US012599678B2

(12) United States Patent
Getts et al.

(10) Patent No.: US 12,599,678 B2
(45) Date of Patent: *Apr. 14, 2026

(54) METHODS AND COMPOSITIONS FOR GENOMIC INTEGRATION

(71) Applicant: CREATE Medicines, Inc., Cambridge, MA (US)

(72) Inventors: Daniel Getts, Medfield, MA (US); Yuxiao Wang, Belmont, MA (US); Namita Bisaria, Somerville, MA (US); Inna Shcherbakova, Holliston, MA (US); Socheata Ly, North Billerica, MA (US)

(73) Assignee: CREATE Medicines, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/313,126

(22) Filed: May 5, 2023

(65) Prior Publication Data

US 2023/0364266 A1     Nov. 16, 2023

Related U.S. Application Data

(63) Continuation of application No. 17/855,423, filed on Jun. 30, 2022, now abandoned, which is a continuation of application No. 17/499,232, filed on Oct. 12, 2021, now Pat. No. 11,672,874, which is a continuation-in-part of application No. PCT/US2020/049240, filed on Sep. 3, 2020.

(60) Provisional application No. 63/039,261, filed on Jun. 15, 2020, provisional application No. 62/908,800, filed on Oct. 1, 2019, provisional application No. 62/895,441, filed on Sep. 3, 2019.

(51) Int. Cl.
| | |
|---|---|
| *A61K 48/00* | (2006.01) |
| *A61K 31/711* | (2006.01) |
| *A61K 31/713* | (2006.01) |
| *A61K 38/17* | (2006.01) |
| *A61K 38/45* | (2006.01) |
| *A61K 38/46* | (2006.01) |
| *A61K 39/395* | (2006.01) |
| *C07K 14/725* | (2006.01) |
| *C07K 16/32* | (2006.01) |
| *C12N 9/12* | (2006.01) |
| *C12N 9/22* | (2006.01) |
| *C12N 15/11* | (2006.01) |
| *C12N 15/113* | (2010.01) |
| *C12N 15/85* | (2006.01) |
| *C12N 15/90* | (2006.01) |

(52) U.S. Cl.
CPC .......... *A61K 48/005* (2013.01); *A61K 31/711* (2013.01); *A61K 31/713* (2013.01); *A61K 38/1774* (2013.01); *A61K 38/45* (2013.01); *A61K 38/465* (2013.01); *A61K 39/39558*

(2013.01); *C07K 14/7051* (2013.01); *C07K 16/32* (2013.01); *C12N 9/1276* (2013.01); *C12N 9/22* (2013.01); *C12N 15/11* (2013.01); *C12N 15/113* (2013.01); *C12N 15/85* (2013.01); *C12N 15/90* (2013.01); *C12N 15/907* (2013.01); *C12Y 207/07049* (2013.01); *A61K 48/00* (2013.01); *C07K 2319/03* (2013.01); *C07K 2319/09* (2013.01); *C07K 2319/30* (2013.01); *C07K 2319/33* (2013.01); *C12N 2310/14* (2013.01); *C12N 2310/20* (2017.05); *C12N 2320/31* (2013.01); *C12N 2800/80* (2013.01); *C12N 2800/90* (2013.01); *C12N 2830/50* (2013.01); *C12N 2840/203* (2013.01)

(58) Field of Classification Search
CPC ........ C12N 15/85; C12N 9/1276; C12N 9/22; C12N 15/11; C12N 15/113; C12N 15/907; C12N 2310/14; C12N 2310/20; C12N 2320/31; C12N 2800/80; C12N 2800/90; C12N 2830/50; C12N 2840/203; A61K 31/711; A61K 31/713; A61K 38/1774; A61K 38/45; A61K 38/465; A61K 39/39558; A61K 48/00; C07K 14/7051; C07K 16/32; C07K 2319/03; C07K 2319/09; C07K 2319/30; C07K 2319/33; C12Y 207/07049

See application file for complete search history.

(56) References Cited

U.S. PATENT DOCUMENTS

| | | | | |
|---|---|---|---|---|
| 10,214,591 | B1 * | 2/2019 | Spadafora | .............. C07K 16/34 |
| 10,617,749 | B1 | 4/2020 | Hanks et al. | |
| 10,925,944 | B2 | 2/2021 | De Vries et al. | |
| 11,034,749 | B2 | 6/2021 | Gill et al. | |
| 11,517,589 | B2 | 12/2022 | Wagner et al. | |
| 11,672,874 | B2 | 6/2023 | Getts et al. | |

(Continued)

FOREIGN PATENT DOCUMENTS

| | | |
|---|---|---|
| CN | 1951499 A | 4/2007 |
| EP | 4025686 A2 | 7/2022 |

(Continued)

OTHER PUBLICATIONS

Ade et al. Gene 2018, vol. 642, pp. 188-198. (Year: 2018).*

(Continued)

*Primary Examiner* — Christopher M Babic
*Assistant Examiner* — Alyssa G Weston
(74) *Attorney, Agent, or Firm* — Wilson Sonsini Goodrich & Rosati

(57) ABSTRACT

Methods and composition for modulating a target genome and stable integration of a transgene of interest into the genome of a cell are disclosed.

22 Claims, 64 Drawing Sheets

Specification includes a Sequence Listing.

(56) References Cited

U.S. PATENT DOCUMENTS

| | | | |
|---|---|---|---|
| 12,319,925 B2 | 6/2025 | Getts et al. | |
| 2002/0132224 A1 | 9/2002 | Poznansky et al. | |
| 2006/0183226 A1* | 8/2006 | Fujiwara | C12N 15/87 |
| | | | 435/456 |
| 2011/0045591 A1* | 2/2011 | Schumann | C12N 15/85 |
| | | | 435/320.1 |
| 2012/0045389 A1* | 2/2012 | Gassull Duro | C12N 15/86 |
| | | | 977/773 |
| 2014/0037606 A1 | 2/2014 | Amiel | |
| 2014/0141046 A1 | 5/2014 | Karlsson-Parra et al. | |
| 2016/0038541 A1 | 2/2016 | Stripecke et al. | |
| 2018/0186855 A1 | 7/2018 | Rosenthal | |
| 2020/0101147 A1 | 4/2020 | Zeng | |
| 2020/0109398 A1* | 4/2020 | Rubens | C12N 15/102 |
| 2020/0239592 A1 | 7/2020 | Vale et al. | |
| 2020/0345773 A1 | 11/2020 | Getts et al. | |
| 2020/0390072 A1* | 12/2020 | Kotin | C12N 15/861 |
| 2021/0038702 A1 | 2/2021 | De Vries et al. | |
| 2022/0001021 A1 | 1/2022 | Uhl et al. | |
| 2022/0001031 A1 | 1/2022 | Getts et al. | |
| 2022/0118010 A1 | 4/2022 | Wagner et al. | |
| 2022/0145293 A1 | 5/2022 | Abudayyeh et al. | |
| 2022/0152199 A1 | 5/2022 | Getts et al. | |
| 2022/0154224 A1 | 5/2022 | Abudayyeh et al. | |
| 2022/0175830 A1 | 6/2022 | Wagner et al. | |
| 2022/0175831 A1 | 6/2022 | Wagner et al. | |
| 2022/0184230 A1 | 6/2022 | Getts et al. | |
| 2022/0202856 A1 | 6/2022 | Wagner et al. | |
| 2022/0233586 A1 | 7/2022 | Wagner et al. | |
| 2022/0241428 A1 | 8/2022 | Getts et al. | |
| 2022/0364110 A1 | 11/2022 | Getts et al. | |
| 2022/0378824 A1 | 12/2022 | Getts et al. | |
| 2022/0411817 A1 | 12/2022 | Getts et al. | |
| 2023/0046472 A1 | 2/2023 | Getts et al. | |
| 2023/0141052 A1 | 5/2023 | Getts et al. | |
| 2023/0277659 A1 | 9/2023 | Getts et al. | |
| 2023/0364265 A1 | 11/2023 | Getts et al. | |
| 2024/0327482 A1 | 10/2024 | Getts et al. | |
| 2025/0250584 A1 | 8/2025 | Getts et al. | |

FOREIGN PATENT DOCUMENTS

| | | | | |
|---|---|---|---|---|
| EP | 4337268 A1 | 3/2024 | | |
| JP | 2015513916 A | 5/2015 | | |
| JP | 2022546592 A | 11/2022 | | |
| WO | WO-2004072290 A1 | 8/2004 | | |
| WO | WO-2006069812 A2 | 7/2006 | | |
| WO | WO-2009056321 A1 | 5/2009 | | |
| WO | WO-2013151736 A2 | 10/2013 | | |
| WO | WO-2016030501 A1 * | 3/2016 | A61K 48/0058 | |
| WO | WO-2016126213 A1 | 8/2016 | | |
| WO | WO-2016138491 A1 | 9/2016 | | |
| WO | WO-2019023164 A1 | 1/2019 | | |
| WO | WO-2019079215 A1 | 4/2019 | | |
| WO | WO-2020131662 A1 | 6/2020 | | |
| WO | WO-2020131862 A1 | 6/2020 | | |
| WO | WO-2020150534 A9 * | 8/2020 | A61K 35/17 | |
| WO | WO-2020191234 A1 | 9/2020 | | |
| WO | WO-2022087235 A1 | 4/2022 | | |
| WO | WO-2025128722 A2 | 6/2025 | | |

OTHER PUBLICATIONS

Ade; Catherine M. et al.: Evaluating different DNA binding domains to modulate L1 ORF2p-driven site-specific retrotransposition events in human cells. Gene 642:188-198 (2018). https://doi.org/10.1016/j.gene.2017.11.033.

Bucheton et al.: The molecular basis of I-R hybrid Dysgenesis in Drosophila melanogaster: Identification, cloning, and properties of the I factor. 38(1):153-163 (1984). Abstract. DOI: https://doi.org/10.1016/0092-8674(84)90536-1.

Chadwick et al.: Safety of a single aerosol administration of escalating doses of the cationic lipid GL-67/DOPE/DMPE-PEG5000 formulation to the lungs of normal volunteers. Gene Therapy 4(9):937-42 (1997). doi: 10.1038/sj.gt.3300481.

Gao et al.: Cationic liposome-mediated gene transfer. Gene Therapy 2(10):710-722 (1995). Abstract.

Onodera et al.: Successful Peripheral T-Lymphocyte-Directed Gene Transfer for a Patient With Severe Combined Immune Deficiency Caused by Adenosine Deaminase Deficiency. Blood 91(1):30-36 (1998). https://doi.org/10.1182/blood.V91.1.30.

PCT/US2022/028831 International Search Report and Written Opinion dated Sep. 2, 2022.

U.S. Appl. No. 18/313,126 Office Action dated May 31, 2024.

U.S. Appl. No. 18/157,052 Office Action dated May 15, 2024.

U.S. Appl. No. 18/313,087 Office Action dated Feb. 12, 2024.

U.S. Appl. No. 18/313,087 Office Action dated Jun. 27, 2024.

Meyer, Thomas J. et al. Heads or tails: L1 insertion-associated 5' homopolymeric sequences. Mob DNA 1(1):7 (2010).

PCT/US2020/030837 International Search Report and Written Opinion dated Oct. 10, 2020.

Strauss et al.: The immunophenotype of antigen presenting cells of the mononuclear phagocyte system in a normal human liver—A systematic review. Journal of Hepatology 62:458-468 (2015).

U.S. Appl. No. 18/157,052 Office Action dated Sep. 5, 2024.

1-(3,4-dichlorophenyl)-3-(4-methoxyphenyl)-4-(4-morpholinyl)-1H-pyrrole-2,5-dione (CAS 1417162) 1 page, Retrieved URL https://www.caymanchem.com/product/18397/ri-2.

6-hydroxyDL-dopa (CAS 21373-30-8). 3 Pages. Retrieved URL: https://www.rndsystems.com/products/6-hydroxy-dl-dopa_5740.

B02 (Cas 1290541-46-6). 4 Pages. Retrieved URL: https://www.rndsystems.com/products/b02_6392.

Benzamide for synthesis. CAS No. 55-21-0, EC No. 200-227-7. 3 Pages. Retrieved URL: https://www.merckmillipore.com/IN/en/product/Benzamide,MDA_CHEM-802191.

Camptothecin (CPT) (CAS 7689-03-4). 8 Pages. Retrieved URL: https://www.tcichemicals.com/IN/en/p/C1495.

DIDS (CAS 67483-13-0). 4 Pages. Retrieved URL: https://www.tocris.com/products/dids_4523.

GenBank Accession No. AAC51261. Version No. AAC51261.1. Putative p150 [Homo sapiens]. 2 pages. Retrieved from URL: https://www.ncbi.nlm.nih.gov/protein/AAC51261.

GenBank Accession No. AAC51262. Version No. AAC51262.1. p40 [Homo sapiens]. 2 pages. Retrieved from URL: https://www.ncbi.nlm.nih.gov/protein/AAC51262.

GenBank Accession No. AAC51263. Version No. AAC51263.1. Putative p150 [Homo sapiens]. 2 pages. Retrieved from URL: https://www.ncbi.nlm.nih.gov/protein/AAC51263.

GenBank Accession No. AAC51264. Version No. AAC51264.1. Putative p150 [Homo sapiens]. 2 pages. Retrieved from URL: https://www.ncbi.nlm.nih.gov/protein/AAC51264.

GenBank Accession No. AAC51265. Version No. AAC51265.1. p40 [Homo sapiens]. 2 pages. Retrieved from URL: https://www.ncbi.nlm.nih.gov/protein/AAC51265.

GenBank Accession No. AAC51266. Version No. AAC51266.1. p40 [Homo sapiens]. 2 pages. Retrieved from URL: https://www.ncbi.nlm.nih.gov/protein/AAC51266.

GenBank Accession No. AAC51267. Version No. AAC51267.1. Putative p150 [Homo sapiens]. 2 pages. Retrieved from URL: https://www.ncbi.nlm.nih.gov/protein/AAC51267.

GenBank Accession No. AAC51268. Version No. AAC51268.1. p40 [Homo sapiens]. 2 pages. Retrieved from URL: https://www.ncbi.nlm.nih.gov/protein/AAC51268.

GenBank Accession No. AAC51269. Version No. AAC51269.1. Putative p150 [Homo sapiens]. 2 pages. Retrieved from URL: https://www.ncbi.nlm.nih.gov/protein/AAC51269.

GenBank Accession No. AAC51270. Version No. AAC51270.1. p40 [Homo sapiens]. 2 pages. Retrieved from URL: https://www.ncbi.nlm.nih.gov/protein/AAC51270.

GenBank Accession No. AAC51271. Version No. AAC51271.1. Putative p150 [Homo sapiens]. 2 page. Retrieved from URL: https://www.ncbi.nlm.nih.gov/protein/AAC51271.

GenBank Accession No. AAC51272. Version No. AAC51272.1. p40 [Homo sapiens]. 1 page. Retrieved from URL: https://www.ncbi.nlm.nih.gov/protein/AAC51272.

(56) References Cited

OTHER PUBLICATIONS

GenBank Accession No. AAC51273. Version No. AAC51273.1. Putative p150 [*Homo sapiens*]. 2 page. Retrieved from URL: https://www.ncbi.nlm.nih.gov/protein/AAC51273.

GenBank Accession No. AAC51274. Version No. AAC51274.1. p40 [*Homo sapiens*]. 2 page. Retrieved from URL: https://www.ncbi.nlm.nih.gov/protein/AAC51274.

GenBank Accession No. AAC51275. Version No. AAC51275.1. p40 [*Homo sapiens*]. 1 page. Retrieved from URL: https://www.ncbi.nlm.nih.gov/protein/AAC51275.

GenBank Accession No. AAC51276. Version No. AAC51276.1. Putative p150 [*Homo sapiens*]. 2 page. Retrieved from URL: https://www.ncbi.nlm.nih.gov/protein/AAC51276.

GenBank Accession No. AAC51277. Version No. AAC51277.1. p40 [*Homo sapiens*]. 2 page. Retrieved from URL: https://www.ncbi.nlm.nih.gov/protein/AAC51277.

GenBank Accession No. AAC51278. Version No. AAC51278.1. p40 [*Homo sapiens*]. 2 page. Retrieved from URL: https://www.ncbi.nlm.nih.gov/protein/AAC51278.

GenBank Accession No. AAC51279. Version No. AAC51279.1. Putative p150 [*Homo sapiens*]. 2 page. Retrieved from URL: https://www.ncbi.nlm.nih.gov/protein/AAC51279.

Irinotecan (CAS 100286-90-6). 7 Pages. Retrived URL: https://www.sigmaaldrich.com/IN/en/product/sigma/i1406.

ML216 (CAS 1430213-30-1). 2 Pages. Retrived URL: https://www.scbt.com/p/ml-216-1430213- 30-1.

Niraparib (MK-827 Tesaro) CAS 1038915-60- 4). 2 Pages. Retrived URL: https://www.bldpharm.com/products/1038915-60-4.html.

NSC 19630 (CAS 72835-26-8). 2 Pages. Retrived URL: https://www.merckmillipore.com/IN/en/product/WRN-Helicase-Inhibitor-NSC-19630-CAS-72835-26-8-Calbiochem,EMD_BIO-681647.

NSC 617145 (CAS 203115-63-3). 3 Pages. Retrived URL: https://www.rndsystems.com/products/nsc-617145_5340.

Olaparib (Lynparza) (CAS 763113-22-0). 54 Pages. Retrieved URL: https://pubchem.ncbi.nlm.nih.gov/compound/Olaparib.

PF-01367338 Pfizer. 3 Pages. Retrived URL: https://www.pfizer.com/news/press-release/press-release-detail/clovis-oncology-inc-receives-license-worldwide-development.

RI-1 (CAS 415713-60-9). 3 Pages. Retrived URL: https://www.rndsystems.com/products/ri-1_6168.

Sambrook, Joseph et al. Molecular Cloning: A Laboratory Manual, 2nd Edition. Chapter 15. Cold Spring Harbor Laboratory Press : 1-30 (1989).

Streptonigrin (SN) (CAS 3930-19-6). 2 Pages. Retrived URL: https://medkoo.com/products/15240.

Topotecan (Hycamtin® GlaxoSmithKline) (CAS 123948-87-8). 2 Pages. Retrived URL: https://www.scbt.com/p/topotecan-123948-87-8.

Veliparib (ABT-888 Abbvie) (CAS 912444-00-9). 4 Pages. Retrived URL: https://www.selleckchem.com/products/ABT-888.html.

www.kazusa.orjp/codon.

Final Office Action issued in counterpart U.S. Appl. No. 17/499,232 dated Dec. 8, 2022.

Final Office Action issued in counterpart U.S. Appl. No. 17/499,232 dated Jul. 7, 2022.

International Search Report for PCT/US2020/037312 issued Nov. 30, 2020.

Non-Final Office Action issued in counterpart U.S. Appl. No. 17/499,232 dated May 4, 2022.

Non-Final Office Action issued in counterpart U.S. Appl. No. 17/499,232 dated Sep. 26, 2022.

Non-Final Office Action issued in counterpart U.S. Appl. No. 17/855,230 dated Oct. 26, 2022.

Non-Final Office Action issued in counterpart U.S. Appl. No. 17/855,423 dated Nov. 7, 2022.

Carisma Therapeutics. Carisma Therapeutics Corporate Overview. Nov. 2018.

EP20861388 European Extended Search Report dated Aug. 11, 2023.

European Patent Application No. 20861388.5 Extended European Search Report dated Aug. 11, 2023.

Gordon, S., Phagocytosis an immunobiologic process. Immunity 44, Mar. 15, 2016 p. 463-475.

Great Britain Patent Application No. GB2203647.9 Examination Report dated Jan. 24, 2024.

Laborde, Rebecca R. et al.: Cancer Vaccines in the World of Immune Suppressive Monocytes (CD14+HLA-DRIo/neg Cells): The Gateway to Improved Responses. Frontiers in Immunology vol. 5 (2014). https://doi.org/10.3389/fimmu.2014.00147.

Nakamizo et al.: Single-cell analysis of human skin identifies CD14+ type 3 dendritic cells co-producing IL1B and IL23A in psoriasis. J Exp Med 218(9):e20202345 (2021). https://doi.org/10.1084/jem.20202345.

Oates et al.: Characterizing the polarization continuum of macrophage subtypes M1, M2a and M2c. bioRxiv (2022). doi: https://doi.org/10.1101/2022.06.13.495868.

Office Action dated Dec. 8, 2022 issued in U.S. Appl. No. 17/499,232.

Office Action dated Oct. 7, 2022 issued in U.S. Appl. No. 17/855,423.

Sica, F., Fingolimod Immune Effects Beyond Its Sequestration Ability, Neurol Ther (2019) 8:231-240.

Silverstein RL., Mechanisms of Cell Signaling By the Scavenger Receptor CD36: Implications in Atherosclerosis and Thrombosis, Transactions of the American Clinical and Climatological Association, vol. 121, 2010.

Supplementary European Search Report dated Dec. 16, 2022 issued in European Patent Application No. 20798060.

Boross, P. et al.: Anti-tumor activity of human IgG1 anti-gp75 TA99 mAb against B16F10 melanoma in human FcgammaRI transgenic mice. Immunol. Lett. 2014 160:151-157. (Abstract).

Jain et al.: Preclinical pharmacologic evaluation of pralatrexate and romidepsin confirms potent synergy of the combination in a murine model of human T-cell lymphoma. Clin Cancer Res. 21(9):2096-2106 (2015).

Mantovani et al.: Tumour-associated macrophages as treatment targets in oncology. Nat Rev Clin Oncol. 14(7):399-416 (2017).

Pathria et al.: Targeting Tumor-Associated Macrophages in Cancer. Trends Immunol. 40(4):310-327 (2019).

Studnicka, Gary M. et al.: Human-engineered Monoclonal Antibodies Retain Full Specific Binding Activity by Preserving non-CDR Complementarity-modulating Residues. Protein Eng. 7(6):805-814 (1994).

Takechi et al.: A melanosomal membrane protein is a cell surface target for melanoma therapy. Clin Cancer Res. 2(11):1837-1842 (1996).

U.S. Appl. No. 18/157,052 Notice of Allowance dated Jan. 29, 2025.

Goodwin, Timothy J.D. et al.: A yeast model for target-primed (non-LTR) retrotransposition. BMC Genomics 8(1):263 (2007). DOI:10.1186/1471-2164-8-263.

Chen, Peter J. et al.: Enhanced prime editing systems by manipulating cellular determinants of editing outcomes. Cell 184:5635-565 (2021). https://doi.org/10.1016/j.cell.2021.09.018.

Ioannidi, Eleonora I. et al.: Drag-and-drop genome insertion without DNA cleavage with CRISPR directed integrases. bioRxiv, Nov. 1, 2021. https://doi.org/10.1101/2021.11.01.466786.

Jiang, Kaiyi et al.: Programmable RNA-guided DNA endonucleases are widespread in eukaryotes and their viruses. Science Advances 9(eadk0171):1-14 (2023). https://www.science.org/doi/pdf/10.1126/sciadv.adk0171.

Kaur, Davneet et al.: IS200/IS605 Family-Associated TnpB Increases Transposon Activity and Retention. doi: https://doi.org/10.1101/2022.10.12.511977.

Kim, Sun Chang et al.: Modifications of mRNA vaccine structural elements for improving mRNA stability and translation efficiency. Molecular & Cellular Toxicology 18:1-8 (2022). https://doi.org/10.1007/s13273-021-00171-4.

Kuroki-Kami, Azusa et al.: Targeted gene knockin in zebrafish using the 28S rDNA-specific non-LTR retrotransposon R2OI. Mobile DNA 10:23 (2019).

Li, Xiaoyi et al.: The MOV10 Helicase Inhibits LINE-1 Mobility. Journal of Biological Chemistry 288(29):21148-21160 (2013).

(56) References Cited

OTHER PUBLICATIONS

Nigumann, Pilvi et al.: Many human genes are transcribed from the antisense promoter of L1 retrotransposon. Genomics 79(5):628-34 (2002). doi: 10.1006/geno.2002.6758 (Abstract).

Pavani, Giulia et al.: Targeted Gene Delivery: Where to Land. Frontier in Genome Editing 2:609650 (2021). doi: 10.3389/fgeed. 2020.609650.

U.S. Appl. No. 18/313,087 Office Action dated Dec. 23, 2024.

Wang; Yuxiao et al.: CRISPR-Enabled Autonomous Transposable Element (CREATE) for RNA-based gene editing and delivery. Cold Spring Harbor Laboratory May 4, 2024. bioRxiv preprint doi: https://doi.org/10.1101/2024.01.29.577809.

Wilkinson, Max E. et al.: Structure of the R2 non-LTR retrotransposon initiating target-primed reverse transcription. Science 380(6642):301-308 (2023). DOI: 10.1126/science.adg7883.

Xiao, Qingquan et al.: Engineered IscB-wRNA system with expanded target range for base editing. Nature Chemical Biology 21:100-108 (2025). https://www.nature.com/articles/s41589-024-01706-1.

Xie, Kabin et al.: Boosting CRISPR/Cas9 multiplex editing capability with the endogenous tRNA-processing system. PNAS 112(11):3570-3575 (2015). https://www.pnas.org/doi/10.1073/pnas. 1420294112.

Yin, Shuming et al.: Engineering of efficiency-enhanced Cas9 and base editors with improved gene therapy efficacies. Mol. Ther. 31(3):744-759 (2022). doi: 10.1016/j.ymthe.2022.11.014.

Zhao, Zhihan et al.: Prime editing: advances and therapeutic applications. Trends in Biotechnology 41(8):1000-1012 https://www.cell. com/trends/biotechnology/pdf/S0167-7799(23)00085-9.

Adikusuma, Fatwa et al.: Versatile single-step-assembly CRISPR/ Cas9 vectors for dual gRNA expression. PLoS One 12(12):e0187236 (2017). https://doi.org/10.1371/journal.pone.0187236.

Beucher, Anthony et al.: One-step dual CRISPR/Cas9 guide RNA cloning protocol. Imperial College London, posted Jun. 26, 2019. DOI: https://doi.org/10.21203/rs.2.1831/v1.

Garfinkel, David J. et al.: Ty element transposition: reverse transcriptase and virus-like particles. Cell 42(2):507-517 (1985). https://doi.org/ 10.1016/0092-8674(85)90108-4.

Yates, John L. et al.: Stable replication of plasmids derived from EpsteinBarr virus in various mammalian cell. Nature 313:812-815 (1985)—Abstract.

Extended European Search Report dated May 7, 2025 issued in European Patent Application No. EP22808288.9.

Han, Jeffrey et al.: A highly active synthetic mammalian retrotransposon. Nature 429:314-318 (2004).

PCT/US2024/059602 International Search Report and Written Opinion dated Jul. 10, 2025.

U.S. Appl. No. 17/687,395 Office Action dated May 16, 2025.

U.S. Appl. No. 18/313,087 Office Action dated Jun. 9, 2025.

Wagstaff, Bradley et al.: Rescuing Alu: Recovery of New Inserts Shows LINE-1Preserves Alu Activity through A-Tail Expansion. PLOS Genetics 8(8):e1002842. doi:10.1371/journal.pgen.1002842. t004.

Wang, Yuxiao et al.: CRISPR-Enabled Autonomous Transposable Element(CREATE) for RNA-based gene editing and delivery. EMBO reports 26:1062-1083 (2025).

Zheng, Feiyang et al.: LINE-1 vectors mediate recombinant antibody gene transfer by retrotransposition in Chinese hamster ovary cells. Biotechnology Journal vol. 16, No. 7 (2021). Abstract.

* cited by examiner

Cis strategy:

CMV/T7    ORF1    ORF2    CMV G FP

Trans strategy:

CMV/T7    ORF1    ORF2

+

CMV/T7    Any gene    CMV G FP

LINE-1 binding domain

FIG. 1D

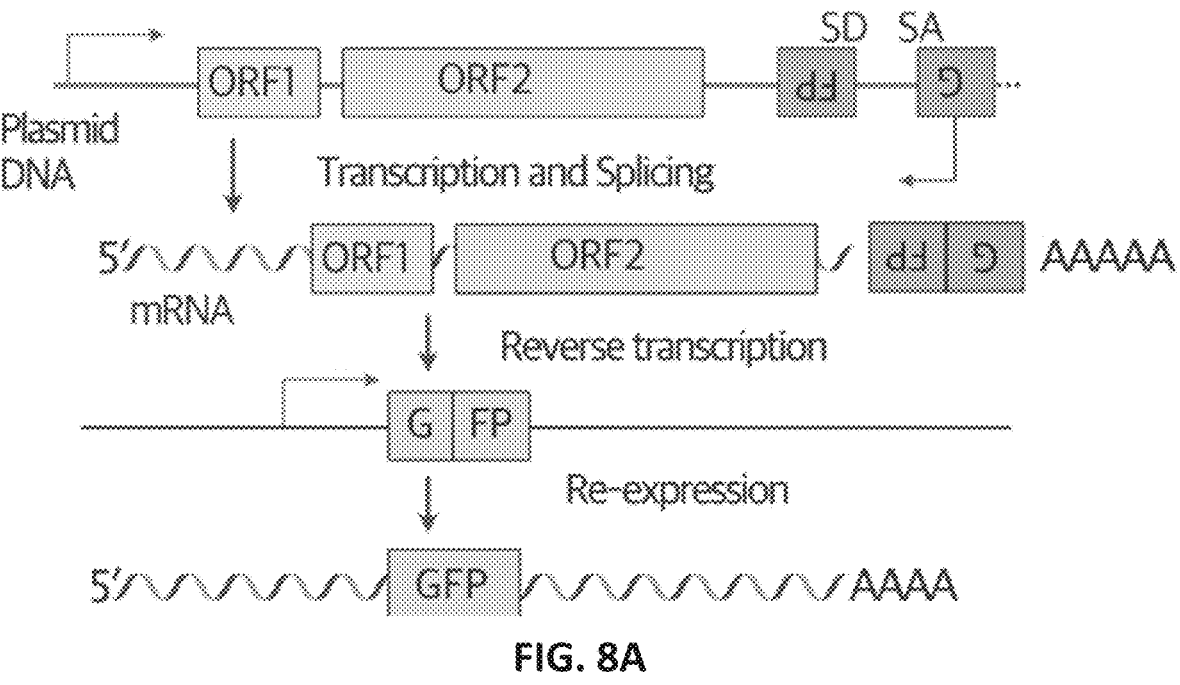
FIG. 8A
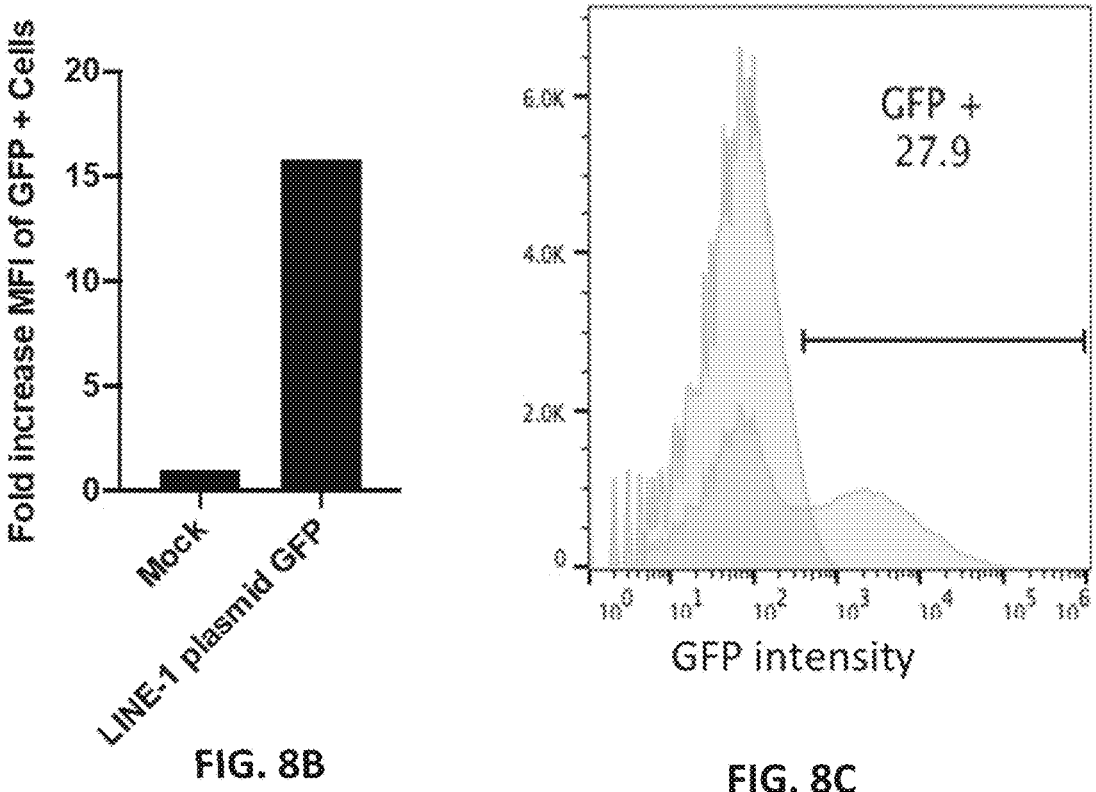
FIG. 8B                    FIG. 8C

CD5 protein-AF647 intensity

METHODS AND COMPOSITIONS FOR GENOMIC INTEGRATION

CROSS REFERENCE

This application is a continuation of U.S. application Ser. No. 17/855,423 filed on Jun. 30, 2022, which is a continuation of U.S. application Ser. No. 17/499,232 filed on Oct. 12, 2021, which is a Continuation-in-part of and claims priority to International Application No. PCT/US2020/049240, filed Sep. 3, 2020, which claims priority to U.S. Provisional Application No. 62/895,441, filed on Sep. 3, 2019, U.S. Provisional Application No. 62/908,800, filed on Oct. 1, 2019, and U.S. Provisional Application No. 63/039,261, filed on Jun. 15, 2020, each of which is incorporated herein by reference in its entirety.

SEQUENCE LISTING

The instant application contains a Sequence Listing which has been filed electronically in XML format and is hereby incorporated by reference in its entirety. Said XML copy, created on May 15, 2025, is named Final 56371-706305_SL.xml and is 326,121 bytes in size.

BACKGROUND

Cell therapy is a rapidly developing field for addressing difficult to treat diseases, such as cancer, persistent infections and certain diseases that are refractory to other forms of treatment. Cell therapy often utilizes cells that are engineered ex vivo and administered to an organism to correct deficiencies within the body. An effective and reliable system for manipulation of a cell's genome is crucial, in the sense that when the engineered cell is administered into an organism, it functions optimally and with prolonged efficacy. Likewise, reliable mechanisms of genetic manipulation form the cornerstone in the success of gene therapy. However, severe deficiencies exist in methods for delivering nucleic acid cargo (e.g., large cargo) in a therapeutically safe and effective manner. Viral delivery mechanisms are frequently used to deliver large nucleic acid cargo in a cell but are tied to safety issues and cannot be used to express the cargo in some cell types. Additionally, subjecting a cell to repeated gene manipulation can affect cell health, induce alterations of cell cycle and render the cell unsuitable for therapeutic use. Advancements are continually sought in the area for efficacious delivery and stabilization of an exogenously introduced genetic material for therapeutic purposes.

SUMMARY

Provided herein are compositions and methods for stable, non-viral transfer and integration of genetic material into a cell. In one aspect, the genetic material is a self-integrating polynucleotide. The genetic material can be stably integrated in the genome of the cell. The cell may be a human cell. The method is designed for a safe and reliable integration of a genetic material into the genome of a cell.

Provided herein is pharmaceutical composition comprising a therapeutically effective amount of one or more polynucleic acids, or at least one vector encoding the one or more polynucleic acids, the one or more polynucleic acids comprising: (a) a mobile genetic element comprising a sequence encoding a polypeptide; and (b) an insert sequence, wherein the insert sequence comprises a sequence that is a reverse complement of a sequence encoding an exogenous therapeutic polypeptide, wherein the polypeptide encoded by the sequence of the mobile genetic element promotes integration of the insert sequence into a genome of a cell; and wherein the pharmaceutical composition is substantially non-immunogenic to a human subject.

In some embodiments, the polypeptide encoded by the sequence of the mobile genetic element comprises one or more long interspersed nuclear element (LINE) polypeptides, wherein the one or more LINE polypeptides comprises: (i) human ORF1p or a functional fragment thereof, and (ii) human ORF2p or a functional fragment thereof.

In some embodiments, the insert sequence stably integrates and/or is retrotransposed into the genome of a human cell.

In some embodiments, the human cell is an immune cell selected from the group consisting of a T cell, a B cell, a myeloid cell, a monocyte, a macrophage and a dendritic cell.

In some embodiments, the insert sequence is integrated into the genome (i) by cleavage of a DNA strand of a target site by an endonuclease encoded by the one or more polynucleic acids, (ii) via target-primed reverse transcription (TPRT) or (iii) via reverse splicing of the insert sequence into a DNA target site of the genome.

In some embodiments, the insert sequence is integrated into the genome at a poly T site using specificity of an endonuclease domain of the human ORF2p.

In some embodiments, the poly T site comprises the sequence TTTTTA.

In some embodiments, the one or more polynucleic acids comprises homology arms complementary to a target site in the genome.

In some embodiments, the insert sequence integrates into: (a) the genome at a locus that is not a ribosomal locus; (b) a gene or regulatory region of a gene of the genome, thereby disrupting the gene or downregulating expression of the gene; (c) a gene or regulatory region of a gene of the genome, thereby upregulating expression of the gene; or (d) the genome and replaces a gene of the genome.

In some embodiments, the pharmaceutical composition further comprises (i) one or more siRNAs and/or (ii) an RNA guide sequence or a polynucleic acid encoding the RNA guide sequence, and wherein the RNA guide sequence targets a DNA target site of the genome and the insert sequence is integrated into the genome at the DNA target site of the genome.

In some embodiments, the one or more polynucleic acids have a total length of from 3 kb to 20 kb.

In some embodiments, the one or more polynucleic acids comprises one or more polyribonucleic acids, one or more RNAs or one or more mRNAs.

In some embodiments, the exogenous therapeutic polypeptide is selected from the group consisting of a ligand, an antibody, a receptor, an enzyme, a transport protein, a structural protein, a hormone, a contractile protein, a storage protein and a transcription factor.

In some embodiments, the exogenous therapeutic polypeptide is a receptor selected from the group consisting of a chimeric antigen receptor (CAR) and a T cell receptor (TCR).

In some embodiments, the one or more polynucleic acids comprises a first expression cassette comprising a promoter sequence, a 5' UTR sequence, a 3' UTR sequence and a poly A sequence; wherein: (i) the promoter sequence is upstream of the 5' UTR sequence, (ii) the 5' UTR sequence is upstream of the sequence of the mobile genetic element encoding a polypeptide, (iii) the 3' UTR sequence is downstream of the insert sequence; and (iv) the 3' UTR is upstream of the poly A sequence; and wherein the 5' UTR sequence, the 3' UTR sequence or the poly A sequence comprises a binding site for a human ORF2p or a functional fragment thereof.

In some embodiments, the insert sequence comprises a second expression cassette comprising a sequence that is a reverse complement of a promoter sequence, a sequence that is a reverse complement of a 5' UTR sequence, a sequence that is a reverse complement of a 3' UTR sequence and a sequence that is a reverse complement of a poly A sequence; wherein: (i) the sequence that is a reverse complement of a promoter sequence is downstream of the sequence that is a reverse complement of a 5' UTR sequence, (ii) the sequence that is a reverse complement of a 5' UTR sequence is downstream of the sequence that is a reverse complement of a sequence encoding an exogenous therapeutic polypeptide (iii) the sequence that is a reverse complement of a 3' UTR sequence is upstream of the sequence that is a reverse complement of a sequence encoding an exogenous thera- peutic polypeptide, and (iv) the sequence that is a reverse complement of a poly A sequence is upstream of the sequence that is a reverse complement of a 3' UTR sequence and downstream of the sequence of the mobile genetic encoding a polypeptide.

In some embodiments, the promoter sequence of the first expression cassette is different from the promoter sequence of the second expression cassette.

In some embodiments, the one or more LINE polypep- tides comprises a first LINE polypeptide comprising the human ORF1p or functional fragment thereof and a second LINE polypeptide comprising the human ORF2p or func- tional fragment thereof, wherein the first LINE polypeptide and the second LINE polypeptide are translated from dif- ferent open reading frames (ORFs).

In some embodiments, the one or more polynucleic acids comprises a first polynucleic acid molecule encoding the human ORF1p or functional fragment thereof and a second polynucleic acid molecule encoding the human ORF2p or functional fragment thereof.

In some embodiments, the one or more polynucleic acids comprises a 5' UTR sequence and a 3' UTR sequence, wherein (a) the 5' UTR comprises a 5' UTR from LINE-1 or a sequence with at least 80% sequence identity to ACUC-CUCCCCAUCCUCUCCCUCUGUCCCUCUGUCCCU-CUGACCCUGCACUGUCCCAGCACC (SEQ ID NO: 86); and/or (b) the 3' UTR comprises a 3' UTR from LINE-1 or a sequence with at least 80% sequence identity to (SEQ ID NO: 87)
CAGGACACAGCCUUGGAUCAGGACAGAGACUUGGGGGCCAUCCUGCCCC

UCCAACCCGACAUGUGUACCUCAGCUUUUUCCCUCACUUGCAUCAAUAA

AGCUUCUGUGUUUGGAACAG.

In some embodiments, the sequence encoding the exog- enous therapeutic polypeptide does not comprise introns.

In some embodiments, the polypeptide encoded by the sequence of the mobile genetic element comprises a C-ter- minal nuclear localization signal (NLS), an N-terminal NLS or both.

In some embodiments, the sequence encoding the exog- enous polypeptide is not in frame with a sequence encoding the ORF1p or functional fragment thereof and/or is not in frame with a sequence encoding the ORF2p or functional fragment thereof.

In some embodiments, the one or more polynucleic acids comprises a sequence encoding a nuclease domain, a nucle- ase domain that is not derived from ORF2p, a megaTAL nuclease domain, a TALEN domain, a Cas9 domain, a Cas6 domain, a Cas7 domain, a Cas8 domain, a zinc finger binding domain from an R2 retroelement, or a DNA binding domain that binds to repeat sequences.

In some embodiments, the one or more polynucleic acids comprises a sequence encoding the nuclease domain, wherein the nuclease domain does not have nuclease activity or comprises a mutation that reduces activity of the nuclease domain compared to the nuclease domain without the muta- tion.

In some embodiments, the ORF2p or functional fragment thereof lacks endonuclease activity or comprises a mutation selected from the group consisting of S228P and Y1180A, and/or wherein the ORF1p or functional fragment comprises a K3R mutation.

In some embodiments, the insert sequence comprises a sequence that is a reverse complement of a sequence encod- ing two or more exogenous therapeutic polypeptides.

In some embodiments, the one or more polynucleic acids comprises one or more polyribonucleic acids, wherein the exogenous therapeutic polypeptide is a receptor selected from the group consisting of a chimeric antigen receptor (CAR) and a T cell receptor (TCR), and wherein the pharmaceutical composition is formulated for systemic administration to a human subject.

In some embodiments, the one or more polynucleic acids (i) are formulated in a nanoparticle selected from the group consisting of a lipid nanoparticle and a polymeric nanopar- ticle; and/or (ii) comprises one or more polynucleic acids selected from the group consisting of glycosylated RNAs, circular RNAs and self-replicating RNAs.

Also provided herein is a method of treating a disease or condition in a human subject in need thereof comprising administering a pharmaceutical composition described herein to the human subject.

Also provided herein is a method of modifying a popu- lation of human cells ex vivo comprising contacting a composition to a population of human cell ex vivo, thereby forming an ex vivo modified population of human cells, the composition comprising one or more polynucleic acids, or at least one vector encoding the one or more polynucleic acids, the one or more polynucleic acids comprising: (a) a mobile genetic element comprising a sequence encoding a polypep- tide; and (b) an insert sequence, wherein the insert sequence is a reverse complement of a sequence encoding an exog- enous therapeutic polypeptide, wherein the ex vivo modified population of human cells is substantially non-immunogenic to a human subject.

In one aspect, provided herein are compositions and methods that allow integration of genetic material into the genome of a cell, wherein the genetic material that can be integrated is not specifically restricted by size. In some aspects, the method described herein provides a one-step, single polynucleotide-mediated delivery and integration of genetic "cargo" in the genome of a cell. The genetic material may comprise a coding sequence, e.g., a sequence encoding a transgene, a peptide, a recombinant protein, or an antibody or fragments thereof, wherein the method and compositions ensure stable expression of the transcribed product encoded by the coding sequence. The genetic material may comprise a non-coding sequence, for example, a regulatory RNA sequences, e.g., a regulatory small inhibitory RNA (siRNA), microRNA (miRNA), long non-coding RNA (lncRNA), or one or more transcription regulators such as a promoter and/or an enhancer, and may also include, but not limited to structural biomolecules such as ribosomal RNA (rRNA), transfer RNA (tRNA) or a fragment thereof or a combination thereof.

In another aspect, provided herein are methods and compositions for site-specific integration of a genetic material that may not be specifically restricted by size, into the genome of a cell via a non-viral delivery that ensures both safety and efficacy of the transfer. Provided methods and compositions may be particularly useful in developing a therapeutic, such as a therapeutic comprising a polynucleotide comprising a genetic material and a machinery that allows transfer into a cell and stable integration into the genome of the cell into which the polynucleotide or an mRNA encoding the polynucleotide is transferred. In some embodiments, the therapeutic may be a cell that comprises a polynucleotide that has been stably integrated into the genome of the cell using the methods and compositions described herein.

In one aspect, the present disclosure provides compositions and methods for stable gene transfer into a cell. In some embodiments, the compositions and methods are for stable gene transfer into an immune cell. In some cases, the immune cell is a myeloid cell. In some cases, the methods described herein relate to development of myeloid cells for immunotherapy.

Provided herein is a method of treating a disease in a subject in need thereof, comprising: administering a pharmaceutical composition to the subject wherein the pharmaceutical composition comprises a polycistronic mRNA sequence encoding a gene or fragment thereof, operably linked to a sequence encoding an L1 retrotransposon; wherein the gene or the fragment thereof is at least 10.1 kb in length.

Provided herein is a method for integrating a nucleic acid sequence into the genome of a cell, comprising contacting the cell with a composition comprising a polycistronic mRNA sequence encoding a gene or fragment thereof, operably linked to a sequence encoding an L1 retrotransposon; wherein the gene or the fragment thereof is at least 10.1 kb in length. In some embodiments, the gene or the fragment thereof (e.g., the payload) is at least about 10.2 kb, 10.3 kb, 10.4 kb, 10.5 kb, 10.6 kb, 10.7 kb, 10.8 kb, 10.9 kb, 11 kb, 12 kb, 13 kb, 14 kb, 15 kb, 16 kb, 17 kb, 18 kb, 19 kb, 20 kb or more in length.

Provided herein is a method for integrating a nucleic acid sequence into the genome of a cell, comprising contacting the cell with a composition comprising a polycistronic mRNA sequence encoding a gene or fragment thereof, operably linked to a sequence encoding an L1 retrotransposon; wherein the gene or the fragment thereof is selected from a group consisting of ABCA4, MY07A, CEP290, CDH23, EYS, USH2a, GPR98, ALMS1, GDE, OTOF, and F8.

Provided herein is a method of expressing a protein encoded by a recombinant nucleic acid in a cell, the method comprising integrating a nucleic acid sequence into the genome of a cell by contacting the cell with a composition comprising a polycistronic mRNA sequence encoding a gene or fragment thereof, operably linked to a sequence encoding an L1 retrotransposon; and expressing a protein encoded by the gene or fragment thereof, wherein expression of the protein is detectable more than 30 days after (a).

In one embodiment of a method described herein, the disease is a genetic disease.

Provided herein is a method of treating Stargardt disease, LCA10, USH1D, DFNB12, retinitis pigmentosa (RP)

USH2A, USH2C, Alstrom syndrome, Glycogen storage disease III, Non-syndromic deafness, Hemophilia A, or Leber congenital aumaurosis in a subject, the method comprising: (i) introducing into the subject an mRNA encoding a suitable gene or a fragment thereof, operably linked to a human L1 transposon, or (ii) introducing to the subject a population of cells comprising an mRNA encoding a suitable gene or a fragment thereof, operably linked to a human L1 transposon.

In one embodiment of a method described herein, the method comprises treating Stargardt disease in a subject in need thereof, and wherein the mRNA encodes an ABCA4 gene, or a fragment thereof.

In one embodiment of a method described herein, the method comprises treating Usher Syndrome Type 1b (Usher 1b) disease in a subject in need thereof, and wherein the mRNA encodes an MY07A gene, or a fragment thereof.

In one embodiment of a method described herein, the method comprises treating Leber congenital amaurosis (LCA)10 disease in a subject in need thereof, and wherein the mRNA encodes a CEP290 gene, or a fragment thereof.

In one embodiment of a method described herein, the method comprises treating a User Syndrome Type 1D (USH1D) non-syndromic deafness or hearing loss USH1D, DFN12 disease in a subject in need thereof, and wherein the mRNA encodes a CDH23 gene, or a fragment thereof.

In one embodiment of a method described herein, the method comprises treating a retinitis pigmentose (RP) disease in a subject in need thereof, and wherein the mRNA encodes an EYS gene, or a fragment thereof.

In one embodiment of a method described herein, the method comprises treating a User Syndrome Type 2A (USH2A) and wherein the mRNA encodes an USH2a gene, or a fragment thereof.

In one embodiment of a method described herein, the method comprises treating a User Syndrome Type 2C (USH2C) and wherein the mRNA encodes a GPR98 gene, or a fragment thereof.

In one embodiment of a method described herein, the method comprises treating an Altrom Syndrome, and wherein the mRNA encodes an ALMS1 gene, or a fragment thereof.

In one embodiment of a method described herein, the method comprises treating a Glycogen Storage Disease III, and wherein the mRNA encodes a GDE gene, or a fragment thereof.

In one embodiment of a method described herein, the method comprises treating a non-syndromic deafness or hearing loss and wherein the mRNA encodes an OTOF gene, or a fragment thereof.

In one embodiment of a method described herein, the method comprises treating Hemophilia A, and the mRNA encodes an Factor VIII (F8) gene, or a fragment thereof.

Provided herein is a method for targeted replacement of a genomic nucleic acid sequence of a cell, the method comprising: (A) introducing to the cell a polynucleotide sequence encoding a first protein complex comprising a targeted excision machinery for excising from the genome of the cell a nucleic acid sequence comprising one or more mutations; and (B) a recombinant mRNA encoding a second protein complex, wherein the recombinant mRNA comprises: (i) a nucleic acid sequence comprising the excised nucleic acid sequence in (A) that does not contain the one or more mutations, and (ii) a sequence encoding an L1 retrotransposon ORF2 protein under the influence of an independent promoter.

In one embodiment of a method described herein, the nucleic acid sequence comprising the one or more mutations comprises a pathogenic variant of a cellular gene.

In one embodiment of a method described herein, the a nucleic acid sequence in (B) comprising the nucleic acid sequence that does not contain the one or more mutations is operably linked to the ORF2 sequence.

In one embodiment of a method described herein, the method further comprising introducing a sequence comprising a plurality of thymidine residues at the excision site.

In some embodiment, introducing the sequence comprises introducing at least four thymidine residues.

In one embodiment of a method described herein, the targeted excision machinery comprises a sequence guided site-specific excision endonuclease.

In one embodiment of a method described herein, the targeted excision machinery comprises a CRISPR-CAS system.

In some embodiments, the targeted excision machinery is a modified recombinant LINE 1 (L1) endonuclease.

In some embodiments, introducing the sequence comprising a plurality of thymidine residues comprises base extension by prime editing at the excision site.

In some embodiments, the mRNA sequence encoding an L1 retrotransposon ORF2 protein further comprises a sequence encoding the L1 retrotransposon ORF1 protein.

In some embodiments, the mRNA comprises a sequence for an inducible promoter.

In one embodiment of a method described herein, the excised sequence is greater than 1000 bases.

In one embodiment of a method described herein, the excised sequence is greater than 6 kb.

In one embodiment of a method described herein, the excised sequence is about 10 kb.

In some embodiments, the cell is a lymphocyte. In some embodiments, the cell is a myeloid cell. In some embodiments, the cell is an epithelial cell. In some embodiments, the cell is a cancer cell.

In some embodiments, the nucleic acid sequence encodes an ATP-binding cassette (ABC) transporter gene, (ABCA4) gene, or a fragment thereof.

In some embodiments, the nucleic acid sequence encodes an MY07A, CEP290, CDH23, EYS, USH2a, GPR98, ALMS1, GDE, OTOF or an F8 gene or a fragment thereof.

In some embodiments, introducing comprises introducing to the cell ex vivo. In some embodiments, introducing comprises electroporation. In some embodiments, introducing comprises introducing to the cell in vivo. In some embodiments, expression of the nucleic acid sequence comprising the sequence that does not contain the one or more mutations, is detectable at least 35 days after introducing to the cell. In some embodiments, introducing into the subject comprises direct administration of the mRNA systemically.

In some embodiments, introducing into the subject comprises local administration of the mRNA.

In some embodiments, the mRNA sequence comprises a cell targeting moiety.

In some embodiments, the cell targeting moiety is an aptamer.

In some embodiments, introducing into the subject comprises introducing the mRNA in the retina of the subject.

Provided herein is a method of integrating a nucleic acid sequence into a genome of a cell, the method comprising introducing a recombinant mRNA or a vector encoding an mRNA into the cell, wherein the mRNA comprises: (a) an insert sequence, wherein the insert sequence comprises (i) an exogenous sequence, or (ii) a sequence that is a reverse complement of the exogenous sequence; (b) a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell, wherein the insert sequence is a gene selected from a group consisting of ABCA4, MY07A, CEP290, CDH23, EYS, USH2a, GPR98, ALMS1, GDE, OTOF, and F8.

In some embodiments, the 5' UTR sequence or the 3' UTR sequence comprises a binding site for human ORF2p.

Provided herein is a method for integrating a nucleic acid sequence into the genome of an immune cell, the method comprising introducing a recombinant mRNA or a vector encoding an mRNA, wherein the mRNA comprises: (a) an insert sequence, wherein the insert sequence comprises (i) an exogenous sequence or (ii) a sequence that is a reverse complement of the exogenous sequence; (b) 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the insert sequence is integrated into the genome of the immune cell, wherein the insert sequence is a gene selected from a group consisting of ABCA4, MY07A, CEP290, CDH23, EYS, USH2a, GPR98, ALMS1, GDE, OTOF, and F8.

Provided herein is a method for integrating a nucleic acid sequence into the genome of a cell, the method comprising introducing a recombinant mRNA or a vector encoding an mRNA, wherein the mRNA comprises: (a) an insert sequence, wherein the insert sequence comprises (i) an exogenous sequence or (ii) a sequence that is a reverse complement of the exogenous sequence; (b) a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell, wherein the insert sequence is a gene selected from a group consisting of ABCA4, MY07A, CEP290, CDH23, EYS, USH2a, GPR98, ALMS1, GDE, OTOF, and F8.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence.

In some embodiments, the sequence of a human retrotransposon is upstream of the 3' UTR sequence. In some embodiments, the sequence of a human retrotransposon encodes for two proteins that are translated from a single RNA containing two ORFs. In some embodiments, the two ORFs are non-overlapping ORFs.

In some embodiments, the sequence of a human retrotransposon comprises a sequence of a non-LTR retrotransposon. In some embodiments, the sequence of a human retrotransposon encodes comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase.

In some embodiments, the endonuclease and/or a reverse transcriptase is ORF2p.

In some embodiments, the reverse transcriptase is a group II intron reverse transcriptase domain.

In some embodiments, the endonuclease and/or a reverse transcriptase is a minke whale endonuclease and/or a reverse transcriptase.

In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA. In some embodiments, the retrotransposon comprises an ORF1p and/or the ORF2p fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences.

Provided herein is a composition comprising a recombinant mRNA or vector encoding an mRNA, wherein the mRNA comprises a human LINE-1 transposon sequence comprising: (i) a human LINE-1 transposon 5' UTR sequence, (ii) a sequence encoding ORF1p downstream of the human LINE-1 transposon 5' UTR sequence, (iii) an inter-ORF linker sequence downstream of the sequence encoding ORF1p, (iv) a sequence encoding ORF2p downstream of the inter-ORF linker sequence, and (v) a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element, wherein the insert sequence is a gene selected from a group consisting of ABCA4, MY07A, CEP290, CDH23, EYS, USH2a, GPR98, ALMS1, GDE, OTOF, and F8.

Provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic, wherein the insert sequence is a gene selected from a group consisting of ABCA4, MY07A, CEP290, CDH23, EYS, USH2a, GPR98, ALMS1, GDE, OTOF, and F8.

Immunotherapy using phagocytic cells involves making and using engineered myeloid cells, such as macrophages or other phagocytic cells that attack and kill diseased cells, such as cancer cells, or infected cells. Engineered myeloid cells, such as macrophages and other phagocytic cells are prepared by incorporating in them via recombinant nucleic acid technology, a synthetic, recombinant nucleic acid encoding an engineered protein, such as a chimeric antigen receptor, that comprises a targeted antigen binding extracellular domain that is designed to bind to specific antigens on the surface of a target, such as a target cell, such as a cancer cell. Binding of the engineered chimeric receptor to an antigen on a target, such as cancer antigen (or likewise, a disease target), initiates phagocytosis of the target. This triggers two fold action: one, phagocytic engulfment and lysis of the target destroys the target and eliminates it as a first line of immune defense; two, antigens from the target are digested in the phagolysosome of the myeloid cell, are presented on the surface of the myeloid cell, which then leads to activation of T cells and further activation of the immune response and development of immunological memory. Chimeric receptors are engineered for enhanced phagocytosis and immune activation of the myeloid cell in which it is incorporated and expressed. Chimeric antigen receptors of the disclosure are variously termed herein as a chimeric fusion protein, CFP, phagocytic receptor (PR) fusion protein (PFP), or chimeric antigen receptor for phagocytosis (CAR-P), while each term is directed to the concept of a recombinant chimeric and/or fusion receptor protein. In some embodiments, genes encoding non-receptor proteins are also co-expressed in the myeloid cells, typically for an augmentation of the chimeric antigen receptor function. In summary, contemplated herein are various engineered receptor and non-receptor recombinant proteins that are designed to augment phagocytosis and or immune response of a myeloid cell against a disease target, and methods and compositions for creating and incorporating recombinant nucleic acids that encode the engineered receptors or non-receptor recombinant protein, such that the methods and compositions are suitable for creating an engineered myeloid cell for immunotherapy.

In one aspect, the present disclosure provides compositions and methods for stable gene transfer into a cell, where the cell can be any somatic cell. In some embodiments the compositions and methods are designed for cell-specific or tissue-specific delivery. In some cases, the methods described herein relate to supplying a functional protein or a fragment thereof to compensate for an absent or defective (mutated) protein in vivo, e.g., for a protein replacement therapy.

Incorporation of a recombinant nucleic acid in a cell can be accomplished by one or more gene transfer techniques that are available in the state of the art. However, incorporation of exogenous genetic (e.g., nucleic acid) elements into the genome for therapeutic purposes still faces several challenges. Achieving stable integration in a safe and dependable manner, and efficient and prolonged expression are a few among them. Most of the successful gene transfer systems aimed at genomic integration of the cargo nucleic acid sequence rely on viral delivery mechanisms, which have some inherent safety and efficacy issues. Delivery and integration of long nucleic acid sequences cannot be achieved by current gene editing systems.

Little attention has so far been devoted to making and using engineered myeloid cells for stable long-term gene transfer and expression of the transgene. For example, gene transfer to differentiated mammalian cells ex vivo for cell therapy can be accomplished via viral gene transfer mechanisms. However, there are several strategic disadvantages associated with the use of viral gene-transfer vectors, including an undesired potential for transgene silencing over time, the preferential integration into transcriptionally active sites of the genome with associated undesired activation of other genes (e.g. oncogenes) and genotoxicity. In addition to the safety issues increased expense and cumbersome effort of manufacturing, storing and handling integrating viruses often stand in the way of large-scale use of viral vector mediated of gene-modified cells in therapeutic applications. These persistent concerns associated with viral vectors regarding safety, as well as cost and scale of vector production necessitates alternative methods for effective therapy.

Integration of a transgene into the genome of a cell to be used for an immunotherapy can be advantageous in the sense that it is stable and a lower number of cells is required for delivery during the therapy. On the other hand, integrating a transgene in a non-dividing cell can be challenging in both affecting the health and function of the cell as well as the ultimate lifespan of the cell in vivo, and therefore affects its overall utility as the therapeutic. In some embodiments, the methods described herein for generating a myeloid cell for immunotherapy can be a cumulative product of a number of steps and compositions involving but not limited to, for example, selecting a myeloid cell for modifying; method and compositions for incorporating a recombinant nucleic acid in a myeloid cell; methods and compositions for enhancing expression of the recombinant nucleic acid; methods and compositions for selecting and modifying vectors; methods of preparing a recombinant nucleic acid suitable for in vivo administration for uptake and incorporation of the recombinant nucleic acid by a myeloid cell in vivo and therefore generating a myeloid cell for therapy. In some aspects, one or more embodiments of the various inventions described herein are transferrable among each other, and one of skill in the art is expected to use them in alternatives, combinations or interchangeably without the necessity of undue experimentation. All such variations of the disclosed elements are contemplated and fully encompassed herein.

In one aspect, transposons, or transposable elements (TEs) are considered herein, for means of incorporating a heterologous, synthetic or recombinant nucleic acid encoding a transgene of interest in a myeloid cell. Transposon, or transposable elements are genetic elements that have the capability to transpose fragments of genetic material into the genome by use of an enzyme known as transposase. Mammalian genomes contain a high number of transposable element (TE)-derived sequences, and up to 70% of our genome represents TE-derived sequences (de Koning et al. 2011; Richardson et al. 2015). These elements could be exploited to introduce genetic material into the genome of a cell. The TE elements are capable of mobilization, often termed as "jumping" genetic material within the genome. TEs generally exist in eukaryotic genomes in a reversibly inactive, epigenetically silenced form. In the present disclosure methods and compositions for efficient and stable integration of transgenes into macrophages and other phagocytic cells. The method is based on use of a transposase and transposable elements mRNA-encoded transposase. In some embodiments, Long Interspersed Element-1 (L1) RNAs are used for stable integration and/or retrotransposition of the transgene into a cell (e.g., a macrophage or phagocytic cell).

Contemplated herein are methods for retrotransposon mediated stable integration of an exogenous nucleic acid sequence into the genome of a cell. The method may take advantage of the random genomic integration machinery of the retrotransposon into the cell without creating an adverse effect. Methods described herein can be used for robust and versatile incorporation of an exogenous nucleic acid sequence into a cell, such that the exogenous nucleic acid is incorporated at a safe locus within the genome and is expressed without being silenced by the cell's inherent defense mechanism. The method described herein can be used to incorporate an exogenous nucleic acid that is about 1 kb, about 2 kb, about 3 kb, about 4 kb, about 5 kb, about 6 kb, about 7 kb about 8 kb, about 9 kb, about 10 kb, or more in size. In some embodiments, the exogenous nucleic acid is not incorporated within a ribosomal locus. In some embodiments, the exogenous nucleic acid is not incorporated within a ROSA26 locus, or another safe harbor locus. In some embodiments, the methods and compositions described herein can incorporate an exogenous nucleic acid sequence anywhere within the genome of the cell. Furthermore, contemplated herein is a retrotransposition system that is developed to incorporate an exogenous nucleic acid sequence into a specific predetermined site within the genome of a cell, without creating an adverse effect. The disclosed methods and compositions incorporate several mechanisms of engineering the retrotransposons for highly specific incorporation of the exogenous nucleic acid into a cell with high fidelity. Retrotransposons chosen for this purpose may be a human retrotransposon.

Methods and compositions described herein represent a salient breakthrough in the molecular systems and mechanisms for manipulating the genome of a cell. Shown here for the first time is a method that exploits a human retrotransposon system into non-virally delivering and stably integrating a large fragment of exogenous nucleic acid sequence (at least greater than 100 nucleobases, at least greater than 1 kb, at least greater than 2 kb, at least greater than 3 kb, etc.) into a non-conserved region of the genome that is not an rDNA or a ribosomal locus or a designated safe-harbor locus such as the ROSA 26 locus.

In some embodiments, a retrotransposable system is used to stably incorporate into the genome and express a non-endogenous nucleic acid, where the non-endogenous nucleic acid comprises retrotransposable elements within the nucleic acid sequence. In some embodiments, a cell's endogenous retrotransposable system (e.g., proteins and enzymes) is used to stably express a non-endogenous nucleic acid in the cell. In some embodiments, a cell's endogenous retrotransposable system (e.g., proteins and enzymes, such as a LINE-1 retrotransposition system) is used, but may further express one or more components of the retrotransposable system to stably express a non-endogenous nucleic acid in the cell.

In some embodiments, a synthetic nucleic acid is provided herein, the synthetic nucleic acid encoding a transgene, and encoding one or more components for genomic integration and/or retrotransposition.

In one aspect, provided herein is a method of integrating a nucleic acid sequence into a genome of a cell, the method comprising introducing a recombinant mRNA or a vector encoding an mRNA into the cell, wherein the mRNA comprises: an insert sequence, wherein the insert sequence comprises an exogenous sequence, or a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell. In some embodiments, the 5' UTR sequence or the 3' UTR sequence comprises a binding site for human ORF2p.

In one aspect, provided herein is a method for integrating a nucleic acid sequence into the genome of an immune cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the transgene sequence is integrated into the genome of the immune cell.

In one aspect, provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence. In some embodiments, the sequence of a human retrotransposon is upstream of the 3' UTR sequence. In some embodiments, the polynucleotide sequence that is desired to be transferred and incorporated into the genome of a cell (e.g., the insert) is inserted at a site 3' to the sequence encoding ORF1 in a recombinant nucleic acid construct. In some embodiments, the polynucleotide sequence that is desired to be transferred and incorporated into the genome of a cell is inserted at a site 3' to the sequence encoding ORF2 in a recombinant nucleic acid construct. In some embodiments the sequence that is desired to be transferred and incorporated into the genome of a cell is inserted within the 3'-UTR of ORF1 or ORF2, or both. In some embodiments, the polynucleotide sequence that is sequence that is desired to be transferred and incorporated into the genome of a cell is inserted upstream of the poly A tail of ORF2 in a recombinant nucleic acid construct.

In some embodiments, the sequence of a human retrotransposon encodes for two proteins that are translated from a single RNA containing two ORFs. In some embodiments, the two ORFs are non-overlapping ORFs. In some embodiments, the two ORFs are ORF1 and ORF2. In some embodiments, the ORF1 encodes ORF1p and ORF2 encodes ORF2p.

In some embodiments, the sequence of a human retrotransposon comprises a sequence of a non-LTR retrotransposon. In some embodiments, the sequence of a human retrotransposon comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase. In some embodiments, the endonuclease and/or a reverse transcriptase is ORF2p. In some embodiments, the reverse transcriptase is a group II intron reverse transcriptase domain. In some embodiments, the endonuclease and/or a reverse transcriptase is a minke whale endonuclease and/or a reverse transcriptase. In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA.

In some embodiments, provided herein is a polynucleotide construct comprising an mRNA wherein the mRNA comprises a sequence encoding a human retrotransposon, wherein, (i) the sequence of a human retrotransposon comprises a sequence encoding ORF1p, (ii) the mRNA does not comprise a sequence encoding ORF1p, or (iii) the mRNA comprises a replacement of the sequence encoding ORF1p with a 5' UTR sequence from the complement gene. In some embodiments, the mRNA comprises a first mRNA molecule encoding ORF1p, and a second mRNA molecule encoding an endonuclease and/or a reverse transcriptase. In some embodiments, the mRNA is an mRNA molecule comprising a first sequence encoding ORF1p, and a second sequence encoding an endonuclease and/or a reverse transcriptase. In some embodiments, the first sequence encoding ORF1p and the second sequence encoding an endonuclease and/or a reverse transcriptase are separated by a linker sequence.

In some embodiments, the linker sequence comprises an internal ribosome entry sequence (IRES). In some embodiments, the IRES is an IRES from CVB3 or EV71. In some embodiments, the linker sequence encodes a self-cleaving peptide sequence. In some embodiments, the linker sequence encodes a T2A, a E2A or a P2A sequence In some embodiments, the sequence of a human retrotransposon comprises a sequence that encodes ORF1p fused to an additional protein sequence and/or a sequence that encodes ORF2p fused to an additional protein sequence. In some embodiments, the ORF1p and/or the ORF2p is fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences. In some embodiments, the 5' UTR sequence or the 3' UTR sequence comprises a sequence that promotes or enhances interaction of a poly A tail of the mRNA with the endonuclease and/or a reverse transcriptase. In some embodiments, the 5' UTR sequence or the 3' UTR sequence comprises a sequence that promotes or enhances interaction of a poly-A-binding proteins (e.g., PABP) with the endonuclease and/or a reverse transcriptase. In some embodiments, the 5' UTR sequence or the 3' UTR sequence comprises a sequence that increases specificity of the endonuclease and/or a reverse transcriptase to the mRNA relative to another mRNA expressed by the cell. In some embodiments, the 5' UTR sequence or the 3' UTR sequence comprises an Alu element sequence.

In some embodiments, the first sequence encoding ORF1p and the second sequence encoding an endonuclease and/or a reverse transcriptase have the same promoter. In some embodiments, the insert sequence has a promoter that is different from the promoter of the first sequence encoding ORF1p. In some embodiments, the insert sequence has a promoter that is different from the promoter of the second sequence encoding an endonuclease and/or a reverse transcriptase. In some embodiments, the first sequence encoding ORF1p and/or the second sequence encoding an endonuclease and/or a reverse transcriptase have a promoter or transcription initiation site selected from the group consisting of an inducible promoter, a CMV promoter or transcription initiation site, a T7 promoter or transcription initiation site, an EF1a promoter or transcription initiation site and combinations thereof. In some embodiments, the insert sequence has a promoter or transcription initiation site selected from the group consisting of an inducible promoter, a CMV promoter or transcription initiation site, a T7 promoter or transcription initiation site, an EF1a promoter or transcription initiation site and combinations thereof.

In some embodiments, the first sequence encoding ORF1p and the second sequence encoding an endonuclease and/or a reverse transcriptase are codon optimized for expression in a human cell.

In some embodiments, the mRNA comprises a WPRE element. In some embodiments, the mRNA comprises a selection marker. In some embodiments, the mRNA comprises a sequence encoding an affinity tag. In some embodiments, the affinity tag is linked to the sequence encoding an endonuclease and/or a reverse transcriptase.

In some embodiments, the 3' UTR comprises a poly A sequence or wherein a poly A sequence is added to the mRNA in vitro. In some embodiments, the poly A sequence is downstream of a sequence encoding an endonuclease and/or a reverse transcriptase. In some embodiments, the insert sequence is upstream of the poly A sequence.

In some embodiments, the 3' UTR sequence comprises the insert sequence. In some embodiments, the insert sequence comprises a sequence that is a reverse complement of the sequence encoding the exogenous polypeptide. In some embodiments, the insert sequence comprises a polyadenylation site. In some embodiments, the insert sequence comprises an SV40 polyadenylation site. In some embodiments, the insert sequence comprises a polyadenylation site upstream of the sequence that is a reverse complement of the sequence encoding the exogenous polypeptide. In some embodiments, the insert sequence is integrated into the genome at a locus that is not a ribosomal locus. In some embodiments, the insert sequence is integrated into the genome at a locus that is not a rDNA locus. In some embodiments, the insert sequence integrates into a gene or regulatory region of a gene, thereby disrupting the gene or downregulating expression of the gene. In some embodiments, the insert sequence integrates into a gene or regulatory region of a gene, thereby upregulating expression of the gene. In some embodiments, the insert sequence integrates into the genome and replaces a gene. In some embodiments, the insert sequence is stably integrated into the genome. In some embodiments, the insert sequence is retrotransposed into the genome. In some embodiments, the insert sequence is integrated into the genome by cleavage of a DNA strand of a target site by an endonuclease encoded by the mRNA. In some embodiments, the insert sequence is integrated into the genome via target-primed reverse transcription (TPRT). In some embodiments, the insert sequence is integrated into the genome via reverse splicing of the mRNA into a DNA target site of the genome.

In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell.

In some embodiments, the mRNA is a self-integrating mRNA. In some embodiments, the method comprises introducing into the cell the mRNA. In some embodiments, the method comprises introducing into the cell the vector encoding the mRNA. In some embodiments, the method comprises introducing the mRNA or the vector encoding the mRNA into a cell ex vivo. In some embodiments, the method further comprises administering the cell to a human subject. In some embodiments, the method comprises administering the mRNA or the vector encoding the mRNA to a human subject. In some embodiments, an immune response is not elicited in the human subject. In some embodiments, the mRNA or the vector is substantially non-immunogenic.

In some embodiments, the vector is a plasmid or a viral vector. In some embodiments, the vector comprises a non-LTR retrotransposon. In some embodiments, the vector comprises a human L1 element. In some embodiments, the vector comprises a L1 retrotransposon ORF1 gene. In some embodiments, the vector comprises a L1 retrotransposon ORF2 gene. In some embodiments, the vector comprises a L1 retrotransposon. In some embodiments, provided herein is an mRNA comprising sequences encoding human LINE 1 retrotransposition elements, and a payload comprising a nucleic acid sequence which can be retrotransposed and integrated into a genome of a cell comprising the mRNA. In some embodiments, provided herein is an mRNA that can be delivered into a living cell, e.g., a human cell, wherein, the mRNA comprises sequences encoding human LINE 1 retrotransposition elements, and a payload comprising a nucleic acid sequence which can be retrotransposed and integrated into the genome of the cell. In some embodiments, the sequences encoding human LINE 1 retrotransposition elements comprise a L1 retrotransposon ORF1 sequence or a fragment thereof. In some embodiments, the sequences encoding human LINE 1 retrotransposition elements comprise a L1 retrotransposon ORF2 sequence or a fragment thereof. In some embodiments, the sequences encoding human LINE 1 retrotransposition elements comprise a L1 retrotransposon ORF1 sequence or a fragment thereof and a L1 retrotransposon ORF2 sequence or a fragment thereof, and a nucleic acid "payload" sequence which is a heterologous sequence which is integrated into the genome of cell by retrotransposition. (See, for example, FIG. 1B).

In some embodiments, the mRNA is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases. In some embodiments, the mRNA is at least about 5.1, 5.2, 5.3, 5.4, 5.5, 5.6, 5.7, 5.8, 5.9 or 6 kilobases. In some embodiments, the mRNA is at least about 6.1, 6.2, 6.3, 6.4, 6.5, 6.6, 6.7, 6.8, 6.9 or 7 kilobases. In some embodiments, the mRNA is at least about 7.1, 7.2, 7.3, 7.4, 7.5, 7.6, 7.7, 7.8, 7.9 or 8 kilobases. In some embodiments, the mRNA is at least about 8.1, 8.2, 8.3, 8.4, 8.5, 8.6, 8.7, 8.8, 8.9 or 9 kilobases. In some embodiments, the mRNA is at least about 9.1, 9.2, 9.3, 9.4, 9.5, 9.6, 9.7, 9.8, 9.9 or 10 kilobases.

In some embodiments, the mRNA comprises a sequence that inhibits or prevents degradation of the mRNA. In some embodiments, the sequence that inhibits or prevents degradation of the mRNA inhibits or prevents degradation of the mRNA by an exonuclease or an RNAse. In some embodiments, the sequence that inhibits or prevents degradation of the mRNA is a G quadruplex, pseudoknot or triplex sequence. In some embodiments, the sequence the sequence that inhibits or prevents degradation of the mRNA is an exoribonuclease-resistant RNA structure from a flaviviral RNA or an ENE element from KSV. In some embodiments, the sequence that inhibits or prevents degradation of the mRNA inhibits or prevents degradation of the mRNA by a deadenylase. In some embodiments, the sequence that inhibits or prevents degradation of the mRNA comprises non-adenosine nucleotides within or at a terminus of a poly A tail of the mRNA. In some embodiments, the sequence that inhibits or prevents degradation of the mRNA increases stability of the mRNA. In some embodiments, the exogenous sequence comprises a sequence encoding an exogenous polypeptide. In some embodiments, the sequence encoding an exogenous polypeptide is not in frame with a sequence encoding an endonuclease and/or a reverse transcriptase. In some embodiments, the sequence encoding an exogenous polypeptide is not in frame with a sequence encoding an endonuclease and/or a reverse transcriptase. In some embodiments, the exogenous sequence does not comprise introns. In some embodiments, the exogenous sequence comprises a sequence encoding an exogenous polypeptide selected from the group consisting of an enzyme, a receptor, a transport protein, a structural protein, a hormone, an antibody, a contractile protein and a storage protein. In some embodiments, the exogenous sequence comprises a sequence encoding an exogenous polypeptide selected from the group consisting of a chimeric antigen receptor (CAR), a ligand, an antibody, a receptor, and an enzyme. In some embodiments, the exogenous sequence comprises a regulatory sequence. In some embodiments, the regulatory sequence comprises a cis-acting regulatory sequence. In some embodiments, the regulatory sequence comprises a cis-acting regulatory sequence selected from the group consisting of an enhancer, a silencer, a promoter or a response element. In some embodiments, the regulatory sequence comprises a trans-acting regulatory sequence. In some embodiments, the regulatory sequence comprises a trans-acting regulatory sequence that encodes a transcription factor.

In some embodiments, integration of the insert sequence does not adversely affect cell health. In some embodiments, the endonuclease, the reverse transcriptase or both are capable of site-specific integration of the insert sequence.

In some embodiments, the mRNA comprises a sequence encoding an additional nuclease domain or a nuclease domain that is not derived from ORF2. In some embodiments, the mRNA comprises a sequence encoding a mega-TAL nuclease domain, a TALEN domain, a Cas9 domain, a zinc finger binding domain from an R2 retroelement, or a DNA binding domain that binds to repetitive sequences such as a Rep78 from AAV. In some embodiments, the endonuclease comprises a mutation that reduces activity of the endonuclease compared to the endonuclease without the mutation. In some embodiments, the endonuclease is an ORF2p endonuclease and the mutation is S228P. In some embodiments, the mRNA comprises a sequence encoding a domain that increases fidelity and/or processivity of the reverse transcriptase. In some embodiments, the reverse transcriptase is a reverse transcriptase from a retroelement other than ORF2 or reverse transcriptase that has higher fidelity and/or processivity compared to a reverse transcriptase of ORF2p. In some embodiments, the reverse transcriptase is a group II intron reverse transcriptase. In some embodiments, the group II intron reverse transcriptase is a group IIA intron reverse transcriptase, a group IIB intron reverse transcriptase, or a group IIC intron reverse transcriptase. In some embodiments, the group II intron reverse transcriptase is TGIRT-II or TGIRT-III.

In some embodiments, the mRNA comprises a sequence comprising an Alu element and/or a ribosome binding aptamer. In some embodiments, the mRNA comprises a sequence encoding a polypeptide comprising a DNA binding domain. In some embodiments, the 3' UTR sequence is derived from a viral 3' UTR or a beta-globin 3' UTR.

In one aspect, provided herein is a composition comprising a recombinant mRNA or vector encoding an mRNA, wherein the mRNA comprises a human LINE-1 transposon sequence comprising a human LINE-1 transposon 5' UTR sequence, a sequence encoding ORF1p downstream of the human LINE-1 transposon 5' UTR sequence, an inter-ORF linker sequence downstream of the sequence encoding ORF1p, a sequence encoding ORF2p downstream of the inter-ORF linker sequence, and a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element.

In some embodiments, the insert sequence integrates into the genome of a cell when introduced into the cell. In some embodiments, the insert sequence integrates into a gene associated a condition or disease, thereby disrupting the gene or downregulating expression of the gene. In some embodiments, the insert sequence integrates into a gene, thereby upregulating expression of the gene. In some embodiments, the recombinant mRNA or vector encoding the mRNA is isolated or purified.

In one aspect, provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic.

In some embodiments, the composition comprises human ORF1p and human ORF2p proteins. In some embodiments, the composition comprises a ribonucleoprotein (RNP) comprising human ORF1p and human ORF2p complexed to the nucleic acid. In some embodiments, the nucleic acid is mRNA.

In one aspect, provided herein is a composition comprising a cell comprising a composition described herein. In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell. In some embodiments, the insert sequence is a reverse complement of a sequence encoding an exogenous polypeptide and the exogenous polypeptide is a chimeric antigen receptor (CAR).

In one aspect, provided herein is a pharmaceutical composition comprising a composition described herein, and a pharmaceutically acceptable excipient. In some embodiments, the pharmaceutical composition is for use in gene therapy. In some embodiments, the pharmaceutical composition is for use in the manufacture of a medicament for treating a disease or condition. In some embodiments, the pharmaceutical composition is for use in treating a disease or condition. In one aspect, provided herein is a method of treating a disease in a subject, comprising administering a pharmaceutical composition described herein to a subject with a disease or condition. In some embodiments, the method increases an amount or activity of a protein or functional RNA in the subject. In some embodiments, the subject has a deficient amount or activity of a protein or functional RNA. In some embodiments, the deficient amount or activity of a protein or functional RNA is associated with or causes the disease or condition.

In some embodiments, the method further comprising administering an agent that inhibits human silencing hub (HUSH) complex, an agent that inhibits FAM208A, or an agent that inhibits TRIM28. In some embodiments, the agent that inhibits human silencing hub (HUSH) complex is an agent that inhibits Periphilin, TASOR and/or MPP8. In some embodiments, the agent that inhibits human silencing hub (HUSH) complex inhibits assembly of the HUSH complex. In some embodiments, the agent inhibits the fanconia anemia complex. In some embodiments, the agent inhibits FANCD2-FANC1 heterodimer monoubiquitination. In some embodiments, the agent inhibits FANCD2-FANC1 heterodimer formation. In some embodiments the agent inhibits the Fanconi Anemia (FA) core complex. FA core complex is a component of the fanconi anemia DNA damage repair pathway, e.g., in chemotherapy induced DNA inter-strand crosslinks. The FA core complex comprises two central dimers of the FANCB and FA-associated protein of 100 kDa (FAAP100) subunits, flanked by two copies of the RING finger subunit, FANCL. These two heterotrimers act as a scaffold to assemble the remaining five subunits, resulting in an extended asymmetric structure. Destabilization of the scaffold would disrupt the entire complex, resulting in a non-functional FA pathway. Examples of agents that can inhibit the FA core complex include Bortezomib and curcumin analogs EF24 and 4H-TTD.

Accordingly, it is an object of the present invention to provide novel transposon-based vectors useful in providing gene therapy to an animal. It is an object of the present invention to provide novel transposon-based vectors for use in the preparation of a medicament useful in providing gene therapy to an animal or human. It is another object of the present invention to provide novel transposon-based vectors that encode for the production of desired proteins or peptides in cells. Yet another object of the present invention to provide novel transposon-based vectors that encode for the production of desired nucleic acids in cells. It is a further object of the present invention to provide methods for cell and tissue specific incorporation of transposon-based DNA or RNA constructs comprising targeting a selected gene to a specific cell or tissue of an animal. It is yet another object of the present invention to provide methods for cell and tissue specific expression of transposon-based DNA or RNA constructs comprising designing a DNA or RNA construct with cell specific promoters that enhance stable incorporation of the selected gene by the transposase and expressing the selected gene in the cell. It is an object of the present invention to provide gene therapy for generations through germ line administration of a transposon-based vector. Another object of the present invention is to provide gene therapy in animals through non germ line administration of a transposon-based vector. Another object of the present invention is to provide gene therapy in animals through administration of a transposon-based vector, wherein the animals produce desired proteins, peptides or nucleic acids. Yet another object of the present invention is to provide gene therapy in animals through administration of a transposon-based vector, wherein the animals produce desired proteins or peptides that are recognized by receptors on target cells. Still another object of the present invention is to provide gene therapy in animals through administration of a transposon-based vector, wherein the animals produce desired fusion proteins or fusion peptides, a portion of which are recognized by receptors on target cells, in order to deliver the other protein or peptide component of the fusion protein or fusion peptide to the cell to induce a biological response. Yet another object of the present invention is to provide a method for gene therapy of animals through administration of transposon-based vectors comprising tissue specific promoters and a gene of interest to facilitate tissue specific incorporation and expression of a gene of interest to produce a desired protein, peptide or nucleic acid. Another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid. Still another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid, wherein the desired protein, peptide or nucleic acid has a desired biological effect in the animal.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." herein), of which:

Figure 1D:
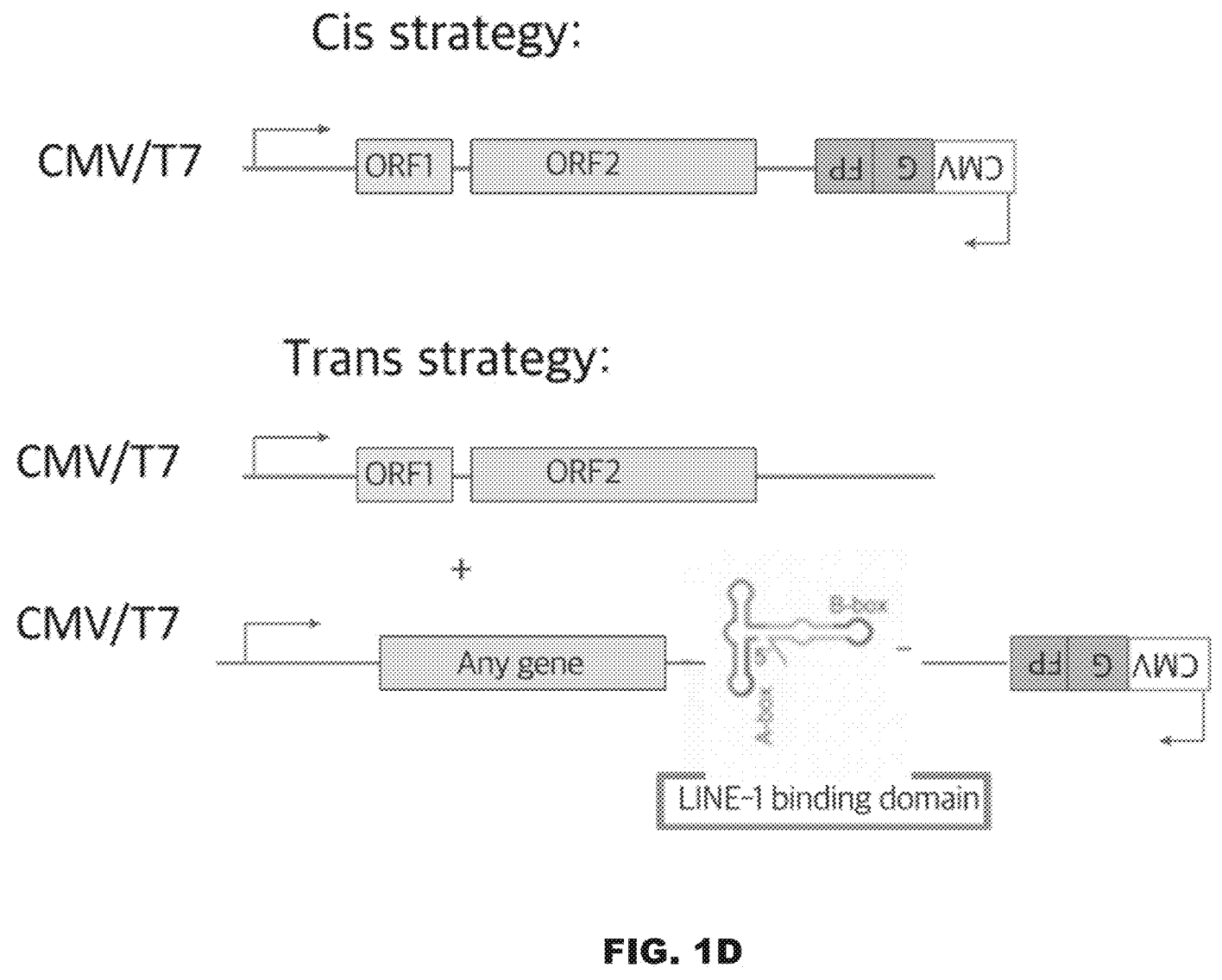

FIG. 1D illustrates various exemplary designs for integrating an mRNA encoding a transgene into the genome of a cell. GFP shown here in a box is an exemplary transgene.

FIG. 8A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding GFP, where the coding sequence of GFP is interrupted with an intron. The GFP is not expressed until the sequence is integrated in the genome and the intron is spliced.

FIG. 8B shows exemplary results showing successful integration of the mRNA transcript encoded by the plasmid shown in FIG. 8A and expression of GFP relative to mock-transfected cells (fold increase in mean fluorescence intensity of GFP positive cells is shown). Mock transfected cells were transfected by the vector lacking the GFP cargo sequence.

FIG. 8C shows exemplary flow cytometry results from the results shown in FIG. 8B.

Figures 17A, 17B:
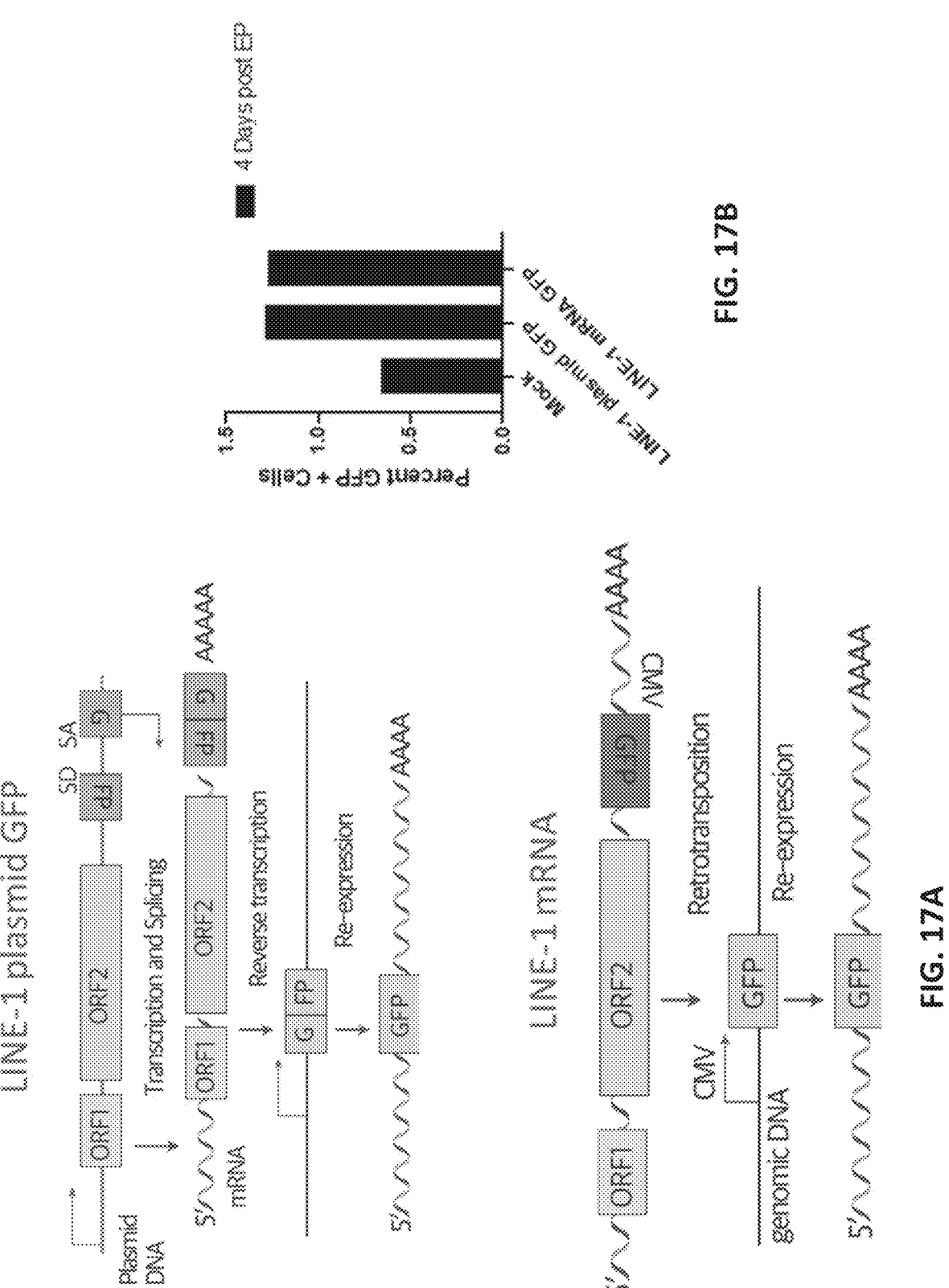
FIG. 17A depicts an exemplary plasmid construct encoding a LINE-1 mRNA transcript comprising ORF1 and ORF2 protein encoding sequences on a single mRNA molecule with a GFP sequence (top panel) and an exemplary LINE-1 mRNA transcript comprising ORF1 and ORF2 protein encoding sequences on a single mRNA molecule with a GFP sequence.

FIG. 17B depicts exemplary data showing expression of GFP (fold increase in mean fluorescence intensity of GFP positive cells is shown) in Jurkat cells using the constructs depicted in FIG. 17A. The plasmid construct was transfected, and the mRNA construct was electroporated.

Figure 18A:
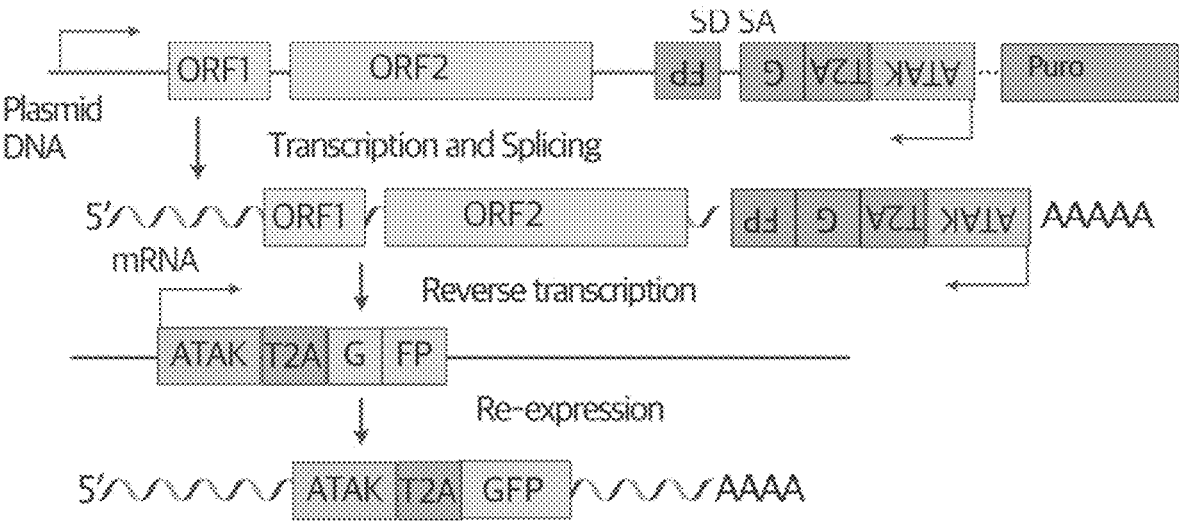

FIG. 18A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) followed by a T2A self-cleavage sequence followed by a split GFP sequence (all in a reverse orientation relative to the LINE-1 sequence). The coding sequence of the GFP is interrupted with an intron. Expected mRNA after reverse transcription and integration of the cargo are depicted.

Figures 10A, 10B, 10C, 10D:
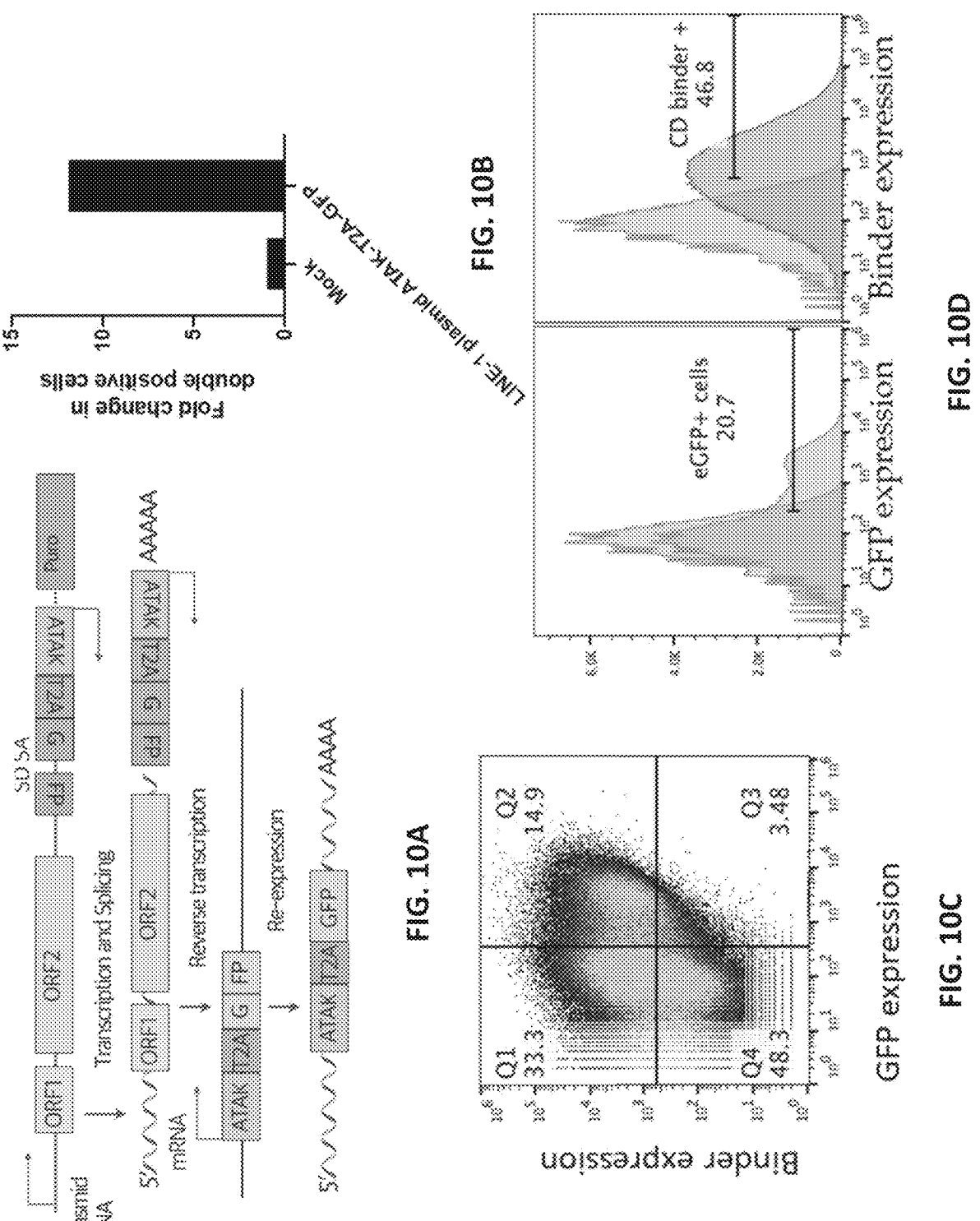
FIG. 10A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) followed by a T2A self-cleavage sequence followed by a split GFP sequence (all in a reverse orientation relative to the LINE-1 sequence). The coding sequence of the GFP is interrupted with an intron. Expected mRNA after reverse transcription and integration of the cargo are depicted.
FIG. 10B shows exemplary results showing successful integration of the mRNA transcript encoded by the plasmid shown in FIG. 10A and expression of ATAK-T2A-GFP relative to mock-transfected cells (fold change in GFP and ATAK double positive cells is shown). Mock transfected cells were transfected by the vector lacking the ATAK cargo sequence. Expression of ATAK receptor protein was detected by binding with a labeled CD5 antibody.
FIG. 10C shows representative flow cytometry data from two separate experimental runs for expression of both GFP and CD5 binder (ATAK) using the experimental setup shown in FIG. 10A.
FIG. 10D shows representative flow cytometry data from two separate experimental runs for expression of both GFP and CD5 binder (ATAK) using the experimental setup shown in FIG. 10A.
Figure 18B:
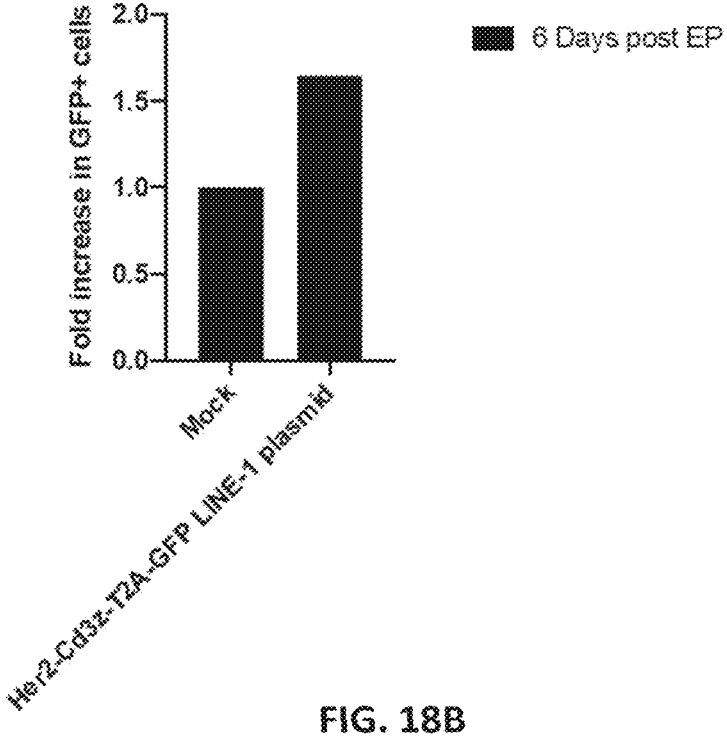

FIG. 18B shows exemplary results showing successful integration of the mRNA transcript encoded by the plasmid shown in FIG. 10A and expression of ATAK-T2A-GFP relative to mock-transfected cells (fold change in GFP and ATAK double positive cells is shown) in a myeloid cell line (THP-1). Data represents expression at 6 days post transfection, normalized over mock plasmid transfected cells wherein the mock plasmid does not have GFP coding sequence.

Figure 19:
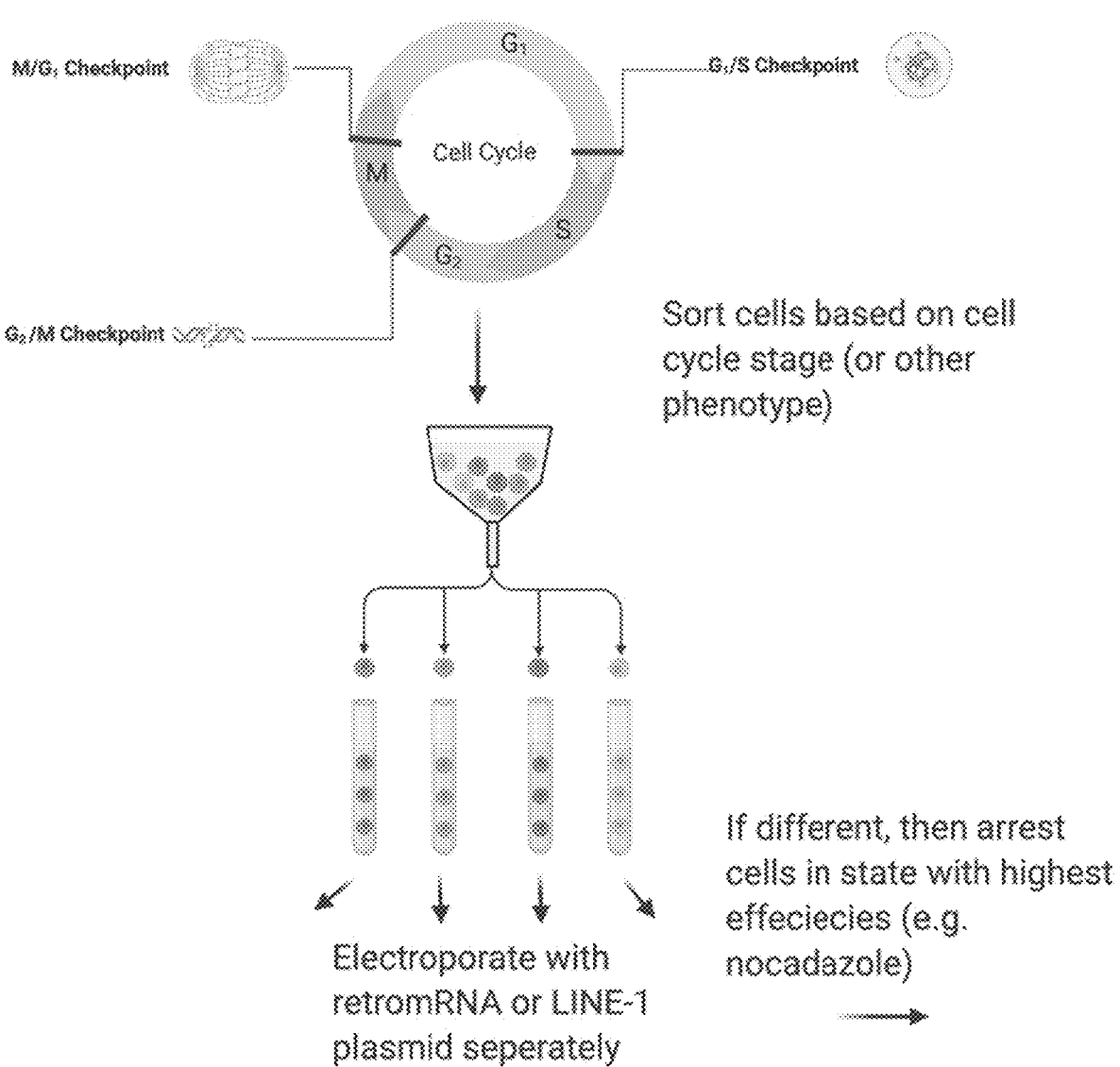

FIG. 19 illustrates an exemplary experimental set up for cell synchronization. A heterogenous cell population is sorted based on cell cycle stage, prior to delivery of an exogenous nucleic acid. Cell cycle synchronization is expected to result in higher expression and stabilization of the exogenous nucleic acid delivered. If cells are not homogeneous after cell sorting, then cells can be further incubated with a suitable agent that arrests cell cycle at a stage.

Figures 20, 21:
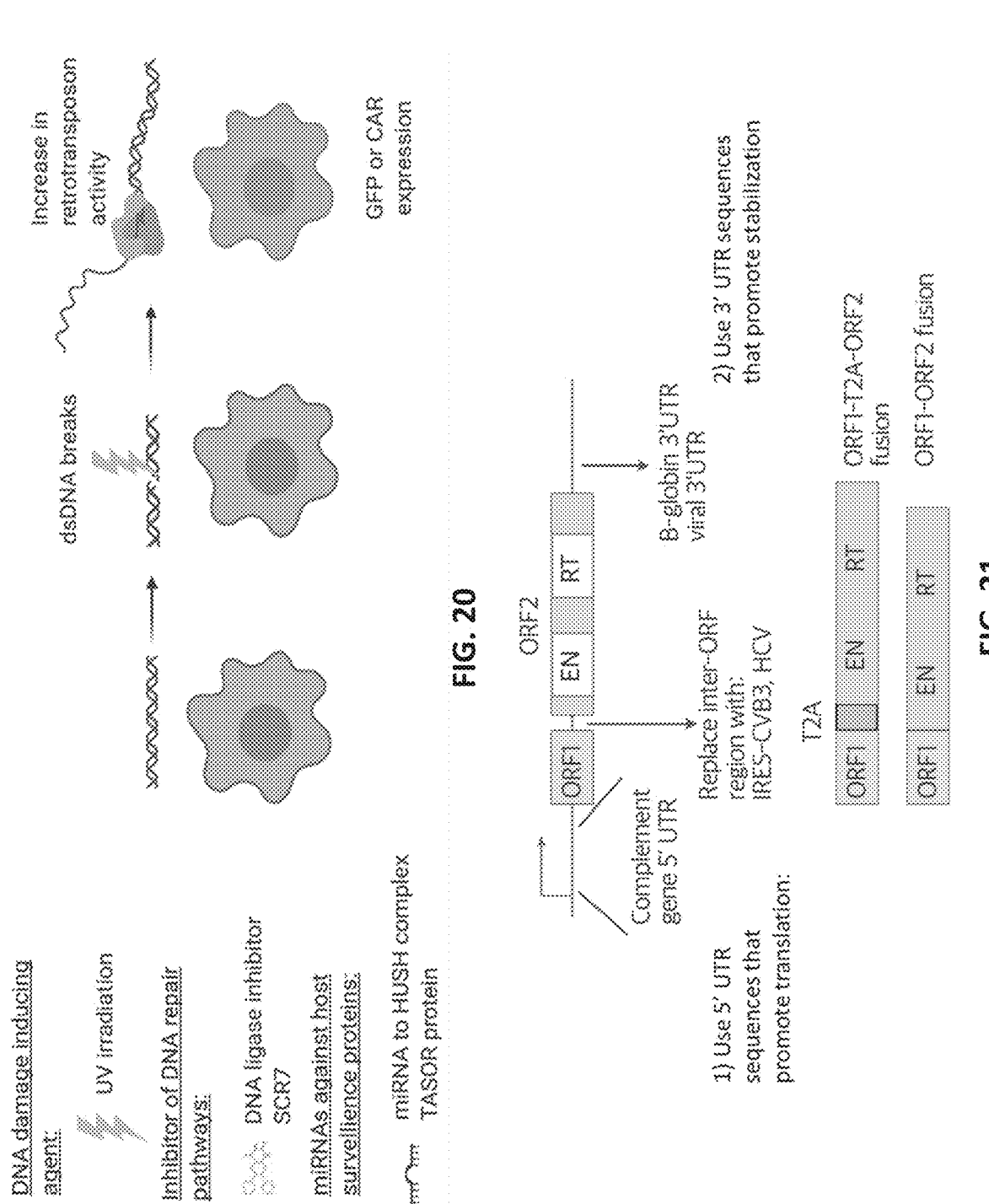

FIG. 20 illustrates an exemplary method for increasing retrotransposon efficiency by inducing DNA double stranded breaks, with or without inhibiting DNA repair pathways, such as by inducing DNA ligase inhibitor SCR7 or inhibiting host surveillance proteins, for example, using miRNA to HUSH complex TASOR protein.

FIG. 21 illustrates exemplary constructs for integrating an mRNA encoding a transgene into the genome of a cell.

Figures 22, 23:
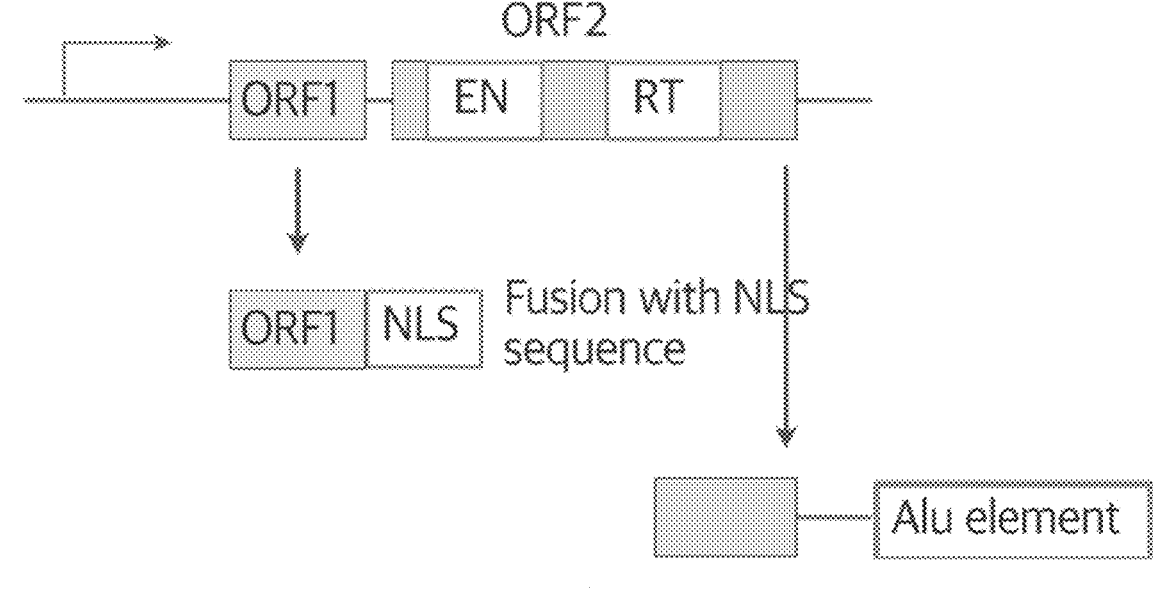

FIG. 22 illustrates exemplary constructs for integrating an mRNA encoding a transgene into the genome of a cell.

FIG. 23 illustrates exemplary constructs for integrating an mRNA encoding a transgene into the genome of a cell.

Figure 24:
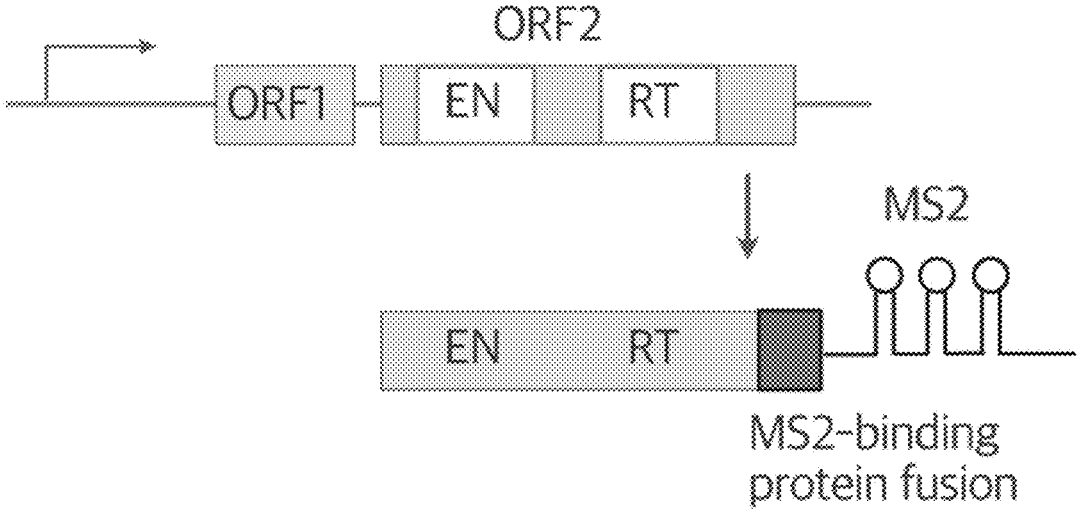

FIG. 24 illustrates exemplary constructs for integrating an mRNA encoding a transgene into the genome of a cell.

Figure 25:
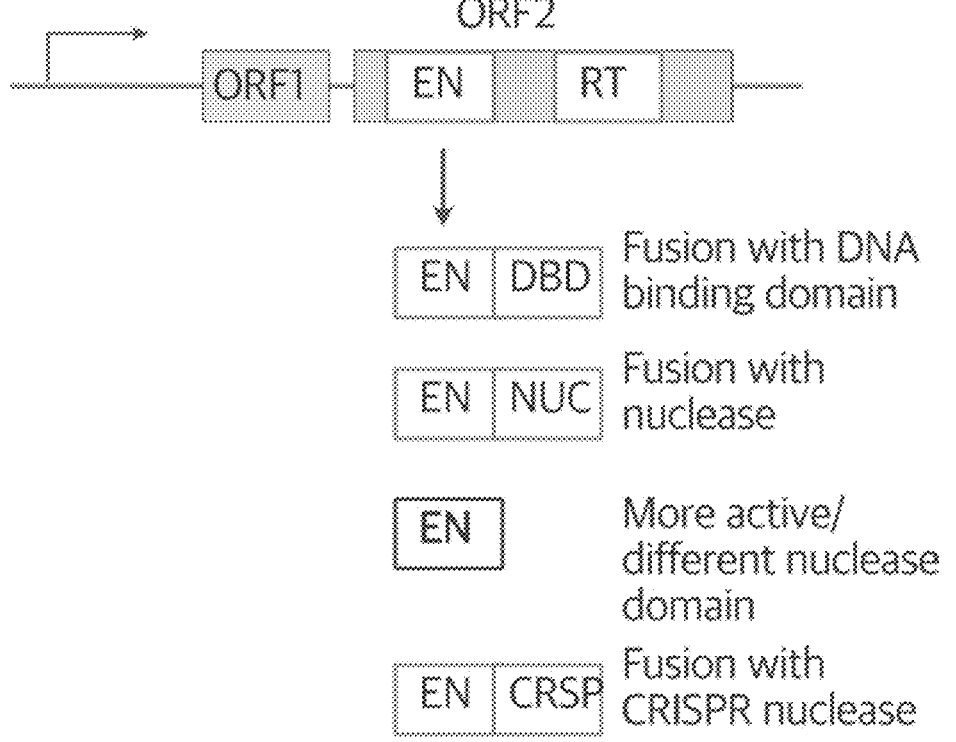

FIG. 25 illustrates exemplary constructs for integrating an mRNA encoding a transgene into the genome of a cell.

Figure 26:
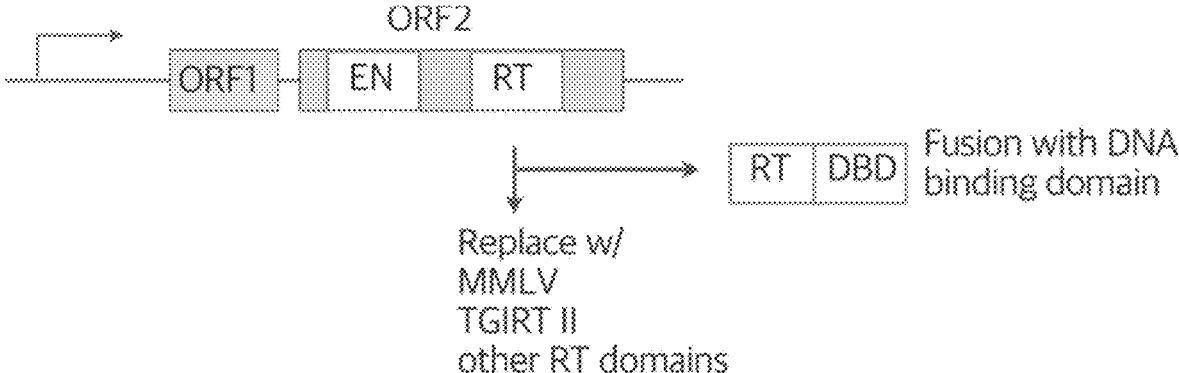

FIG. 26 illustrates exemplary constructs for integrating an mRNA encoding a transgene into the genome of a cell.

Figure 27:
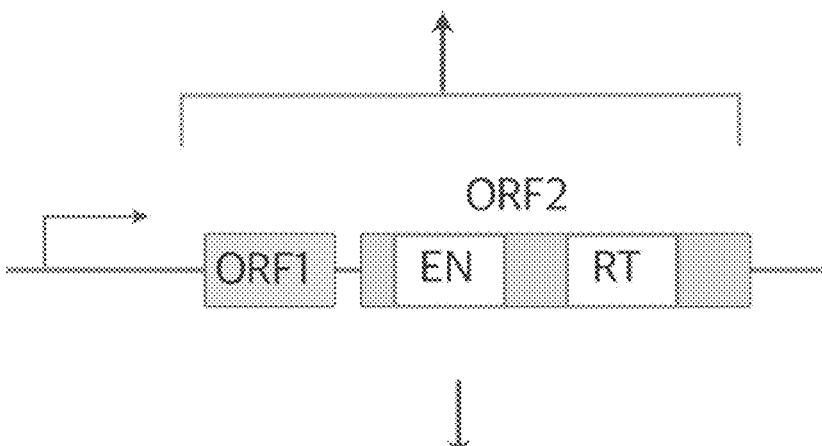

FIG. 27 illustrates exemplary constructs for integrating an mRNA encoding a transgene into the genome of a cell.

Figure 28:
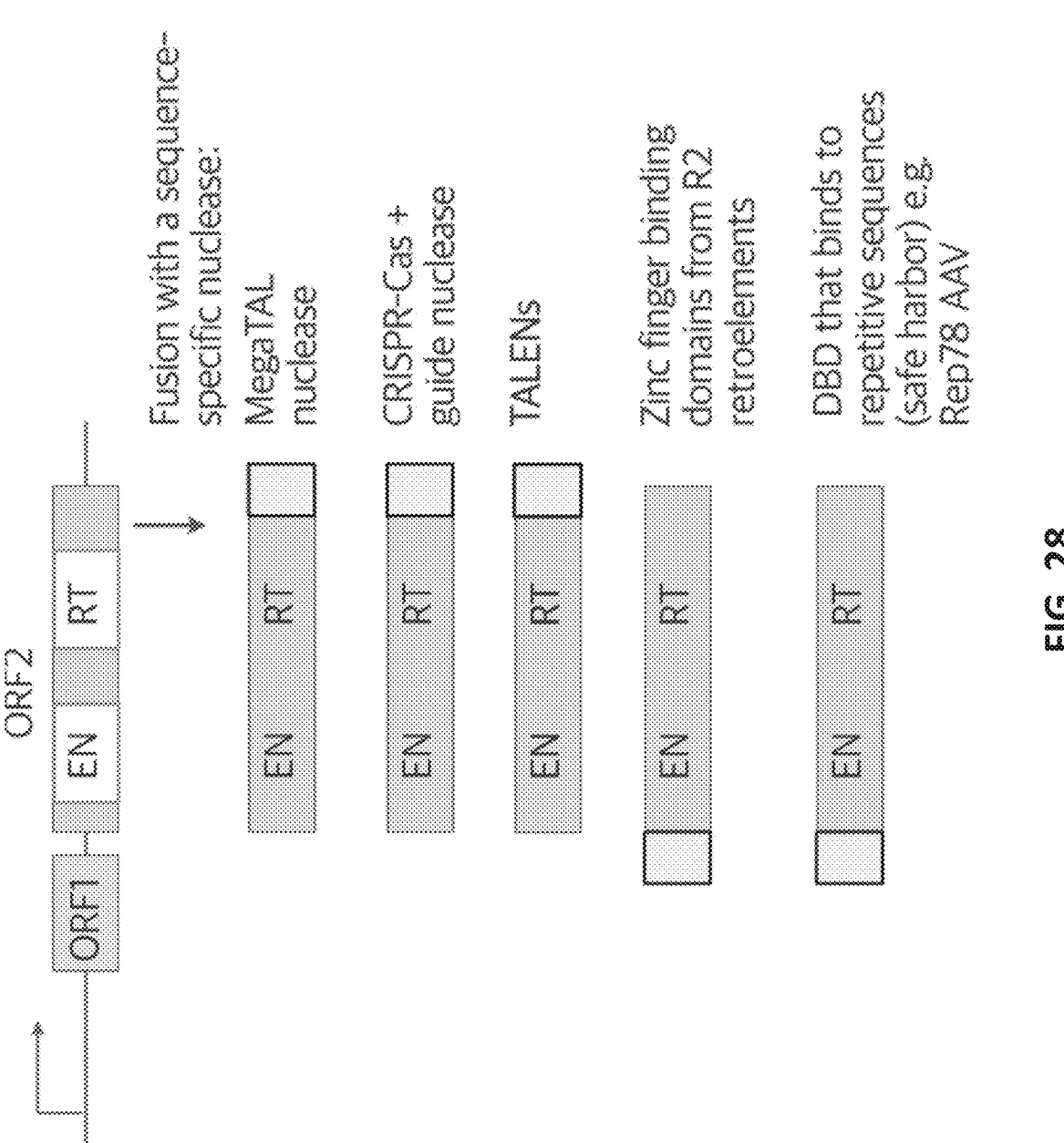

FIG. 28 illustrates exemplary constructs for integrating an mRNA encoding a transgene into the genome of a cell.

Figure 29:
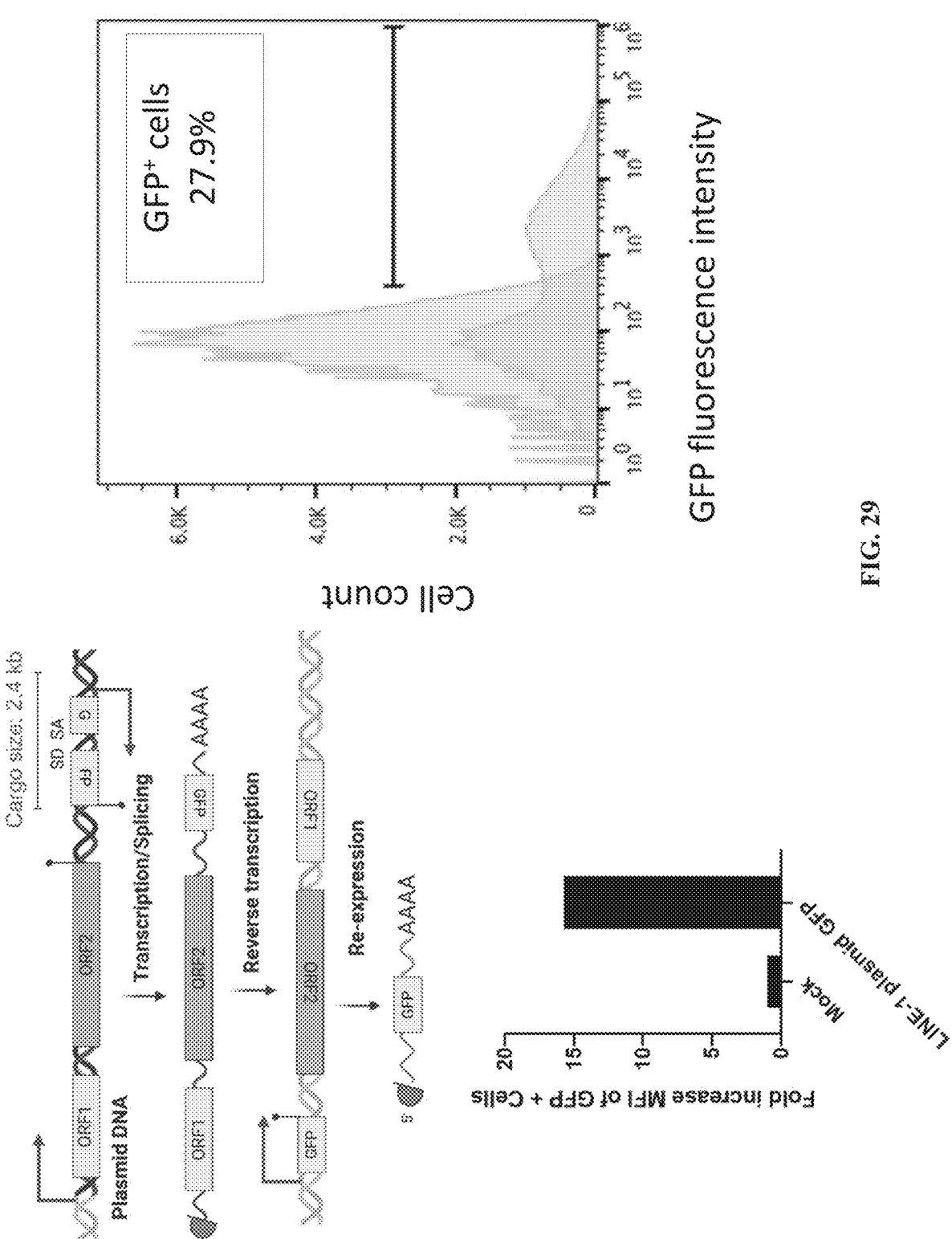

FIG. 29 illustrates exemplary retrotransposon constructs (left) with a 2.4 kb cargo with a general mechanism of action of the retrotransposon, and a representative data (right) for expression of a fluorescent GFP marker encoded by the cargo from a nucleic acid sequence integrated into the genome in HEK293 cells. Placement of an antisense GFP gene split with an intron in the sense direction and a promoter sequence in the 3'UTR of the LINE-1 leads to reconstitution and retrotransposition of the GFP cargo. GFP expression in 293T cells transfected with the construct shown on the left, as measured by flow cytometry (right) and quantitated bar graphs (bottom left). Data collected 35 days after doxycycline induction of the ORF.

Figure 30:
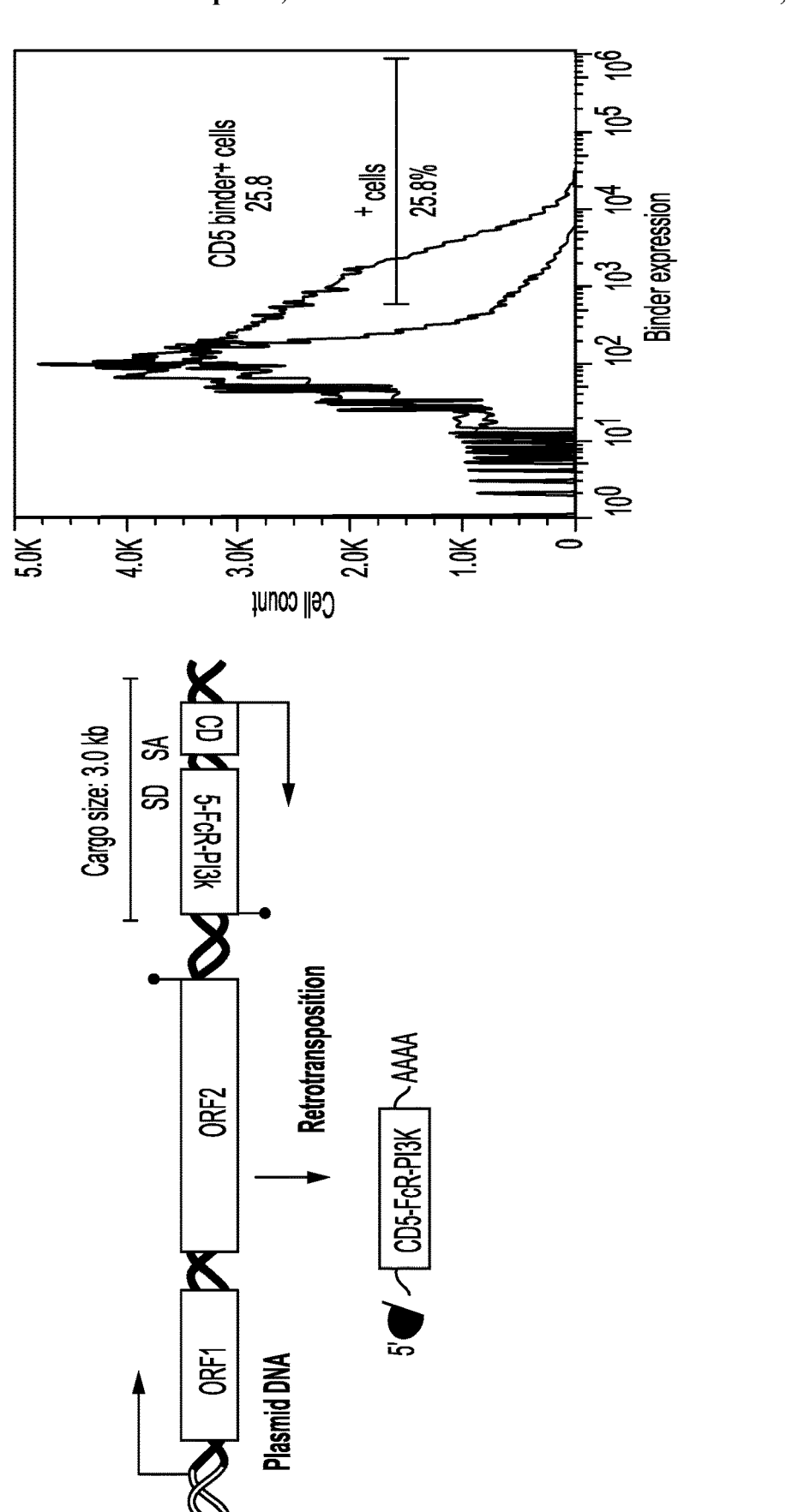

FIG. 30 illustrates exemplary retrotransposon constructs (left) with a 3.0 kb cargo comprising a membrane protein (CD5 binder chimeric antigen receptor, CD5-CAR), and a representative flow cytometry data for expression of the CD5 binder (right) from the nucleic acid sequence integrated into the genome in HEK293 cells. % of CD5 binder positive (+) cells is indicated in the inset.

Figure 31:
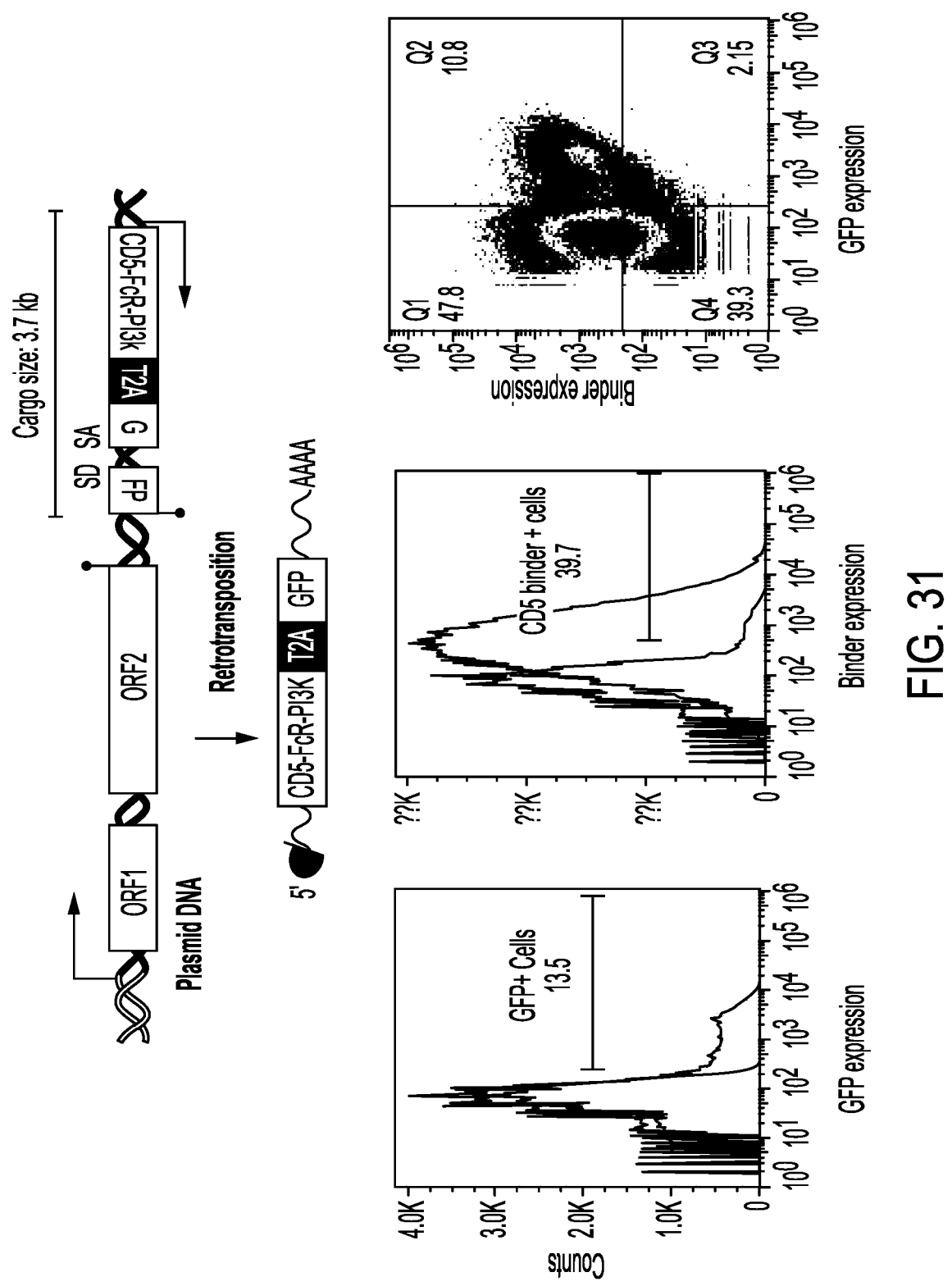

FIG. 31 illustrates an exemplary retrotransposon construct (top) with a 3.7 kb cargo comprising a membrane protein (CD5 binder chimeric antigen receptor, CD5-CAR and a GFP separated by an auto-cleavable T2A element), and a representative flow cytometry data (bottom) demonstrating the expression of the CD5 binder and GFP.

Figure 32:
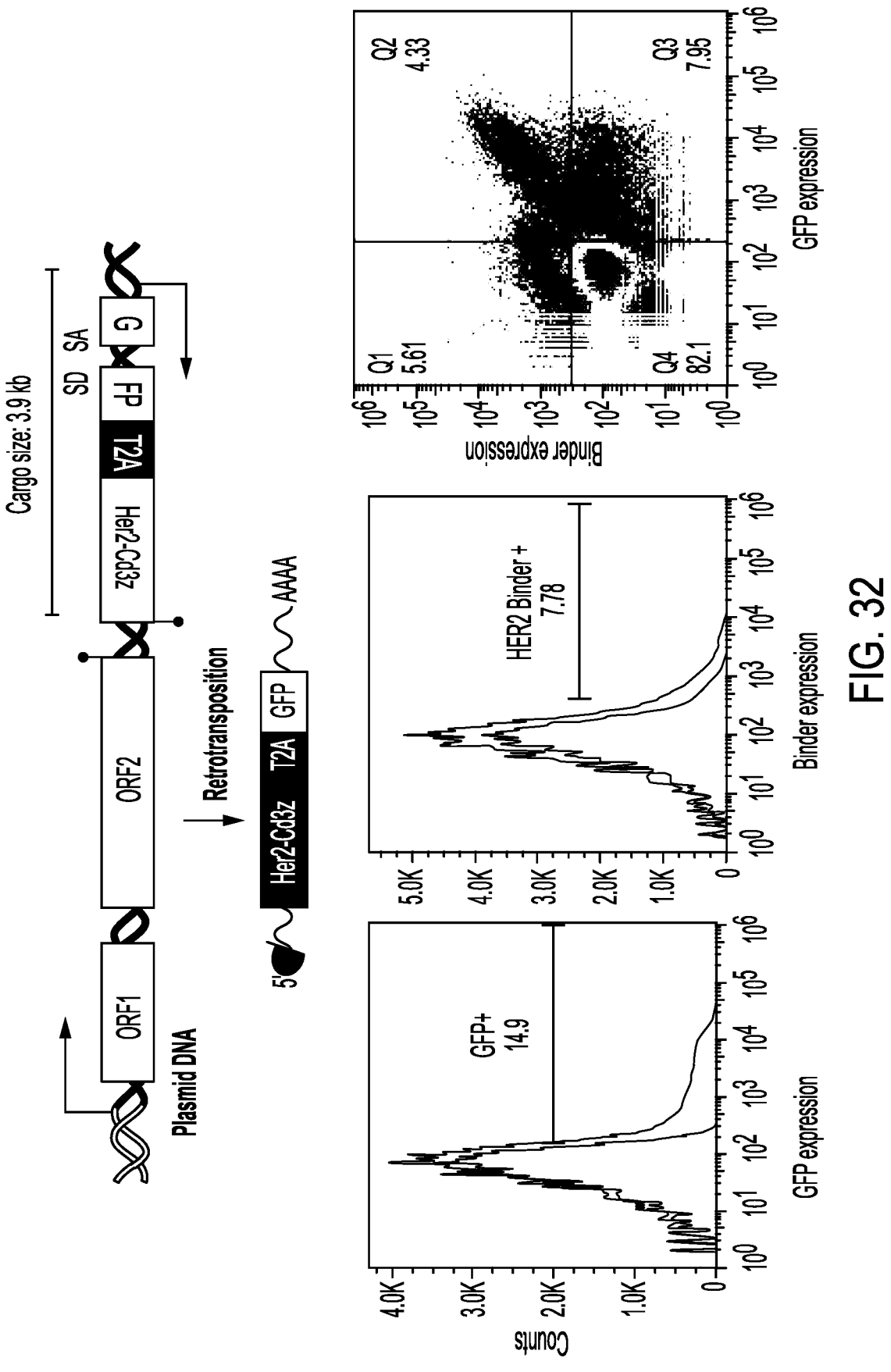

FIG. 32 illustrates an exemplary retrotransposon construct (top) with a 3.9 kb cargo comprising a membrane protein (HER2 binder chimeric antigen receptor, and a GFP separated by an auto-cleavable T2A element), and a representative flow cytometry data (bottom) demonstrating the expression of the HER2 binder and GFP.

Figure 33A:
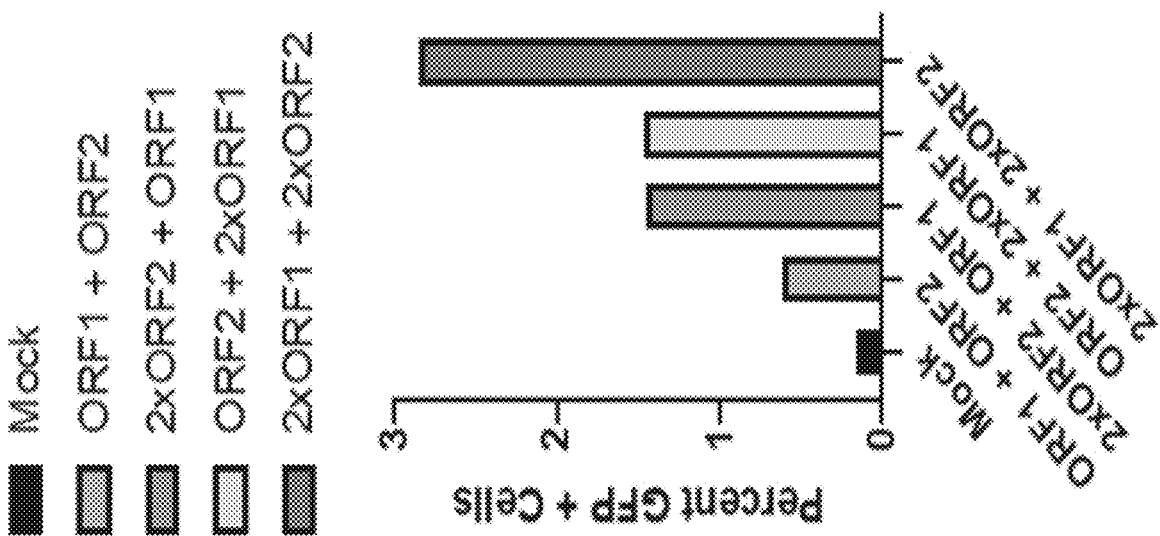

FIG. 33A shows exemplary data for delivery of retrotransposon elements delivered as mRNA.

Figure 33B:
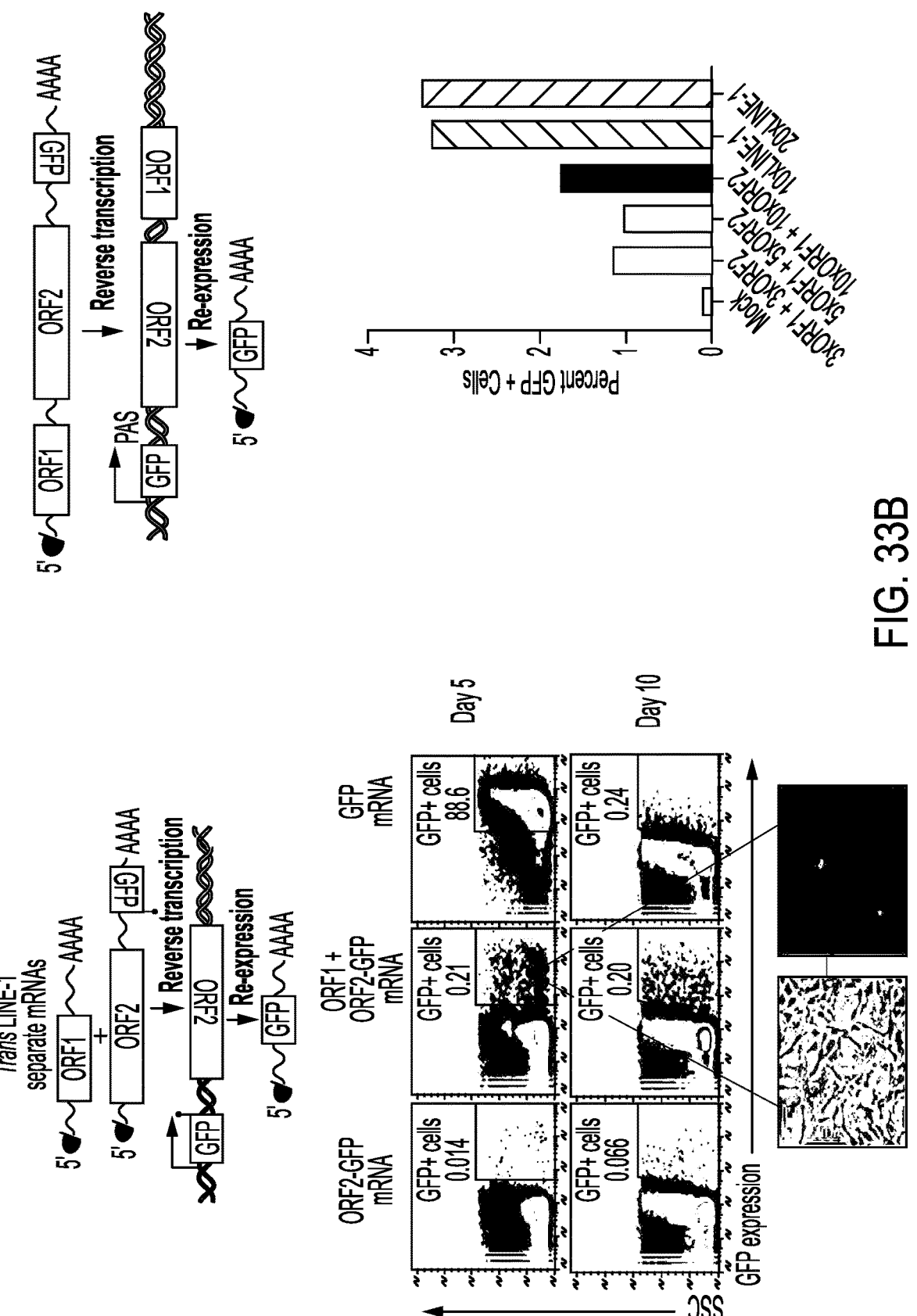

FIG. 33B shows schematic diagram showing a trans and a cis mRNA design for delivery of LINE 1 mRNA with GFP cargo (top panel). Representative results of electroporation of 293T cells with trans mRNAs with separate ORF1 and ORF2 mRNAs. 293T cells were electroporated with 100 μg/mL of mRNA either with ORF2 alone, ORF1+ORF2 mRNAs, each at 100 μg/mL, or a GFP-encoding mRNA with the same 5' and 3'UTRs as the ORF1 mRNA (left panel of data plots). Retrotransposition events result in GFP-positive cells. Cells were assayed for GFP fluorescence by flow cytometry 4 days and 10 days post-electroporation. Mock electroporated cells serve as the negative control population for gating. Bar graph on the right shows results from a representative experiment indicating titration of trans mRNAs and cis ORF1 and ORF2 containing mRNA concentration during electroporation. Trans mRNAs solid bars and cis mRNA stripes. 20× is 2000 μg/mL in the electroporation reaction.

Figure 33C:
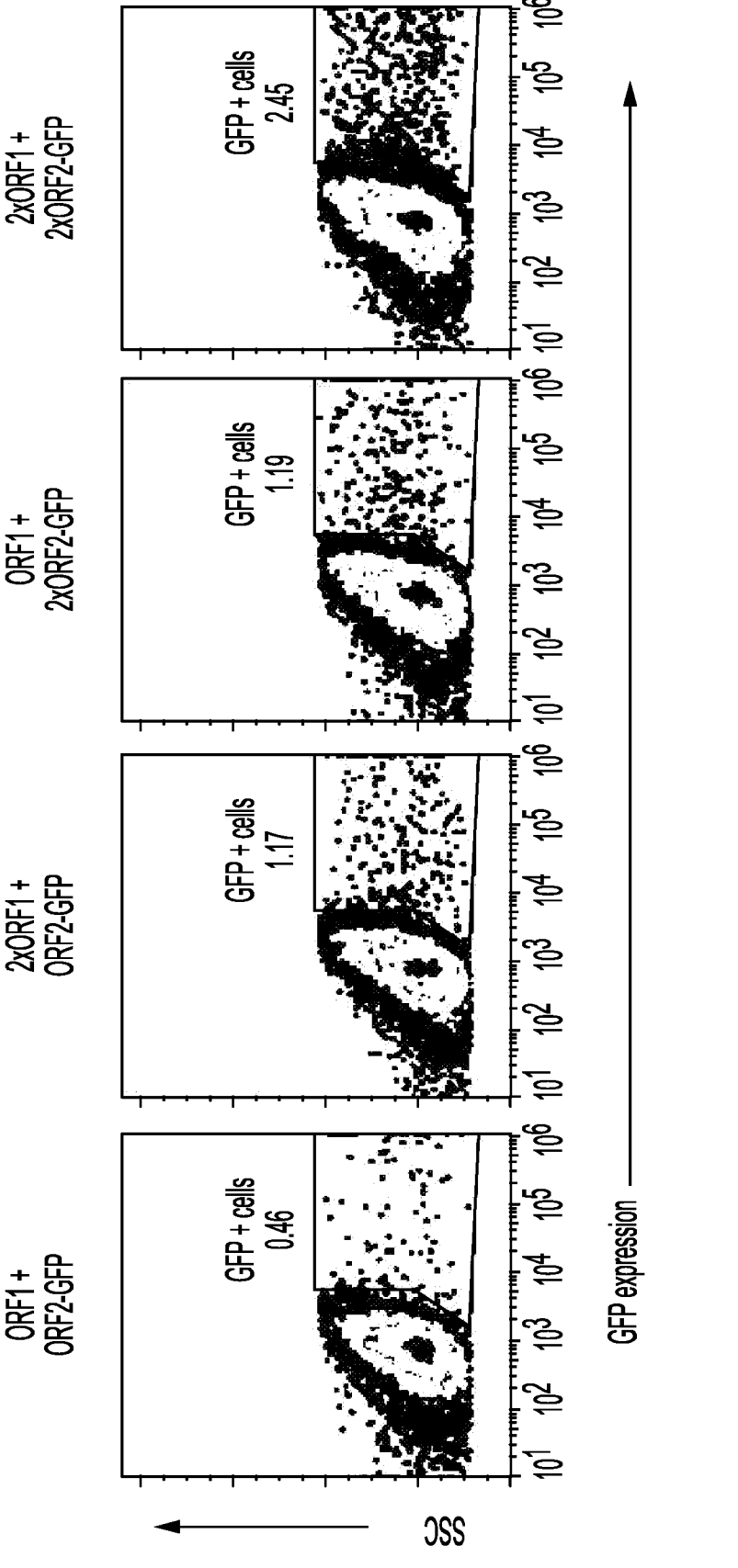

FIG. 33C shows titration of the ORF1 and ORF2-GFPai trans mRNAs. Increasing the concentration separately and together during the electroporation to 200 μg/mL increases retrotransposition of the GFP gene cargo.

Figure 33D:
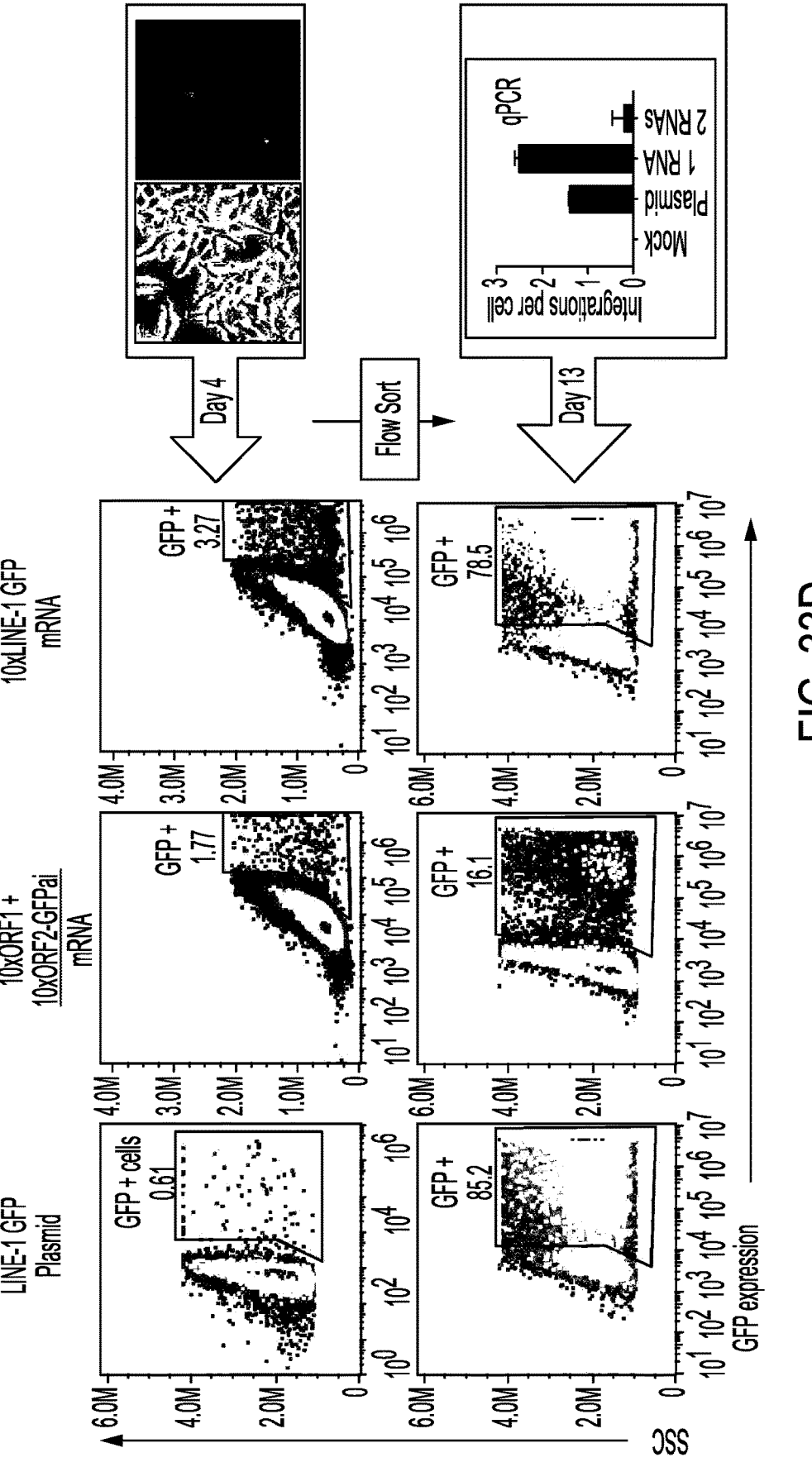

FIG. 33D illustrates an exemplary data for the different constructs indicated above each flow cytometry data plot in the figure, the top panel on day 4, and the bottom panel on day 13. Right hand figures illustrate light and fluorescent microscopic images of a the GFP expressing cells in culture. Copies of integrated cargo per construct is demonstrated in the bottom right at day 13. qPCR assay for genomic DNA integration from different LINE-1 plasmid transfected, LINE-1 mRNA (retro-mRNA), and ORF1 and ORF2-GFP mRNA electroporated cells is shown. Two qPCR primer-probe sets were used, one for the housekeeping gene RPS30 and the other for the GFP gene. Plasmid-transfected cells use a plasmid that does not contain and SV40 maintenance sequence. Integration per cell is calculated from determining copy numbers per samples through interpolation of a standard curve of plasmid and genomic DNA, and normalizing for the two copies of RPS30 per 293T cell. Error bard denote standard deviation of three technical replicate measurements.

Figure 34:
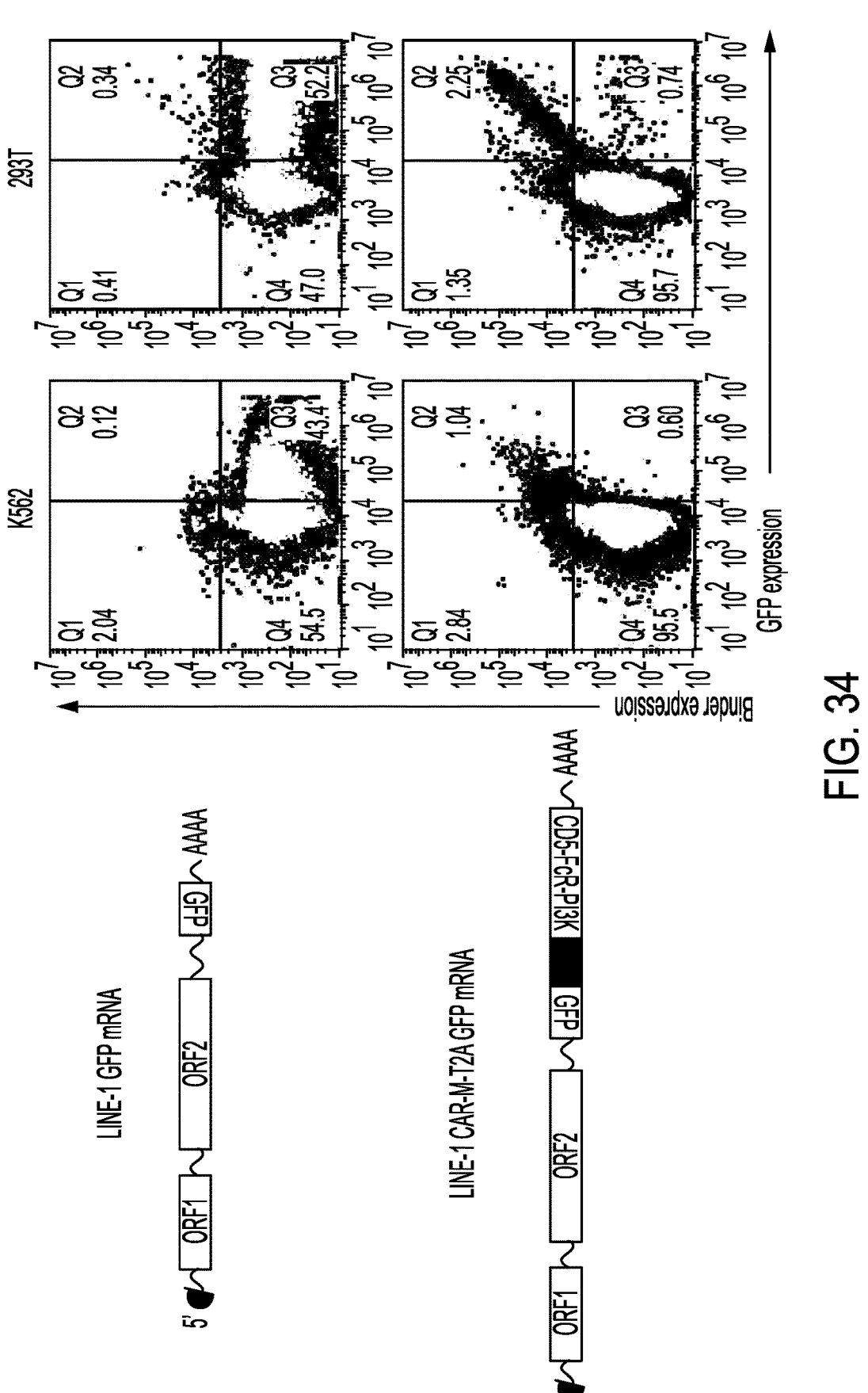

FIG. 34 illustrates exemplary retrotransposon construct (left) and expression data (right) in the indicated cell lines.

Figure 35:
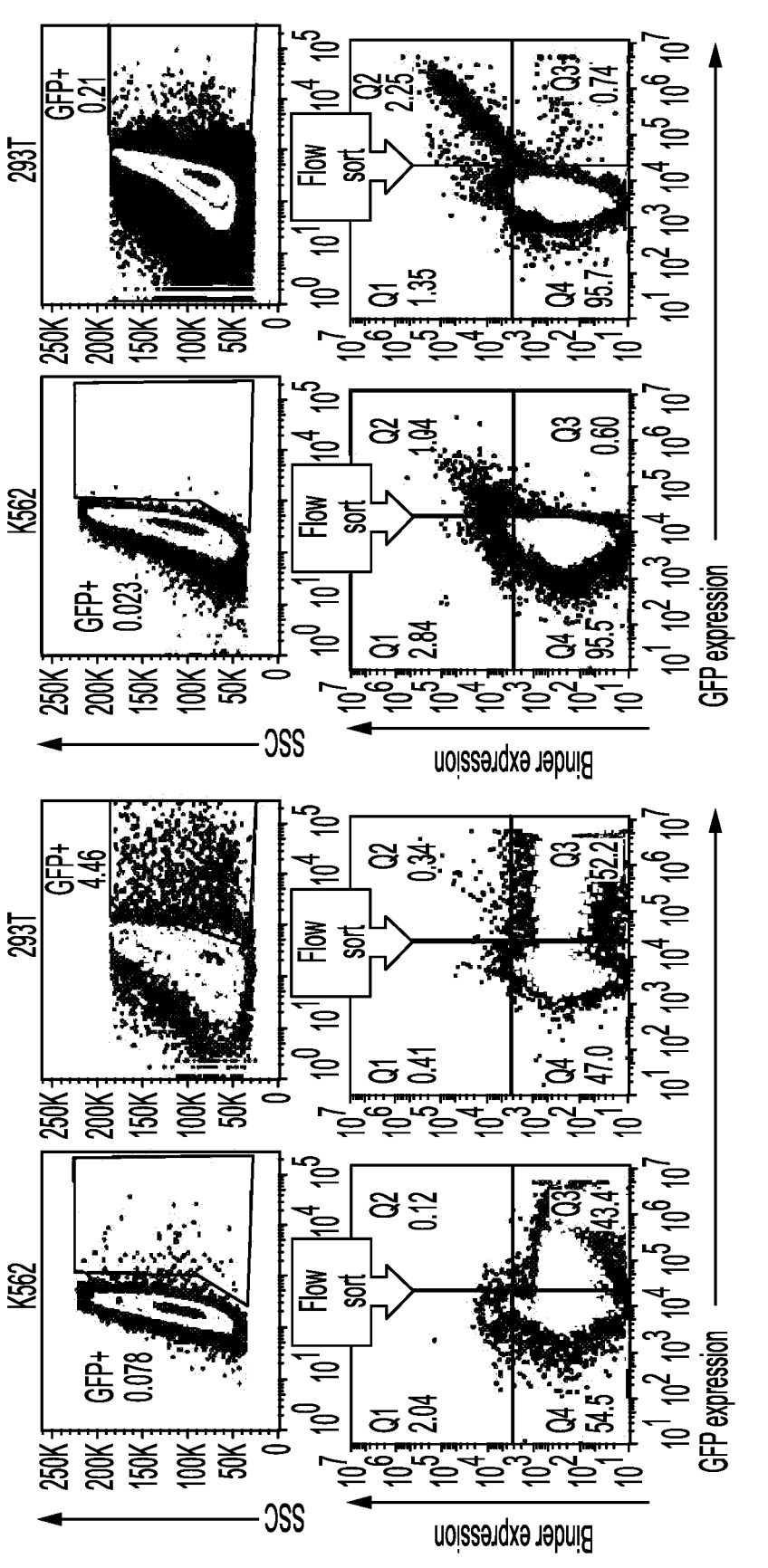
Figure 35:
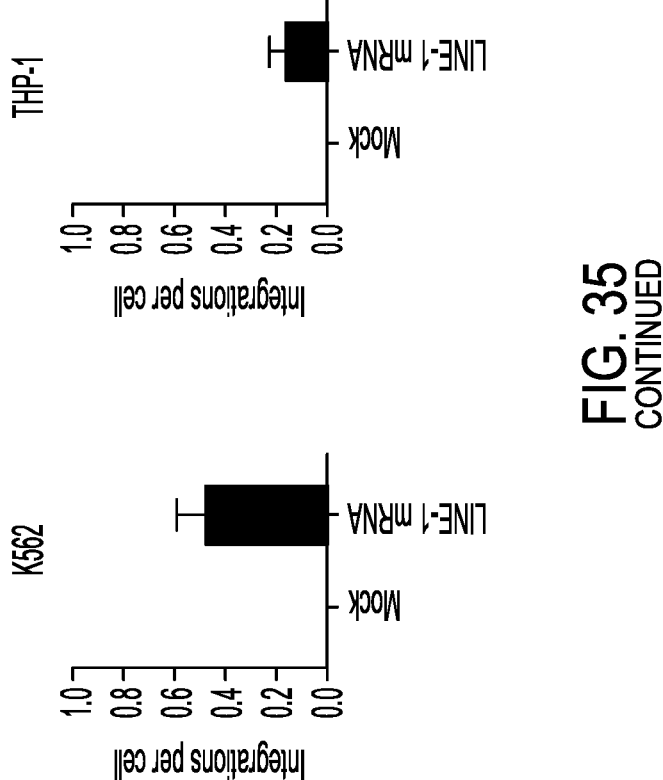

FIG. 35 illustrates flow cytometry data showing expression of LINE 1 GFP constructs in K562, 293T and THP1 cells (upper panel); and number of integrations of LINE-2-GFP mRNA per cell in K562 and THP-1 cell lines (lower panel).

Figure 36:
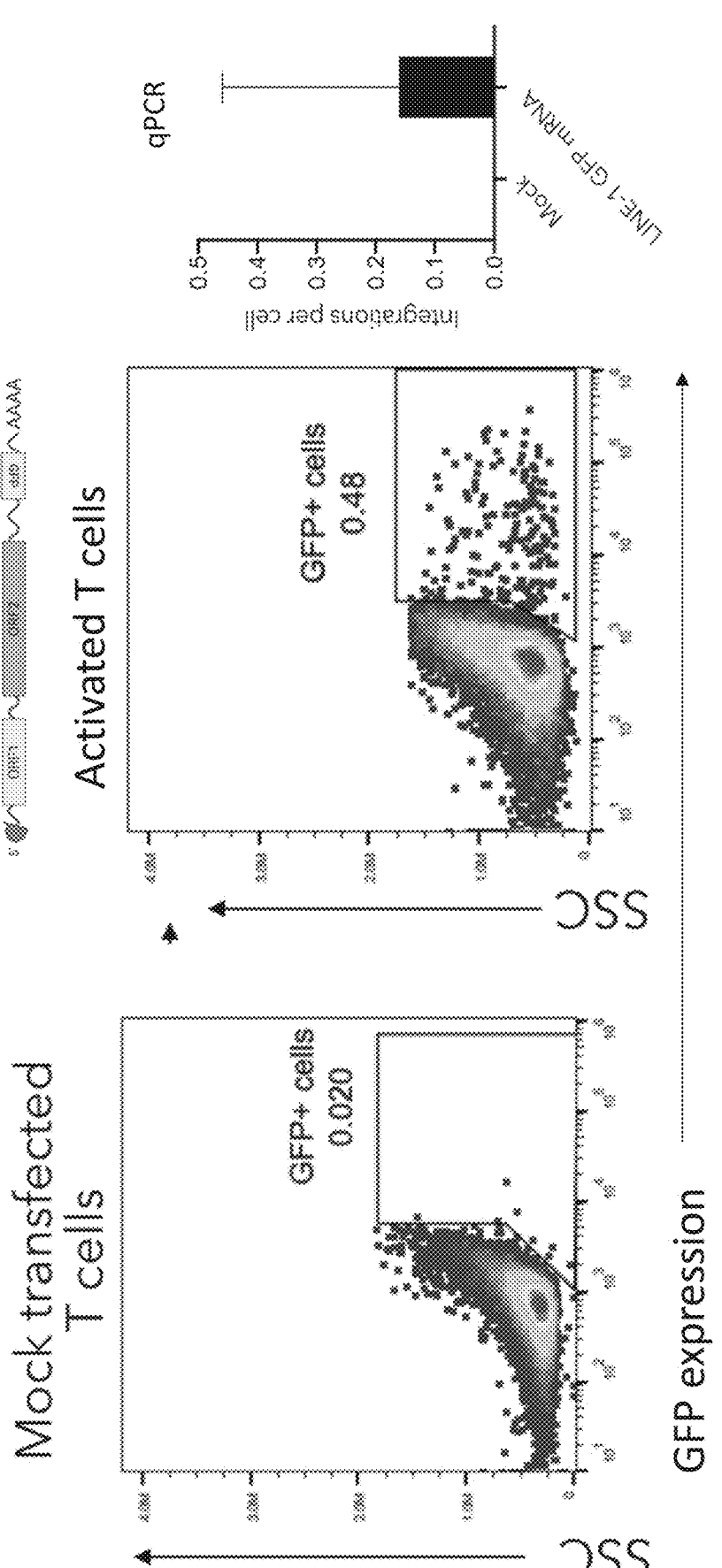

FIG. 36 illustrates flow cytometry data showing expression of LINE 1 GFP constructs in primary T cells (left). Integrations per cell are indicated in the graph on the right. Data was collected on day 6 after electroporation.

Figure 37A:
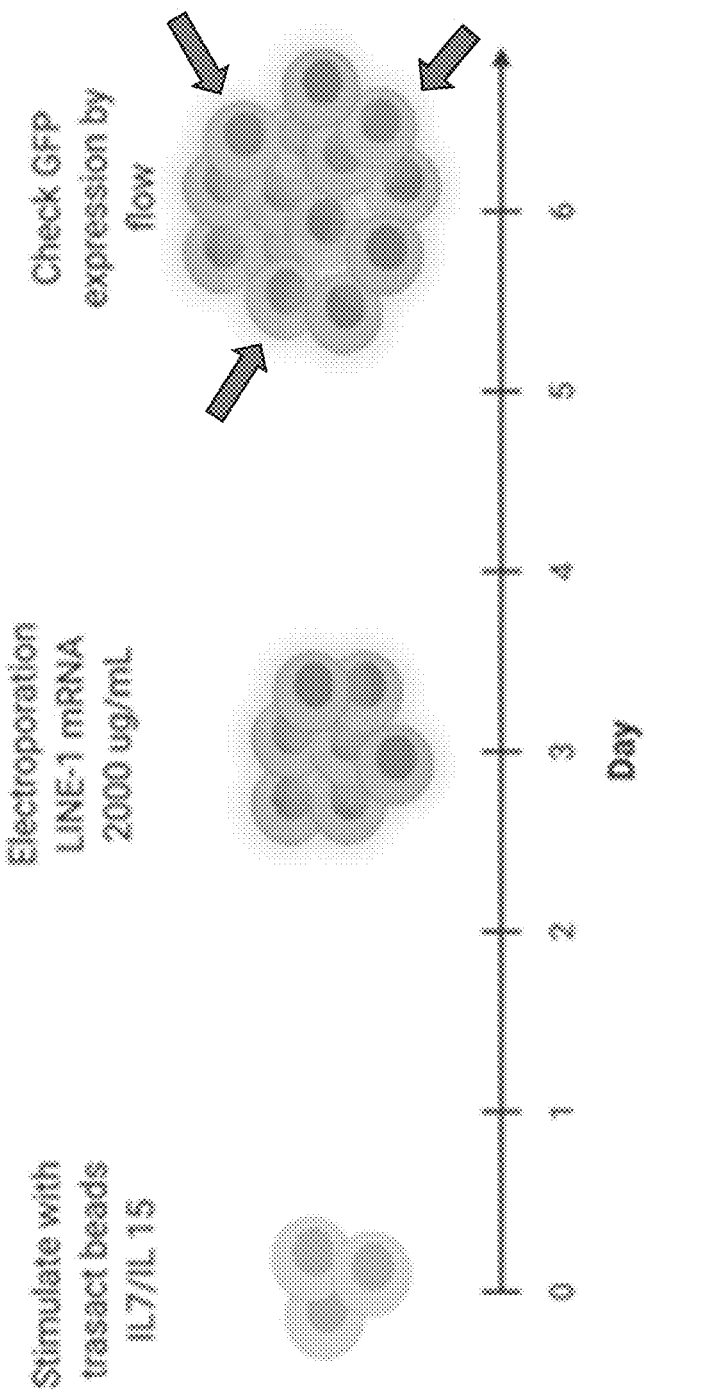

FIG. 37A shows a schematic of activation, culture times, electroporation, and GFP expression assay of isolated primary T cells.

Figure 37B:
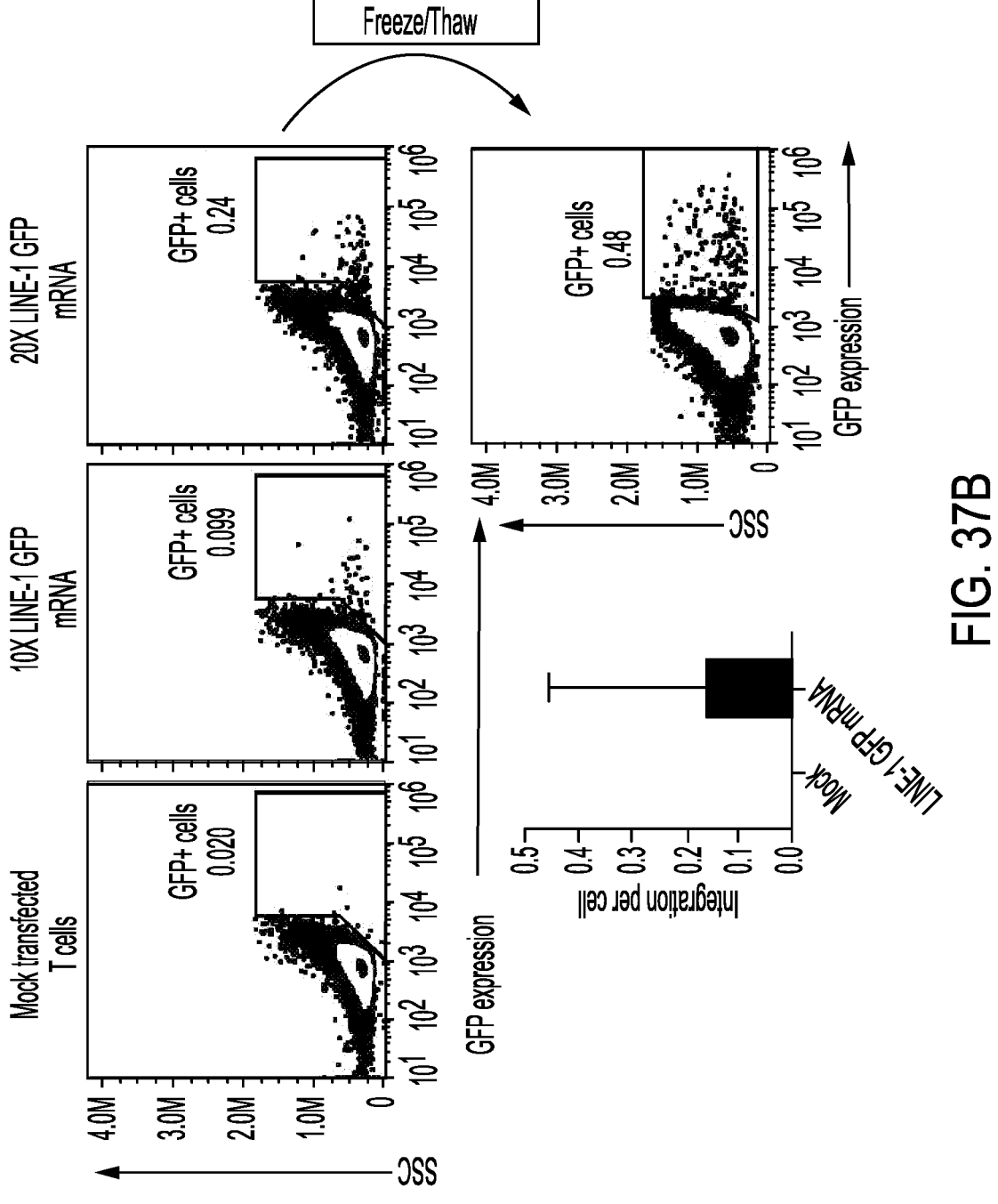

FIG. 37B illustrates flow cytometry data showing expression of LINE 1 GFP mRNA constructs in primary T cells at the indicated concentrations and before and after freeze-thaw as indicated in the figure. Integrations per cell is shown in the bar diagram. GFP expression using a retro-mRNA electroporation with a GFP cargo. GFP expression was assayed 4 days post electroporation and 15 days of culturing post electroporation. Primary T cells were cryo-preserved and thawed during this time. qPCR integration assay for GFP integration. Genomic DNA from the 20× sample was isolated and assayed for copies of GFP.

Figure 38:
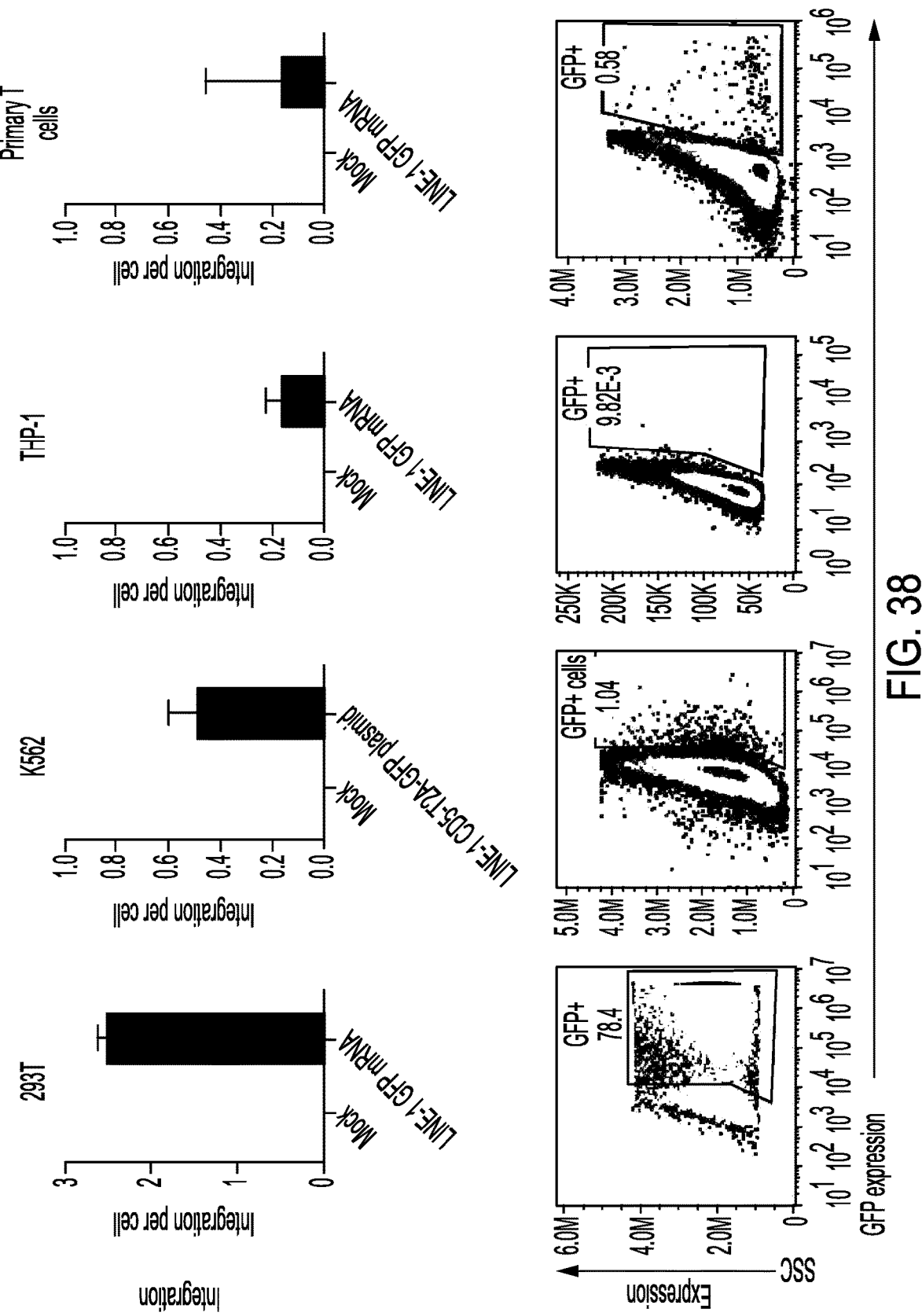

FIG. 38 demonstrates a summary of results of retrotransposon integration and expression across cell types.

Figure 39:
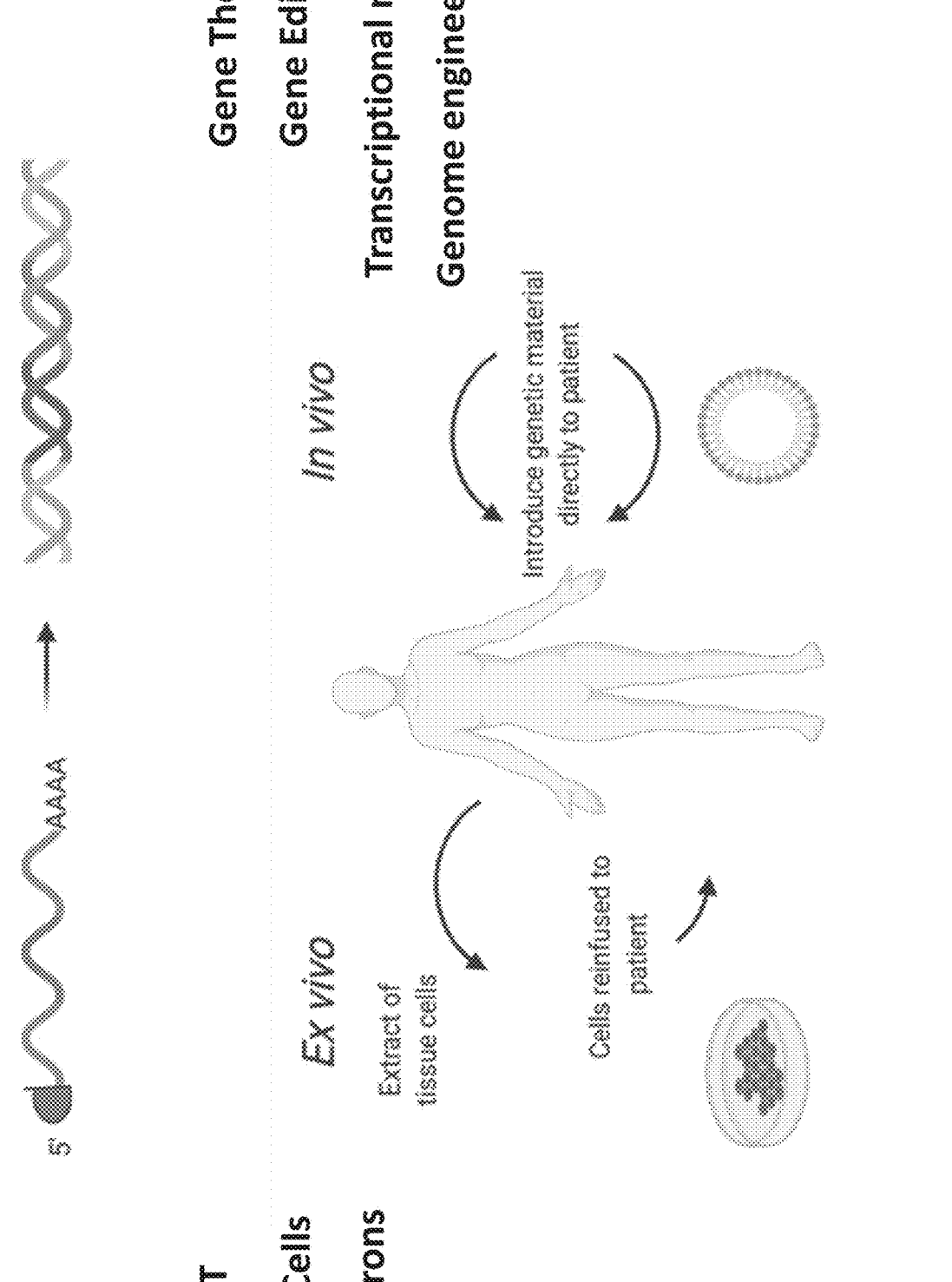

FIG. 39 shows various applications of the technology described herein, including but not limited to use of CART cells, NK cells, neurons and other cells for cell therapy, and use of in vivo applications in including but not limited to gene therapy, gene editing, transcription regulation, and genome engineering.

Figure 40:
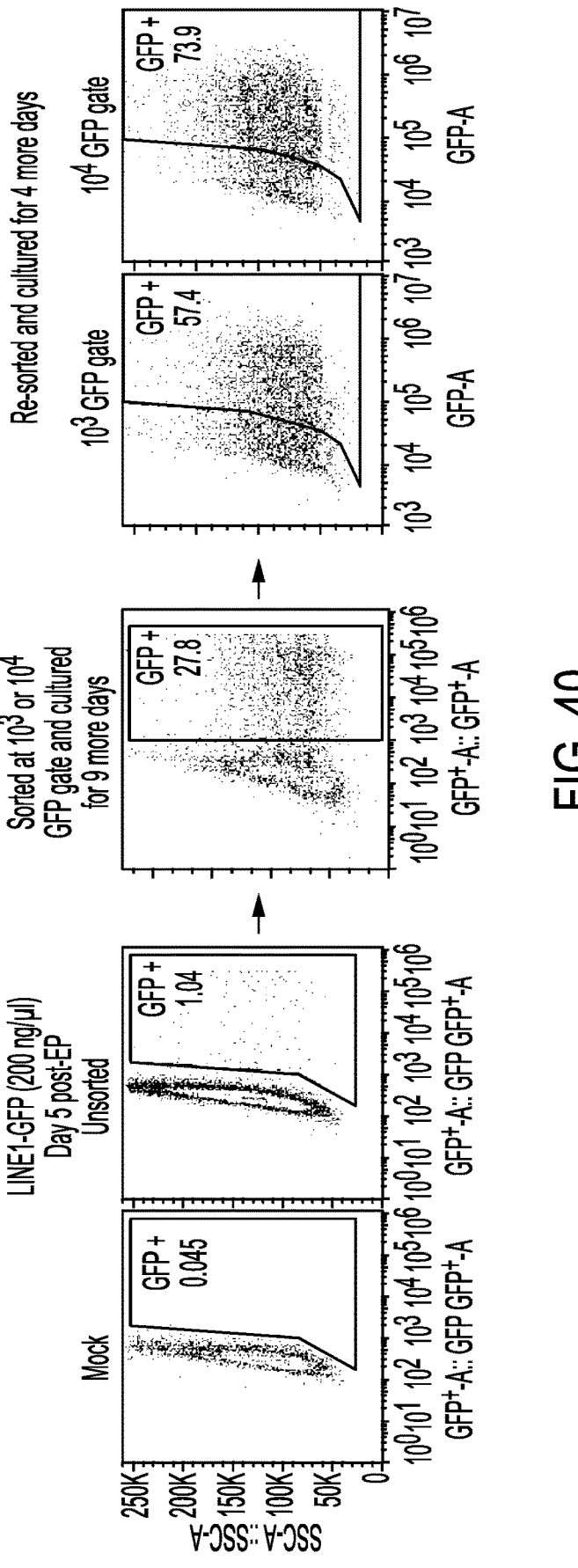

FIG. 40 depicts exemplary flow cytometry data showing sorting and enriching GFP+293T cells electroporated with 2000 ng/μL LINE1-GFP mRNA. The first panel shows flow cytometry data for mock electroporated cells in the absence of LINE1-GFP mRNA. The second panel shows flow cytometry data collected 5 days post electroporation for unsorted cells electroporated with LINE1-GFP mRNA. The GFP+ cells from the second panel were sorted and the flow cytometry data are shown in the third panel. The GFP+ cells from the third panel were cultured for 9 days post sorting and resorted using 10^3 or 10^4 GFP fluorescence intensity gate. The fourth panel shows flow cytometry data for cells resorted using GFP+ at 10^3 GFP gate collected 4 days after resorting. The fifth panel shows flow cytometry data for cells resorted using GFP+ at 10^3 GFP gate collected 4 days after resorting.

Figures 41A, 41B:
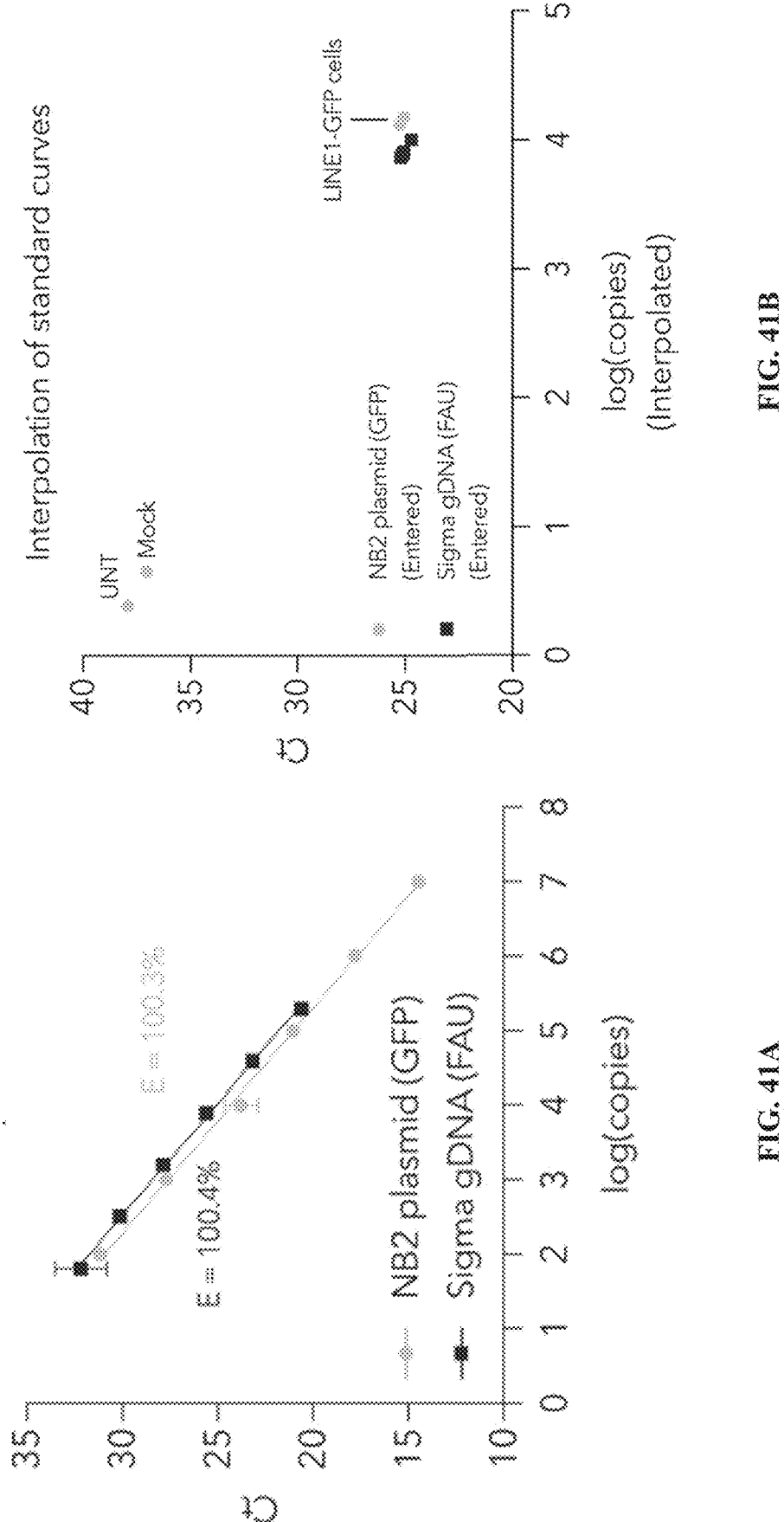

FIG. 41A shows a standard curve for GFP (NB2 plasmid) and a housekeeping gene (FAU) for evaluating genomic integration of GFP-encoding nucleic acid per cell using quantitative PCR.

FIG. 41B shows results of an exemplary graph depicting interpolation of the standard curves of FIG. 41A for quantitation of genomic integration.

Figure 41C:
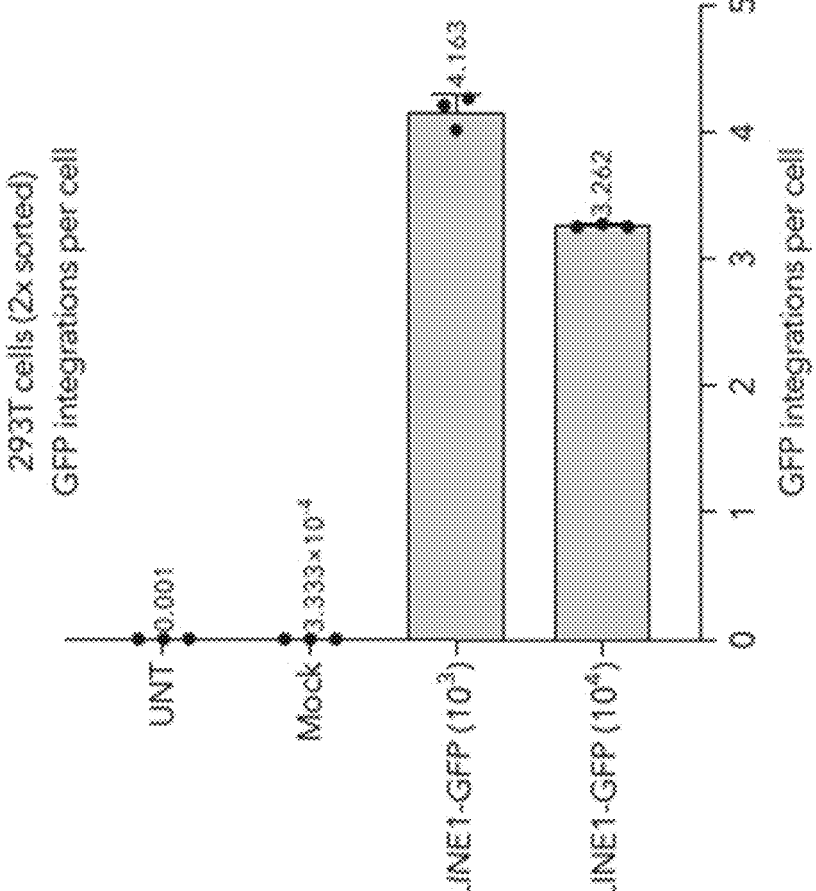

FIG. 41C shows the number of the GFP gene integrated into genome of 293T cells following LINE1-GFP mRNA electroporation and double sorting as shown in FIG. 40. The average number of GFP integrations per cell when gated at 10^3 GFP+ cells and at 10∝GFP+ cells according to qPCR are shown.

Figure 42:
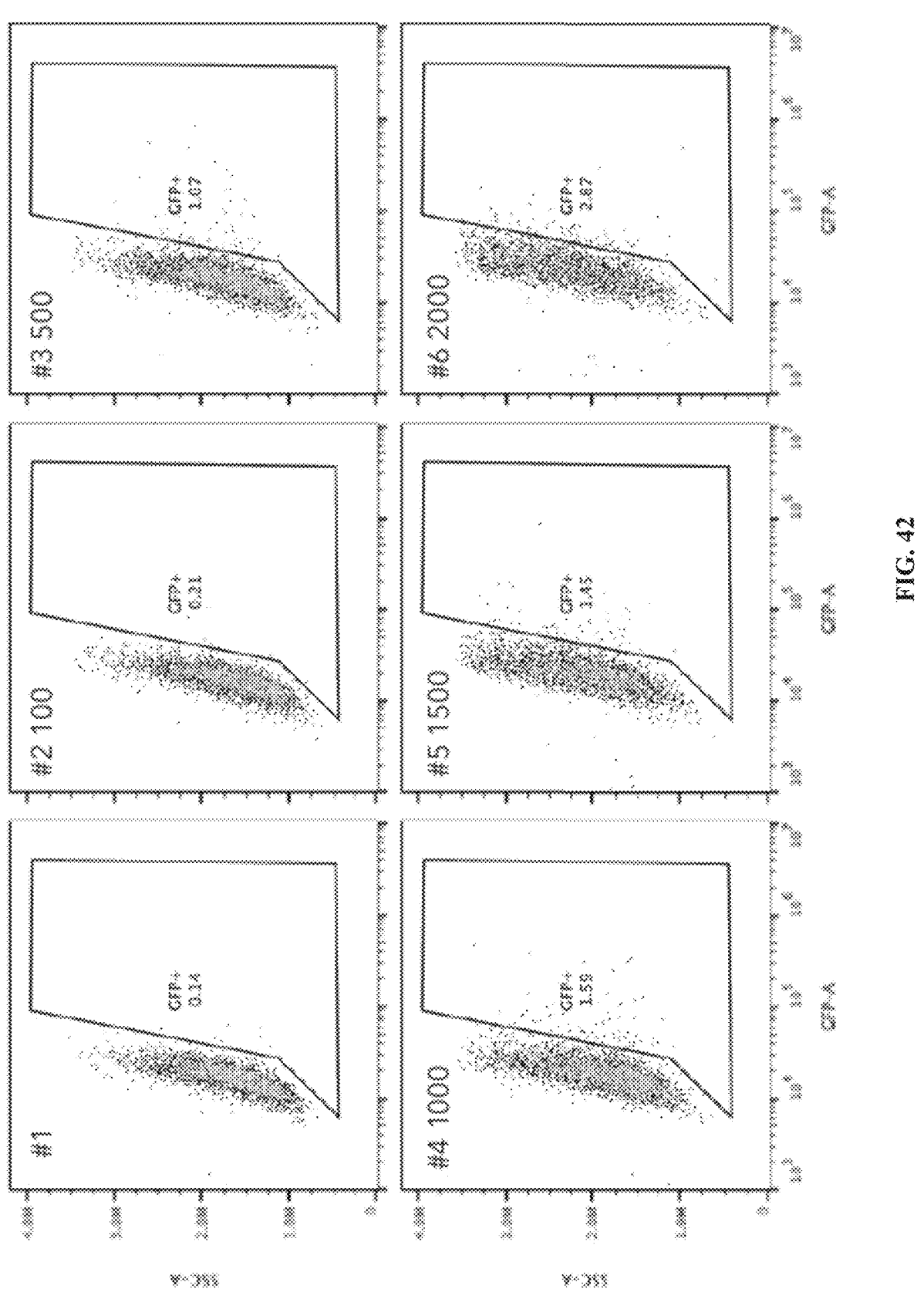

FIG. 42 depicts exemplary flow cytometry data showing GFP+293T cells electroporated with the indicated titrated amounts of LINE1-GFP mRNA, in ng/μL in electroporation solution, after culturing for 3 days post-electroporation.

Figure 43:
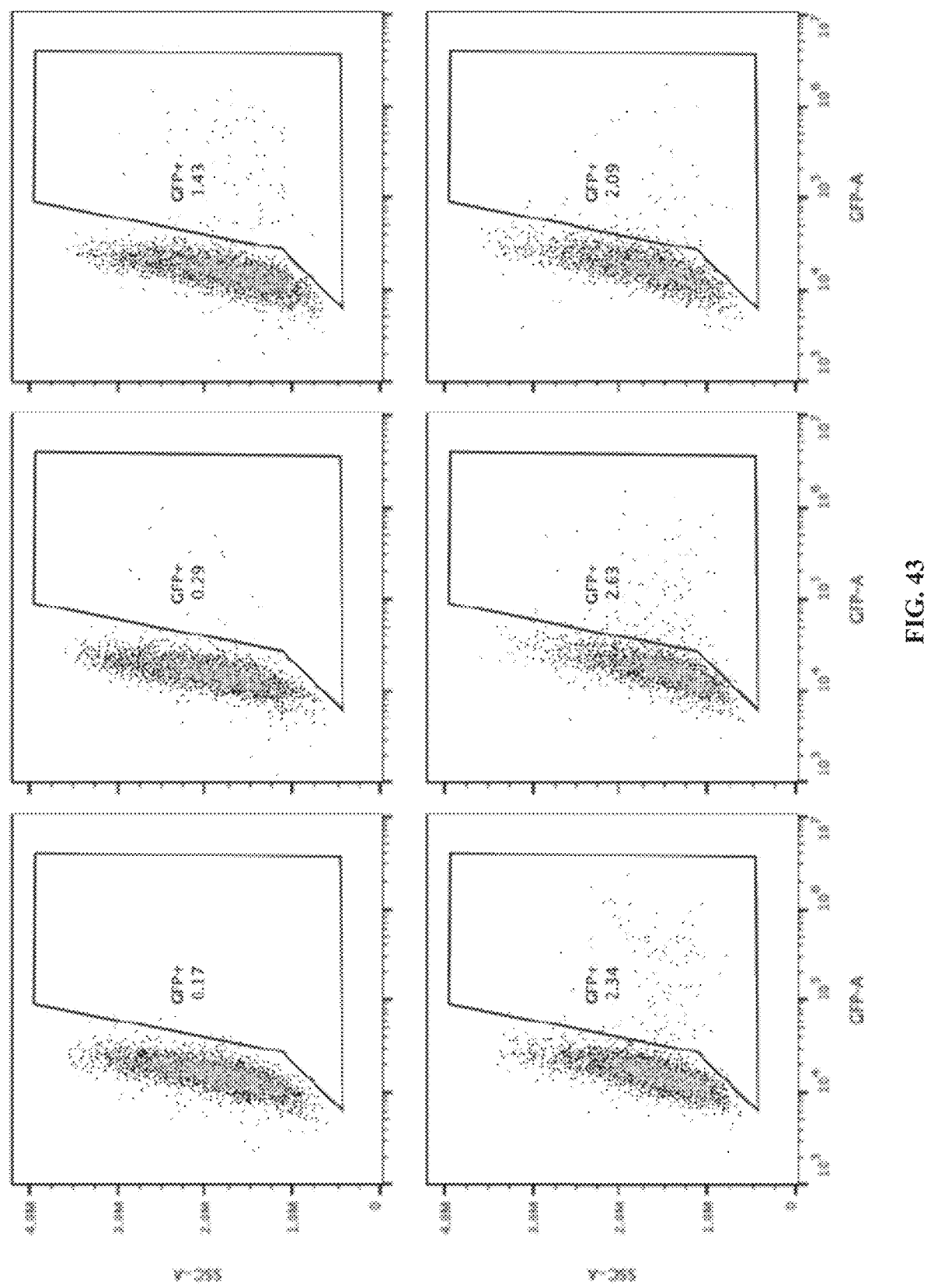

FIG. 43 depicts exemplary flow cytometry data showing GFP+293T cells electroporated with the indicated titrated amounts of LINE1-GFP mRNA, in ng/μL in electroporation solution, after culturing for 5 days post-electroporation.

Figure 44:
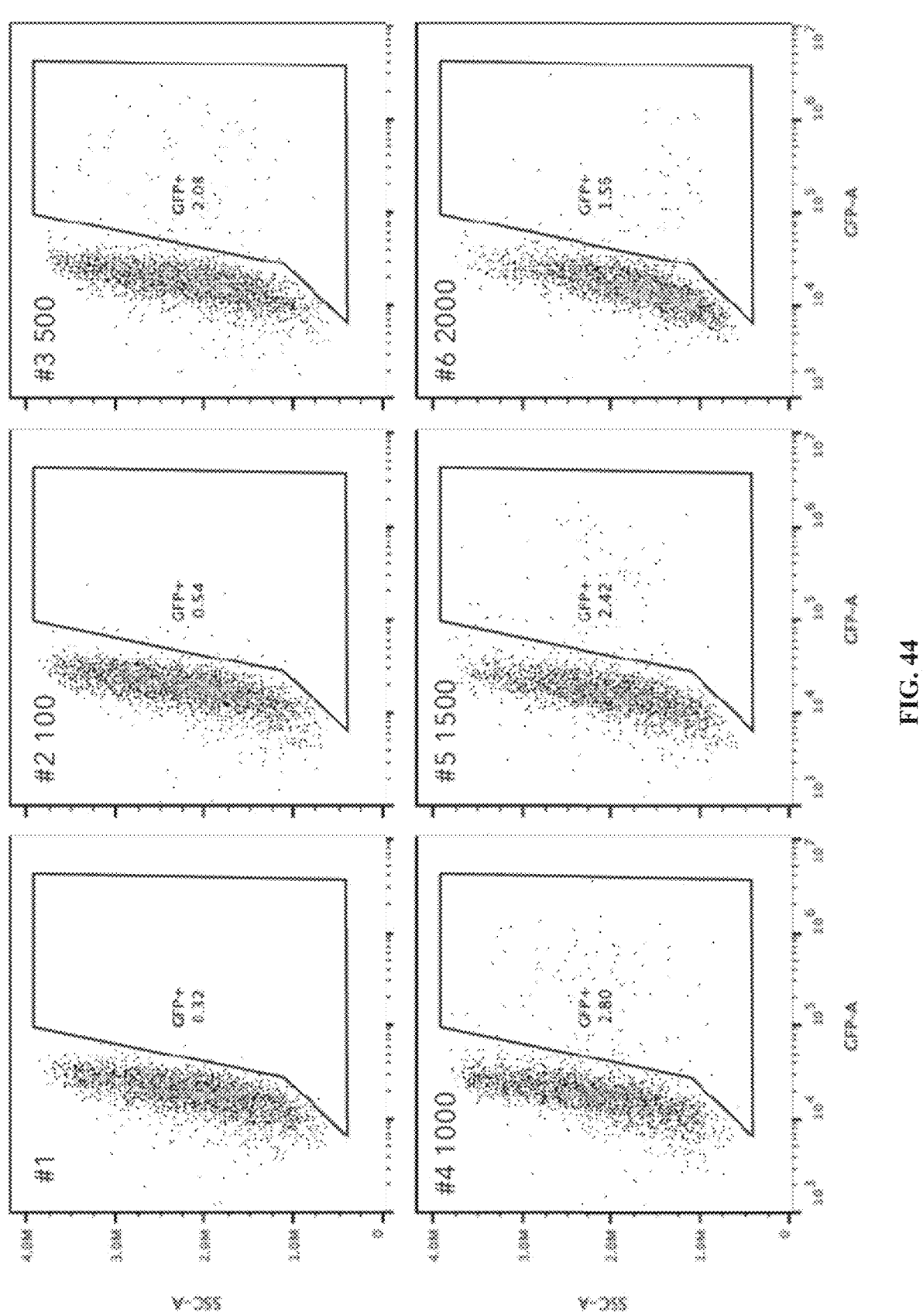

FIG. 44 depicts exemplary flow cytometry data showing GFP+293T cells electroporated with the indicated titrated amounts of LINE1-GFP mRNA, in ng/μL in electroporation solution, after culturing for 7 days post-electroporation.

Figure 45:
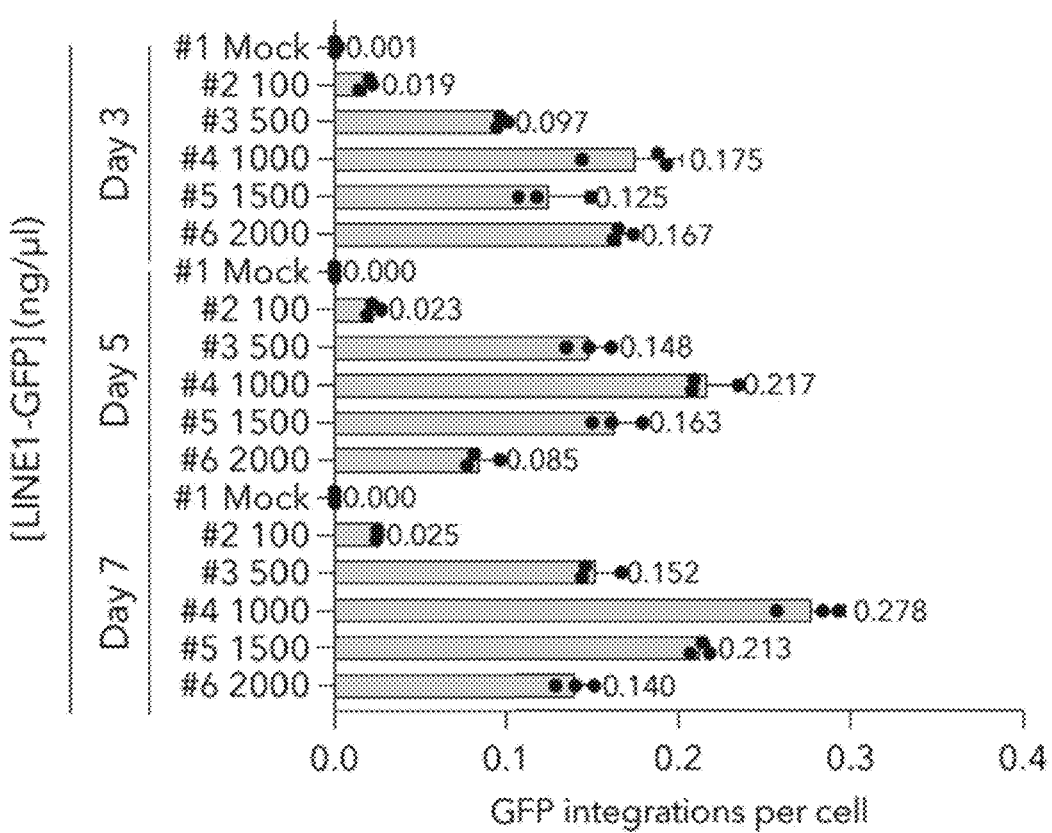
Figure 45:
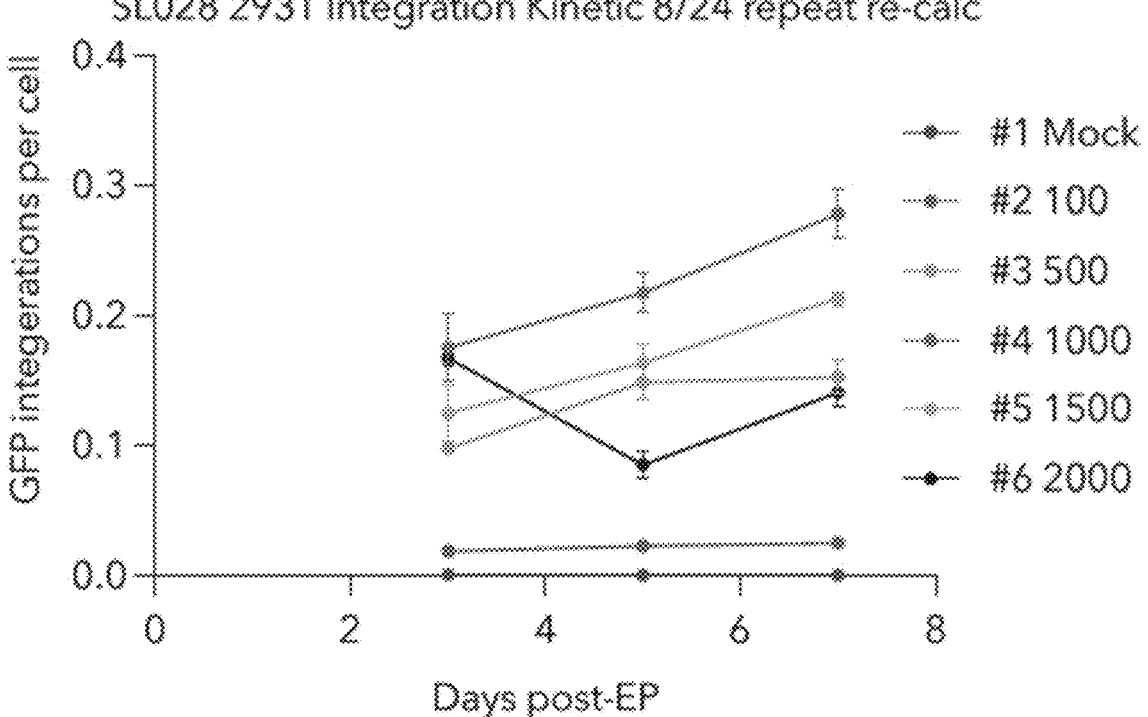

FIG. 45 shows a graph of the number of GFP integrations per genome of 293T cells electroporated with the indicated titrated amounts of LINE1-GFP mRNA, in ng/μL in electroporation solution, according to qPCR after culturing for 3, 5 or 7 days post-electroporation according to FIGS. 42-44 (top) and a graph of the integration kinetics (bottom) according to the data from FIGS. 42-44.

Figure 46:
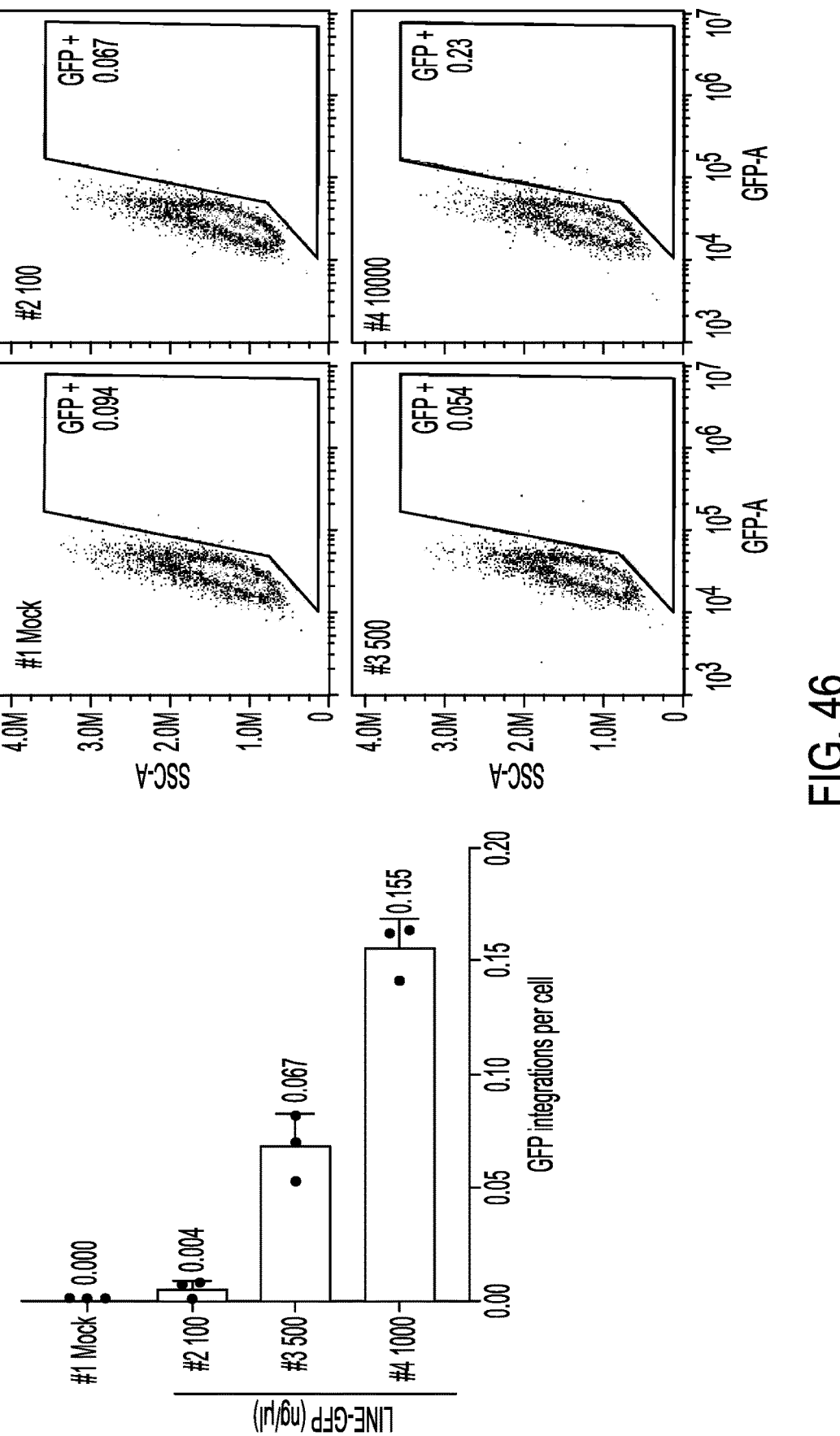

FIG. 46 depicts exemplary flow cytometry data (right) showing GFP+K562 cells electroporated with the indicated titrated amounts of LINE1-GFP mRNA, in ng/μL in electroporation solution, after culturing for 6 days post-electroporation, and a graph of the number of GFP integrations per genome according to qPCR (left).

Figure 47:
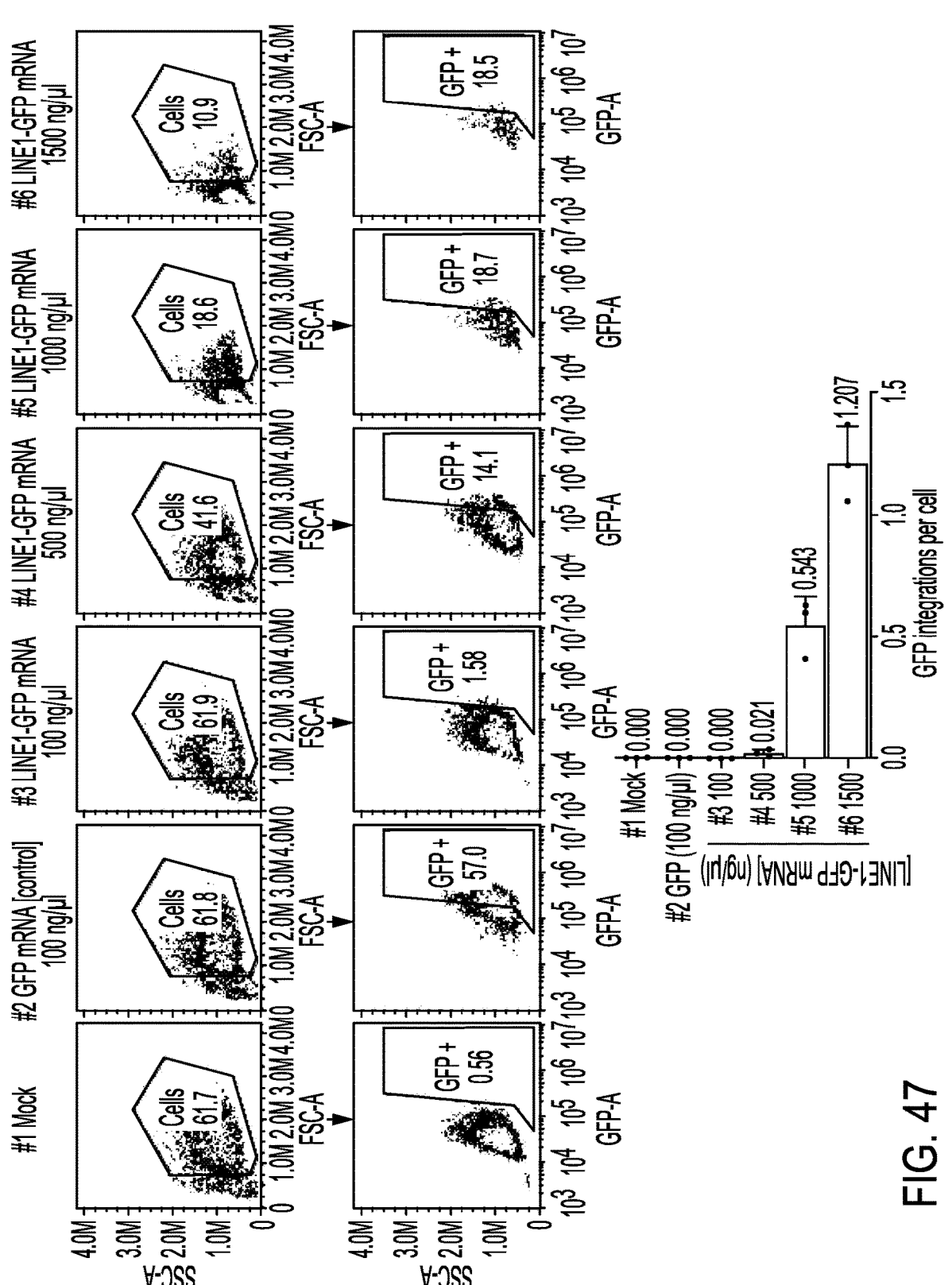

FIG. 47 depicts exemplary flow cytometry data (top) showing GFP+ human primary monocytes electroporated with the indicated titrated amounts of LINE1-GFP mRNA after culturing for 3 days post-electroporation, and a graph of the number of GFP integrations per genome according to qPCR (bottom).

Figure 48:
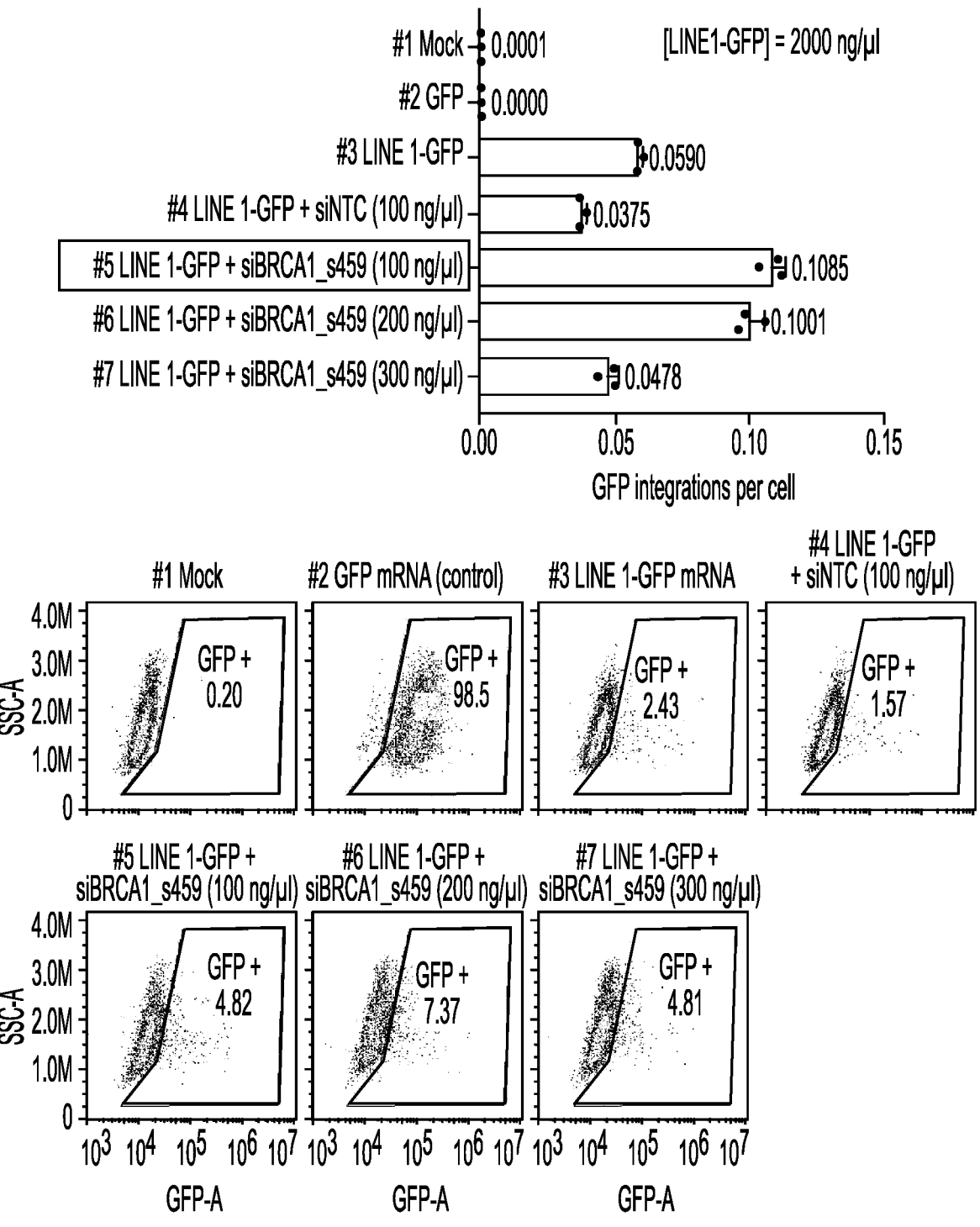

FIG. 48 depicts exemplary flow cytometry data (bottom) showing GFP+293T cells electroporated with 2000 ng/μL LINE1-GFP mRNA and 100 ng/μL, 200 ng/μL or 300 ng/μL of an siRNA targeting BRCA1 (siBRCA1) after culturing for 4 days post-electroporation and a graph of the number of GFP integrations per genome according to qPCR (top).

Figure 49:
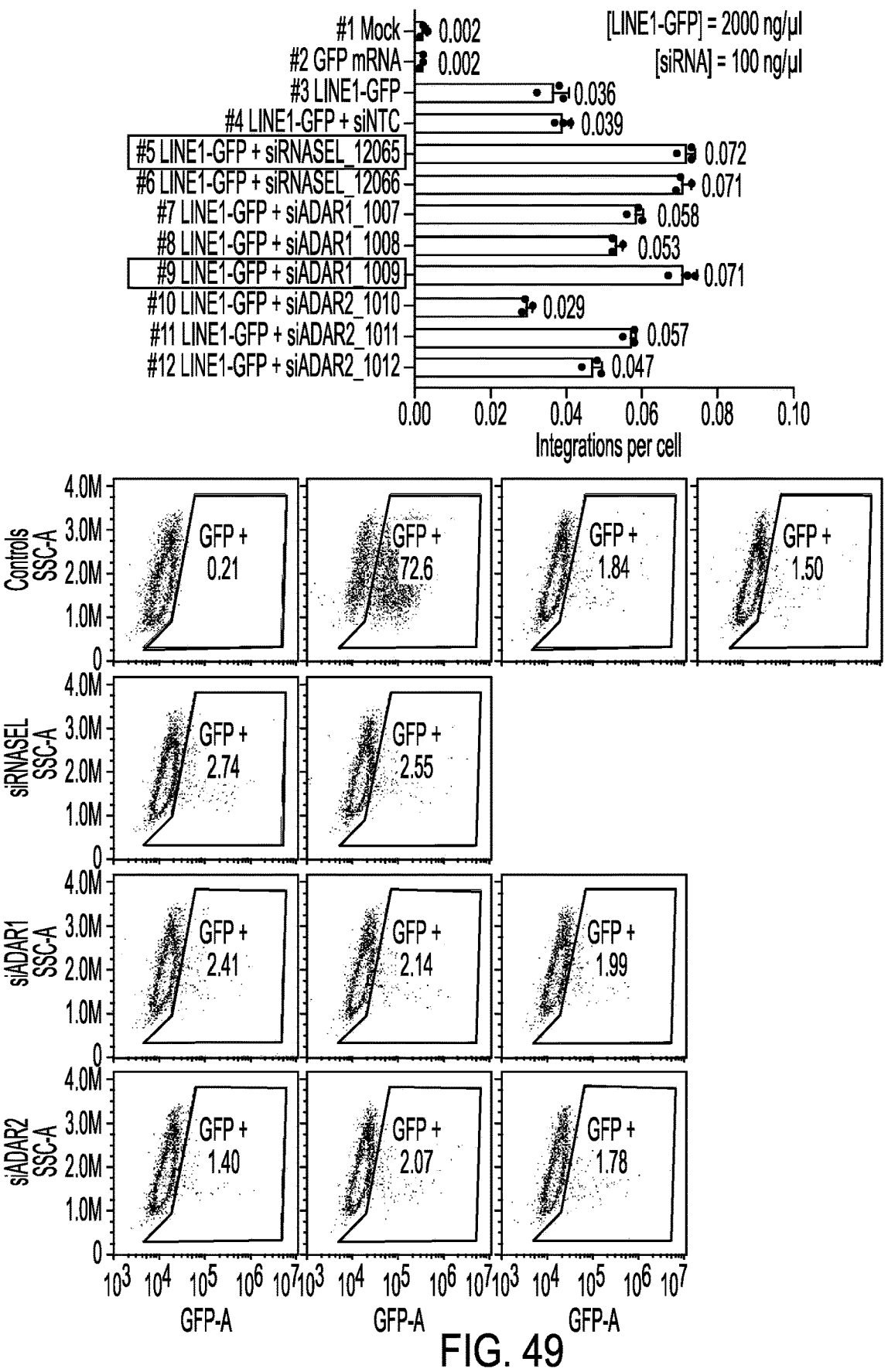

FIG. 49 depicts exemplary flow cytometry data (bottom) showing GFP+293T cells electroporated with 2000 ng/μL LINE1-GFP mRNA and 100 ng/μL of an siRNA targeting RNASEL (siRNASEL), ADAR1 (siADAR1), or ADAR2 (siADAR2) after culturing for 6 days post-electroporation and a graph of the number of GFP integrations per genome according to qPCR (top).

Figure 50:
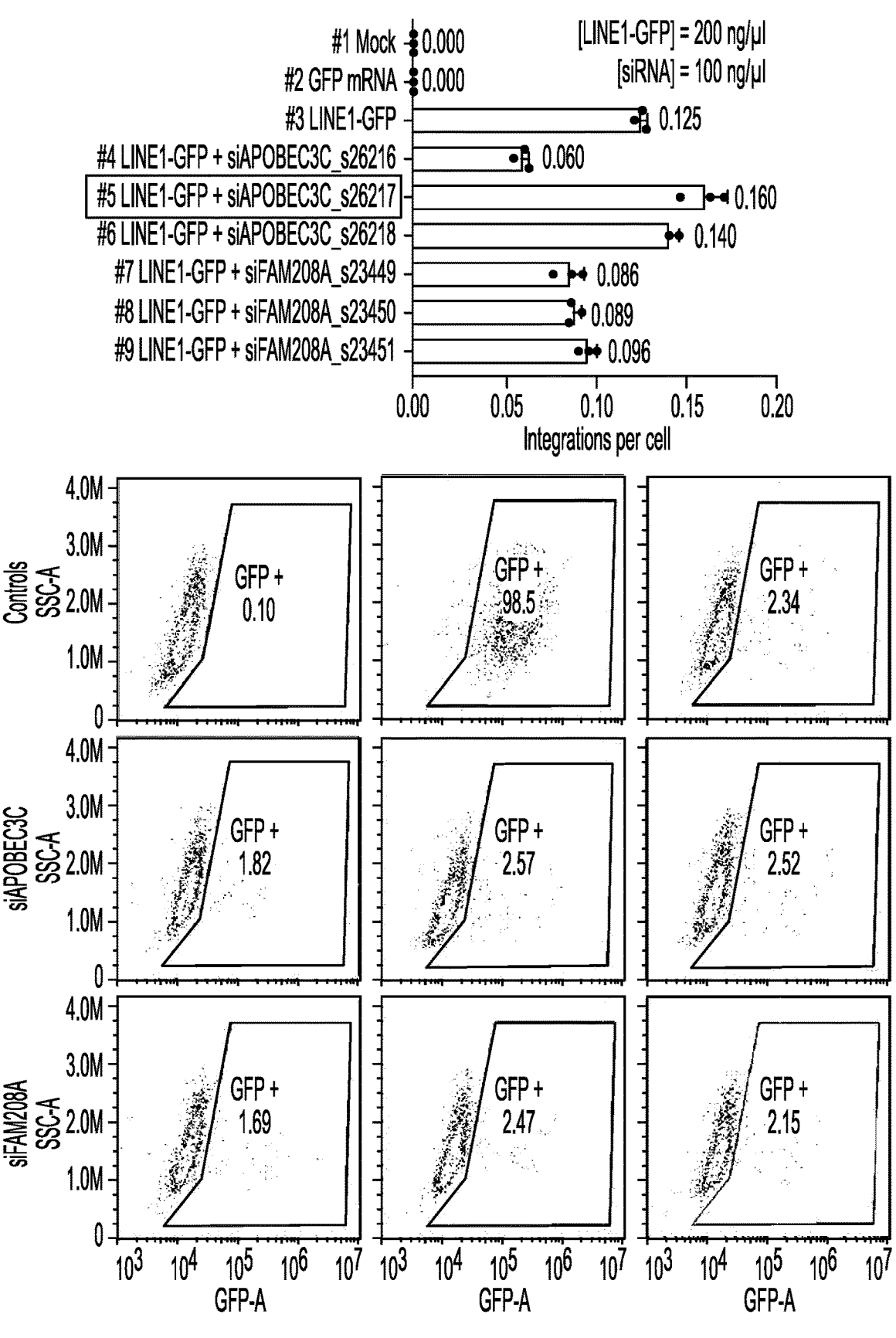

FIG. 50 depicts exemplary flow cytometry data (bottom) showing GFP+293T cells electroporated with 2000 ng/μL LINE1-GFP mRNA and 100 ng/μL of an siRNA targeting APOBEC3C (siAPOBEC3C) or FAM208A (siFAM208A) after culturing for 6 days post-electroporation and a graph of the number of GFP integrations per genome according to qPCR (top).

Figure 51:
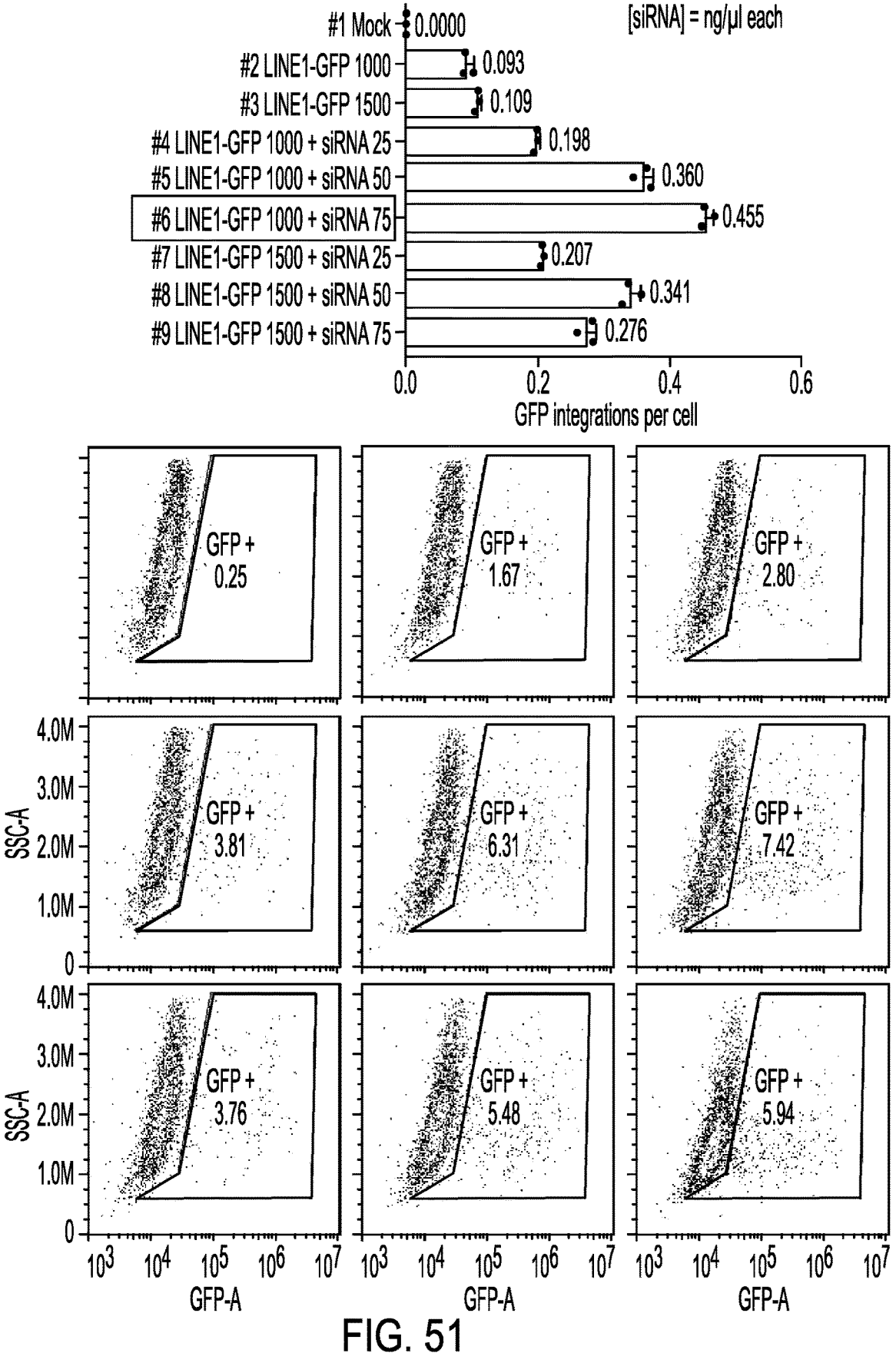

FIG. 51 depicts exemplary flow cytometry data (bottom) showing GFP+293T cells electroporated with 1000 ng/μL or 1500 ng/μL LINE1-GFP mRNA and an siRNA cocktail with 25 ng/μL, 50 ng/μL or 75 ng/μL of each siRNA targeting RNASEL (siRNASEL), ADAR1 (siADAR1), ADAR2 (siADAR2) and BRCA1 (siBRCA1) after culturing for 6 days post-electroporation and a graph of the number of GFP integrations per genome according to qPCR (top).

Figure 52:
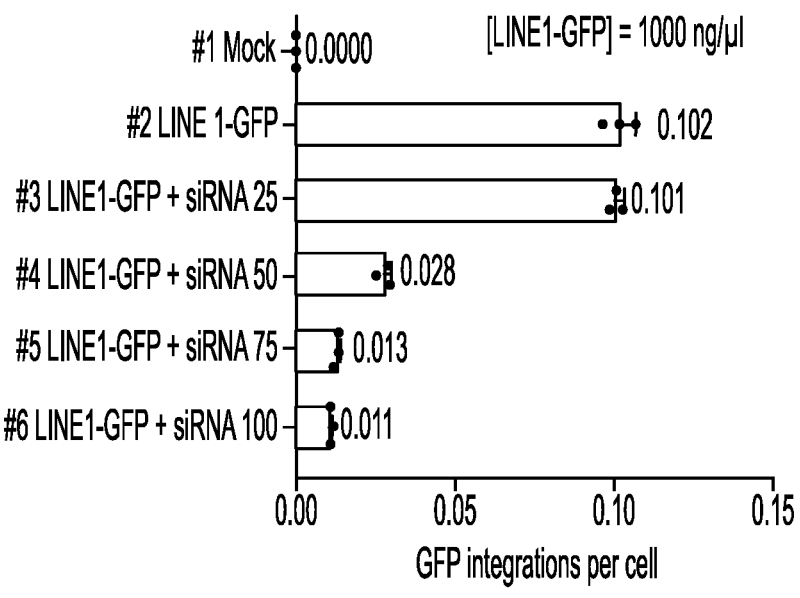
Figure 52:
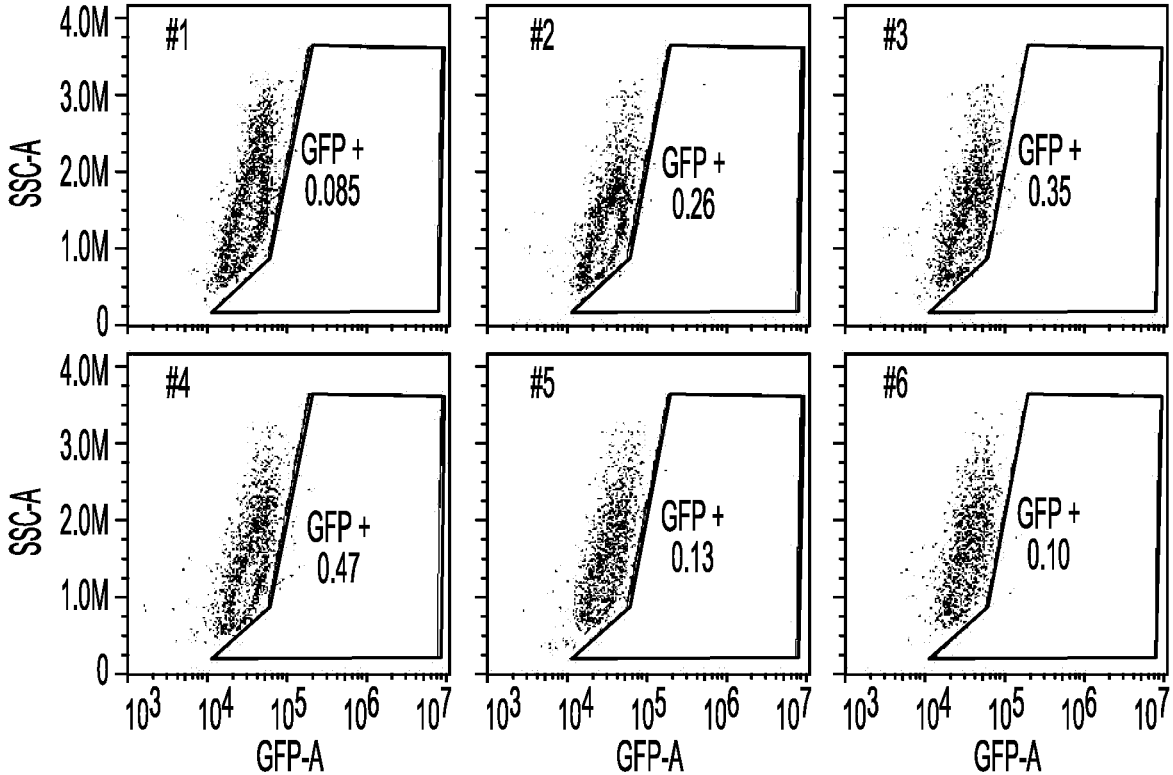

FIG. 52 depicts exemplary flow cytometry data (bottom) showing GFP+K562 cells electroporated with 1000 ng/μL LINE1-GFP mRNA and an siRNA cocktail with 25 ng/μL, 50 ng/μL or 75 ng/μL of each siRNA targeting RNASEL (siRNASEL), ADAR1 (siADAR1), ADAR2 (siADAR2) and BRCA1 (siBRCA1) after culturing for 5 days post-electroporation and a graph of the number of GFP integrations per cell according to qPCR (top).

Figure 53:
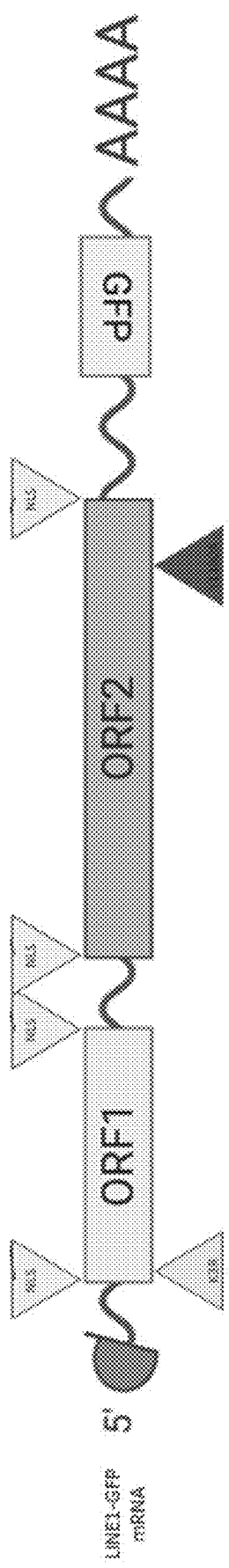

FIG. 53 depicts a schematic showing exemplary locations of extraneous nuclear localization sequences (NLS) and exemplary ORF1p and ORF2p mutations of an exemplary LINE1-GFP mRNA construct.

DETAILED DESCRIPTION

The present invention arises in part from the exciting discovery that a polynucleotide could be designed and developed to accomplish transfer and integration of a genetic cargo (e.g., large genetic cargo) into the genome of a cell. In some embodiments, the polynucleotide comprises (i) a genetic material for stable expression, and (ii) a self-integrating genomic integration machinery that allows stable integration of the genetic material into a cell by non-viral means, that is both safe and efficacious. Moreover, the genetic material may be integrated at a locus other than a ribosomal locus; the genetic material may be integrated site-specifically; and/or the integrated genetic material appear to express without triggering a cell's natural silencing machinery.

Clustered Regularly-Interspaced Short Palindromic Repeats (CRISPR) revolutionized the molecular biology field and has developed into a potent gene editing too. It utilizes homology-directed repair (HDR) and can be directed to a genomic site. CRISPR/Cas9 is a naturally occurring RNA-guided endonuclease. While the CRISPR/Cas9 system has demonstrated great promise for site-specific gene editing and other applications, there are several factors that influence its efficacy which must be addressed, especially if it is to be used for in vivo human gene therapy. These factors include target DNA site selection, sgRNA design, off-target cutting, incidence/efficiency of HDR vs. NHEJ, Cas9 activity, and the method of delivery. Delivery remains the major obstacle for use of CRISPR for in vivo applications. Zinc finger nucleases ZFNs are a fusion protein of Cys2-His2 zinc finger proteins (ZFPs) and a non-specific DNA restriction enzyme derived from FokI endonucleases. Challenges with ZFPs include design and engineering of the ZFP for high-affinity binding of the desired sequence, which is non-trivial. Also, not all sequences are available for ZFP binding, so site selection is limited. Another significant challenge is off-target cutting. Transcription activator-like effector nucleases (TALENs) are a fusion protein comprised of a TALE and a FokI nuclease. While off-target cutting remains a concern, TALENs have been shown in one side-by-side comparison study to be more specific and less cytotoxic than ZFNs. However, TALENs are substantially larger, and the cDNA encoding TALEN only is 3 kb. This makes delivery of a pair of TALENs more challenging than a pair of ZFNs due to delivery vehicle cargo size limitations. Further, packaging and delivery of TALENs in some viral vectors may be problematic due to the high level of repetition in the TALENs sequence. A mutant Cas9 system, a fusion protein of inactive dCas9 and a FokI nuclease dimer increase specificity and reduce off-target cutting, the number of potential target sites is lower due to PAM and other sgRNA design constraints.

The present invention addresses the problems described above by providing new, effective and efficient compositions comprising transposon-based vectors for providing therapy, including gene therapy, to animals and humans. The present invention provides methods of using these compositions for providing therapy to animals and humans. These transposon-based vectors can be used in the preparation of a medicament useful for providing a desired effect to a recipient following administration. Gene therapy includes, but is not limited to, introduction of a gene, such as an exogenous gene, into an animal using a transposon-based vector. These genes may serve a variety of functions in the recipient such as coding for the production of nucleic acids, for example RNA, or coding for the production of proteins and peptides.

The present invention can facilitate efficient incorporation of the polynucleotide sequences, including the genes of interest, promoters, insertion sequences, poly A and any regulatory sequences. The invention is based on the finding that human LINE-1 elements are capable of retrotransposition in human cells as well as cells of other animal species and can be manipulated in a versatile manner to achieve efficient delivery and integration of a genetic cargo into the genome of a cell. Such LINE-1 elements have a variety of uses in human and animal genetics including, but not limited to, uses in diagnosis and treatment of genetic disorders and in cancer. The LINE-1 elements of the invention are also useful for the treatment of various phenotypic effects of various diseases. For example, LINE-1 elements may be used for transfer of DNA encoding anti-tumorigenic gene products into cancer cells. Other uses of the LINE-1 elements of the invention will become apparent to the skilled artisan upon a reading of the present specification.

In general, a human LINE-1 element comprises a 5' UTR with an internal promoter, two non-overlapping reading frames (ORF1 and ORF2), a 200 bp 3' UTR and a 3' poly A tail. The LINE-1 retrotransposon can also comprise an endonuclease domain at the LINE-1 ORF2 N-terminus. The finding that LINE-1 encodes an endonuclease demonstrates that the element is capable of autonomous retrotransposition. LINE-1 is a modular protein that contains non-overlapping functional domains which mediate its reverse transcription and integration. In some embodiments, the sequence specificity of the LINE-1 endonuclease itself can be altered or the LINE-1 endonuclease can be replaced with another site-specific endonuclease.

The LINE-1 retrotransposon may be manipulated using recombinant DNA technology to comprise and/or be contiguous with, other DNA elements which render the retrotransposon suitable for insertion of substantial lengths (up to 1 kb, or greater than 1 kb) of heterologous or homologous DNA into the genome of a cell. The LINE-1 retrotransposon may also be manipulated using the same type of technology such that insertion of the DNA into the genome of a cell is site-directed (site into which such DNA is inserted is known). Alternatively, the LINE-1 retrotransposon may be manipulated such that the insertion site of the DNA is random. The retrotransposon may also be manipulated to effect insertion of a desired DNA sequence into regions of DNA which are normally transcriptionally silent, wherein the DNA sequence is expressed in a manner such that it does not disrupt the normal expression of genes in the cell. In some embodiments, the integration or retrotransposition is in the trans orientation. In some embodiments, the integration or retrotransposition occurs in the cis orientation.

Since LINE-1 is native to human cells, when the constructs are placed into human cells, they should not be rejected by the immune system as foreign. In addition, the mechanism of LINE-1 retro-integration ensures that only one copy of the gene is integrated at any specific chromosomal location. Accordingly, there is a copy number control built into the system. In contrast, gene transfer procedures using ordinary plasmids offer little or no control regarding copy number and often result in complex arrays of DNA molecules tandemly integrated into the same genomic location.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, may be used interchangeably. These terms may convey that any combination is specifically contemplated. Solely for illustrative purposes, the following phrases "A, B, and/or C" or "A, B, C, or any combination thereof" may mean "A individually; B individually; C individually; A and B; B and C; A and C; and A, B, and C." The term "or" may be used conjunctively or disjunctively, unless the context specifically refers to a disjunctive use.

The term "about" or "approximately" may mean within an acceptable error range for the particular value as determined by one of ordinary skill in the art, which will depend in part on how the value is measured or determined, i.e., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Alternatively, particularly with respect to biological systems or processes, the term may mean within an order of magnitude, within 5-fold, and more preferably within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification may be implemented with respect to any method or composition of the present disclosure, and vice versa. Furthermore, compositions of the present disclosure may be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Applications of the present disclosure encompasses, but are not limited to methods and compositions related to expression of an exogenous nucleic acid in a cell. In some embodiments, the exogenous nucleic acid is configured for stable integration in the genome of a cell, such as a myeloid cell. In some embodiments, the stable integration of the exogenous nucleic acid may be at specific targets within the genome. In some embodiments, the exogenous nucleic acid comprises one or more coding sequences. In some embodiments, the exogenous nucleic acid may comprise one or more coding comprising a nucleic acid sequence encoding an immune receptor. In some embodiments, the present disclosure provides methods and compositions for a stable incorporation of a nucleic acid encoding a transmembrane receptor implicated in an immune response function (e.g. a phagocytic receptor or synthetic chimeric antigen receptor) into human macrophage or dendritic cell or a suitable myeloid cell or a myeloid precursor cell. An exogenous nucleic acid can refer to a nucleic acid that was not originally in a cell and is added from outside the cell, irrespective of whether it comprises a sequence that may already be present in the cell endogenously. An exogenous nucleic acid may be a DNA or an RNA molecule. An exogenous nucleic acid may comprise a sequence encoding a transgene. An exogenous nucleic acid may encode a recombinant protein, such as a recombinant receptor, or a chimeric antigen receptor (CAR). An exogenous nucleic acid may be referred to as a "genetic cargo" in the context of the exogenous nucleic acid being delivered inside a cell. The genetic cargo may be a DNA or an RNA. Genetic material can generally be delivered inside a cell ex vivo by a few different known techniques using either chemical ($CaCl_2$)-medicated transfection), or physical (electroporation), or biological (e.g. viral infection or transduction) means.

In one aspect, provided herein are methods and compositions for delivery inside a cell, for example a myeloid cell and stable incorporation of one or more nucleic acids, comprising nucleic acid sequences encoding one or more proteins, wherein the stable incorporation may be via non-viral mechanisms. In some embodiments, the delivery of a nucleic acid composition into a myeloid cell is via a non-viral mechanism. In some embodiments, the delivery of the nucleic acids may further bypass plasmid mediated delivery. A "plasmid," as used herein, refers to a non-viral expression vector, e.g., a nucleic acid molecule that encodes for genes and/or regulatory elements necessary for the expression of genes. A "viral vector," as used herein, refers to a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

In some embodiments, provided herein is a method of delivering a composition inside a cell, such as in a myeloid cell, the composition comprising one or more nucleic acid sequences encoding one or more proteins, wherein the one or more nucleic acid sequences is an RNA. In some embodiments, the RNA is mRNA. In some embodiments, one or more mRNA comprising one or more nucleic acid sequences are delivered. In some embodiments, the one or more mRNA may comprise at least one modified nucleotide. The term "nucleotide," as used herein, refers to a base-sugar-phosphate combination. A nucleotide may comprise a synthetic nucleotide. A nucleotide may comprise a synthetic nucleotide analog. Nucleotides may be monomeric units of a nucleic acid sequence (e.g. deoxyribonucleic acid (DNA) and ribonucleic acid (RNA)). The term nucleotide may include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, or derivatives thereof. Such derivatives may include, for example, [aS]dATP, 7-deaza-dGTP and 7-deaza-dATP, and nucleotide derivatives that confer nuclease resistance on the nucleic acid molecule containing them. The term nucleotide as used herein may refer to dideoxyribonucleoside triphosphates (ddNTPs) and their derivatives. Illustrative examples of dideoxyribonucleoside triphosphates may include, but are not limited to, ddATP, ddCTP, ddGTP, ddITP, and ddTTP. A nucleotide may be unlabeled or detectably labeled by well-known techniques. Labeling may also be carried out with quantum dots. Detectable labels may include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,NcN'-tetramethyl-6-carboxy-rhodamine (TAMRA), 6-carboxy-X-rhodamine (ROX), 4-(4'dimethylaminophenylazo)benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides may include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAN1RA] ddGTP, [ROX]ddTTP, [dR6G]ddATP, [dR110]ddCTP, [dTAMRA]ddGTP, and [dROX]ddTTP available from Perkin Elmer, Foster City, Calif FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, TR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-1 4-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides may also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-cICTP, biotin-14-dCTP), and biotin-dUTP (e.g. biotin-11-dUTP, biotin-1.6-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide may be exogenous or endogenous to a cell. A polynucleotide may exist in a cell-free environment. A polynucleotide may be a gene or fragment thereof. A polynucleotide may be DNA. A polynucleotide may be RNA. A polynucleotide may have any three-dimensional structure, and may perform any function, known or unknown. A polynucleotide may comprise one or more analogs (e.g. altered backbone, sugar, or nucleobase). If present, modifications to the nucleotide structure may be imparted before or after assembly of the polymer. Some non-limiting examples of modified nucleotides or analogs include: pseudouridine, 5-bromouracil, 5-methylcytosine, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, eDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides may be interrupted by non-nucleotide components.

In some embodiments, the nucleic acid composition may comprise one or more mRNA, comprising at least one mRNA encoding a transmembrane receptor implicated in an immune response function (e.g. a phagocytic receptor or synthetic chimeric antigen receptor) into human macrophage or dendritic cell or a suitable myeloid cell or a myeloid precursor cell. In some embodiments, the nucleic acid composition comprises one or more mRNA, and one or more lipids for delivery of the nucleic acid into a cell of hematopoietic origin, such as a myeloid cell or a myeloid cell precursor cell. In some embodiments, the one or more lipids may form a liposomal complex.

As used herein, the composition described herein may be used for delivery inside a cell. A cell may originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell may not be originating from a natural organism (e.g. a cell may be a synthetically made, sometimes termed an artificial cell). In some embodiments, the cell referred to herein is a mammalian cell. In some embodiments, the cell is a human cell. The methods and compositions described herein relates to incorporating a genetic material in a cell, more specifically a human cell, wherein the human cell can be any human cell. As used herein, a human cell may be of any origin, for example, a somatic cell, a neuron, a fibroblast, a muscle cell, an epithelial cell, a cardiac cell, or a hematopoietic cell. The methods and compositions described herein can also be applicable to and useful for incorporating exogenous nucleic acid in hard-to-transfect human cell. The methods are simple and universally applicable, once a suitable exogenous nucleic acid construct has been designed and developed. The methods and compositions described herein are applicable to incorporate an exogenous nucleic acid in a cell ex vivo. In some embodiments, the compositions may be applicable for systemic administration in an organism, where the nucleic acid material in the composition may be taken up by a cell in vivo, whereupon it is incorporated in cell in vivo.

In some embodiments, the methods and compositions described herein may be directed to incorporating an exogenous nucleic acid in a human hematopoietic cell, for example, a human cell of hematopoietic origin, such as a human myeloid cell or a myeloid cell precursor. However, the methods and compositions described herein can be used or made suitable for use in any biological cell with minimum modifications. Therefore, a cell as may refer to any cell that is a basic structural, functional and/or biological unit of a living organism.

In one aspect, provided herein are methods and compositions for utilizing transposable elements for stable incorporation of one or more nucleic acids into the genome of a cell, where the cell is a member of a hematopoietic cells, for example a myeloid cell. In some embodiments, the one or more nucleic acids comprise at least one nucleic acid sequence encoding a transmembrane receptor protein having a role in immune response. In some embodiments, the methods and compositions are directed to using a retrotransposable element for incorporating one or more nucleic acid sequences into a myeloid cell. The nucleic acid composition may comprise one or more nucleic sequences, such as a gene, where the gene is a transgene. The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and may include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes nontranscribed regions including upstream and downstream regulatory regions, enhancers and promoters. A gene may refer to an "endogenous gene" or a native gene in its natural location in the genome of an organism. A gene may refer to an "exogenous gene" or a non-native gene. A non-native gene may refer to a gene not normally found in the host organism, but which is introduced into the host organism by gene transfer. A non-native gene may also refer to a gene not in its natural location in the genome of an organism. A non-native gene may also refer to a naturally occurring nucleic acid or polypeptide sequence that comprises mutations, insertions and/or deletions (e.g., non-native sequence).

The term "transgene" refers to any nucleic acid molecule that is introduced into a cell, that may be intermittently termed herein as a recipient cell. The resultant cell after receiving a transgene may be referred to a transgenic cell. A transgene may include a gene that is partly or entirely heterologous (i.e., foreign) to the transgenic organism or cell, or may represent a gene homologous to an endogenous gene of the organism or cell. In some cases, transgenes include any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription). Transcripts and encoded polypeptides may be collectively referred to as "gene product." If the polynucleotide is derived from genomic DNA, expression may include splicing of the mRNA in a eukaryotic cell. "Up-regulated," with reference to expression, refers to an increased expression level of a polynucleotide (e.g., RNA such as mRNA) and/or polypeptide sequence relative to its expression level in a wild-type state while "down-regulated" refers to a decreased expression level of a polynucleotide (e.g., RNA such as mRNA) and/or polypeptide sequence relative to its expression in a wild-type state. Expression of a transfected gene may occur transiently or stably in a cell. During "transient expression" the transfected gene is not transferred to the daughter cell during cell division. Since its expression is restricted to the transfected cell, expression of the gene is lost over time. In contrast, stable expression of a transfected gene may occur when the gene is co-transfected with another gene that confers a selection advantage to the transfected cell. Such a selection advantage may be a resistance towards a certain toxin that is presented to the cell. Where a transfected gene is required to be expressed, the application envisages the use of codon-optimized sequences. An example of a codon optimized sequence may be a sequence optimized for expression in a eukaryote, e.g., humans (i.e. being optimized for expression in humans), or for another eukaryote, animal or mammal. Codon optimization for a host species other than human, or for codon optimization for specific organs is known. In some embodiments, the coding sequence encoding a protein may be codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. Codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell may generally reflect the codons used most frequently in peptide synthesis. Accordingly, genes may be tailored for optimal gene expression in a given organism based on codon optimization. Codon usage tables are readily available, for example, at the "Codon Usage Database" available at kazusa (dot)org(slash)codon and these tables may be adapted in a number of ways. Computer algorithms for codon optimizing a particular sequence for expression in a particular host cell are also available, such as Gene Forge (Aptagen; Jacobus, PA), are also available.

A "multicistronic transcript" as used herein refers to an mRNA molecule that contains more than one protein coding region, or cistron. A mRNA comprising two coding regions is denoted a "bicistronic transcript." The "5'-proximal"

coding region or cistron is the coding region whose translation initiation codon (usually AUG) is closest to the 5' end of a multicistronic mRNA molecule. A "5'-distal" coding region or cistron is one whose translation initiation codon (usually AUG) is not the closest initiation codon to the 5' end of the mRNA.

The terms "transfection" or "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The term "promoter," as used herein, refers to a polynucleotide sequence capable of driving transcription of a coding sequence in a cell. Thus, promoters used in the polynucleotide constructs of the disclosure include cis-acting transcriptional control elements and regulatory sequences that are involved in regulating or modulating the timing and/or rate of transcription of a gene. For example, a promoter may be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions, developmental conditions, or drug or chemical conditions. Exemplary inducible promoter may be a doxycycline or a tetracycline inducible promoter. Tetracycline regulated promoters may be both tetracycline inducible or tetracycline repressible, called the tet-on and tet-off systems. The tet regulated systems rely on two components, i.e., a tetracycline-controlled regulator (also referred to as transactivator) (tTA or rtTA) and a tTA/rtTA-dependent promoter that controls expression of a downstream cDNA, in a tetracycline-dependent manner. tTA is a fusion protein containing the repressor of the Tn10 tetracycline-resistance operon of *Escherichia coli* and a carboxyl-terminal portion of protein 16 of herpes simplex virus (VP16). The tTA-dependent promoter consists of a minimal RNA polymerase II promoter fused to tet operator (tetO) sequences (an array of seven cognate operator sequences). This fusion converts the tet repressor into a strong transcriptional activator in eukaryotic cells. In the absence of tetracycline or its derivatives (such as doxycycline), tTA binds to the tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. In contrast, in the tet-ON system, a mutant form of tTA, termed rtTA, has been isolated using random mutagenesis. In contrast to tTA, rtTA is not functional in the absence of doxycycline but requires the presence of the ligand for transactivation. The term "exon" refers to a nucleic acid sequence found in genomic DNA that is bioinformatically predicted and/or experimentally confirmed to contribute contiguous sequence to a mature mRNA transcript. The term "intron" refers to a sequence present in genomic DNA that is bioinformatically predicted and/or experimentally confirmed to not encode part of or all of an expressed protein, and which, in endogenous conditions, is transcribed into RNA (e.g. pre-mRNA) molecules, but which is spliced out of the endogenous RNA (e.g. the pre-mRNA) before the RNA is translated into a protein.

The term "splice acceptor site" refers to a sequence present in genomic DNA that is bioinformatically predicted and/or experimentally confirmed to be the acceptor site during splicing of pre-mRNA, which may include identified and unidentified natural and artificially derived or derivable splice acceptor sites.

An "internal ribosome entry site" or "IRES" refers to a nucleotide sequence that allows for 5'-end/cap-independent initiation of translation and thereby raises the possibility to express 2 proteins from a single messenger RNA (mRNA) molecule. IRESs are commonly located in the 5' UTR of positive-stranded RNA viruses with uncapped genomes. Another means to express 2 proteins from a single mRNA molecule is by insertion of a 2A peptide(-like) sequence in between their coding sequence. 2A peptide(-like) sequences mediate self-processing of primary translation products by a process variously referred to as "ribosome skipping", "stop-go" translation and "stop carry-on" translation. 2A peptide (-like) sequences are present in various groups of positive- and double-stranded RNA viruses including Picornaviridae, Flaviviridae, Tetraviridae, Dicistroviridae, Reoviridae and Totiviridae.

The term "2A peptide" refers to a class of 18-22 amino-acid (AA)-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (*Thosea asigna* virus 2A) were also identified. The mechanism of 2A-mediated "self-cleavage" is believed to be ribosome skipping the formation of a glycyl-prolyl peptide bond at the C-terminus of the 2A sequence. 2A peptide(-like) sequences mediate self-processing of primary translation products by a process variously referred to as "ribosome skipping", "stop-go" translation and "stop carry-on" translation. 2A peptide(-like) sequences are present in various groups of positive- and double-stranded RNA viruses including Picornaviridae, Flaviviridae, Tetraviridae, Dicistroviridae, Reoviridae and Totiviridae.

As used herein, the term "operably linked" refers to a functional relationship between two or more segments, such as nucleic acid segments or polypeptide segments. Typically, it refers to the functional relationship of a transcriptional regulatory sequence to a transcribed sequence.

The term "termination sequence" refers to a nucleic acid sequence which is recognized by the polymerase of a host cell and results in the termination of transcription. The termination sequence is a sequence of DNA that, at the 3' end of a natural or synthetic gene, provides for termination of mRNA transcription or both mRNA transcription and ribosomal translation of an upstream open reading frame. Prokaryotic termination sequences commonly comprise a GC-rich region that has a two-fold symmetry followed by an AT-rich sequence. A commonly used termination sequence is the T7 termination sequence. A variety of termination sequences are known in the art and may be employed in the nucleic acid constructs of the present invention, including the TINT3, TL13, TL2, TR1, TR2, and T6S termination signals derived from the bacteriophage lambda, and termination signals derived from bacterial genes, such as the trp gene of *E. coli*.

The terms "polyadenylation sequence" (also referred to as a "poly A site" or "poly A sequence") refers to a DNA sequence which directs both the termination and polyadenylation of the nascent RNA transcript. Efficient polyadenylation of the recombinant transcript is desirable, as transcripts lacking a poly A tail are typically unstable and rapidly degraded. The poly A signal utilized in an expression vector may be "heterologous" or "endogenous". An endogenous poly A signal is one that is found naturally at the 3' end of the coding region of a given gene in the genome. A heterologous poly A signal is one which is isolated from one gene and placed 3' of another gene, e.g., coding sequence for a protein. A commonly used heterologous poly A signal is the SV40 poly A signal. The SV40 poly A signal is contained on a 237 bp BamHI/BclI restriction fragment and directs both termination and polyadenylation; numerous vectors contain the SV40 poly A signal. Another commonly used heterologous poly A signal is derived from the bovine growth hormone (BGH) gene; the BGH poly A signal is also available on a number of commercially available vectors. The poly A signal from the Herpes simplex virus thymidine kinase (HSV tk) gene is also used as a poly A signal on a number of commercial expression vectors. The polyadenylation signal facilitates the transportation of the RNA from within the cell nucleus into the cytosol as well as increases cellular half-life of such an RNA. The polyadenylation signal is present at the 3'-end of an mRNA.

The terms "complement," "complements," "complementary," and "complementarity," as used herein, refer to a sequence that is complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner available at ebi(dot)ac(dot)uk, the BLAST algorithm (BLAST alignment tool), or the Smith-Waterman algorithm (see e.g. the EMBOSS Water aligner available at ebi(dot)ac(dot)uk, optionally with default settings). Optimal alignment can be assessed using any suitable parameters of a chosen algorithm, including default parameters.

Complementarity may be perfect or substantial/sufficient. Perfect complementarity between two nucleic acids may mean that the two nucleic acids may form a duplex in which every base in the duplex is bonded to a complementary base by Watson-Crick pairing. Substantial or sufficient complementary may mean that, a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions may be predicted by using the sequences and standard mathematical calculations to predict the melting temperature ($T_m$) of hybridized strands, or by empirical determination of $T_m$ by using routine methods. [00254]"Transposons" as used herein are segments within the chromosome that can translocate within the genome, also known as "jumping gene". There are two different classes of transposons: class 1, or retrotransposons, that mobilize via an RNA intermediate and a "copy-and-paste" mechanism, and class II, or DNA transposons, that mobilize via excision integration, or a "cut-and-paste" mechanism (Ivics Nat Methods 2009). Bacterial, lower eukaryotic (e.g. yeast) and invertebrate transposons appear to be largely species specific, and cannot be used for efficient transposition of DNA in vertebrate cells. "Sleeping Beauty" (Ivics Cell 1997), was the first active transposon that was artificially reconstructed by sequence shuffling of inactive TEs from fish. This made it possible to successfully achieve DNA integration by transposition into vertebrate cells, including human cells. Sleeping Beauty is a class II DNA transposon belonging to the Tcl/mariner family of transposons (Ni Genomics Proteomics 2008). In the meantime, additional functional transposons have been identified or reconstructed from different species, including *Drosophila*, frog and even human genomes, that all have been shown to allow DNA transposition into vertebrate and also human host cell genomes. Each of these transposons have advantages and disadvantages that are related to transposition efficiency, stability of expression, genetic payload capacity etc. Exemplary class II transposases that have been created include Sleeping Beauty, PiggyBac, Frog Prince, Himarl, Passport, Minos, hAT, Tol1, Tol2, AciDs, PIF, Harbinger, Harbinger3-DR, and Hsmarl.

"Heterologous" as used herein, includes molecules such as DNA and RNA which may not naturally be found in the cell into which it is inserted. For example, when mouse or bacterial DNA is inserted into the genome of a human cell, such DNA is referred to herein as heterologous DNA. In contrast, the term "homologous" as used herein, denotes molecules such as DNA and RNA that are found naturally in the cell into which it is inserted. For example, the insertion of mouse DNA into the genome of a mouse cell constitutes insertion of homologous DNA into that cell. In the latter case, it is not necessary that the homologous DNA be inserted into a site in the cell genome in which it is naturally found; rather, homologous DNA may be inserted at sites other than where it is naturally found, thereby creating a genetic alteration (a mutation) in the inserted site.

A "transposase" is an enzyme that is capable of forming a functional complex with a transposon end-containing composition (e.g., transposons, transposon ends), and catalyze insertion or transposition of the transposon end-containing composition into double stranded DNA which is incubated with an in vitro transposon reaction. The term "transposon end" means a double-stranded DNA that contains the nucleotide sequences (the "transposon end sequences") necessary to form the complex with the transposase or integrase enzyme that is functional in an in vitro transposition reaction.

A transposon end forms a complex or a synaptic complex or a transposon complex or a transposon composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a transferred transposon end sequence or transferred strand and a non-transferred transposon end sequence, or non-transferred strand For example, one transposon end that forms a complex with a hyperactive Tn5 transposase that is active in an in vitro transposition reaction comprises a transferred strand that exhibits a transferred transposon end sequence as follows: 5' AGATGTGTATAAGAGACAG 3' (SEQ ID NO: 51), and a non-transferred strand that exhibits a "non-transferred transposon end sequence" as follows: 5' CTGTCTCTTATACACATCT 3 (SEQ ID NO: 52)'. The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure. As used herein an "cleavage domain" refers to a nucleic acid sequence that is susceptible to cleavage by an agent, e.g., an enzyme.

A "restriction site domain" means a tag domain that exhibits a sequence for the purpose of facilitating cleavage using a restriction endonuclease. For example, in some embodiments, the restriction site domain is used to generate di-tagged linear ssDNA fragments. In some embodiments, the restriction site domain is used to generate a compatible double-stranded 5'-end in the tag domain so that this end can be ligated to another DNA molecule using a template-dependent DNA ligase. In some embodiments, the restriction site domain in the tag exhibits the sequence of a restriction site that is present only rarely, if at all, in the target DNA (e.g., a restriction site for a rare-cutting restriction endonuclease such as NotI or AscI).

As used herein, the term "recombinant nucleic acid molecule" refers to a recombinant DNA molecule or a recombinant RNA molecule. A recombinant nucleic acid molecule is any nucleic acid molecule containing joined nucleic acid molecules from different original sources and not naturally attached together. Recombinant RNA molecules include RNA molecules transcribed from recombinant DNA molecules. A recombinant nucleic acid may be synthesized in the laboratory. A recombinant nucleic acid can be prepared by using recombinant DNA technology by using enzymatic modification of DNA, such as enzymatic restriction digestion, ligation, and DNA cloning. A recombinant DNA may be transcribed in vitro, to generate a messenger RNA (mRNA), the recombinant mRNA may be isolated, purified and used to transfect a cell. A recombinant nucleic acid may encode a protein or a polypeptide. A recombinant nucleic acid, under suitable conditions, can be incorporated into a living cell, and can be expressed inside the living cell. As used herein, "expression" of a nucleic acid usually refers to transcription and/or translation of the nucleic acid. The product of a nucleic acid expression is usually a protein but can also be an mRNA. Detection of an mRNA encoded by a recombinant nucleic acid in a cell that has incorporated the recombinant nucleic acid, is considered positive proof that the nucleic acid is "expressed" in the cell. The process of inserting or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the forced introduction of small molecules such as DNA, RNA, or antibodies into eukaryotic cells. Just to make life confusing, 'transfection' also refers to the introduction of bacteriophage into bacterial cells. 'Transduction' is mostly used to describe the introduction of recombinant viral vector particles into target cells, while 'infection' refers to natural infections of humans or animals with wild-type viruses.

A "stem-loop" sequence refers to a nucleic acid sequence (e.g., RNA sequence) with sufficient self-complementarity to hybridize and form a stem and the regions of non-complementarity that bulges into a loop. The stem may comprise mismatches or bulges.

The term "vector" refers to a nucleic acid molecule capable of transporting or mediating expression of a heterologous nucleic acid. A "vector sequence" as used herein, refers to a sequence of nucleic acid comprising at least one origin of replication and at least one selectable marker gene. Vectors capable of directing the expression of genes and/or nucleic acid sequence to which they are operatively linked are referred to herein as "expression vectors".

A plasmid is a species of the genus encompassed by the term "vector." In general, expression vectors of utility are often in the form of "plasmids" which refer to circular double stranded DNA molecules which, in their vector form are not bound to the chromosome, and typically comprise entities for stable or transient expression of the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the cell. A vector can be a DNA or RNA vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked. A safe harbor locus is a region within the genome where additional exogenous or heterologous nucleic acid sequence can be inserted, and the host genome is able to accommodate the inserted genetic material. Exemplary safe harbor sites include but are not limited to: AAVS1 site, GGTA1 site, CMAH site, B4GALNT2 site, B2M site, ROSA26 site, COLA1 site, and TIGRE site. For example, the heterologous nucleic acid described in this disclosure may be integrated at one or more sites in the genome of the cell, wherein the one or more locations is selected from the group consisting of: AAVS1 site, GGTA1 site, CMAH site, B4GALNT2 site, B2M site, ROSA26 site, COLA1 site, and TIGRE site. In some embodiments, the nucleic acid cargo comprising the transgene may be delivered to a R2D locus.

In some embodiments, the nucleic acid cargo comprising the transgene may be delivered to the genome in an intergenic or intragenic region. In some embodiments the nucleic acid cargo comprising the transgene is integrated into the genome 5' or 3' within 0.1 kb, 0.25 kb, 0.5 kb, 0.75, kb, 1 kb, 2 kb, 3 kb, 4 kb, 5 kb, 7.5 kb, 10 kb, 15 kb, 20 kb, 25 kb, 50, 75 kb, or 100 kb of an endogenous active gene. In some embodiments the nucleic acid cargo comprising the transgene is integrated into the genome 5' or 3' within 0.1 kb, 0.25 kb, 0.5 kb, 0.75, kb, 1 kb, 2 kb, 3 kb, 4 kb, 5 kb, 7.5 kb, 10 kb, 15 kb, 20 kb, 25 kb, 50, 75 kb, or 100 kb of an endogenous promoter or enhancer. In some embodiments the nucleic acid cargo comprising the transgene is 50-50,000 base pairs, e.g., between 50-40,000 bp, between 500-30,000 bp between 500-20,000 bp, between 100-15,000 bp, between 500-10,000 bp, between 50-10,000 bp, between 50-5,000 bp. In some embodiments the nucleic acid cargo comprising the transgene is less than 1,000, 1,300, 1500, 2,000, 3,000, 4,000, 5,000, or 7,500 nucleotides in length.

L1 and Non-L1 Retrotransposon Systems

Retrotransposons can contain transposable elements that are active participants in reorganizing their resident genomes. Broadly, retrotransposons can refer to DNA sequences that are transcribed into RNA and translated into protein and have the ability to reverse-transcribe themselves back into DNA. Approximately 45% of the human genome is comprised of sequences that result from transposition events. Retrotransposition occasionally generates target site deletions or adds non-retrotransposon DNA to the genome by processes termed 5'- and 3'-transduction. Recombination between non-homologous retrotransposons causes deletions, duplications or rearrangements of gene sequence. Ongoing retrotransposition can generate novel splice sites, polyadenylation signals and promoters, and so builds new transcription modules.

Generally, retrotransposons may be grouped into two classes, the retrovirus-like LTR retrotransposons, and the non-LTR elements such as human L1 elements, *Neurospora* TAD elements (Kinsey, 1990, Genetics 126:317-326), I factors from *Drosophila* (Bucheton et al., 1984, Cell 38:153-163), and R2Bm from *Bombyx mori* (Luan et al., 1993, Cell 72: 595-605). These two types of retrotransposons are structurally different and also retrotranspose using radically different mechanisms. Exemplary, non-limiting examples of LINE-encoded polypeptides are found in GenBank Accession Nos. AAC51261, AAC51262, AAC51263, AAC51264, AAC51265, AAC51266, AAC51267, AAC51268, AAC51269, AAC51270, AAC51271, AAC51272, AAC51273, AAC51274, AAC51275, AAC51276, AAC51277, AAC51278 and AAC51279.

The decision to focus on LINE-1 to develop into a system as described in the disclosure for a number of reasons at least some of which are exemplified below: (a) LINE-1 (or L1-) elements are autonomous as they encode all of the machinery alone to complete this reverse transcription and integration process; (b) L1 elements are abundant in the human genome, such that these elements may be considered as a naturalized element of the genome; (c) L1 retrotransposon retrotransposes its own mRNA with high degree of specificity, compared to other mRNAs floating around in the cells.

The L1 expresses a 6-kb bicistronic RNA that encodes the 40 kDa Open Reading Frame-1 RNA-binding protein (ORF1p) of essential but uncertain function, and a 150 kDa ORF2 protein with endonuclease and reverse transcriptase (RT) activities. L1 retrotransposition is a complex process involving transcription of the L1, transport of its RNA to the cytoplasm, translation of the bicistronic RNA, formation of a ribonucleoprotein (RNP) particle, its re-import to the nucleus and target-primed reverse transcription at the integration site. A few transcription factors that interact with L Is have been identified. Transcribed L1 RNA forms an RNP in cis with the proteins that are translated from the transcript. L1 integrates into genomic DNA by target-site primer reverse transcription (TPRT) by ORF2p cleavage at the 5'-TTTT-3' where a poly A sequence of L1 RNA anneals and primes reverse transcriptase (RT) activity to make L1 cDNA.

Other mobile elements of the genome can "hijack" the L1 ORF for retrotransposition. For example, Alu elements are such mobile DNA elements that belong to the class of short interspersed elements (SINEs) that are non-autonomous retrotransposons and acquire trans-factors to integrate. Alu elements and SINE-1 elements can associate with the L1 ribonucleoproteins in trans to be also retrotransposed by ORF1p and ORF2p. Somewhat similar to the L1 RNA, the Alu element ends with a long A-run, often referred to as the A-tail, and it also has a smaller A-rich region (indicated by AA) separating the two halves of a diverged dimer structure. Alu elements are likely to have the internal components of an RNA polymerase III promoter (such as, commonly designated as an A box and a B box promoters), but they do not encode a terminator for RNA polymerase III. They may utilize a stretch of T nucleotides at various distances downstream of the Alu element to terminate a transcription. A typical Alu transcript encompasses the entire Alu, including the A-tail, and has a 3' region that is unique for each locus. The Alu RNA folds into separate structures for each monomer unit. The RNA has been shown to bind the 7SL RNA SRP9 and 14 heterodimer, as well as poly A-binding protein (PABP). The poly A tail of Alu primes with T rich (TTTT) region of the genome and attracts ORF2p to bind to the primed region and cleaves at the T rich region via its endonuclease activity. The T-rich region primes reverse transcription by ORF2p on the 3' A-tail region of the Alu element. This creates a cDNA copy of the body of the Alu element. A nick occurs by an unknown mechanism on the second strand and second-strand synthesis is primed. The new Alu element is then flanked by short direct repeats that are duplicates of the DNA sequence between the first and second nicks. Alu elements are extremely prevalent within RNA molecules, owing to their preference for gene-rich regions. A full-length Alu (~300 bp) is derived from the signal recognition particle RNA 7SL and consists of two similar monomers with an A-rich linker in-between, A- and B-boxes present in the 5' monomer, and a poly-A tail lacking the preceding polyadenylation signal resulting in an elongated tail (up to 100 bp in length). Alus can be transcribed by RNA polymerase III using the internal promoters within the A- and B-boxes; however, Alus contain no ORFs and therefore do not encode for protein products.

Other non-L1 transposons include SVAs and HERV-Ks. A full-length SVA (SINE-VNTR-Alu) element (~2-3 kb) is a composite unit that contains a CCCTCT repeat, two Alu-like sequences, a VNTR, a SINE-R region with env (envelope) gene, the 3' LTR of HERV-K10, and a polyadenylation signal followed by a poly-A tail. It is most likely that SVAs are transcribed by RNA polymerase II, although it is unknown whether SVA elements carry an internal promoter.

A full-length HERV-K element (~9-10 kb) is comprised of ancient remnants of endogenous retroviral sequences and includes two flanking LTR regions surrounding three retroviral ORFs: (1) gag encoding the structural proteins of a retroviral capsid; (2) pol-pro encoding the enzymes: protease, RT, and integrase; and (3) env encoding proteins allowing for horizontal transfer. The LTR of HERV-K contains an internal, bidirectional promoter that appears to be under the transcriptional control of RNA polymerase II.

L1 retrotransposition and RNA binding can take place at or near poly-A tail. The 3'-UTR plays a role in the recognition of stringent-type LINE RNA of ORF1 protein (ORF1p). Stringent-type LINEs can contain a stem-loop structure located at the end of the 3'UTR. Branched molecules consisting of junctions between transposon 3'-end cDNA and the target DNA, as well as specific positioning of L1 RNA within ORF2 protein (ORF2p), were detected during initial stages of L1 retrotransposition in vitro. Secondary or tertiary RNA structure shared by L1 and Alu are likely to be responsible for recognition by and binding of ORF2, possibly along with a poly-A tail. In some embodiments, the stem-loop structure located downstream of the poly-A sequence correlates with cleavage intensity.

Mechanisms for restricting or resolving L1 integration have also evolved for the sake of maintaining genetic integrity and stability of the genome. Non-homologous end-joining repair proteins, such as XRCC1, Ku70 and DNA-PK, have been implicated in resolution of the L1 integrate at the time of insertion. In addition, the cell has evolved a number of proteins that stand against unrestricted retrotransposition, including the APOBEC3 family of cytosine deaminases, adenosine deaminase ADAR1, chromatin-remodeling factors and members of the piRNA pathway for post-transcription gene silencing that functions in the male germ line.

I. Compositions Comprising Nucleic Acid Constructs and Methods Involved for Stable Expression of Encoded Protein Provided herein is a recombinant nucleic acid encoding one or more proteins for expression in a cell, such as a myeloid cell. In one embodiment, the recombinant nucleic acid is designed for stable expression of the one or more proteins or polypeptides encoded by the recombinant nucleic acid. In some embodiments, the stable expression is achieved by incorporation of recombinant nucleic acid within the genome of the cell.

It can be easily understood by one of skill in the art that the compositions and methods described herein can be utilized to design products in which the recombinant nucleic acid may comprise one or more sequences that do not translate as a protein or a polypeptide component, but may encode an oligonucleotide that can be a regulatory nucleic acid, such as an inhibitor oligonucleotide product, such as an activator oligonucleotide.

In one aspect, provided herein is a composition comprising a synthetic nucleic acid, comprising a nucleic acid sequence encoding a gene of interest and one or more retrotransposable elements to stably incorporate a non-endogenous nucleic acid into a cell. In some embodiments, the cell is a hematopoietic cell. In some embodiments, the cell is a myeloid cell. In some embodiments, the cell is a precursor cell. In some embodiments, the cell is undifferentiated. In some embodiments, the cell has further differentiation potential. In some embodiments, the cell is not a stem cell.

A. LINE/Alu Retrotransposon Construct

In some embodiments, the present disclosure may utilize a retrotransposable system to stably incorporate into the genome and express a non-endogenous nucleic acid, where the non-endogenous nucleic acid comprises retrotransposable elements within the nucleic acid sequence. In some embodiments, the present disclosure may utilize a cell's endogenous retrotransposable system (e.g., proteins and enzymes), to stably express a non-endogenous nucleic acid in the cell. In some embodiments, the present disclosure may utilize a cell's endogenous retrotransposable system (e.g., proteins and enzymes, such as a LINE1 retrotransposition system), but may further express one or more components of the retrotransposable system to stably express a non-endogenous nucleic acid in the cell.

In some embodiments, a synthetic nucleic acid is provided herein, the synthetic nucleic acid encoding a transgene, and encoding one or more components for retrotransposition. The synthetic nucleic acid described herein is interchangeably termed as a nucleic acid construct, transgene or the exogenous nucleic acid.

In one aspect, provided herein is a method of integrating a nucleic acid sequence into a genome of a cell, the method comprising introducing a recombinant mRNA or a vector encoding an mRNA into the cell, wherein the mRNA comprises: an insert sequence, wherein the insert sequence comprises an exogenous sequence, or a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell.

In some embodiments, the 5' UTR sequence or the 3' UTR sequence comprises a binding site for human ORF2p.

In one aspect, provided herein is a method for integrating a nucleic acid sequence into the genome of an immune cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the transgene sequence is integrated into the genome of the immune cell.

In one aspect, provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence. In some embodiments, the sequence of a human retrotransposon is upstream of the 3' UTR sequence.

In some embodiments, the sequence of a human retrotransposon encodes for two proteins that are translated from a single RNA containing two ORFs. In some embodiments, the two ORFs are non-overlapping ORFs. In some embodiments, the two ORFs are ORF1 and ORF2. In some embodiments, the ORF1 encodes ORF1p and ORF2 encodes ORF2p.

In some embodiments, the sequence of a human retrotransposon comprises a sequence of a non-LTR retrotransposon. In some embodiments, the sequence of a human retrotransposon encodes comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase. In some embodiments, the endonuclease and/or a reverse transcriptase is ORF2p. In some embodiments, the reverse transcriptase is a group II intron reverse transcriptase domain. In some embodiments, the endonuclease and/or a reverse transcriptase is a minke whale endonuclease and/or a reverse transcriptase. In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA.

In some embodiments, (i) the sequence of a human retrotransposon comprises a sequence encoding ORF1p, (ii) the mRNA does not comprise a sequence encoding ORF1p, or (iii) the mRNA comprises a replacement of the sequence encoding ORF1p with a 5' UTR sequence from the complement gene. In some embodiments, the mRNA comprises a first mRNA molecule encoding ORF1p, and a second mRNA molecule encoding an endonuclease and/or a reverse transcriptase. In some embodiments, the mRNA is an mRNA molecule comprising a first sequence encoding ORF1p, and a second sequence encoding an endonuclease and/or a reverse transcriptase. In some embodiments, the first sequence encoding ORF1p and the second sequence encoding an endonuclease and/or a reverse transcriptase are separated by a linker sequence.

In some embodiments, the linker sequence comprises an internal ribosome entry sequence (IRES). In some embodiments, the IRES is an IRES from CVB3 or EV71. In some embodiments, the linker sequence encodes a self-cleaving peptide sequence. In some embodiments, the linker sequence encodes a T2A, a E2A or a P2A sequence In some embodiments, the sequence of a human retrotransposon comprises a sequence that encodes ORF1p fused to an additional protein sequence and/or a sequence that encodes ORF2p fused to an additional protein sequence. In some embodiments, the ORF1p and/or the ORF2p is fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences. In some embodiments, the 5' UTR sequence or the 3' UTR sequence comprises a sequence that promotes or enhances interaction of a poly A tail of the mRNA with the endonuclease and/or a reverse transcriptase. In some embodiments, the 5' UTR sequence or the 3' UTR sequence comprises a sequence that promotes or enhances interaction of a poly-A-binding protein (PABP) with the endonuclease and/or a reverse transcriptase. In some embodiments, the 5' UTR sequence or the 3' UTR sequence comprises a sequence that increases specificity of the endonuclease and/or a reverse transcriptase to the mRNA relative to another mRNA expressed by the cell. In some embodiments, the 5' UTR sequence or the 3' UTR sequence comprises an Alu element sequence.

In some embodiments, the first sequence encoding ORF1p and the second sequence encoding an endonuclease and/or a reverse transcriptase have the same promoter. In some embodiments, the insert sequence has a promoter that is different from the promoter of the first sequence encoding ORF1p. In some embodiments, the insert sequence has a promoter that is different from the promoter of the second sequence encoding an endonuclease and/or a reverse transcriptase. In some embodiments, the first sequence encoding ORF1p and/or the second sequence encoding an endonuclease and/or a reverse transcriptase have a promoter or transcription initiation site selected from the group consisting of an inducible promoter, a CMV promoter or transcription initiation site, a T7 promoter or transcription initiation site, an EF1a promoter or transcription initiation site and combinations thereof. In some embodiments, the insert sequence has a promoter or transcription initiation site selected from the group consisting of an inducible promoter, a CMV promoter or transcription initiation site, a T7 promoter or transcription initiation site, an EF1a promoter or transcription initiation site and combinations thereof.

In some embodiments, the first sequence encoding ORF1p and the second sequence encoding an endonuclease and/or a reverse transcriptase are codon optimized for expression in a human cell.

In some embodiments, the mRNA comprises a WPRE element. In some embodiments, the mRNA comprises a selection marker. In some embodiments, the mRNA comprises a sequence encoding an affinity tag. In some embodiments, the affinity tag is linked to the sequence encoding an endonuclease and/or a reverse transcriptase.

In some embodiments, the 3' UTR comprises a poly A sequence or wherein a poly A sequence is added to the mRNA in vitro. In some embodiments, the poly A sequence is downstream of a sequence encoding an endonuclease and/or a reverse transcriptase. In some embodiments, the insert sequence is upstream of the poly A sequence.

In some embodiments, the 3' UTR sequence comprises the insert sequence. In some embodiments, the insert sequence comprises a sequence that is a reverse complement of the sequence encoding the exogenous polypeptide. In some embodiments, the insert sequence comprises a polyadenylation site. In some embodiments, the insert sequence comprises an SV40 polyadenylation site. In some embodiments, the insert sequence comprises a polyadenylation site upstream of the sequence that is a reverse complement of the sequence encoding the exogenous polypeptide. In some embodiments, the insert sequence is integrated into the genome at a locus that is not a ribosomal locus. In some embodiments, the insert sequence integrates into a gene or regulatory region of a gene, thereby disrupting the gene or downregulating expression of the gene. In some embodiments, the insert sequence integrates into a gene or regulatory region of a gene, thereby upregulating expression of the gene. In some embodiments, the insert sequence integrates into the genome and replaces a gene. In some embodiments, the insert sequence is stably integrated into the genome. In some embodiments, the insert sequence is retrotransposed into the genome. In some embodiments, the insert sequence is integrated into the genome by cleavage of a DNA strand of a target site by an endonuclease encoded by the mRNA. In some embodiments, the insert sequence is integrated into the genome via target-primed reverse transcription (TPRT). In some embodiments, the insert sequence is integrated into the genome via reverse splicing of the mRNA into a DNA target site of the genome.

In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell.

In some embodiments, the mRNA is a self-integrating mRNA. In some embodiments, the method comprises introducing into the cell the mRNA. In some embodiments, the method comprises introducing into the cell the vector encoding the mRNA. In some embodiments, the method comprises introducing the mRNA or the vector encoding the mRNA into a cell ex vivo. In some embodiments, the method further comprises administering the cell to a human subject. In some embodiments, the method comprises administering the mRNA or the vector encoding the mRNA to a human subject. In some embodiments, an immune response is not elicited in the human subject. In some embodiments, the mRNA or the vector is substantially non-immunogenic.

In some embodiments, the vector is a plasmid or a viral vector. In some embodiments, the vector comprises a non-LTR retrotransposon. In some embodiments, the vector comprises a human L1 element. In some embodiments, the vector comprises a L1 retrotransposon ORF1 gene. In some embodiments, the vector comprises a L1 retrotransposon ORF2 gene. In some embodiments, the vector comprises a L1 retrotransposon.

In some embodiments, the mRNA is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases.

In some embodiments, the mRNA comprises a payload that is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases. In some embodiments, the mRNA is at least about 5.1, 5.2, 5.3, 5.4, 5.5, 5.6, 5.7, 5.8, 5.9 or 6 kilobases. In some embodiments, the mRNA is at least about 6.1, 6.2, 6.3, 6.4, 6.5, 6.6, 6.7, 6.8, 6.9 or 7 kilobases. In some embodiments, the mRNA is at least about 7.1, 7.2, 7.3, 7.4, 7.5, 7.6, 7.7, 7.8, 7.9 or 8 kilobases. In some embodiments, the mRNA is at least about 8.1, 8.2, 8.3, 8.4, 8.5, 8.6, 8.7, 8.8, 8.9 or 9 kilobases. In some embodiments, the mRNA is at least about 9.1, 9.2, 9.3, 9.4, 9.5, 9.6, 9.7, 9.8, 9.9 or 10 kilobases. In some embodiments, the mRNA is at least about 10.1, 10.2, 10.3, 10.4, 10.5, 10.6, 10.7, 10.8, 10.9 or 11 kilobases. In some embodiments, the mRNA is at least about 11.1, 11.2, 11.3, 11.4, 11.5, 11.6, 11.7, 11.8, 11.9 or 12 kilobases. In some embodiments, the mRNA comprises a payload of about 6.8 kB, e.g., a sequence encoding a ABCA4 gene product. In some embodiments, the mRNA comprises a payload of about 6.7 kB, e.g., a sequence encoding a MY07A gene product. In some embodiments, the mRNA comprises a payload of about 7.5 kB, e.g., a sequence encoding a CEP290 gene product. In some embodiments, the mRNA comprises a payload of about 10.1 kB, e.g., a sequence encoding a CDH23 gene product. In some embodiments, the mRNA comprises a payload of about 9.4 kB, e.g., a sequence encoding a EYS gene product. In some embodiments, the mRNA comprises a payload of about 15.6 kB, e.g., a sequence encoding a USH2a gene product. In some embodiments, the mRNA comprises a payload of about 12.5 kB, e.g., a sequence encoding a ALMS1 gene product. In some embodiments, the mRNA comprises a payload of about 4.6 kB, e.g., a sequence encoding a GDE gene product. In some embodiments, the mRNA comprises a payload of about 6 kB, e.g., a sequence encoding the OTOF gene product. In some embodiments, the mRNA comprises a payload of about 7.1 kB, e.g., a sequence encoding a F8 gene product.

One of the advantages of using the method of integration of a nucleic acid into the genome using retrotransposition is that it can be designed as described herein to deliver a nucleic acid cargo that is much larger than that using any other existing methods. For example, lentiviral and adeno-associated viral (AAV) gene delivery method are not expected to deliver a nucleic acid cargo of greater than 4 kB. In addition, lentiviral delivery entails risk of insertional mutagenesis and other toxicities. AAV mediated delivery entails unresolved liver and CNS toxicity. On the other hand, retrotransposition mediated method (Retro-T) using mRNA as described herein is rapid, safer and less complex than these viral methods.

In some embodiments, the mRNA comprises a sequence that inhibits or prevents degradation of the mRNA. In some embodiments, the sequence that inhibits or prevents degradation of the mRNA inhibits or prevents degradation of the mRNA by an exonuclease or an RNAse. In some embodiments, the sequence that inhibits or prevents degradation of the mRNA is a G quadruplex, pseudoknot or triplex sequence. In some embodiments, the sequence the sequence that inhibits or prevents degradation of the mRNA is an exoribonuclease-resistant RNA structure from a flaviviral RNA or an ENE element from KSV. In some embodiments, the sequence that inhibits or prevents degradation of the mRNA inhibits or prevents degradation of the mRNA by a deadenylase. In some embodiments, the sequence that inhibits or prevents degradation of the mRNA comprises non-adenosine nucleotides within or at a terminus of a poly A tail of the mRNA. In some embodiments, the sequence that inhibits or prevents degradation of the mRNA increases stability of the mRNA. In some embodiments, the exogenous sequence comprises a sequence encoding an exogenous polypeptide. In some embodiments, the sequence encoding an exogenous polypeptide is not in frame with a sequence encoding an endonuclease and/or a reverse transcriptase. In some embodiments, the sequence encoding an exogenous polypeptide is not in frame with a sequence encoding an endonuclease and/or a reverse transcriptase. In some embodiments, the exogenous sequence does not comprise introns. In some embodiments, the exogenous sequence comprises a sequence encoding an exogenous polypeptide selected from the group consisting of an enzyme, a receptor, a transport protein, a structural protein, a hormone, an antibody, a contractile protein and a storage protein. In some embodiments, the exogenous sequence comprises a sequence encoding an exogenous polypeptide selected from the group consisting of a chimeric antigen receptor (CAR), a ligand, an antibody, a receptor, and an enzyme. In some embodiments, the exogenous sequence comprises a regulatory sequence. In some embodiments, the regulatory sequence comprises a cis-acting regulatory sequence. In some embodiments, the regulatory sequence comprises a cis-acting regulatory sequence selected from the group consisting of an enhancer, a silencer, a promoter or a response element. In some embodiments, the regulatory sequence comprises a trans-acting regulatory sequence. In some embodiments, the regulatory sequence comprises a trans-acting regulatory sequence that encodes a transcription factor.

In some embodiments, integration of the insert sequence does not adversely affect cell health. In some embodiments, the endonuclease, the reverse transcriptase or both are capable of site-specific integration of the insert sequence.

In some embodiments, the mRNA comprises a sequence encoding an additional nuclease domain or a nuclease domain that is not derived from ORF2. In some embodiments, the mRNA comprises a sequence encoding a mega-TAL nuclease domain, a TALEN domain, a Cas9 domain, a zinc finger binding domain from an R2 retroelement, or a DNA binding domain that binds to repetitive sequences such as a Rep78 from AAV. In some embodiments, the endonuclease comprises a mutation that reduces activity of the endonuclease compared to the endonuclease without the mutation. In some embodiments, the endonuclease is an ORF2p endonuclease and the mutation is S228P. In some embodiments, the mRNA comprises a sequence encoding a domain that increases fidelity and/or processivity of the reverse transcriptase. In some embodiments, the reverse transcriptase is a reverse transcriptase from a retroelement other than ORF2 or reverse transcriptase that has higher fidelity and/or processivity compared to a reverse transcriptase of ORF2p. In some embodiments, the reverse transcriptase is a group II intron reverse transcriptase. In some embodiments, the group II intron reverse transcriptase is a group IIA intron reverse transcriptase, a group IIB intron reverse transcriptase, or a group IIC intron reverse transcriptase. In some embodiments, the group II intron reverse transcriptase is TGIRT-II or TGIRT-III.

In some embodiments, the mRNA comprises a sequence comprising an Alu element and/or a ribosome binding aptamer. In some embodiments, the mRNA comprises a sequence encoding a polypeptide comprising a DNA binding domain. In some embodiments, the 3' UTR sequence is derived from a viral 3' UTR or a beta-globin 3' UTR.

In one aspect, provided herein is a composition comprising a recombinant mRNA or vector encoding an mRNA, wherein the mRNA comprises a human LINE-1 transposon sequence comprising a human LINE-1 transposon 5' UTR sequence, a sequence encoding ORF1p downstream of the human LINE-1 transposon 5' UTR sequence, an inter-ORF linker sequence downstream of the sequence encoding ORF1p, a sequence encoding ORF2p downstream of the inter-ORF linker sequence, and a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element.

In some embodiments, the insert sequence integrates into the genome of a cell when introduced into the cell. In some embodiments, the insert sequence integrates into a gene associated a condition or disease, thereby disrupting the gene or downregulating expression of the gene. In some embodiments, the insert sequence integrates into a gene, thereby upregulating expression of the gene. In some embodiments, the recombinant mRNA or vector encoding the mRNA is isolated or purified.

In one aspect, provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic.

In some embodiments, the composition comprises human ORF1p and human ORF2p proteins. In some embodiments, the composition comprises a ribonucleoprotein (RNP) comprising human ORF1p and human ORF2p complexed to the nucleic acid. In some embodiments, the nucleic acid is mRNA.

In one aspect, provided herein is a composition comprising a cell comprising a composition described herein. In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell. In some embodiments, the insert sequence is a reverse complement of a sequence encoding an exogenous polypeptide and the exogenous polypeptide is a chimeric antigen receptor (CAR).

In one aspect, provided herein is a pharmaceutical composition comprising a composition described herein, and a pharmaceutically acceptable excipient. In some embodiments, the pharmaceutical composition is for use in gene therapy. In some embodiments, the pharmaceutical composition is for use in the manufacture of a medicament for treating a disease or condition. In some embodiments, the pharmaceutical composition is for use in treating a disease or condition. In one aspect, provided herein is a method of treating a disease in a subject, comprising administering a pharmaceutical composition described herein to a subject with a disease or condition. In some embodiments, the method increases an amount or activity of a protein or functional RNA in the subject. In some embodiments, the subject has a deficient amount or activity of a protein or functional RNA. In some embodiments, the deficient amount or activity of a protein or functional RNA is associated with or causes the disease or condition.

In some embodiments, the method further comprising administering an agent that inhibits human silencing hub (HUSH) complex, an agent that inhibits FAM208A, or an agent that inhibits TRIM28. In some embodiments, the agent that inhibits human silencing hub (HUSH) complex is an agent that inhibits Periphilin, TASOR and/or MPP8. In some embodiments, the agent that inhibits human silencing hub (HUSH) complex inhibits assembly of the HUSH complex.

In some embodiments, the agent inhibits the fanconia anemia complex. In some embodiments, the agent inhibits FANCD2-FANC1 heterodimer monoubiquitination. In some embodiments, the agent inhibits FANCD2-FANC1 heterodimer formation. In some embodiments the agent inhibits the Fanconi Anemia (FA) core complex. FA core complex is a component of the fanconi anemia DNA damage repair pathway, e.g., in chemotherapy induced DNA inter-strand crosslinks. The FA core complex comprises two central dimers of the FANCB and FA-associated protein of 100 kDa (FAAP100) subunits, flanked by two copies of the RING finger subunit, FANCL. These two heterotrimers act as a scaffold to assemble the remaining five subunits, resulting in an extended asymmetric structure. Destabilization of the scaffold would disrupt the entire complex, resulting in a non-functional FA pathway. Examples of agents that can inhibit the FA core complex include Bortezomib and curcumin analogs E3F24 and 4H-TTD.

In some embodiments, the sequences to be inserted may be placed under the control of tissue-specific elements, such that the entire inserted DNA is only functional in those cells in which the tissue-specific element is active.

In one aspect, provided herein are method and compositions for stable gene transfer to a cell by introducing to the cell a heterologous nucleic acid or gene of interest (e.g., a transgene, a regulatory sequence, for example, a sequence for an inhibitory nucleic acid, an siRNA, a miRNA), flanked by sequences that cause retrotransposition of the heterologous nucleic acid sequence into the genome of the cell. In some embodiments, the heterologous nucleic acid is termed insert for the purpose of the description in this document, where the insert is the nucleic acid sequence that will be reverse transcribed and inserted into the genome of the cell by the intended design of the constructs described herein. In some embodiments, the heterologous nucleic acid is also termed the cargo, or cargo sequence for the purpose of the description in this document. The cargo can comprise the sequence of the heterologous nucleic acid that that is inserted in the genome. In some embodiments, the cell may be a cell mammalian cell. The mammalian cell may be of epithelial, mesothelial or endothelial origin. In some embodiments, the cell may be a stem cell. In some embodiments, the cell may be a precursor cell. In some embodiments, the cell may be a cell that is terminally differentiated. In some embodiments, the cell may be a muscle cell, a cardiac cell, an epithelial cell, a hematopoietic cell, a mucous cell, an epidermal cell, a squamous cell, a cartilage cell, a bone cell, or any cell of mammalian origin. In some embodiments, the cell is of hematopoietic lineage. In some embodiments, the cell is of myeloid lineage, or a phagocytic cell, for example a monocyte, macrophage, a dendritic cell or a myeloid precursor cell. In some embodiments, the nucleic acid encoding the transgene is an mRNA.

In some embodiments, the retrotransposable elements may be derived from a non-LTR retrotransposon.

Provided herein is a method of integrating a nucleic acid sequence into a genome of a cell, the method comprising introducing a recombinant mRNA or a vector encoding an mRNA into the cell, wherein the mRNA comprises an insert sequence and wherein the insert sequence is integrated into the genome of the cell. In some embodiments, the insert sequence comprises (i) an exogenous sequence, or (ii) a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein. In some embodiments, the ORF protein is a human LINE 1 ORF2 protein. In some embodiments, the ORF protein is a non-human ORF protein. In some embodiments, the ORF protein is a chimeric protein, a recombinant protein or an engineered protein.

Provided herein is a method for integrating a nucleic acid sequence into the genome of an immune cell, the method comprising introducing a recombinant mRNA or a vector encoding an mRNA, wherein the mRNA comprises, (a) an insert sequence, wherein the insert sequence comprises (i) an exogenous sequence or (ii) a sequence that is a reverse complement of the exogenous sequence; (b) 5' UTR sequence and a 3' UTR sequence downstream of the 5' UTR sequence, wherein the 5' UTR sequence or the 3' UTR sequence comprises an endonuclease binding site and a reverse transcriptase binding site, and wherein the transgene sequence is integrated into the genome of the immune cell.

In some embodiments, the structural elements that mediate RNA integration or transposition may be encoded in a synthetic construct and are relied upon to deliver a heterologous gene of interest to the cell. In some embodiments, the synthetic construct may comprise a nucleic acid encoding the heterologous gene of interest and the structural elements that cause integration or retrotransposition of a heterologous gene of interest into the genome. In some embodiments, the structural elements that cause integration or retrotransposition may include a 5' L1 RNA region, and a 3'-L1 region, the latter comprising a poly A 3' region for priming. In some embodiments, the 5' L1 RNA region may comprise one or more stem loop regions. In some embodiments, the L1-3' region may comprise one or more stem loop regions. In some embodiments, the 5'- and 3' L1 regions are constructed as flanking the nucleic acid sequence encoding the heterologous gene of interest (the transgene). In some embodiments, the structural elements may include a region from an L1 or an Alu RNA comprising the hairpin loop structure that includes the A-Box and the B-Box elements that are ribosomal binding sites In some embodiments, the synthetic nucleic acid may comprise a L1-Ta promoter.

There may be two types of LINE RNA recognition by ORF2p—the stringent and the relaxed. In the stringent type RT recognizes its own 3'UTR tail, and in the relaxed type RT does not require any specific recognition except for the poly-A tail. Division into the stringent and the relaxed type came from the observation that some LINE/SINE pairs share the same 3'-end. For the stringent type, the experimental studies showed that a 3'UTR stem-loop promotes retrotransposition. The 5'-UTR of the LINE retrotransposition sequences have been shown to contain three conserved stem loop regions.

In some embodiments, the transgene, or transcript of interest may be flanked by transposable elements from a L1 or an Alu sequence at the 5' and the 3' end. In some embodiments, the 5' region of a retrotransposon comprises an Alu sequence. In some embodiments, the 3' region of a retrotransposon comprises an Alu sequence. In some embodiments, the 5' region of a retrotransposon comprises an L1 sequence. In some embodiments, the 3' region of a retrotransposon comprises an L1 sequence. In some embodiments, the transgene or transcript of interest is flanked by an SVA transposon sequence.

In some embodiments, the transcript of interest may comprise an L1 or an Alu sequence, encoding the binding regions for ORF2p and the 3'-poly A priming regions. In some embodiments, the heterologous nucleic acid encoding the transgene of interest may be flanked by an L1 or an Alu sequence, encoding the binding regions for ORF1p and the 3'-poly A priming regions. The 3'-region may comprise one or more stem loop structures. In some embodiments, the transcript of interest is structured for cis integration or retrotransposition. In some embodiments, the transcript of interest is structured for trans integration or retrotransposition.

In some embodiments, the retrotransposon is a human retrotransposon. The sequence of a human retrotransposon can comprise a sequence encoding an endonuclease and/or a reverse transcriptase. The sequence of a human retrotransposon can encode for two proteins that are translated from a single RNA containing two non-overlapping ORFs. In some embodiments, the two ORFs are ORF1 and ORF2.

Accordingly, provided herein is a method for stably integrating a heterologous nucleic acid encoding a transgene into the genome of a cell, such as a myeloid cell, the method comprising introducing to the cell a nucleic acid encoding: the transgene; one or more 5'nucleic acid sequences flanking the region encoding the transgene, comprising a 5' region of a retrotransposon; and one or more 3' nucleic acid sequence flanking the region encoding the transgene, comprising a 3' region of a retrotransposon, wherein the 3' region of the retrotransposon comprises a genomic DNA priming sequence and a LINE transposase binding sequence, having the respective endonuclease and reverse transcriptase (RT) activity.

Provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; (b) a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and a reverse transcriptase binding site, and wherein the sequence of a human retrotransposon encodes for two proteins that are translated from a single RNA containing two ORFs, and wherein the insert sequence is integrated into the genome of the cell.

In some embodiments, the method comprising using a single nucleic acid molecule for delivering and integrating the insert sequence into the genome of a cell. The single nucleic acid molecule may be a plasmid vector. The single nucleic acid may be DNA or an RNA molecule. The single nucleic acid may be an mRNA.

In some embodiments, the method comprises introducing into a cell one or more polynucleotides comprising the human retrotransposon and a heterologous nucleic acid sequence. In some embodiments, the one or more polynucleotides comprises (i) a first nucleic acid molecule encoding an ORF1p; (ii) a second nucleic acid molecule encoding an ORF2p and a sequence encoding a cargo. In some embodiments, the first nucleic acid and the second nucleic acid are mRNA. In some embodiments, the first nucleic acid and the second nucleic acid are DNA, e.g., encoded in separate plasmid vectors.

Provided herein is a self-integrating polynucleotide that comprises a sequence which is inserted into the genome of a cell, and insert is stably integrated into the genome by the self-integrating naked polynucleotide. In some embodiments, the polynucleotide is an RNA. In some embodiments, the polynucleotide is an mRNA. In some embodiments, the polynucleotide is an mRNA that has modifications. In some embodiments, the modifications ensure protection against RNases in the intracellular milieu. In some embodiments, the modifications include substituted modified nucleotides, e.g., 5-methylcytidine, pseudouridine or 2-thiouridine.

In some embodiments, a single polynucleotide is used for delivery and genomic integration of the insert (or cargo) nucleic acid. In some embodiments, the single polynucleotide is bicistronic. In some embodiments, the single polynucleotide is tricistronic. In some embodiments, the single polynucleotide is multi-cistronic. In some embodiments, a two or more polynucleotide molecules are used for delivery and genomic integration of the insert (or cargo) nucleic acid.

In some embodiments, a retrotransposable genetic element may be generated, the retrotransposable genetic element comprising (i) a heterologous nucleic acid encoding a transgene or a non-coding sequence to be inserted into the genome of a cell (the insert); (ii) a nucleic sequence encoding one or more retrotransposon ORF-encoding sequences; (iii) one or more UTR regions of the ORF-coding sequences, such that the heterologous nucleic acid encoding a transgene or a non-coding sequence to be inserted is comprised within the UTR sequences; wherein the 3' region of the retrotransposon ORF-encoding sequences comprises a genomic DNA priming sequence.

In some embodiments, the retrotransposable genetic element may be introduced into a cell for stably integrating the transgene into the genomic DNA. In some embodiments, the retrotransposable genetic element comprises (a) a retrotransposon protein coding sequence, and a 3' UTR; and (b) a sequence comprising a heterologous nucleic acid that is to be inserted (e.g, integrated) within the genome of a cell. The retrotransposon protein coding sequence, and the 3' UTR may be a complete and sufficient unit for delivering the heterologous nucleic acid sequence within the genome of the cell, and comprise the retrotransposable elements, such as an endonuclease, a reverse transcriptase, a sequence in the 3' UTR for binding to and priming the genomic DNA at the region cleaved by the endonuclease to start reverse transcribing and incorporating the heterologous nucleic acid.

In some embodiments, the coding sequence of the insert is in forward orientation with respect to the coding sequence of the one or more ORFs. In some embodiments, the coding sequence of the insert is in reverse orientation with respect to the coding sequence of the one or more ORFs. The coding sequence of the insert and the coding sequence of the one or more ORFs may comprise distinct regulatory elements, including 5' UTR, 3' UTR, promoter, enhancer, etc. In some embodiments, the 3' UTR or the 5'-UTR of the insert may comprise the coding sequence of the one or more ORFs, and likewise, the coding sequence of the insert may be situated within in the 3' UTR of the coding sequence of the one or more ORFs.

In some embodiments, a retrotransposable genetic element may be generated, the retrotransposable genetic element comprising: (a) an insert sequence, comprising (i) an exogenous sequence, a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein.

In some embodiments, the retrotransposon may comprise a SINE or LINE element. In some embodiments, the retrotransposon comprises a SINE or LINE stem loop structure, such as an Alu element.

In some embodiments, the retrotransposon is a LINE-1 (L1) retrotransposon. In some embodiments, the retrotransposon is human LINE-1. Human LINE-1 sequences are abundant in the human genome. There are approximately 13,224 total human L1s, of which 480 are active, which make up about 3.6%. Therefore, human L1 proteins are well tolerated and non-immunogenic in humans. Moreover, a tight regulation of random transposition in human ensures that random transposase activity will not be triggered by introduction of the L1 system as described herein. In addition, the retrotransposable constructs designed herein may comprise targeted and specific incorporation of the insert sequence. In some embodiments, the retrotransposable genetic element may comprise designs intended to overcome the silencing machinery actively prevalent in human cells, while being careful that random integration resulting in genomic instability is not initiated.

Accordingly, the retrotransposable constructs may comprise a sequence encoding a human LINE-1 ORF1 protein; and a human LINE-1 ORF2 protein. In some embodiments, the construct comprises a nucleic acid sequence encoding an ORF1p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to MGKKQNRKTGNSKTQSASPPPK-ERSSSPATEQSWMENDFDELREEGFRRSNYSEL-REDIQTKGK EVENFEKNLEEC-ITRITNTEKCLKELMELKTKARELREECRSLRSRCDQ LEERVSAMEDEMNEM KREGKFREKRIKR-NEQSLQEIWDYVKRPNLRLIGVPESD-VENGTKLENTLQDIIQENFPNLARQA NVQIQEIQRTPQRYSSRRAT-PRHIIVRFTKVEMKEKMLRAAREKGRVTLKGK-PIRLTVDLSAETL QARREWGPIFNILKEKNFQPRI-SYPAKLSFISEGEIKYFIDKQMLRDFVTTRPALKELLK EALNME RNNRYQPLQNHAKM (SEQ ID NO: 53). In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to

```
                                        (SEQ ID NO: 54)
atgggcaagaagcaaaatcgcaagacggggaattccaagacacaatccgc tagcccaccacctaaagagcgttctagctccctgctactgagcagtcct ggatggaaaacgacttcgatgaactccgggaagagggatttaggcgatcc aactattcagaactccgcgaagatatccagacaaaggggaaggaagtcga gaatttcgagaagaacctcgaggagtgcatcacccgtatcacaaacactg agaaatgtctcaaagaactcatggaacttaagacaaaagccagggagctt cgagaggagtgtcggagtctgagatccaggtgtgaccagctcgaggagcg cgtgagcgcgatggaagacgagatgaacgagatgaaaagagagggcaaat tcagggagaagcgcattaagaggaacgaacagagtctgcaggagatttgg gattacgtcaagaggcctaacctgcggttgatcggcgtccccgagagcga cgtagaaaacgggactaaactggagaatacacttcaagacatcattcaag aaaattttccaaacctggctcggcaagctaatgtgcaaatccaagagatc caacgcacaccccagcggtatagctctcggcgtgccacccctaggcatat tatcgtgcgctttactaaggtggagatgaaagagaagatgctgcgagccg ctcgggaaaagggaagggtgactttgaagggcaaacctattcggctgacg gttgaccttagcgccgagacactccaggcacgccgggaatggggccccat ctttaatatcctgaaggagaagaacttccagccacgaatctcttaccctg caaagttgagttttatctccgagggtgagattaagtatttcatcgataaa cagatgctgcgagacttcgtgacaactcgcccagctctcaaggaactgct caaagaggctcttaatatggagcgcaataatagatatcaacccttgcaga accacgcaaagatgtga.
```

In some embodiments, the construct comprises a nucleic acid sequence encoding an ORF2p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to MTGSNSHIT-ILTLNINGLNSAIKRHRLASWIKSQDPSVCCIQETHLT-CRDTHRLKIKGWRKIYQAN GKQKKAGVAIL-VSDKTDFKPTKIKRDKEGHYIMVKGSIQQEELTILNI YAPNTGAPRFIKQVLSDL QRDLDSHTLIMGDFNTPL-STLDRSTRQKVNKDTQELNSALHQAD-LIDIYRTLHPKSTEYTFFSAP HHTYSKIDHIVGSKALL-SKCKRTEIIT- NYLSDHSAIKLELRIKNLTQSRSTTWKLNNLLLNDY
WV HNEMKAEIKMFFETNENKDT-
TYQNLWDAFKAVCRGKFIALNAYKRKQERSKIDTLT-
SQLKELE KQEQTHSKASRRQEITKIRAELKEI-
ETQKTLQKINESRSWFFERINKIDRPLARLIKKKREKN
QIDTI KNDKGDITTDPTEIQTTIREYYKHLYANKLEN-
LEEMDTFLDTYTLPRLNQEEVESLNRPITGSEIV AIIN-
SLPTKKSPGPDGFTAEFYQRYMEELVP-
FLLKLFQSIEKEGILPNSFYEASIILIPKPGRDTTKKE
NFRPISLMNIDAKILNKILANRIQQHIKKLIHHDQVG-
FIPGMQGWFNIRKSINVIQHINRAKDKNH MIISI-
DAEKAFDKIQQPFMLKTLNKLGIDGTYFKII-
RAIYDKPTANIILNGQKLEAFPLKTGTRQGC
PLSPLLFNIVLEVLARAIRQEKEIKGIQLGKEEVKLSL-
FADDMIVYLENPIVSAQNLLKLISNFSKV SGYK-
INVQKSQAFLYTNNRQTESQIMGELPFVIASKRI-
KYLGIQLTRDVKDLFKENYKPLLKEIKE
DTNKWKNIPCSWVGRINIVKMAILPKVIYRFNAIP-
IKLPMTFFTELEKTTLKFIWNQKRARIAKSIL SQKNK-
AGGITLPDFKLYYKATVTKTAWYWYQNR-
DIDQWNRTEPSEIMPHIYNYLIFDKPEKNK
QWGKDSLFNKWCWENWLAICRKLKLDPFLTPYT-
KINSRWIKDLNVKPKTIKTLEENLGITIQDIG
VGKDFMSKTPKAMATKDKIDKWDLIKLKSFCTA-
KETTIRVNRQPTTWEKIFATYSSDKGLISRIY
NELKQIYKKKTNNPIKKWAKDMNRHFSKEDI-
YAAKKHMKKCSSSLAIREMQIKTTMRYHLTPV
RMAIIKKSGNNRCWRGCGEIGTLLHCWWDCK-
LVQPLWKSVWRFLRDLELEIPFDPAIPLLGIYP
NEYKSCCYKDTCTRMFIAALFTIAKTWNQPKCPT-
MIDWIKKMWHIYTMEYYAAIKNDEFISFVG
TWMKLETIILSKLSQEQKTKHRIFSLIGGN (SEQ ID
NO: 55). In some embodiments, the construct comprises a
nucleic acid sequence with at least 80%, at least 81%, at
least 82%, at least 83%, at least 84%, at least 85%, at least
86%, at least 87%, at least 88%, at least 89%, at least 90%,
at least 91%, at least 92%, at least 93%, at least 94%, at least
95%, at least 96%, at least 97%, at least 98%, at least 99%,
or 100% sequence identity to (SEQ ID NO: 56)
atgaccggctctaactcacatatcaccatccttacacttaacattaacgg cctcaactcagctatcaagcgccatcggctggccagctggatcaaatcac aggatccaagcgtttgttgcatccaagagacccacctgacctgtagagat actcaccgcctcaagatcaaggatggcgaaagatttatcaggcgaacgg taagcagaagaaagccggagtcgcaattctggtctcagacaagacggatt tcaagcccaccaaaattaagcgtgataaggaaggtcactatattatggtg aaaggcagcatacagcaggaagaacttaccatattgaacatctacgcgcc aaacaccggcgcacctcgctttatcaaacaggtcctgtccgatctgcagc gagatctggattctcatacgttgattatgggtgatttcaatacaccattg agcaccctggatcgcagcaccaggcaaaaggtaaataaagacacgcaaga gctcaatagcgcactgcatcaggcagatctcattgatatttatcgcactc ttcatcctaagagtaccgagtacacattcttcagcgccccacatcataca tactcaaagatcgatcatatcgtcggctcaaaggctctgctgtcaaagtg caagcgcacagagataattacaaattacctgtcagatcatagcgcgatca agctcgagctgagaatcaagaacctgacccagagccggagtaccacttgg -continued
aagcttaataacctgctgctcaacgattattgggtccacaatgagatgaa ggcagagattaaaatgttcttcgaaacaaatgagaataaggatactacct atcaaaacctttgggatgcctttaaggccgtctgcagaggcaagttcatc gccctcaacgcctataaaagaaaacaagagagatctaagatcgatactct cacctctcagctgaaggagttggagaaacaggaacagacccactccaagg cgtcaagacggcaggagatcacaaagattcgcgccgagttgaaagagatc gaaacccaaaagactcttcagaaaattaacgagtctcgtagttggttctt cgagcggattaataagatagacagacctctggcacgactgattaagaaga agcgcgaaaagaaccagattgataccatcaagaacgacaagggcgacatc actactgacccgaccgagatccagaccactattcgggagtattataagca tttgtatgctaacaagcttgagaacctggaagagatggacacttttctgg atacctatactctgccacggcttaatcaagaggaagtcgagtccctcaac cgcccaattacaggaagcgagattgtggccataattaactccctgccgac aaagaaatctcctggtccggacgggtttacagctgagtttatcaacggt atatggaagagcttgtaccgtttctgctcaagctctttcagtctatagaa aaggaaggcatcttgcccaattccttctacgaagcttctataatacttat tcccaaaccaggacgcgataccacaaagaaggaaaacttccggcccatta gtctcatgaatatcgacgctaaaatattgaacaagattctcgccaacaga atccaacaacatattaagaaattgatacatcacgaccaggtggggtttat acctggcatgcagggctggtttaacatccggaagagtattaacgtcattc aacacattaatagagctaaggataagaatcatatgatcatctctatagac gcggaaaaggcattcgataagattcagcagccatttatgctcaagactct gaacaaactcggcatcgacggaacatattttaagattattcgcgcaattt acgataagccgactgctaacattatccttaacggccaaaagctcgaggcc tttccgctcaagactggaacccgccaaggctgtcccctctccccgctttt gtttaatattgtactcgaggtgctggctagggctattcgtcaagagaaag agattaaagggatacagctcgggaaggaagaggtcaagctttccttgttc gccgatgatatgattgtgtacctggagaatcctattgtgtctgctcagaa ccttcttaaacttatttctaactttagcaaggtcagcggctataagatta acgtccagaaatctcaggcctttctgtacacaaataatcgacagaccgaa tcccagataatgggtgagcttccgtttgtcatagccagcaaaaggataaa gtatctcggaatccagctgacacgagacgttaaagatttgtttaaggaaa attacaagcctctcctgaaagagattaaggaagatactaataagtggaag aatatccctgttcatgggttggcagaatcaacatagtgaagatggcaat acttcctaaagtgatatatcgctttaacgccatcccaattaaactgccta tgaccttctttacggagctcgagaaaatgtattataaagccacagtaact aagacagcctggtattggtatcagaatagagacatcgaccagtggaatcg gaccgaaccatcagagataatgccccacatctataattaccttatattcg ataagccagaaaagaataaacagtggggcaaagacagcctcttcaacaag tggtgttgggagaattggctggccatatgccggaaactcaagctcgaccc -continued

```
ctttcttacaccctacactaaaatcaacagtaggtggatcaaggacttga atgtcaagccaaagactataaagacactggaagagaatcttgggatcaca atacaagatataggcgtcggcaaagattttatgtcaaagacgcccaaggc catggccactaaggataagattgataagtgggaccttattaagctcaaaa gcttctgtactgccaaggagaccacgatcagagttaataggcagcccact acatgggaaagattttcgccacttattcatcagataaggggttgataag cagaatatataacgagctgaagcagatctacaagaagaaaacgaataatc ccatcaagaagtgggcaaaagatatgaacaggcattttagcaaagaggat atctacgccgcgaagaagcatatgaagaagtgtagttcaagcttggccat tcgtgagatgcagattaagacgaccatgcgataccaccttaccccagtga ggatggcaattatcaagaaatctggcaataatagatgttggcggggctgt ggcgagattggcaccctgctccattgctggtgggattgcaagctggtgca gccgctttggaaatcagtctggcgctttctgagggacctcgagcttgaga ttccttcgatcccgcaattccttgctcggaatctatcctaacgaatac aagagctgttgttacaaggatacgtgtacccggatgttcatcgcggcctt gtttacgatagctaagacgtggaatcagcctaagtgccccacaatgatcg attggatcaagaaatgtggcatatttataccatggagtattacgcagca attaagaatgacgaatttatttccttcgttgggacctggatgaagctgga gactattattctgagcaagctgtctcaggagcaaaagacaaagcatagaa tcttctctctcattggtggtaactaa.
```

In some embodiments, the construct comprises a nucleic acid sequence encoding an ORF2p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to MVIGTY-ISIITLNVNGLNAPTKRHRLAEWIQKQDPYIC-CLQETHFRPRDTYRLKVRGWKKIFHAN GNQKK-AGVAILISDKIDFKIKNVTRDKEGHYIMIQGSIQEEDITI-INIYAPNIGAPQYIRQLLTAIKE EIDSNTIIVGDFNTSLTPMDRSSKMKINKETEAL-NDTIDQIDLIDIYRTFHPKTADYTFFSSAHGTFS RIDHILGHKSSLSKFKKIEIISSIFSDHNAMR-LEMNHREKNVKKTNTWRLNNTLLNNQEITEEIKQ EIKKYLETNDNENTTTQNLWDAAKAVLRGKFIAI-QAYLKKQEKSQVNNLTLHLKKLEKEEQTK PKVSRRKEIIKIRAEINEIETKK-TIAKINKTKSWFFEKINKIDKPLARLIKKKR-ERTQINKIRNEKGE VTTDTAEIQNILRDYYKQLY-ANKMDNLEEMDKFLERYNLPRLNQEETENINRPITS NEIETVIKNL PTNKSPGPDGFTGEFYQTFREELT-PILLKLFQKIAEEGTLPNSFYEATI-TLIPKPDKDTTKKENYRPI SLMNIDAKILNKILAN-RIQQHIKRIIHHDQVGFIPGMQGFFNIRKSINVIHHIN KLKKKNHMIISIDA EKAFD-KIQHPFMIKTLQKVGIEGTYLNIIKAIYDKP-TANIILNGEKLKAFPLRSGTRQGCPLSPLLF NIVLEV-LATAIREEKEIKGIQIGKEEVKLSLFADDMILYIENPK TATRKLLELINEYGKVAGYKINA QKSLAFLY-TNDEKSEREIMETLPFTIATKRIKYLGINLPKETKDLY-AENYKTLMKEIKDDTNRWR DIPCSWIGRINIVKM-SILPKAIYRFNAIPIKLPMAFFTELEQIILKFVWRHKR PRIAKAVLRQKNGA GGIRLPDFRLYYKATVIKTIWY- WHKNRNIDQWNKIESPEIN-PRTYGQLIYDKGGKDIQWRKDSLF NKWC-WENWTATCKRMKLEYSLTPYTKINSKWIRDLNIRLD TIKLLEENIGRTLFDINHSKIFFDPP PRVMEIKT-KINKWDLMKLQSFCTAKETINKTKRQPSEWEKI-FANESTDKGLISKIYKQLIQLNIKE TNTPIQKWAE-DLNRHFSKEDIQTATKHMKRCSTSLIIREMQIKTTMR YHLTPVRMGIIRKSTNNK CWRGCGEKGTLLHCWWECK-LIQPLWRTIWRFLKKLKIELPYDPAIPLLGIYPEKT-VIQKDTCTR MFIAALFTIARSWKQPKCPSTDEWIK-KMWYIYTMEYYSAIKRNEIGSFLETWMDLETVIQSE VSQ KEKNKYRILTHICGTWKNGTDEPVCRTEIETQM (SEQ ID NO: 57). In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to

```
(SEQ ID NO: 58)
atggtcataggaacatacatatcgataattaccttaaacgtgaatggatt aaatgccccaaccaaaagacatagactggctgaatggatacaaaaacaag acccatatatatgctgtctacaagagacccacttcagacctagggacaca tacagactgaaagtgaggggatggaaaaagatattccatgcaaatggaaa tcaaaagaaagctggagtagctatactcatatcagataaaatagacttta aaataaagaatgttacaagagacaaggaaggacactacataatgatccag ggatcaatccaagaagaagatataacaattataaatatatatgcacccaa cataggagcacctcaatacataaggcaactgctaacagctataaaagagg aaatcgacagtaacacaataatagtgggggactttaacacctcacttaca ccaatggacagatcatccaaaatgaaaataaataaggaaacagaagcttt aaatgacacaatagaccagatagatttaattgatatatataggacattcc atccaaaaacagcagattacacgttcttctcaagtgcgcacggaacattc tccaggatagatcacatcttgggtcacaaatcaagcctcagtaaatttaa gaaaattgaaatcatatcaagcatcttttctgaccacaacgctatgagat tagaaatgaatcacagggaaaaaaacgtaaaaaagacaaacacatggagg ctaaacaatacgttactaaataaccaagagatcactgaagaaatcaaaca ggaaataaaaaaatacctagagacaaatgacaatgaaaacacgacgaccc aaaacctatgggatgcagcaaaagcggttctaagagggaagtttatagct atacaagcctacctaaagaaacaagaaaaatctcaagtaaacaatctaac cttacacctaaagaaactagagaagaagaacaaacaaaacccaaagtta gcagaaggaaagaaatcataaagatcagagcagaaataaatgaaatagaa acaaagaaacaatagcaaagatcaataaaactaaaagttggttctttga gaagataaacaaaattgataagccattagccagactcatcaagaaaaga gggagaggactcaaatcaataaaatcagaaatgaaaaaggagaagttaca acagacaccgcagaaatacaaaacatcctaagagactactacaagcaact ttatgccaataaaatggacaacctggaagaaatggacaaattcttagaaa
```

-continued

```
ggtataaccttccaagactgaaccaggaagaaacagaaaatatcaacaga ccaatcacaagtaatgaaattgaaactgtgattaaaaatcttccaacaaa caaaagtccaggaccagatggcttcacaggtgaattctatcaaacattta gagaagagctaacacccatccttctcaaactcttccaaaaaattgcagaa gaaggaacactcccaaactcattctatgaggccaccatcaccctgatacc aaaaccagacaaagacactacaaaaaaagaaaattacagaccaatatcac tgatgaatatagatgcaaaaatcctcaacaaaatactagcaaacagaatc caacaacacattaaaaggatcatacaccacgatcaagtgggatttatccc agggatgcaaggattcttcaatatacgcaaatcaatcaatgtgatacacc atattaacaaattgaagaagaaaaaccatatgatcatctcaatagatgca gaaaaagcttttgacaaaattcaacacccatttatgataaaaactctcca gaaagtgggcatagagggaacctacctcaacataataaaggccatatatg acaaacccacagcaaacatcattctcaatggtgaaaaactgaaagcattt cctctaagatcaggaacgagacaaggatgtccactctcaccactattatt caacatagttctggaagtcctagccacggcaatcagagaagaaaaagaaa taaaaggaatacaaattggaaaagaagaagtaaaactgtcactgtttgcg gatgacatgatactatacatagagaatcctaaaactgccaccagaaaact gctagagctaattaatgaatatggtaaagttgcaggttacaaaattaatg cacagaaatctcttgcattcctatacactaatgatgaaaaatctgaaaga gaaattatggaaacactcccatttaccattgcaacaaaaagaataaaata cctaggaataaacctacctaaggagacaaaagacctgtatgcagaaaact ataagacactgatgaaagaaattaaagatgataccaacagatggagagat ataccatgttcttggattggaagaatcaacattgtgaaaatgagtatact acccaaagcaatctacagattcaatgcaatccctatcaaattaccaatgg cattttttacggagctagaacaaatcatcttaaaatttgtatggagacac aaaagaccccgaatagccaaagcagtcttgaggcaaaaaaatggagctgg aggaatcagactccctgacttcagactatactacaaagctacagtaatca agacaatatggtactggcacaaaaacagaaacatagtcaatggaacaag atagaaagcccagagattaacccacgcacctatggtcaactaatctatga caaaggaggcaaagatatacaatggagaaaagacagtctcttcaataagt ggtgctgggaaaactggacagccacatgtaaaagaatgaaattagaatac tccctaacaccatacacaaaaataaactcaaaatggattagagacctaaa tataagactggacactataaaactcttagaggaaaacataggaagaacac tctttgacataaatcacagcaagatcttttttcgatccacctcctagagta atggaaataaaaacaaaaataaacaagtgggacctaatgaaacttcaaag cttttgcacagcaaaggaaaccat+aaacaagacgaaaagacaaccctcag aatgggagaaatatttgcaaatgaatcaacggacaaaggattaatctcc aaaatatataaacagctcattcagctcaatatcaaagaaacaaacacccc aatccaaaaatgggcagaagacctaaatagacatttctccaaagaagaca tacagacggccacgaagcacatgaaaaagatgctcaacatcactaattatt agagaaatgcaaatcaaaactacaatgaggtatcacctcactcctgttag
```

In some embodiments, the construct comprises a nucleic acid sequence encoding a nuclear localization sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to PAAKRVKLD ((SEQ ID NO: 59). In some embodiments, the nuclear localization sequence is fused to the ORF2p sequence. In some embodiments, the construct comprises a nucleic acid sequence encoding a flag tag having the sequence DYKDDDDK (SEQ ID NO: 60). In some embodiments, the flag tag is fused to the ORF2p sequence. In some embodiments, the flag tag is fused to the nuclear localization sequence.

In some embodiments, the construct comprises a nucleic acid sequence encoding an MS2 coat protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to ASNFTQFVLVDNGGTGDVTVAPSNFANGIAEWISSN-SRSQAYKVTCSVRQSSAQNRKYTIKVEV PKGAWR-SYLNMELTIPIFATNSDCELIVKAMQGLLKDGNPIP-SAIAANSGIYAMASNFTQFVLVD NGGTGDVTVAPSNFANGIAEWISSNSR-SQAYKVTCSVRQSSAQNRKYTIKVEVPKGAWRSYLN MELTIPIFATNSDCELIVKAMQGLLKDGNPIPSA-IAANSGIY (SEQ ID NO: 61). In some embodiments, the MS2 coat protein sequence is fused to the ORF2p sequence.

In some embodiments, the transgene may comprise a flanking sequence which comprises an Alu ORF2p recognition sequence.

In some embodiments, additional elements may be introduced into the mRNA. In some embodiments, the additional elements may be an IRES element or a T2A element. In some embodiments, the mRNA transcript comprises one, two, three or more stop codons at the 3'-end.

In some embodiments, the one, two, three or more stop codons are designed to be in tandem. In some embodiments, the one, two, three or more stop codons are designed to be in all three reading frames. In some embodiments, the one, two, three or more stop codons may be designed to be both in multiple reading frames and in tandem.

In some embodiments, one or more target specific nucleotides may be added at the priming end of the L1 or the Alu RNA priming region.

-continued

```
aatgggcatcatcagaaaatctacaaacaacaaatgctggagagggtgtg gagaaaagggaaccctcttgcactgttggtgggaatgtaaattgatacag ccactatggagaacaatatggaggttccttaaaaaactaaaaatagaatt accatatgacccagcaatcccactactgggcatatacccagagaaaaccg taattcaaaaagacacatgcacccgaatgttcattgcagcactatttaca atagccaggtcatggaagcaacctaaatgcccatcgacagacgaatggat aaagaagatgtggtacatatatacaatggaatattactcagccataaaaa ggaacgaaattgggtcatttttagagacgtggatggatctagagactgtc atacagagtgaagtaagtcagaaagagaaaaacaaatatcgtatattaac gcatatatgtggaacctggaaaaatggtacagatgaaccggtctgcagga cagaaattgagacacaaatgtaa.
```

In some embodiments, the 5' UTR sequence or the 3' UTR sequence in addition to be able to bind the ORF protein may also be capable of binding to one or more endogenous proteins that regulate gene retrotransposition and/or stable integration. In some embodiments, the flanking sequence is capable of binding to a PABP protein.

In some embodiments, the 5' region flanking the transcript may comprise a strong promoter. In some embodiments, the promoter is a CMV promoter.

In some embodiments, an additional nucleic encoding L1 ORF2p is introduced into the cell. In some embodiments, the sequence encoding L1 ORF1 is omitted, and only L1-ORF2 is included. In some embodiments, the nucleic acid encoding the transgene with the flanking elements is mRNA. In some embodiments, the endogenous L1-ORF1p function may be suppressed or inhibited.

In some embodiments, the nucleic acid encoding the transgene with the retrotransposition flanking elements comprise one or more nucleic acid modifications. In some embodiments, the nucleic acid encoding the transgene with the retrotransposition flanking elements comprises one or more nucleic acid modifications in the transgene. In some embodiments, the modifications comprise codon optimization of the transgene sequence. In some embodiments, the codon optimization is for more efficient recognition by the human translational machinery, leading to more efficient expression in a human cell. In some embodiments, the one or more nucleic acid modification is performed in the 5'-flanking sequence or the 3'-flanking sequence including one or more stem-loop regions. the nucleic acid encoding the transgene with the retrotransposition flanking elements comprise one, two, three, four, five, six, seven eight, nine, ten or more nucleic acid modifications.

In some embodiments, the retrotransposed transgene is stably expressed for the life of the cell. In some embodiments, the cell is a myeloid cell. In some embodiments, the myeloid cell is a monocyte precursor cell. In some embodiments, the myeloid cell is an immature monocyte. In some embodiments, the monocyte is an undifferentiated monocyte. In some embodiments, the myeloid cell is a CD14+ cell. In some embodiments, the myeloid cell does not express CD16 marker. In some embodiments, the myeloid cell is capable of remaining functionally active for a desired period of greater than 3 days, greater than 4 days, greater than 5 days, greater than 6 days, greater than 7 days, greater than 8 days, greater than 9 days, greater than 10 days, greater than 11 days, greater than 12 days, greater than 13 days, greater than 14 days or more under suitable conditions. A suitable condition may denote an in vitro condition, or an in vivo condition or a combination of both.

In some embodiments, the retrotransposed transgene may be stably expressed in the cell for about 2 days, about 3 days, about 4 days, about 5 days, about 6 days, about 7 days, about 8 days, about 9 days or about 10 days. In some embodiments, the retrotransposed transgene is stably expressed in the cell for more than 10 days. In some embodiments, the retrotransposed transgene is stably expressed in the cell for more than 2 weeks. In some embodiments, the retrotransposed transgene is stably expressed in the cell for about 1 month.

In some embodiments, the retrotransposed transgene may be modified for stable expression. In some embodiments, the retrotransposed transgene may be modified for resistant to in vivo silencing.

In some embodiments, the expression of the retrotransposed transgene may be controlled by a strong promoter. In some embodiments, the expression of the retrotransposed transgene may be controlled by a moderately strong promoter. In some embodiments, the expression of the retrotransposed transgene may be controlled by a strong promoter that can be regulated in an in vivo environment. In some embodiments, the promoter is a CMV promoter. In some embodiments, the promoter is a L1-Ta promoter.

In some embodiments, the ORF1p may be overexpressed. In some embodiments, the ORF2 may be overexpressed. In some embodiments, the ORF1p or ORF2p or both are overexpressed. In some embodiments, upon overexpression of an ORF1, ORF1p is at least 1.1 fold, 1.5 fold, 2 fold, 3 fold, 4 fold, 5 fold, 6 fold, 7 fold, 8 fold, 9 fold, 10 fold, 12 fold, 14 fold, 16 fold, 18 fold, 20 fold, 30 fold, 40 fold, 50 fold, 60 fold, 70 fold, 80 fold, 90 fold, or at least 100 fold higher than a cell not overexpressing and ORF1.

In some embodiments, upon overexpression of an ORF2 sequence, ORF2p is at least 1.1 fold, 1.5 fold, 2 fold, 3 fold, 4 fold, 5 fold, 6 fold, 7 fold, 8 fold, 9 fold, 10 fold, 12 fold, 14 fold, 16 fold, 18 fold, 20 fold, 30 fold, 40 fold, 50 fold, 60 fold, 70 fold, 80 fold, 90 fold, or at least 100 fold higher than a cell not overexpressing and ORF2p.

Retrotransposition Fidelity and Target Specificity

The LINE-1 elements can bind to their own mRNA poly A tail to initiate retrotransposition. LINE-1 elements preferably retrotranspose their own mRNA over random mRNAs (Dewannieux et al., 2013, 3,000-fold higher LINE-1 retrotransposition as compared to random mRNAs). In addition, LINE-1 elements can also integrate non-specific poly-A sequences within a genome.

In one aspect, provided herein are retrotransposition compositions and methods of using the same with increased retrotransposition specificity. For example, retrotransposition compositions with high specificity may be used for highly specific and efficient reverse transcription and subsequently, integration into genome of a target cell, e.g., a myeloid cell. In some embodiments, a retrotransposition composition provided herein comprises a retrotransposition cassette that comprises one or more additional components that increases integration or retrotransposing specificity. For example, the retrotransposon cassette may encode one or more additional elements that allows for high affinity RNA-protein interaction to out compete non-specific binding between poly-A sequences and ORF2.

Accordingly, several measures are disclosed herein for enhancing integration or retrotransposition efficiency.

One exemplary measure for enhancing integration or retrotransposition efficiency is external manipulation of the cells. The endonuclease function of the retrotransposition machinery delivered in a cell may likely be subject to inhibition by the cell's transposition silencing machinery, such as DNA repair pathways. For example, small molecules can be used to modulate or inhibit DNA repair pathways in the cells prior to introducing the nucleic acid. For example, cell sorting and/or synchronization can be used prior to introducing the nucleic acid, such as by electroporation, as cell cycle synchronized cell populations were shown to increase gene transfer to the cells. Cell sorting may be utilized to synchronize or homogenize the cell types and increase uniform transfer and expression of the exogenous nucleic acid. Uniformity may be achieved sorting stem cells from non-stem cells. Another exemplary measure for enhancing integration or retrotransposition efficiency is to enhance biochemical activity. For example, this may be achieved by increasing reverse-transcriptase processivity or DNA cleavage (endonuclease) activity. Another exemplary measure for enhancing integration or retrotransposition efficiency is to subvert endogenous silencing mechanisms. For example, this may be achieved by replacing entire LINE-1 sequence with a different organisms' LINE-1. Another exemplary measure for enhancing integration or retrotrans-position efficiency is to enhance translation and ribosome binding. For example, this may be achieved by increasing expression of LINE-1 proteins, increasing LINE protein binding LINE-1 mRNA, or increasing LINE-1 complex binding to ribosomes. Another exemplary measure for enhancing integration or retrotransposition efficiency is to increase nuclear import or retention. For example, this may be achieved by fusing the LINE-1 sequence to a nuclear retention signal sequence. Another exemplary measure for enhancing integration or retrotransposition efficiency is to enhance sequence-specific insertion. For example, this may be achieved by fusing a targeting domain to ORF2 to increase sequence specific retrotransposition.

In one embodiment, the method encompasses enhancing the retrotransposon for increasing specificity and robustness of expression of the cargo by modifying the UTR sequence of the LINE-1 ORFs. In some embodiments, the 5'UTR upstream of ORF1 or ORF2 encoding sequence may be further modified to comprise a sequence that is complementary to the sequence of a target region within the genome that helps in homologous recombination at the specific site where the ORF nuclease can act and the retrotransposition can take place. In some embodiments, the sequence that can bind to a target sequence by homology is between 2-15 nucleotides long. In some embodiments, the sequence having homology to a genomic target that is included in the 5'UTR of an ORF1 mRNA may be about 3 nucleotides, about 4 nucleotides, about 5 nucleotides, about 6 nucleotides, about 7 nucleotides, about 8 nucleotides, about 9 nucleotides or about 10 nucleotides long. In some embodiments, the sequence having homology to a genomic target is about 12 or about 15 nucleotides long. In some embodiments, the sequence having homology to a genomic target is at least about 10, 15, 20, 25, 30, 35, 40, 45, 50, 55, 60, 65, 70, 75, 80, 85, 90, 95, 100, 105, 110, 115, 1120 or 125 nucleotides in length. In some embodiments, the sequence having homology to a genomic target comprises about 2-5, about 2-6, about 2-8 or about 2-10, or about 2-12 contiguous nucleotides that share complementarity with the respective target region within the genome. In some embodiments, the sequence having homology to a genomic target is at least about or about 10, 15, 20, 25, 30, 35, 40, 45, 50, 55, 60, 65, 70, 75, 80, 85, 90, 95, 100, 105, 110, 115, 1120 or 125 contiguous nucleotides that share complementarity with the respective target region within the genome.

In some embodiments, an ORF2 is associated with or fused to an additional protein domain that comprises RNA binding activity. In some embodiments, the retrotransposon cassette comprises a cognate RNA sequence that comprises affinity with the additional protein domain associated with or fused to the ORF2. In some embodiments, the ORF2 is associated with or fused to a MS2-MCP coat protein. In some embodiments, the retrotransposon cassette further comprises a MS2 hairpin RNA sequence in the 3' or 5' UTR sequence that interacts with the MS2-MCP coat protein. In some embodiments, the ORF2 is associated with or fused to a PP7 coat protein. In some embodiments, the retrotranspo-son cassette further comprises a PP7 hairpin RNA sequence in the 3' or 5' UTR sequence that interacts with the MS2-MCP coat protein. In some embodiments, the one or more additional elements increases retrotransposition specificity by at least 1.5 fold, at least 2 fold, at least 3 fold, at least 4 fold, at least 5 fold, at least 10 fold, at least 20 fold, at least 30 fold, at least 50 fold, at least 100 fold, at least 200 fold, at least 300 fold, at least 500 fold, at least 1000 fold, at least 1500 fold, at least 2000 fold, at least 3000 fold, at least 5000 fold or more as compared to a retrotransposon cassette without the one or more additional elements.

The DNA endonuclease domain appears to have speci-ficity for a series of purines 3' of the target site followed by a series of pyrimidines $(Py)_n \downarrow (Pu)_n$. An exemplary sequence may be $(Adenosine)_n \downarrow (Thymidine)_n$.

In one aspect, provided herein are methods of using retrotransposition having high target specificity. Conse-quently, provided herein is a method and compositions for stable incorporation of a transgene into the genome of a myeloid cell, such as a monocyte or macrophage, wherein the method comprises incorporating the transgene using a non-LTR retrotransposon system, wherein the retrotranspo-sition occurs at a specific genomic locus with a target specificity, high precision and fidelity. Therefore, in some embodiments, the method comprises administration to the cell a composition comprising a system having at least one transgene, flanked with one or more retrotransposable ele-ments, and one or more nucleic acids encoding one or more proteins for increasing the transposition specificity, and/or further comprising modifying one or more genes associated with the retrotransposition.

The nucleic acid comprising the transgene, situated in 3' UTR region of the retrotransposable elements is often referred to as a retrotransposition cassette. Accordingly, in some embodiments, the retrotransposition cassette com-prises the nucleic acid encoding the transgene and flanking Alu transposable elements. The retrotransposable elements comprise a sequence for binding the retrotransposons, for example, L1-transposons, such as L1-ORF proteins, ORF1p and ORF2p. ORF proteins are known to bind to their own mRNA sequence for retrotransposition. Therefore, the ret-rotransposition cassette comprises the nucleic acid encoding the transgene; a flanking L1-ORF2p binding sequence, and/or a L1-ORF1p binding sequence, comprising a sequence encoding a L1-ORF1p encoding sequence and a L1-ORF2p encoding sequence outside the transgene sequence. In some embodiments, the L1-ORF1 and L1-ORF2 are interspersed by a spacer region, also termed as an ORF1-ORF2 inter-region. In some embodiments, the L1-ORF1 and L1-ORF2 coding sequences are in an opposite orientation with respect to the coding region of the trans-gene. The retrotransposition cassette can comprise a poly A region downstream of the L1-ORF2-coding sequence and the transgene sequence is placed downstream of the poly A sequence. The L1-ORF2 comprises a nucleic acid sequence that encodes an endonuclease (EN) and a reverse tran-scriptase (RT) followed by the poly A sequence. In some embodiments, the L1-ORF2 sequence in the retrotransposi-tion cassette described herein is a complete (intact) sequence, that is, encodes the full length native (WT) L1-ORF2 sequence. In some embodiments, the L1-ORF2 sequence in the retrotransposition cassette described herein comprises a partial or modified sequence.

The system described herein can comprise a promoter for expressing the L1-ORF1p and L1-ORF2p. In some embodi-ments, the transgene expression is driven by a separate promoter. In some embodiments, the transgene and the ORFs are in tandem orientation. In some embodiments, the transgene and the ORFs are in opposite orientation.

In some embodiments, the method comprises incorporat-ing one or more elements in addition to the retrotransposon cassette. In some embodiments, the one or more additional elements comprise a nucleic acid sequence encoding one or more domains of a heterologous protein. The heterologous protein may be a sequence specific nucleic acid binding protein, for example, a sequence specific DNA binding protein domain (DBD). In some embodiments, the heterologous protein is a nuclease or a fragment thereof. In some embodiments, the additional elements comprise a nucleic acid sequence encoding one or more nuclease domains or fragments thereof from a heterologous protein. In some embodiments, the heterologous nuclease domain has reduced nuclease activity. In some embodiments, the heterologous nuclease domain is rendered inactive. In some embodiments, the ORF2 nuclease is rendered inactive; whereas one or more nuclease domains from the heterologous protein is configured to render specificity to the retrotransposition. In some embodiments, one or more nuclease domains or fragments thereof from the heterologous protein targets a specific desired polynucleotide within the genome where retrotransposition and incorporation of the polynucleotide of interest is to be incorporated. In some embodiments, the one or more nuclease domains from the heterologous protein comprise a mega-TAL nuclease domain, TALENs, or a zinc finger nuclease domain, for example, a mega-TAL, a TALE, or a zinc finger domain fused to or associated with a nuclease domain, e.g., a FokI nuclease domain. In some embodiments, the one or more nuclease domains from the heterologous protein comprise a CRISPR-Cas protein domain loaded with a specific guide nucleic acid, e.g., a guide RNA (gRNA) for a specific target locus. In some embodiments, the CRISPR-Cas protein is a Cas9, a Cas12a, a Cas12b, a Cas13, a CasX, or a CasY protein domain. In some embodiments, the one or more nuclease domains from the heterologous protein has target specificity.

In some embodiments, the additional nuclease domain may be incorporated into the ORF2 domain. In some embodiments, the additional nuclease may be fused with the ORF2p domain. In some embodiments, the additional nuclease domain may be fused to an ORF2p, wherein the ORF2p includes a mutation in the ORF2p endonuclease domain. In some embodiments, the mutation inactivates the ORF2p endonuclease domain. In some embodiments, the mutation is a point mutation. In some embodiments, the mutation is a deletion. In some embodiments, the mutation is an insertion. In some embodiments, the mutation abrogates the ORF2 endonuclease (nickase) activity. In some embodiments, a mutation inactivates the DNA target recognition of ORF2p endonuclease. In some embodiments, the mutation covers a region associated with ORF2p nuclease-DNA recognition. In some embodiments, a mutation reduces the DNA target recognition of ORF2p endonuclease. In some embodiments, the ORF2p endonuclease domain mutation is in the N-terminal region of the protein. In some embodiments, the ORF2p endonuclease domain mutation is in a conserved region of the protein. In some embodiments, the ORF2p endonuclease domain mutation is in the conserved N-terminal region of the protein. In some embodiments, the mutation comprises the N14 amino acid within L1 endonuclease domain. In some embodiments, the mutation comprises 2, 3, 4, 5, 6, 7, 8, 9, 10, 11, 12, 13, 14, 15, 16, 17, 18, 19, 20 or more consecutive amino acids including the N14 amino acid within L1 endonuclease domain. In some embodiments, the mutation comprises the comprises the E43 amino acid within L1 endonuclease. In some embodiments, the mutation comprises 2, 3, 4, 5, 6, 7, 8, 9, 10, 11, 12, 13, 14, 15, 16, 17, 18, 19, 20 or more consecutive amino acids including the E43 amino acid within L1 endonuclease domain. In some embodiments, the mutation comprises 2 or more amino acids in the L1 endonuclease domain including N14, or E43 or a combination thereof. In some embodiments, the mutation comprises D145 of the L1 endonuclease domain. In some embodiments, the mutation may be D145A. In some embodiments, the may be a comprise D205 of the L1 endonuclease domain. In some embodiments, the mutation may be D205G. In some embodiments, the mutation may comprise H230 of L1 endonuclease domain. In some embodiments, the may be a comprise S228 of the L1 endonuclease domain. In some embodiments, the mutation may be S228P.

In some embodiments, a mutation reduces the DNA target recognition of ORF2p endonuclease by at least 50%. In some embodiments, a mutation reduces the DNA target recognition of ORF2p endonuclease by at least 60%. In some embodiments, a mutation reduces the DNA target recognition of ORF2p endonuclease by at least 70%. In some embodiments, a mutation reduces the DNA target recognition of ORF2p endonuclease 80%. In some embodiments, a mutation reduces the DNA target recognition of ORF2p endonuclease 90%. In some embodiments, a mutation reduces the DNA target recognition of ORF2p by 95%. In some embodiments, a mutation reduces the DNA target recognition of ORF2p by 100%.

In some embodiments, the mutation is a deletion. In some embodiments, the deletion is complete, i.e., 100% of the L1 endonuclease domain is deleted. In some embodiments, the deletion is partial. In some embodiments, the about 98%, about 95%, about 94%, about 93%, about 92% about 91%, about 90%, about 85%, about 80%, about 75%, about 70%, about 65%, about 60%, or about 50% of the ORF2 endonuclease domain is deleted.

In some embodiments, an additional nuclease domain is inserted into the ORF2 protein sequence. In some embodiments, ORF2 endonuclease domain is deleted, and is replaced with an endonuclease domain from a heterologous protein. In some embodiments, the ORF2 endonuclease is partially deleted and replaced with an endonuclease domain from a heterologous protein. The endonuclease domain from a heterologous protein may be a mega-TAL nuclease domain. The endonuclease domain from a heterologous protein may be a TALENs. The endonuclease domain from a heterologous protein may be a Cas9 loaded with a specific gRNA for a locus.

In some embodiments, the endonuclease is an endonuclease that has (i) a specific target on the genome and (ii) it creates a 5'-P and a 3'-OH terminus at the cleavage site.

In some embodiments, the additional endonuclease domain from a heterologous protein is an endonuclease domain from a related retrotransposon.

In some embodiments, the endonuclease domain from a heterologous protein may comprise a bacterial endonuclease engineered for targeting a specific site. In some embodiments, the endonuclease domain from a heterologous protein may comprise a domain of a homing endonuclease or a fragment thereof. In some embodiments, the endonuclease is a homing endonuclease. In some embodiments, the homing endonuclease is an engineered LAGLIDADG (SEQ ID NO: 62) homing endonucleases (LHEs) or a fragment thereof. In some embodiments, additional endonucleases may be a restriction endonuclease, Cre, Cas TAL or fragments thereof. In some embodiments, the endonuclease may comprise a Group II intron encoded protein (ribozyme) or a fragment thereof.

An engineered or modified L1-ORF2p as discussed in the preceding paragraphs, that is endowed with specific DNA targeting capability due to the additional/heterologous endonuclease is expected to be highly advantageous in driving targeted stable integration of a transgene into the genome.

The engineered L1-ORF2p can generate much reduced off-target effects when expressed in a cell than using a native, non-engineered L1-ORF2p. In some embodiments, the engineered L1-ORF2p generates no off-target effect.

In some embodiments, the engineered or modified L1-ORF2p targets a recognition site that is other than the usual $(Py)_n\downarrow(Pu)_n$ site. In some embodiments, engineered L1-ORF2p targets a recognition site that comprises the $(Py)_n\downarrow(Pu)_n$ site, for example, TTTT/AA site, such as a hybrid target site. In some embodiments, the engineered L1-ORF2p targets a recognition site having at least one nucleotide in addition to the conventional L1-ORF2 $(Py)_n\downarrow$ $(Pu)_n$ site, for example TTTT/AAG, or TTTT/AAC, or TTTT/AAT, TTTT/AAA, GTTTT/AA, CTTTT/AA, ATTTT/AA, or TTTTT/AA. In some embodiments, the engineered L1-ORF2p targets a recognition site that is in addition to the conventional L1-ORF2p $(Py)_n\downarrow(Pu)_n$ site. In some embodiments, the engineered L1-ORF2p targets a recognition site that is other than to the conventional L1-ORF2p $(Py)_n\downarrow(Pu)_n$ site. In some embodiments, the engineered L1-ORF2p targets a recognition site that is 4, 5, 6, 7, 8, 9, 10 or more nucleotides long. In some embodiments, the engineered or modified L1-ORF2p recognition site may be 11, 12, 13, 14, 15, 16, 17, 18, 19, 20 or more nucleotides.

The engineered L1-ORF2p can be engineered to retain its ability to bind to its own mRNA after translation and reverse transcribe with high efficiency. In some embodiments, the engineered L1-ORF2p has enhanced efficiency of reverse transcription compared to a native (WT) L1-ORF2p.

In some embodiments, the system comprising a retrotransposable element further comprises a gene modification that reduces non-specific retrotransposition. In some embodiments, the gene modification may comprise a sequence encoding the L1-ORF2p. In some embodiments, the modification may comprise mutation of one or more amino acids that are essential for binding to a protein that helps ORF2p binding to the target genomic DNA. A protein that helps ORF2p binding to the target genomic DNA may be part of the chromatin-ORF interactome. In some embodiments, the modification may comprise one or more amino acids that are essential for binding to a protein that helps ORF2p DNA endonuclease activity. In some embodiments, the modification may comprise one or more amino acids that are essential for binding to a protein that helps ORF2p RT activity. In some embodiments, the modification may comprise at a protein binding site on ORF2p such that the association of a protein with ORF2p is altered, wherein binding of the protein to ORF2p is required for binding to chromatin. In some embodiments, the modification may comprise at a protein binding site on ORF2p such that the association of the protein with ORF2p is more stringent and/or specific than in absence of the modification. In some embodiments, as a consequence of altered association of ORF2p with the protein owing to the modification of ORF2p coding sequence at the protein binding site, the binding of ORF2p to the target DNA has increased specificity. In some embodiments, the modification may reduce binding of ORF2 to one or more proteins that are part of the ORF2p chromatin interactome.

In some embodiments, the gene modification may be in the PIP domain of ORF2p.

In some embodiments, the gene modification may be in one or more genes encoding a protein that binds to an ORF2p and helps in the recognition, binding, endonuclease or RT activity of ORF2p. In some embodiments, the gene modification may be in one or more genes encoding PCNA, PARP1, PABP, MCM, TOP1, RPA, PURA, PURB, RUVBL2, NAP1, ZCCHC3, UPF1 or MOV10 proteins at an ORF2p interacting site for each protein or at a site that affects the protein's interaction with ORF2p or the interaction of ORF2p with target DNA. In some embodiments, the modification may be on an ORF2p binding domain of PCNA at an ORF2p interacting site or at a site that affects the protein's interaction with ORF2p or the interaction of ORF2p with target DNA. In some embodiments, the modification may be on an ORF2p binding domain of TOP1. In some embodiments, the modification may be on an ORF2p binding domain of RPA. In some embodiments, the modification may be on an ORF2p binding domain of PARP1 at an ORF2p interacting site or at a site that affects the protein's interaction with ORF2p or the interaction of ORF2p with target DNA. In some embodiments, the modification may be on an ORF2p binding domain of PABP (e.g., PABPC1) at an ORF2p interacting site or at a site that affects the protein's interaction with ORF2p or the interaction of ORF2p with target DNA. In some embodiments, the gene modification may be on an MCM gene. In some embodiments, the gene modification may be on a gene encoding MCM3 protein at an ORF2p interacting site or at a site that affects the protein's interaction with ORF2p or the interaction of ORF2p with target DNA. In some embodiments, the gene modification may be on a gene encoding MCM5 protein at an ORF2p interacting site or at a site that affects the protein's interaction with ORF2p or the interaction of ORF2p with target DNA. In some embodiments, the gene modification may be on a gene encoding MCM6 protein at an ORF2p interacting site or at a site that affects the protein's interaction with ORF2p or the interaction of ORF2p with target DNA. In some embodiments, the gene modification may be on a gene encoding MEPCE protein at an ORF2p interacting site or at a site that affects the protein's interaction with ORF2p or the interaction of ORF2p with target DNA. In some embodiments, the gene modification may be on a gene encoding on a gene encoding RUVBL1 or RUVBL2 protein at an ORF2p interacting site or at a site that affects the protein's interaction with ORF2p or the interaction of ORF2p with target DNA. In some embodiments, the gene modification may be on a gene encoding on a gene encoding TROVE protein at an ORF2p interacting site or at a site that affects the protein's interaction with ORF2p or the interaction of ORF2p with target DNA.

In some embodiments, the retrotransposition system disclosed herein comprises one or more elements that increase the fidelity of reverse transcription.

In some embodiments, the L1-ORF2 RT domain is modified. In some embodiments, the modification includes one or more of: increasing fidelity, increasing processivity, increasing DNA-RNA substrate affinity; or inactivating RNase H activity.

In some embodiments, the modification comprises introducing one or more mutations in the RT domain of the L1-ORF2, such that the fidelity of the RT is increased. In some embodiments, the mutation comprises a point mutation. In some embodiments, the mutation comprises alteration, such as substitution of one, two three, four, five, six or more amino acids in the L1-ORF2p RT domain. In some embodiments, the mutation comprises deletion of one or more amino acids, for example, one, two, three, four, five, six, seven, eight, nine, ten or more amino acids in the L1-ORF2p RT domain. In some embodiments, the mutation may comprise an in-del mutation. In some embodiments, the mutation may comprise a frame-shift mutation.

In some embodiments, the modification may comprise inclusion of an additional RT domain or fragment thereof from a second protein. In some embodiments, the second protein is a viral reverse transcriptase. In some embodiments, the second protein is a non-viral reverse transcriptase. In some embodiments, the second protein is a retrotransposable element. In some embodiments, the second protein is a non-LTR retrotransposable element. In some embodiments, the second protein is a group II intron protein. In some embodiments, the group II intron is as TGIRTII. In some embodiments, the second protein is a Cas nickase, wherein the retrotransposable system further comprises introducing a guide RNA. In some embodiments, the second protein is a Cas9 endonuclease, wherein the retrotransposable system further comprises introducing a guide RNA. In some embodiments, the second protein or fragment thereof is fused to the N-terminus of the L1-ORF2 RT domain or the modified L1-ORF2 RT domain. In some embodiments, the second protein or fragment thereof is fused to the C-terminus of the L1-ORF2 RT domain or the modified L1-ORF2 RT domain.

In some embodiments, the additional RT domain or fragment thereof from the second protein is incorporated in the retrotransposition system in addition to the full-length WT L1-ORF2p RT domain. In some embodiments, the additional RT domain or fragment thereof from the second protein is incorporated in presence of a modified (engineered) L1-ORF2p RT domain or a fragment thereof, where the modification (or engineering) may comprise a mutation for enhancement of the L1-ORF2p RT processivity, stability and/or fidelity of the modified L1-ORF2p RT compared to the native or WT ORF2p.

In some embodiments, the reverse transcriptase domain could be replaced with other more highly processive and high-fidelity RT domains from other retroelements or group II introns, such as TGIRTII.

In some embodiments, the modification may comprise a fusion with an additional RT domain or fragment thereof from a second protein. In some embodiments, the second protein may comprise a retroelement. The additional RT domain or fragment thereof from a second protein is configured to increase the fidelity of reverse transcription of the fused L1-ORF2p RT domain. In some embodiments, the nucleic acid encoding the additional RT domain or fragment thereof is fused to a native or WT L1-ORF2 encoding sequence. In some embodiments, the nucleic acid encoding the additional RT domain or fragment thereof from a second protein is fused to a modified L1-ORF2 encoding sequence. In some embodiments, the modification comprises introducing one or more mutations in the RT domain of the L1-ORF2 or fragment thereof, such that the fidelity of the fused RT is increased. In some embodiments, the mutation in the RT domain of the L1-ORF2 or fragment thereof comprises a point mutation. In some embodiments, the mutation comprises alteration, such as substitution of one, two three, four, five, six or more amino acids in the L1-ORF2p RT domain. In some embodiments, the mutation comprises deletion of one or more amino acids, for example, one, two, three, four, five, six, seven, eight, nine, ten or more amino acids in the L1-ORF2p RT domain. In some embodiments, the mutation may comprise an in-del mutation. In some embodiments, the mutation may comprise a frame-shift mutation.

In some embodiments, the modified L1-ORF2p RT domain has increased processivity than the WT L1-ORF2p RT domain.

In some embodiments, the modified L1-ORF2p RT domain has at least 10% higher processivity and/or fidelity over the WT L1-ORF2p RT domain. In some embodiments, the modified L1-ORF2p RT domain has at least 20%, 30%, 40%, 50%, 60%, 70%, 80%, 90%, 100%, 110%, 120%, 150%, 200%, 300%, 400%, 500%, 1000% or higher processivity and/or fidelity over the WT L1-ORF2p RT domain. In some embodiments, the modified RT can process greater than 6 kb nucleic acid stretch. In some embodiments, the modified RT can process greater than 7 kb nucleic acid stretch. In some embodiments, the modified RT can process greater than 8 kb nucleic acid stretch. In some embodiments, the modified RT can process greater than 9 kb nucleic acid stretch. In some embodiments, the modified RT can process greater than 10 kb nucleic acid stretch.

B. Group II Introns and Ribozymes

Group II enzymes are mobile ribozymes that self-splice precursor RNAs, yielding excised intron lariat RNAs. The introns encode a reverse transcriptase. The reverse transcriptase may stabilize the RNA for forward and reverse splicing, and later in converting the integrated intron RNA to DNA.

Group II RNAs are characterized by a conserved secondary structure spanning 400-800 nucleotides. The secondary structure is formed by six domains DI-VI, and is organized in a structure resembling a wheel, where the domains radiate from a central point. The domains interact to form a conserved tertiary structure that brings together distant sequences to form an active site. The active site binds the splice sites and branch point residue nucleotide and in association of Mg2+ cations, activate catalysis of splicing. The DV domain is within the active site, which has the conserved catalytic AGC and an AY bulge and both these regions bind Mg2+ ions necessary for the catalysis. DI is the largest domain with upper and lower halves separated by kappa and zeta motifs. The lower half contains the ε' motif, which is associated with an active site. The upper half contains sequence elements that bind to the 5' and 3' exons at the active sites. DIV encodes the intron-encoded protein (IEP) with subdomain IVa near the 5'-end containing the high affinity binding site for IEP. Group II introns have conserved 5'- and 3'-end sequences, GUGYG and AY respectively.

Group II RNA introns can be utilized to retrotranspose a sequence of interest into DNA via target primed reverse transcription. This process of transposition by Group II RNA introns is often referred to as retrohoming. Group II introns recognize DNA target sites by base pairing of the intron RNA to the DNA target sequence, they can be modified to retarget a specific sequence carried within the intron to a desired DNA site.

In some embodiments, the method and compositions for retrotransposition described herein may comprise a Group II intron sequence, a modified Group II intron sequence or a fragment thereof. Exemplary Group II IEPs (maturase) include but are not limited to bacterial, fungal, yeast IEPs, that are functional in human cells. In particular, the nuclease leaves a 3'-OH at the cleavage site of the DNA which can be utilized by another RT for priming and reverse transcription. An exemplary Group II maturase may be TGIRT (thermally stable group II intron maturase).

In one or more embodiments of several aspects described herein, the nucleic acid construct comprises an RNA. In one or more embodiments of several aspects of the disclosure, the nucleic acid construct is an RNA. In one or more embodiments of several aspects of the disclosure, the nucleic acid construct is an mRNA. In one aspect, the mRNA comprises a sequence of a heterologous gene or portion thereof, wherein the heterologous gene or portion thereof encodes a polypeptide or protein. In some embodiments, the mRNA comprises a sequence encoding a fusion protein. In some embodiments, the mRNA comprises a sequence encoding a recombinant protein. In some embodiments, the mRNA comprises a sequence encoding a synthetic protein. In some embodiments, the nucleic acid comprises one or more sequences, wherein the one or more sequences encode on or more heterologous proteins, one or more recombinant proteins, or one or more synthetic proteins or a combination thereof. In some embodiments, the nucleic acid comprises one or more sequences, wherein the one or more sequences encode on or more heterologous proteins comprising a synthetic protein or a recombinant protein. In some embodiments, the synthetic or recombinant protein is a recombinant fusion protein.

In one or more of embodiments of several aspects of the disclosure, the nucleic acid construct is developed for expressing in a eukaryotic cell. In some embodiments, the nucleic acid construct is developed for expressing in a human cell. In some embodiments, the nucleic acid construct is developed for expressing in a hematopoietic cell. In some embodiments, the nucleic acid construct is developed for expressing in a myeloid cell. In some embodiments, the myeloid cell is a human cell.

II. Modifications in Nucleic Acid Constructs for Methods of Enhancement of Expression of Encoded Protein In some aspects of the disclosure, the recombinant nucleic acid is modified for enhanced expression of the protein encoded by a sequence of the nucleic acid. Enhanced expression of the protein encoded therein can be a function of the nucleic acid stability, translation efficiency and the stability of the translated protein. A number of modifications are contemplated herein for incorporation in the design of the nucleic acid construct that can confer nucleic acid stability, such as stability of the messenger RNA encoding the exogenous or heterologous protein, which may be a synthetic recombinant protein or a fragment thereof.

In some embodiments, the nucleic acid is mRNA, comprising one or more sequences, wherein the one or more sequences encode one or more heterologous proteins comprising a synthetic or a recombinant fusion protein.

In some embodiments, one or more modifications are made in the mRNA comprising a sequence encoding a recombinant or fusion protein to increase the mRNA half-life.

Structural Elements to Block 5'- and 3'-Degradations by Exonucleases: 5'-Cap and 3' UTR Modifications A proper 5'-cap structure is important in the synthesis of functional messenger RNA. In some embodiments, the 5'-cap comprises a guanosine triphosphate arranged as GpppG at the 5'terminus of the nucleic acid. In some embodiments, the mRNA comprises a 5' 7-methylguanosine cap, m7-GpppG. A 5' 7-methylguanosine cap increases mRNA translational efficiency and prevents degradation of mRNA 5'-3'exonucleases. In some embodiments, the mRNA comprises "anti-reverse" cap analog (ARCA, m$^{7,3'}$-₀GpppG). Translational efficiency, however, can be markedly increased by usage of the ARCA. In some embodiments, the guanosine cap is a Cap 0 structure. In some embodiments, the guanosine cap is a Cap 1 structure. In addition to its essential role of cap-dependent initiation of protein synthesis, the mRNA cap also functions as a protective group from 5' to 3' exonuclease cleavage and a unique identifier for recruiting protein factors for pre-mRNA splicing, polyadenylation and nuclear export. It acts as the anchor for the recruitment of initiation factors that initiate protein synthesis and the 5' to 3' looping of mRNA during translation. Three enzymatic activities are required to generate the Cap 0 structure, namely, RNA triphosphatase (TPase), RNA guanylyltransferase (GTase) and guanine-N7 methyltransferase (guanine-N7 MTase). Each of these enzyme activities carries out an essential step in the conversion of the 5' triphosphate of nascent RNA to the Cap 0 structure. RNA TPase removes the γ-phosphate from the 5' triphosphate to generate 5' diphosphate RNA. GTase transfers a GMP group from GTP to the 5' diphosphate via a lysine-GMP covalent intermediate. The guanine-N7 MTase then adds a methyl group to the N7 amine of the guanine cap to form the cap 0 structure. For Cap 1 structure, m7G-specific TO methyltransferase (TO MTase) methylates the +1 ribonucleotide at the 2'O position of the ribose to generate the cap 1 structure. The nuclear RNA capping enzyme interacts with the polymerase subunit of RNA polymerase II complex at phosphorylated Ser5 of the C-terminal heptad repeats. RNA guanine-N7 methyltransferase also interacts with the RNA polymerase II phosphorylated heptad repeats. In some embodiments, the cap is a G-quadruplex cap.

In some embodiments, the mRNA is synthesized by in vitro transcription (IVT). In some embodiments, mRNA synthesis and capping may be performed in one step. Capping may occur in the same reaction mixture as IVT. In some embodiments, mRNA synthesis and capping may be performed in separate steps. mRNA thus formed by IVT is purified and then capped.

In some embodiments, the nucleic acid construct, e.g., the mRNA construct, comprises one or more sequences encoding a protein or a polypeptide of interest can be designed to comprise elements that protect, prevent, inhibit or reduce degradation of the mRNA by endogenous 5'-3' exoribonucleases, for example, Xrn1. Xrn1 is a cellular enzyme in the normal RNA decay pathways that degrades 5' monophosphorylated RNAs. However, some viral RNA structural elements are found to be particularly resistant to such RNases, for example, the Xrn1-resistant structure in flaviviral sfRNAs, called the 'xrRNA'. For example, the mosquito-borne flaviviruses (MBFV) genomes contain discrete RNA structures in their 3'-untranslated region (UTR) that block the progression of Xrn1. These RNA elements are sufficient to block Xrn1 without the use of accessory proteins. xrRNAs halt the enzyme at a defined location such that the viral RNA located downstream of the xrRNAs is protected from degradation. The xrRNAs from Zika virus or Murray Valley encephalitis virus, for example, comprise three-way junction and multiple pseudoknot interactions that create an unusual and complex fold that requires a set of nucleotides conserved across the MBFVs structure. xrRNAs halt the enzyme at a defined location such that the viral RNA located downstream of the xrRNAs is protected from degradation. The 5'-end of the RNA passes through a ring-like structure of the fold and is believed to remain protected from the Xrn1-like exonuclease.

In some embodiments, the nucleic acid construct comprising the one or more sequences that encode a protein of interest may comprise one or more xrRNA structures incorporated therein. In some embodiments, the xrRNA is a stretch of nucleotides having the conserved regions of the 3' UTR of one or more viral xrRNA sequences. In some embodiments, 1, 2, 3, 4, 5, 6, 7, 8, 9, 10 or more xrRNA elements are incorporated within the nucleic acid construct. In some embodiments, 2 or more xrRNA elements are incorporated in tandem within the nucleic acid construct. In some embodiments, the xrRNA comprise one or more regions comprising conserved sequences or fragments thereof or modifications thereof. In some embodiments, the xrRNA is placed at the 3'UTR of a retrotransposon element. In some embodiments, the xrRNA is placed at upstream of the sequences encoding the one or more proteins or poly-peptides. In some embodiments, the xrRNA is placed in the 3'UTR of a retrotransposon element, such as an ORF2 sequence, and upstream of the sequences encoding the one or more proteins or polypeptides.

In some embodiments, the xrRNA structure comprises a MBFV xrRNA sequence, or a sequence that is at least 90% identical thereof. In some embodiments, the xrRNA struc-ture comprises a tick-borne flaviviruses (TBFVs) xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a xrRNA sequence from a member of no known arthropod vector flaviviruses (NKVFVs), or a sequence that is at least 90% identical thereof. In some embodiments, the xrRNA structure com-prises a xrRNA sequence from a member of insect-specific flaviviruses (ISFVs), or a sequence that is at least 90% identical thereof. In some embodiments, the xrRNA struc-ture comprises a Zikavirus xrRNA sequence, or a sequence that is at least 90% identical thereof. It is hereby contem-plated that any known xrRNA structural elements or con-ceivable non-obvious variations thereof may be used for the purpose described herein.

Several messenger RNAs from different organisms exhibit one or more pseudoknot structures that exhibits resistance from 5'-3' exonuclease. A pseudoknot is a RNA structure that is minimally composed of two helical seg-ments connected by single-stranded regions or loops. Although several distinct folding topologies of pseudoknots exist.

Poly a Tail Modifications

The poly A structure in the 3'UTR of an mRNA is an important regulator of mRNA half-life. Deadenylation of the 3' end of the poly A tail is the first step of the intracellular mRNA degradation. In some embodiments, the length of the poly A tail of the mRNA construct is taken into critical consideration and designed for maximizing the expression of the protein encoded by the mRNA coding region, and the mRNA stability. In some embodiments, the nucleic acid construct comprises one or more poly A sequences. In some embodiments, the poly A sequence at the 3'UTR of the sequences encoding the one or more proteins or polypep-tides comprise 20-200 adenosine nucleobases. In some embodiments, the poly A sequence comprises 30-200 adenosine nucleobases. In some embodiments, the poly A sequence comprises 50-200 adenosine nucleobases. In some embodiments, the poly A sequence comprises 80-200 adenosine nucleobases. In some embodiments, the mRNA segment comprising the sequences that encode one or more proteins or polypeptides comprises a 3'-UTR having a poly-A tail comprising about 180 adenosine nucleobases, or about 140 adenosine nucleobases, or about 120 adenosine nucleobases. In some embodiments, the poly A tail com-prises about 122 adenosine nucleobases. In some embodi-ments, the poly A sequence comprises 50 adenosine nucle-obases. In some embodiments, the poly A sequence comprises 30 adenosine nucleobases. In some embodiments, the adenosine nucleobases in the poly A tail are placed in tandem, with or without intervening non-adenosine bases. In some embodiments, one or more non-adenosine nucleobases are incorporated in the poly A tail, which confer further resistance to certain exonucleases.

In some embodiments, the stretch of adenosines in poly A tail of the construct comprises one or more non-adenosine (A) nucleobase. In some embodiments, the non-A nucle-obase is present at −3, −2, −1, and/or +1 position at the poly A 3'-terminal region. In some embodiments, the non-A bases comprise a guanosine (G) or a cytosine (C) or an uracil base (U). In some embodiments, the non-A base is a G. In some embodiments, the non-A base more than one, in tandem, for example, GG. In some embodiments, the modification at the 3' end of the poly A tail with one or more non-A base is directed at disrupting the A base stacking at the poly A tail. The poly A base stacking promotes deadenylation by various deadenylating enzymes, and therefore 3' end of poly A tail ending in -AAAG, -AAAGA, or -AAAGGA are effective in conferring stability against deadenylation. In some organ-isms, a GC sequence intervening a poly A sequence is shown to effectively show down 3'-5' exonuclease mediated decay. A modification contemplated herein comprises an interven-ing non-A residue, or a non-A residue duplex intervening a poly A stretch at the 3'end.

In some embodiments, a triplex structure is introduced in the 3' UTR which effectively stalls or slows down exonu-clease activity involving the 3' end.

In some embodiments, the mRNA with the modifications described above has an extended half-life and demonstrates stable expression over a longer period than the unmodified mRNA. In some embodiments, the mRNA stably expresses for greater than 2 days, 3 days, 4 days, 5 days, 6 days, 7 days, 8 days 9 days or 10 days or more, and the mRNA or its protein product is detectable in vivo. In some embodiments, the mRNA is detected up to 3 days, 4 days, 5 days, 6 days, 7 days, 8 days, 9 days, 10 days, 11 days, 12 days, 13 days, 14 days or 15 days in vivo. In some embodiments, a protein product of the mRNA is detected up to 3 days, 4 days, 5 days, 6 days, 7 days, 8 days, 9 days, 10 days, 11 days, 12 days, 13 days, 14 days, 15 days, 16 days, 17 days, 18 days, 20 days, 25 days or 30 days in vivo.

CircRNA and tectoRNA

Figure 3A:
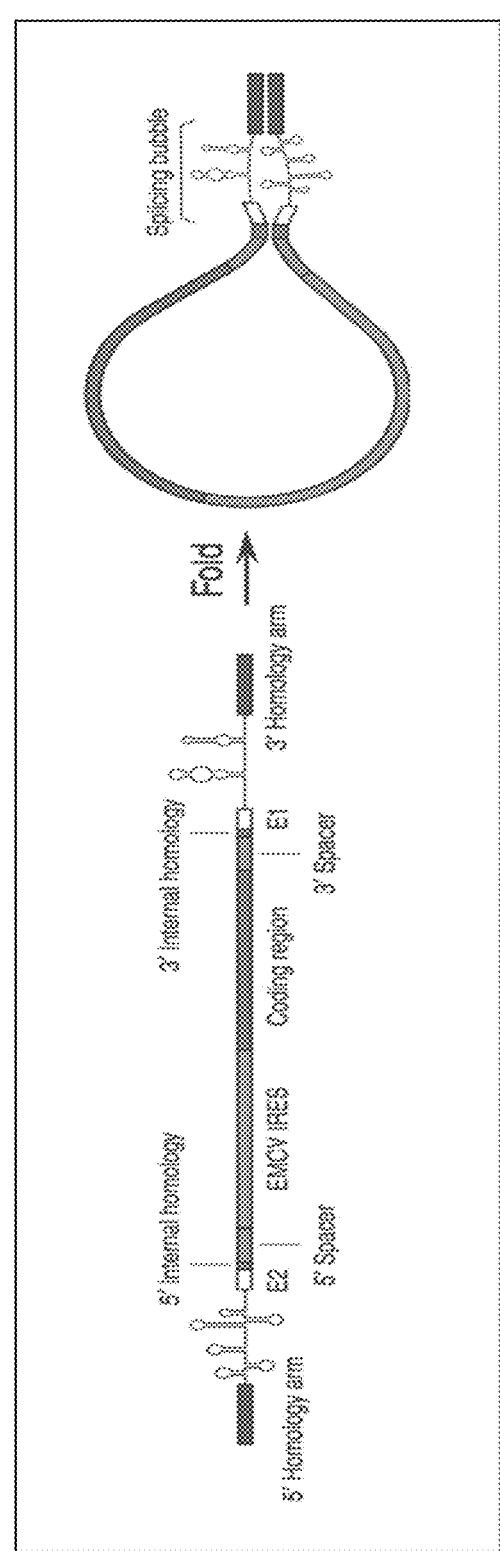
FIG. 3A illustrates an exemplary diagram of conventional circRNA structure and formation.

Circular RNA is useful in the design and production of stable form of RNA used as a messenger RNA to direct synthesis protein chains, such as long, multiply repeating protein chains. There are few methods to make circular RNA (circRNA). They include protein-mediated ligation of RNA ends using RNA ligase and using a split self-splicing intron, such that if the two halves of the intron are located and the ends of a transcribed mRNA, the intron will splice itself out and leave a ligated product (FIG. 3A). Another technique relies on the ability of T4 DNA ligase to act as an RNA ligase when the RNA ends to be ligated are held together by an oligonucleotide. Both these techniques suffer from inef-ficiency and require a large amount of enzyme. A third technique uses the cyclization or circularization activity of group I introns where most of the intron sequences that carry out the reaction must remain a part of the circle. Group I introns share a complex set of secondary and tertiary struc-tures containing a series of conserved RNA stem loops which form the catalytic core. Many of these introns are self-splicing in vitro and can splice and form two ligated exons as RNA with no accessory protein factors. The products created by the group I autocatalytic reaction are (1) an upstream exon ligated at the 5' splice site to the 3' splice site of a downstream exon and (2) a linear intron that can undergo further reversible auto-catalysis to form a circular intron. The presence of such a large highly structured nucleic acid sequence severely limits the types of RNA sequences that can be made circular by that technique. In addition, the catalytic activity of the intron may remain and interfere with structure and function of the circular RNA.

It is useful to increase the rate of the reaction, and thus the overall efficiency, by bringing the ends of the RNA in closer proximity. Previous work has achieved this by including complementary RNA sequences 3' and 5' to the ends of the mRNA such that upon hybridization of these sequences, the ends of the mRNA are in closer proximity such that it can undergo the ligation or self-splicing reaction with an overall faster rate compared to without the complementary sequences. These are called homology arms (FIG. 3A) of the self-splicing version of the circularization reaction. A major issue with such hybridization strategy is that if there are complementary sequences within the coding region to either of the homology arms, hybridization would actually inhibit the splicing reaction and the arms would need to be optimized for each new coding region. An alternative to this strategy described herein is the use of RNA sequences that fold a three-dimensional structure to form a stable binding interaction that is independent of sequence.

Non-Watson-Crick RNA tertiary interactions can be exploited to construct 'tectoRNA' molecular units, defined as RNA molecules capable of self-assembly. The use of such type of tertiary interactions allows one to control and modulate the assembly process by manipulating cation concentration (e.g. $Mg^{2+}$), and/or suitable temperature and employing modularly designed 'selector' RNA molecules. For the self-assembly of one-dimensional arrays, a basic modular unit was designed that comprises a 4-way junction with an interacting module on each helical arm. In some embodiments, the interacting module is a GAAA loop or a specific GAAA loop receptor. Each tectoRNA can interact with two other tectoRNAs via the formation of four loop-receptor interactions, two with each partner molecule.

In some embodiments, the tectoRNA structures are suitably selected, and integrated in the RNA comprising the exon and intron to form a circRNA. In some embodiments, the integration is done by well-known molecular biology techniques such as ligation. In some embodiments, the tectoRNA forms a stable structure at high temperatures. The tectoRNA structure do not compete with internal RNA sequences, thereby creating high efficiency circularization and splicing.

The circRNA can comprise a coding sequence described in any of the preceding sections. For example, it can comprise a sequence encoding fusion protein comprising a tethering or a receptor molecule. The receptor can be a phagocytic receptor fusion protein.

In some embodiments, the intron is a self-splicing intron.

In some embodiments, the terminal regions having the tertiary structures, also termed scaffolding regions for the circRNA, are about 30 nucleotides to about 100 nucleotides long. In some embodiments, the tertiary structure motif is about 45 nucleotides, about 50 nucleotides, about 55 nucleotides, about 60 nucleotides, about 65 nucleotides, about 70 nucleotides or about 75 nucleotides long. In some embodiments, the tertiary motifs are formed at high temperatures. In some embodiments, the tertiary motifs are stable.

In some embodiments, the nucleic acid construct having the one or more modifications as described herein and comprising one or more sequences encoding one or more proteins or polypeptides, is stable when administered in vivo. In some embodiments, the nucleic acid is an mRNA. In some embodiments, the mRNA comprising one or more sequences encoding one or more proteins or polypeptides is stable in vivo for more than 2 days, for more than 3 days, more than 4 days, more than 5 days, more than 6 days, more than 7 days, more than 8 days, more than 9 days, more than 10 days, more than 11 days, more than 12 days, more than 13 days, more than 14 days, more than 15 days, more than 16 days, more than 17 days, more than 18 days, more than 19 days, or more than 20 days. In some embodiments, the protein encoded by the sequences in the mRNA can be detected in vivo at greater than 3 days, 4 days, 5 days, 6 days, 7 days, 8 days, 9 days, 10 days, 11 days, 12 days, 13 days, 14 days, 15 days, 16 days, 17 days, 18 days, 19 days, or 20 days. In some embodiments, the protein encoded by the sequences in the mRNA can be detected in vivo for about 7 days after the mRNA is administered. In some embodiments, the protein encoded by the sequences in the mRNA can be detected in vivo for about 14 days after the mRNA is administered. In some embodiments, the protein encoded by the sequences in the mRNA can be detected in vivo for about 21 days after the mRNA is administered. In some embodiments, the protein encoded by the sequences in the mRNA can be detected in vivo for about 30 days after the mRNA is administered. In some embodiments, the protein encoded by the sequences in the mRNA can be detected in vivo for more than about 30 days after the mRNA is administered.

In some aspects, enhancing nucleic acid uptake or incorporation within the cell is contemplated for enhancing expression of the retrotransposition. One of the methods include obtaining a homogenous population of cells to initiate incorporation of the nucleic acid, e.g. via transfection, in case of plasmid vector constructs, or via electroporation or any other means that may be used suitably to deliver a nucleic acid molecule into the cell. In some embodiments, cell cycle synchronization may be sought. Cell cycle synchronization may be accomplished by sorting cells for a certain common phenotype. In some embodiments, the cell population may be subjected to a treatment with a reagent that can stall cell cycle progression of all cells at a certain stage. Exemplary reagents can be found in commercial databases, such as tocris(dot)com, or scbt(dot)com. For example, itraconazole or nocodazole inhibits cell cycle at G1 phase, or reagents that arrest cell cycle at G0/G1 phase, for example, 5-[(4-Ethylphenyl)methylene]-2-thioxo-4-thiazolidinone (compound 10058-F4) (Tocris Bioscience); or a G2M cell cycle blocker, such as AZD 5438 (chemical name, 4-[2-Methyl-1-(1-methylethyl)-1H-imidazol-5-yl]-N-[4-(methylsulfonyl)phenyl]-2-pyrimidinamine) which blocks cell cycle at G2M, G1 or S phases, to name a few. Cyclosporin, hydroxyurea, thymidine, are well known reagents that can cause cell cycle arrests. Some reagents may irreversibly alter a cell state or may be toxic for the cells. Serum deprivation of cells for about 2-16 hours prior to electroporation or transfection, depending on the cell type, may also be an easy and reversible strategy for cell synchronization.

In some embodiments, retrotransposition efficiency may be increased by encouraging generation of DNA double stranded breaks to a cell that has been transfected with or electroporated with the retrotransposition constructs as described herein and/or modulating the DNA repair machinery. Application of these techniques may be limited depending on end uses of the cell that would undergo the genetic manipulation ex vivo for stable incorporation of a nucleic acid sequence by this method. In some cases, use of such techniques may be contemplated where robust expression of the protein or transcript encoded by the incorporated nucleic acid is expected as an outcome for a determined period of time. Method of introducing double stranded breaks in a cell include subjecting the cell to controlled ionizing radiation of about 0.1 Gy or less for a short period.

In some embodiments, efficiency of LINE-1 mediated retrotransposition may be increased by treating the cell with small molecule inhibitors of DNA repair proteins to increase the window for the reverse transcriptase to act. Exemplary small molecule inhibitors of DNA repair proteins may be Benzamide (CAS 55-21-0), Olaparib (Lynparza) (CAS 763113-22-0), Rucaparib (Clovis—AG014699, PF-01367338 Pfizer), Niraparib (MK-827 Tesaro) CAS 1038915-60-4); Veliparib (ABT-888 Abbvie) (CAS 912444-00-9); Camptothecin (CPT) (CAS 7689-03-4); Irinotecan (CAS 100286-90-6); Topotecan (Hycamtin®️ GlaxoSmithKline) (CAS 123948-87-8); NSC 19630 (CAS 72835-26-8); NSC 617145 (CAS 203115-63-3); ML216 (CAS 1430213-30-1); 6-hydroxyDL-dopa (CAS 21373-30-8); D-103; D-G23; DIDS (CAS 67483-13-0); B02 (CAS 1290541-46-6); RI-1 (CAS 415713-60-9); RI-2 (CAS 1417162-36-7); Streptonigrin (SN) (CAS 3930-19-6).

III. Nucleic Acid Cargo:

A. Transgene

In one aspect the transgene or noncoding sequence that is the heterologous nucleic acid sequence to be inserted within the genome of a cell is delivered as an mRNA. The mRNA may comprise greater than about 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000 bases. In some embodiments, the mRNA may be more than 10,000 bases long. In some embodiments, the mRNA may be about 11,000 bases long. In some embodiments, the mRNA may be about 12,000 bases long. In some embodiments, the mRNA comprises a transgene sequence that encodes a fusion protein. In some embodiments, the nucleic acid is delivered as a plasmid.

In some embodiments, the nucleic acid is delivered in the cell by transfection. In some embodiments, the nucleic acid is delivered in the cell by electroporation. In some embodiments, the transfection or electroporation is repeated more than once to enhance incorporation of the nucleic acid into the cell.

Contemplated herein are retrotransposon mediated stable integration of a recombinant nucleic acid encoding a phagocytic or tethering receptor (PR) fusion protein (CFP). In some embodiments, the CFPs comprise: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked.

In some embodiments, the nucleic acid comprises a sequence encoding a chimeric fusion protein (CFP), the CFP comprising an extracellular domain comprising a CD5 binding domain, and a transmembrane domain operatively linked to the extracellular domain. In some embodiments, the CD5 binding domain is a CD5 binding protein, such as an antigen binding fragment of an antibody, a Fab fragment, an scFv domain or an sdAb domain. In some embodiments, wherein the CD5 binding domain comprises an scFv comprising (i) a variable heavy chain (VH) sequence with at least 90% sequence identity to EIQLVQSGG-GLVKPGGSVRISCAASGYTFTNYGMNWVRQAPGK-GLEWMGWINTHTGEPTYAD SFKGRFTFSLDDSKN-TAYLQINSLRAEDTAVYFCTRRGYDWYFDVWGQGT TVTV (SEQ ID NO: 63); and (ii) a variable light chain (VL) sequence with at least 90% sequence identity to DIQMTQSPSSLSASVGDRVTITCRASQDIN-SYLSWFQQKPGKAPKTLIYRANRLESGVPSRFSGSG SGTDYTLTISSLQYEDFGIYYCQQYDESPWTFGGGT KLEIK (SEQ ID NO: 64). In some embodiments, the CFP further comprises an intracellular domain, wherein the intracellular domain comprises one or more intracellular signaling domains, and wherein a wild-type protein comprising the intracellular domain does not comprise the extracellular domain. In some embodiments, the one or more intracellular signaling domains comprises a phagocytic signaling domain. In some embodiments, the phagocytosis signaling domain comprises an intracellular signaling domain derived from a receptor other than Megf10, MerTk, FcaR, and Bai1. In some embodiments, the phagocytosis signaling domain comprises an intracellular signaling domain derived from FcγR, FcαR or FcεR. In some embodiments, the phagocytosis signaling domain comprises an intracellular signaling domain with at least 90% sequence identity to LYCRRLKIQVRKAAITSYEKSDGVYTGLSTRNQETY-ETLKHEKPP (SEQ ID NO: 65). In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence with at least 90% sequence identity to YEDMRGILYAAPQLRSIRGQPGPNHEEDADSYENM (SEQ ID NO: 66). In some embodiments, the proinflammatory signaling domain is derived from an intracellular signaling domain of CD40. In some embodiments, the proinflammatory signaling domain comprises a sequence with at least 90% sequence identity to KVAKKPTNKAPHPKQEPQEINFPDDLPGSN-TAAPVQETLHGCQPVTQEDGKESRISVQERQ (SEQ ID NO: 67). In some embodiments, the transmembrane domain comprises a CD8 transmembrane domain. In some embodiments, the transmembrane domain comprises a sequence with at least 90% sequence identity to IYI-WAPLAGTCGVLLLSLVIT (SEQ ID NO: 68). In some embodiments, the extracellular domain further comprises a hinge domain derived from CD8, wherein the hinge domain is operatively linked to the transmembrane domain and the CD5 binding domain. In some embodiments, the extracellular domain comprises a sequence with at least 90% sequence identity to ALSNSIMYFSHFVPVFLPAKPTTT-PAPRPPTPAPTIASQPLSLRPEACRPAAGGAVHTRGLD (SEQ ID NO: 69). In some embodiments, the CFP comprises an extracellular domain comprising a scFv that specifically binds CD5, and a hinge domain derived from CD8; a hinge domain derived from CD28 or at least a portion of an extracellular domain from CD68; a CD8 transmembrane domain, a CD28 transmembrane domain or a CD68 transmembrane domain; and an intracellular domain comprising at least two intracellular signaling domains, wherein the at least two intracellular signaling domains comprise: a first intracellular signaling domain derived from FcγR or FcεR, and a second intracellular signaling domain comprising a PI3K recruitment domain, or derived from CD40. In some embodiments, the recombinant polynucleic acid is an mRNA or circRNA. In some embodiments, the nucleic acid is delivered into a myeloid cell. In some embodiments, the nucleic acid is delivered into a CD14+ cell, a CD14+CD16- cell, an M0 macrophage, an M2 macrophage, an M1 macrophage or a mosaic myeloid cell/macrophage. In some embodiments, the fusion protein comprises a sequence with at least 90% sequence identity to EIQLVQSGG-GLVKPGGSVRISCAASGYTFTNYGMNWVRQAPGK-

81

GLEWMGWINTHTGEPTYAD SFKGRFTFSLDDSKN-TAYLQINSLRAEDTAVYFCTRRGYDWYFDVWGQGT TVTVSSGGGGSGG GGSGGGGSDIQMTQSPSSL-SASVGDRVTITCRASQDIN-SYLSWFQQKPGKAPKTLIYRANRLESG VPSRFSGSGSGTDYTLTISSLQYEDFGIYYCQQYDES PWTFGGGTKLEIKSGGGGSGALSNSIMYF SHFVPVFLPAKPTTTPAPRPPTPAPTIA-SQPLSLRPEACRPAAGGAVHTRGLDIYI-WAPLAGTCGV LLLSLVITLYCRRLKIQVRKAAIT-SYEKSDGVYTGLSTRNQETYETLKHEKPPQGSGSY EDMRGI LYAAPQLRSIRGQPGPNHEEDADSYENM (SEQ ID NO: 70). In some embodiments, the fusion protein comprises a sequence with at least 90% sequence identity to

```
                                    (SEQ ID NO: 71)
EIQLVQSGGGLVKPGGSVRISCAASGYTFTNYGMNWVRQAPGKGLEWMGW

INTHTGEPTYADSFKGRFTFSLDDSKNTAYLQINSLRAEDTAVYFCTRRG

YDWYFDVWGQGTTVTVSSGGGGSGGGGSGGGGSDIQMTQSPSSLSASVGD

RVTITCRASQDINSYLSWFQQKPGKAPKTLIYRANRLESGVPSRFSGSGS

GTDYTLTISSLQYEDFGIYYCQQYDESPWTFGGGTKLEIKSGGGGSGALS

NSIMYFSHFVPVFLPAKPTTTPAPRPPTPAPTIASQPLSLRPEACRPAAG

GAVHTRGLDIYIWAPLAGTCGVLLLSLVITLYCRLKIQVRKAAITSYEKS

DGVYTGLSTRNQETYETLKHEKPPQKKVAKKPTNKAPHPKQEPQEINFPD

DLPGSNTAAPVQETLHGCQPVTQEDGKESRISVQERQ
or
                                    (SEQ ID NO: 72)
EIQLVQSGGGLVKPGGSVRISCAASGYTFTNYGMNWVRQAPGKGLEWMGW

INTHTGEPTYADSFKGRFTFSLDDSKNTAYLQINSLRAEDTAVYFCTRRG

YDWYFDVWGQGTTVTVSSGGGGSGGGGSGGGGSDIQMTQSPSSLSASVGD

RVTITCRASQDINSYLSWFQQKPGKAPKTLIYRANRLESGVPSRFSGSGS

GTDYTLTISSLQYEDFGIYYCQQYDESPWTFGGGTKLEIKSGGGGSGALS

NSIMYFSHFVPVFLPAKPTTTPAPRPPTPAPTIASQPLSLRPEACRPAAG

GAVHTRGLDIYIWAPLAGTCGVLLLSLVITLYCRRLKIQVRKAAITSYEK

SDGVYTGLSTRNQETYETLKHEKPPQKKVAKKPTNKAPHPKQEPQEINFP

DDLPGSNTAAPVQETLHGCQPVTQEDGKESRISVQERQ.
```

In some embodiments, the fusion protein is a transmembrane protein, an intracellular protein or an intracellular protein. In one embodiment the fusion protein is directed to enhancing the function of an immune cell, e.g., a myeloid cell, selected from monocyte, macrophages dendritic cells or precursors thereof. In one embodiment the fusion protein augments a cellular function of an immune cell, such as phagocytosis. The disclosure is not limited by the transgenes that can be expressed using the methods and compositions described. The transgenes indicated in this section are exemplary.

Provided herein are exemplary transgene candidates, for stable integration into the genome of a phagocytic cell. In one embodiment the transgene is a recombinant nucleic acid encoding a phagocytic receptor (PR) fusion protein (CFP). The recombinant nucleic acid has a PR subunit comprising: (i) a transmembrane domain, and (ii) an intracellular domain comprising a phagocytic receptor intracellular signaling domain; and an extracellular antigen binding domain specific to an antigen of a target cell; wherein the transmembrane domain and the extracellular antigen binding domain are operatively linked such that antigen binding to the target by the extracellular antigen binding domain of the fused receptor activated in the intracellular signaling domain of the phagocytic receptor. In some embodiments, the recombinant nucleic acid encodes a chimeric antigen receptor. In some embodiments, the chimeric antigen receptor is a chimeric antigen receptor (phagocytosis) (CAR-P). In some embodiments, the fusion protein is a recombinant protein for locking anti-phagocytic signals. In some embodiments, the fusion protein is a phagocytosis enhancing chimeric protein. In some embodiments, the chimeric protein has intracellular domains comprising active phagocytosis signal transduction domains. In some embodiments, the chimeric protein enhances the phagocytic potential by enhancing the inflammatory potential of the phagocytic cell in which it expresses. In some embodiments, the transgene is designed to express a chimeric protein which is activated by contact with an antigen in a target cell, whereupon the phagocytic cell phagocytoses the target cell and kills the target cell.

The terms "spacer" or "linker" as used in reference to a fusion protein refers to a peptide sequence that joins the protein domains of a fusion protein. Generally, a spacer has no specific biological activity other than to join or to preserve some minimum distance or other spatial relationship between the proteins or RNA sequences. However, in some embodiments, the constituent amino acids of a spacer can be selected to influence some property of the molecule such as the folding, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. The linker is used to separate two antigenic peptides by a distance sufficient to ensure that, in some embodiments, each antigenic peptide properly folds. Exemplary peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also can be used in the linker sequence.

The various exemplary proteins encoded by a transgene that can be expressed for enhancing the immune potential of a phagocytic cell are described below. This is not an exhaustive list but serves as an exemplary list for transgene design within the scope of the present disclosure.

In some embodiments, the PSP subunit comprises a transmembrane (TM) domain of a phagocytic receptor.

In some embodiments, the PSP subunit comprises an ICD domain of a phagocytic receptor.

In some embodiments, the ICD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), and CD169 receptor.

In some embodiments, the ICD comprises the signaling domain derived from any one or more of: lectin, dectin 1, mannose receptor (CD206), scavenger receptor A1 (SRA1), MARCO (Macrophage Receptor with Collagenous Structure, aliases: SRA6, SCARA2), CD36 (Thrombospondin receptor, aliases: Scavenger Receptor class B, member 3), CD163 (Scavenger receptor, cysteine rich-type 1), MSR1, SCARA3, COLEC12 (aliases: Scavenger Receptor With C-Type Lectin, SCARA4, or Collectin 12), SCARA5, SCARB1, SCARB2, CD68 (SCARD, microsialin), OLR1 (Oxidized Low Density Lipoprotein Receptor 1, LOX1, or C-Type Lectin Domain Family 8 Member A), SCARF1, SCARF2, SRCRB4D, SSC5D, and CD169 (aliases, Sialoadhesin receptor, SIGLEC1).

In some embodiments, the recombinant nucleic acid encodes, for example, an intracellular domain of human MARCO. The PSR subunit comprises an intracellular domain having a 44 amino acid ICD of human MARCO having an amino acid sequence: MRNKKILKEDELL-SETQQAAFHQIAMEPFEINVPKPKRRNGVNF (SEQ ID NO: 73). In some embodiments, the PSR subunit comprises a variant which is at least 70%, 75%, 80%, 85%, 90% or 95% identical to the intracellular domain of MARCO.

In some embodiments, for example, the PSR (phagocytic scavenger receptor) comprises a transmembrane region of human MARCO.

In some embodiments, the recombinant nucleic acid encodes an intracellular domain of human SRA1. The PSR subunit comprises an intracellular domain having a 50 amino acid ICD of human SRA1 having an amino acid sequence: MEQWDHFHNQQEDTDSCSESVKF-DARSMTALLPPNPKNSPSLQEKLKSFK (SEQ ID NO: 74). In some embodiments, the PSR subunit comprises a variant which is at least 70%, 75%, 80%, 85%, 90% or 95% identical to the intracellular domain of human SRA1. The intracellular region of SRA has a phosphorylation site.

In some embodiments, the PSR comprises a transmembrane region of human SRA1.

In some embodiments, for example, the recombinant nucleic acid comprises an intracellular domain of CD36. In some embodiments, the recombinant nucleic acid comprises a TM domain of CD36. Naturally occurring full length CD36 has two TM domains and two short intracellular domains, and an extracellular domain of CD36 binds to oxidized LDL. Both of the intracellular domains contain pairs of cysteines that are fatty acid acylated. It lacks known signaling domains (e.g. kinase, phosphatase, g-protein binding, or scaffolding domains). N-terminal cytoplasmic domain is extremely short (5-7 amino acid residues) and is closely associated with the internal leaflet of the plasma membrane. The carboxy-terminal domain contains 13 amino acids, containing a CXCX5K motif homologous to a region in the intracellular domain of CD4 and CD8 that is known to interact with signaling molecules. The intracellular domain of CD36 is capable of assembling a signaling complex that activates lyn kinases, MAP kinases and Focal Adhesion Kinases (FAK), and inactivation of src homology 2-containing phosphotyrosine phosphatase (SHP-2). Members of the guanine nucleotide exchange factors (GEFs) have been identified as potential key signaling intermediates.

In some embodiments, the recombinant nucleic acid encodes for example, an intracellular domain of human SCARA3. In some embodiments, the PSR subunit comprises a variant which is at least 70%, 75%, 80%, 85%, 90% or 95% identical to the intracellular domain of human SCARA3. In some embodiments, the PSR comprises the TM domain of SCARA3. In some embodiments, the TM domains are about 20-30 amino acids long.

Scavenger receptors may occur as homo or hetero dimers. MARCO, for example occurs as a homo trimer.

In some embodiments, the TM domain or the ICD domain of the PSP is not derived from FcR, Megf10, Bai1 or MerTK. In some embodiments, the ICD of the PSR does not comprise a CD3 zeta intracellular domain.

In some embodiments, the intracellular domain and transmembrane domains are derived from FcR beta.

In one aspect the recombinant nucleic acid encodes a chimeric antigenic receptor for enhanced phagocytosis (CAR-P), which is a phagocytic scavenger receptor (PSR) fusion protein (CFP) comprising: (a) an extracellular domain comprising an extracellular antigen binding domain specific to an antigen of a target cell, (b) a transmembrane domain, and (c) a recombinant PSR intracellular signaling domain, wherein the recombinant PSR intracellular signaling domain comprises a first portion derived from a phagocytic and a second portion derived from non-phagocytic receptor.

In some embodiments, the second portion is not a PI3K recruitment domain. In some embodiments, the second portion is a PI3K recruitment domain.

The second portion derived from non-phagocytic receptor may comprise an intracellular signaling domain that enhances phagocytosis, and/or inflammatory potential of the engineered phagocytic cells expressing the recombinant nucleic acid. In some embodiments, the second portion derived from non-phagocytic receptor comprises more than one intracellular domain (ICD). In some embodiments, the second portion derived from non-phagocytic receptor comprises a second ICD. In some embodiments, the second portion derived from non-phagocytic receptor comprises a second and a third ICD. In some embodiments, the second portion derived from non-phagocytic receptor comprises a second, a third and a fourth ICD, wherein the second portion is encoded by the recombinant nucleic acid. The respective second portions comprising a second, or third or fourth ICD derived from non-phagocytic receptor are described as follows.

Chimeric Antigen Receptors for Enhancing Intracellular Signaling and Inflammation Activation In one aspect, the recombinant nucleic acid encodes a second intracellular domain in addition to the phagocytic ICD, which confers capability of potent pro-inflammatory immune activation, such as when macrophages engage in fighting infection. The second intracellular domain (second ICD) is fused to the cytoplasmic terminus of the first phagocytic ICD. The second intracellular domain provides a second signal is necessary to trigger inflammasomes and pro-inflammatory signals. Nod-like receptors (NLRs) are a subset of receptors that are activated in innate immune response, and oligomerize to form multi-protein complexes that serve as platforms to recruit proinflammatory caspases and induce their cleavage and activation. This leads to direct activation of ROS, and often result in a violent cell death known as pyroptosis. There are four inflammasome complexes, NLRP1m, NLRP3, IPAF and AIM2.

The tumor microenvironment (TME) constitutes an immunosuppressive environment. Influence of IL-10, glucocorticoid hormones, apoptotic cells, and immune complexes can interfere with innate immune cell function. Immune cells, including phagocytic cells settle into a tolerogenic phenotype. In macrophages, this phenotype, commonly known as the M2 phenotype is distinct from the M1 phenotype, where the macrophages are potent and capable of killing pathogens. Macrophages exposed to LPS or IFN-gamma, for example, can polarize towards an M1 phenotype, whereas macrophages exposed to IL-4 or IL-13 will polarize towards an M2 phenotype. LPS or IFN-gamma can interact with Toll-like receptor 4 (TLR4) on the surface of macrophages inducing the Trif and MyD88 pathways, inducing the activation of transcription factors IRF3, AP-1, and NFKB and thus activating TNFs genes, interferon genes, CXCL10, NOS2, IL-12, etc., which are necessary in a pro-inflammatory M1 macrophage response. Similarly, IL-4 and IL-13 bind to IL-4R, activation the Jak/Stat6 pathway, which regulates the expression of CCL17, ARGI, IRF4, IL-10, SOCS3, etc., which are genes associated with an anti-inflammatory response (M2 response). Expression of CD14, CD80, D206 and low expression of CD163 are indicators of macrophage polarization towards the M1 phenotype.

In some embodiments, the recombinant nucleic acid encodes one or more additional intracellular domains, comprising a cytoplasmic domain for inflammatory response. In some embodiments, expression of the recombinant nucleic acid encoding the phagocytic receptor (PR) fusion protein (CFP) comprising the cytoplasmic domain for inflammatory response in the engineered macrophages confers potent pro-inflammatory response similar to the M1 phenotype.

In some embodiments, the cytoplasmic domain for inflammatory response can be the signal transducing domains or regions of TLR3, 4, 9, MYD88, TRIF, RIG-1, MDA5, CD40, IFN receptor, NLRP-1-14, NOD1, NOD2, Pyrin, AIM2, NLRC4, CD40.

In some embodiments, the expression of the recombinant nucleic acid encoding the phagocytic scavenger receptor (PSR) fusion protein (CFP) comprises a pro-inflammatory cytoplasmic domain for activation of IL-1 signaling cascade.

In some embodiments, the cytoplasmic portion of the chimeric receptor (for example, phagocytic receptor (PR) fusion protein (CFP)) comprises a cytoplasmic domain from a toll-like receptor, such as the intracellular signaling domains of toll-like receptor 3 (TLR3), toll-like receptor 4 (TLR4), toll-like receptor 7 (TLR7), toll-like receptor 8 (TLR8), toll-like receptor 9 (TLR9). In some embodiments, the cytoplasmic portion of the chimeric receptor comprises a suitable region from interleukin-1 receptor-associated kinase 1 (IRAK1). In some embodiments, the cytoplasmic portion of the chimeric receptor comprises a suitable region from differentiation primary response protein (MYD88). In some embodiments, the cytoplasmic portion of the chimeric receptor comprises a suitable region from myelin and lymphocyte protein (MAL). In some embodiments, the cytoplasmic portion of the chimeric receptor comprises a suitable region from retinoic acid inducible gene (RIG-1).

In some embodiments, the transmembrane domain of the PSR comprises the transmembrane domain of any one of MYD88, TLR3, TLR4, TLR7, TLR8, TLR9, MAL, IRAK1, proteins.

In some embodiments, the recombinant PSR intracellular signaling domain comprises a first portion derived from a phagocytic and a second portion derived from non-phagocytic receptor wherein the second portion derived from non-phagocytic receptor comprises a phosphorylation site. In some embodiments, the phosphorylation site comprises amino acid sequences suitable for an autophosphorylation site. In some embodiments, the phosphorylation site comprises amino acid sequences suitable phosphorylation by Src family kinases. In some embodiments, the phosphorylation site comprises amino acid sequences, which upon phosphorylation are capable of binding to SH2 domains in a kinase. In some embodiments, a receptor tyrosine kinase domain is fused at the cytoplasmic end of the CFP in addition to the first cytoplasmic portion. In some embodiments, the phosphorylation is a tyrosine phosphorylation.

In some embodiments, the second intracellular domain is an Immune receptor Tyrosine Activation Motif (ITAM). The ITAM motif is present in mammalian a and 0 immunoglobulin proteins, TCR γ receptors, FCR γ receptors subunits, CD3 chains receptors and NFAT activation molecule.

In some embodiments, the CFP intracellular domain comprises one ITAM motif. In some embodiments, the CFP intracellular domain comprises more than one ITAM motifs. In some embodiments, the CFP intracellular domain comprises two or more ITAM motifs. In some embodiments, the CFP intracellular domain comprises three or more ITAM motifs. In some embodiments, the CFP intracellular domain comprises four or more ITAM motifs. In some embodiments, the CFP intracellular domain comprises five or more ITAM motifs. In some embodiments, the CFP intracellular domain comprises six or more ITAM motifs. In some embodiments, the CFP intracellular domain comprises seven or more ITAM motifs. In some embodiments, the CFP intracellular domain comprises eight or more ITAM motifs. In some embodiments, the CFP intracellular domain comprises nine or more ITAM motifs. In some embodiments, the CFP intracellular domain comprises ten or more ITAM motifs.

In some embodiments, one or more domains in the first phagocytic ICD comprises a mutation.

In some embodiments, one or more domains in the second ICD comprises a mutation to enhance a kinase binding domain, to generate a phosphorylation site, to generate an SH2 docking site or a combination thereof.

Co-Expression of an Inflammatory Gene

In one aspect, the recombinant nucleic acid comprises a coding sequence for a pro-inflammatory gene, which is co-expressed with the CFP in the engineered cell. In some embodiments, the pro-inflammatory gene is a cytokine. Examples include but not limited to TNF-α, IL-1α, IL-1β, IL-6, CSF, GMCSF, or IL-12 or interferons.

The recombinant nucleic acid encoding the proinflammatory gene can be monocistronic, wherein the two coding sequences for (a) the PSP and (b) the proinflammatory gene are post-transcriptionally or post-translationally cleaved for independent expression.

In some embodiments, the two coding sequences comprise a self-cleavage domain, encoding a P2A sequence, for example.

In some embodiments, the two coding regions are separated by an IRES site.

In some embodiments, the two coding sequences are encoded by a bicistronic genetic element. The coding regions for (a) the PSP and (b) the proinflammatory gene can be unidirectional, where each is under a separate regulatory control. In some embodiments, the coding regions for both are bidirectional and drive in opposite directions. Each coding sequence is under a separate regulatory control.

Co-expression of the proinflammatory gene is designed to confer strong inflammatory stimulation of the macrophage and activate the surrounding tissue for inflammation.

Integrin Activation Domains

Cell-cell and cell-substratum adhesion is mediated by the binding of integrin extracellular domains to diverse protein ligands; however, cellular control of these adhesive interactions and their translation into dynamic cellular responses, such as cell spreading or migration, requires the integrin cytoplasmic tails. These short tails bind to intracellular ligands that connect the receptors to signaling pathways and cytoskeletal networks (Calderwood DA, 2004, Integrin Activation, Journal of Cell Science 117, 657-666). Integrins are heterodimeric adhesion receptors formed by the non-covalent association of a and 0 subunits. Each subunit is a type I transmembrane glycoprotein that has relatively large extracellular domains and, with the exception of the β4 subunit, a short cytoplasmic tail. Individual integrin family members have the ability to recognize multiple ligands. Integrins can bind to a large number of extracellular matrix proteins (bone matrix proteins, collagens, fibronectins, fibrinogen, laminins, thrombospondins, vitronectin, and von Willebrand factor), reflecting the primary function of integrins in cell adhesion to extracellular matrices. Many "counter-receptors" are ligands, reflecting the role of integrins in mediating cell-cell interactions. Integrins undergo conformational changes to increase ligand affinity.

The Integrin R2 subfamily consists of four different integrin receptors, $\alpha_M\beta_2$ (CD11b/CD18, Mac-1, CR3, Mo-1), $\alpha_L\beta_2$ (CD11a/CD18, LFA-1), $\alpha_x\beta_2$ (CD11c/CD18), and $\alpha_D\beta_2$ (CD11d/CD18). These leukocyte integrins are involved in virtually every aspect of leukocyte function, including the immune response, adhesion to and transmigration through the endothelium, phagocytosis of pathogens, and leukocyte activation.

The a subunits of all $\beta_2$ integrins contain an inserted region of ~200 amino acids, termed the I or A domain. Highly conserved I domains are found in several other integrin α subunits and other proteins, such as certain coagulation and complement proteins. I domains mediate protein-protein interactions, and in integrins, they are integrally involved in the binding of protein ligands. Although the I domains dominate the ligand binding functions of their integrins, other regions of the a subunits do influence ligand recognition. As examples, in $\alpha_M\beta_2$ a mAb (OKM1) recognizing an epitope outside the I domain but in the αM subunit inhibits ligand binding; and the EF-hand regions in $\alpha_L\beta_2$ and $\alpha_2\beta_1$, integrins with I domains in their a subunits, contribute to ligand recognition. The am subunit, and perhaps other a subunits, contains a lectin-like domain, which is involved in engagement of non-protein ligands, and occupancy may modulate the function of the I domain.

As integrins lack enzymatic activity, signaling is instead induced by the assembly of signaling complexes on the cytoplasmic face of the plasma membrane. Formation of these complexes is achieved in two ways; first, by receptor clustering, which increases the avidity of molecular interactions thereby increasing the on-rate of binding of effector molecules, and second, by induction of conformational changes in receptors that creates or exposes effector binding sites. Within the ECM, integrins have the ability to bind fibronectin, laminins, collagens, tenascin, vitronectin and thrombospondin. Clusters of integrin/ECM interactions form focal adhesions, concentrating cytoskeletal components and signaling molecules within the cell. The cytoplasmic tail of integrins serve as a binding site for α-actinin and talin which then recruit vinculin, a protein involved in anchoring F-actin to the membrane. Talin is activated by kinases such as protein kinase C (PKCα).

Integrins are activated by selectins. Leucocytes express L-selectin, activated platelets express P-selectin, and activated endothelial cells express E- and P-selectin. P-selectin-mediated adhesion enables chemokine- or platelet-activating factor-triggered activation of β2 integrins, which stabilizes adhesion. It also facilitates release of chemokines from adherent leucocytes. The cytoplasmic domain of P-selectin glycoprotein ligand 1 formed a constitutive complex with Nef-associated factor 1. After binding of P-selectin, Src kinases phosphorylated Nef-associated factor 1, which recruit the phosphoinositide-3-OH kinase p85-p1106 heterodimer and result in activation of leukocyte integrins. E-selectin ligands transduce signals that also affect β2 integrin function. Selectins trigger activation of Src family kinases. SFKs activated by selectin engagement phosphorylate the immunoreceptor tyrosine-based activation motifs (ITAMs) in the cytoplasmic domains of DAP12 and FcRγ. In some respects, CD44 is sufficient to transduce signals from E-selectin. CD44 triggers the inside-out signaling of integrins. A final common step in integrin activation is binding of talin to the cytoplasmic tail of the β subunit. Kindlins, another group of cytoplasmic adaptors, bind to a different region of integrin β tails. Kindlins increase the clustering of talin-activated integrins. Kindlins are responsive to selectin signaling, however, kindlins are found mostly in hematopoietic cells, such as neutrophils. Selectin signaling as well as signaling upon integrin activation by chemokines components have shared components, including SFKs, Syk, and SLP-76.

In some embodiments, the intracellular domain of the recombinant PSR fusion protein comprises an integrin activation domain. The integrin activation domain comprises an intracellular domain of a selectin, for example, a P-selectin, L-selectin or E-selectin.

In some embodiments, the intracellular domain of the recombinant PSR fusion protein comprises an integrin activation domain of laminin.

In some embodiments, the intracellular domain of the recombinant PSR fusion protein comprises an integrin activation domain for activation of Talin.

In some embodiments, the intracellular domain of the recombinant PSR fusion protein comprises an integrin activation domain fused to the cytoplasmic end of the phagocytic receptor ICD domain.

Chimeric Receptor for Enhancing Antigen Cross Presentation

In some embodiments, the recombinant nucleic acid encodes a domain capable of enabling cross presentation of antigens. In general, MHC class I molecules present self- or pathogen-derived antigens that are synthesized within the cell, whereas exogenous antigens derived via endocytic uptake are loaded onto MHC class II molecules for presentation to CD4+ T cells. MHC I-restricted presentation of endogenous antigens, in which peptides are generated by the proteasome. However, in some cases, DC can process exogenous antigens into the MHC-I pathway for presentation to CD8+ T cells. This is referred to as cross presentation of antigens. Soluble or exogenous antigenic components may get degraded by lysosomal proteases in the vacuoles and cross presented by DCs, instead of following the endocytotic pathway. In some instances, chaperones, such as heat shock protein 90 (Hsp90) have shown to help cross present antigens by certain APCs. HSP-peptide complexes are known to be internalized by a distinct group of receptors compared to free polypeptides. These receptors are from the scavenger receptor families and included LOX-1, SREC-I/SCARF-I, and FEEL1/Stabilin-1. Both SREC-I and LOX-1 have been shown to mediate the cross presentation of molecular chaperone bound antigens and lead to activation of CD8+T lymphocytes.

SREC-1 (scavenger receptor expressed by endothelial cells) has no significant homology to other types of scavenger receptors but has unique domain structures. It contains 10 repeats of EGF-like cysteine-rich motifs in the extracellular domain. Recently, the structure of SREC-I was shown to be similar to that of a transmembrane protein with 16 EGF-like repeats encoded by the *Caenorhabditis elegans* gene ced-I, which functions as a cell surface phagocytic receptor that recognizes apoptotic cells.

Cross presentation of cancer antigens through the Class-I MHC pathway results in enhanced CD8+ T cell response, which is associated with cytotoxicity and therefore beneficial in tumor regression. In some embodiments, the intracellular domain of the CFP comprises a SREC1 intracellular domain. In some embodiments, the intracellular domain of the CFP comprises a SRECII intracellular domain.

In some embodiments, the PSR subunit comprises: an intracellular domain comprising a PSR intracellular signaling domain from SREC1 or SRECII.

In some embodiments, the PSR subunit comprises: (i) a transmembrane domain, and (ii) an intracellular domain comprising a PSR intracellular signaling domain from SREC1 or SRECII.

In some embodiments, the PSR subunit comprises: (i) a transmembrane domain, (ii) an intracellular domain comprising a PSR intracellular signaling domain, and (iii) an extracellular domain from SREC1 or SRECII.

Transmembrane Domain of a CFP Fusion Protein

In some embodiments, the TM encoded by the recombinant nucleic acid comprises a domain of a scavenger receptor (SR). In some embodiments, the TM can be the TM domain of or derived from any one or more of: lectin, dectin 1, mannose receptor (CD206), SRA1, MARCO, CD36, CD163, MSR1, SCARA3, COLEC12, SCARA5, SCARB1, SCARB2, CD68, OLR1, SCARF1, SCARF2, SRCRB4D, SSC5D, and CD169.

In some embodiments, the TM domains are about 20-30 amino acids long. TM domains of SRs are about 20-30 amino acids long.

The TM domain or the ICD domain of the PSP is not derived from Megf10, Bai1 or MerTK. The ICD of the PSR does not comprise a CD3 zeta intracellular domain.

In some embodiments, the TM is derived from the same phagocytic receptor as the ICD.

In some embodiments, the TM region is derived from a plasma membrane protein. The TM can be selected from an Fc receptor (FcR). In some embodiments, nucleic acid sequence encoding domains from specific FcRs are used for cell-specific expression of a recombinant construct. An FCR-alpha region comprising the TM domain may be used for macrophage specific expression of the construct. FcRβ recombinant protein expresses in mast cells.

In some embodiments, the CFP comprises the TM of an FCR-beta (FcRβ).

In some embodiments, the CFP comprises both the FcRβ TM and ICD domains.

In some embodiments, the TM domain is derived from CD8.

In some embodiments, the TM is derived from CD2.

In some embodiments, the TM is derived from FCR alpha.

Extracellular Domain of a CFP Fusion Protein

The extracellular domain comprises an antigen binding domain that binds to one or more target antigens on a target cell. The target binding domain is specific for the target. The extracellular domain can include an antibody or an antigen-binding domain selected from intrabodies, peptibodies, nanobodies, single domain antibodies. SMIPs, and multi-specific antibodies.

In some embodiments, the extracellular domain includes a Fab binding domain. In yet other such embodiments, the extracellular domain includes a scFv.

In some embodiments, the chimeric antigen receptor comprises an extracellular antigen binding domain is derived from the group consisting of an antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof. In some embodiments, the antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof specifically bind to one or more antigens.

In some embodiments, the antigens are cancer antigens, and the target cell is a target cancer cell. In some embodiments, the antigen for a target cancer cell is selected from the group consisting of CD3, CD4, CD5, CD7, CD19, CCR2, CCR4, CD30, CD37, TCRB1/2, TCR, TCR. CD22, HER2 (ERBB2/neu), Mesothelin, PSCA, CD123, CD30, CD171, CD138, CS-1, CLECL1, CD33, CD79b, EGFRvIII, GD2, GD3, BCMA, PSMA, ROR1, FLT3, TAG72, CD38, CD44v6, CEA, EPCAM, B7H3 (CD276), KIT (CD 117), CD213A2, IL-1 IRa, PRSS21, VEGFR2, CD24, MUC-16, PDGFR-beta, SSEA-4, CD20, MUC1, EGFR, NCAM, Prostase, PAP, ELF2M, Ephrin B2, FAP, EphA2, GM3, TEM1/CD248, TEM7R, CLDN6, TSHR, GPRC5D, CD97, CD179a, ALK, and IGLL1.

Various cancer antigen targets can be selected from cancer antigens known to one of skill in the art. Depending on the cancer and the cell type involved cancer antigens are mutated native proteins. The antigen binding domains are screened for specificity towards mutated/cancer antigens and not the native antigens.

In some embodiments, for example, the cancer antigen for a target cancer cell can be one or more ofthe mutated/cancer antigens: MUC16, CCAT2, CTAG1A, CTAG1B, MAGE A1, MAGEA2, MAGEA3, MAGE A4, MAGEA6, PRAME, PCA3, MAGE C1, MAGEC2, MAGED2, AFP, MAGEA8, MAGE9, MAGEA11, MAGEA12, IL13RA2, PLAC1, SDCCAG8, LSP1, CT45A1, CT45A2, CT45A3, CT45A5, CT45A6, CT45A8, CT45A10, CT47A1, CT47A2, CT47A3, CT47A4, CT47A5, CT47A6, CT47A8, CT47A9, CT47A10, CT47A11, CT47A12, CT47B1, SAGE1, and CT55.

In some embodiments, for example, the cancer antigen for a target cancer cell can be one or more of the mutated/cancer antigens: CD2, CD3, CD4, CD5, CD7, CD8, CD20, CD30, CD45, CD56, where the cancer is a T cell lymphoma.

In some embodiments, for example, the cancer antigen for a target cancer cell can be one or more of the mutated/cancer antigens: IDH1, ATRX, PRL3, or ETBR, where the cancer is a glioblastoma.

In some embodiments, for example, the cancer antigen for a target cancer cell can be one or more of the mutated/cancer antigens: CA125, beta-hCG, urinary gonadotropin fragment, AFP, CEA, SCC, inhibin or extradiol, where the cancer is ovarian cancer.

In some embodiments, the cancer antigen for a target cancer cell may be HER2.

In some embodiments, the cancer antigen for a target cancer cell may be EGFR Variant III.

In some embodiments, the cancer antigen for a target cancer cell may be CD19.

In some embodiments, the SR subunit region comprises an extracellular domain (ECD) of the scavenger receptor. In some embodiments, the ECD of the scavenger receptor comprises an ECD domain of the SR comprising the ICD and the TM domains. In some embodiments, the SR-ECD contributes to the binding of the phagocyte to the target cell, and in turn is activated, and activates the phagocytosis of the target cell.

In some embodiments, the PSR domain optionally comprises the ECD domain or portion thereof of the respective scavenger receptor the ICD and TM domains of which is incorporated in the PSR. Therefore, in some embodiments, In some embodiments, the ECD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), and CD169 receptor. The extra-cellular domains of most macrophage scavenger receptors contain scavenger receptors with a broad binding specificity that may be used to discriminate between self and non-self in the nonspecific antibody-independent recognition of for-eign substances. The type I and II class A scavenger recep-tors (SR-AII and SR-AII) are trimeric membrane glycopro-teins with a small NH2-terminal intracellular domain, and an extracellular portion containing a short spacer domain, an α-helical coiled-coil domain, and a triple-helical collag-enous domain. The type I receptor additionally contains a cysteine-rich COOH-terminal (SRCR) domain. These recep-tors are present in macrophages in diverse tissues throughout the body and exhibit an unusually broad ligand binding specificity. They bind a wide variety of polyanions, includ-ing chemically modified proteins, such as modified LDL, and they have been implicated in cholesterol deposition during atherogenesis. They may also play a role in cell adhesion processes in macrophage-associated host defense and inflammatory conditions.

In some embodiments, the SR ECD is designed to bind to pro-apoptotic cells. In some embodiments, the scavenger receptor ECD comprises a binding domain for a cell surface molecule of a cancer cell or an infected cell.

In some embodiments, the extracellular domain of the PR subunit is linked by a linker to a target cell binding domain, such as an antibody or part thereof, specific for a cancer antigen.

In some embodiments, the extracellular antigen binding domain comprises one antigen binding domain. In some embodiments, the extracellular antigen binding domain comprises more than one binding domain. In some embodi-ments, the binding domain is an scFv. In some embodiments, the binding domain is an single domain antibody (sdAb). In some embodiments, the binding domain is fused to the recombinant PR at the extracellular domain. In some embodiments, the binding domain (e.g., scFv) and the extracellular domain of the PR are linked via a linker.

In some embodiments, the ECD antigen binding domain can bind to an intracellular antigen. In some embodiments, the intracellular antigen is a cancer antigen.

In some embodiments, the extracellular antigen binding domain binds to the target ligand with an affinity of less than 1000 nM. In some embodiments, the extracellular antigen binding domain binds to the target ligand with an affinity of less than 500 nM. In some embodiments, the extracellular antigen binding domain binds to the target ligand with an affinity of less than 450 nM. In some embodiments, the extracellular antigen binding domain binds to the target ligand with an affinity of less than 400 nM. In some embodiments, the extracellular antigen binding domain binds to the target ligand with an affinity of less than 350 nM. In some embodiments, the extracellular antigen binding domain binds to the target ligand with an affinity of less than 250 nM. In some embodiments, the extracellular antigen binding domain binds to the target ligand with an affinity of less than 200 nM. In some embodiments, the extracellular antigen binding domain binds to the target ligand with an affinity of less than 100 nM. In some embodiments, the extracellular antigen binding domain binds to the target ligand with an affinity ranging between than 200 nM to 1000 nM. In some embodiments, the extracellular antigen binding domain binds to the target ligand with an affinity ranging between than 300 nM to 1.5 mM. In some embodiments, the antigen binding domain binds to the target ligand with an affinity>200 nM, >300 nM or >500 nM.

Peptide Linker

In some embodiments, the extracellular antigen binding domains, scfvs are linked to the TM domain or other extracellular domains by a linker. In some embodiments, where there are more than one scfv at the extracellular antigen binding domain the more than scfvs are linked with each other by linkers.

In some embodiments, the linkers are flexible. In some embodiments, the linkers comprise a hinge region. Linkers are usually short peptide sequences. In some embodiments, the linkers are stretches of Glycine and one or more Serine residues. Other amino acids preferred for short peptide linkers include but are not limited to threonine (Thr), serine (Ser), proline (Pro), glycine (Gly), aspartic acid (Asp), lysine (Lys), glutamine (Gln), asparagine (Asn), and alanine (Ala) arginine (Arg), phenylalanine (Phe), glutamic acid (Glu). Of these Pro, Thr, and Gln are frequently used amino acids for natural linkers. Pro is a unique amino acid with a cyclic side chain which causes a very restricted conforma-tion. Pro-rich sequences are used as interdomain linkers, including the linker between the lipoyl and E3 binding domain in pyruvate dehydrogenase $(GA_2PA_3PAKQEA_3PAPA_2KAEAPA_3PA_2KA)$ (SEQ ID NO: 75). For the purpose of the disclosure, the empirical linkers may be flexible linkers, rigid linkers, and cleavable linkers. Sequences such as (G4S)x (SEQ ID NO: 76) (where x is multiple copies of the moiety, designated as 1, 2, 3, 4, and so on) comprise a flexible linker sequence. Other flexible sequences used herein include several repeats of glycine, e.g., (Gly)6(SEQ ID NO: 77) or (Gly)8 (SEQ ID NO: 78). On the other hand, a rigid linker may be used, for example, a linker (EAAAK)x (SEQ ID NO: 79), where x is an integer, 1, 2, 3, 4 etc. gives rise to a rigid linker.

In some embodiments, the linker comprises at least 2, or at least 3 amino acids. In some embodiments, the linker comprises 4 amino acids. In some embodiments, the linker comprises 5 amino acids. In some embodiments, the linker comprises 6 amino acids. In some embodiments, the linker comprises 7 amino acids. In some embodiments, the linker comprises 8 amino acids. In some embodiments, the linker comprises 9 amino acids. In some embodiments, the linker comprises 8 amino acids. In some embodiments, the linker comprises 10 amino acids. In some embodiments, the linker comprises 11 amino acids. In some embodiments, the linker comprises 12 amino acids. In some embodiments, the linker comprises 13 amino acids. In some embodiments, the linker comprises 14 amino acids. In some embodiments, the linker comprises 15 amino acids. In some embodiments, the linker comprises 16 amino acids. In some embodiments, the linker comprises 17 amino acids. In some embodiments, the linker comprises 18 amino acids. In some embodiments, the linker comprises 19 amino acids. In some embodiments, the linker comprises 20 amino acids.

As contemplated herein, any suitable ECD, TM or ICD domain can be cloned interchangeably in the suitable portion of any one of the CARP receptors described in the disclosure to obtain a protein with enhanced phagocytosis compared to an endogenous receptor.

Characteristics of the Fusion Proteins:

The CFP can structurally incorporate into the cell mem-brane of the cell in which it is expressed. Specific leader sequences in the nucleic acid construct, such as the signal peptide can be used to direct plasma membrane expression of the encoded protein. The transmembrane domain encoded by the construct can incorporate the expressed protein in the plasma membrane of the cell.

In some embodiments, the transmembrane domain comprises a TM domain of an FcRalpha receptor, which dimerizes with endogenous FcR-gamma receptors in the macrophages, ensuring macrophage specific expression.

The CFP can render the cell that expresses it as potently phagocytic. When the recombinant nucleic acid encoding the CFP is expressed in a cell, the cell can exhibit an increased phagocytosis of a target cell having the antigen of a target cell, compared to a cell not expressing the recombinant nucleic acid. When the recombinant nucleic acid is expressed in a cell, the cell can exhibit an increased phagocytosis of a target cell having the antigen of a target cell, compared to a cell not expressing the recombinant nucleic acid. In some embodiments, the recombinant nucleic acid when expressed in a cell, the cell exhibits at least 2-fold increased phagocytosis of a target cell having the antigen of a target cell, compared to a cell not expressing the recombinant nucleic acid. In some embodiments, the recombinant nucleic acid when expressed in a cell, the cell exhibits at least 3-fold, 4-fold, 5-fold, 6-fold, 7-fold, 8-fold, 9-fold, 10-fold, 20-fold 30-fold or at least 5-fold increased phagocytosis of a target cell having the antigen of a target cell, compared to a cell not expressing the recombinant nucleic acid.

In some embodiments, expression of SIRP-AICD enhances phagocytosis of the cell expressing it by 1.1 fold or more, 1.2 fold or more, 1.3 fold or more, q.4 fold or more, 1.5 fold or more, by 1.6 fold or more, 1.7 fold or more, 1.8 fold or more, 1.9 fold or more, 2 fold or more, 3 fold or more, 4 fold or more, 5 fold or more, 8 fold or more, 10 fold or more, 15 fold or more, 20 fold or more, 30 fold or more, 40 fold or more, 50 fold or more, 60 fold or more, 70 fold or more 80 fold or more, 90 fold or more, 100 fold or more, compared to a cell not expressing SIRP-ΔICD.

In some embodiments, the cells co-expressing SIRP-ΔICD and a CFP encoding a phagocytic receptor as described herein exhibits an augmented phagocytosis compared to a cell that does not express either of the proteins. In some embodiments, co-expressing SIRP-ΔICD and a CFP encoding a phagocytic receptor as described herein exhibits more than 2-fold, more than 3-fold, more than 4-fold, more than 5-fold, more than 6-fold, more than 7-fold, more than 8-fold, more than 9-fold, more than 10-fold, more than 20-fold, more than 30-fold, more than 40-fold, more than 50-fold, more than 60-fold, more than 70-fold, more than 80-fold, more than 90-fold, more than 100-fold, or more than 150-fold or more than 200-fold increase in phagocytic potential (measured in fold change of phagocytic index) compared to a cell that does not express either the SIRP-ΔICD or the CFP encoding a phagocytic receptor.

In some embodiments, expression of the any one of a CFP expressing a CD47 blocking extracellular domain of SIRPα and an intracellular domain of a phagocytic receptor augments phagocytic activity of a cell expressing it by at least 1.5 fold or more, 1.6 fold or more, 1.7 fold or more, 1.8 fold or more, 1.9 fold or more, 2 fold or more, 3 fold or more, 4 fold or more, 5 fold or more, 8 fold or more, 10 fold or more, 15 fold or more, 20 fold or more, 30 fold or more, 40 fold or more, 50 fold or more, 60 fold or more, 70 fold or more 80 fold or more, 90 fold or more, 100 fold or more, compared to a cell not expressing the CFP, or compared to a cell expressing SIRP-ΔICD.

In some embodiments, the enhancement in phagocytosis of target cells by a cell expressing either SIRP-ΔICD is highly increased compared to a phagocytic cell not expressing SIRP-ΔICD.

In some embodiments, the enhancement in phagocytosis of target cells by a cell expressing a CFP comprising a CD47 blocking extracellular domain of SIRPα and an intracellular domain of a phagocytic receptor is highly increased compared to a control phagocytic cell not expressing the fusion protein or a control phagocytic cell expressing the SIRP-ΔICD.

In some embodiments, when the recombinant nucleic acid described herein is expressed in a cell, the cell exhibits an increased cytokine production. The cytokine can comprise any one of: IL-1, IL-6, IL-12, IL-23, TNF, CXCL9, CXCL10, CXCL11, IL-18, IL-23, IL-27 and interferons.

In some embodiments, when the recombinant nucleic acid described herein is expressed in a cell, the cell exhibits an increased cell migration.

In some embodiments, when the recombinant nucleic acid described herein is expressed in a cell, the cell exhibits an increased immune activity. In some embodiments, when the recombinant nucleic acid is expressed in a cell, the cell exhibits an increased expression of MHC II. In some embodiments, when the recombinant nucleic acid is expressed in a cell, the cell exhibits an increased expression of CD80. In some embodiments, when the recombinant nucleic acid is expressed in a cell, the cell exhibits an increased expression of CD86. In some embodiments, when the recombinant nucleic acid is expressed in a cell, the cell exhibits an increased iNOS production.

In some embodiments, when the recombinant nucleic acid is expressed in a cell, the cell exhibits decreased trogocytosis of a target cell expressing the antigen of a target cell compared to a cell not expressing the recombinant nucleic acid.

In embodiments, the chimeric receptors may be glycosylated, pegylated, and/or otherwise post-translationally modified. In further embodiments, glycosylation, pegylation, and/or other posttranslational modifications may occur in vivo or in vitro and/or may be performed using chemical techniques. In additional embodiments, any glycosylation, pegylation and/or other posttranslational modifications may be N-linked or O-linked. In embodiments any one of the chimeric receptors may be enzymatically or functionally active such that, when the extracellular domain is bound by a ligand, a signal is transduced to polarize a macrophage.

In some embodiments, the chimeric fusion protein (CFP) comprises an extracellular domain (ECD) targeted to bind to CD5 (CD5 binding domain), for example, comprising a heavy chain variable region (VH) having an amino acid sequence as set forth in SEQ ID NO: 1. In some embodiments, the chimeric CFP comprises a CD5 binding heavy chain variable domain comprising an amino acid sequence that has at least 80%, 85%, 90%, 95%, 96%, 97%, 98%, 99% sequence identity to SEQ ID NO: 1. In some embodiments, the extracellular domain (ECD) targeted to bind to CD5 (CD5 binding domain) comprises a light chain variable domain (VL) having an amino acid sequence as set forth in SEQ ID NO: 2. In some embodiments, the chimeric CFP comprises a CD5 binding light chain variable domain comprising an amino acid sequence that has at least 80%, 85%, 90%, 95%, 96%, 97%, 98%, 99% sequence identity to SEQ ID NO: 2.

In some embodiments, the CFP comprises an extracellular domain targeted to bind to HER2 (HER2 binding domain) having for example a heavy chain variable domain amino acid sequence as set forth in SEQ ID NO: 8 and a light chain variable domain amino acid sequence as set forth in SEQ ID NO: 9. In some embodiments, the CFP comprises a HER2 binding heavy chain variable domain comprising an amino acid sequence that has at least 80%, 85%, 90%, 95%, 96%, 97%, 98%, 99% sequence identity to SEQ ID NO: 8. In some embodiments, the CFP comprises a HER2 binding light chain variable domain comprising an amino acid sequence that has at least 80%, 85%, 90%, 95%, 96%, 97%, 98%, 99% sequence identity to SEQ ID NO: 9.

In some embodiments, the CFP comprises a hinge connecting the ECD to the transmembrane (TM). In some embodiments the hinge comprises the amino acid sequence of the hinge region of a CD8 receptor. In some embodiments, the CFP may comprise a hinge having the amino acid sequence set forth in SEQ ID NO: 7 (CD8a chain hinge domain). In some embodiments, the PFP hinge region comprises an amino acid sequence that is at least 80%, 85%, 90%, 95%, 96%, 97%, 98%, 99% sequence identity to SEQ ID NO: 7.

In some embodiments, the CFP comprises a CD8 transmembrane region, for example having an amino acid sequence set forth in SEQ ID NO: 6. In some embodiments, the CFP TM region comprises an amino acid sequence that is at least 80%, 85%, 90%, 95%, 96%, 97%, 98%, 99% sequence identity to SEQ ID NO: 6.

In some embodiments, the CFP comprises an intracellular domain having an FcR domain. In some embodiments, the CFP comprises an FcR domain intracellular domain comprises an amino acid sequence set forth in SEQ ID NO: 3, or at least a sequence having 80%, 85%, 90%, 95%, 96%, 97%, 98%, 99% sequence identity to SEQ ID NO: 3.

In some embodiments, the CFP comprises an intracellular domain having a PI3K recruitment domain. In some embodiments the PI3K recruitment domain comprises an amino sequence set forth in SEQ ID NO: 4. In some embodiments the PI3K recruitment domain comprises an amino acid sequence that has at least 80%, 85%, 90%, 95%, 96%, 97%, 98%, 99% sequence identity to SEQ ID NO: 4.

In some embodiments, the CFP comprises an intracellular domain having a CD40 intracellular domain. In some embodiments the CD40 ICD comprises an amino sequence set forth in SEQ ID NO: 5. In some embodiments the CD40 ICD comprises an amino acid sequence that has at least 80%, 85%, 90%, 95%, 96%, 97%, 98%, 99% sequence identity to SEQ ID NO: 5.

In some embodiments, the CD5 binding domain comprises an scFv comprising: (i) a variable heavy chain (VH) sequence of SEQ ID NO: 1 or with at least 90% sequence identity to SEQ ID NO: 1; and (ii) a variable light chain (VL) sequence of SEQ ID NO: 2 or with at least 70%, 75%, 80%, 85%, 90%, 91%, 92%, 93%, 94%, 95%, 96%, 97%, 98% or 99% sequence identity to SEQ ID NO: 2. In some embodiments, the CD5 binding domain comprises an scFv comprising SEQ ID NO: 33 or with at least 70%, 75%, 80%, 85%, 90%, 91%, 92%, 93%, 94%, 95%, 96%, 97%, 98% or 99% sequence identity to SEQ ID NO: 33. In some embodiments, the HER2 binding domain comprises an scFv comprising: (i) a variable heavy chain (VH) sequence of SEQ ID NO: 8 or with at least 70%, 75%, 80%, 85%, 90%, 91%, 92%, 93%, 94%, 95%, 96%, 97%, 98% or 99% sequence identity to SEQ ID NO: 8; and (ii) a variable light chain (VL) sequence of SEQ ID NO: 9 or with at least 70%, 75%, 80%, 85%, 90%, 91%, 92%, 93%, 94%, 95%, 96%, 97%, 98% or 99% sequence identity to SEQ ID NO: 9. In some embodiments, the CD5 binding domain comprises an scFv comprising SEQ ID NO: 32 or with at least 70%, 75%, 80%, 85%, 90%, 91%, 92%, 93%, 94%, 95%, 96%, 97%, 98% or 99% sequence identity to SEQ ID NO: 32. In some embodiments, the CFP further comprises an intracellular domain, wherein the intracellular domain comprises one or more intracellular signaling domains, and wherein a wild-type protein comprising the intracellular domain does not comprise the extracellular domain.

In some embodiments, the extracellular domain further comprises a hinge domain derived from CD8, wherein the hinge domain is operatively linked to the transmembrane domain and the anti-CD5 binding domain. In some embodiments, the extracellular hinge domain comprises a sequence of SEQ ID NO: 7 or with at least 70%, 75%, 80%, 85%, 90%, 91%, 92%, 93%, 94%, 95%, 96%, 97%, 98% or 99% sequence identity to SEQ ID NO: 7.

In some embodiments, the CFP comprises an extracellular domain fused to a transmembrane domain of SEQ ID NO: 30 or with at least 70%, 75%, 80%, 85%, 90%, 91%, 92%, 93%, 94%, 95%, 96%, 97%, 98% or 99% sequence identity to SEQ ID NO: 30. In some embodiments, the CFP comprises an extracellular domain fused to a transmembrane domain of SEQ ID NO: 31 or with at least 70%, 75%, 80%, 85%, 90%, 91%, 92%, 93%, 94%, 95%, 96%, 97%, 98% or 99% sequence identity to SEQ ID NO: 31.

In some embodiments, the transmembrane domain comprises a CD8 transmembrane domain. In some embodiments, the transmembrane domain comprises a sequence of SEQ ID NO: 6 or 29 or with at least 70%, 75%, 80%, 85%, 90%, 91%, 92%, 93%, 94%, 95%, 96%, 97%, 98% or 99% sequence identity to SEQ ID NO: 6 or 29. In some embodiments, the transmembrane domain comprises a sequence of SEQ ID NO: 18 or with at least 70%, 75%, 80%, 85%, 90%, 91%, 92%, 93%, 94%, 95%, 96%, 97%, 98% or 99% sequence identity to SEQ ID NO: 18. In some embodiments, the transmembrane domain comprises a sequence of SEQ ID NO: 34 or with at least 70%, 75%, 80%, 85%, 90%, 91%, 92%, 93%, 94%, 95%, 96%, 97%, 98% or 99% sequence identity to SEQ ID NO: 34. In some embodiments, the transmembrane domain comprises a sequence of SEQ ID NO: 19 or with at least 70%, 75%, 80%, 85%, 90%, 91%, 92%, 93%, 94%, 95%, 96%, 97%, 98% or 99% sequence identity to SEQ ID NO: 19.

In some embodiments, the CFP comprises one or more intracellular signaling domains that comprise a phagocytic signaling domain. In some embodiments, the phagocytosis signaling domain comprises an intracellular signaling domain derived from a receptor other than Megf10, MerTk, FcRα, and Bai1. In some embodiments, the phagocytosis signaling domain comprises an intracellular signaling domain derived from a receptor other than Megf10, MerTk, an FcR, and Bai1. In some embodiments, the phagocytosis signaling domain comprises an intracellular signaling domain derived from a receptor other than CD3ζ. In some embodiments, the phagocytosis signaling domain comprises an intracellular signaling domain derived from FcRγ, FcRα or FcRε. In some embodiments, the phagocytosis signaling domain comprises an intracellular signaling domain derived from CD3ζ. In some embodiments, the CFP comprises an intracellular signaling domain of any one of SEQ ID NOs: 3, 20, 27 and 28 or with at least 70%, 75%, 80%, 85%, 90%, 91%, 92%, 93%, 94%, 95%, 96%, 97%, 98% or 99% sequence identity to any one of SEQ ID NOs: 3, 20, 27 and 28. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence of SEQ ID NO: 4 or with at least 70%, 75%, 80%, 85%, 90%, 91%, 92%, 93%, 94%, 95%, 96%, 97%, 98% or 99% sequence identity to SEQ ID NO: 4. In some embodiments, the proinflammatory signaling domain is derived from an intracellular signaling domain of CD40. In some embodiments, the proinflammatory signaling domain comprises a sequence of SEQ ID NO: 5 or with at least 70%, 75%, 80%, 85%, 90%, 91%, 92%, 93%, 94%, 95%, 96%, 97%, 98% or 99% sequence identity to SEQ ID NO: 5. In some embodiments, the CFP comprises an intracellular signaling domain of SEQ ID NO: 21 or with at least 70%, 75%, 80%, 85%, 90%, 91%, 92%, 93%, 94%, 95%, 96%, 97%, 98% or 99% sequence identity to SEQ ID NO: 21. In some embodiments, the CFP comprises an intracellular signaling domain of SEQ ID NO: 23 or with at least 70%, 75%, 80%, 85%, 90%, 91%, 92%, 93%, 94%, 95%, 96%, 97%, 98% or 99% sequence identity to SEQ ID NO: 23.

In some embodiments, the CFP comprises a sequence of SEQ ID NO: 14 or with at least 70%, 75%, 80%, 85%, 90%, 91%, 92%, 93%, 94%, 95%, 96%, 97%, 98% or 99% sequence identity to SEQ ID NO: 14. In some embodiments, the CFP comprises a sequence of SEQ ID NO: 15 or with at least 70%, 75%, 80%, 85%, 90%, 91%, 92%, 93%, 94%, 95%, 96%, 97%, 98% or 99% sequence identity to SEQ ID NO: 15. In some embodiments, the CFP comprises a sequence of SEQ ID NO: 16 or with at least 70%, 75%, 80%, 85%, 90%, 91%, 92%, 93%, 94%, 95%, 96%, 97%, 98% or 99% sequence identity to SEQ ID NO: 16. In some embodiments, the CFP comprises a sequence of SEQ ID NO: 24 or with at least 70%, 75%, 80%, 85%, 90%, 91%, 92%, 93%, 94%, 95%, 96%, 97%, 98% or 99% sequence identity to SEQ ID NO: 24. In some embodiments, the CFP comprises a sequence of SEQ ID NO:25 or with at least 70%, 75%, 80%, 85%, 70%, 75%, 80%, 85%, 90%, 91%, 92%, 93%, 94%, 95%, 96%, 97%, 98% or 99%, 91%, 92%, 93%, 94%, 95%, 96%, 97%, 98% or 99% sequence identity to SEQ ID NO: 25.

In some embodiments, the CFP comprises: (a) an extracellular domain comprising: (i) a scFv that specifically binds CD5, and (ii) a hinge domain derived from CD8; a hinge domain derived from CD28 or at least a portion of an extracellular domain from CD68; (b) a CD8 transmembrane domain, a CD28 transmembrane domain, a CD2 transmembrane domain or a CD68 transmembrane domain; and (c) an intracellular domain comprising at least two intracellular signaling domains, wherein the at least two intracellular signaling domains comprise: (i) a first intracellular signaling domain derived from FcRα, FcRγ or FcRε, and (ii) a second intracellular signaling domain: (A) comprising a PI3K recruitment domain, or (B) derived from CD40. In some embodiments, the CFP comprises as an alternative (c) to the above: an intracellular domain comprising at least two intracellular signaling domains, wherein the at least two intracellular signaling domains comprise: (i) a first intracellular signaling domain derived from a phagocytic receptor intracellular domain, and (ii) a second intracellular signaling domain derived from a scavenger receptor phagocytic receptor intracellular domain comprising: (A) comprising a PI3K recruitment domain, or (B) derived from CD40. Exemplary scavenger receptors from which an intracellular signaling domain may be derived may be found in Table 2. In some embodiments, the CFP comprises and intracellular signaling domain derived from an intracellular signaling domain of an innate immune receptor.

In some embodiments, the recombinant polynucleic acid is an mRNA. In some embodiments, the recombinant polynucleic acid is a circRNA. In some embodiments, the recombinant polynucleic acid is a viral vector. In some embodiments, the recombinant polynucleic acid is delivered via a viral vector.

In some embodiments, the myeloid cell is a CD14+ cell, a CD14+/CD16− cell, a CD14+/CD16+ cell, a CD14−/CD16+ cell, CD14−/CD16− cell, a dendritic cell, an M0 macrophage, an M2 macrophage, an M1 macrophage or a mosaic myeloid cell/macrophage/dendritic cell.

In one aspect, provided herein is a method of treating cancer in a human subject in need thereof comprising administering a pharmaceutical composition to the human subject, the pharmaceutical composition comprising: (a) a myeloid cell comprising a recombinant polynucleic acid sequence, wherein the polynucleic acid sequence comprises a sequence encoding a chimeric fusion protein (CFP), the CFP comprising: (i) an extracellular domain comprising an anti-CD5 binding domain, and (ii) a transmembrane domain operatively linked to the extracellular domain; and (b) a pharmaceutically acceptable carrier; wherein the myeloid cell expresses the CFP.

In some embodiments, upon binding of the CFP to CD5 expressed by a target cancer cell of the subject killing or phagocytosis activity of the myeloid cell is increased by greater than 20% compared to a myeloid cell not expressing the CFP. In some embodiments, growth of a tumor is inhibited in the human subject.

In some embodiments, the cancer is a CD5+ cancer. In some embodiments, the cancer is leukemia, T cell lymphoma, or B cell lymphoma. In some embodiments, the CFP comprises one or more sequences shown in Table A and/or Table B below.

TABLE A

| Exemplary sequences of CFPs and domains thereof | | |
| --- | --- | --- |
| SEQ ID NO | PFP/Domain | Sequence |
| 1 | Anti-CD5 heavy chain variable domain | EIQLVQSGGGLVKPGGSVRISCAASGYTFTNYGMNWVRQA PGKGLEWMGWINTHTGEPTYADSFKGRFTFSLDDSKNTAY LQINSLRAEDTAVYFCTRRGYDWYFDVWGQGTTVTV |
| 2 | Anti-CD5 light chain variable domain | DIQMTQSPSSLSASVGDRVTITCRASQDINSYLSWFQQKPG KAPKTLIYRANRLESGVPSRFSGSGSGTDYTLTISSLQYEDF GIYYCQQYDESPWTFGGGTKLEIK |
| 33 | Anti-CD5 scFv | EIQLVQSGGGLVKPGGSVRISCAASGYTFTNYGMNWVRQA PGKGLEWMGWINTHTGEPTYADSFKGRFTFSLDDSKNTAY LQINSLRAEDTAVYFCTRRGYDWYFDVWGQGTTVTV*SSGG GGSGGGGSGGGGS*DIQMTQSPSSLSASVGDRVTITCRASQDI |

TABLE A-continued

Exemplary sequences of CFPs and domains thereof

| SEQ ID NO | PFP/Domain | Sequence |
|---|---|---|
| | | NSYLSWFQQKPGKAPKTLIYRANRLESGVPSRFSGSGSGTD YTLTISSLQYEDFGIYYCQQYDESPWTFGGGTKLEIK |
| 3 | FcRγ-chain intracellular signaling domain | LYCRRLKIQVRKAAITSYEKSDGVYTGLSTRNQETYETLKH EKPPQ |
| 20 | FcRγ-chain intracellular signaling domain | LYCRLKIQVRKAAITSYEKSDGVYTGLSTRNQETYETLKHE KPPQ |
| 27 | FcRγ-chain intracellular signaling domain | RLKIQVRKAAITSYEKSDGVYTGLSTRNQETYETLKHEKPP Q |
| 28 | FcRγ-chain intracellular signaling domain | RLKIQVRKAAITSYEKSDGVYTGLSTRNQETYETLKHEKPP Q |
| 4 | PI3K recruitment domain | YEDMRGILYAAPQLRSIRGQPGPNHEEDADSYENM |
| 5 | CD40 intra-cellular domain | KKVAKKPTNKAPHPKQEPQEINFPDDLPGSNTAAPVQETLH GCQPVTQEDGKESRISVQERQ |
| 6 | CD8α chain transmembrane domain | IYIWAPLAGTCGVLLLSLVIT |
| 29 | CD8α chain transmembrane domain | IYIWAPLAGTCGVLLLSLVITLYC |
| 7 | CD8α chain hinge domain | ALSNSIMYFSHFVPVFLPAKPTTTPAPRPPTPAPTIASQPLSL RPEACRPAAGGAVHTRGLD |
| 8 | Anti-HER2 heavy chain variable domain | DIQMTQSPSSLSASVGDRVTITCRASQDVNTAVAWYQQKP GKAPKLLIYSASFLYSGVPSRFSGSRSGTDFTLTISSLQPEDF ATYYCQQHYTTPPTFGQGTKVEIKRTGSTSGSGKPGSGEGS EVQLVE |
| 9 | Anti-HER2 light chain variable domain | LVQPGGSLRLSCAASGFNIKDTYIHWVRQAPGKGLEWVAR IYPTNGYTRYADSVKGRFTISADTSKNTAYLQMNSLRAEDT AVYYCSRWGGDGFYAMDVWGQGTLVTV |
| 32 | Anti-HER2 scFv | DIQMTQSPSSLSASVGDRVTITCRASQDVNTAVAWYQQKP GKAPKLLIYSASFLYSGVPSRFSGSRSGTDFTLTISSLQPEDF ATYYCQQHYTTPPTFGQGTKVEIKRTGSTSGSGKPGSGEGS EVQLVE*SSGGGGSGGGGSGGGGS*LVQPGGSLRLSCAASGFN IKDTYIHWVRQAPGKGLEWVARIYPTNGYTRYADSVKGRF TISADTSKNTAYLQMNSLRAEDTAVYYCSRWGGDGFYAM DVWGQGTLVTV |
| 17 | GMCSF Signal peptide | MWLQSLLLLGTVACSIS |
| 18 | CD28 transmembrane domain | FWVLVVVGGVLACYSLLVTVAFIIFWV |
| 34 | CD2 Transmembrane domain | IYLIIGICGGGSLLMVFVALLVFYIT |
| 19 | CD68 transmembrane domain | ILLPLIIGLILLGLLALVLIAFCII |
| 21 | TNFR1 intracellular domain | QRWKSKLYSIVCGKSTPEKEGELEGTTTKPLAPNPSFSPTPG FTPTLGFSPVPSSTFTSSSTYTPGDCPNFAAPRREVAPPYQG ADPILATALASDPIPNPLQKWEDSAHKPQSLDTDDPATLYA VVENVPPLRWKEFVRRLGLSDHEIDRLELQNGRCLREAQY SMLATWRRRTPRREATLELLGRVLRDMDLLGCLEDIEEAL CGPAALPPAPSLLR |

TABLE A-continued

Exemplary sequences of CFPs and domains thereof

| SEQ ID NO | PFP/Domain | Sequence |
|---|---|---|
| 22 | TNFR2 intracellular domain | PLCLQREAKVPHLPADKARGTQGPEQQHLLITAPSSSSSSLE SSASALDRRAPTRNQPQAPGVEASGAGEARASTGSSDSSPG GHGTQVNVTCIVNVCSSSDHSSQCSSQASSTMGDTDSSPSE SPKDEQVPFSKEECAFRSQLETPETLLGSTEEKPLPLGVPDA GMKPS |
| 23 | MDA5 intracellular domain | MSNGYSTDENFRYLISCFRARVKMYIQVEPVLDYLTFLPAE VKEQIQRTVATSGNMQAVELLLSTLEKGVWHLGWTREFVE ALRRTGSPLAARYMNPELTDLPSPSFENAHDEYLQLLNLLQ PTLVDKLLVRDVLDKCMEEELLTIEDRNRIAAAENNGNESG VRELLKRIVQKENWFSAFLNVLRQTGNNELVQELTGSDCSE SNAEIEN |
| 30 | CD8α chain hinge domain + transmembrane domain | ALSNSIMYFSHFVPVFLPAKPTTTPAPRPPTPAPTIASQPLSL RPEACRPAAGGAVHTRGLDIYIWAPLAGTCGVLLLSLVITL YC |
| 31 | CD8α chain hinge domain + transmembrane domain | ALSNSIMYFSHFVPVFLPAKPTTTPAPRPPTPAPTIASQPLSL RPEACRPAAGGAVHTRGLDIYIWAPLAGTCGVLLLSLVIT |
| 14 | CD5-FcRγ-PI3K | MWLQSLLLLGTVACSISEIQLVQSGGGLVKPGGSVRISCAA SGYTFTNYGMNWVRQAPGKGLEWMGWINTHTGEPTYAD SFKGRFTFSLDDSKNTAYLQINSLRAEDTAVYFCTRRGYDW YFDVWGQGTTVTV*SSGGGGSGGGGSGGGGS*DIQMTQSPSS LSASVGDRVTITCRASQDINSYLSWFQQKPGKAPKTLIYRA NRLESGVPSRF*SGSGSG*TDYTLTISSLQYEDFGIYYCQQYDE SPWTFGGGTKLEIK*SGGGGS*GALSNSIMYFSHFVPVFLPAKP TTTPAPRPPTPAPTIASQPLSLRPEACRPAAGGAVHTRGLDI YIWAPLAGTCGVLLLSLVITLYCRRLKIQVRKAAITSYEKSD GVYTGLSTRNQETYETLKHEKPPQ*GSGS*YEDMRGILYAAPQ LRSIRGQPGPNHEEDADSYENM |
| 15 | HER2-FCRγ-PI3K | MWLQSLLLLGTVACSISDIQMTQSPSSLSASVGDRVTITCRA SQDVNTAVAWYQQKPGKAPKLLIYSASFLYSGVPSRFSGSR SGTDFTLTISSLQPEDFATYYCQQHYTTPPTFGQGTKVEIKR TGSTSGSGKPGSGEGSEVQLVE*SGGG*LVQPGGSLRLSCAAS GFNIKDTYIHWVRQAPGKGLEWVARIYPTNGYTRYADSVK GRFTISADTSKNTAYLQMNSLRAEDTAVYYCSRWGGDGFY AMDVWGQGTLVTV*SSSGGGGSG*ALSNSIMYFSHFVPVFLP AKPTTTPAPRPPTPAPTIASQPLSLRPEACRPAAGGAVHTRG LDIYIWAPLAGTCGVLLLSLVITLYCRRLKIQVRKAAITSYE KSDGVYTGLSTRNQETYETLKHEKPPQ*GSGS*YEDMRGILYA APQLRSIRGQPGPNHEEDADSYENM |
| 16 | CD5-FcRγ-CD40 | MWLQSLLLLGTVACSISEIQLVQSGGGLVKPGGSVRISCAA SGYTFTNYGMNWVRQAPGKGLEWMGWINTHTGEPTYAD SFKGRFTFSLDDSKNTAYLQINSLRAEDTAVYFCTRRGYDW YFDVWGQGTTVTV*SSGGGGSGGGGSGGGGS*DIQMTQSPSS LSASVGDRVTITCRASQDINSYLSWFQQKPGKAPKTLIYRA NRLESGVPSRFSGSGSGTDYTLTISSLQYEDFGIYYCQQYDE SPWTFGGGTKLEIK*SGGGGS*GALSNSIMYFSHFVPVFLPAKP TTTPAPRPPTPAPTIASQPLSLRPEACRPAAGGAVHTRGLDI YIWAPLAGTCGVLLLSLVITLYCRLKIQVRKAAITSYEKSDG VYTGLSTRNQETYETLKHEKPPQKKVAKKPTNKAPHPKQE PQEINFPDDLPGSNTAAPVQETLHGCQPVTQEDGKESRISVQ ERQ |
| 24 | CD5-FcRγ-MDA5 | MWLQSLLLLGTVACSISEIQLVQSGGGLVKPGGSVRISCAA SGYTFTNYGMNWVRQAPGKGLEWMGWINTHTGEPTYAD SFKGRFTFSLDDSKNTAYLQINSLRAEDTAVYFCTRRGYDW YFDVWGQGTTVTVSSGGGGSGGGGSGGGGSDIQMTQSPSS LSASVGDRVTITCRASQDINSYLSWFQQKPGKAPKTLIYRA NRLESGVPSRFSGSGSGTDYTLTISSLQYEDFGIYYCQQYDE SPWTFGGGTKLEIKSGGGGSGALSNSIMYFSHFVPVFLPAKP TTTPAPRPPTPAPTIASQPLSLRPEACRPAAGGAVHTRGLDI YIWAPLAGTCGVLLLSLVITLYCRLKIQVRKAAITSYEKSDG VYTGLSTRNQETYETLKHEKPPQGSGSMSNGYSTDENFRY LISCFRARVKMYIQVEPVLDYLTFLPAEVKEQIQRTVATSG NMQAVELLLSTLEKGVWHLGWTREFVEALRRTGSPLAAR YMNPELTDLPSPSFENAHDEYLQLLNLLQPTLVDKLLVRDV |

TABLE A-continued

Exemplary sequences of CFPs and domains thereof

| SEQ ID NO | PFP/Domain | Sequence |
|---|---|---|
| | | LDKCMEEELLTIEDRNRIAAAENNGNESGVRELLKRIVQKE NWFSAFLNVLRQTGNNELVQELTGSDCSESNAEIEN |
| 25 | CD5-FcRγ-TNFR1 | MWLQSLLLLGTVACSISEIQLVQSGGGLVKPGGSVRISCAA SGYTFTNYGMNWVRQAPGKGLEWMGWINTHTGEPTYAD SFKGRFTFSLDDSKNTAYLQINSLRAEDTAVYFCTRRGYDW YFDVWGQGTTVTVSSGGGGSGGGGSGGGGSDIQMTQSPSS LSASVGDRVTITCRASQDINSYLSWFQQKPGKAPKTLIYRA NRLESGVPSRFSGSGSGTDYTLTISSLQYEDFGIYYCQQYDE SPWTFGGGTKLEIKSGGGGSGALSNSIMYFSHFVPVFLPAKP TTTPAPRPPTPAPTIASQPLSLRPEACRPAAGGAVHTRGLDI YIWAPLAGTCGVLLLSLVITLYCRLKIQVRKAAITSYEKSDG VYTGLSTRNQETYETLKHEKPPQGSGSQRWKSKLYSIVCG KSTPEKEGELEGTTTKPLAPNPSFSPTPGFTPTLGFSPVPSSTF TSSSTYTPGDCPNFAAPRREVAPPYQGADPILATALASDPIP NPLQKWEDSAHKPQSLDTDDPATLYAVVENVPPLRWKEFV RRLGLSDHEIDRLELQNGRCLREAQYSMLATWRRRTPRRE ATLELLGRVLRDMDLLGCLEDIEEALCGPAALPPAPSLLR |
| 26 | CD5-FcRγ-TNFR2 | MWLQSLLLLGTVACSISEIQLVQSGGGLVKPGGSVRISCAA SGYTFTNYGMNWVRQAPGKGLEWMGWINTHTGEPTYAD SFKGRFTFSLDDSKNTAYLQINSLRAEDTAVYFCTRRGYDW YFDVWGQGTTVTVSSGGGGSGGGGSGGGGSDIQMTQSPSS LSASVGDRVTITCRASQDINSYLSWFQQKPGKAPKTLIYRA NRLESGVPSRFSGSGSGTDYTLTISSLQYEDFGIYYCQQYDE SPWTFGGGTKLEIKSGGGGSGALSNSIMYFSHFVPVFLPAKP TTTPAPRPPTPAPTIASQPLSLRPEACRPAAGGAVHTRGLDI YIWAPLAGTCGVLLLSLVITLYCRLKIQVRKAAITSYEKSDG VYTGLSTRNQETYETLKHEKPPQGSGSPLCLQREAKVPHLP ADKARGTQGPEQQHLLITAPSSSSSSLESSASALDRRAPTRN QPQAPGVEASGAGEARASTGSSDSSPGGHGTQVNVTCIVN VCSSSDHSSQCSSQASSTMGDTDSSPSESPKDEQVPFSKEEC AFRSQLETPETLLGSTEEKPLPLGVPDAGMKPS |

TABLE B

Linker sequences

| SEQ ID | Sequence |
|---|---|
| 10 | SSGGGGSGGGGSGGGGS |
| 11 | SGGGGSG |
| 12 | SGGG |
| 13 | GSGS |

IV. Noncoding exogenous sequence for delivery and incorporation into the genome of a cell.

A noncoding sequence may be delivered into the cell and designed to be incorporated in the genome of the cell. The noncoding sequence as used herein, is a sequence that does not result in a translated protein product, but may have regulatory elements, such as transcribed products, such as inhibitory RNA. In some embodiments, such a sequence may be a miRNA sequence. In some embodiments, the sequence may be a sequence for siRNA generation. In some embodiments, the sequence may comprise an intronic sequence, or a binding site created, such that one or more DNA binding proteins can dock on the site and influence the nature and behavior of the adjoining regions. In some embodiments, the sequence may be a transcription factor binding site. In some embodiments, the sequence may comprise an enhancer binding site. In some embodiments, the sequence may comprise a binding site for topoisomerase, gyrase, reverse transcriptase, polymerase, poly A binding protein, guanylyl cyclase, ligase, restriction enzymes, DNA methylase, HDAC enzymes, and many others. In some embodiments, the noncoding sequence may be directed to manipulating heterochromatin. A noncoding insert sequence, as it may also be referred to here, may be a few nucleotides to 5 kB in length.

V. Plasmid Design and Recombinant Nucleic Acid Design Comprising an Insert Sequence The nucleic acid construct comprising one or more sequences encoding one or more proteins or polypeptides is incorporated in a plasmid for transcription and generating an mRNA. mRNA can be transcribed in an in vitro system using synthetic system of cell extracts. Alternatively, mRNA can be generated in a cell and harvested. The cell can be a prokaryotic cell, such as a bacterial cell. In some embodiments, the cell is a eukaryotic cell. In some embodiments, the transcription occurs in a synthetic system. Provided herein are exemplary plasmid design.

In some embodiments, of the various aspects of the disclosure, a plasmid is designed for expression of the mRNA molecule comprising a heterologous sequence of interest that encodes a protein or a polypeptide. The plasmid comprises, inter alia, the sequences for genomic integration elements for integration of the heterologous sequence of interest that encodes a protein or a polypeptide; the sequence comprising the transgene or fragment thereof, operably linked to its separate promoter and regulatory elements that are required for its expression in the host following integration in the host genome, (such as, the subject who is administered the mRNA); one or more regulatory elements for transcription and generation of the mRNA including a promoter for expression of the mRNA, e.g. in a bacterial cell or cell extract, and 3' stabilizing elements; sequences for one or more detection marker and/or selection markers.

As is known to one of skill in the art, a plasmid backbone can be an available vector, such as an in-house or commercially developed vector, that can be improved in various ways for best expression of the transcribed sequences, for example, (but not limited to), by introducing one or more desirable restriction digestion sites in the MCS (multiple cloning site), introducing a desired promoter for overall mRNA transcription, such as the T7 promoter, exchanging an existing sequence within the plasmid vector for one or more desired sequences, or introducing one or more desired segments, such as a selection marker sequence.

The plasmid comprises transcription regulatory elements, such as a promoter at the 5' region, and a 3'-stabilizing element. In some embodiments, the promoter is chosen for enhanced mRNA transcription in the desired cell, such as an *E. coli* bacterial cell. In some embodiments, the promoter for transcription of the plasmid is selected from a T7 promoter, a Sp6 promoter, pL (lambda) promoter, T3 promoter, trp promoter, araBad promoter, lac promoter or a Ptac promoter. In some embodiments, the promoter is a T7 promoter. T7 or Sp6 promoters are constitutive promoters and are useful for high level transcription or in vitro transcription. In some embodiments, the 3' stabilizing element is a sequence from BGH 3' element, WPRE 3' element, SV40 element, hGH element and other elements. The 3' element comprises the necessary poly A and transcription termination sequences.

Exemplary selection markers include antibiotic selection marker and/or expression detection marker. Antibiotic selection markers include but are not limited to ampicillin resistance gene sequence (beta lactamase gene or fragment thereof) conferring resistance to ampicillin, for example G418 selection marker, tetracycline resistance gene sequence conferring resistance to tetracycline, kanamycin resistance gene sequence conferring resistance to kanamycin, erythromycin resistance gene sequence conferring resistance to erythromycin, chloramphenicol resistance gene sequence conferring resistance to chloramphenicol, neomycin resistant gene sequence conferring resistance to neomycin, and others. Exemplary expression detection marker include FLAG, HA, GFP and others.

In some embodiments, the and other tags that can be fused to one or more coding sequences to function as a surrogate for the expression of the desired protein or peptide to which it is fused.

In some embodiments, the plasmid is less than 20 kb in length. In some embodiments, the plasmid is less than 19 kb in length. In some embodiments, the plasmid is less than 20 kb in length. In some embodiments, the plasmid is less than 18 kb in length. In some embodiments, the plasmid is less than 20 kb in length. In some embodiments, the plasmid is less than 17 kb in length. In some embodiments, the plasmid is less than 20 kb in length. In some embodiments, the plasmid is less than 16 kb in length. In some embodiments, the plasmid is less than 15 kb in length. In some embodiments, the plasmid is less than 14 kb in length. In some embodiments, the plasmid is less than 13 kb in length. In some embodiments, the plasmid is less than 12 kb in length. In some embodiments, the plasmid is about 15 kb, about 14 kb, about 13 kb, about 12 kb or about 10 kb in length.

In some embodiments, the codon is optimized for maximized transcription suitable for the transcription system.

VI. Features Related to the Expression of the Transgene In Vivo

Transcription Regulatory Elements in the Recombinant Nucleic Acid Construct (Transgene)

In some embodiments, the recombinant nucleic comprises one or more regulatory elements within the noncoding regions that can be manipulated for desired expression profiles of the encoded proteins. In some embodiments, the noncoding region may comprise suitable enhancer. In some embodiments, the enhancer comprises a binding region for a regulator protein or peptide may be added to the cell or the system comprising the cell, for commencement of expression of the protein encoded under the influence of the enhancer. Conversely, a regulatory element may comprise a protein binding domain that remains bound with the cognate protein and continue to inhibit transcription and/or translation of recombinant protein until an extracellular signal is provided for the protein to decouple from the bound position to allow commencement of the protein synthesis. Examples include but are not limited to Tetracycline-inducible (Tet-Inducible or Tet-on) and Tetracycline repressible (Tet-off) systems known to one of skill in the art.

Construct comprising metabolic switch: In some embodiments, the 5' and 3' untranslated regions flanking the coding regions of the construct may be manipulated for regulation of expression of the recombinant protein encoded by the nucleic acid constructs described above. For instance, the 3'UTR may comprise one or more elements that are inserted for stabilizing the mRNA. In some embodiments, AU-Rich Elements (ARE) sequences are inserted in the 3' UTR that result in binding of RNA binding proteins that stabilize or destabilize the mRNA, allowing control of the mRNA half-life.

In some embodiments, the 3'UTR may comprise a conserved region for RNA binding proteins (e.g. GAPDH) binding to mature mRNA strand preventing translation. In some embodiments, glycolysis results in the uncoupling of the RNA binding proteins (e.g. GAPDH) allowing for mRNA strand translation. The principle of the metabolic switch is to trigger expression of target genes when a cell enters a certain metabolic state. In resting cells, for example, GAPDH is an RNA binding protein (RBP). It binds to ARE sequences in the 3'UTR, preventing translation of mRNA. When the cell enters glycolysis, GAPDH is required to convert glucose into ATP, coming off the mRNA allowing for translation of the protein to occur. In some embodiments, the environment in which the cell comprising the recombinant nucleic acid is present, provides the metabolic switch to the gene expression. For example, hypoxic condition can trigger the metabolic switch inducing the disengaging of GAPDH from the mRNA. The expression of the mRNA therefore can be induced only when the macrophage leaves the circulation and enters into a tumor environment, which is hypoxic. This allows for systemic administration of the nucleic acid or a cell comprising the nucleic acid, but ensures a local expression, specifically targeting the tumor environment.

In some embodiments, the nucleic acid construct can be a split construct, for example, allowing a portion of the construct to be expressed under the control of a constitutive expression system whereas another portion of the nucleic acid is expressed under control of a metabolic switch, as described above. In some embodiments, the nucleic acid may be under bicistronic control. In some embodiments, the bicistronic vector comprises a first coding sequence under a first regulatory control, comprising the coding sequence of a target recognition moiety which may be under constitutive control; and a second coding sequence encoding an inflammatory gene expression which may be under the metabolic switch. In some embodiments, the bicistronic vector may be unidirectional. In some embodiments, the bicistronic vector may be bidirectional.

In some embodiments, the ARE sequences comprise protein binding motifs for binding ARE sequence that bind to ADK, ALDH18A1, ALDH6A1, ALDOA, ASSI, CCBL2, CS, DUT, ENO1, FASN, FDPS, GOT2, HADHB, HK2, HSD17B10, MDH2, NME1, NQO1, PKM2, PPP1CC, SUCLG1, TP11, GAPDH, or LDH.

Pharmaceutical Compositions and Immunotherapy

In one aspect provided herein is a pharmaceutical composition comprising (i) the nucleic acid encoding the transgene is incorporated in a transpositioning or retrotranspositioning system comprising the transgene, the 5'- and 3'-flanking transposition or retrotranspositioning elements, the expression regulation elements, such as promoters, introns; and a nucleic acid encoding the transposase or retrotransposase, (ii) a nucleic acid delivery vehicle and a pharmaceutically acceptable salt or excipient.

In some embodiments, the pharmaceutical composition comprises cells comprising the nucleic acid encoding the transgene that is stably integrated in the genome of the cell and a pharmaceutically acceptable excipient. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995), using viral vectors (Monahan, et al, Gene Therapy 4:40-49, 1997; Onodera, et al, Blood 91:30-36, 1998), by uptake of "naked DNA", and the like. Techniques well known in the art for the transformation of cells (see discussion above) can be used for the ex vivo administration of nucleic acid constructs. The exact formulation, route of administration and dosage can be chosen empirically. (See e.g. Fingl et al., 1975, in "The Pharmacological Basis of Therapeutics", Ch. 1 pl).

In some embodiments, the nucleic acid comprising the transgene and the transposable elements is introduced or incorporated in the cell by known methods of nucleic acid transfer inside a cell, such as using lipofectamine, or calcium phosphate, or via physical means such as electroporation or nucleofection. In some embodiments, the nucleic acid is encapsulated in liposomes or lipid nanoparticles. LNPs are 100-300 nm in diameter provide efficient means of mRNA delivery to various cell types, including macrophages. In some embodiments, the nucleic acid is transferred by other nanoparticles. In some embodiments, the vector for expression of the CFP is of a viral origin, namely a lentiviral vector or an adenoviral vector. In some embodiments, the nucleic acid encoding the recombinant nucleic acid is encoded by a lentiviral vector. In some embodiments, the lentiviral vector is prepared in-house and manufactured in large scale for the purpose. In some embodiments, commercially available lentiviral vectors are utilized, as is known to one of skill in the art.

In some embodiments, the viral vector is an Adeno-Associated Virus (AAV) vector.

The methods find use in a variety of applications in which it is desired to introduce an exogenous nucleic acid into a target cell and are particularly of interest where it is desired to express a protein encoded by an expression cassette in a target cell, where the target cell or cells are part of a multicellular organism. The transposase system may be administered to the organism or host in a manner such that the targeting construct is able to enter the target cell(s), e.g., via an in vivo or ex vivo protocol. Such cells or organs are typically returned to a living body.

In some embodiments, the transgene encoding a fusion protein related to immune function is stably integrated in a living cell of a subject ex vivo, following which the cell comprising the transgene is returned to the subject. Of exemplary importance, the CFP transgene (phagocytic receptor fusion protein) is intended for expression in an immune cell, such as a myeloid cell, a phagocytic cell, a macrophage, a monocyte or a cell of dendritic cell lineage is contacted ex vivo with the recombinant nucleic acids for stable transfer of the transgene and re-introduced in the same subject for combating a disease of the subject. The diseases contemplated comprises infectious diseases, cancer and autoimmune diseases. The nucleic acid encoding the PSR subunit comprising fusion protein (CFP) described herein is used to generate engineered phagocytic cells for treating cancer.

Cancers include, but are not limited to T cell lymphoma, cutaneous lymphoma, B cell cancer (e.g., multiple myeloma, Waldenstrom's macroglobulinemia), the heavy chain diseases (such as, for example, alpha chain disease, gamma chain disease, and mu chain disease), benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

In general, cellular immunotherapy comprises providing the patient a medicament comprising live cells, which should be HLA matched for compatibility with the subject, and such that the cells do not lead to graft versus Host Disease, GVHD. A subject arriving at the clinic for personalized medicine and immunotherapy as described above, is routinely HLA typed for determining the HLA antigens expressed by the subject.

Therapeutic Advantages of mRNA Driven Delivery

In one embodiment, provided herein is a method of introducing a nucleic acid sequence into a cell for sustained gene expression in the cell without adverse effects. In some embodiments, the cell is within a living system, e.g., a host organism such as a human. The nucleic acid sequence is an mRNA.

In particular, delivery via retrotransposon poses to be a highly lucrative mode. mRNA driven delivery simplifies gene delivery. While other technologies require expensive and sophisticated design and manufacturing, and a solution for delivery of the nucleic acid into the cell, and gene editing technologies to assist in integration, retrotransposon mediated delivery itself encodes for the editing machinery, encodes for new genes to be delivered. In addition, a single mRNA may be sufficient for gene delivery and editing.

In one embodiment, mRNA delivery is advantageous in that it can ensure introduction of a nucleic acid cargo without size restraint.

Table 9 summarizes some of the advantages over the other existing methods of nucleic acid deliveries.

TABLE 9

Advantages of retrotransposon mediated gene delivery

| | Lentiviral delivery | AAV-delivery | Retrotransposon delivery |
|---|---|---|---|
| Payload | ~4 kb | ~4 kb | >10 kb |
| Toxicity | Insertional mutagenesis | Unresolved liver & CNS toxicity | Unknown, pending clinical development |
| Manufacturing | Complex, expensive | Complex, expensive | Inexpensive, rapid |

Retrotransposons are advantageous for applications across multiple modalities. Gene manipulation using this method is easily attained both in vivo and ex vivo. In one embodiment, the application of retrotransposon may be in vivo, a piece of genetic material encoded in an mRNA can be directly introduced into a patient by systemic or local introduction. In contrast, cells can be taken out from a subject, and manipulated ex vivo and then introduced either to the same subject (autologous) or to another human (heterologous).

In one embodiment, retrotransposons and the related methods described herein may be instrumental in gene therapy. With the advantage of capacity to introduce large payloads, large sections of DNA carrying a gene encoding an entire protein may be introduced in one shot without requiring multiple introductions and multiple editing events. In one embodiment, for example, a gene that encodes a defective protein may be excised, the correct gene may be introduced in the correct site in one integration event using a retrotransposon mediated delivery. In one example, CRISPR editing may be used to excise a gene from precise locus and retrotransposition may be used to replace the correct genes. In some embodiments, a preferred retrotransposon integration site may be introduced at the excision site.

In one embodiment, retrotransposons and the related methods described herein may be instrumental in gene editing.

In one embodiment, retrotransposons and the related methods described herein may be instrumental in transcriptional regulation.

In one embodiment, retrotransposons and the related methods described herein may be instrumental in genome engineering.

In one embodiment, retrotransposons and the related methods described herein may be instrumental in developing cell therapy, for example chimeric antigen receptor (CAR)T cells, in NK cell therapy or in myeloid cell therapy. In one embodiment, retrotransposons and the related methods described herein may be instrumental in delivery of genes into neurons, which are difficult to access by existing technologies.

In one aspect, provided herein is a method for targeted replacement of a genomic nucleic acid sequence of a cell, the method comprising: (A) introducing to the cell a polynucleotide sequence encoding a first protein complex comprising a targeted excision machinery for excising from the genome of the cell a nucleic acid sequence comprising one or more mutations; and (B) a recombinant mRNA encoding a second protein complex, wherein the recombinant mRNA comprises: (i) a nucleic acid sequence comprising the excised nucleic acid sequence in (A) that does not contain the one or more mutations, and (ii) a sequence encoding an L1 retrotransposon ORF2 protein under the influence of an independent promoter.

In one embodiment, the first protein complex may be an endonuclease complex independent of the second protein complex. In one embodiment, the first protein complex comprises a CRISPR-CAS system that uses sequence guided genomic DNA excision. In one embodiment, the methods described herein couples a CRISPR CAS system or any other gene editing system with a Lil transposon machinery (e.g., the second protein complex) that delivers a replacement gene with a payload capacity of greater than 4 kb, or 5 kb, or 6 kb, or 7 kb, or 8 kb or 9 kb or 10 kb. This coupling can be utilized in precisely excising a large fragment (a mutated gene causing a disease) from the genomic locus and integrating a large fragment of a gene or an entire gene that encodes a correct, non-mutated sequence.

A large number of genetic diseases may require delivery of gene delivery of large payloads, often exceeding the functional capacity of existing methods. Contemplated herein are methods and compositions disclosed herein that can be instrumental in further designing therapy for such diseases using retrotransposons. An exemplary list of genetic diseases include but are not limited to the ones listed in Table 10.

TABLE 10

| List of potential gene therapy applications | | | | |
|---|---|---|---|---|
| Disease | Gene | CDS | Expression | Prevalence |
| Stargardt | ABCA4 | 6.8 kb | Rod and Cone PRs | 1:8000 |
| Usher 1B | MYO7A | 6.7 kb | RPE and PRs | 3.2:100,000 |
| LCA10 | CEP290 | 7.4 kb | PR (pan retinal) | 1:50,000 |
| USH1D, DFNB12 | CDH23 | 10.1 kb | PR | 3:100,000 |
| RP | EYS | 9.4 kb | PR ECM | 1:50,000 |
| USH2A | USH2a | 15.6 kb | Rod and Cone PRs | 4:100,000 |
| USH2C | GPR98 | 18.0 kb | Mainly PRs | 1:100,000 |
| Alstrom syndrome | ALMS1 | 12.5 kb | Rod and Cone PRs | 1:1,000,000 |
| Glycogen storage disease III | GDE | 4.6 kb | Muscle, Liver | 1:8000 |
| Non-syndromic deafness | OTOF | 6.0 kb | Ear | 14:100,000 |
| Hemophilia A | F8 | 7.1 kb | Liver | 1:10,000 |
| Leber congenital aumaurosis | CEP290 | 7.5 kb | Retina | 5:100,000 |

Provided herein is a method for targeted replacement of a genomic nucleic acid sequence in a cell. In one embodiment, the method comprises: (A) excising from the genome of the cell a nucleic acid sequence comprising one or more mutations and (B) introducing into the cell a recombinant mRNA encoding: (i) a nucleic acid sequence comprising a wild type sequence relative to the sequence excised in (A) that does not contain the one or more mutation, (ii) a sequence encoding an L1 retrotransposon ORF2 protein under the influence of an independent promoter. In one embodiment, Step (A) further comprises introducing a short sequence comprising at least a plurality of adenylate residues at the excision site. In one embodiment, the In one embodiment, the nucleic acid sequence comprising a wild type sequence is operably linked with the ORF2 encoding sequence in a way such that the ORF2 reverse transcriptase integrates the sequence comprising the wild type non-mutated sequence into the genome.

In one embodiment, the cell is a lymphocyte.

In one embodiment, the cell is an epithelial cell. In some embodiments the cell is a retinal pigmented epithelial cell (RPE).

In one embodiment, the cell is a neuron.

In one embodiment, the cell is a myeloid cell.

In one embodiment, the cell is a stem cell.

In one embodiment, the cell is a cancer cell.

In one embodiment, the gene is selected from a group consisting of ABCA4, MYO7A, CEP290, CDH23, EYS, USH2a, GPR98, ALMS1, GDE, OTOF and F8.

In one embodiment, the mRNA comprises a sequence for an inducible promoter.

In one embodiment, the expression of the nucleic acid sequence comprising a non-mutated sequence is detectable at least 20, 21, 22, 23, 24, 25, 26, 27, 28, 29, 30, 31, 32, 33, 34 or 35 days post infection.

In one embodiment, the method comprises introducing into the cell a recombinant mRNA in vivo.

In one embodiment, the method comprises introducing into the cell a recombinant mRNA ex vivo.

Provided herein is a method of treating a genetic disease in a subject in need thereof, comprising: introducing into the subject a composition comprising a polycistronic mRNA encoding a gene or fragment thereof, operably linked to a sequence encoding an L1 retrotransposon; wherein the gene or the fragment thereof is at least 10.1 kb in length.

In one embodiment, the method comprises directly introducing the mRNA systemically.

In one embodiment, the method comprises directly introducing the mRNA locally.

In one embodiment, the genetic disease is a retinal disease. For example, the disease is macular dystrophy. In one embodiment, the disease is stargardt disease, also known as juvenile macular degeneration, or fundus flavimaculatus. The disease causes progressive degeneration and damage of the macula. The condition has a genetic basis due to mutation in the ATP-binding cassette (ABC) transporter gene, (ABCA4) gene, and arises from the deposition of lipofuscin-like substance in the retinal pigmented epithelium (RPE) with secondary photoreceptor cell death. In some embodiments, the method comprises direct delivery of the mRNA to the retina.

In one embodiment, the method comprises treating a nonsyndromic autosomal recessive deafness (DFNB12) and deafness associated with retinitis pigmentosa and vestibular dysfunction (USH1D). In one embodiment, provided herein is a method of treating non-syndromic deafness (DFNB12) or Usher syndrome (USH1D), the method comprises introducing an mRNA comprising a copy of CDH23 or a fragment thereof operably linked to a sequence encoding an L1 retrotransposon.

EXAMPLES

It should be appreciated that the invention should not be construed to be limited to the examples which are now described; rather, the invention should be construed to include any and all applications provided herein and all equivalent variations within the skill of the ordinary artisan.

Example 1. Exemplary Retrotransposon Designs Constructs

Figure 1A:
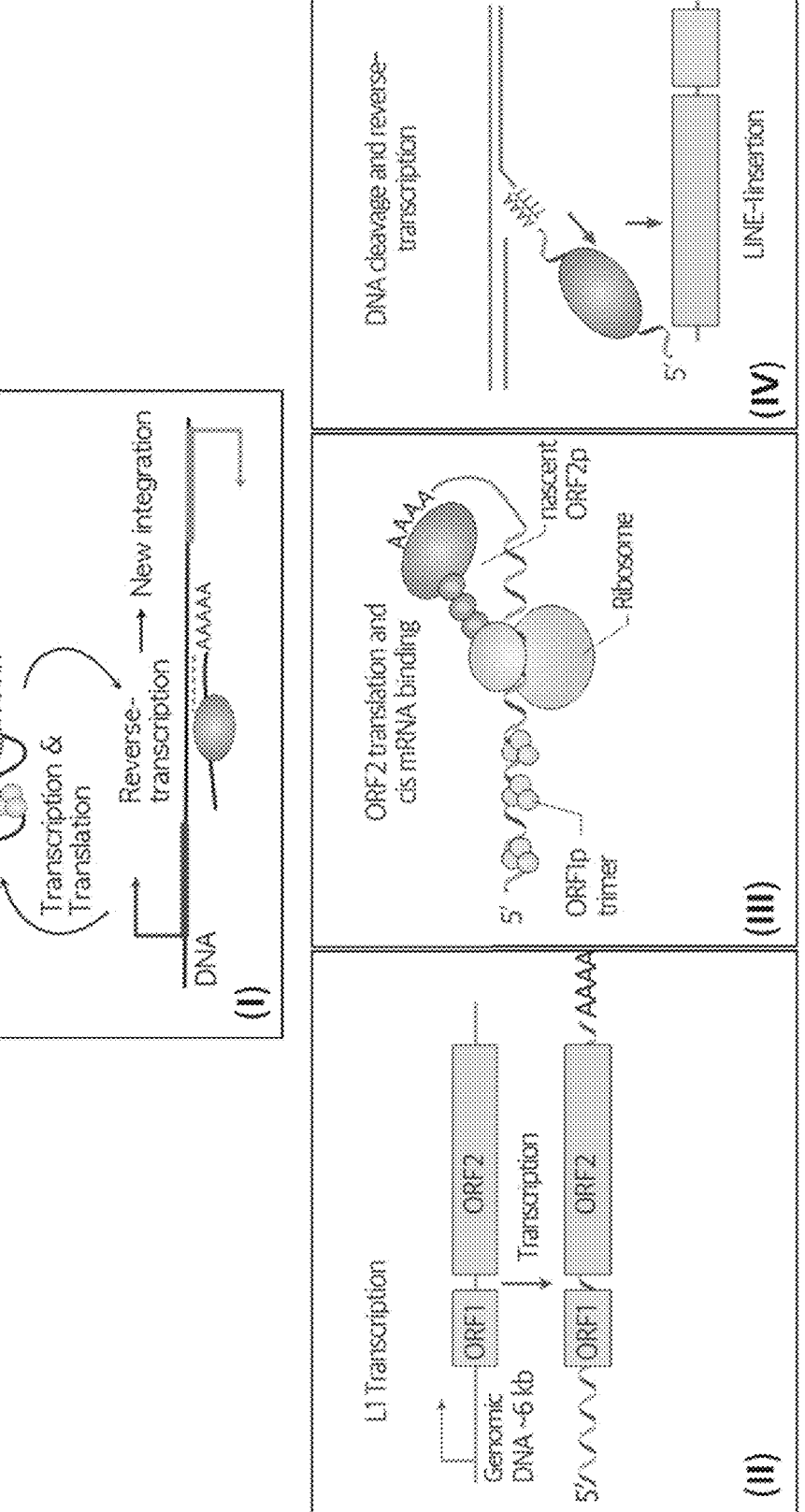
FIG. 1A illustrates a general mechanism of action of retrotransposons. (I) is a schematic representing the overall lifecycle of an autonomous retrotransposon. (II) LINE-1 retrotransposon comprises LINE-1 elements, which encode two proteins ORF1p and ORF2p that are expressed as mRNAs. The bicistronic mRNA is translated into the two proteins, and when ORF2p is translated by a read-through event by the ribosome, it binds the 3'end of its own mRNA through the poly A tail (III). ORF2p cleaves at a consensus sequence TAAAA, where the poly A at the 3' end of the mRNA hybridizes and primes the reverse transcriptase activity of the ORF2 protein. The protein reverse-transcribes the mRNA back into DNA leading to an insertion of the LINE-1 sequence back into a new location in the genome (IV).
Figure 1B:
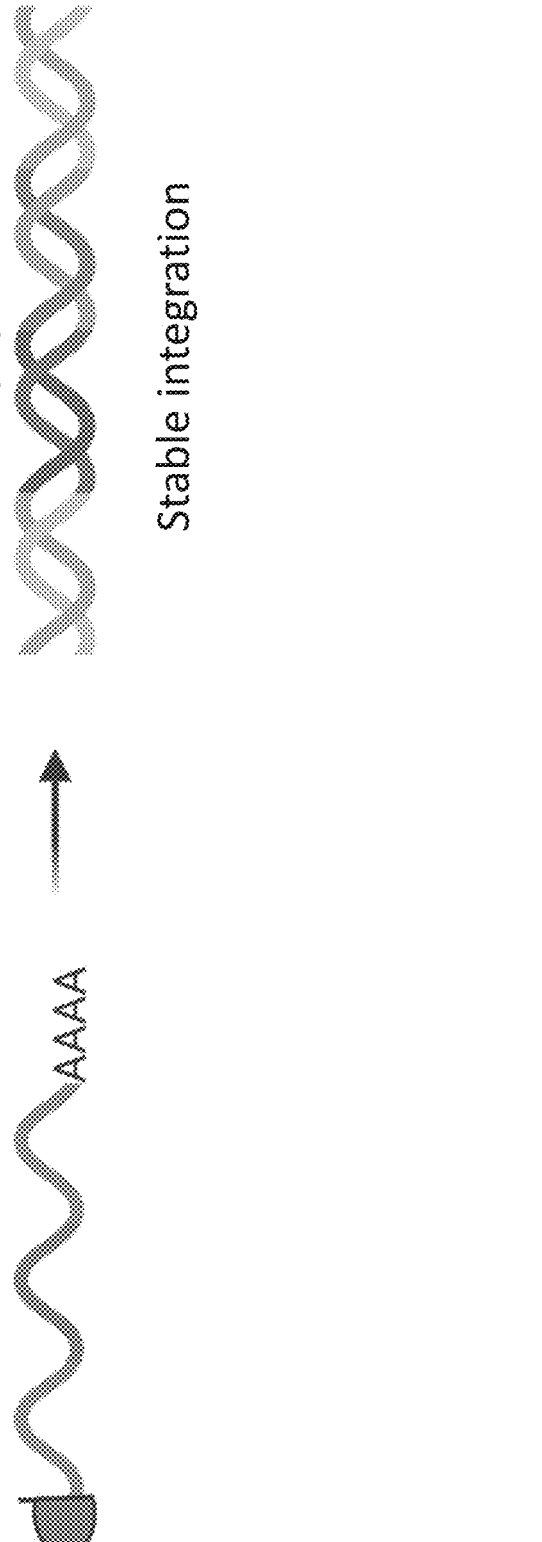
FIG. 1B is an illustration of a schematic diagram of an mRNA construct that comprises a genetic payload (left) that can be designed for integration into the genome (right).
Figure 1C:
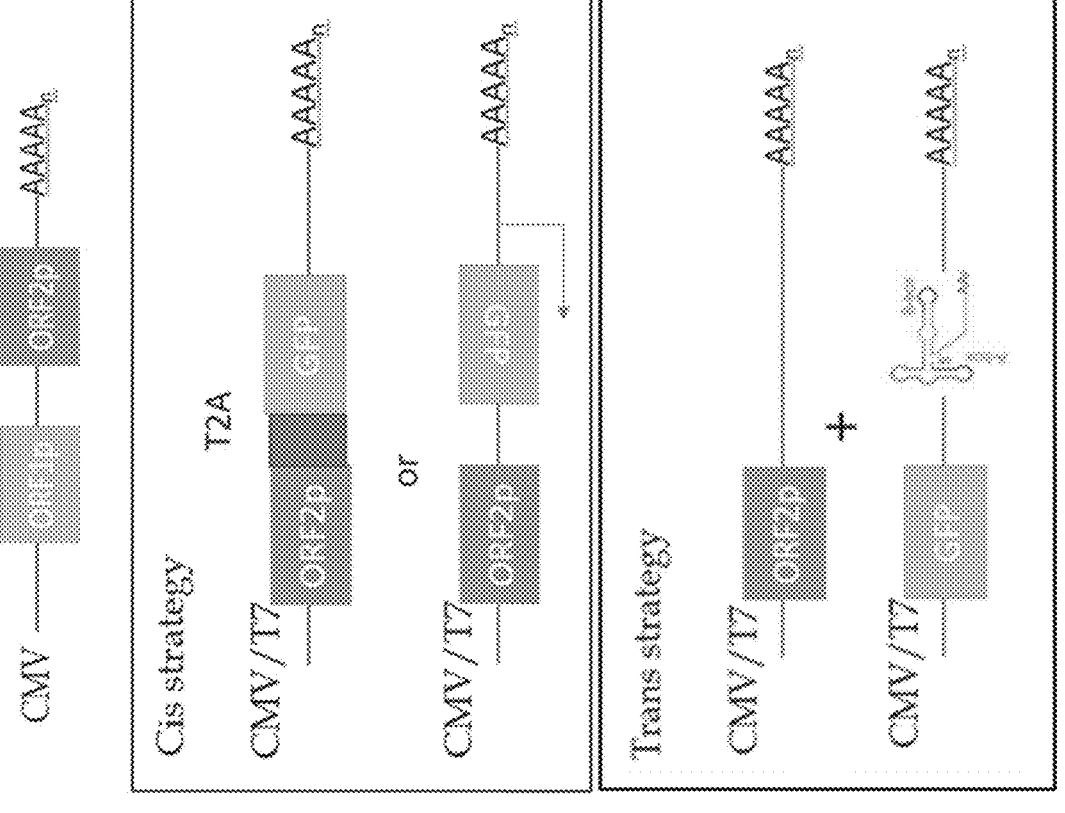
FIG. 1C illustrates various exemplary designs for integrating an mRNA encoding a transgene into the genome of a cell. GFP shown here in a box is an exemplary transgene.
Figure 1E:
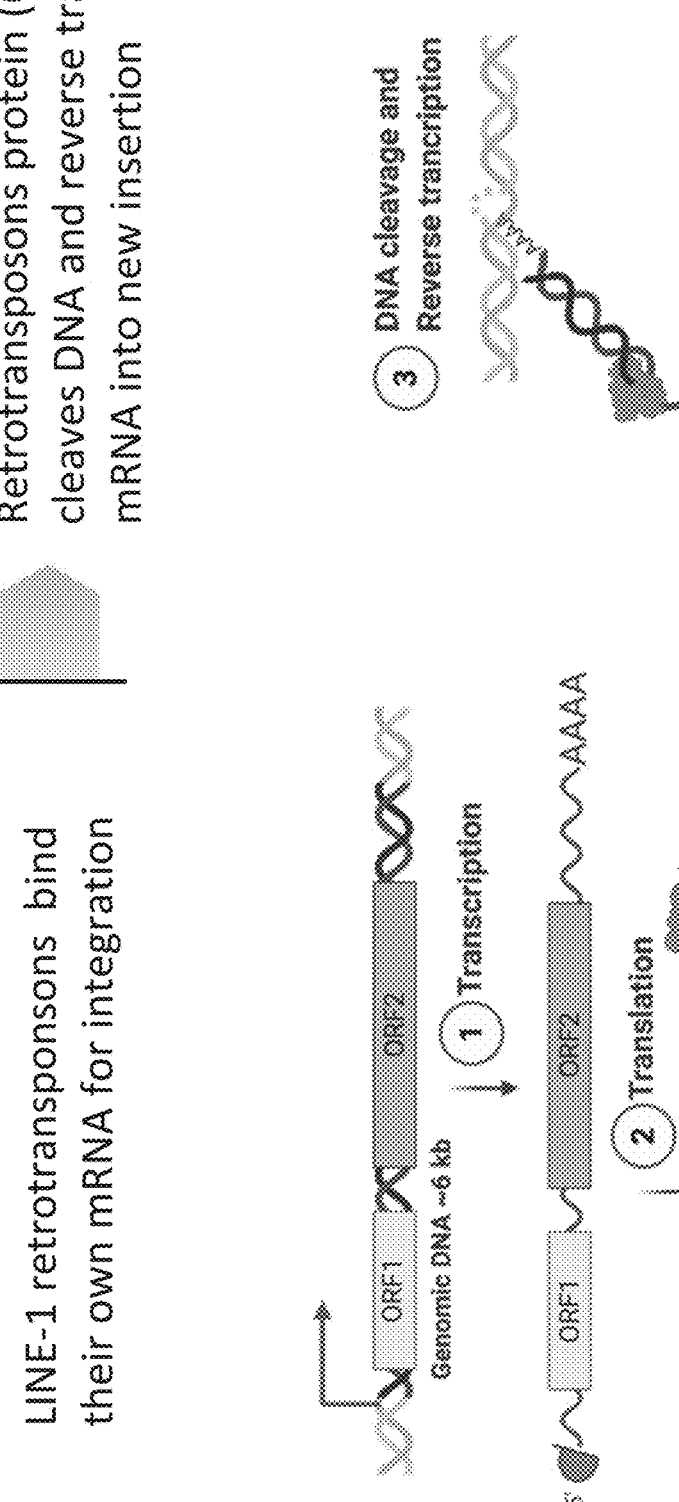
FIG. 1E is an illustration a schematic of the LINE-1 retrotransposition cycle showing the mechanism of action of the LINE transposons and introduction of a transgene cargo into a retrotransposon cite. LINE-1 retrotransposons are genomic sequences that encode for two proteins, ORF1 and ORF2. These elements are transcribed and translated into proteins that form an RNA-protein complex with the LINE-1 mRNA, ORF1 trimers, and ORF2, a reverse-transcriptase endonuclease. This complex translocates back into the nuclease where it cleaves DNA at a 5'-TTTT N-3' motif and is primed for reverse-transcription of the LINE-1 RNA by the ORF2 protein by making an RNA-DNA hybrid with the poly A tail of the mRNA and the resected cleaved DNA. Reverse-transcription of the LINE-1 into cDNA leads to a new LINE-1 integration event.

Provided here are exemplary strategies of designing retrotransposon constructs for incorporating into the genome of a cell and expressing an exemplary transgene. FIG. 1B and FIG. 1C illustrates various strategic designs for integrating an mRNA encoding transgene into the genome of a cell. GFP shown here in a box is an exemplary transgene. The mRNA encoding the transgene (e.g., GFP) can be co-expressed with a nucleic acid sequence encoding an ORF2p protein, in either sense or antisense orientation; the respective coding sequences may be in a monocistronic or bicistronic construct shown under exemplary Cis-strategies (FIG. 1B and FIG. 1C). CMV/T7 are promoters.

Figure 2A:
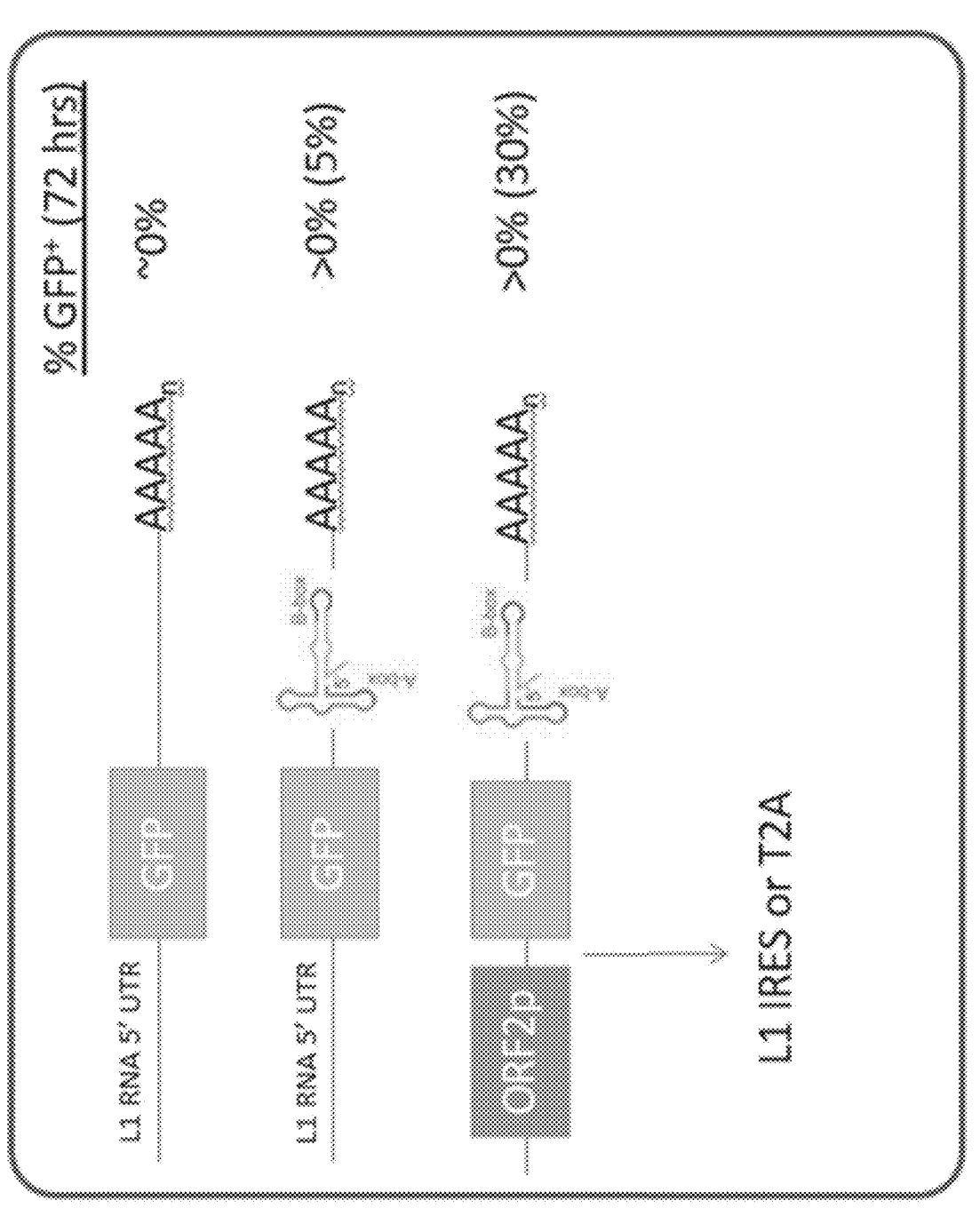
FIG. 2A illustrates three exemplary designs for expressing an exemplary transgene GFP by stably incorporating the sequence encoding GFP using the constructs. Expected GFP expression levels at 72 hours are shown on the right side.
Figure 2B:
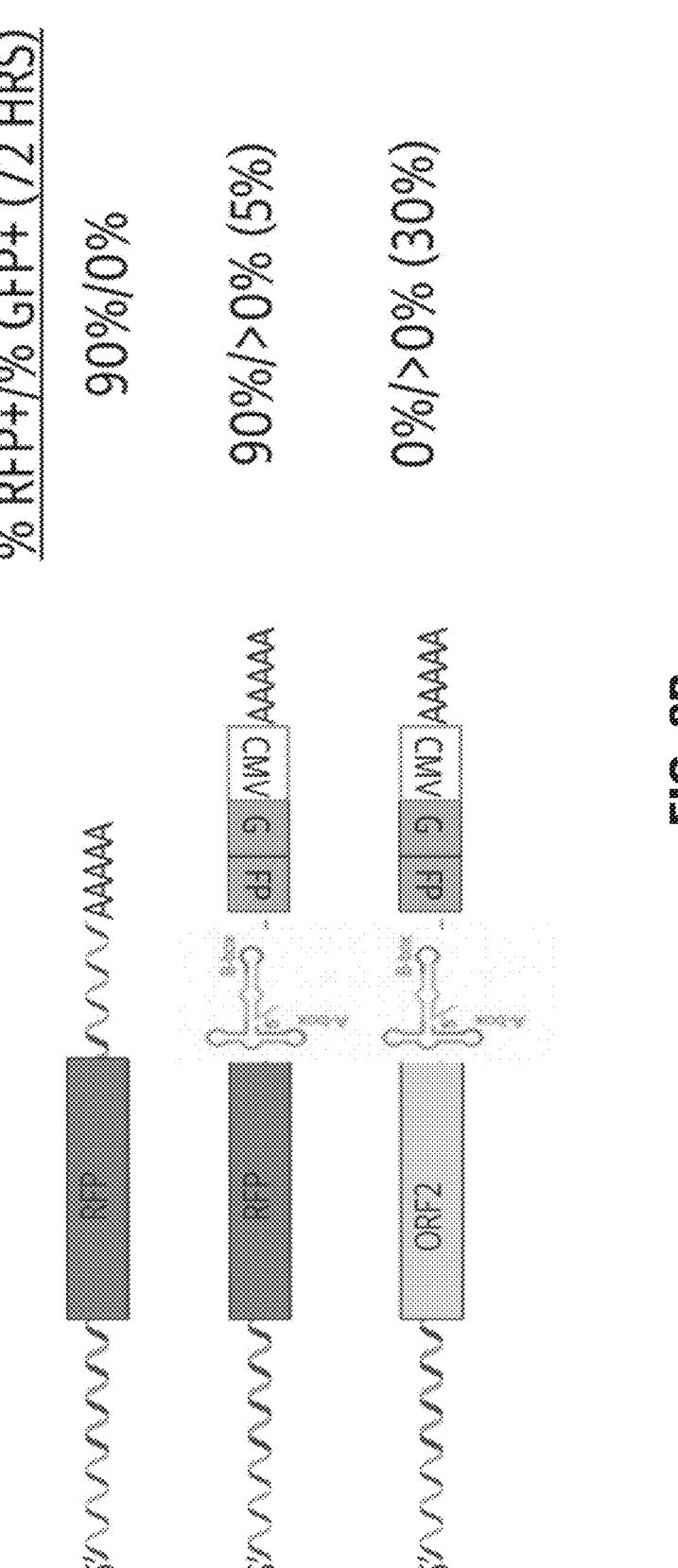
FIG. 2B illustrates three exemplary designs for expressing an exemplary transgene GFP by stably incorporating the sequence encoding RFP, RFP and GFP or ORF2p and GFP using the constructs. Expected GFP and RFP expression levels at 72 hours are shown on the right side.

On the other hand, the same could be directed to be expressed in a trans manner. The trans-strategy can include a sequence encoding an ORF2p protein or both ORF 1p and ORF2p proteins from a bicistronic sequence and an mRNA encoding a GFP in a sense or antisense direction in the 3'UTR of any gene. The transgene is flanked by a retrans-posing sequence comprising transposase binding sequences, an A-box and B-box, and a poly A tail. FIG. 2A illustrates three exemplary designs for expressing an exemplary trans-gene GFP by stably incorporating the sequence encoding GFP using the constructs. The first construct comprises a sequence encoding GFP, flanked by L1 5'-UTR; and a poly A sequence at the 3' UTR, in absence of any transposase binding elements. The second and the third constructs com-prise a sequence encoding GFP, a 3'UTR an A Box and a B-box, and a poly A sequence at the 3' UTR. The third construct comprises an additional sequence encoding ORF2p. Expected GFP expression levels at 72 hours are shown on the right side. FIG. 2B illustrates three exemplary designs for expressing an exemplary transgene GFP in an mRNA that either encodes RFP or ORF2p by stably incor-porating the sequence encoding GFP using the constructs. The first construct comprises a sequence encoding RFP, and a poly A sequence at the 3' UTR, in absence of any L1 elements. The second and the third constructs comprise a 3'UTR comprising an A Box and a B-box, and a poly A sequence at the 3' UTR. The second construct comprises a sequence encoding RFP and the third construct comprises a sequence encoding ORF2p. Expected RFP and GFP expres-sion levels at 72 hours are shown on the right side.

Example 2. Exemplary circRNA Designs Constructs

In this example, modular designs for circRNA are dem-onstrated, which incorporate a stretch of about 50 nucleotide long RNA having naturally occurring tertiary structures in order to prepare a circRNA. Use of the tertiary-structure forming RNA makes the circRNA formation process inde-pendent of sequence mediated hybridization for circulariza-tion. These RNA motifs having tertiary structures can be incorporated in the desired RNA having an exon and an intron in place of the 5' and 3' homology arms, thereby forming the terminal RNA scaffolds for circularization.

Figure 3C:
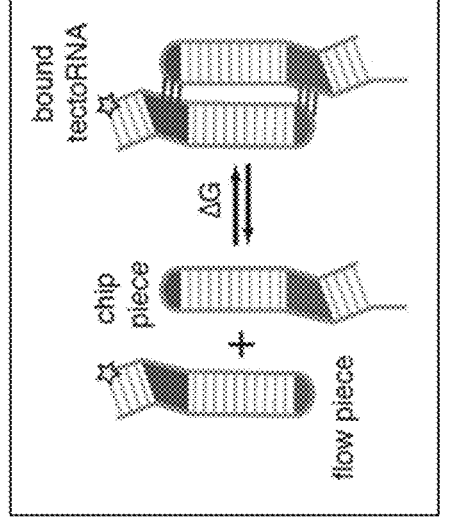
FIG. 3C illustrates exemplary structures of chip-flow piece RNAs as platforms for testing potential tectoRNA.
Figure 3B:
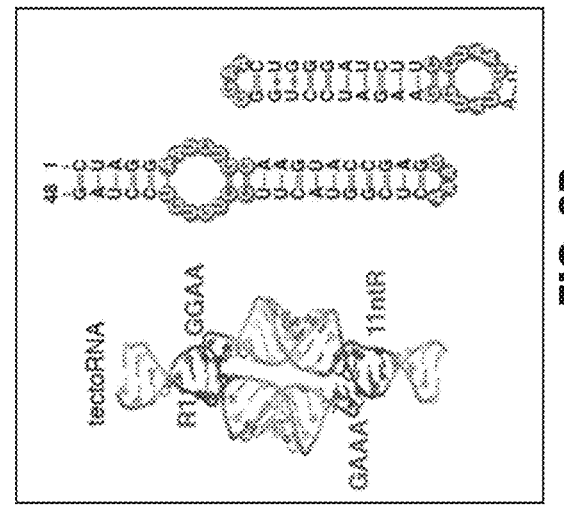
FIG. 3B illustrates two views of an exemplary RL-GAAA tectoRNA motif designs.

TectoRNA: RNA-RNA binding interfaces are constructed by combining pairs of GNRA loop/loop-receptor interaction motifs, yielding high affinity, high specificity tertiary struc-tures. (FIG. 3B). Pairs of GNRA loop/loop-receptor inter-action motifs are fused using the four-way junction from the hairpin ribozyme to create divalent, self-assembling scaf-folding units ('tectoRNA') which help form a closed coop-eratively assembling ring-shaped complexes. Using two orthogonal loop/loop-receptor interaction motifs, RNA monomers are designed that are capable of directional assembly in either the parallel ('up-up') or anti-parallel ('up-down') assembly modes. In anti-parallel assembly of interacting molecules, each incorporated monomer switches the directionality of the growing chain and thus compensates for its intrinsic bending, producing long, relatively straight multi-unit chains. For selecting a tectoRNA scaffolds having minimum occurrences of alternative secondary structures, sequences are checked by submitting them to the RNA folding program Mfold (bioinfo.math.rpi.edu/~zukerm/ma/mfold) which predicts the thermodynamically favored sec-ondary structure of a given RNA sequence. A thermody-namically favored structure is selected for scaffolding that has minimum alternative secondary structures (typically but not exclusively, no other secondary structure is closer than 15% in energy to the lowest energy structure). RNA mol-ecule is prepared by conventional methods, such as in vitro run-off transcription using T7 RNA polymerase. FIG. 3B shows a RL-GAAA loop structure. In order to profile tectoRNA heterodimers a fluorescence-based chip-flow piece testing method is utilized. In this method, a library of potential variants of the structured RNA (chip piece) is synthesized as DNA templates and amplified to include sequencing adapters and regions for RNAP initiation. Each DNA variant is transcribed in situ into RNA, enabling display of sequence-identified clusters of RNA on the sur-face of the sequencing chip. The fluorescently-labeled tec-toRNA binding partner, the "flow piece", is introduced to the sequencing chip flow cell at increasing concentrations, allowing quantification of bound fluorescence to each cluster of RNA after equilibration. These fluorescence values are used to derive the affinity of the flow piece to each chip piece variant (FIG. 3C), in terms of the dissociation constant ($K_d$) and binding free energy, ($\Delta G = RT \log(K_d)$).

The selected terminal RNA scaffold segments comprising the tertiary structures are incorporated using T7 transcription or ligated at the 5' and 3' ends of the desired RNA to be circularized; or are incorporated in the desired RNA by any known molecular biology techniques.

Example 3: Exemplary Retrotransposon Designs with Enhanced Specificity

In this example, designs for a nucleic acid construct for L1-mediated retrotransposon for enhanced target specificity is demonstrated. An mRNA is designed comprising ORF2 encoding sequence and a sequence encoding a gene of interest, to incorporate the gene of interest into the genome of a cell using ORF2. In one exemplary design, the construct comprises an ORF2 that is further modified.

Figure 4A:
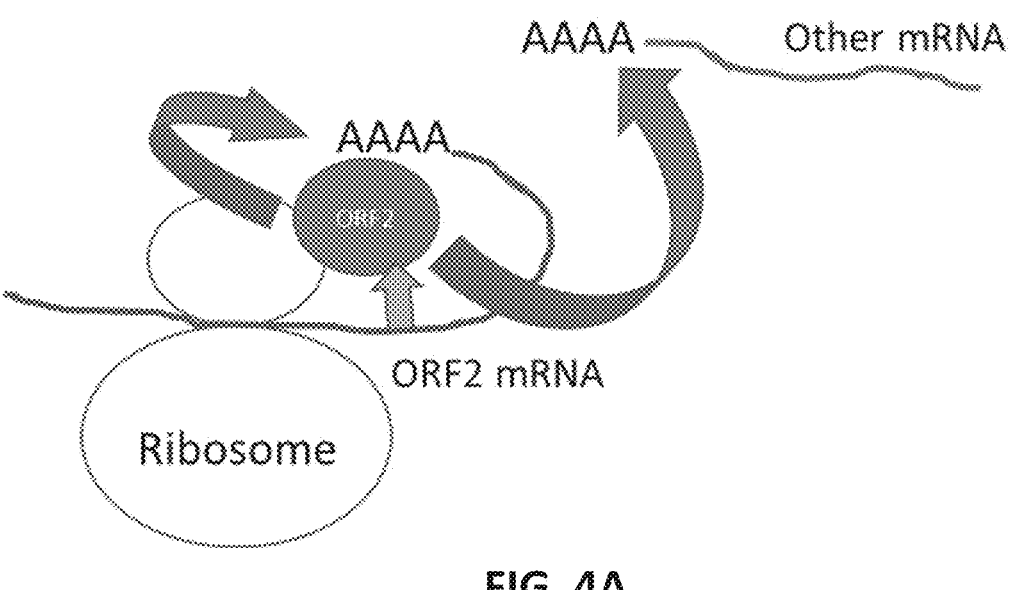
FIG. 4A illustrates an exemplary schematic showing ORF2p binding to an ORF2 poly A region.

As shown in FIG. 4A, ORF2 protein initiates retrotrans-position by binding to its own poly A sequence. However, because poly A is abundantly present in mRNAs, a non-specific binding and integration becomes a possibility. To increase the specificity, a recombinant ORF2 is designed comprising an mRNA-binding domain of a heterologous protein, and the cognate mRNA sequence for the heterolo-gous mRNA-binding domain is inserted near the poly A sequence in the 3'-UTR and the ORF2 poly A binding site.

Figure 4B:
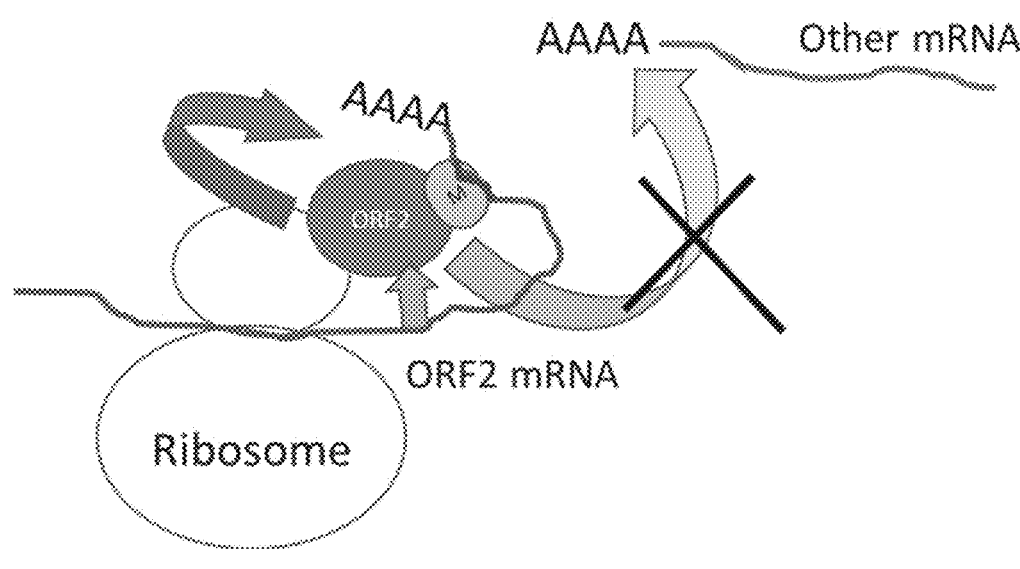
FIG. 4B illustrates an exemplary schematic showing how a fusion of ORF2p with an MS2 RNA binding domain binds to an MS2 binding RNA sequence in the 3'UTR of an mRNA encoding the ORF2 an increase specificity.

A chimeric ORF2 is thereby generated as shown in (FIG. 4B), in which a high affinity RNA-binding domain of a heterologous protein encoding sequence is incorporated or fused to the ORF2 sequence and cognate RNA sequences corresponding to the high affinity RNA-binding protein is incorporated in the 3'UTR region of the mRNA, proximal to the poly A region. In this example the heterologous high affinity RNA-binding domain is derived from MCP coat protein MS2 (shown as M in the figure), is incorporated within the ORF2 sequence and the cognate sequence, the MS2 hairpin, is included in the 3' UTR sequence of the mRNA (FIG. 4B). The MS2 binds to the cognate sequence, increasing the specificity of the chimeric ORF2 to its own mRNA for reverse transcribing and incorporating the respec-tive sequence associated with the ORF2 mRNA in the mammalian cell genome (FIG. 4B).

Figure 4C:
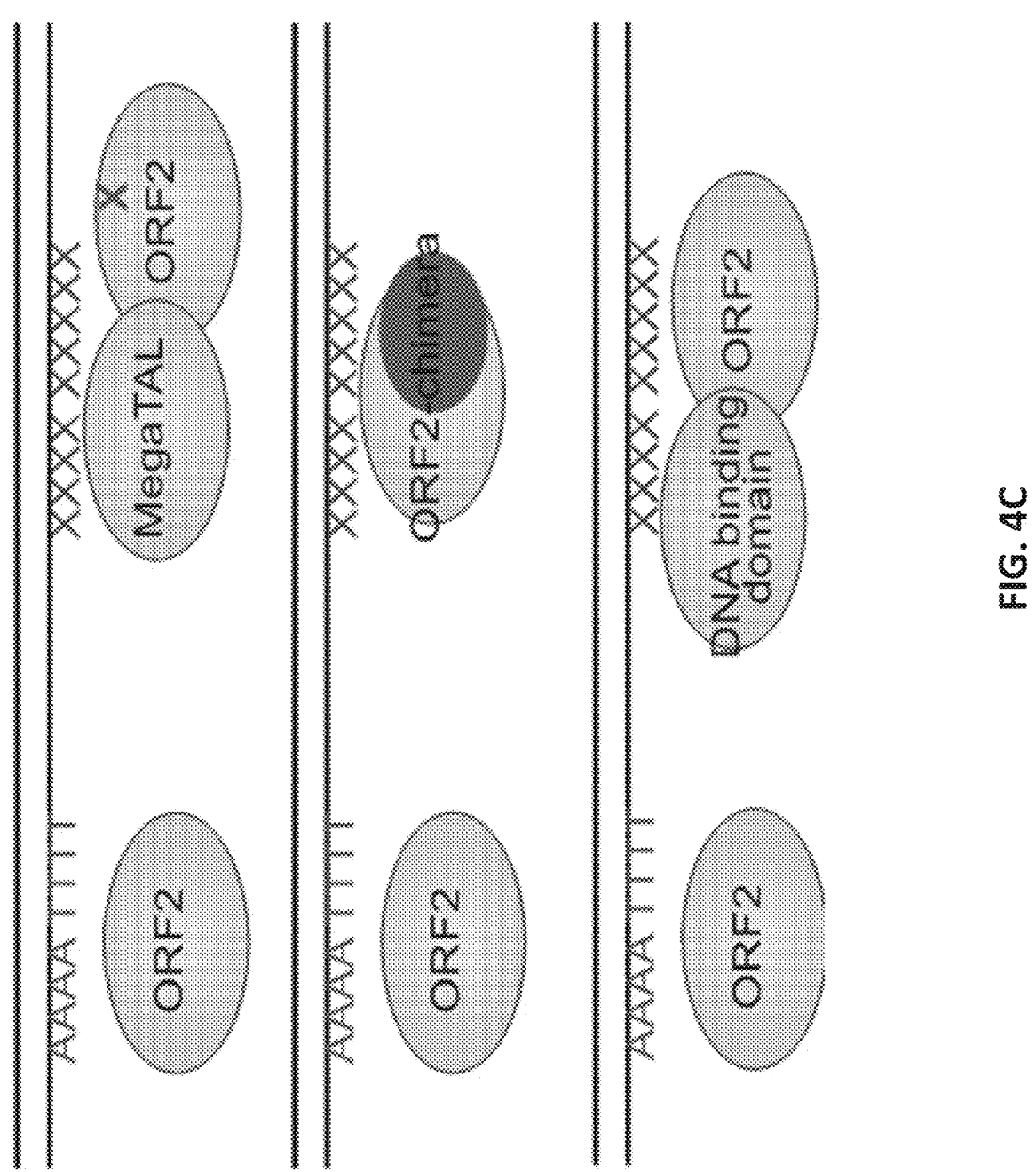
FIG. 4C illustrates exemplary designs of retrotransposon systems for stably integrating a nucleic acid into the genome of a cell at specific sites. The upper panel shows a design using an ORFp2-MegaTAL DNA binding domain fusion where the DNA binding and endonuclease activity of ORF2p is mutated to be inactive. The middle panel shows a chimeric ORF2p where the endonuclease domain has been replaced with a high specificity and high-fidelity nuclease domain of another protein. The lower panel shows a fusion of a DNA binding domain of a heterologous protein with ORF2p such that the fusion protein binds to ORF2 binding site as well additional DNA sequences in the vicinity of the ORF2 site.

In other exemplary designs, attempts to increase speci-ficity of integration of the transgene by the ORF2 within the genome of a target cell is undertaken. In one exemplary design, Mega TAL encoding sequence fused to an ORF2 as shown in FIG. 4C (upper panel). Along with that, the ORF2 is mutated to remove its ability to recognize and bind to RNA sequence that has less specificity. The fused protein is directed to the TAL binding sequence incorporated within the 3'UTR and perform endonuclease function. The Mega TAL DNA binding sequence is targeted by the fusion protein. Likewise, other chimera (FIG. 4C (middle panel)) and fusion protein with a specific DNA binding domain FIG. 4C (lower panel) are designed.

Example 4. Exemplary Plasmid Design and Developments for LINE-1 Mediated Retrotransposition of an Exogenous Nucleic Acid Sequence In this example plasmid vectors are generated for delivery and incorporation of a recombinant LINE-1 construct comprising an ORF2 transposon element operably linked to a transgene transposable into a mammalian cell, and regulatory elements for mRNA transcription and stabilization. The mRNA can be transcribed in a bacterial host cell, which can be further processed and/or purified for introduction into a mammalian cell in vitro or administration in an organism, such as a mammal, a rodent, sheep, pig or a human.

Any suitable vector backbone is used for incorporating the recombinant nucleic acid sequence as insert and transcribing in a bacterial system for mRNA generation; or in vitro transcription system may be utilized to generate an mRNA comprising the recombinant nucleic acid sequence. Several features are added to the plasmid. Upon successful scalable mRNA production, and purification, the mRNA may be introduced in a mammalian cell of interest, such as a myeloid cell.

Plasmids traditionally used in the field of study for retrotransposition lack designer genes, gene blocks, and Gibson assembly methods were used regularly to insert different features. A new vector that takes features from the old vectors but has flexibility to insert new features can be beneficial both for the study and optimization of LINE-1 elements as a gene delivery system. Below is an outline of base features and additional features that can increase retrotransposition frequency, both using the plasmid alone or the mRNA transcribed from the plasmid. In an exemplary plasmid design shown graphically in FIG. 5(I), which contains the natural LINE-1 sequence with the original 5'UTR, 3'UTR and interORF sequence with no restriction sites to swap out any of these features. New optimized plasmid Removed Dox inducible promoter, replaced with CMV or EIF1a or EF1a promoter Added a T7 site to make mRNA Codon optimized ORF1 and ORF2

Added a WPRE element to stabilize mRNA

Added FLAG tag to ORF2 to help with protein detection

Decreased size from 18 kb to 14 kb

Figure 5:
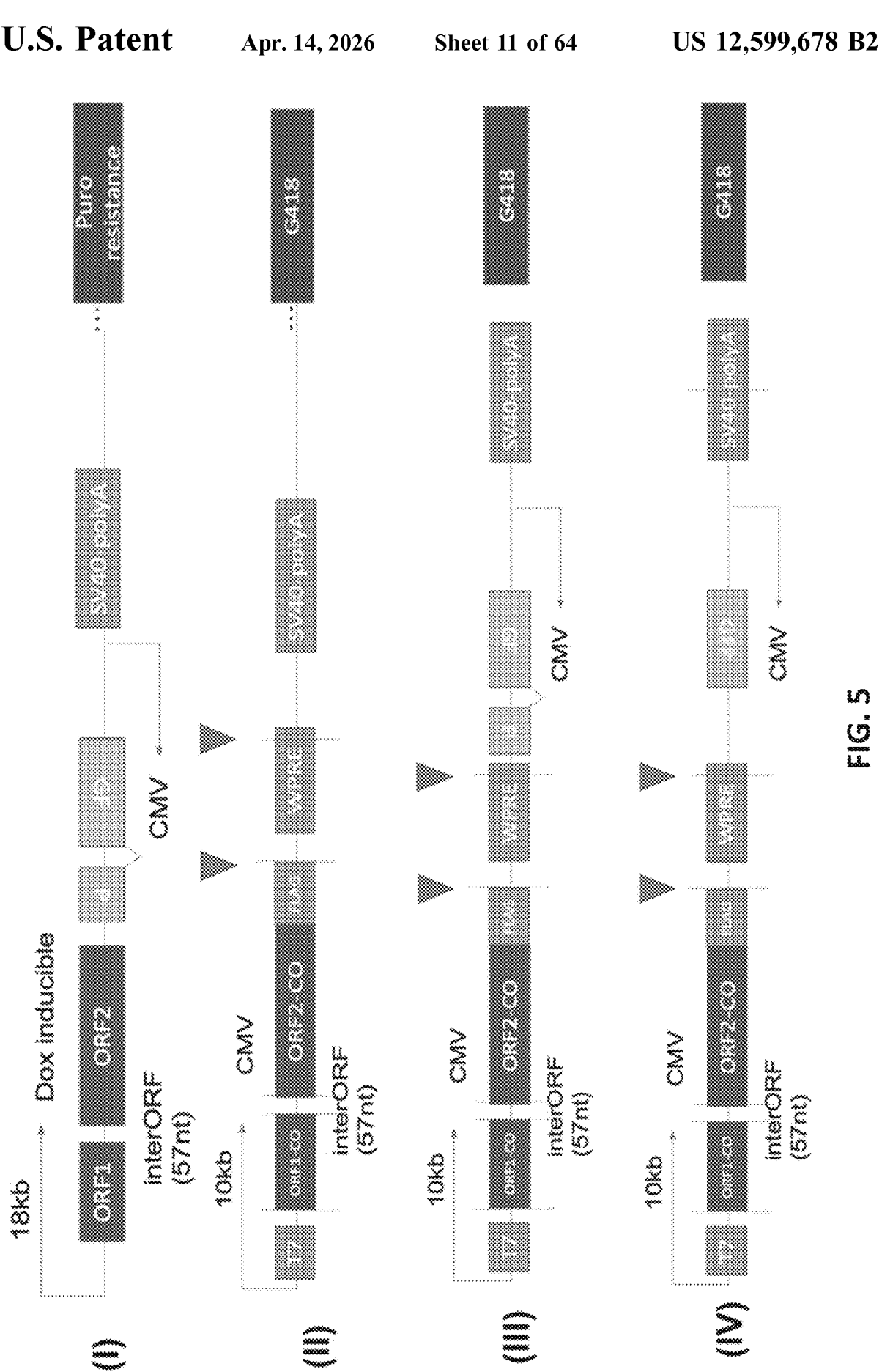
FIG. 5 illustrates exemplary constructs (I)-(X) for integrating an mRNA encoding a transgene into the genome of a cell.
Figure 5:
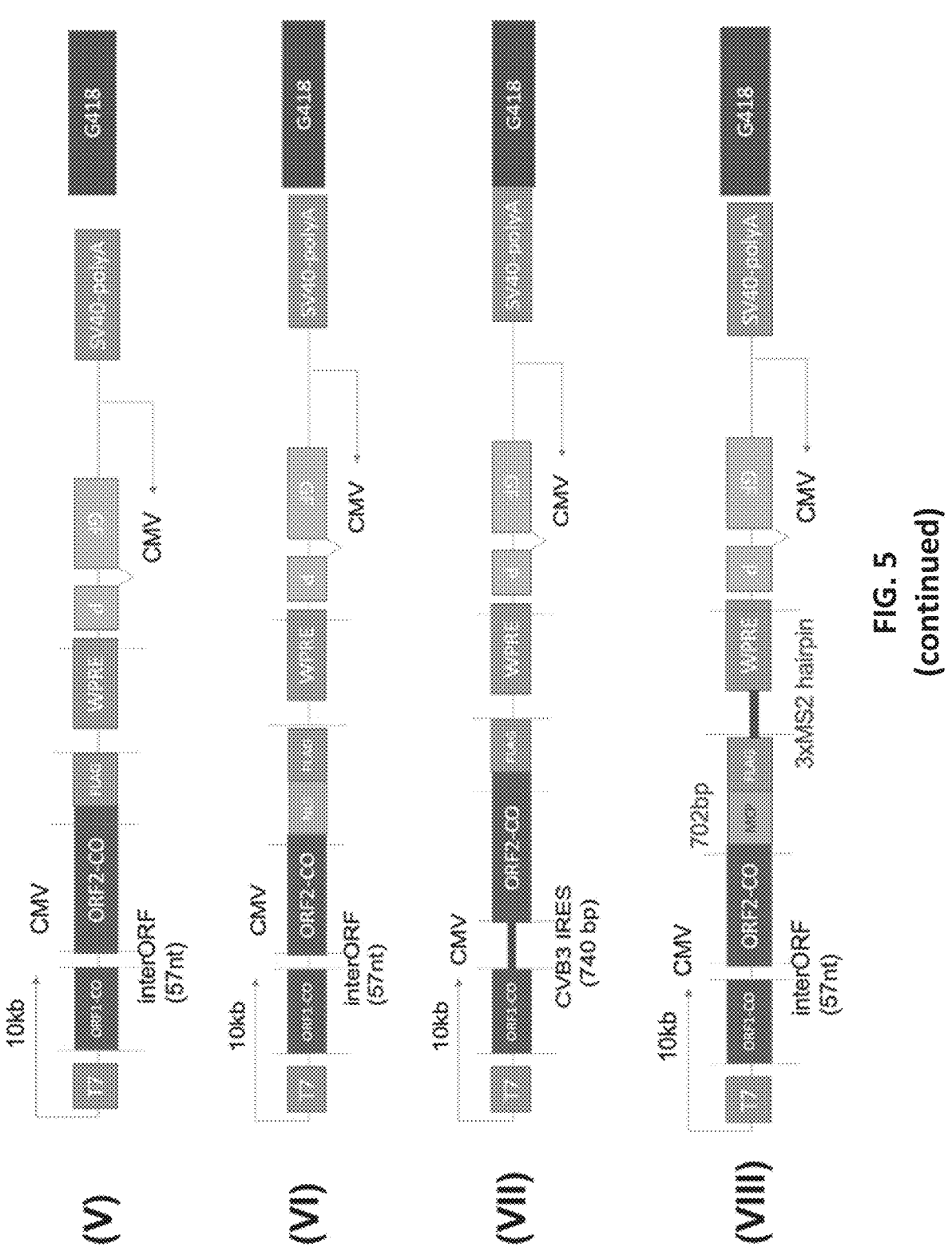
Figure 5:
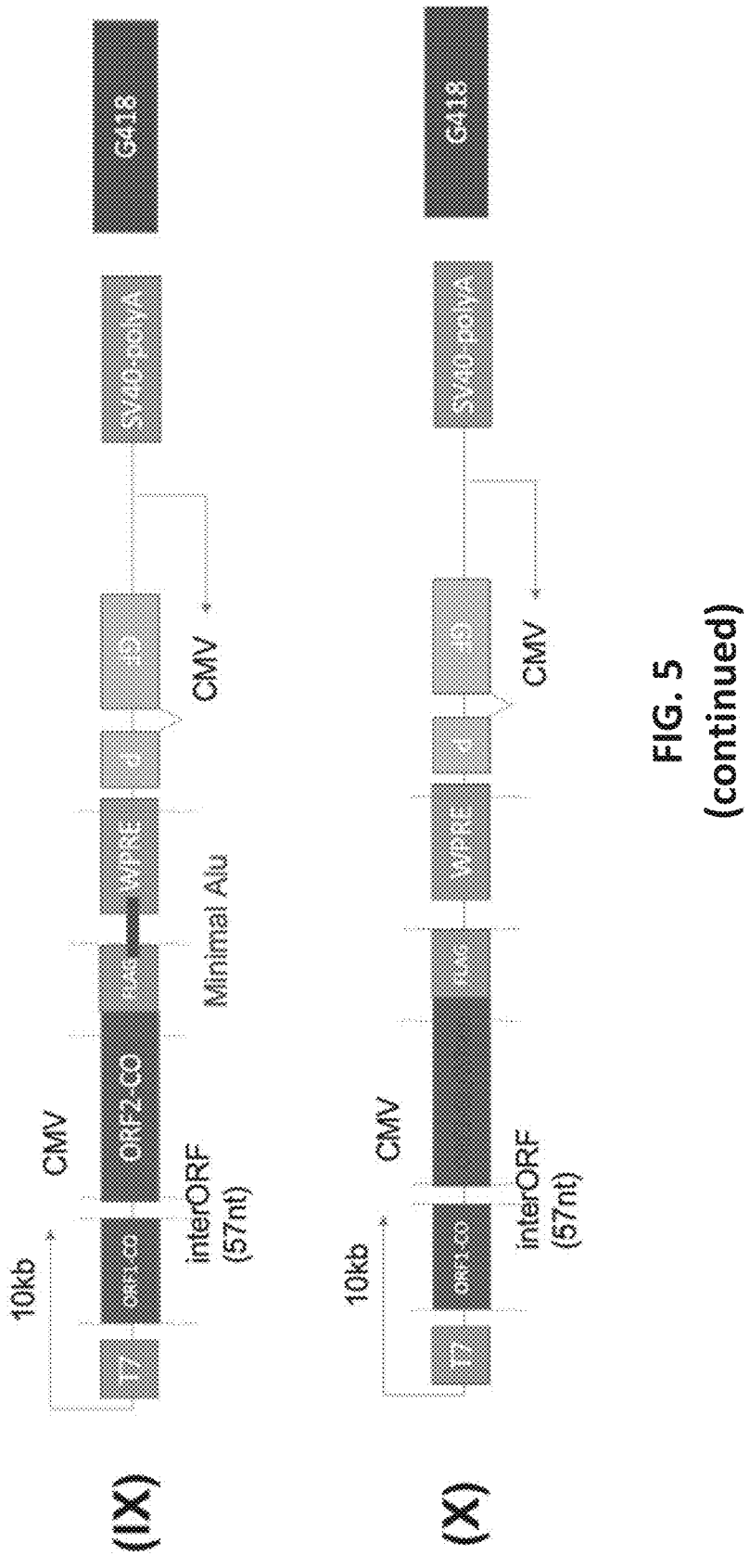

Added blunt restriction sites (dotted lines with blunt arrows) at each feature to facilitate insertions Includes a G418 selection marker The plasmid is shown in FIG. 5 (II).

With Gibson a reverse split GFP is inserted for plasmid reporter gene as shown in FIG. 5 (III). A complete reverse GFP for the mRNA reporter is inserted as in FIG. 5 (IV).

Using the plasmid construct in FIG. 5 (V) as parent, a nuclear localization sequence (NLS) is inserted at the N terminus of ORF2 to help with nuclear import (FIG. 5 (VI)). An IRES or another termination/promoter sequence is inserted to increase expression of ORF2 (FIG. 5 (VII)). To facilitate stronger interactions between ORF2 and the mRNA, MS2 hairpins are inserted in the 3'UTR and a MS2 coat protein sequence in the N terminus of the ORF2 protein (FIG. 5 (VIII)). A corresponding exemplary ORF2 with enhanced specificity and its mechanism of action is disclosed in the preceding example and in FIG. 4B. To facilitate stronger interactions of the mRNA with the translating ribosome and to stall translation so that nascent ORF2 will more likely bind the mRNA, an Alu element is inserted in the 3'UTR of the mRNA (FIG. 5 (IX)). To potentially use a more active ORF2 protein, the ORF2's RT domain is replaced with the Group II intron's reverse transcriptase domain (FIG. 5 (X)). Additionally, the minke whale genome has the highest number and percentage of active LINE elements (~5,000 with 60% active compared to humans that have 480 with 3.6% active). The two sequences are 67% identical and the whale sequence has the active endonuclease and reverse-transcriptase residues. The respective minke whale domains can be used to replace native ORF2 endonuclease and/or RT domains or design a chimera domain.

Figures 6A, 6B:
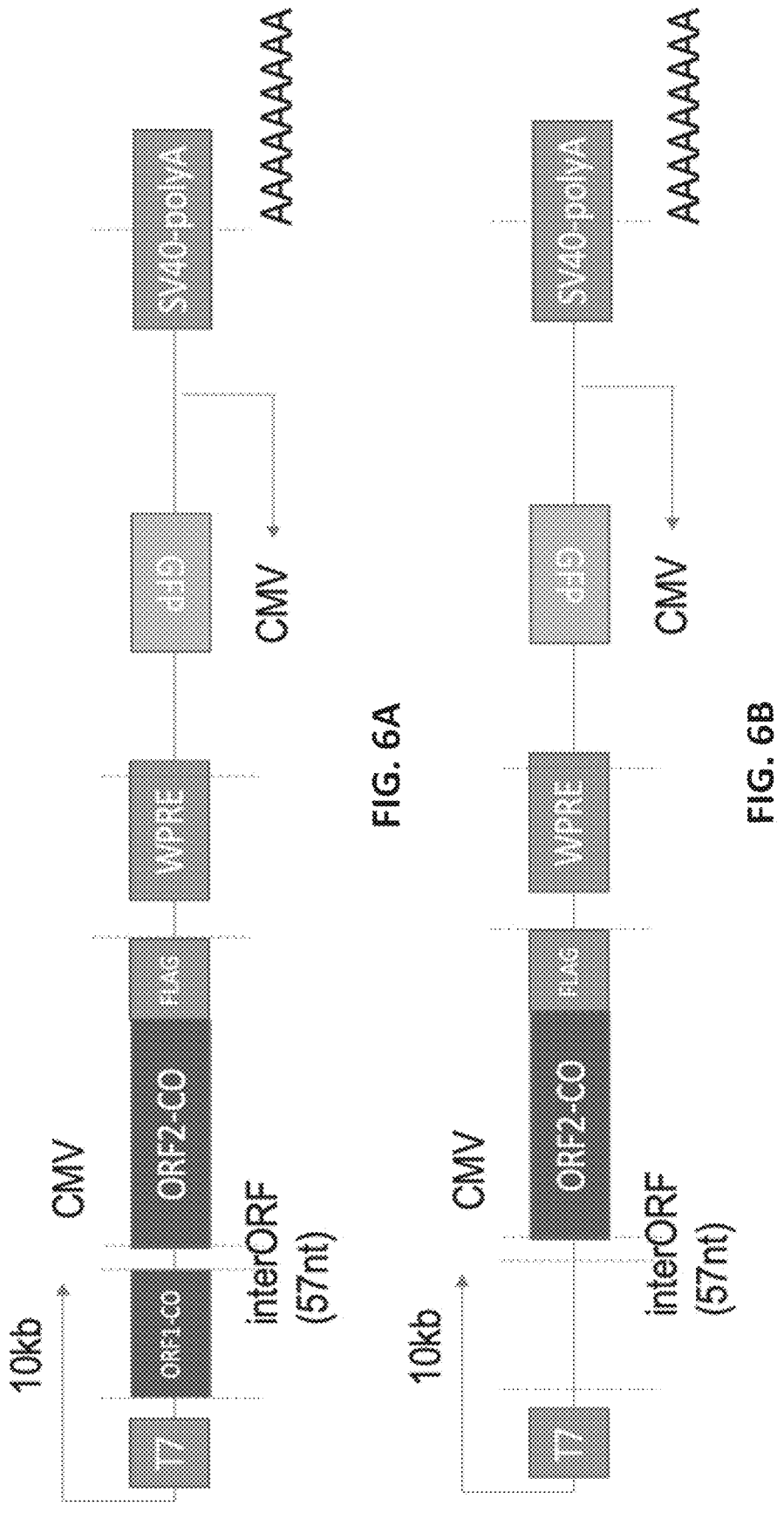
FIG. 6A illustrates an exemplary construct with a sequence encoding ORF1p for integrating an mRNA encoding a transgene into the genome of a cell.
FIG. 6B illustrates an exemplary construct without a sequence encoding ORF1p for integrating an mRNA encoding a transgene into the genome of a cell.

Example 5. MRNA Design Synthetic mRNA Generation mRNA can be strategically designed for synthetic production by oligosynthesis and or ligation of oligonucleotides. Additionally, such designs are useful for in vitro transcription (IVT) mediated mRNA generation. The mRNA strategy can include the same variants as the plasmid strategy discussed in the previous example. The main differences are that the reporter GFP sequence does not include an intron (FIG. 6A) and that the constructs can be delivered without the ORF1 coding region (FIG. 6B).

Example 6. Structural Features for Increased mRNA Half-Life

In this example, structural features are introduced in the mRNA comprising the retrotransposition elements and/or the transgene for increasing the mRNA half-life. The goal is to increase the duration of protein expression from the mRNA in primary monocytes from three days to at least 5 days with an ultimate goal of 10 days.

Figure 7A:
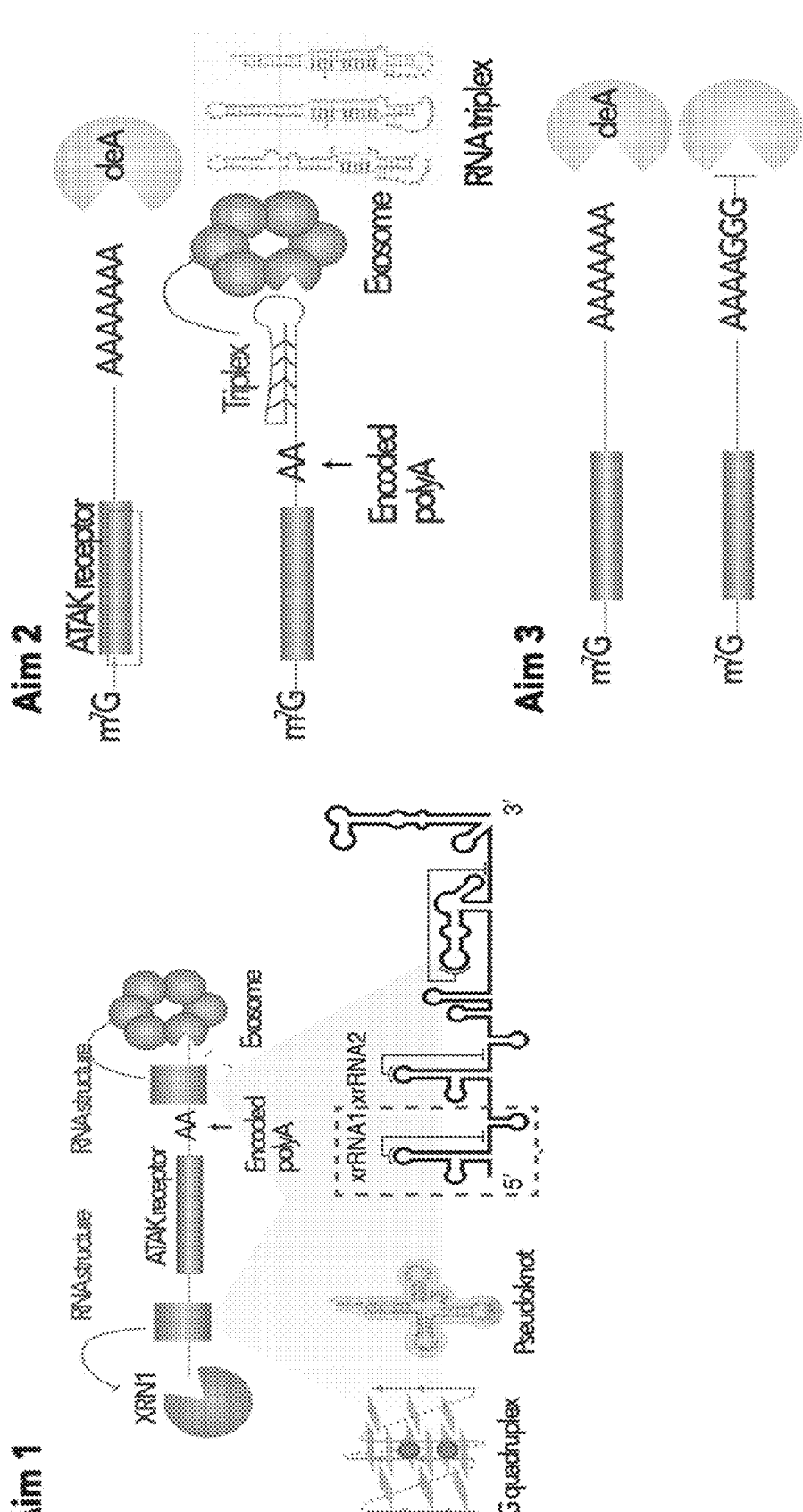
FIG. 7A illustrates exemplary methods of improving mRNA half-life by inhibiting degradation by 5'-3' exonucleases, such as XRN1, or 3'-5' exosomal degradation, by introducing structures corresponding to a G-quadruplex, or, a pseudoknot (SEQ ID NO: 82) in the 5'UTR; and/or xrRNAs, a triplex motifs (SEQ ID NOS. 83-85 in order of appearance) and/or a non-A nucleotide residues in the 3'UTR.
Figures 7B, 7C:
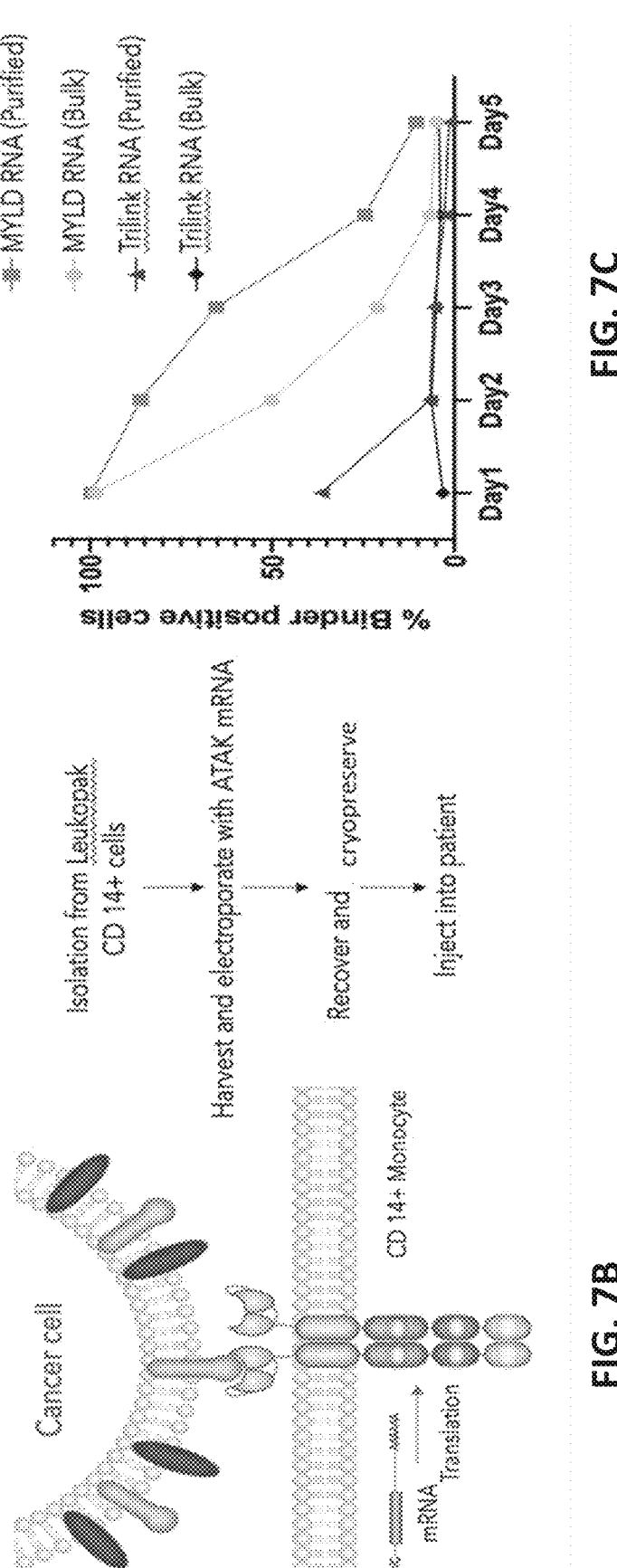
FIG. 7B illustrates an exemplary schematic of a myeloid cell expressing a transgene encoding a chimeric receptor that binds a cancer cell and induces anti-cancer activity.
FIG. 7C shows expected results of introducing bulk or purified RNA encoding a chimeric receptor that binds a cancer cell as described in FIG. 7B on increased and prolonged expression of the chimeric receptors.

As shown in FIG. 7B (left), the mRNA comprising a sequence encoding the transgene when introduced into a CD14+ myeloid cell (monocyte), is translated and expresses a chimeric receptor (an ATAK construct) capable of binding to an antigen on a cancer cell.

A number of mRNA designs are generated by synthesizing various gene blocks comprising singly, or combinations of one or more of: (i) a G-quadruplex, (ii) a viral pseudoknot structure in the 5' UTR; and/or (iii) one or (iv) more xrRNA loop structures in the 3' UTR (v) a triplex RNA structure as shown in FIG. 7A; and cloned into the transcription vector at the respective UTRs adjoining the coding sequence of the transgene. These constructs are individually prepared by an off-site vendor and tested in-house for determining stability of the mRNA, as measured by the expression of the chimeric receptor (An exemplary receptor and its function is depicted graphically in FIG. 7B (left). The process flow chart is shown on FIG. 7B (right). In short, constructs are cloned into plasmids, with encoded or modified poly A tails. The mRNA was transcribed and purified. Meanwhile, frozen monocytes are thawed and harvested. Harvested cells were electroporated with the purified mRNA (5-10 ug), and cultured for 1, 2, 3, 5 days. Cells positive for the chimeric receptor (binder positive cells), are detected by means of their ability to bind to a target cell or a substrate coated with the target antigen. The expected results are shown in FIG.

7C. Bulk or purified mRNA expressing one or more of the structural features outlined in (i)-(v) (data denoted by solid squares) or a combination thereof outperforms the commercially available counterparts that do not contain any of the features outlined in (i)-(v) (data denoted by triangles).

Example 7. LINE-1 Retrotransposon Plasmid Mediated Delivery of GFP Gene

In this test run, genomic integration of a GFP cargo and expression the GFP protein using a LINE-1 retrotransposon system was verified. The LINE-1-GFP construct (LINE-1 plasmid GFP) is exemplified in FIG. 8A: A plasmid construct having a LINE-1 sequence encoding ORF1p (ORF1), a sequence encoding ORF2p (ORF2), and a CMV promoter driven split GFP gene situated in the 3'UTR of the LINE-1 in reverse orientation with respect to the ORFs. The split GFP is designed to have an intronic sequence inserted in between a splice donor and acceptor sites, which ensures that the GFP is expressed only after integration and splicing mediated removal of the noncoding sequence in the middle of the coding sequence. In this case the cargo is 2.1 kb. HEK293T cells were transfected with the plasmid using Fugene reagent, and plasmid positive cells were selected by puromycin. The mRNA generated from a genome integrated GFP successfully translates and is measured by flow cytometry, as indicated as change in mean fluorescence intensity (MFI) (FIG. 8B) and fraction of cells with GFP fluorescence intensity compared to mock transfected cells (FIG. 8C). Mock transfected cells received the plasmid that lack the GFP sequence.

Figure 9A:
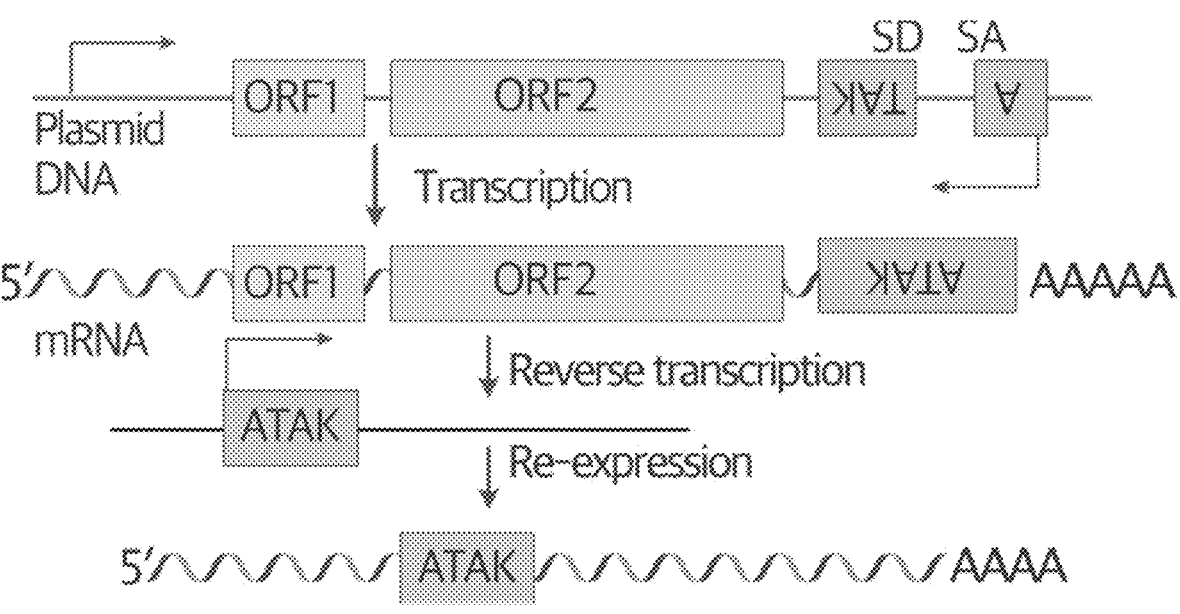
FIG. 9A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) that has extracellular region capable of binding to CD5 and an intracellular region comprising an FCR intracellular domain and a PI3 kinase recruitment domain. The coding sequence of the ATAK receptor is interrupted with an intron.
Figure 9B:
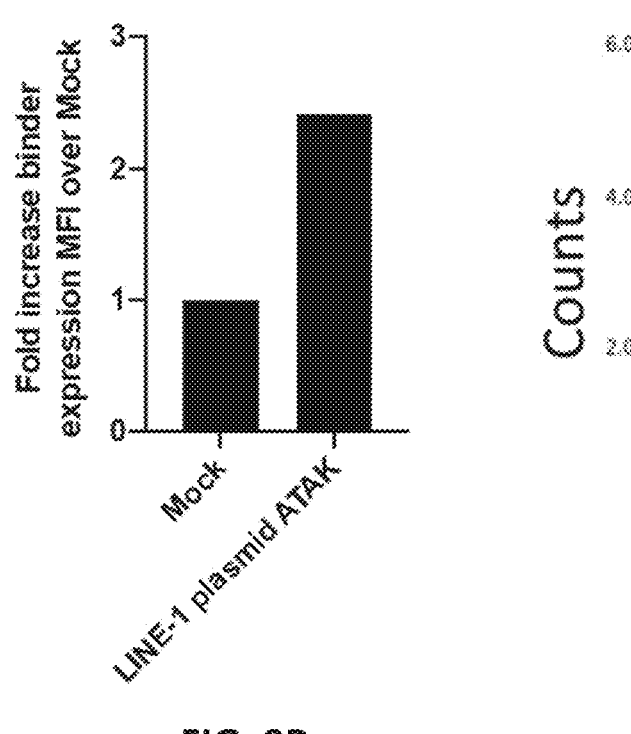
FIG. 9B shows exemplary results showing successful integration of the mRNA transcript encoded by the plasmid shown in FIG. 9A and expression of ATAK relative to mock-transfected cells (fold increase in mean fluorescence intensity of ATAK positive cells is shown). Mock transfected cells were transfected by the vector lacking the ATAK cargo sequence. Expression of ATAK receptor protein was detected by binding with a labeled CD5 antibody.
Figure 9C:
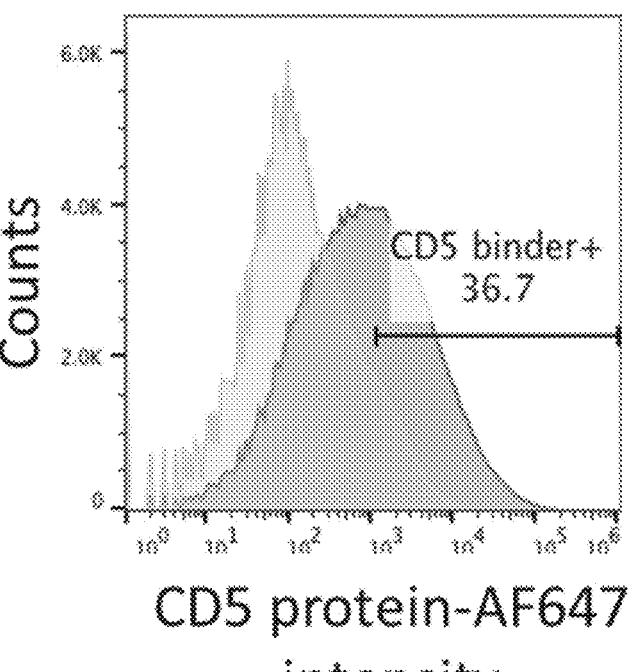
FIG. 9C shows exemplary flow cytometry results from the results shown in FIG. 9B.

Example 8. LINE-1 Retrotransposon Plasmid Mediated Delivery of a Chimeric Receptor Gene This example demonstrates that a recombinant gene can be successfully expressed using the LINE-1 sequence in a cell. HEK 293 cells were transfected with a plasmid having the LINE-1 elements, with a 3 kb cargo sequence encoding recombinant receptor protein CD5-intron-fcr-PI3K (ATAK) that is interrupted by an intron sequence in the CD5 binding domain. The cargo is a chimeric receptor that has a CD5 binding extracellular domain, a FCRγ transmembrane domain, and an intracellular domain having a PI3-kinase recruitment domain. The schematic representation of the retrotransposon plasmid is shown in FIG. 9A. As in the design of the experiment above, the ATAK receptor cannot express unless it is integrated in the genome and the intron is spliced off. Following transfection in HEK293T cells, the receptor expression is detected using labeled CD5 as bait for the CD5 binding extracellular domain. Results shown in FIGS. 9B and 9C show successful integration and expression of the receptor. 36.5% cells were ATAK (CD5 binder) positive (FIG. 9C).

In a further modification, a LINE-1 construct (LINE-1plasmid-cd5 fcr-pi3k_t2a_GFPintron) with a longer 3.7 kb cargo sequence encoding a non-interrupted recombinant receptor protein CD5-intron-fcr-PI3K and an interrupted GFP sequence with a T2A sequence between receptor and the GFP sequences (FIG. 10A). Normalized against mock-transfected cells, there was a greater than 10-fold increase of the ATAK receptor and GFP double-positive cells was noted (FIG. 10B). Exemplary fluorescence identification of GFP and fluorescent tagged CD5 binding and gating quantitation for experimental runs are shown in FIG. 10C and FIG. 10D.

Figure 11A:
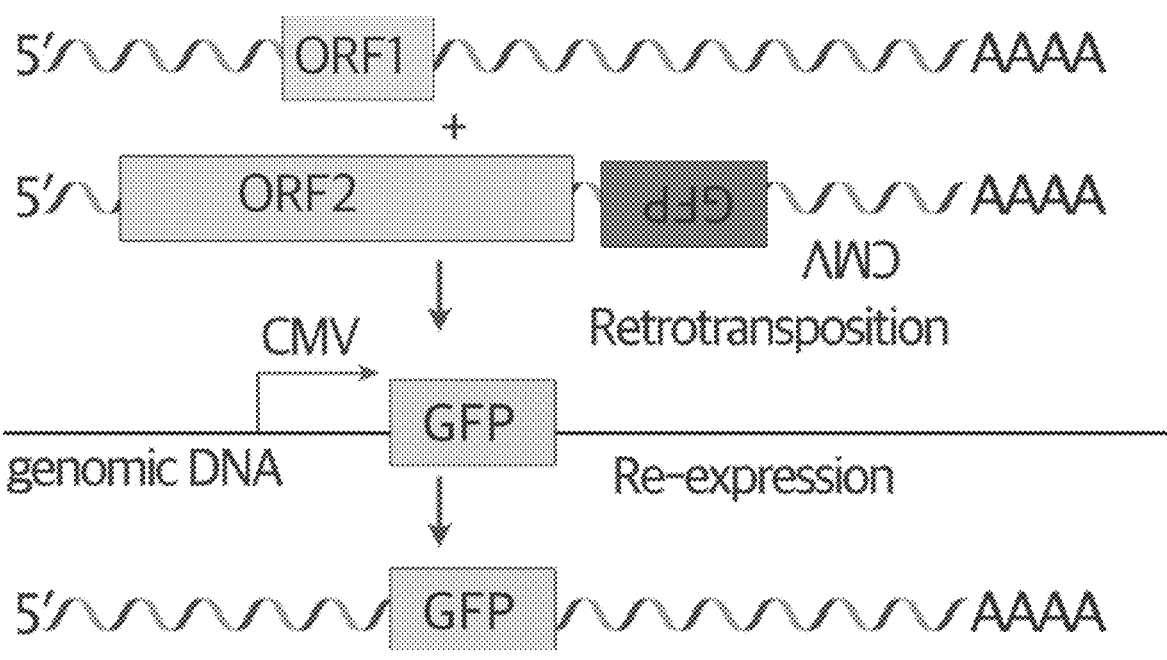
FIG. 11A shows exemplary mRNA constructs for retrotransposition-based gene delivery. The ORF1 and ORF2 sequences are in two difference mRNA molecules. The ORF2p (ORF2) coding mRNA comprises and inverted GFP coding sequence.
Figure 11B:
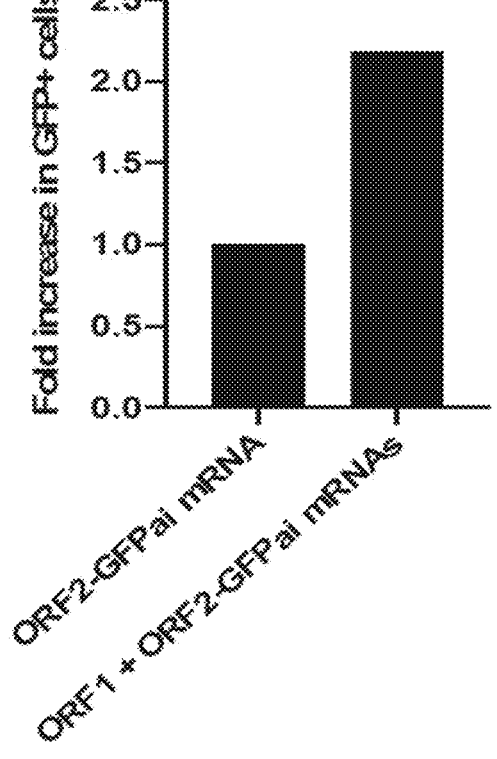
FIG. 11B depicts exemplary data showing expression of GFP (fold increase in mean fluorescence intensity of GFP positive cells is shown) upon electroporating both ORF1-mRNA and ORF2-FLAG-GFPai mRNA normalized to electroporation of ORF2-FLAG-GFPai mRNA only.

Example 9. MRNA Encoding LINE-1 Retrotransposon for Delivery of a Cargo Gene In this assay, capability of delivering and expressing a LINE-1 retrotransposable gene sequence as an mRNA was tested. An mRNA encoding an ORF1 (ORF1-FLAG-mRNA), and an mRNA encoding ORF2 and GFP in the antisense direction with a CMV promoter sequence (ORF2-FLAG-GFPai) are designed as shown in FIG. 11A. The cargo size in this assay was 2.4 kb, and GFP is in antisense orientation with respect to ORF2 sequence. The mRNAs were electroporated in 293T cells and the reporter genes expression was demonstrated as shown in FIG. 11B. This experimental set up demonstrated that no ORF1-read-through is necessary for the expression of the ORF2p, and expression of ORF2p from a different mRNA molecule can allow higher expression of ORF2p and GFP. With these results, a successful delivery of the LINE-1 and cargo in the form of mRNA was achieved.

Figure 12A:
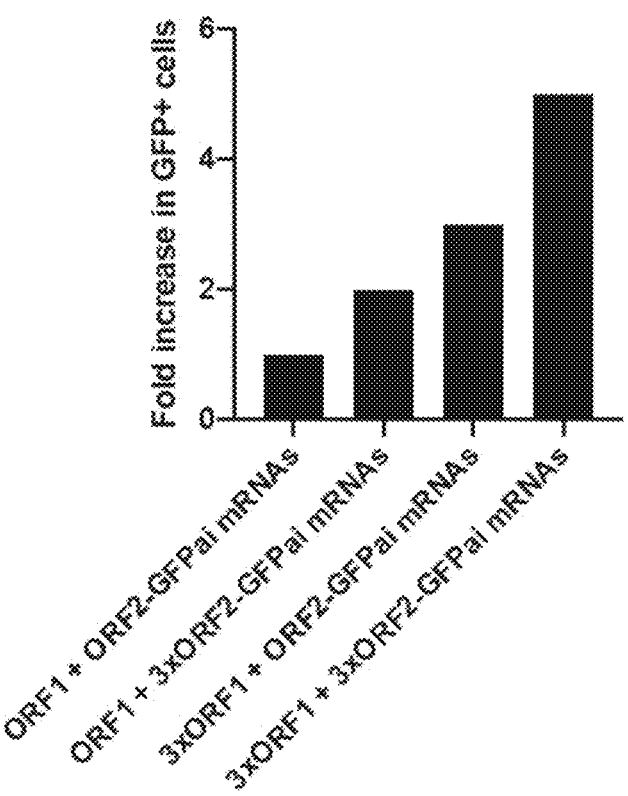
FIG. 12A depicts exemplary data showing expression of GFP (fold increase in mean fluorescence intensity of GFP positive cells is shown) upon electroporating ORF1-mRNA and ORF2-FLAG-GFPai mRNA at different amounts. Fold increase is relative to 1×ORF2-GFPao and 1×ORF1 mRNA.
Figure 12B:
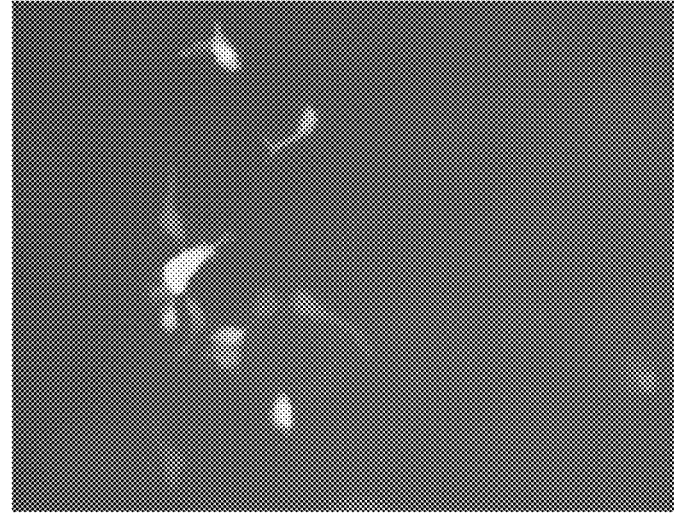
FIG. 12B shows an exemplary fluorescent microscopy image of GFP+ cells following electroporation of the mRNA depicted in FIG. 11A.

In order to determine whether the relative levels of ORF1 and ORF2 mRNA affected GFP expression an experiment was set up to test the varying amounts of ORF1 and ORF2 mRNAs (FIG. 11A). 3×the amount of each and together is tested for increases in GFP+ cells and results are shown in FIG. 12A. Fold increase is relative to 1×ORF2-GFP and 1×ORF 1 mRNA. GFP expression was higher when 3×ORF 1 was used with 1×ORF2, but not the reverse; whereas having both 3×ORF1 and 3×ORF2 showed the maximum level of GFP expression in the sets compared. The cargo size here is 2.4 kb. FIG. 12B shows fluorescent microscopy image of GFP+ cells following retrotransposon mRNA electroporation.

Figures 13A, 13B:
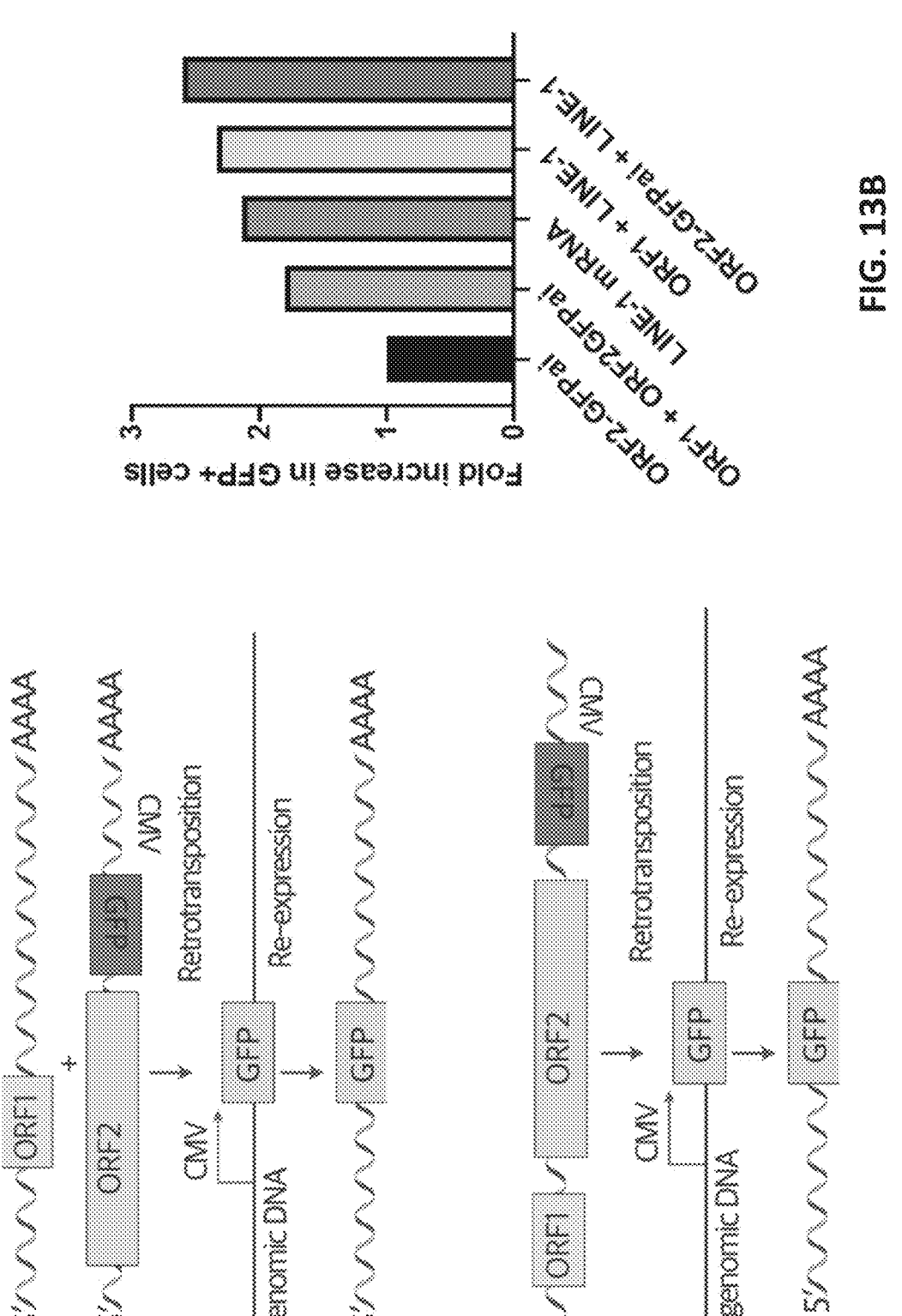
FIG. 13A shows exemplary mRNA constructs where the ORF1 and ORF2 sequences are in two difference mRNA molecules (top panel) and a LINE-1 mRNA transcript comprising ORF1 and ORF2 protein encoding sequences on a single mRNA molecule (bottom panel) for gene delivery. mRNA contains the bicistronic ORF1 and ORF2 sequence with a CMV-GFP sequence in the 3'UTR going from 3'-5'. Upon retrotransposition of the delivered ORF2-cmv-GFP antisense (LINE-1 mRNA), cells are expected to express GFP.
FIG. 13B depicts exemplary data showing expression of GFP (fold increase in mean fluorescence intensity of GFP positive cells is shown) upon electroporating the constructs depicted in FIG. 13A.

A complete LINE-1 mRNA encoding both ORF1 and ORF2 and GFP transgene in antisense orientation in a single mRNA molecule (LINE 1-GFP mRNA construct) was tested for delivery and genomic integration in a cell. mRNA contains the bicistronic ORF1 and ORF2 sequence with a CMV-GFP sequence in the 3'UTR going from 3'-5' (FIG. 13A). In this study the cargo size is 2.4 kb. As shown in FIG. 13B, upon retrotransposition of the delivered ORF2-cmv-GFP antisense (LINE-1 mRNA), third bar from left, cells expressed higher GFP compared to ORF1 and ORF2 being on separate mRNA molecules (graph bar 1, 2). Inclusion of ORF1 in a separate mRNA in addition to LINE-1 complete mRNA increased GFP expression over LINE-1 alone. Inclusion of ORF2+GFP expectantly showed higher GFP which could be the contribution of the additional ORF2 with the GFP cargo encoding mRNA.

Figure 14B:
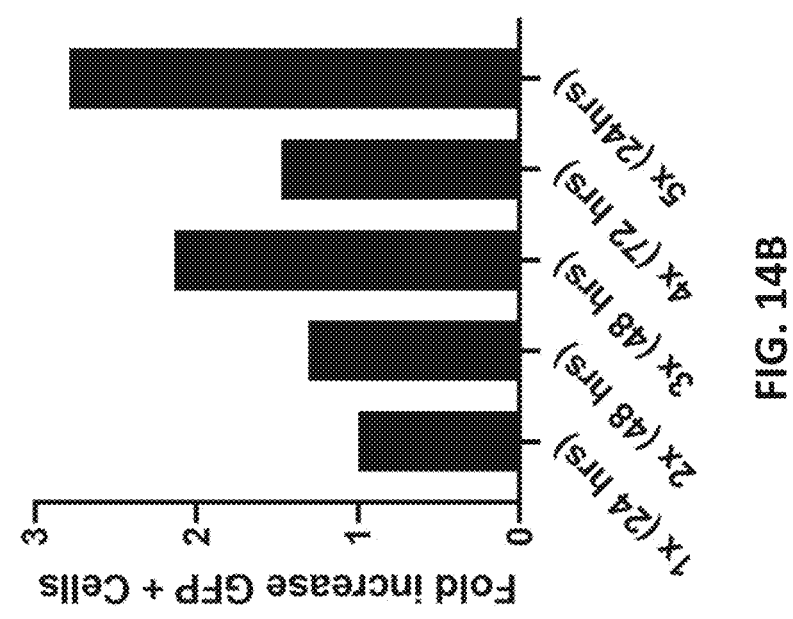
FIG. 14B depicts exemplary data showing expression of GFP at the indicated times (fold increase in mean fluorescence intensity of GFP positive cells is shown) upon electroporating 1-5 times according to FIG. 14A.
Figure 14A:
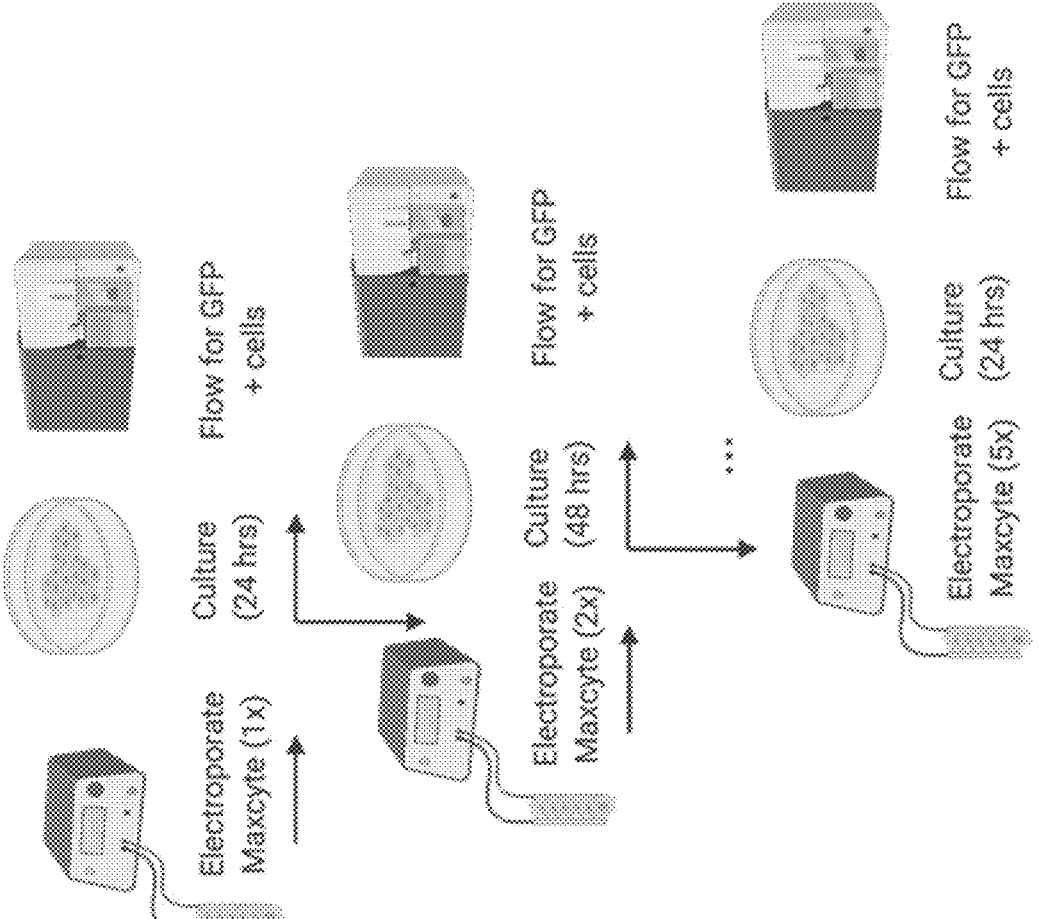
FIG. 14A shows an exemplary experimental design for testing whether multiple electroporations increases retrotransposition efficiency. HEK293T cells were electroporated every 48 hours with the Maxcyte system and assessed for GFP positive cells using flow after culturing for 24-72 hrs.

To test whether subsequent electroporation increases retrotransposition efficiency, cells were electroporation every 48 hours. GFP positive cells were assessed using flow after culturing for 24-72 hrs. The fluorescence data were normalized to the values in the set with a single electroporation event. As shown in FIGS. 14A and 14B, multiple electroporation led to an upward trend in the expression of the transposed gene, but the changes were modest.

Figure 15A:
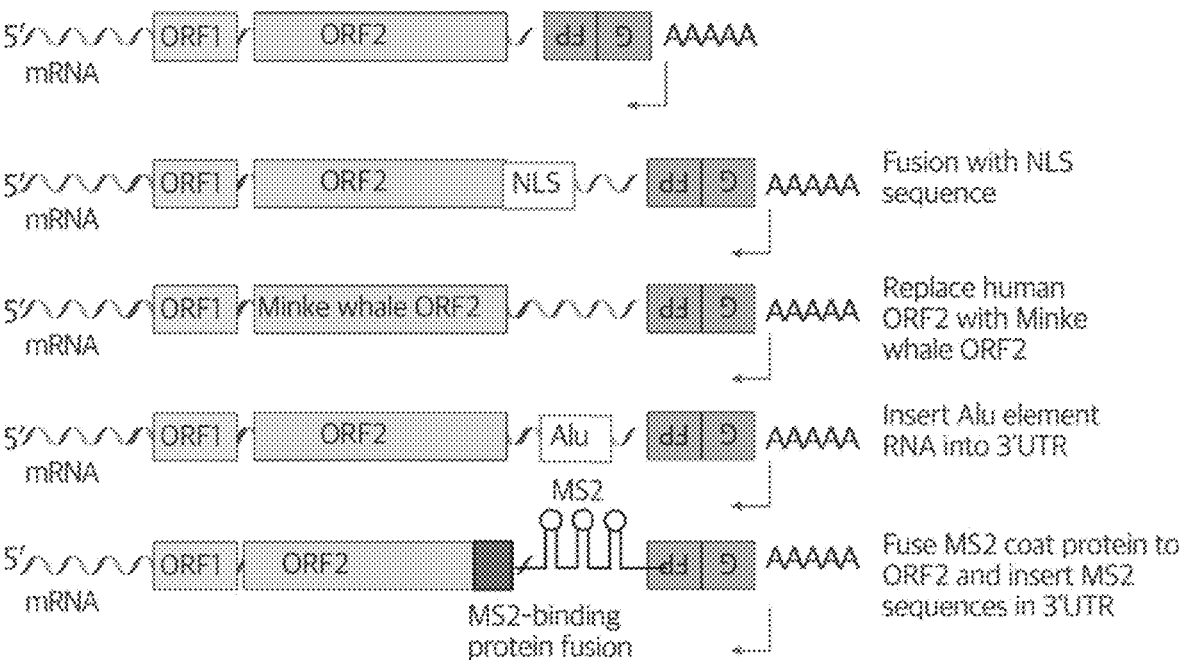
FIG. 15A depicts exemplary constructs to enhance retrotransposition via mRNA delivery. In one construct a nuclear localization signal (NLS) sequence is fused to the C terminus of the ORF2 sequence (ORF2-NLS fusion). In one construct a Minke whale ORF2 sequence was used in place of the human ORF2. In one construct a minimal sequence of the Alu element (AJL-H33delta) is inserted in the 3'UTR of the LINE-1 sequence. In one construct MS2 hairpins are inserted in the 3'UTR of the LINE-1 sequence and an MS2 hairpin binding protein (MCP) sequence is fused to the ORF2 sequence.

Example 10. Modifications to the ORF2 Protein Sequence to Enhance Retrotransposition by mRNA Modification of the LINE-1 sequence to enhance retrotransposition via mRNA delivery were tested using GFP reporter as readout. The experiment was performed as follows. All modifications were in the context of the bicistronic ORF1 and ORF2 sequence. (i) ORF2-NLS fusion was created by inserting C-terminal NLS sequence to the ORF2 sequence. (ii) Human ORF2 was replaced with Minke whale ORF2; (Ivancevic et al., 2016). (iii) Incorporation of an Alu element in the 3'UTR: Using a minimal sequence of the Alu element (AJL-H33A; Ahl et al., 2015) in the 3'UTR of the LINE-1. (iv) MS2-hairpin in the 3'UTR+ORF2-MCP fusion: MS2 hairpins in the 3'UTR of the LINE-1 sequence and a MS2 hairpin binding protein (MCP) fused to the ORF2 sequence (FIG. 15A). The mock construct had the wild-type human ORF2 sequence.

Figure 15B:
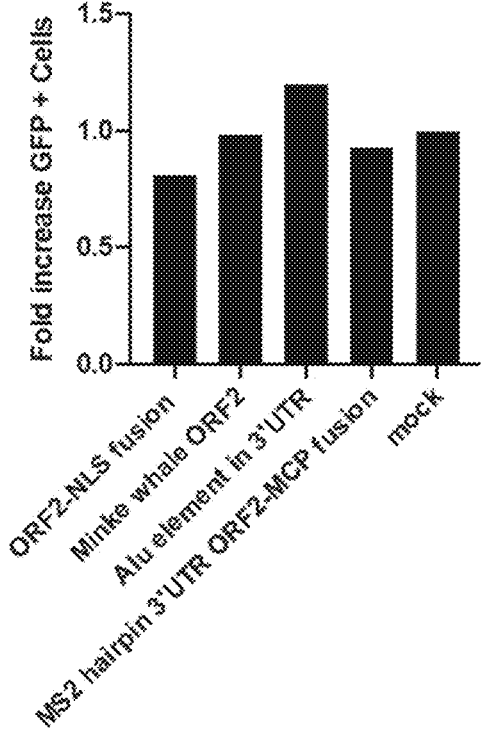
FIG. 15B depicts exemplary data showing expression of GFP (fold increase in mean fluorescence intensity of GFP positive cells is shown) using the constructs depicted in FIG. 15A.

Quantification of the fold increase in the fraction of GFP positive cells relative to mock construct electroporated cells are shown in FIG. 15B.

Example 11. Retrotransposition in an Immune Cell

Figures 16A, 16B:
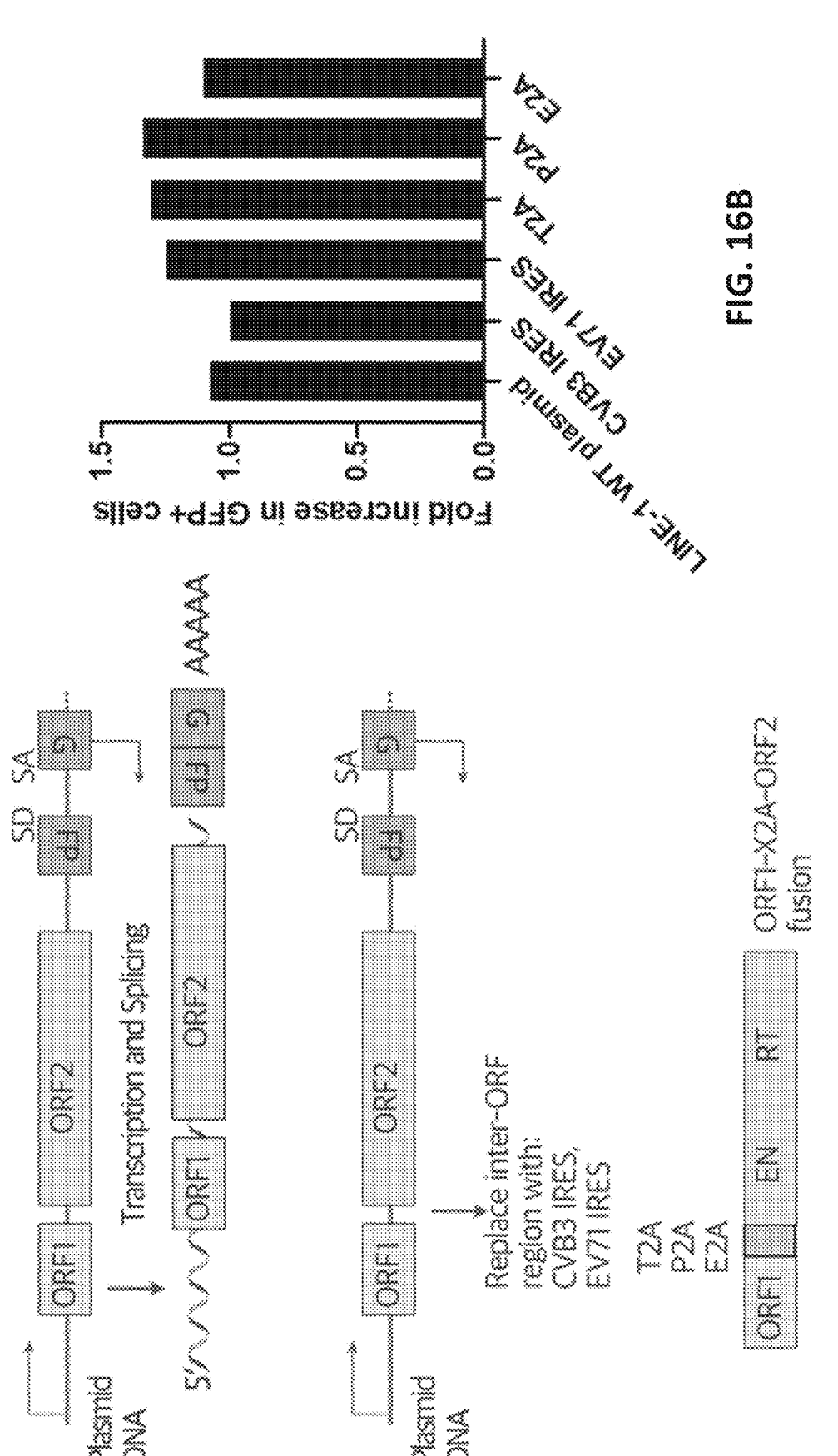
FIG. 16A shows exemplary plasmid constructs where the ORF1 and ORF2 sequences are in two difference plasmid molecules (top panel) and a plasmid encoding a LINE-1 mRNA transcript comprising ORF1 and ORF2 protein encoding sequences on a single mRNA molecule with various replacements of the inter-ORF sequence between ORF1 and ORF2 (bottom panel) for gene delivery.
FIG. 16B depicts exemplary data showing expression of GFP (fold increase in mean fluorescence intensity of GFP positive cells is shown) using the constructs depicted in FIG. 16A.

In this experiment, the inter-ORF region is further manipulated to determine if any of the changes improve GFP expression after transfection of the HEK cells. Taking LINE-1plasmid GFP, the inter-ORF region is manipulated as follows: (a) In one construct the inter-ORF region is replaced with an IRES from CVB3; (b) In another construct, the inter-ORF region is replaced with an IRES from EV71; (c) In three separate constructs, an E2A or P2A or T2A self-cleavage sequence is intercalated in the inter-ORF region. Result are as shown in FIG. 16. Compared to the LINE-1 plasmid GFP (LINE-1 wild type plasmid) led to only modest changes in the GFP readout, especially with T2A sequence insertion. Insertion of EV71 IRES sequence improved GFP expression, while CVB3 IRES did not show any improvement.

Example 12. Retrotransposition in an Immune Cell

To test retrotransposition in immune cells, LINE-1 plasmid and mRNA were tested with the CMV-GFP antisense reporter cargo by electroporating into Jurkat cells, which is a T cell lymphoma line (FIG. 17A-FIG. 17B). Mock set were electroporated with a plasmid with no GFP sequence. GFP expression in the transfected cells was assessed, representative data at 4 days post electroporation is shown in FIG. 17B. Fold increase is reported relative to mock transfected cells. Both plasmid and mRNA delivery modes resulted in successful GFP expression.

Next, THP-1 cells (a myeloid, monocytic cell line) were electroporated with a plasmid having LINE-1 sequences and a 3.7 kb cargo encoding a chimeric HER-2 binding receptor, and a split GFP (LINE-1 plasmid Her2-Cd3z-T2A-GFPintron) (FIG. 18A). The cargo is a chimeric receptor that comprises a HER2 binding extracellular domain, a CD3z transmembrane domain, and split GFP reporter. The plasmid was successfully integrated into the genome and showed prolonged expression, as demonstrated in FIG. 18B. Representative expression at day 6 post transfection is shown in the figure. From these studies, it was demonstrated that LINE-1 mediated gene delivery can result in successful stable genomic integration in various cell types, including epithelial cell types (HEK-293T cells); T cells (e.g., Jurkat cells); and cells of myeloid lineage (e.g., THP-1 cells) and results in prolonged expression. Moreover, unlike CRISPR dependent technologies such as Prime editing, retrotransposition can result in integration of large genetic cargo, and, these can be delivered as a single nucleic acid construct.

Example 13. External Methods for Further Enhancing Efficiency of LINE-1 Mediated Retrotransposition of the Cargo Sequences In this section, methods for further enhancing the efficiency of retrotransposition of cargo sequences into the genome of cells are detailed.

Cell cycle synchronization by selection of cells in a population that are in a certain stage of cell cycle or G1 arrest by a suitable agent can lead to higher nucleic acid uptake efficiency, e.g., plasmid vector transfection efficiency or electroporation efficiency. In this assay, cells are presorted and each group is separately electroporated to ensure uniform electroporation. The efficiencies of electroporation are compared between these groups and a cell cycle stage that results in highest efficiency as determined by the expression of the GFP test plasmid or mRNA is selected (FIG. 19).

In another variation of this experiment, cells are synchronized with or without sorting by treating the cells, with a cell cycle arrest reagent for a few hours prior to electroporation. An exemplary list of cell cycle arrest reagents is provided in Table 1. The list is non-exhaustive, and is inclusive of reagents that can be proapoptotic, and hence careful selection suitable for the purpose and dose and time of incubation is optimized for use in the particular context.

TABLE 1

| Exemplary non-exhaustive list of small molecule reagents that are used for inhibiting cell cycle | | |
| --- | --- | --- |
| Agent | Cell cycle | Mechanism |
| 5-[(4-Ethylphenyl)methylene]-2-thioxo-4-thiazolidinone | Arrests cell cycle at G0-G1 | Inhibits c-Myc-Max dimerization |
| Itraconazole | Inhibits cell cycle at G1 | SMO antagonist |
| ABT 751 (Tocris Bioscience, cat #4138) | Blocks cell cycle at G2M | Inhibits microtubule proliferation |
| Artesunate | Arrests cell cycle at G2M | Suppresses ROS-induced NLRP3 |
| AZD 5438 | Blocks cell cycle at G2M, M, S and G1 phases | Inhibits Cdk |
| Baicalein | Arrests cell cycle at G1 and G2 phases | Inhibits lipoxygenases |
| CPI 203 (alternative name: TEN 101) | Arrests cell cycle at G1 phase | BET bromodomain inhibitor |
| Diadzein | Arrests cell cycle at G1 | Estrogen receptor agonist |
| DIM | Blocks cell cycle at G2M | Induces EGFR activation |
| Epothilone B | Arrests cell cycle at G2M | Inhibits tubulin proliferation |

TABLE 1-continued

Exemplary non-exhaustive list of small molecule
reagents that are used for inhibiting cell cycle

| Agent | Cell cycle | Mechanism |
|---|---|---|
| Indirubin-3'-oxime | Antiproliferative | Inhibits GSK3b |
| MPC 6827 hydrochloride | Cell cycle arrest | Inhibits microtubule proliferation |
| Pladienolide | Inhibits G1 and G2/M | Decreases mRNA splicing |
| Plumbagin | Induces G2/M arrest | Inhibits TOR signaling and others |
| Temsirolimus | Induces G1/S | mTOR inhibitor |
| Toceranib | Cell cycle arrest | Inhibits PDGFR and VEGFR |
| WYE 687 dihydrochloride | Induces Gl arrest | mTOR inhibitor |
| YC1 | Induces Gl arrest | Guanylyl cyclase activator |

For certain ex vivo usages, retrotransposition is enhanced by inducing DNA double stranded breaks (DSB) in a cell that expresses a retrotransposition machinery as described in any of the examples above by controlled irradiation, which create opportunities for the homologous recombination and priming for the reverse transcriptase (FIG. 20). In another example, cells transfected with LINE-1 plasmid GFP construct and subjected to an irradiation pulse. GFP expression is monitored. The intensity and time of irradiation is optimized for obtaining the maximum benefit, as indicated by higher GFP expression.

In another example, cells transfected with LINE-1 plasmid GFP were divided into experimental sets that are treated as follows (i) irradiation in order to induce DSB (as described above); (ii) treat cells in this set with a small molecule, such as SCR7, that blocks DNA ligase and therefore inhibits the DNA damage repair machinery. Prereplaced with an UTR of a complement gene; (b) In another construct, the 3' UTR is replaced with the UTR sequence of B-globin gene for increased stability; (c) In another construct the inter-ORF region is replaced with an IRES from CVB3; (d) In another construct, the inter-ORF region is replaced with an IRES from EV71 (e) In three separate constructs, an E2A or P2A or T2A self-cleavage sequence is intercalated in the inter-ORF region as shown in a diagrammatic representation in FIG. 21. In addition to the above, various combinations of (a)-(e) and additional combinations listed in Table 2 are tested using the same set-up as above. GFP expressions are monitored after transfection of the constructs in parallel test sets into HEK293T cells to see if any of these constructs increased GFP expression compared to the LINE-1 plasmid GFP alone. The combinations that show improvement are adopted.

TABLE 2

Exemplary combinations of 5' and 3' UTR and inter-ORF insertion elements
for inclusion in the LINE-1 construct for increase in retrotransposition efficiency.

| 5'-UTR sequences selected from sequences | 3'-UTR sequences | Inter-ORF sequences |
|---|---|---|
| Complement 5'UTR | WPRE | T2A, E2A, P2A |
| Covid-19 5' leader sequence | B-globin 3'UTR | CVB3 IRES |
| CYBA 5'UTR | RSV RSE | EV71 IRES |
| CYP2E1 5' UTR | AREs | EMCV IRES |
| | RNA zipcodes for the ER | PV IRES |
| | mtRNR1-AES | CSFV IRES |
| | | HRV2 IRES |
| | | AAA (tri alanine fusion or any fusion-linker sequence) | venting protective repair mechanism from inhibiting the progress of the retrotransposition is expected to enhance GFP expression: (iii) irradiate the cells then treat the cells with SCR7, combination of the two is expected to show a more robust effect. GFP expression is monitored over a period of 6 days, and the set that shows maximum GFP fluorescence over the longest period indicates a condition that is adopted in further studies.

Example 14. Enhancing Efficiency of LINE-1 Mediated Retrotransposition of the Cargo Sequences by Further Modification of the Construct I. Enhancing non-coding regions of the construct to offer stability and higher expression. In this example a LINE-1 plasmid-GFP is further modified to test for increased GFP expression as follows: (a) In one construct, the 5'UTR is II. Enhancing localization and retention of the ORFs in the nucleus. In this example, LINE-1 plasmid-GFP is further modified to test for increased GFP expression as follows: (a) the ORF2 encoding sequence is fused with a nuclear localization sequence (NLS) (graphically represented in FIG. 15A second construct from top). (b) the ORF 1 encoding sequence is fused with a nuclear localization sequence (NLS), graphically represented in FIG. 22; and (c) An Alu binding sequence is inserted 3' of the sequence encoding ORF2 reverse transcriptase (graphically represented in FIG. 15A, fourth construct from the top; (d) Both (a) and (c) together (not shown); (e) Both (b) and (c) together, the NLS sequence is fused to the ORF1 N-terminus, and an Alu binding sequence is inserted 3' of the sequence encoding ORF2 reverse transcriptase (FIG. 22) and (f) Integrating a SINE-derived nuclear RNA LOcalizatIoN (SIRLOIN) sequence in LINE-1 3' UTR. HEK-293T cells were transfected with constructs (a)-(f) and the LINE-plasmid GFP construct in parallel. GFP expression is monitored after transfection into HEK293T cells. The set that shows maximum GFP fluorescence over the longest period is adopted.

III. Modifying construct to increase LINE-1-protein-RNA complex binding to the ribosome. In this example, an additional sequence is inserted in the 3'UTR of the LINE-1 construct to increase association of the LINE-1 protein RNA construct to the ribosomes, the sequence is an Alu element, or a ribosome binding aptamer (FIG. 23).

For enhancing LINE-1 protein-RNA complex binding to the ribosome, insertion of the following elements in the 3' UTR of the mRNA is done and tested similar to the experiments above. Insertion of Alu elements is described above. In separate constructs, Alu element truncations, Ribosome binding aptamers (109.2-3) and Ribosome expansion segments (ES9S) binding sequence are inserted and each tested for increase in GFP expression.

IV. Enhancing binding of ORF2 to its own mRNA for retrotransposition. In this example, a sequence containing MS2 binding loop structure is introduced into the 3'UTR of the LINE-1, and a sequence encoding MS2 RNA binding domain is fused to the RNA binding domain of the ORF2p-RT (graphically represented in FIGS. 4A and 4B, and FIG. 24, construct SEQ ID NO: 15). The fused protein will specifically attach to the MS2-binding structural motif in the 3' UTR, and therefore any non-specific binding and retrotransposition is minimized (FIG. 24). GFP expression is monitored after transfection into HEK293T cells. Following a similar design, the ORF is fused with the protein binding sequences shown in left column of Table 3 below, combined with a cognate sequence inserted in the 3'UTR region of the ORF2 shown in the corresponding right column in the same row.

TABLE 3

| Exemplary list of elements to enhance translation efficiency and stability of the LINE-1 proteins and increased expression of LINE-1 proteins. | |
| --- | --- |
| Elements to be fused with the LINE-1 ORF2 | 3' UTR sequence recognizable by the element |
| PP7 coat protein | PP7 |
| Streptavidin | S1m aptamer |
| Tobramycin | Tobramycin aptamer |

V. Modifying the endonuclease function of the retrotransposon. In this example, the constructs are modified to test increase in GFP expression as follows. In a first experimental set, the LINE-1 plasmid GFP is cut at the 3'end of the endonuclease coding sequence of ORF2, and a sequence encoding the DNA binding domain (DBD) of a heterologous zinc finger protein (ZFP) is inserted. In another experimental set, the endonuclease domain is fused with a CRISPR nuclease. A variety of nucleases can be tested by modifying the LINE-1 plasmid GFP ORF by creating a fusion protein using DNA binding domains and cleavage domain as shown in a non-exhaustive list in Table 4, In addition, two ORF-2 domains are encoded in one set to facilitate dimerization. The construct that has higher GFP expression than the ORF2 endonuclease can be further selected. The plasmid designs are graphically represented in FIG. 25. GFP expression is monitored after transfection of the plasmids into HEK293T cells, and the set that yielded best.

TABLE 4

| Exemplary non-exhaustive list of additional DNA cleavage domains/enzymes that can be fused to or inserted in place of LINE-1 endonuclease. | |
| --- | --- |
| Gene/Enzyme | Description |
| FokI | Class II endonuclease from Flavobacterium okeanokoites, recognition and cleavage sequence are separated by a few nucleotides; recognizes DNA sequence 5-GGATG-3' |
| Restriction enzymes, LAGLIDADG family nuclease A | e.g., HindII, EcoR1, BamH1 Intron encoded homing proteins found in various genera including bacteria |
| GIY-YIG | This domain is found in the amino terminal region of excinuclease abc subunit c (uvrC), bacteriophage T4, endonuclease segA, segB, seg C, seg D, and seg E and group I introns of fungi and phage. |
| His-Cys box | Homing endonucleases containing two clusters of conserved histidine and cysteine residues over a 100 amino acid region. |
| H—N—H | Widely present nuclease in phage DNA. Crucial component of the terminase packaging reaction of *E. coli* phage HK97. |
| PD-(D/E)xK | Phosphodiesterases, present in a large number of proteins, e.g., DUF4420, DUF3883, DUF4263, COG5482, COG1395, Tsp45I, HaeII, Eco47II, ScaI, HpaII. |
| Vsr-like/EDxHD | C-terminal nuclease domain that displays recognizable homology to bacterial Very short repair (Vsr) endonucleases |

VI. Modifying the reverse transcriptase function of the retrotransposon. In this example, the reverse transcriptase domain of ORF2 is modified for increasing its efficiency. In one experimental set, the sequence encoding the human ORF2 in LINE-1plasmid GFP is excised and replaced with a sequence encoding MMLV or TGIRTII In another experimental set, the OR2 reverse transcriptase domain is fused with a DNA binding domain of a heterologous protein. The reverse transcriptase domains and/or the DNA binding domains can be selected from anon-exhaustive list provided in Table5A-Table5B. The constructs are graphically exemplified in FIG. 26. GFP expression is monitored after transfection into HEK293T cells.

TABLE 5A

Selected non-exhaustive list of reverse transcriptase
for replacing the LINE-1 RT for higher efficiency

| Reverse Transcriptase | Description |
| --- | --- |
| M-MLV-RT | Murine leukemia virus |
| TGIRT-II | Thermostable group II intron reverse transcriptase with high fidelity and processivity |
| AMV-RT | Avian Myeloblastosis Virus reverse transcriptase |
| Group II intron maturase RT | Derived from *Eubacterium rectale* |
| HIV-RT | Efficient RT derived from HIV |
| TERT | Catalyzes the RNA-dependent extension of 3'-chromosomal termini with the 6-nucleotide telomeric repeat unit, 5'-TTAGGG-3'. |

TABLE 5B

Selected non-exhaustive list of DNA-binding domains
for fusing to a RT for higher efficiency

| DNA binding domains (DBD) |
| --- |
| Zinc finger domains |
| Leucine zipper (bZip) |
| Helix-turn-helix domain |
| HMG-box |
| R2 retroelement DBD |
| Sso7d |
| Protein A (ssDNA) |
| OB-fold (ssDNA) |

VII. Replacing human LINE-1 with LINE-1 from other organisms. In this example, the sequence encoding human LINE-1 is replaced by a LINE-1 from a different organism. In one example, the human LINE-1 construct is compared with a construct where the human LINE-1 is replaced by a minke whale LINE-1 sequence (FIG. 27). Using the same experimental framework, a number of ORFs are tested. An exemplary non-exhaustive list is provided in Table 6 below. A further comprehensive list is available in Ivancevic A. et al., Genome Biol Evol 8(11):3301-3322.

TABLE 6

Exemplary LINE-1 elements from organism for
use in replacement of the human LINE-1

| Species Name | No of total LINE-1/No active/percent active |
| --- | --- |
| *Balaenoptera acutorostrata scammoni* | 8,012/5,006/62.4% |
| *Rhinopithecus roxellana* | 11,115/2,954/26.5% |
| *Mus musculus* | 18,280/4,143/22.66% |
| *Aedes aegypti* | 519/184/35.4% |
| *Zea mays* | 744/165/22.17% |
| *Brassica napus* | 1,929/565/29.2% |
| *Brassica rapa* | 543/228/41.9% |
| *Danio rerio* | 590/268/45.4% |

In another set, human LINE-1 is retained as in the GFP plasmid, but an inhibitor of human LINE-1 silencer is utilized to prevent recognition by endogenous proteins like HUSH complex TASOR protein. In this case, the TASOR inhibitor is an inhibitory RNA, such as a miRNA.

VIII. LINE-1 fusion proteins for target specificity. In this example, the LINE-1 plasmid GFP ORF2 is fused with a domain of a MegaTAL nuclease, a CRISPR-CAS nuclease, a TALEN, R2 retroelement binding zinc finger binding domain, or a DNA binding domain that can bind to repetitive elements such as Rep78 AAV. FIG. 28 exemplifies the deigns. Table 7 provides a list of the different elements that can be fused to increase sequence specific retrotransposition.

TABLE 7

Exemplary proteins with DNA binding domains to be fused
to ORF2 for increasing retrotransposition specificity

| Elements |
| --- |
| Transcription Factors |
| MegaTAL nucleases |
| TALENs |
| Zinc finger binding domains from other retroelements |
| Safe harbor binding proteins |
| Cfp1 |

Each plasmid is transfected into HEK293 cells and GFP expression is monitored.

The modifications described in this section under (I)-(VIII) are designed to test for increase in retrotransposition efficiency, using GFP as readout. Following this, a number of useful modifications from (I)-(VIII) are incorporated into a single retrotransposition construct, tested with GFP as insert for the outcome, and the GFP sequence is replaced by the desired insert sequence.

Example 15. Delivering a Large Payload for Prolonged Expression Using Retrotransposon Technology Provided here are exemplary demonstrations of retrotransposon constructs are versatile for incorporating nucleic acid payloads into the genome of a cell and expressing an exemplary transgene. Retrotransposon constructs were designed as elaborated elsewhere in the disclosure.

Briefly, in one set of validation experiments, GFP encoding payloads were constructed as follows: an antisense promoter sequence under doxycycline inducible control followed by antisense GFP gene split with an intron in the sense direction was placed downstream of the LINE-1 ORFs (FIG. 29). Splicing donor (SD) and splicing acceptor (SA) sequences are recognized and spliced out only when the mRNA is produced from the promoter in the top strand, therefore only the GFP gene integrated into genome from spliced mRNA generates fluorescent signal. As shown in the representative flow cytometry data in FIG. 29, the GFP expression was measured 35 days post doxycycline induction of the ORF expression using flow cytometry (histogram) compared to a negative control plasmid (histogram). In this case, the cargo size was 2.4 kb.

The cargo GFP gene in the previous construct was replaced with intron interrupted CD5-FcR-PI3K CAR-M sequence (Morrissey et al., 2018). The CD5 binder expression was measured by flow cytometry using a Alexa647-conjugated CD5 protein such that retrotransposed cells are CD5-AF647 positive (histogram) compared with a plasmid transfected negative control cell population (histogram) (FIG. 30). Successful expression of the 3.0 kb construct was demonstrated as shown in the figure.

The cargo gene length was extended by adding the intron-interrupted GFP gene after the T2A sequence downstream of the CD5-FcR-PI3K CAR-M sequence (FIG. 31). The CD5 binder expression was measured by flow cytometry using a Alexa647-conjugated CD5 protein. The CD5 binder positive cells shown by histogram, in comparison with a negative control (histogram). The GFP expression is measured using flow cytometry (histogram) compared to a negative control plasmid transfected cells (histogram). The flow cytometry signal in the Q2 showed that 10.8% cells express both CAR-M and GFP proteins.

As shown in FIG. 32, the payload size limit has not been reached with retrotransposon delivery and integration (Retro-T delivery) with a 3.9 kb payload. The delivery mechanism described here was successful for expression of the first generation CART construct and GFP (separated by T2A site). In this example, different constructs were tested for retrotransposition efficiency of the insert sequence. FIG. 33A shows gene delivery as mRNA results in successful integration. This data is the first to show that Retro T can be delivered as mRNA. A trans strategy of using separate mRNAs encoding for ORF1 and ORF2 with antisense promoter and GFP cargo (ORF2-GFPai) in the 3' UTR for gene delivery was explored, as exemplified graphically in FIG. 33B (top panel). FIGS. 33B-33D demonstrate experimental results from multiple representative assays. Separate mRNAs that expression the LINE-1 proteins could reconstitute the RNA-protein complex required for retrotransposition. The cis strategy uses a single bicistronic LINE-1 mRNA with the antisense promoter and GFP gene cargo in the 3'UTR. Constructs comprising variable amounts and proportions of ORF2 and ORF1 were compared as shown in FIG. 33B and FIG. 33C with GFP encoding sequence as payload. FIG. 33D shows that introducing a single mRNA yields higher number of integrations per cell. Sorting of 293T GFP cells to enrich for retrotransposed cells for biochemical and integration assays. Cells are the same as in FIG. 33B and show GFP expression 4 days post-sort in bottom panels. The graph shows qPCR assay for genomic DNA integration from different LINE-1 plasmid transfected, LINE-1 mRNA (retro-mRNA), and ORF1 and ORF2-GFP mRNA electroporated cells. Two qPCR primer-probe sets were used, one for the housekeeping gene RPS30 and the other for the GFP gene. Plasmid-transfected cells use a plasmid that does not contain and SV40 maintenance sequence. Integration per cell is calculated from determining copy numbers per samples through interpolation of a standard curve of plasmid and genomic DNA and normalizing for the two copies of RPS30 per 293T cell. Error bar denote standard deviation of three technical replicate measurements.

Example 16. Delivery to Diverse Cell Types

As shown in FIGS. 34-38, the mRNA constructs comprising a gene of interest, e.g. encoding a CAR protein, or for example, a GFP protein can be efficiently expressed in diverse cell types, such as epithelial cells (e.g., HEK 293 cells), monocytic cells lines (e.g., THP-1 cells), lymphoblastic cell lines (e.g., K562 cells), and primary lymphocytes (T cells). Activated primary T cells were also successfully transfected with mRNA with genomic integration and expression of GFP (FIG. 36). Primary T cells were isolated and expanded using IL7/IL15; and a $1^{st}$ Gen CAR construct was delivered on day 2 post activation. Cells sorted and frozen. GFP expression was detectable after a freeze-thaw cycle (FIG. 37A-B). This indicates the versatile nature of mRNA mediated delivery and L1-transposon mediated integration. FIG. 38 shows a representative assay of GFP mRNA integration and expression in 293T cells, K562 cells, THP-1 cells and Primary T cells.

Exemplary Sequences

Following are exemplary sequences of the constructs used in the examples. These sequences are for reference exemplary purposes and sequence variations and optimizations that are conceivable by one of skill in the art without undue experimentation are contemplated and encompassed by the disclosure. Where mRNA sequences are referred in the sequence title, the construct recites nucleotides of a DNA template and one of skill in the art can easily derive the corresponding mRNA sequence.

TABLE 8

| Plasmid and mRNA construct sequences |
| --- |
| ORF1-FLAG- mRNA (Codon Optimized human ORF1 coding sequence-FLAG) (SEQ ID NO: 35): |

```
  1 TAATACGACT CACTATAGGG AGAAAGACGC CACCATGGGC AAGAAGCAAA ATCGCAAGAC

61 GGGGAATTCC AAGACACAAT CCGCTAGCCC ACCACCTAAA GAGCGTTCTA GCTCCCCTGC

121 TACTGAGCAG TCCTGGATGG AAAACGACTT CGATGAACTC CGGGAAGAGG GATTTAGGCG

181 ATCCAACTAT TCAGAACTCC GCGAAGATAT CCAGACAAAG GGGAAGGAAG TCGAGAATTT

241 CGAGAAGAAC CTCGAGGAGT GCATCACCCG TATCACAAAC ACTGAGAAAT GTCTCAAAGA

301 ACTCATGGAA CTTAAGACAA AAGCCAGGGA GCTTCGAGAG GAGTGTCGGA GTCTGAGATC

361 CAGGTGTGAC CAGCTCGAGG AGCGCGTGAG CGCGATGGAA GACGAGATGA ACGAGATGAA

421 AAGAGAGGGC AAATTCAGGG AGAAGCGCAT TAAGAGGAAC GAACAGAGTC TGCAGGAGAT

481 TTGGGATTAC GTCAAGAGGC CTAACCTGCG GTTGATCGGC GTCCCCGAGA GCGACGTAGA

541 AAACGGGACT AAACTGGAGA ATACACTTCA AGACATCATT CAAGAAAATT TTCCAAACCT

601 GGCTCGGCAA GCTAATGTGC AAATCCAAGA GATCCAACGC ACACCCCAGC GGTATAGCTC

661 TCGGCGTGCC ACCCCTAGGC ATATTATCGT GCGCTTTACT AAGGTGGAGA TGAAAGAGAA

721 GATGCTGCGA GCCGCTCGGG AAAAGGGAAG GGTGACTTTG AAGGGCAAAC CTATTCGGCT

781 GACGGTTGAC CTTAGCGCCG AGACACTCCA GGCACGCCGG GAATGGGGCC CCATCTTTAA
```

TABLE 8-continued

| Plasmid and mRNA construct sequences |
| --- |

```
 841 TATCCTGAAG GAGAAGAACT TCCAGCCACG AATCTCTTAC CCTGCAAAGT TGAGTTTTAT

901 CTCCGAGGGT GAGATTAAGT ATTTCATCGA TAAACAGATG CTGCGAGACT TCGTGACAAC

961 TCGCCCAGCT CTCAAGGAAC TGCTCAAAGA GGCTCTTAAT ATGGAGCGCA ATAATAGATA

1021 TCAACCCTTG CAGAACCACG CAAAGATGGA TTATAAGGAT GACGATGATA AATGA
(SEQ ID NO: 35)
```

ORF2-FLAG-GFPai mRNA (Codon Optimized human ORF2 coding sequence)
(SEQ ID NO: 36)

```
   1 TAATACGACT CACTATAGGG AGAAAGACGC CACCATGACA GGTTCAAATA GTCACATTAC

61 GATTCTCACT CTGAATATAA ATGGGCTGAA TTCTGCAATT AAACGGCACA GGCTTGCTTC

121 CTGGATAAAG TCTCAAGACC CCTCAGTGTG CTGTATTCAG GAAACGCATC TCACGTGCAG

181 GGACACCCAT CGGCTGAAAA TAAAAGGCTG GCGGAAGATC TACCAAGCCA ATGGAAAACA

241 AAAGAAGGCT GGGGTGGCGA TACTTGTAAG CGATAAAACA GACTTTAAAC CAACTAAGAT

301 CAAACGGGAC AAAGAGGGCC ATTACATCAT GGTAAAGGGT AGTATTCAAC AAGAGGAGCT

361 GACTATCCTG AATATTTATG CACCTAATAC TGGAGCCCCC AGATTCATAA AGCAAGTGTT

421 GAGTGACCTT CAACGCGACC TCGACTCCCA CACTCTGATC ATGGGAGACT TTAACACCCC

481 GCTGTCCACT CTCGACAGAT CTACTAGACA GAAAGTCAAC AAGGATACAC AGGAACTGAA

541 CAGTGCTCTC CACCAAGCGG ACCTTATCGA CATCTACAGA ACACTCCACC CCAAAAGCAC

601 AGAATATACC TTCTTTTCAG CCCCTCACCA CACCTATTCC AAAATTGACC ACATTGTGGG

661 GAGTAAAGCC CTTCTCTCCA AATGTAAACG GACCGAAATT ATCACTAACT ATCTCTCCGA

721 CCACAGTGCA ATAAAACTTG AATTGCGAAT TAAGAATCTC ACTCAAAGTA GATCCACGAC

781 ATGGAAACTG AACAATCTCC TCTTGAATGA CTACTGGGTG CATAACGAAA TGAAGGCTGA

841 AATAAAGATG TTCTTTGAGA CCAACGAAAA CAAAGACACC ACGTACCAGA TCTCTGGGA

901 CGCTTTCAAA GCAGTGTGTC GAGGAAAATT TATTGCACTG AATGCTTACA AGCGGAAGCA

961 GGAAAGATCC AAAATAGACA CCCTGACTAG CCAACTTAAA GAACTGGAAA AGCAAGAGCA

1021 AACTCATAGC AAAGCTAGCC GTCGCCAAGA AATTACGAAA ATCAGAGCTG AACTGAAGGA

1081 AATTGAGACA CAGAAACCC TGCAAAGAT AAATGAAAGC CGCAGCTGGT CTTTGAACG

1141 CATCAACAAA ATCGATAGGC CACTTGCTCG CCTTATCAAG AAGAAAGGG AGAAGAATCA

1201 AATCGACACT ATAAAGAATG ATAAAGGCGA TATAACCACC GATCCCACAG AAATTCAAAC

1261 AACCATACGC GAATACTACA AACACCTCTA CGCCAATAAA CTCGAAAATC TCGAGGAAAT

1321 GGATACATTC CTCGACACGT ACACCCTTCC CAGGCTGAAC CAGGAAGAAG TTGAATCACT

1381 GAATCGGCCT ATCACGGGGA GTGAAATAGT AGCTATCATC AATTCACTCC CTACCAAGAA

1441 GTCACCCGGA CCTGATGGAT TCACCGCCGA ATTCTACCAG AGATACATGG AAGAACTGGT

1501 GCCCTTCTTG CTGAAACTTT TCCAAAGTAT TGAGAAAGAG GGAATACTTC CAAACTCATT

1561 TTATGAGGCA TCCATCATTC TGATCCCGAA GCCCGGCAGG GACACGACCA AGAAAGAGAA

1621 TTTTCGACCA ATCTCATTGA TGAACATTGA TGCAAAGATC CTCAATAAAA TACTGGCAAA

1681 TCGGATTCAG CAGCACATAA AGAAGCTGAT CCACCATGAT CAAGTAGGCT TCATCCCCGG

1741 TATGCAAGGT TGGTTCAATA TACGAAAATC AATCAATGTT ATCCAGCATA TAAACCGGGC

1801 CAAAGACAAG AACCACATGA TTATTAGTAT CGATGCTGAG AAAGCCTTTG ACAAAATACA

1861 ACAACCCTTC ATGCTGAAAA CATTGAATAA GCTGGGAATT GATGGCACCT ACTTCAAAAT

1921 CATCAGAGCC ATATATGACA AACCAACAGC AAATATCATT CTGAATGGTC AGAAATTGGA
```

TABLE 8-continued

Plasmid and mRNA construct sequences

```
1981 AGCATTCCCC TTGAAAACCG GCACACGGCA GGGTTGCCCT CTGTCACCAC TCCTCTTCAA

2041 CATCGTGTTG GAAGTTCTTG CCCGCGCAAT CCGGCAGGAA AAGGAAATCA AGGGCATTCA

2101 ACTGGGCAAA GAGGAAGTTA AATTGAGCCT GTTTGCAGAC GACATGATCG TCTATTTGGA

2161 AAACCCCATA GTTAGTGCAC AAAATCTGCT GAAGTTGATC AGTAATTTCT CCAAAGTGAG

2221 TGGGTACAAA ATCAATGTGC AAAAGAGCCA AGCTTTCTTG TACACCAACA ACAGGCAAAC

2281 TGAGTCTCAA ATCATGGGCG AACTCCCCTT CGTGATTGCA TCCAAGCGGA TCAAATACCT

2341 GGGGATTCAA TTGACTCGTG ATGTGAAGGA CCTCTTCAAG GAGAACTACA AACCCCTGCT

2401 CAAGGAAATC AAAGAGGACA CAAACAAATG GAAGAACATT CCATGCTCTT GGGTGGGAAG

2461 GATCAATATC GTCAAATGG CCATCCTGCC CAAGGTAATT TACAGGTTCA ATGCTATACC

2521 CATCAAGCTC CCCATGACAT TCTTCACAGA ACTTGAAAAG ACGACGCTGA AGTTCATTTG

2581 GAACCAGAAA CGTGCCAGGA TTGCTAAATC TATTCTCTCC CAAAAGAACA AAGCTGGCGG

2641 AATCACACTC CCAGACTTCA AACTTTACTA CAAGGCGACC GTGACGAAAA CGGCTTGGTA

2701 CTGGTACCAA AACAGGGATA TAGATCAATG GAACCGAACG GAGCCCAGCG AAATTATGCC

2761 TCATATATAC AACTATCTGA TCTTTGACAA ACCGGAGAAG AACAAGCAAT GGGGAAAGGA

2821 TAGTCTGTTT AATAAATGGT GCTGGGAAAA CTGGCTCGCA ATCTGTAGGA AGCTGAAACT

2881 GGATCCATTC TTGACGCCTT ATACAAAGAT AAATTCCCGA TGGATTAAAG ATCTCAACGT

2941 GAAACCCAAA ACAATTAAAA CCCTCGAGGA AAACCTGGGT ATTACGATTC AGGACATTGG

3001 GGTGGGAAAG GACTTCATGT CCAAAACCCC AAAAGCGATG GCAACCAAAG ACAAAATCGA

3061 CAAATGGGAT CTCATAAAAC TTAAGTCATT TTGCACAGCT AAAGAAACGA CAATTAGGGT

3121 GAACCGACAA CCGACCACTT GGGAGAAAAT CTTCGCAACA TACAGTTCTG ACAAAGGCCT

3181 GATTTCCAGG ATCTACAATG AATTGAAACA AATTTACAAG AAGAAGACGA ACAACCCTAT

3241 AAAGAAATGG GCCAAGGACA TGAACAGACA CTTCTCTAAG GAAGACATTT ATGCAGCCAA

3301 GAAACACATG AAGAAATGCA GCTCTTCACT GGCAATCAGG GAAATGCAAA TCAAAACAAC

3361 AATGAGATAT CATCTCACAC CCGTCAGAAT GGCCATCATT AAGAAGAGCG GAAACAACCG

3421 GTGCTGGCGT GGTTGCGGAG AAATCGGTAC TCTCCTTCAC TGTTGGTGGG ACTGTAAACT

3481 CGTTCAACCA CTGTGGAAGT CTGTGTGGCG GTTCCTCAGA GATCTGGAAC TCGAAATCCC

3541 ATTTGACCCA GCCATCCCTC TCCTGGGTAT ATACCCGAAT GAGTATAAAT CCTGCTGCTA

3601 TAAAGACACC TGCACAAGGA TGTTTATTGC AGCTCTCTTC ACAATCGCGA AGACGTGGAA

3661 CCAACCCAAA TGTCCGACTA TGATTGACTG GATTAAGAAG ATGTGGCACA TATACACTAT

3721 GGAATACTAT GCTGCGATCA AGAACGATGA GTTCATATCA TTTGTGGGCA CATGGATGAA

3781 ACTCGAAACC ATCATACTCT CTAAATTGAG TCAAGAACAG AAAACTAAAC ACCGTATATT

3841 TTCCCTGATC GGTGGGAATT AGCTACAAAG ACGATGACGA CAAGGACCAT GGAGACGGTG

3901 AGAGACACAA AAAATTCCAA CACACTATTG CAATGAAAAT AAATTTCCTT TATTAGCCAG

3961 AAGTCAGATG CTCAAGGGGC TTCATGATGT CCCCATAATT TTTGGCAGAG GGAAAAAGAT

4021 CTCAGTGGTA TTTGTGAGCC AGGGCATTGG CCTTCTGATA GGCAGCCTGC ACCTGAGGAG

4081 TGCGGCCGCT TTACTTGTAC AGCTCGTCCA TGCCGAGAGT GATCCCGGCG CGGTCACGA

4141 ACTCCAGCAG GACCATGTGA TCGCGCTTCT CGTTGGGGTC TTTGCTCAGG GCGGACTGGG

4201 TGCTCAGGTA GTGGTTGTCG GGCAGCAGCA CGGGGCCGTC GCCGATGGGG GTGTTCTGCT

4261 GGTAGTGGTC GGCGAGCTGC ACGCTGCCGT CCTCGATGTT GTGGCGGATC TTGAAGTTCA
```

TABLE 8-continued

Plasmid and mRNA construct sequences

```
4321 CCTTGATGCC GTTCTTCTGC TTGTCGGCCA TGATATAGAC GTTGTGGCTG TTGTAGTTGT

4381 ACTCCAGCTT GTGCCCCAGG ATGTTGCCGT CCTCCTTGAA GTCGATGCCC TTCAGCTCGA

4441 TGCGGTTCAC CAGGGTGTCG CCCTCGAACT TCACCTCGGC GCGGGTCTTG TAGTTGCCGT

4501 CGTCCTTGAA GAAGATGGTG CGCTCCTGGA CGTAGCCTTC GGGCATGGCG GACTTGAAGA

4561 AGTCGTGCTG CTTCATGTGG TCGGGGTAGC GGCTGAAGCA CTGCACGCCG TAGGTCAGGG

4621 TGGTCACGAG GGTGGGCCAG GGCACGGGCA GCTTGCCGGT GGTGCAGATG AACTTCAGGG

4681 TCAGCTTGCC GTAGGTGGCA TCGCCCTCGC CCTCGCCGGA CACGCTGAAC TTGTGGCCGT

4741 TTACGTCGCC GTCCAGCTCG ACCAGGATGG GCACCACCCC GGTGAACAGC TCCTCGCCCT

4801 TGCTCACCAT GGTGGCGGGA TCTGACGGTT CACTAAACCA GCTCTGCTTA TATAGACCTC

4861 CCACCGTACA CGCCTACCGC CCATTTGCGT CAATGGGCG GAGTTGTTAC GACATTTTGG

4921 AAAGTCCCGT TGATTTTGGT GCCAAAACAA ACTCCCATTG ACGTCAATGG GGTGGAGACT

4981 TGGAAATCCC CGTGAGTCAA ACCGCTATCC ACGCCCATTG ATGTACTGCC AAAACCGCAT

5041 CACCATGGTA ATAGCGATGA CTAATACGTA GATGTACTGC CAAGTAGGAA AGTCCCATAA

5101 GGTCATGTAC TGGGCATAAT GCCAGGCGGG CCATTTACCG TCATTGACGT CAATAGGGGG

5161 CGTACTTGGC ATATGATACA CTTGATGTAC TGCCAAGTGG GCAGTTTACC GTAAATACTC

5221 CACCCATTGA CGTCAATGGA AAGTCCCTAT TGGCGTTACT ATGGGAACAT ACGTCATTAT

5281 TGACGTCAAT GGGCGGGGGT CGTTGGGCGG TCAGCCAGGC GGGCCATTTA CCGTAAGTTA

5341 TGTAACGACG TCTCAGCTGA CAATGAGATC ACATGGACAC AGGAAGGGGA ATATCACACT

5401 CTGGGGACTG TGGTGGGGTC GGGGGAGGGG GGAGGGATAG CATTGGGAGA TATACCTAAT

5461 GCTAGATGAC ACATTAGTGG GTGCAGCGCA CCAGCATGGC ACATGTATAC ATATGTAACT

5521 AACCTGCACA ATGTGCACAT GTACCCTAAA ACTTAGAGTA TAATGGATCC GCAGGCCTCT

5581 GCTAGCTTGA CTGACTGAGA TACAGCGTAC CTTCAGCTCA CAGACATGAT AAGATACATT

5641 GATGAGTTTG GACAAACCAC AACTAGAATG CAGTGAAAAA AATGCTTTAT TTGTGAAATT

5701 TGTGATGCTA TTGCTTTATT TGTAACCATT ATAAGCTGCA ATAAACAAGT T
(SEQ ID NO: 36)
```

LINE-1 plasmid GFP (SEQ ID NO: 37)

```
  1 CGGCCGCGGG GGGAGGAGCC AAGATGGCCG AATAGGAACA GCTCCGGTCT ACAGCTCCCA

61 GCGTGAGCGA CGCAGAAGAC GGTGATTTCT GCATTTCCAT CTGAGGTACC GGGTTCATCT

121 CACTAGGGAG TGCCAGACAG TGGGCGCAGG CCAGTGTGTG TGCGCACCGT GCGCGAGCCG

181 AAGCAGGGCG AGGCATTGCC TCACCTGGGA AGCGCAAGGG GTCAGGGAGT TCCCTTTCCG

241 AGTCAAAGAA AGGGGTGACG GACGCACCTG AAAATCGGG TCACTCCCAC CCGAATATTG

301 CGCTTTTCAG ACCGGCTTAA GAAACGGCGC ACCACGAGAC TATATCCCAC ACCTGGCTCG

361 GAGGGTCCTA CGCCCACGGA ATCTCGCTGA TTGCTAGCAC AGCAGTCTGA GATCAAACTG

421 CAAGGCGGCA ACGAGGCTGG GGGAGGGGCG CCCGCCATTG CCCAGGCTTG CTTAGGTAAA

481 CAAAGCAGCA GGGAAGCTCG AACTGGGTGG AGCCCACCAC AGCTCAAGGA GGCCTGCCTG

541 CCTCTGTAGG CTCCACCTCT GGGGGCAGGG CACAGACAAA CAAAAAGACA GCAGTAACCT

601 CTGCAGACTT AAGTGTCCCT GTCTGACAGC TTTGAAGAGA GCAGTGGTTC TCCCAGCACG

661 CAGCTGGAGA TCTGAGAACG GCAGACTGC CTCCTCAAGT GGGTCCCTGA CCCCTGACCC

721 CCGAGCAGCC TAACTGGGAG GCACCCCCCA GCAGGGGCAC ACTGACACCT CACACGGCAG

781 GGTATTCCAA CAGACCTGCA GCTGAGGGTC CTGTCTGTTA GAAGGAAAAC TAACAACCAG
```

TABLE 8-continued

Plasmid and mRNA construct sequences

```
 841 AAAGGACATC TACACCGAAA ACCCATCTGT ACATCACCAT CATCAAAGAC CAAAAGTAGA

901 TAAAACCACA AAGATGGGGA AAAAACAGAA CAGAAAAACT GGAAACTCTA AAACGCAGAG

961 CGCCTCTCCT CCTCCAAAGG AACGCAGTTC CTCACCAGCA ACAGAACAAA GCTGGATGGA

1021 GAATGATTTT GATGAGCTGA GAGAAGAAGG CTTCAGACGA TCAAATTACT CTGAGCTACG

1081 GGAGGACATT CAAACCAAAG GCAAAGAAGT TGAAAACTTT GAAAAAAATT TAGAAGAATG

1141 TATAACTAGA ATAACCAATA CAGAGAAGTG CTTAAAGGAG CTGATGGAGC TGAAAACCAA

1201 GGCTCGAGAA CTACGTGAAG AATGCAGAAG CCTCAGGAGC CGATGCGATC AACTGGAAGA

1261 AAGGGTATCA GCAATGGAAG ATGAAATGAA TGAAATGAAG CGAGAAGGGA AGTTTAGAGA

1321 AAAAAGAATA AAAAGAAATG AGCAAAGCCT CCAAGAAATA TGGGACTATG TGAAAAGACC

1381 AAATCTACGT CTGATTGGTG TACCTGAAAG TGATGTGGAG AATGGAACCA AGTTGGAAAA

1441 CACTCTGCAG GATATTATCC AGGAGAACTT CCCCAATCTA GCAAGGCAGG CCAACGTTCA

1501 GATTCAGGAA ATACAGAGAA CGCCACAAAG ATACTCCTCG AGAAGAGCAA CTCCAAGACA

1561 CATAATTGTC AGATTCACCA AAGTTGAAAT GAAGGAAAAA ATGTTAAGGG CAGCCAGAGA

1621 GAAAGGTCGG GTTACCCTCA AAGGAAAGCC CATCAGACTA ACAGCGGATC TCTCGGCAGA

1681 AACCCTACAA GCCAGAAGAG AGTGGGGGCC AATATTCAAC ATTCTTAAAG AAAAGAATTT

1741 TCAACCCAGA ATTTCATATC CAGCCAAACT AAGCTTCATA AGTGAAGGAG AAATAAAATA

1801 CTTTATAGAC AAGCAAATGT TGAGAGATTT TGTCACCACC AGGCCTGCCC TAAAAGAGCT

1861 CCTGAAGGAA GCGCTAAACA TGGAAAGGAA CAACCGGTAC CAGCCGCTGC AAAATCATGC

1921 CAAAATGTAA AGACCATCAA GACTAGGAAG AAACTGCATC AACTAATGAG CAAAATCACC

1981 AGCTAACATC ATAATGACAG GATCAACTTC ACACATAACA ATATTAACTT TAAATATAAA

2041 TGGACTAAAT TCTGCAATTA AAAGACACAG ACTGGCAAGT TGGATAAAGA GTCAAGACCC

2101 ATCAGTGTGC TGTATTCAGG AAACCCATCT CACGTGCAGA GACACACATA GGCTCAAAAT

2161 AAAAGGATGG AGGAAGATCT ACCAAGCCAA TGGAAAACAA AAAAAGGCAG GGGTTGCAAT

2221 CCTAGTCTCT GATAAAACAG ACTTTAAACC AACAAAGATC AAAAGAGACA AAGAAGGCCA

2281 TTACATAATG GTAAAGGGAT CAATTCAACA AGAGGAGCTA ACTATCCTAA ATATTTATGC

2341 ACCCAATACA GGAGCACCCA GATTCATAAA GCAAGTCCTC AGTGACCTAC AAAGAGACTT

2401 AGACTCCCAC ACATTAATAA TGGGAGACTT TAACACCCCA CTGTCAACAT TAGACAGATC

2461 AACGAGACAG AAAGTCAACA AGGATACCCA GGAATTGAAC TCAGCTCTGC ACCAAGCAGA

2521 CCTAATAGAC ATCTACGAAA CTCTCCACCC CAAATCAACA GAATATACAT TTTTTTCAGC

2581 ACCACACCAC ACCTATTCCA AAATTGACCA CATAGTTGGA AGTAAAGCTC TCCTCAGCAA

2641 ATGTAAAAGA ACAGAAATTA TAACAAACTA TCTCTCAGAC CACAGTGCAA TCAAACTAGA

2701 ACTCAGGATT AAGAATCTCA CTCAAAGCCG CTCAACTACA TGGAAACTGA CAACCTGCT

2761 CCTGAATGAC TACTGGGTAC ATAACGAAAT GAAGGCAGAA ATAAAGATGT TCTTTGAAAC

2821 CAACGAGAAC AAAGACACCA CATACCAGAA TCTCTGGGAC GCATTCAAAG CAGTGTGTAG

2881 AGGGAAATTT ATAGCACTAA ATGCCTACAA GAGAAAGCAG GAAGATCCA AAATTGACAC

2941 CCTAACATCA CAATTAAAAG AACTAGAAAA GCAAGAGCAA ACACATTCAA AAGCTAGCAG

3001 AAGGCAAGAA ATAACTAAAA TCAGAGCAGA ACTGAAGGAA ATAGAGACAC AAAAAACCCT

3061 TCAAAAAATC AATGAATCCA GGAGCTGGTT TTTTGAAAGG ATCAACAAAA TTGATAGACC

3121 GCTAGCAAGA CTAATAAAGA AAAAAGAGA GAAGAATCAA ATAGACACAA TAAAAAATGA
```

TABLE 8-continued

Plasmid and mRNA construct sequences

```
3181 TAAAGGGGAT ATCACCACCG ATCCCACAGA AATACAAACT ACCATCAGAG AATACTACAA

3241 ACACCTCTAC GCAAATAAAC TAGAAAATCT AGAAGAAATG GATACATTCC TCGACACATA

3301 CACTCTCCCA AGACTAAACC AGGAAGAAGT TGAATCTCTG AATCGACCAA TAACAGGCTC

3361 TGAAATTGTG GCAATAATCA ATAGTTTACC AACCAAAAAG AGTCCAGGAC CAGATGGATT

3421 CACAGCCGAA TTCTACCAGA GGTACAAGGA GGAACTGGTA CCATTCCTTC TGAAACTATT

3481 CCAATCAATA GAAAAGAGG GAATCCTCCC TAACTCATTT TATGAGGCCA GCATCATTCT

3541 GATACCAAAG CCGGGCAGAG ACACAACCAA AAAGAGAAT TTTAGACCAA TATCCTTGAT

3601 GAACATTGAT GCAAAAATCC TCAATAAAAT ACTGGCAAAC CGAATCCAGC AGCACATCAA

3661 AAAGCTTATC CACCATGATC AAGTGGGCTT CATCCCTGGG ATGCAAGGCT GGTTCAATAT

3721 ACGCAAATCA ATAAATGTAA TCCAGCATAT AAACAGAGCC AAAGACAAAA ACCACATGAT

3781 TATCTCAATA GATGCAGAAA AAGCCTTTGA CAAAATTCAA CAACCCTTCA TGCTAAAAAC

3841 TCTCAATAAA TTAGGTATTG ATGGGACGTA TTTCAAAATA ATAAGAGCTA TCTATGACAA

3901 ACCCACAGCC AATATCATAC TGAATGGGCA AAAACTGGAA GCATTCCCTT TGAAAACCGG

3961 CACAAGACAG GGATGCCCTC TCTCACCGCT CCTATTCAAC ATAGTGTTGG AAGTTCTGGC

4021 CAGGGCAATC AGGCAGGAGA AGGAAATAAA GGGTATTCAA TTAGGAAAAG AGGAAGTCAA

4081 ATTGTCCCTG TTTGCAGACG ACATGATTGT TTATCTAGAA AACCCCATCG TCTCAGCCCA

4141 AAATCTCCTT AAGCTGATAA GCAACTTCAG CAAAGTCTCA GGATACAAAA TCAATGTACA

4201 AAAATCACAA GCATTCTTAT ACACCAACAA CAGACAAACA GAGAGCCAAA TCATGGGTGA

4261 ACTCCCATTC ACAATTGCTT CAAAGAGAAT AAAATACCTA GGAATCCAAC TTACAAGGGA

4321 TGTGAAGGAC CTCTTCAAGG AGAACTACAA ACCACTGCTC AAGGAAATAA AAGAGGAGAC

4381 AAACAAATGG AAGAACATTC CATGCTCATG GGTAGGAAGA ATCAATATCG TGAAAATGGC

4441 CATACTGCCC AAGGTAATTT ACAGATTCAA TGCCATCCCC ATCAAGCTAC CAATGACTTT

4501 CTTCACAGAA TTGGAAAAAA CTACTTTAAA GTTCATATGG AACCAAAAAA GAGCCCGCAT

4561 TGCCAAGTCA ATCCTAAGCC AAAAGAACAA AGCTGGAGGC ATCACACTAC CTGACTTCAA

4621 ACTATACTAC AAGGCTACAG TAACCAAAAC AGCATGGTAC TGGTACCAAA CAGAGATAT

4681 AGATCAATGG AACAGAACAG AGCCCTCAGA AATAATGCCG CATATCTACA ACTATCTGAT

4741 CTTTGACAAA CCTGAGAAAA ACAAGCAATG GGGAAAGGAT TCCCTATTTA ATAAATGGTG

4801 CTGGGAAAAC TGGCTAGCCA TATGTAGAAA GCTGAAACTG GATCCCTTCC TTACACCTTA

4861 TACAAAAATC AATTCAAGAT GGATTAAAGA TTTAAACGTT AAACCTAAAA CCATAAAAAC

4921 CCTAGAAGAA AACCTAGGCA TTACCATTCA GGACATAGGC GTGGGCAAGG ACTTCATGTC

4981 CAAAACACCA AAAGCAATGG CAACAAAAGA CAAAATTGAC AAATGGGATC TAATTAAACT

5041 AAAGAGCTTC TGCACAGCAA AAGAAACTAC CATCAGAGTG AACAGGCAAC CTACAACATG

5101 GGAGAAAATT TTTGCAACCT ACTCATCTGA CAAAGGGCTA ATATCCAGAA TCTACAATGA

5161 ACTCAAACAA ATTTACAAGA AAAAAACAAA CAACCCCATC AAAAAGTGGG CGAAGGACAT

5221 GAACAGACAC TTCTCAAAAG AAGACATTTA TGCAGCCAAA AACACATGA AGAAATGCTC

5281 ATCATCACTG GCCATCAGAG AAATGCAAAT CAAAACCACT ATGAGATATC ATCTCACACC

5341 AGTTAGAATG GCAATCATTA AAAGTCAGG AAACAACAGG TGCTGGAGAG GATGCGGAGA

5401 AATAGGAACA CTTTTACACT GTTGGTGGGA CTGTAAACTA GTTCAACCAT TGTGGAAGTC

5461 AGTGTGGCGA TTCCTCAGGG ATCTAGAACT AGAAATACCA TTTGACCCAG CCATCCCATT
```

US 12,599,678 B2

139

140

TABLE 8-continued

Plasmid and mRNA construct sequences

5521 ACTGGGTATA TACCCAAATG AGTATAAATC ATGCTGCTAT AAAGACACAT GCACACGTAT

5581 GTTTATTGCG GCACTATTCA CAATAGCAAA GACTTGGAAC CAACCCAAAT GTCCAACAAT

5641 GATAGACTGG ATTAAGAAAA TGTGGCACAT ATACACCATG GAATACTATG CAGCCATAAA

5701 AAATGATGAG TTCATATCCT TTGTAGGGAC ATGGATGAAA TTGGAAACCA TCATTCTCAG

5761 TAAACTATCG CAAGAACAAA AAACCAAACA CCGCATATTC TCACTCATAG GTGGGAATTG

5821 AACAATGAGA TCACATGGAC ACAGGAAGGG GAATATCACA CTCTGGGGAC TGTGGTGGGG

5881 TCGGGGGAGG GGGGAGGGAT AGCATTGGGA GATATACCTA ATGCTAGATG ACACATTAGT

5941 GGGTGCAGCG CACCAGCATG GCACATGTAT ACGGATCCGA ATTCTCGACG GATCGATCCG

6001 AACAAACGAC CCAACACCCG TGCGTTTTAT TCTGTCTTTT TATTGCCGAT CCCCTCAGAA

6061 GAACTCGTCA AGAAGGCGAT AGAAGGCGAT GCGCTGCGAA TCGGGAGCGG CGATACCGTA

6121 AAGCACGAGG AAGCGGTCAG CCCATTCGCC GCCAAGCTCT TCAGCAATAT CACGGGTAGC

6181 CAACGCTATG TCCTGATAGC GGTCGGCCGC TTTACTTGTA CAGCTCGTCC ATGCCGAGAG

6241 TGATCCCGGC GGCGGTCACG AACTCCAGCA GGACCATGTG ATCGCGCTTC TCGTTGGGGT

6301 CTTTGCTCAG GGCGGACTGG GTGCTCAGGT AGTGGTTGTC GGGCAGCAGC ACGGGGCCGT

6361 CGCCGATGGG GGTGTTCTGC TGGTAGTGGT CGGCCAGGTG AGTCCAGGAG ATGTTTCAGC

6421 ACTGTTGCCT TTAGTCTCGA GGCAACTTAG ACAACTGAGT ATTGATCTGA GCACAGCAGG

6481 GTGTGAGCTG TTTGAAGATA CTGGGGTTGG GGGTGAAGAA ACTGCAGAGG ACTAACTGGG

6541 CTGAGACCCA GTGGCAATGT TTTAGGGCCT AAGGAATGCC TCTGAAAATC TAGATGGACA

6601 ACTTTGACTT TGAGAAAAGA GAGGTGGAAA TGAGGAAAAT GACTTTTCTT TATTAGATTT

6661 CGGTAGAAAG AACTTTCATC TTTCCCCTAT TTTTGTTATT CGTTTTAAAA CATCTATCTG

6721 GAGGCAGGAC AAGTATGGTC ATTAAAAAGA TGCAGGCAGA AGGCATATAT TGGCTCAGTC

6781 AAAGTGGGGA ACTTTGGTGG CCAAACATAC ATTGCTAAGG CTATTCCTAT ATCAGCTGGA

6841 CACATATAAA ATGCTGCTAA TGCTTCATTA CAAACTTATA TCCTTTAATT CCAGATGGGG

6901 GCAAAGTATG TCCAGGGGTG AGGAACAATT GAAACATTTG GGCTGGAGTA GATTTTGAAA

6961 GTCAGCTCTG TGTGTGTGTG TGTGTGTGTG TGTGTGAGAG CGTGTGTTTC TTTTAACGTT

7021 TTCAGCCTAC AGCATACAGG GTTCATGGTG GCAAGAAGAT AACAAGATTT AAATTATGGC

7081 CAGTGACTAG TGCTGCAAGA AGAACAACTA CCTGCATTTA ATGGGAAAGC AAAATCTCAG

7141 GCTTTGAGGG AAGTTAACAT AGGCTTGATT CTGGGTGGAA GCTGGGTGTG TAGTTATCTG

7201 GAGGCCAGGC TGGAGCTCTC AGCTCACTAT GGGTTCATCT TTATTGTCTC CTTTCATCTC

7261 AACAGCTGCA CGCTGCCGTC CTCGATGTTG TGGCGGATCT TGAAGTTCAC CTTGATGCCG

7321 TTCTTCTGCT TGTCGGCCAT GATATAGACG TTGTGGCTGT TGTAGTTGTA CTCCAGCTTG

7381 TGCCCCAGGA TGTTGCCGTC CTCCTTGAAG TCGATGCCCT TCAGCTCGAT GCGGTTCACC

7441 AGGGTGTCGC CCTCGAACTT CACCTCGGCG CGGGTCTTGT AGTTGCCGTC GTCCTTGAAG

7501 AAGATGGTGC GCTCCTGGAC GTAGCCTTCG GGCATGGCGG ACTTGAAGAA GTCGTGCTGC

7561 TTCATGTGGT CGGGGTAGCG GCTGAAGCAC TGCACGCCGT AGGTCAGGGT GGTCACGAGG

7621 GTGGGCCAGG GCACGGGCAG CTTGCCGGTG GTGCAGATGA ACTTCAGGGT CAGCTTGCCG

7681 TAGGTGGCAT CGCCCTCGCC CTCGCCGGAC ACGCTGAACT TGTGGCCGTT TACGTCGCCG

7741 TCCAGCTCGA CCAGGATGGG CACCACCCCG GTGAACAGCT CCTCGCCCTT GCTCACCATG

7801 GTGGCGAATT CGAAGCTTGA GCTCGAGATC TGAGTCCGGT AGCGCTAGCG GATCTGACGG

TABLE 8-continued

Plasmid and mRNA construct sequences

```
 7861 TTCACTAAAC CAGCTCTGCT TATATAGACC TCCCACCGTA CACGCCTACC GCCCATTTGC

7921 GTCAATGGGG CGGAGTTGTT ACGACATTTT GGAAAGTCCC GTTGATTTTG GTGCCAAAAC

7981 AAACTCCCAT TGACGTCAAT GGGGTGGAGA CTTGGAAATC CCCGTGAGTC AAACCGCTAT

8041 CCACGCCCAT TGATGTACTG CCAAAACCGC ATCACCATGG TAATAGCGAT GACTAATACG

8101 TAGATGTACT GCCAAGTAGG AAAGTCCCAT AAGGTCATGT ACTGGGCATA ATGCCAGGCG

8161 GGCCATTTAC CGTCATTGAC GTCAATAGGG GGCGTACTTG GCATATGATA CACTTGATGT

8221 ACTGCCAAGT GGGCAGTTTA CCGTAAATAC TCCACCCATT GACGTCAATG GAAAGTCCCT

8281 ATTGGCGTTA CTATGGGAAC ATACGTCATT ATTGACGTCA ATGGGCGGGG TCGTTGGGC

8341 GGTCAGCCAG GCGGGCCATT TACCGTAAGT TATGTAACGC GGAACTCCAT ATATGGGCTA

8401 TGAACTAATG ACCCCGTAAT TGATTACTAT TAGCCCGGGG GATCCAGACA TGATAAGATA

8461 CATTGATGAG TTTGGACAAA CCACAACTAG AATGCAGTGA AAAAAATGCT TTATTTGTGA

8521 AATTTGTGAT GCTATTGCTT TATTTGTAAC CATTATAAGC TGCAATAAAC AAGTTAACAA

8581 CAACAATTGC ATTCATTTTA TGTTTCAGGT TCAGGGGGAG GTGTGGGAGG TTTTTTAAAG

8641 CAAGTAAAAC CTCTACAAAT GTGGTATGGC TGATTATGAT CCGGCTGCCT CGCGCGTTTC

8701 GGTGATGACG GTGAAAACCT CTGACACATG CAGCTCCCGG AGACGGTCAC AGCTTGTCTG

8761 TAAGCGGATG CCGGGAGCAG ACAAGCCCGT CAGGGCGCGT CAGCGGGTGT TGGCGGGTGT

8821 CGGGGCGCAG CCATGAGGTC GATCGACTCT AGAGGATCGA TCCCCGCCCC GGACGAACTA

8881 AACCTGACTA CGACATCTCT GCCCCTTCTT CGCGGGGCAG TGCATGTAAT CCCTTCAGTT

8941 GGTTGGTACA ACTTGCCAAC TGGGCCCTGT TCCACATGTG ACACGGGGGG GGACCAAACA

9001 CAAAGGGGTT CTCTGACTGT AGTTGACATC CTTATAAATG GATGTGCACA TTTGCCAACA

9061 CTGAGTGGCT TTCATCCTGG AGCAGACTTT GCAGTCTGTG GACTGCAACA CAACATTGCC

9121 TTTATGTGTA ACTCTTGGCT GAAGCTCTTA CACCAATGCT GGGGGACATG TACCTCCCAG

9181 GGGCCCAGGA AGACTACGGG AGGCTACACC AACGTCAATC AGAGGGGCCT GTGTAGCTAC

9241 CGATAAGCGG ACCCTCAAGA GGGCATTAGC AATAGTGTTT ATAAGGCCCC CTTGTTAACC

9301 CTAAACGGGT AGCATATGCT TCCCGGGTAG TAGTATATAC TATCCAGACT AACCCTAATT

9361 CAATAGCATA TGTTACCCAA CGGGAAGCAT ATGCTATCGA ATTAGGGTTA GTAAAAGGGT

9421 CCTAAGGAAC AGCGATATCT CCCACCCCAT GAGCTGTCAC GGTTTTATTT ACATGGGGTC

9481 AGGATTCCAC GAGGGTAGTG AACCATTTTA GTCACAAGGG CAGTGGCTGA AGATCAAGGA

9541 GCGGGCAGTG AACTCTCCTG AATCTTCGCC TGCTTCTTCA TTCTCCTTCG TTTAGCTAAT

9601 AGAATAACTG CTGAGTTGTG AACAGTAAGG TGTATGTGAG GTGCTCGAAA ACAAGGTTTC

9661 AGGTGACGCC CCCAGAATAA AATTTGGACG GGGGGTTCAG TGGTGGCATT GTGCTATGAC

9721 ACCAATATAA CCCTCACAAA CCCCTTGGGC AATAAATACT AGTGTAGGAA TGAAACATTC

9781 TGAATATCTT TAACAATAGA AATCCATGGG GTGGGGACAA GCCGTAAAGA CTGGATGTCC

9841 ATCTCACACG AATTTATGGC TATGGGCAAC ACATAATCCT AGTGCAATAT GATACTGGGG

9901 TTATTAAGAT GTGTCCCAGG CAGGGACCAA GACAGGTGAA CCATGTTGTT ACACTCTATT

9961 TGTAACAAGG GGAAAGAGAG TGGACGCCGA CAGCAGCGGA CTCCACTGGT TGTCTCTAAC

10021 ACCCCCGAAA ATTAAACGGG GCTCCACGCC AATGGGGCCC ATAAACAAAG ACAAGTGGCC

10081 ACTCTTTTTT TTGAAATTGT GGAGTGGGGG CACGCGTCAG CCCCCACACG CCGCCCTGCG

10141 GTTTTGGACT GTAAAATAAG GGTGTAATAA CTTGGCTGAT TGTAACCCCG CTAACCACTG
```

TABLE 8-continued

Plasmid and mRNA construct sequences

```
10201 CGGTCAAACC ACTTGCCCAC AAAACCACTA ATGGCACCCC GGGGAATACC TGCATAAGTA

10261 GGTGGGCGGG CCAAGATAGG GGCGCGATTG CTGCGATCTG GAGGACAAAT TACACACACT

10321 TGCGCCTGAG CGCCAAGCAC AGGGTTGTTG GTCCTCATAT TCACGAGGTC GCTGAGAGCA

10381 CGGTGGGCTA ATGTTGCCAT GGGTAGCATA TACTACCCAA ATATCTGGAT AGCATATGCT

10441 ATCCTAATCT ATATCTGGGT AGCATAGGCT ATCCTAATCT ATATCTGGGT AGCATATGCT

10501 ATCCTAATCT ATATCTGGGT AGTATATGCT ATCCTAATTT ATATCTGGGT AGCATAGGCT

10561 ATCCTAATCT ATATCTGGGT AGCATATGCT ATCCTAATCT ATATCTGGGT AGTATATGCT

10621 ATCCTAATCT GTATCCGGGT AGCATATGCT ATCCTAATAG AGATTAGGGT AGTATATGCT

10681 ATCCTAATTT ATATCTGGGT AGCATATACT ACCCAAATAT CTGGATAGCA TATGCTATCC

10741 TAATCTATAT CTGGGTAGCA TATGCTATCC TAATCTATAT CTGGGTAGCA TAGGCTATCC

10801 TAATCTATAT CTGGGTAGCA TATGCTATCC TAATCTATAT CTGGGTAGTA TATGCTATCC

10861 TAATTTATAT CTGGGTAGCA TAGGCTATCC TAATCTATAT CTGGGTAGCA TATGCTATCC

10921 TAATCTATAT CTGGGTAGTA TATGCTATCC TAATCTGTAT CCGGGTAGCA TATGCTATCC

10981 TCATGCATAT ACAGTCAGCA TATGATACCC AGTAGTAGAG TGGGAGTGCT ATCCTTTGCA

11041 TATGCCGCCA CCTCCCAAGG GGGCGTGAAT TTTCGCTGCT TGTCCTTTTC CTGCATGCTG

11101 GTTGCTCCCA TTCTTAGGTG AATTTAAGGA GGCCAGGCTA AAGCCGTCGC ATGTCTGATT

11161 GCTCACCAGG TAAATGTCGC TAATGTTTTC CAACGCGAGA AGGTGTTGAG CGCGGAGCTG

11221 AGTGACGTGA CAACATGGGT ATGCCCAATT GCCCCATGTT GGGAGGACGA AAATGGTGAC

11281 AAGACAGATG GCCAGAAATA CACCAACAGC ACGCATGATG TCTACTGGGG ATTTATTCTT

11341 TAGTGCGGGG GAATACACGG CTTTTAATAC GATTGAGGGC GTCTCCTAAC AAGTTACATC

11401 ACTCCTGCCC TTCCTCACCC TCATCTCCAT CACCTCCTTC ATCTCCGTCA TCTCCGTCAT

11461 CACCCTCCGC GGCAGCCCCT TCCACCATAG GTGGAAACCA GGGAGGCAAA TCTACTCCAT

11521 CGTCAAAGCT GCACACAGTC ACCCTGATAT TGCAGGTAGG AGCGGGCTTT GTCATAACAA

11581 GGTCCTTAAT CGCATCCTTC AAAACCTCAG CAAATATATG AGTTTGTAAA AAGACCATGA

11641 AATAACAGAC AATGGACTCC CTTAGCGGGC CAGGTTGTGG GCCGGGTCCA GGGGCCATTC

11701 CAAAGGGGAG ACGACTCAAT GGTGTAAGAC GACATTGTGG AATAGCAAGG GCAGTTCCTC

11761 GCCTTAGGTT GTAAAGGGAG GTCTTACTAC CTCCATATAC GAACACACCG GCGACCCAAG

11821 TTCCTTCGTC GGTAGTCCTT TCTACGTGAC TCCTAGCCAG GAGAGCTCTT AAACCTTCTG

11881 CAATGTTCTC AAATTTCGGG TTGGAACCTC CTTGACCACG ATGCTTTCCA AACCACCCTC

11941 CTTTTTTGCG CCTGCCTCCA TCACCCTGAC CCCGGGGTCC AGTGCTTGGG CCTTCTCCTG

12001 GGTCATCTGC GGGGCCCTGC TCTATCGCTC CCGGGGGCAC GTCAGGCTCA CCATCTGGGC

12061 CACCTTCTTG GTGGTATTCA AAATAATCGG CTTCCCCTAC AGGGTGGAAA AATGGCCTTC

12121 TACCTGGAGG GGGCCTGCGC GGTGGAGACC CGGATGATGA TGACTGACTA CTGGGACTCC

12181 TGGGCCTCTT TTCTCCACGT CCACGACCTC TCCCCCTGGC TCTTTCACGA CTTCCCCCCC

12241 TGGCTCTTTC ACGTCCTCTA CCCCGGCGGC CTCCACTACC TCCTCGACCC CGGCCTCCAC

12301 TACCTCCTCG ACCCCGGCCT CCACTGCCTC CTCGACCCCG GCCTCCACCT CCTGCTCCTG

12361 CCCCTCCTGC TCCTGCCCCT CCTCCTGCTC CTGCCCCTCC TGCCCCTCCT GCTCCTGCCC

12421 CTCCTGCCCC TCCTGCTCCT GCCCCTCCTG CCCCTCCTGC TCCTGCCCCT CCTGCCCCTC

12481 CTCCTGCTCC TGCCCCTCCT GCCCCTCCTC CTGCTCCTGC CCCTCCTGCC CCTCCTGCTC
```

TABLE 8-continued

Plasmid and mRNA construct sequences

12541 CTGCCCCTCC TGCCCCTCCT GCTCCTGCCC CTCCTGCCCC TCCTGCTCCT GCCCCTCCTG

12601 CTCCTGCCCC TCCTGCTCCT GCCCCTCCTG CTCCTGCCCC TCCTGCCCCT CCTGCCCCTC

12661 CTCCTGCTCC TGCCCCTCCT GCTCCTGCCC CTCCTGCCCC TCCTGCCCCT CCTGCTCCTG

12721 CCCCTCCTCC TGCTCCTGCC CCTCCTGCCC CTCCTGCCCC TCCTCCTGCT CCTGCCCCTC

12841 CTCCTCCTGC TCCTGCCCCT CCTGCCCCTC CTCCTGCTCC TGCCCCTCCT CCTGCTCCTG

12901 CCCCTCCTGC CCCTCCTGCC CCTCCTCCTG CTCCTGCCCC TCCTCCTGCT CCTGCCCCTC

12961 CTGCCCCTCC TGCCCCTCCT GCCCCTCCTC CTGCTCCTGC CCCTCCTCCT GCTCCTGCCC

13021 CTCCTGCTCC TGCCCCTCCC GCTCCTGCTC CTGCTCCTGT TCCACCGTGG GTCCCTTTGC

13081 AGCCAATGCA ACTTGGACGT TTTTGGGGTC TCCGGACACC ATCTCTATGT CTTGGCCCTG

13141 ATCCTGAGCC GCCCGGGGCT CCTGGTCTTC CGCCTCCTCG TCCTCGTCCT CTTCCCCGTC

13201 CTCGTCCATG GTTATCACCC CCTCTTCTTT GAGGTCCACT GCCGCCGGAG CCTTCTGGTC

13261 CAGATGTGTC TCCCTTCTCT CCTAGGCCAT TTCCAGGTCC TGTACCTGGC CCCTCGTCAG

13321 ACATGATTCA CACTAAAAGA GATCAATAGA CATCTTTATT AGACGACGCT CAGTGAATAC

13381 AGGGAGTGCA GACTCCTGCC CCCTCCAACA GCCCCCCCAC CCTCATCCCC TTCATGGTCG

13441 CTGTCAGACA GATCCAGGTC TGAAAATTCC CCATCCTCCG AACCATCCTC GTCCTCATCA

13501 CCAATTACTC GCAGCCCGGA AAACTCCCGC TGAACATCCT CAAGATTTGC GTCCTGAGCC

13561 TCAAGCCAGG CCTCAAATTC CTCGTCCCCC TTTTTGCTGG ACGGTAGGGA TGGGGATTCT

13621 CGGGACCCCT CCTCTTCCTC TTCAAGGTCA CCAGACAGAG ATGCTACTGG GGCAACGGAA

13681 GAAAAGCTGG GTGCGGCCTG TGAGGATCAG CTTATCGATG ATAAGCTGTC AAACATGAGA

13741 ATTCTTGAAG ACGAAAGGGC CTCGTGATAC GCCTATTTTT ATAGGTTAAT GTCATGATAA

13801 TAATGGTTTC TTAGACGTCA GGTGGCACTT TTCGGGGAAA TGTGCGCGGA ACCCCTATTT

13861 GTTTATTTTT CTAAATACAT TCAAATATGT ATCCGCTCAT GAGACAATAA CCCTGATAAA

13921 TGCTTCAATA ATATTGAAAA AGGAAGAGTA TGAGTATTCA ACATTTCCGT GTCGCCCTTA

13981 TTCCCTTTTT TGCGGCATTT TGCCTTCCTG TTTTTGCTCA CCCAGAAACG CTGGTGAAAG

14041 TAAAAGATGC TGAAGATCAG TTGGGTGCAC GAGTGGGTTA CATCGAACTG GATCTCAACA

14101 GCGGTAAGAT CCTTGAGAGT TTTCGCCCCG AAGAACGTTT TCCAATGATG AGCACTTTTA

14161 AAGTTCTGCT ATGTGGCGCG GTATTATCCC GTGTTGACGC CGGGCAAGAG CAACTCGGTC

14221 GCCGCATACA CTATTCTCAG AATGACTTGG TTGAGTACTC ACCAGTCACA GAAAAGCATC

14281 TTACGGATGG CATGACAGTA AGAGAATTAT GCAGTGCTGC CATAACCATG AGTGATAACA

14341 CTGCGGCCAA CTTACTTCTG ACAACGATCG GAGGACCGAA GGAGCTAACC GCTTTTTTGC

14401 ACAACATGGG GGATCATGTA ACTCGCCTTG ATCGTTGGGA ACCGGAGCTG AATGAAGCCA

14461 TACCAAACGA CGAGCGTGAC ACCACGATGC CTGCAGCAAT GGCAACAACG TTGCGCAAAC

14521 TATTAACTGG CGAACTACTT ACTCTAGCTT CCCGGCAACA ATTAATAGAC TGGATGGAGG

14581 CGGATAAAGT TGCAGGACCA CTTCTGCGCT CGGCCCTTCC GGCTGGCTGG TTTATTGCTG

14641 ATAAATCTGG AGCCGGTGAG CGTGGGTCTC GCGGTATCAT TGCAGCACTG GGGCCAGATG

14701 GTAAGCCCTC CCGTATCGTA GTTATCTACA CGACGGGGAG TCAGGCAACT ATGGATGAAC

14761 GAAATAGACA GATCGCTGAG ATAGGTGCCT CACTGATTAA GCATTGGTAA CTGTCAGACC

14821 AAGTTTACTC ATATATACTT TAGATTGATT TAAAACTTCA TTTTTAATTT AAAAGGATCT

14881 AGGTGAAGAT CCTTTTTGAT AATCTCATGA CCAAAATCCC TTAACGTGAG TTTTCGTTCC

TABLE 8-continued

Plasmid and mRNA construct sequences

```
14941 ACTGAGCGTC AGACCCCGTA GAAAAGATCA AAGGATCTTC TTGAGATCCT TTTTTTCTGC

15001 GCGTAATCTG CTGCTTGCAA ACAAAAAAAC CACCGCTACC AGCGGTGGTT TGTTTGCCGG

15061 ATCAAGAGCT ACCAACTCTT TTTCCGAAGG TAACTGGCTT CAGCAGAGCG CAGATACCAA

15121 ATACTGTCCT TCTAGTGTAG CCGTAGTTAG GCCACCACTT CAAGAACTCT GTAGCACCGC

15181 CTACATACCT CGCTCTGCTA ATCCTGTTAC CAGTGGCTGC TGCCAGTGGC GATAAGTCGT

15241 GTCTTACCGG GTTGGACTCA AGACGATAGT TACCGGATAA GGCGCAGCGG TCGGGCTGAA

15301 CGGGGGGTTC GTGCACACAG CCCAGCTTGG AGCGAACGAC CTACACCGAA CTGAGATACC

15361 TACAGCGTGA GCTATGAGAA AGCGCCACGC TTCCCGAAGG GAGAAAGGCG GACAGGTATC

15421 CGGTAAGCGG CAGGGTCGGA ACAGGAGAGC GCACGAGGGA GCTTCCAGGG GGAAACGCCT

15481 GGTATCTTTA TAGTCCTGTC GGGTTTCGCC ACCTCTGACT TGAGCGTCGA TTTTTGTGAT

15541 GCTCGTCAGG GGGGCGGAGC CTATGGAAAA ACGCCAGCAA CGCGGCCTTT TTACGGTTCC

15601 TGGCCTTTTG CTGGCCTTTT GCTCACATGT TCTTTCCTGC GTTATCCCCT GATTCTGTGG

15661 ATAACCGTAT TACCGCCTTT GAGTGAGCTG ATACCGCTCG CCGCAGCCGA ACGACCGAGC

15721 GCAGCGAGTC AGTGAGCGAG GAAGCGGAAG AGCGCCTGAT GCGGTATTTT CTCCTTACGC

15781 ATCTGTGCGG TATTTCACAC CGCATATGGT GCACTCTCAG TACAATCTGC TCTGATGCCG

15841 CATAGTTAAG CCAGCTGTGG AATGTGTGTC AGTTAGGGTG TGGAAAGTCC CCAGGCTCCC

15901 CAGCAGGCAG AAGTATGCAA AGCATGCATC TCAATTAGTC AGCAACCAGG TGTGGAAAGT

15961 CCCCAGGCTC CCCAGCAGGC AGAAGTATGC AAAGCATGCA TCTCAATTAG TCAGCAACCA

16021 TAGTCCCGCC CCTAACTCCG CCCATCCCGC CCCTAACTCC GCCCAGTTCC GCCCATTCTC

16081 CGCCCCATGG CTGACTAATT TTTTTTATTT ATGCAGAGGC CGAGGCCGCC TCGGCCTCTG

16141 AGCTATTCCA GAAGTAGTGA GGAGGCTTTT TTGGAGGCCT AGGCTTTTGC AAAAAGCTTG

16201 CATGCCTGCA GGTCGGCCGC CACGACCGGT GCCGCCACCA TCCCCTGACC CACGCCCCTG

16261 ACCCCTCACA AGGAGACGAC CTTCCATGAC CGAGTACAAG CCCACGGTGC GCCTCGCCAC

16321 CCGCGACGAC GTCCCCCGGG CCGTACGCAC CCTCGCCGCC GCGTTCGCCG ACTACCCCGC

16381 CACGCGCCAC ACCGTCGACC CGGACCGCCA CATCGAGCGG GTCACCGAGC TGCAAGAACT

16441 CTTCCTCACG CGCGTCGGGC TCGACATCGG CAAGGTGTGG GTCGCGGACG ACGGCGCCGC

16501 GGTGGCGGTC TGGACCACGC CGGAGAGCGT CGAAGCGGGG GCGGTGTTCG CCGAGATCGG

16561 CCCGCGCATG GCCGAGTTGA GCGGTTCCCG GCTGGCCGCG CAGCAACAGA TGGAAGGCCT

16621 CCTGGCGCCG CACCGGCCCA AGGAGCCCGC GTGGTTCCTG GCCACCGTCG GCGTCTCGCC

16681 CGACCACCAG GGCAAGGGTC TGGGCAGCGC CGTCGTGCTC CCCGGAGTGG AGGCGGCCGA

16741 GCGCGCCGGG GTGCCCGCCT TCCTGGAGAC CTCCGCGCCC CGCAACCTCC CCTTCTACGA

16801 GCGGCTCGGC TTCACCGTCA CCGCCGACGT CGAGGTGCCC GAAGGACCGC GCACCTGGTG

16861 CATGACCCGC AAGCCCGGTG CCTGACGCCC GCCCCACGAC CCGCAGCGCC CGACCGAAAG

16921 GAGCGCACGA CCCCATGGCT CCGACCGAAG CCGACCCGGG CGGCCCCGCC GACCCCGCAC

16981 CCGCCCCCGA GGCCCACCGA CTCTAGAGGA TCATAATCAG CCATACCACA TTTGTAGAGG

17041 TTTTACTTGC TTTAAAAAAC CTCCCACACC TCCCCCTGAA CCTGAAACAT AAAATGAATG

17101 CAATTGTTGT TGTTAACTTG TTTATTGCAG CTTATAATGG TTACAAATAA AGCAATAGCA

17161 TCACAAATTT CACAAATAAA GCATTTTTTT CACTGCATTC TAGTTGTGGT TTGTCCAAAC

17221 TCATCAATGT ATCTTATCAT GTCTGGATCA CTCGCCGATA GTGGAAACCG ACGCCCCAGC
```

TABLE 8-continued

Plasmid and mRNA construct sequences

```
17281 ACTCGTCCGA GGGCAAAGGA ATAGGGGAGA TGGGGGAGGC TAACTGAAAC ACGGAAGGAG

17341 ACAATACCGG AAGGAACCCG CGCTATGACG GCAATAAAAA GACAGAATAA AACGCACGGG

17401 TGTTGGGTCG TTTGTTCATA AACGCGGGGT TCGGTCCCAG GGCTGGCACT CTGTCGATAC

17461 CCCACCGAGA CCCCATTGGG GCCAATACGC CCGCGTTTCT TCCTTTTCCC CACCCCACCC

17521 CCCAAGTTCG GGTGAAGGCC CAGGGCTCGC AGCCAACGTC GGGGCGGCAG GCCCTGCCAT

17581 AGCCACTGGC CCCGTGGGTT AGGGACGGGG TCCCCCATGG GGAATGGTTT ATGGTTCGTG

17641 GGGGTTATTA TTTTGGGCGT TGCGTGGGGT CTGGTCCACG ACTGGACTGA GCAGACAGAC

17701 CCATGGTTTT TGGATGGCCT GGGCATGGAC CGCATGTACT GGCGCGACAC GAACACCGGG

17761 CGTCTGTGGC TGCCAAACAC CCCCGACCCC CAAAAACCAC CGCGCGGATT TCTGGCGTGC

17821 CAAGCTAGTC GACCAATTCT CATGTTTGAC AGCTTATCAT CGCAGATCCG GCAACGTTG

17881 TTGCATTGCT GCAGGCGCAG AACTGGTAGG TATGGAAGAT CTCTAGAAGC TGGGTACCAG

17941 CTGCTAGCAA GCTTGCTAGC GGCCGGCTCG AGTTTACTCC CTATCAGTGA TAGAGAACGT

18001 ATGTCGAGTT TACTCCCTAT CAGTGATAGA GAACGATGTC GAGTTTACTC CCTATCAGTG

18061 ATAGAGAACG TATGTCGAGT TTACTCCCTA TCAGTGATAG AGAACGTATG TCGAGTTTAC

18121 TCCCTATCAG TGATAGAGAA CGTATGTCGA GTTTATCCCT ATCAGTGATA GAGAACGTAT

18181 GTCGAGTTTA CTCCCTATCA GTGATAGAGA ACGTATGTCG AGGTAGGCGT GTACGGTGGG

18241 AGGCCTATAT AAGCAGAGCT CGTTTAGTGA ACCGTCAGAT CGCCG
(SEQ ID NO: 37)
```

LINE 1- GFP mRNA (SEQ ID NO: 38)

```
   1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT

361 CCAGGTGTGA CCAGCTCGAG GAGCGCGTGA GCGCGATGGA AGACGAGATG AACGAGATGA

421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA

721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA

901 TCTCCGAGGG TGAGATTAAG TATTTCATCG ATAAACAGAT GCTGCGAGAC TTCGTGACAA

961 CTCGCCCAGC TCTCAAGGAA CTGCTCAAAG AGGCTCTTAA TATGGAGCGC AATAATAGAT

1021 ATCAACCCTT GCAGAACCAC GCAAAGATGT GAGACAGCCG TCAGACCATC AAGACTAGGA

1081 AGAAACTGCA TCAACTAATG AGCAAAATCA CCAGCTAACA TCATAGTATA CATGACCGGC

1141 TCTAACTCAC ATATCACCAT CCTTACACTT AACATTAACG GCCTCAACTC AGCTATCAAG
```

TABLE 8-continued

Plasmid and mRNA construct sequences

```
1201 CGCCATCGGC TGGCCAGCTG GATCAAATCA CAGGATCCAA GCGTTTGTTG CATCCAAGAG

1261 ACCCACCTGA CCTGTAGAGA TACTCACCGC CTCAAGATCA AGGGATGGCG AAAGATTTAT

1321 CAGGCGAACG GTAAGCAGAA GAAAGCCGGA GTCGCAATTC TGGTCTCAGA CAAGACGGAT

1381 TTCAAGCCCA CCAAAATTAA GCGTGATAAG GAAGGTCACT ATATTATGGT GAAAGGCAGC

1441 ATACAGCAGG AAGAACTTAC CATATTGAAC ATCTACGCGC CAAACACCGG CGCACCTCGC

1501 TTTATCAAAC AGGTCCTGTC CGATCTGCAG CGAGATCTGG ATTCTCATAC GTTGATTATG

1561 GGTGATTTCA ATACACCATT GAGCACCCTG GATCGCAGCA CCAGGCAAAA GGTAAATAAA

1621 GACACGCAAG AGCTCAATAG CGCACTGCAT CAGGCAGATC TCATTGATAT TTATCGCACT

1681 CTTCATCCTA AGAGTACCGA GTACACATTC TTCAGCGCCC CACATCATAC ATACTCAAAG

1741 ATCGATCATA TCGTCGGCTC AAAGGCTCTG CTGTCAAAGT GCAAGCGCAC AGAGATAATT

1801 ACAAATTACC TGTCAGATCA TAGCGCGATC AAGCTCGAGC TGAGAATCAA GAACCTGACC

1861 CAGAGCCGGA GTACCACTTG GAAGCTTAAT AACCTGCTGC TCAACGATTA TTGGGTCCAC

1921 AATGAGATGA AGGCAGAGAT TAAAATGTTC TTCGAAACAA ATGAGAATAA GGATACTACC

1981 TATCAAAACC TTTGGGATGC CTTTAAGGCC GTCTGCAGAG GCAAGTTCAT CGCCCTCAAC

2041 GCCTATAAAA GAAAACAAGA GAGATCTAAG ATCGATACTC TCACCTCTCA GCTGAAGGAG

2101 TTGGAGAAAC AGGAACAGAC CCACTCCAAG GCGTCAAGAC GGCAGGAGAT CACAAAGATT

2161 CGCGCCGAGT TGAAAGAGAT CGAAACCCAA AAGACTCTTC AGAAAATTAA CGAGTCTCGT

2221 AGTTGGTTCT TCGAGCGGAT TAATAAGATA GACAGACCTC TGGCACGACT GATTAAGAAG

2281 AAGCGCGAAA AGAACCAGAT TGATACCATC AAGAACGACA AGGGCGACAT CACTACTGAC

2341 CCGACCGAGA TCCAGACCAC TATTCGGGAG TATTATAAGC ATTTGTATGC TAACAAGCTT

2401 GAGAACCTGG AAGAGATGGA CACTTTTCTG GATACCTATA CTCTGCCACG GCTTAATCAA

2461 GAGGAAGTCG AGTCCCTCAA CCGCCCAATT ACAGGAAGCG AGATTGTGGC CATAATTAAC

2521 TCCCTGCCGA CAAAGAAATC TCCTGGTCCG GACGGGTTTA CAGCTGAGTT TTATCAACGG

2581 TATATGGAAG AGCTTGTACC GTTTCTGCTC AAGCTCTTTC AGTCTATAGA AAAGGAAGGC

2641 ATCTTGCCCA ATTCCTTCTA CGAAGCTTCT ATAATACTTA TTCCCAAACC AGGACGCGAT

2701 ACCACAAAGA AGGAAAACTT CCGGCCCATT AGTCTCATGA ATATCGACGC TAAAATATTG

2761 AACAAGATTC TCGCCAACAG AATCCAACAA CATATTAAGA AATTGATACA TCACGACCAG

2821 GTGGGGTTTA TACCTGGCAT GCAGGGCTGG TTTAACATCC GGAAGAGTAT TAACGTCATT

2881 CAACACATTA ATAGAGCTAA GGATAAGAAT CATATGATCA TCTCTATAGA CGCGGAAAAG

2941 GCATTCGATA AGATTCAGCA GCCATTTATG CTCAAGACTC TGAACAAACT CGGCATCGAC

3001 GGAACATATT TTAAGATTAT TCGCGCAATT TACGATAAGC CGACTGCTAA CATTATCCTT

3061 AACGGCCAAA AGCTCGAGGC CTTTCCGCTC AAGACTGGAA CCCGCCAAGG CTGTCCCCTC

3121 TCCCCGCTTT TGTTTAATAT TGTACTCGAG GTGCTGGCTA GGGCTATTCG TCAAGAGAAA

3181 GAGATTAAAG GGATACAGCT CGGGAAGGAA GAGGTCAAGC TTTCCTTGTT CGCCGATGAT

3241 ATGATTGTGT ACCTGGAGAA TCCTATTGTG TCTGCTCAGA ACCTTCTTAA ACTTATTTCT

3301 AACTTTAGCA AGGTCAGCGG CTATAAGATT AACGTCCAGA AATCTCAGGC CTTTCTGTAC

3361 ACAAATAATC GACAGACCGA ATCCCAGATA ATGGGTGAGC TTCCGTTTGT CATAGCCAGC

3421 AAAAGGATAA AGTATCTCGG AATCCAGCTG ACACGAGACG TTAAAGATTT GTTTAAGGAA

3481 AATTACAAGC CTCTCCTGAA AGAGATTAAG GAAGATACTA ATAAGTGGAA GAATATCCCC
```

TABLE 8-continued

Plasmid and mRNA construct sequences

```
3541 TGTTCATGGG TTGGCAGAAT CAACATAGTG AAGATGGCAA TACTTCCTAA AGTGATATAT

3601 CGCTTTAACG CCATCCCAAT TAAACTGCCT ATGACCTTCT TTACGGAGCT CGAGAAAACA

3661 ACCCTTAAAT TTATATGGAA TCAAAAGAGA GCAAGAATAG CGAAGTCCAT CTTGAGCCAG

3721 AAGAATAAGG CCGGTGGGAT TACTTTGCCT GATTTTAAGT TGTATTATAA AGCCACAGTA

3781 ACTAAGACAG CCTGGTATTG GTATCAGAAT AGAGACATCG ACCAGTGGAA TCGGACCGAA

3841 CCATCAGAGA TAATGCCCCA CATCTATAAT TACCTTATAT TCGATAAGCC AGAAAAGAAT

3901 AAACAGTGGG GCAAAGACAG CCTCTTCAAC AAGTGGTGTT GGGAGAATTG GCTGGCCATA

3961 TGCCGGAAAC TCAAGCTCGA CCCCTTTCTT ACACCCTACA CTAAAATCAA CAGTAGGTGG

4021 ATCAAGGACT TGAATGTCAA GCCAAAGACT ATAAAGACAC TGGAAGAGAA TCTTGGGATC

4081 ACAATACAAG ATATAGGCGT CGGCAAAGAT TTTATGTCAA AGACGCCCAA GGCCATGGCC

4141 ACTAAGGATA AGATTGATAA GTGGGACCTT ATTAAGCTCA AAAGCTTCTG TACTGCCAAG

4201 GAGACCACGA TCAGAGTTAA TAGGCAGCCC ACTACATGGG AAAAGATTTT CGCCACTTAT

4261 TCATCAGATA AGGGGTTGAT AAGCAGAATA TATAACGAGC TGAAGCAGAT CTACAAGAAG

4321 AAAACGAATA ATCCCATCAA GAAGTGGGCA AAAGATATGA ACAGGCATTT TAGCAAAGAG

4381 GATATCTACG CCGCGAAGAA GCATATGAAG AAGTGTAGTT CAAGCTTGGC CATTCGTGAG

4441 ATGCAGATTA AGACGACCAT GCGATACCAC CTTACCCCAG TGAGGATGGC AATTATCAAG

4501 AAATCTGGCA ATAATAGATG TTGGCGGGGC TGTGGCGAGA TTGGCACCCT GCTCCATTGC

4561 TGGTGGGATT GCAAGCTGGT GCAGCCGCTT TGGAAATCAG TCTGGCGCTT TCTGAGGGAC

4621 CTCGAGCTTG AGATTCCCTT CGATCCCGCA ATTCCCTTGC TCGGAATCTA TCCTAACGAA

4681 TACAAGAGCT GTTGTTACAA GGATACGTGT ACCCGGATGT TCATCGCGGC CTTGTTTACG

4741 ATAGCTAAGA CGTGGAATCA GCCTAAGTGC CCCACAATGA TCGATTGGAT CAAGAAAATG

4801 TGGCATATTT ATACCATGGA GTATTACGCA GCAATTAAGA ATGACGAATT TATTTCCTTC

4861 GTTGGGACCT GGATGAAGCT GGAGACTATT ATTCTGAGCA AGCTGTCTCA GGAGCAAAAG

4921 ACAAAGCATA GAATCTTCTC TCTCATTGGT GGTAACGACT ACAAAGACGA TGACGACAAG

4981 TAAAGCGCTT CTAGAAGTTG TCTCCTCCTG CACTGACTGA CTGATACAAT CGATTTCTGG

5041 ATCCGCAGGC CTAATCAACC TCTGGATTAC AAAATTTGTG AAAGATTGAC TGGTATTCTT

5101 AACTATGTTG CTCCTTTTAC GCTATGTGGA TACGCTGCTT TAATGCCTTT GTATCATGCT

5161 ATTGCTTCCC GTATGGCTTT CATTTTCTCC TCCTTGTATA AATCCTGGTT GCTGTCTCTT

5221 TATGAGGAGT TGTGGCCCGT TGTCAGGCAA CGTGGCGTGG TGTGCACTGT GTTTGCTGAC

5281 GCAACCCCCA CTGGTTGGGG CATTGCCACC ACCTGTCAGC TCCTTTCCGG GACTTTCGCT

5341 TTCCCCCTCC CTATTGCCAC GGCGGAACTC ATCGCCGCCT GCCTTGCCCG CTGCTGGACA

5401 GGGGCTCGGC TGTTGGGCAC TGACAATTCC GTGGTGTTGT CGGGGAAGCT GACGTCCTTT

5461 CCATGGCTGC TCGCCTGTGT TGCCACCTGG ATTCTGCGCG GGACGTCCTT CTGCTACGTC

5521 CCTTCGGCCC TCAATCCAGC GGACCTTCCT TCCCGCTGAG AGACACAAAA AATTCCAACA

5581 CACTATTGCA ATGAAAATAA ATTTCCTTTA TTAGCCAGAA GTCAGATGCT CAAGGGGCTT

5641 CATGATGTCC CCATAATTTT TGGCAGAGGG AAAAAGATCT CAGTGGTATT TGTGAGCCAG

5701 GGCATTGGCC TTCTGATAGG CAGCCTGCAC CTGAGGAGTG CGGCCGCTTT ACTTGTACAG

5761 CTCGTCCATG CCGAGAGTGA TCCCGGCGGC GGTCACGAAC TCCAGCAGGA CCATGTGATC

5821 GCGCTTCTCG TTGGGGTCTT TGCTCAGGGC GGACTGGGTG CTCAGGTAGT GGTTGTCGGG
```

TABLE 8-continued

Plasmid and mRNA construct sequences

```
5881 CAGCAGCACG GGGCCGTCGC CGATGGGGGT GTTCTGCTGG TAGTGGTCGG CGAGCTGCAC

5941 GCTGCCGTCC TCGATGTTGT GGCGGATCTT GAAGTTCACC TTGATGCCGT TCTTCTGCTT

6001 GTCGGCCATG ATATAGACGT TGTGGCTGTT GTAGTTGTAC TCCAGCTTGT GCCCCAGGAT

6061 GTTGCCGTCC TCCTTGAAGT CGATGCCCTT CAGCTCGATG CGGTTCACCA GGGTGTCGCC

6121 CTCGAACTTC ACCTCGGCGC GGGTCTTGTA GTTGCCGTCG TCCTTGAAGA AGATGGTGCG

6181 CTCCTGGACG TAGCCTTCGG GCATGGCGGA CTTGAAGAAG TCGTGCTGCT TCATGTGGTC

6241 GGGGTAGCGG CTGAAGCACT GCACGCCGTA GGTCAGGGTG GTCACGAGGG TGGGCCAGGG

6301 CACGGGCAGC TTGCCGGTGG TGCAGATGAA CTTCAGGGTC AGCTTGCCGT AGGTGGCATC

6361 GCCCTCGCCC TCGCCGGACA CGCTGAACTT GTGGCCGTTT ACGTCGCCGT CCAGCTCGAC

6421 CAGGATGGGC ACCACCCCGG TGAACAGCTC CTCGCCCTTG CTCACCATGG TGGCGGGATC

6481 TGACGGTTCA CTAAACCAGC TCTGCTTATA TAGACCTCCC ACCGTACACG CCTACCGCCC

6541 ATTTGCGTCA ATGGGGCGGA GTTGTTACGA CATTTTGGAA AGTCCCGTTG ATTTTGGTGC

6601 CAAAACAAAC TCCCATTGAC GTCAATGGGG TGGAGACTTG AAATCCCCG TGAGTCAAAC

6661 CGCTATCCAC GCCCATTGAT GTACTGCCAA AACCGCATCA CCATGGTAAT AGCGATGACT

6721 AATACGTAGA TGTACTGCCA AGTAGGAAAG TCCCATAAGG TCATGTACTG GGCATAATGC

6781 CAGGCGGGCC ATTTACCGTC ATTGACGTCA ATAGGGGGCG TACTTGGCAT ATGATACACT

6841 TGATGTACTG CCAAGTGGGC AGTTTACCGT AAATACTCCA CCCATTGACG TCAATGGAAA

6901 GTCCCTATTG GCGTTACTAT GGGAACATAC GTCATTATTG ACGTCAATGG GCGGGGGTCG

6961 TTGGGCGGTC AGCCAGGCGG GCCATTTACC GTAAGTTATG TAACGGGCCT GCTGCCGGCT

7021 CTGCGGCCTC TTCCGCGTCT TCGCCTTCGC CCTCAGACGA GTCGGATCTC CCTTTGGGCC

7081 GCCTCCCCGC CTGTCTAGCT TGACTGACTG AGATACAGCG TACCTTCAGC TCACAGACAT

7141 GATAAGATAC ATTGATGAGT TTGGACAAAC CACAACTAGA ATGCAGTGAA AAAAATGCTT

7201 TATTTGTGAA ATTTGTGATG CTATTGCTTT ATTTGTAACC ATTATAAGCT GCAATAAACA

7261 AGTT
```
(SEQ ID NO: 38)

LINE-1-plasmid_CD5-intron-FCR-PI3K (SEQ ID NO: 39)

```
   1 CGGCCGCGGG GGGAGGAGCC AAGATGGCCG AATAGGAACA GCTCCGGTCT ACAGCTCCCA

61 GCGTGAGCGA CGCAGAAGAC GGTGATTTCT GCATTTCCAT CTGAGGTACC GGGTTCATCT

121 CACTAGGGAG TGCCAGACAG TGGGCGCAGG CCAGTGTGTG TGCGCACCGT GCGCGAGCCG

181 AAGCAGGGCG AGGCATTGCC TCACCTGGGA AGCGCAAGGG GTCAGGGAGT TCCCTTTCCG

241 AGTCAAAGAA AGGGGTGACG GACGCACCTG AAAATCGGG TCACTCCCAC CCGAATATTG

301 CGCTTTTCAG ACCGGCTTAA GAAACGGCGC ACCACGAGAC TATATCCCAC ACCTGGCTCG

361 GAGGGTCCTA CGCCCACGGA ATCTCGCTGA TTGCTAGCAC AGCAGTCTGA GATCAAACTG

421 CAAGGCGGCA ACGAGGCTGG GGGAGGGGCG CCCGCCATTG CCCAGGCTTG CTTAGGTAAA

481 CAAAGCAGCA GGGAAGCTCG AACTGGGTGG AGCCCACCAC AGCTCAAGGA GGCCTGCCTG

541 CCTCTGTAGG CTCCACCTCT GGGGGCAGGG CACAGACAAA CAAAAAGACA GCAGTAACCT

601 CTGCAGACTT AAGTGTCCCT GTCTGACAGC TTTGAAGAGA GCAGTGGTTC TCCCAGCACG

661 CAGCTGGAGA TCTGAGAACG GGCAGACTGC CTCCTCAAGT GGGTCCCTGA CCCCTGACCC

721 CCGAGCAGCC TAACTGGGAG GCACCCCCCA GCAGGGGCAC ACTGACACCT CACACGGCAG

781 GGTATTCCAA CAGACCTGCA GCTGAGGGTC CTGTCTGTTA GAAGGAAAAC TAACAACCAG
```

TABLE 8-continued

Plasmid and mRNA construct sequences

```
 841 AAAGGACATC TACACCGAAA ACCCATCTGT ACATCACCAT CATCAAAGAC CAAAAGTAGA

901 TAAAACCACA AAGATGGGGA AAAAACAGAA CAGAAAAACT GGAAACTCTA AAACGCAGAG

961 CGCCTCTCCT CCTCCAAAGG AACGCAGTTC CTCACCAGCA ACAGAACAAA GCTGGATGGA

1021 GAATGATTTT GATGAGCTGA GAGAAGAAGG CTTCAGACGA TCAAATTACT CTGAGCTACG

1081 GGAGGACATT CAAACCAAAG GCAAAGAAGT TGAAAACTTT GAAAAAAATT TAGAAGAATG

1141 TATAACTAGA ATAACCAATA CAGAGAAGTG CTTAAAGGAG CTGATGGAGC TGAAAACCAA

1201 GGCTCGAGAA CTACGTGAAG AATGCAGAAG CCTCAGGAGC CGATGCGATC AACTGGAAGA

1261 AAGGGTATCA GCAATGGAAG ATGAAATGAA TGAAATGAAG CGAGAAGGGA AGTTTAGAGA

1321 AAAAAGAATA AAAAGAAATG AGCAAAGCCT CCAAGAAATA TGGGACTATG TGAAAAGACC

1381 AAATCTACGT CTGATTGGTG TACCTGAAAG TGATGTGGAG AATGGAACCA AGTTGGAAAA

1441 CACTCTGCAG GATATTATCC AGGAGAACTT CCCCAATCTA GCAAGGCAGG CCAACGTTCA

1501 GATTCAGGAA ATACAGAGAA CGCCACAAAG ATACTCCTCG AGAAGAGCAA CTCCAAGACA

1561 CATAATTGTC AGATTCACCA AAGTTGAAAT GAAGGAAAAA ATGTTAAGGG CAGCCAGAGA

1621 GAAAGGTCGG GTTACCCTCA AAGGAAAGCC CATCAGACTA ACAGCGGATC TCTCGGCAGA

1681 AACCCTACAA GCCAGAAGAG AGTGGGGGCC AATATTCAAC ATTCTTAAAG AAAAGAATTT

1741 TCAACCCAGA ATTTCATATC CAGCCAAACT AAGCTTCATA AGTGAAGGAG AAATAAAATA

1801 CTTTATAGAC AAGCAAATGT TGAGAGATTT TGTCACCACC AGGCCTGCCC TAAAAGAGCT

1861 CCTGAAGGAA GCGCTAAACA TGGAAAGGAA CAACCGGTAC CAGCCGCTGC AAAATCATGC

1921 CAAAATGTAA AGACCATCAA GACTAGGAAG AAACTGCATC AACTAATGAG CAAAATCACC

1981 AGCTAACATC ATAATGACAG GATCAACTTC ACACATAACA ATATTAACTT TAAATATAAA

2041 TGGACTAAAT TCTGCAATTA AAAGACACAG ACTGGCAAGT TGGATAAAGA GTCAAGACCC

2101 ATCAGTGTGC TGTATTCAGG AAACCCATCT CACGTGCAGA GACACACATA GGCTCAAAAT

2161 AAAAGGATGG AGGAAGATCT ACCAAGCCAA TGGAAAACAA AAAAAGGCAG GGGTTGCAAT

2221 CCTAGTCTCT GATAAAACAG ACTTTAAACC AACAAAGATC AAAAGAGACA AAGAAGGCCA

2281 TTACATAATG GTAAAGGGAT CAATTCAACA AGAGGAGCTA ACTATCCTAA ATATTTATGC

2341 ACCCAATACA GGAGCACCCA GATTCATAAA GCAAGTCCTC AGTGACCTAC AAAGAGACTT

2401 AGACTCCCAC ACATTAATAA TGGGAGACTT TAACACCCCA CTGTCAACAT TAGACAGATC

2461 AACGAGACAG AAAGTCAACA AGGATACCCA GGAATTGAAC TCAGCTCTGC ACCAAGCAGA

2521 CCTAATAGAC ATCTACGAAA CTCTCCACCC CAAATCAACA GAATATACAT TTTTTTCAGC

2581 ACCACACCAC ACCTATTCCA AAATTGACCA CATAGTTGGA AGTAAAGCTC TCCTCAGCAA

2641 ATGTAAAAGA ACAGAAATTA TAACAAACTA TCTCTCAGAC CACAGTGCAA TCAAACTAGA

2701 ACTCAGGATT AAGAATCTCA CTCAAAGCCG CTCAACTACA TGGAAACTGA ACAACCTGCT

2761 CCTGAATGAC TACTGGGTAC ATAACGAAAT GAAGGCAGAA ATAAAGATGT TCTTTGAAAC

2821 CAACGAGAAC AAAGACACCA CATACCAGAA TCTCTGGGAC GCATTCAAAG CAGTGTGTAG

2881 AGGGAAATTT ATAGCACTAA ATGCCTACAA GAGAAAGCAG GAAGATCCA AAATTGACAC

2941 CCTAACATCA CAATTAAAAG AACTAGAAAA GCAAGAGCAA ACACATTCAA AAGCTAGCAG

3001 AAGGCAAGAA ATAACTAAAA TCAGAGCAGA ACTGAAGGAA ATAGAGACAC AAAAAACCCT

3061 TCAAAAAATC AATGAATCCA GGAGCTGGTT TTTTGAAAGG ATCAACAAAA TTGATAGACC

3121 GCTAGCAAGA CTAATAAAGA AAAAAAGAGA GAAGAATCAA ATAGACACAATAAAAAATGA
```

TABLE 8-continued

Plasmid and mRNA construct sequences

```
3181 TAAAGGGGAT ATCACCACCG ATCCCACAGA AATACAAACT ACCATCAGAG AATACTACAA

3241 ACACCTCTAC GCAAATAAAC TAGAAAATCT AGAAGAAATG GATACATTCC TCGACACATA

3301 CACTCTCCCA AGACTAAACC AGGAAGAAGT TGAATCTCTG AATCGACCAA TAACAGGCTC

3361 TGAAATTGTG GCAATAATCA ATAGTTTACC AACCAAAAAG AGTCCAGGAC CAGATGGATT

3421 CACAGCCGAA TTCTACCAGA GGTACAAGGA GGAACTGGTA CCATTCCTTC TGAAACTATT

3481 CCAATCAATA GAAAAGAGG GAATCCTCCC TAACTCATTT TATGAGGCCA GCATCATTCT

3541 GATACCAAAG CCGGGCAGAG ACACAACCAA AAAAGAGAAT TTTAGACCAA TATCCTTGAT

3601 GAACATTGAT GCAAAAATCC TCAATAAAAT ACTGGCAAAC CGAATCCAGC AGCACATCAA

3661 AAAGCTTATC CACCATGATC AAGTGGGCTT CATCCCTGGG ATGCAAGGCT GGTTCAATAT

3721 ACGCAAATCA ATAAATGTAA TCCAGCATAT AAACAGAGCC AAAGACAAAA ACCACATGAT

3781 TATCTCAATA GATGCAGAAA AAGCCTTTGA CAAAATTCAA CAACCCTTCA TGCTAAAAAC

3841 TCTCAATAAA TTAGGTATTG ATGGGACGTA TTTCAAAATA ATAAGAGCTA TCTATGACAA

3901 ACCCACAGCC AATATCATAC TGAATGGGCA AAAACTGGAA GCATTCCCTT TGAAAACCGG

3961 CACAAGACAG GGATGCCCTC TCTCACCGCT CCTATTCAAC ATAGTGTTGG AAGTTCTGGC

4021 CAGGGCAATC AGGCAGGAGA AGGAAATAAA GGGTATTCAA TTAGGAAAAG AGGAAGTCAA

4081 ATTGTCCCTG TTTGCAGACG ACATGATTGT TTATCTAGAA AACCCCATCG TCTCAGCCCA

4141 AAATCTCCTT AAGCTGATAA GCAACTTCAG CAAAGTCTCA GGATACAAAA TCAATGTACA

4201 AAAATCACAA GCATTCTTAT ACACCAACAA CAGACAAACA GAGAGCCAAA TCATGGGTGA

4261 ACTCCCATTC ACAATTGCTT CAAAGAGAAT AAAATACCTA GGAATCCAAC TTACAAGGGA

4321 TGTGAAGGAC CTCTTCAAGG AGAACTACAA ACCACTGCTC AAGGAAATAA AAGAGGAGAC

4381 AAACAAATGG AAGAACATTC CATGCTCATG GGTAGGAAGA ATCAATATCG TGAAAATGGC

4441 CATACTGCCC AAGGTAATTT ACAGATTCAA TGCCATCCCC ATCAAGCTAC CAATGACTTT

4501 CTTCACAGAA TTGGAAAAAA CTACTTTAAA GTTCATATGG AACCAAAAAA GAGCCCGCAT

4561 TGCCAAGTCA ATCCTAAGCC AAAAGAACAA AGCTGGAGGC ATCACACTAC CTGACTTCAA

4621 ACTATACTAC AAGGCTACAG TAACCAAAAC AGCATGGTAC TGGTACCAAA ACAGAGATAT

4681 AGATCAATGG AACAGAACAG AGCCCTCAGA AATAATGCCG CATATCTACA ACTATCTGAT

4741 CTTTGACAAA CCTGAGAAAA ACAAGCAATG GGGAAAGGAT TCCCTATTTA ATAAATGGTG

4801 CTGGGAAAAC TGGCTAGCCA TATGTAGAAA GCTGAAACTG GATCCCTTCC TTACACCTTA

4861 TACAAAAATC AATTCAAGAT GGATTAAAGA TTTAAACGTT AAACCTAAAA CCATAAAAAC

4921 CCTAGAAGAA AACCTAGGCA TTACCATTCA GGACATAGGC GTGGGCAAGG ACTTCATGTC

4981 CAAAACACCA AAAGCAATGG CAACAAAGA CAAAATTGAC AAATGGGATC TAATTAAACT

5041 AAAGAGCTTC TGCACAGCAA AAGAAACTAC CATCAGAGTG AACAGGCAAC CTACAACATG

5101 GGAGAAAATT TTTGCAACCT ACTCATCTGA CAAAGGGCTA ATATCCAGAA TCTACAATGA

5161 ACTCAAACAA ATTTACAAGA AAAAAACAAA CAACCCCATC AAAAAGTGGG CGAAGGACAT

5221 GAACAGACAC TTCTCAAAAG AAGACATTTA TGCAGCCAAA AAACACATGA AGAAATGCTC

5281 ATCATCACTG GCCATCAGAG AAATGCAAAT CAAAACCACT ATGAGATATC ATCTCACACC

5341 AGTTAGAATG GCAATCATTA AAAAGTCAGG AAACAACAGG TGCTGGAGAG GATGCGGAGA

5401 AATAGGAACA CTTTTACACT GTTGGTGGGA CTGTAAACTA GTTCAACCAT TGTGGAAGTC

5461 AGTGTGGCGA TTCCTCAGGG ATCTAGAACT AGAAATACCA TTTGACCCAG CCATCCCATT
```

TABLE 8-continued

Plasmid and mRNA construct sequences

```
5521 ACTGGGTATA TACCCAAATG AGTATAAATC ATGCTGCTAT AAAGACACAT GCACACGTAT

5581 GTTTATTGCG GCACTATTCA CAATAGCAAA GACTTGGAAC CAACCCAAAT GTCCAACAAT

5641 GATAGACTGG ATTAAGAAAA TGTGGCACAT ATACACCATG GAATACTATG CAGCCATAAA

5701 AAATGATGAG TTCATATCCT TTGTAGGGAC ATGGATGAAA TTGGAAACCA TCATTCTCAG

5761 TAAACTATCG CAAGAACAAA AAACCAAACA CCGCATATTC TCACTCATAG GTGGGAATTG

5821 AACAATGAGA TCACATGGAC ACAGGAAGGG GAATATCACA CTCTGGGGAC TGTGGTGGGG

5881 TCGGGGGAGG GGGGAGGGAT AGCATTGGGA GATATACCTA ATGCTAGATG ACACATTAGT

5941 GGGTGCAGCG CACCAGCATG GCACATGTAT ACGGATCCGA ATTCTCGACG GATCGATCCG

6001 AACAAACGAC CCAACACCCG TGCGTTTTAT TCTGTCTTTT TATTGCCGAT CCCCTCAGAA

6061 GAACTCGTCA AGAAGGCGAT AGAAGGCGAT GCGCTGCGAA TCGGGAGCGG CGATACCGTA

6121 AAGCACGAGG AAGCGGTCAG CCCATTCGCC GCCAAGCTCT TCAGCAATAT CACGGGTAGC

6181 CAACGCTATG TCCTGATAGC GGTCGGCCGC TCATGTTCTC GTAGGAGTCG GCGTCCTCTT

6241 CGTGGTTAGG TCCAGGTTGG CCTCTGATAG ACCGCAGCTG AGGAGCGGCG TACAGAATGC

6301 CTCTCATGTC CTCATAGCTG CCGCTGCCTT GTGGAGGCTT CTCGTGCTTC AGTGTCTCGT

6361 ATGTCTCTTG ATTCCGGGTG CTCAGGCCGG TGTACACGCC ATCAGATTTC TCGTAGCTGG

6421 TGATGGCGGC CTTCCGCACT TGGATCTTCA GCCGTCTGCA GTACAGGGTG ATGACCAGAG

6481 ACAGCAGCAG GACACCACAT GTGCCAGCCA GAGGGGCCCA AATGTAGATA TCCAGGCCTC

6541 TGGTATGCAC AGCTCCGCCT GCAGCAGGTC TACAGGCTTC AGGTCTGAGA GACAGAGGCT

6601 GGCTGGCGAT TGTAGGAGCT GGTGTAGGTG GTCTAGGAGC GGGTGTTGTT GTAGGCTTGG

6661 CGGGCAGAAA CACGGGCACG AAGTGGCTGA AGTACATGAT GCTATTGCTC AGGGCTCCGC

6721 TTCCTCCGCC GCCTGATTTG ATTTCCAGCT TGGTGCCTCC GCCAAATGTC CAAGGGCTCT

6781 CGTCGTACTG CTGGCAGTAG TAGATGCCGA AGTCCTCGTA CTGCAGGCTG CTGATTGTCA

6841 GGGTGTAGTC GGTGCCAGAG CCGCTGCCAG AAAATCTGCT TGGCACGCCG CTTTCCAGTC

6901 TGTTGGCCCG GTAGATCAGT GTCTTAGGGG CCTTGCCAGG CTTCTGCTGG AACCAGCTCA

6961 GGTAGCTGTT GATGTCCTGG CTGGCTCTAC AGGTGATGGT CACTCTATCG CCCACAGAGG

7021 CAGACAGGCT GCTAGGGCTC TGTGTCATCT GGATATCAGA GCCACCACCG CCAGATCCAC

7081 CGCCACCTGA TCCTCCGCCT CCGCTAGAAA CTGTCACTGT GGTGCCCTGG CCCCACACAT

7141 CGAAGTACCA GTCGTAGCCT CTTCTGGTGC AGAAGTACAC GGCGGTATCC TCGGCTCTCA

7201 GGCTGTTGAT CTGCAGGTAG GCGGTGTTCT TGCTGTCGTC CAGGCTGAAG GTGAATCTGC

7261 CCTTAAAGCT ATCGGCGTAG GTTGGCTCGC CGGTGTGGGT ATTGATCCAG CCCATCCACT

7321 CAAGGCCAGG TGAGTCCAGG AGATGTTTCA GCACTGTTGC CTTTAGTCTC GAGGCAACTT

7381 AGACAACTGA GTATTGATCT GAGCACAGCA GGGTGTGAGC TGTTTGAAGA TACTGGGGTT

7441 GGGGGTGAAG AAACTGCAGA GGACTAACTG GGCTGAGACC CAGTGGCAAT GTTTTAGGGC

7501 CTAAGGAATG CCTCTGAAAA TCTAGATGGA CAACTTTGAC TTTGAGAAAA GAGAGGTGGA

7561 AATGAGGAAA ATGACTTTTC TTTATTAGAT TTCGGTAGAA AGAACTTTCA TCTTTCCCCT

7621 ATTTTTGTTA TTCGTTTTAA AACATCTATC TGGAGGCAGG ACAAGTATGG TCATTAAAAA

7681 GATGCAGGCA GAAGGCATAT ATTGGCTCAG TCAAAGTGGG GAACTTTGGT GGCCAAACAT

7741 ACATTGCTAA GGCTATTCCT ATATCAGCTG GACACATATA AAATGCTGCT AATGCTTCAT

7801 TACAAACTTA TATCCTTTAA TTCCAGATGG GGGCAAAGTA TGTCCAGGGG TGAGGAACAA
```

TABLE 8-continued

Plasmid and mRNA construct sequences

```
 7861 TTGAAACATT TGGGCTGGAG TAGATTTTGA AAGTCAGCTC TGTGTGTGTG TGTGTGTGTG

7921 TGTGTGTGAG AGCGTGTGTT TCTTTTAACG TTTTCAGCCT ACAGCATACA GGGTTCATGG

7981 TGGCAAGAAG ATAACAAGAT TTAAATTATG GCCAGTGACT AGTGCTGCAA GAAGAACAAC

8041 TACCTGCATT TAATGGGAAA GCAAAATCTC AGGCTTTGAG GGAAGTTAAC ATAGGCTTGA

8101 TTCTGGGTGG AAGCTGGGTG TGTAGTTATC TGGAGGCCAG GCTGGAGCTC TCAGCTCACT

8161 ATGGGTTCAT CTTTATTGTC TCCTTTTTCC AGGGGCCTGT CGGACCCAGT TCATGCCGTA

8221 GTTGGTGAAG GTGTAGCCGC TGGCGGCACA GCTGATTCTG ACAGATCCGC CAGGTTTCAC

8281 AAGTCCGCCG CCAGACTGAA CCAGCTGGAT CTCAGAGATG CTACAGGCCA CTGTTCCCAG

8341 CAGCAGCAGA GACTGCAGCC ACATCTGGTG GCGAATTCGA AGCTTGAGCT CGAGATCTGA

8401 GTCCGGTAGC GCTAGCGGAT CTGACGGTTC ACTAAACCAG CTCTGCTTAT ATAGACCTCC

8461 CACCGTACAC GCCTACCGCC CATTTGCGTC AATGGGGCGG AGTTGTTACG ACATTTTGGA

8521 AAGTCCCGTT GATTTTGGTG CCAAAACAAA CTCCCATTGA CGTCAATGGG GTGGAGACTT

8581 GGAAATCCCC GTGAGTCAAA CCGCTATCCA CGCCCATTGA TGTACTGCCA AAACCGCATC

8641 ACCATGGTAA TAGCGATGAC TAATACGTAG ATGTACTGCC AAGTAGGAAA GTCCCATAAG

8701 GTCATGTACT GGGCATAATG CCAGGCGGGC CATTTACCGT CATTGACGTC AATAGGGGGC

8761 GTACTTGGCA TATGATACAC TTGATGTACT GCCAAGTGGG CAGTTTACCG TAAATACTCC

8821 ACCCATTGAC GTCAATGGAA AGTCCCTATT GGCGTTACTA TGGGAACATA CGTCATTATT

8881 GACGTCAATG GGCGGGGGTC GTTGGGCGGT CAGCCAGGCG GGCCATTTAC CGTAAGTTAT

8941 GTAACGCGGA ACTCCATATA TGGGCTATGA ACTAATGACC CCGTAATTGA TTACTATTAG

9001 CCCGGGGGAT CCAGACATGA TAAGATACAT TGATGAGTTT GGACAAACCA CAACTAGAAT

9061 GCAGTGAAAA AAATGCTTTA TTTGTGAAAT TTGTGATGCT ATTGCTTTAT TTGTAACCAT

9121 TATAAGCTGC AATAAACAAG TTAACAACAA CAATTGCATT CATTTTATGT TTCAGGTTCA

9181 GGGGGAGGTG TGGGAGGTTT TTTAAAGCAA GTAAAACCTC TACAAATGTG GTATGGCTGA

9241 TTATGATCCG GCTGCCTCGC GCGTTTCGGT GATGACGGTG AAAACCTCTG ACACATGCAG

9301 CTCCCGGAGA CGGTCACAGC TTGTCTGTAA GCGGATGCCG GGAGCAGACA AGCCCGTCAG

9361 GGCGCGTCAG CGGGTGTTGG CGGGTGTCGG GGCGCAGCCA TGAGGTCGAT CGACTCTAGA

9421 GGATCGATCC CCGCCCCGGA CGAACTAAAC CTGACTACGA CATCTCTGCC CCTTCTTCGC

9481 GGGGCAGTGC ATGTAATCCC TTCAGTTGGT TGGTACAACT TGCCAACTGG GCCCTGTTCC

9541 ACATGTGACA CGGGGGGGGA CCAAACACAA AGGGGTTCTC TGACTGTAGT TGACATCCTT

9601 ATAAATGGAT GTGCACATTT GCCAACACTG AGTGGCTTTC ATCCTGGAGC AGACTTTGCA

9661 GTCTGTGGAC TGCAACACAA CATTGCCTTT ATGTGTAACT CTTGGCTGAA GCTCTTACAC

9721 CAATGCTGGG GGACATGTAC CTCCCAGGGG CCCAGGAAGA CTACGGGAGG CTACACCAAC

9781 GTCAATCAGA GGGGCCTGTG TAGCTACCGA TAAGCGGACC CTCAAGAGGG CATTAGCAAT

9841 AGTGTTTATA AGGCCCCCTT GTTAACCCTA AACGGGTAGC ATATGCTTCC CGGGTAGTAG

9901 TATATACTAT CCAGACTAAC CCTAATTCAA TAGCATATGT TACCCAACGG GAAGCATATG

9961 CTATCGAATT AGGGTTAGTA AAAGGGTCCT AAGGAACAGC GATATCTCCC ACCCCATGAG

10021 CTGTCACGGT TTTATTTACA TGGGGTCAGG ATTCCACGAG GGTAGTGAAC CATTTTAGTC

10081 ACAAGGGCAG TGGCTGAAGA TCAAGGAGCG GGCAGTGAAC TCTCCTGAAT CTTCGCCTGC

10141 TTCTTCATTC TCCTTCGTTT AGCTAATAGA ATAACTGCTG AGTIGTGAAC AGTAAGGTGT
```

TABLE 8-continued

Plasmid and mRNA construct sequences

```
10201 ATGTGAGGTG CTCGAAAACA AGGTTTCAGG TGACGCCCCC AGAATAAAAT TTGGACGGGG

10261 GGTTCAGTGG TGGCATTGTG CTATGACACC AATATAACCC TCACAAACCC CTTGGGCAAT

10321 AAATACTAGT GTAGGAATGA AACATTCTGA ATATCTTTAA CAATAGAAAT CCATGGGGTG

10381 GGGACAAGCC GTAAAGACTG GATGTCCATC TCACACGAAT TTATGGCTAT GGGCAACACA

10441 TAATCCTAGT GCAATATGAT ACTGGGGTTA TTAAGATGTG TCCCAGGCAG GGACCAAGAC

10501 AGGTGAACCA TGTTGTTACA CTCTATTTGT AACAAGGGGA AAGAGAGTGG ACGCCGACAG

10561 CAGCGGACTC CACTGGTTGT CTCTAACACC CCCGAAAATT AAACGGGGCT CCACGCCAAT

10621 GGGGCCCATA AACAAAGACA AGTGGCCACT CTTTTTTTTG AAATTGTGGA GTGGGGGCAC

10681 GCGTCAGCCC CCACACGCCG CCCTGCGGTT TTGGACTGTA AAATAAGGGT GTAATAACTT

10741 GGCTGATTGT AACCCCGCTA ACCACTGCGG TCAAACCACT TGCCCACAAA ACCACTAATG

10801 GCACCCCGGG GAATACCTGC ATAAGTAGGT GGGCGGGCCA AGATAGGGGC GCGATTGCTG

10861 CGATCTGGAG GACAAATTAC ACACACTTGC GCCTGAGCGC CAAGCACAGG GTTGTTGGTC

10921 CTCATATTCA CGAGGTCGCT GAGAGCACGG TGGGCTAATG TTGCCATGGG TAGCATATAC

10981 TACCCAAATA TCTGGATAGC ATATGCTATC CTAATCTATA TCTGGGTAGC ATAGGCTATC

11041 CTAATCTATA TCTGGGTAGC ATATGCTATC CTAATCTATA TCTGGGTAGT ATATGCTATC

11101 CTAATTTATA TCTGGGTAGC ATAGGCTATC CTAATCTATA TCTGGGTAGC ATATGCTATC

11161 CTAATCTATA TCTGGGTAGT ATATGCTATC CTAATCTGTA TCCGGGTAGC ATATGCTATC

11221 CTAATAGAGA TTAGGGTAGT ATATGCTATC CTAATTTATA TCTGGGTAGC ATATACTACC

11281 CAAATATCTG GATAGCATAT GCTATCCTAA TCTATATCTG GTAGCATAT GCTATCCTAA

11341 TCTATATCTG GTAGCATAG GCTATCCTAA TCTATATCTG GTAGCATAT GCTATCCTAA

11401 TCTATATCTG GTAGTATAT GCTATCCTAA TTTATATCTG GTAGCATAG GCTATCCTAA

11461 TCTATATCTG GTAGCATAT GCTATCCTAA TCTATATCTG GTAGTATAT GCTATCCTAA

11521 TCTGTATCCG GTAGCATAT GCTATCCTCA TGCATATACA GTCAGCATAT GATACCCAGT

11581 AGTAGAGTGG GAGTGCTATC CTTTGCATAT GCCGCCACCT CCCAAGGGGG CGTGAATTTT

11641 CGCTGCTTGT CCTTTTCCTG CATGCTGGTT GCTCCCATTC TTAGGTGAAT TTAAGGAGGC

11701 CAGGCTAAAG CCGTCGCATG TCTGATTGCT CACCAGGTAA ATGTCGCTAA TGTTTTCCAA

11761 CGCGAGAAGG TGTTGAGCGC GGAGCTGAGT GACGTGACAA CATGGGTATG CCCAATTGCC

11821 CCATGTTGGG AGGACGAAAA TGGTGACAAG ACAGATGGCC AGAAATACAC CAACAGCACG

11881 CATGATGTCT ACTGGGGATT TATTCTTTAG TGCGGGGGAA TACACGGCTT TTAATACGAT

11941 TGAGGGCGTC TCCTAACAAG TTACATCACT CCTGCCCTTC CTCACCCTCA TCTCCATCAC

12001 CTCCTTCATC TCCGTCATCT CCGTCATCAC CCTCCGCGGC AGCCCCTTCC ACCATAGGTG

12061 GAAACCAGGG AGGCAAATCT ACTCCATCGT CAAAGCTGCA CACAGTCACC CTGATATTGC

12121 AGGTAGGAGC GGGCTTTGTC ATAACAAGGT CCTTAATCGC ATCCTTCAAA ACCTCAGCAA

12181 ATATATGAGT TTGTAAAAAG ACCATGAAAT AACAGACAAT GGACTCCCTT AGCGGGCCAG

12241 GTTGTGGGCC GGGTCCAGGG GCCATTCCAA AGGGGAGACG ACTCAATGGT GTAAGACGAC

12301 ATTGTGGAAT AGCAAGGGCA GTTCCTCGCC TTAGGTTGTA AAGGGAGGTC TTACTACCTC

12361 CATATACGAA CACACCGGCG ACCCAAGTTC CTTCGTCGGT AGTCCTTTCT ACGTGACTCC

12421 TAGCCAGGAG AGCTCTTAAA CCTTCTGCAA TGTTCTCAAA TTTCGGGTTG GAACCTCCTT

12481 GACCACGATG CTTTCCAAAC CACCCTCCTT TTTTGCGCCT GCCTCCATCA CCCTGACCCC
```

TABLE 8-continued

Plasmid and mRNA construct sequences

```
12541 GGGGTCCAGT GCTTGGGCCT TCTCCTGGGT CATCTGCGGG GCCCTGCTCT ATCGCTCCCG

12601 GGGGCACGTC AGGCTCACCA TCTGGGCCAC CTTCTTGGTG GTATTCAAAA TAATCGGCTT

12661 CCCCTACAGG GTGGAAAAAT GGCCTTCTAC CTGGAGGGGG CCTGCGCGGT GGAGACCCGG

12721 ATGATGATGA CTGACTACTG GGACTCCTGG GCCTCTTTTC TCCACGTCCA CGACCTCTCC

12781 CCCTGGCTCT TTCACGACTT CCCCCCCTGG CTCTTTCACG TCCTCTACCC CGGCGGCCTC

12841 CACTACCTCC TCGACCCCGG CCTCCACTAC CTCCTCGACC CCGGCCTCCA CTGCCTCCTC

12901 GACCCCGGCC TCCACCTCCT GCTCCTGCCC CTCCTGCTCC TGCCCCTCCT CCTGCTCCTG

12961 CCCCTCCTGC CCCTCCTGCT CCTGCCCCTC CTGCCCCTCC TGCTCCTGCC CCTCCTGCCC

13021 CTCCTGCTCC TGCCCCTCCT GCCCCTCCTC CTGCTCCTGC CCCTCCTGCC CCTCCTCCTG

13081 CTCCTGCCCC TCCTGCCCCT CCTGCTCCTG CCCCTCCTGC CCCTCCTGCT CCTGCCCCTC

13141 CTGCCCCTCC TGCTCCTGCC CCTCCTGCTC CTGCCCCTCC TGCTCCTGCC CCTCCTGCTC

13201 CTGCCCCTCC TGCCCCTCCT GCCCCTCCTC CTGCTCCTGC CCCTCCTGCT CCTGCCCCTC

13261 CTGCCCCTCC TGCCCCTCCT GCTCCTGCCC CTCCTCCTGC TCCTGCCCCT CCTGCCCCTC

13321 CTGCCCCTCC TCCTGCTCCT GCCCCTCCTG CCCCTCCTCC TGCTCCTGCC CCTCCTCCTG

13381 CTCCTGCCCC TCCTGCCCCT CCTGCCCCTC CTCCTGCTCC TGCCCCTCCT GCCCCTCCTC

13441 CTGCTCCTGC CCCTCCTCCT GCTCCTGCCC CTCCTGCCCC TCCTGCCCCT CCTCCTGCTC

13501 CTGCCCCTCC TCCTGCTCCT GCCCCTCCTG CCCCTCCTGC CCCTCCTGCC CCTCCTCCTG

13561 CTCCTGCCCC TCCTCCTGCT CCTGCCCCTC CTGCTCCTGC CCCTCCCGCT CCTGCTCCTG

13621 CTCCTGTTCC ACCGTGGGTC CCTTTGCAGC CAATGCAACT TGGACGTTTT TGGGGTCTCC

13681 GGACACCATC TCTATGTCTT GGCCCTGATC CTGAGCCGCC CGGGGCTCCT GGTCTTCCGC

13741 CTCCTCGTCC TCGTCCTCTT CCCCGTCCTC GTCCATGGTT ATCACCCCCT CTTCTTTGAG

13801 GTCCACTGCC GCCGGAGCCT TCTGGTCCAG ATGTGTCTCC CTTCTCTCCT AGGCCATTTC

13861 CAGGTCCTGT ACCTGGCCCC TCGTCAGACA TGATTCACAC TAAAAGAGAT CAATAGACAT

13921 CTTTATTAGA CGACGCTCAG TGAATACAGG GAGTGCAGAC TCCTGCCCCC TCCAACAGCC

13981 CCCCCACCCT CATCCCCTTC ATGGTCGCTG TCAGACAGAT CCAGGTCTGA AAATTCCCCA

14041 TCCTCCGAAC CATCCTCGTC CTCATCACCA ATTACTCGCA GCCCGGAAAA CTCCCGCTGA

14101 ACATCCTCAA GATTTGCGTC CTGAGCCTCA AGCCAGGCCT CAAATTCCTC GTCCCCCTTT

14161 TTGCTGGACG GTAGGGATGG GGATTCTCGG GACCCCTCCT CTTCCTCTTC AAGGTCACCA

14221 GACAGAGATG CTACTGGGGC AACGGAAGAA AAGCTGGGTG CGGCCTGTGA GGATCAGCTT

14281 ATCGATGATA AGCTGTCAAA CATGAGAATT CTTGAAGACG AAAGGGCCTC GTGATACGCC

14341 TATTTTTATA GGTTAATGTC ATGATAATAA TGGTTTCTTA GACGTCAGGT GGCACTTTTC

14401 GGGGAAATGT GCGCGGAACC CCTATTTGTT TATTTTTCTA AATACATTCA AATATGTATC

14461 CGCTCATGAG ACAATAACCC TGATAAATGC TTCAATAATA TTGAAAAAGG AAGAGTATGA

14521 GTATTCAACA TTTCCGTGTC GCCCTTATTC CCTTTTTTGC GGCATTTTGC CTTCCTGTTT

14581 TTGCTCACCC AGAAACGCTG GTGAAAGTAA AAGATGCTGA AGATCAGTTG GGTGCACGAG

14641 TGGGTTACAT CGAACTGGAT CTCAACAGCG GTAAGATCCT TGAGAGTTTT CGCCCCGAAG

14701 AACGTTTTCC AATGATGAGC ACTTTTAAAG TTCTGCTATG TGGCGCGGTA TTATCCCGTG

14761 TTGACGCCGG GCAAGAGCAA CTCGGTCGCC GCATACACTA TTCTCAGAAT GACTTGGTTG

14821 AGTACTCACC AGTCACAGAA AAGCATCTTA CGGATGGCAT GACAGTAAGA GAATTATGCA
```

TABLE 8-continued

Plasmid and mRNA construct sequences

```
14881 GTGCTGCCAT AACCATGAGT GATAACACTG CGGCCAACTT ACTTCTGACA ACGATCGGAG

14941 GACCGAAGGA GCTAACCGCT TTTTTGCACA ACATGGGGGA TCATGTAACT CGCCTTGATC

15001 GTTGGGAACC GGAGCTGAAT GAAGCCATAC CAAACGACGA GCGTGACACC ACGATGCCTG

15061 CAGCAATGGC AACAACGTTG CGCAAACTAT TAACTGGCGA ACTACTTACT CTAGCTTCCC

15121 GGCAACAATT AATAGACTGG ATGGAGGCGG ATAAAGTTGC AGGACCACTT CTGCGCTCGG

15181 CCCTTCCGGC TGGCTGGTTT ATTGCTGATA AATCTGGAGC CGGTGAGCGT GGGTCTCGCG

15241 GTATCATTGC AGCACTGGGG CCAGATGGTA AGCCCTCCCG TATCGTAGTT ATCTACACGA

15301 CGGGGAGTCA GGCAACTATG GATGAACGAA ATAGACAGAT CGCTGAGATA GGTGCCTCAC

15361 TGATTAAGCA TTGGTAACTG TCAGACCAAG TTTACTCATA TATACTTTAG ATTGATTTAA

15421 AACTTCATTT TTAATTTAAA AGGATCTAGG TGAAGATCCT TTTTGATAAT CTCATGACCA

15481 AAATCCCTTA ACGTGAGTTT TCGTTCCACT GAGCGTCAGA CCCCGTAGAA AAGATCAAAG

15541 GATCTTCTTG AGATCCTTTT TTTCTGCGCG TAATCTGCTG CTTGCAAACA AAAAAACCAC

15601 CGCTACCAGC GGTGGTTTGT TTGCCGGATC AAGAGCTACC AACTCTTTTT CCGAAGGTAA

15661 CTGGCTTCAG CAGAGCGCAG ATACCAAATA CTGTCCTTCT AGTGTAGCCG TAGTTAGGCC

15721 ACCACTTCAA GAACTCTGTA GCACCGCCTA CATACCTCGC TCTGCTAATC CTGTTACCAG

15781 TGGCTGCTGC CAGTGGCGAT AAGTCGTGTC TTACCGGGTT GGACTCAAGA CGATAGTTAC

15841 CGGATAAGGC GCAGCGGTCG GGCTGAACGG GGGGTTCGTG CACACAGCCC AGCTTGGAGC

15901 GAACGACCTA CACCGAACTG AGATACCTAC AGCGTGAGCT ATGAGAAAGC GCCACGCTTC

15961 CCGAAGGGAG AAAGGCGGAC AGGTATCCGG TAAGCGGCAG GGTCGGAACAGGAGAGCGCA

16021 CGAGGGAGCT TCCAGGGGGA AACGCCTGGT ATCTTTATAG TCCTGTCGGG TTTCGCCACC

16081 TCTGACTTGA GCGTCGATTT TTGTGATGCT CGTCAGGGGG GCGGAGCCTA TGGAAAAACG

16141 CCAGCAACGC GGCCTTTTTA CGGTTCCTGG CCTTTTGCTG GCCTTTTGCT CACATGTTCT

16201 TTCCTGCGTT ATCCCCTGAT TCTGTGGATA ACCGTATTAC CGCCTTTGAG TGAGCTGATA

16261 CCGCTCGCCG CAGCCGAACG ACCGAGCGCA GCGAGTCAGT GAGCGAGGAA GCGGAAGAGC

16321 GCCTGATGCG GTATTTTCTC CTTACGCATC TGTGCGGTAT TTCACACCGC ATATGGTGCA

16381 CTCTCAGTAC AATCTGCTCT GATGCCGCAT AGTTAAGCCA GCTGTGGAAT GTGTGTCAGT

16441 TAGGGTGTGG AAAGTCCCCA GGCTCCCCAG CAGGCAGAAG TATGCAAAGC ATGCATCTCA

16501 ATTAGTCAGC AACCAGGTGT GGAAAGTCCC CAGGCTCCCC AGCAGGCAGA AGTATGCAAA

16561 GCATGCATCT CAATTAGTCA GCAACCATAG TCCCGCCCCT AACTCCGCCC ATCCCGCCCC

16621 TAACTCCGCC CAGTTCCGCC CATTCTCCGC CCCATGGCTG ACTAATTTTT TTTATTTATG

16681 CAGAGGCCGA GGCCGCCTCG CCTCTGAGC TATTCCAGAA GTAGTGAGGA GGCTTTTTTG

16741 GAGGCCTAGG CTTTTGCAAA AAGCTTGCAT GCCTGCAGGT CGGCCGCCAC GACCGGTGCC

16801 GCCACCATCC CCTGACCCAC GCCCCTGACC CCTCACAAGG AGACGACCTT CCATGACCGA

16861 GTACAAGCCC ACGGTGCGCC TCGCCACCCG CGACGACGTC CCCCGGGCCG TACGCACCCT

16921 CGCCGCCGCG TTCGCCGACT ACCCCGCCAC GCGCCACACC GTCGACCCGG ACCGCCACAT

16981 CGAGCGGGTC ACCGAGCTGC AAGAACTCTT CCTCACGCGC GTCGGGCTCG ACATCGGCAA

17041 GGTGTGGGTC GCGGACGACG GCGCCGCGGT GGCGGTCTGG ACCACGCCGG AGAGCGTCGA

17101 AGCGGGGGCG GTGTTCGCCG AGATCGGCCC GCGCATGGCC GAGTTGAGCG GTTCCCGGCT

17161 GGCCGCGCAG CAACAGATGG AAGGCCTCCT GGCGCCGCAC CGGCCCAAGG AGCCCGCGTG
```

TABLE 8-continued

Plasmid and mRNA construct sequences

```
17221 GTTCCTGGCC ACCGTCGGCG TCTCGCCCGA CCACCAGGGC AAGGGTCTGG GCAGCGCCGT

17281 CGTGCTCCCC GGAGTGGAGG CGGCCGAGCG CGCCGGGGTG CCCGCCTTCC TGGAGACCTC

17341 CGCGCCCCGC AACCTCCCCT TCTACGAGCG GCTCGGCTTC ACCGTCACCG CCGACGTCGA

17401 GGTGCCCGAA GGACCGCGCA CCTGGTGCAT GACCCGCAAG CCCGGTGCCT GACGCCCGCC

17461 CCACGACCCG CAGCGCCCGA CCGAAAGGAG CGCACGACCC CATGGCTCCG ACCGAAGCCG

17521 ACCCGGGCGG CCCCGCCGAC CCCGCACCCG CCCCCGAGGC CCACCGACTC TAGAGGATCA

17581 TAATCAGCCA TACCACATTT GTAGAGGTTT TACTTGCTTT AAAAAACCTC CCACACCTCC

17641 CCCTGAACCT GAAACATAAA ATGAATGCAA TTGTTGTTGT TAACTTGTTT ATTGCAGCTT

17701 ATAATGGTTA CAAATAAAGC AATAGCATCA CAAATTTCAC AAATAAAGCA TTTTTTTCAC

17761 TGCATTCTAG TTGTGGTTTG TCCAAACTCA TCAATGTATC TTATCATGTC TGGATCACTC

17821 GCCGATAGTG AAACCGACG CCCCAGCACT CGTCCGAGGG CAAAGGAATA GGGGAGATGG

17881 GGGAGGCTAA CTGAAACACG GAAGGAGACA ATACCGGAAG GAACCCGCGC TATGACGGCA

17941 ATAAAAAGAC AGAATAAAAC GCACGGGTGT TGGGTCGTTT GTTCATAAAC GCGGGGTTCG

18001 GTCCCAGGGC TGGCACTCTG TCGATACCCC ACCGAGACCC CATTGGGGCC AATACGCCCG

18061 CGTTTCTTCC TTTTCCCCAC CCCACCCCCC AAGTTCGGGT GAAGGCCCAG GGCTCGCAGC

18121 CAACGTCGGG GCGGCAGGCC CTGCCATAGC CACTGGCCCC GTGGGTTAGG ACGGGGTCC

18181 CCCATGGGGA ATGGTTTATG GTTCGTGGGG GTTATTATTT TGGGCGTTGC GTGGGGTCTG

18241 GTCCACGACT GGACTGAGCA GACAGACCCA TGGTTTTTGG ATGGCCTGGG CATGGACCGC

18301 ATGTACTGGC GCGACACGAA CACCGGGCGT CTGTGGCTGC CAAACACCCC CGACCCCCAA

18361 AAACCACCGC GCGGATTTCT GGCGTGCCAA GCTAGTCGAC CAATTCTCAT GTTTGACAGC

18421 TTATCATCGC AGATCCGGGC AACGTTGTTG CATTGCTGCA GGCGCAGAAC TGGTAGGTAT

18481 GGAAGATCTC TAGAAGCTGG GTACCAGCTG CTAGCAAGCT TGCTAGCGGC CGGCTCGAGT

18541 TTACTCCCTA TCAGTGATAG AGAACGTATG TCGAGTTTAC TCCCTATCAG TGATAGAGAA

18601 CGATGTCGAG TTTACTCCCT ATCAGTGATA GAGAACGTAT GTCGAGTTTA CTCCCTATCA

18661 GTGATAGAGA ACGTATGTCG AGTTTACTCC CTATCAGTGA TAGAGAACGT ATGTCGAGTT

18721 TATCCCTATC AGTGATAGAG AACGTATGTC GAGTTTACTC CCTATCAGTG ATAGAGAACG

18781 TATGTCGAGG TAGGCGTGTA CGGTGGGAGG CCTATATAAG CAGAGCTCGT TTAGTGAACC

18841 GTCAGATCGC CG
(SEQ ID NO: 39)
```

LINE-1plasmid-CD5_FCR-PI3K_T2A-GFPintron (SEQ ID NO: 40)

```
   1 CGGCCGCGGG GGGAGGAGCC AAGATGGCCG AATAGGAACA GCTCCGGTCT ACAGCTCCCA

61 GCGTGAGCGA CGCAGAAGAC GGTGATTTCT GCATTTCCAT CTGAGGTACC GGGTTCATCT

121 CACTAGGGAG TGCCAGACAG TGGGCGCAGG CCAGTGTGTG TGCGCACCGT GCGCGAGCCG

181 AAGCAGGGCG AGGCATTGCC TCACCTGGGA AGCGCAAGGG GTCAGGGAGT TCCCTTTCCG

241 AGTCAAAGAA AGGGGTGACG GACGCACCTG GAAAATCGGG TCACTCCCAC CCGAATATTG

301 CGCTTTTCAG ACCGGCTTAA GAAACGGCGC ACCACGAGAC TATATCCCAC ACCTGGCTCG

361 GAGGGTCCTA CGCCCACGGA ATCTCGCTGA TTGCTAGCAC AGCAGTCTGA GATCAAACTG

421 CAAGGCGGCA ACGAGGCTGG GGGAGGGGCG CCCGCCATTG CCCAGGCTTG CTTAGGTAAA

481 CAAAGCAGCA GGGAAGCTCG AACTGGGTGG AGCCCACCAC AGCTCAAGGA GGCCTGCCTG
```

TABLE 8-continued

Plasmid and mRNA construct sequences

```
 541 CCTCTGTAGG CTCCACCTCT GGGGGCAGGG CACAGACAAA CAAAAAGACA GCAGTAACCT

601 CTGCAGACTT AAGTGTCCCT GTCTGACAGC TTTGAAGAGA GCAGTGGTTC TCCCAGCACG

661 CAGCTGGAGA TCTGAGAACG GGCAGACTGC CTCCTCAAGT GGGTCCCTGA CCCCTGACCC

721 CCGAGCAGCC TAACTGGGAG GCACCCCCCA GCAGGGGCAC ACTGACACCT CACACGGCAG

781 GGTATTCCAA CAGACCTGCA GCTGAGGGTC CTGTCTGTTA GAAGGAAAAC TAACAACCAG

841 AAAGGACATC TACACCGAAA ACCCATCTGT ACATCACCAT CATCAAAGAC CAAAAGTAGA

901 TAAAACCACA AAGATGGGGA AAAAACAGAA CAGAAAAACT GGAAACTCTA AAACGCAGAG

961 CGCCTCTCCT CCTCCAAAGG AACGCAGTTC CTCACCAGCA ACAGAACAAA GCTGGATGGA

1021 GAATGATTTT GATGAGCTGA GAGAAGAAGG CTTCAGACGA TCAAATTACT CTGAGCTACG

1081 GGAGGACATT CAAACCAAAG GCAAAGAAGT TGAAAACTTT GAAAAAAATT TAGAAGAATG

1141 TATAACTAGA ATAACCAATA CAGAGAAGTG CTTAAAGGAG CTGATGGAGC TGAAAACCAA

1201 GGCTCGAGAA CTACGTGAAG AATGCAGAAG CCTCAGGAGC CGATGCGATC AACTGGAAGA

1261 AAGGGTATCA GCAATGGAAG ATGAAATGAA TGAAATGAAG CGAGAAGGGA AGTTTAGAGA

1321 AAAAAGAATA AAAAGAAATG AGCAAAGCCT CCAAGAAATA TGGGACTATG TGAAAAGACC

1381 AAATCTACGT CTGATTGGTG TACCTGAAAG TGATGTGGAG AATGGAACCA AGTTGGAAAA

1441 CACTCTGCAG GATATTATCC AGGAGAACTT CCCCAATCTA GCAAGGCAGG CCAACGTTCA

1501 GATTCAGGAA ATACAGAGAA CGCCACAAAG ATACTCCTCG AGAAGAGCAA CTCCAAGACA

1561 CATAATTGTC AGATTCACCA AAGTTGAAAT GAAGGAAAAA ATGTTAAGGG CAGCCAGAGA

1621 GAAAGGTCGG GTTACCCTCA AAGGAAAGCC CATCAGACTA CAGCGGATC TCTCGGCAGA

1681 AACCCTACAA GCCAGAAGAG AGTGGGGGCC AATATTCAAC ATTCTTAAAG AAAAGAATTT

1741 TCAACCCAGA ATTTCATATC CAGCCAAACT AAGCTTCATA AGTGAAGGAG AAATAAAATA

1801 CTTTATAGAC AAGCAAATGT TGAGAGATTT TGTCACCACC AGGCCTGCCC TAAAAGAGCT

1861 CCTGAAGGAA GCGCTAAACA TGGAAAGGAA CAACCGGTAC CAGCCGCTGC AAAATCATGC

1921 CAAAATGTAA AGACCATCAA GACTAGGAAG AAACTGCATC AACTAATGAG CAAAATCACC

1981 AGCTAACATC ATAATGACAG GATCAACTTC ACACATAACA ATATTAACTT TAAATATAAA

2041 TGGACTAAAT TCTGCAATTA AAAGACACAG ACTGGCAAGT TGGATAAAGA GTCAAGACCC

2101 ATCAGTGTGC TGTATTCAGG AAACCCATCT CACGTGCAGA GACACACATA GGCTCAAAAT

2161 AAAAGGATGG AGGAAGATCT ACCAAGCCAA TGGAAAACAA AAAAAGGCAG GGGTTGCAAT

2221 CCTAGTCTCT GATAAAACAG ACTTTAAACC AACAAAGATC AAAAGAGACA AAGAAGGCCA

2281 TTACATAATG GTAAAGGGAT CAATTCAACA AGAGGAGCTA ACTATCCTAA ATATTTATGC

2341 ACCCAATACA GGAGCACCCA GATTCATAAA GCAAGTCCTC AGTGACCTAC AAAGAGACTT

2401 AGACTCCCAC ACATTAATAA TGGGAGACTT TAACACCCCA CTGTCAACAT TAGACAGATC

2461 AACGAGACAG AAAGTCAACA AGGATACCCA GGAATTGAAC TCAGCTCTGC ACCAAGCAGA

2521 CCTAATAGAC ATCTACGAA CTCTCCACCC CAAATCAACA GAATATACAT TTTTTTCAGC

2581 ACCACACCAC ACCTATTCCA AAATTGACCA CATAGTTGGA AGTAAAGCTC TCCTCAGCAA

2641 ATGTAAAAGA ACAGAAATTA TAACAAACTA TCTCTCAGAC CACAGTGCAA TCAAACTAGA

2701 ACTCAGGATT AAGAATCTCA CTCAAAGCCG CTCAACTACA TGGAAACTGA ACAACCTGCT

2761 CCTGAATGAC TACTGGGTAC ATAACGAAAT GAAGGCAGAA ATAAAGATGT TCTTTGAAAC

2821 CAACGAGAAC AAAGACACCA CATACCAGAA TCTCTGGGAC GCATTCAAAG CAGTGTGTAG
```

TABLE 8-continued

Plasmid and mRNA construct sequences

```
2881 AGGGAAATTT ATAGCACTAA ATGCCTACAA GAGAAAGCAG GAAAGATCCA AAATTGACAC

2941 CCTAACATCA CAATTAAAAG AACTAGAAAA GCAAGAGCAA ACACATTCAA AAGCTAGCAG

3001 AAGGCAAGAA ATAACTAAAA TCAGAGCAGA ACTGAAGGAA ATAGAGACAC AAAAAACCCT

3061 TCAAAAAATC AATGAATCCA GGAGCTGGTT TTTTGAAAGG ATCAACAAAA TTGATAGACC

3121 GCTAGCAAGA CTAATAAAGA AAAAAGAGA GAAGAATCAA ATAGACACAA TAAAAAATGA

3181 TAAAGGGGAT ATCACCACCG ATCCCACAGA AATACAAACT ACCATCAGAG AATACTACAA

3241 ACACCTCTAC GCAAATAAAC TAGAAAATCT AGAAGAAATG GATACATTCC TCGACACATA

3301 CACTCTCCCA AGACTAAACC AGGAAGAAGT TGAATCTCTG AATCGACCAA TAACAGGCTC

3361 TGAAATTGTG GCAATAATCA ATAGTTTACC AACCAAAAAG AGTCCAGGAC CAGATGGATT

3421 CACAGCCGAA TTCTACCAGA GGTACAAGGA GGAACTGGTA CCATTCCTTC TGAAACTATT

3481 CCAATCAATA GAAAAAGAGG GAATCCTCCC TAACTCATTT TATGAGGCCA GCATCATTCT

3541 GATACCAAAG CCGGGCAGAG ACACAACCAA AAAAGAGAAT TTTAGACCAA TATCCTTGAT

3601 GAACATTGAT GCAAAAATCC TCAATAAAAT ACTGGCAAAC CGAATCCAGC AGCACATCAA

3661 AAAGCTTATC CACCATGATC AAGTGGGCTT CATCCCTGGG ATGCAAGGCT GGTTCAATAT

3721 ACGCAAATCA ATAAATGTAA TCCAGCATAT AAACAGAGCC AAAGACAAAA ACCACATGAT

3781 TATCTCAATA GATGCAGAAA AAGCCTTTGA CAAAATTCAA CAACCCTTCA TGCTAAAAAC

3841 TCTCAATAAA TTAGGTATTG ATGGGACGTA TTTCAAAATA ATAAGAGCTA TCTATGACAA

3901 ACCCACAGCC AATATCATAC TGAATGGGCA AAAACTGGAA GCATTCCCTT TGAAAACCGG

3961 CACAAGACAG GGATGCCCTC TCTCACCGCT CCTATTCAAC ATAGTGTTGG AAGTTCTGGC

4021 CAGGGCAATC AGGCAGGAGA AGGAAATAAA GGGTATTCAA TTAGGAAAAG AGGAAGTCAA

4081 ATTGTCCCTG TTTGCAGACG ACATGATTGT TTATCTAGAA AACCCCATCG TCTCAGCCCA

4141 AAATCTCCTT AAGCTGATAA GCAACTTCAG CAAAGTCTCA GGATACAAAA TCAATGTACA

4201 AAAATCACAA GCATTCTTAT ACACCAACAA CAGACAAACA GAGAGCCAAA TCATGGGTGA

4261 ACTCCCATTC ACAATTGCTT CAAAGAGAAT AAAATACCTA GGAATCCAAC TTACAAGGGA

4321 TGTGAAGGAC CTCTTCAAGG AGAACTACAA ACCACTGCTC AAGGAAATAA AAGAGGAGAC

4381 AAACAAATGG AAGAACATTC CATGCTCATG GGTAGGAAGA ATCAATATCG TGAAAATGGC

4441 CATACTGCCC AAGGTAATTT ACAGATTCAA TGCCATCCCC ATCAAGCTAC CAATGACTTT

4501 CTTCACAGAA TTGGAAAAAA CTACTTTAAA GTTCATATGG AACCAAAAAA GAGCCCGCAT

4561 TGCCAAGTCA ATCCTAAGCC AAAAGAACAA AGCTGGAGGC ATCACACTAC CTGACTTCAA

4621 ACTATACTAC AAGGCTACAG TAACCAAAAC AGCATGGTAC TGGTACCAAA ACAGAGATAT

4681 AGATCAATGG AACAGAACAG AGCCCTCAGA AATAATGCCG CATATCTACA ACTATCTGAT

4741 CTTTGACAAA CCTGAGAAAA CAAGCAATG GGGAAAGGAT TCCCTATTTA ATAAATGGTG

4801 CTGGGAAAAC TGGCTAGCCA TATGTAGAAA GCTGAAACTG GATCCCTTCC TTACACCTTA

4861 TACAAAAATC AATTCAAGAT GGATTAAAGA TTTAAACGTT AAACCTAAAA CCATAAAAAC

4921 CCTAGAAGAA AACCTAGGCA TTACCATTCA GGACATAGGC GTGGGCAAGG ACTTCATGTC

4981 CAAAACACCA AAAGCAATGG CAACAAAGA CAAAATTGAC AAATGGGATC TAATTAAACT

5041 AAAGAGCTTC TGCACAGCAA AAGAAACTAC CATCAGAGTG AACAGGCAAC CTACAACATG

5101 GGAGAAAATT TTTGCAACCT ACTCATCTGA CAAAGGGCTA ATATCCAGAA TCTACAATGA

5161 ACTCAAACAA ATTTACAAGA AAAAAACAAA CAACCCCATC AAAAAGTGGG CGAAGGACAT
```

TABLE 8-continued

Plasmid and mRNA construct sequences

```
5221 GAACAGACAC TTCTCAAAAG AAGACATTTA TGCAGCCAAA AAACACATGA AGAAATGCTC

5281 ATCATCACTG GCCATCAGAG AAATGCAAAT CAAAACCACT ATGAGATATC ATCTCACACC

5341 AGTTAGAATG GCAATCATTA AAAAGTCAGG AAACAACAGG TGCTGGAGAG GATGCGGAGA

5401 AATAGGAACA CTTTTACACT GTTGGTGGGA CTGTAAACTA GTTCAACCAT TGTGGAAGTC

5461 AGTGTGGCGA TTCCTCAGGG ATCTAGAACT AGAAATACCA TTTGACCCAG CCATCCCATT

5521 ACTGGGTATA TACCCAAATG AGTATAAATC ATGCTGCTAT AAAGACACAT GCACACGTAT

5581 GTTTATTGCG GCACTATTCA CAATAGCAAA GACTTGGAAC CAACCCAAAT GTCCAACAAT

5641 GATAGACTGG ATTAAGAAAA TGTGGCACAT ATACACCATG GAATACTATG CAGCCATAAA

5701 AAATGATGAG TTCATATCCT TTGTAGGGAC ATGGATGAAA TTGGAAACCA TCATTCTCAG

5761 TAAACTATCG CAAGAACAAA AAACCAAACA CCGCATATTC TCACTCATAG GTGGGAATTG

5821 AACAATGAGA TCACATGGAC ACAGGAAGGG GAATATCACA CTCTGGGGAC TGTGGTGGGG

5881 TCGGGGGAGG GGGGAGGGAT AGCATTGGGA GATATACCTA ATGCTAGATG ACACATTAGT

5941 GGGTGCAGCG CACCAGCATG GCACATGTAT ACGGATCCGA ATTCTCGACG GATCGATCCG

6001 AACAAACGAC CCAACACCCG TGCGTTTTAT TCTGTCTTTT TATTGCCGAT CCCCTCAGAA

6061 GAACTCGTCA AGAAGGCGAT AGAAGGCGAT GCGCTGCGAA TCGGGAGCGG CGATACCGTA

6121 AAGCACGAGG AAGCGGTCAG CCCATTCGCC GCCAAGCTCT TCAGCAATAT CACGGGTAGC

6181 CAACGCTATG TCCTGATAGC GGTCGGCCGC TTTACTTGTA CAGCTCGTCC ATGCCGAGAG

6241 TGATCCCGGC GGCGGTCACG AACTCCAGCA GGACCATGTG ATCGCGCTTC TCGTTGGGGT

6301 CTTTGCTCAG GGCGGACTGG GTGCTCAGGT AGTGGTTGTC GGGCAGCAGC ACGGGGCCGT

6361 CGCCGATGGG GGTGTTCTGC TGGTAGTGGT CGGCCAGGTG AGTCCAGGAG ATGTTTCAGC

6421 ACTGTTGCCT TTAGTCTCGA GGCAACTTAG ACAACTGAGT ATTGATCTGA GCACAGCAGG

6481 GTGTGAGCTG TTTGAAGATA CTGGGGTTGG GGGTGAAGAA ACTGCAGAGG ACTAACTGGG

6541 CTGAGACCCA GTGGCAATGT TTTAGGGCCT AAGGAATGCC TCTGAAAATC TAGATGGACA

6601 ACTTTGACTT TGAGAAAAGA GAGGTGGAAA TGAGGAAAAT GACTTTTCTT TATTAGATTT

6661 CGGTAGAAAG AACTTTCATC TTTCCCCTAT TTTTGTTATT CGTTTTAAAA CATCTATCTG

6721 GAGGCAGGAC AAGTATGGTC ATTAAAAAGA TGCAGGCAGA AGGCATATAT TGGCTCAGTC

6781 AAAGTGGGGA ACTTTGGTGG CCAAACATAC ATTGCTAAGG CTATTCCTAT ATCAGCTGGA

6841 CACATATAAA ATGCTGCTAA TGCTTCATTA CAAACTTATA TCCTTTAATT CCAGATGGGG

6901 GCAAAGTATG TCCAGGGGTG AGGAACAATT GAAACATTTG GGCTGGAGTA GATTTTGAAA

6961 GTCAGCTCTG TGTGTGTGTG TGTGTGTGTG TGTGTGAGAG CGTGTGTTTC TTTTAACGTT

7021 TTCAGCCTAC AGCATACAGG GTTCATGGTG GCAAGAAGAT AACAAGATTT AAATTATGGC

7081 CAGTGACTAG TGCTGCAAGA AGAACAACTA CCTGCATTTA ATGGGAAAGC AAAATCTCAG

7141 GCTTTGAGGG AAGTTAACAT AGGCTTGATT CTGGGTGGAA GCTGGGTGTG TAGTTATCTG

7201 GAGGCCAGGC TGGAGCTCTC AGCTCACTAT GGGTTCATCT TTATTGTCTC CTTTCATCTC

7261 AACAGCTGCA CGCTGCCGTC CTCGATGTTG TGGCGGATCT TGAAGTTCAC CTTGATGCCG

7321 TTCTTCTGCT TGTCGGCCAT GATATAGACG TTGTGGCTGT TGTAGTTGTA CTCCAGCTTG

7381 TGCCCCAGGA TGTTGCCGTC CTCCTTGAAG TCGATGCCCT TCAGCTCGAT GCGGTTCACC

7441 AGGGTGTCGC CCTCGAACTT CACCTCGGCG CGGGTCTTGT AGTTGCCGTC GTCCTTGAAG

7501 AAGATGGTGC GCTCCTGGAC GTAGCCTTCG GGCATGGCGG ACTTGAAGAA GTCGTGCTGC
```

TABLE 8-continued

Plasmid and mRNA construct sequences

```
7561 TTCATGTGGT CGGGGTAGCG GCTGAAGCAC TGCACGCCGT AGGTCAGGGT GGTCACGAGG

7621 GTGGGCCAGG GCACGGGCAG CTTGCCGGTG GTGCAGATGA ACTTCAGGGT CAGCTTGCCG

7681 TAGGTGGCAT CGCCCTCGCC CTCGCCGGAC ACGCTGAACT TGTGGCCGTT TACGTCGCCG

7741 TCCAGCTCGA CCAGGATGGG CACCACCCCG GTGAACAGCT CCTCGCCCTT GCTCACCATA

7801 GGGCCGGGAT TCTCCTCCAC GTCACCGCAT GTTAGAAGAC TTCCTCTGCC CTCCATGTTC

7861 TCGTAGGAGT CGGCGTCCTC TTCGTGGTTA GGTCCAGGTT GGCCTCTGAT AGACCGCAGC

7921 TGAGGAGCGG CGTACAGAAT GCCTCTCATG TCCTCATAGC TGCCGCTGCC TTGTGGAGGC

7981 TTCTCGTGCT TCAGTGTCTC GTATGTCTCT TGATTCCGGG TGCTCAGGCC GGTGTACACG

8041 CCATCAGATT TCTCGTAGCT GGTGATGGCG GCCTTCCGCA CTTGGATCTT CAGCCGTCTG

8101 CAGTACAGGG TGATGACCAG AGACAGCAGC AGGACACCAC ATGTGCCAGC CAGAGGGGCC

8161 CAAATGTAGA TATCCAGGCC TCTGGTATGC ACAGCTCCGC CTGCAGCAGG TCTACAGGCT

8221 TCAGGTCTGA GAGACAGAGG CTGGCTGGCG ATTGTAGGAG CTGGTGTAGG TGGTCTAGGA

8281 GCGGGTGTTG TTGTAGGCTT GGCGGGCAGA AACACGGGCA CGAAGTGGCT GAAGTACATG

8341 ATGCTATTGC TCAGGGCTCC GCTTCCTCCG CCGCCTGATT TGATTTCCAG CTTGGTGCCT

8401 CCGCCAAATG TCCAAGGGCT CTCGTCGTAC TGCTGGCAGT AGTAGATGCC GAAGTCCTCG

8461 TACTGCAGGC TGCTGATTGT CAGGGTGTAG TCGGTGCCAG AGCCGCTGCC AGAAAATCTG

8521 CTTGGCACGC CGCTTTCCAG TCTGTTGGCC CGGTAGATCA GTGTCTTAGG GGCCTTGCCA

8581 GGCTTCTGCT GGAACCAGCT CAGGTAGCTG TTGATGTCCT GGCTGGCTCT ACAGGTGATG

8641 GTCACTCTAT CGCCCACAGA GGCAGACAGG CTGCTAGGGC TCTGTGTCAT CTGGATATCA

8701 GAGCCACCAC CGCCAGATCC ACCGCCACCT GATCCTCCGC CTCCGCTAGA AACTGTCACT

8761 GTGGTGCCCT GGCCCCACAC ATCGAAGTAC CAGTCGTAGC CTCTTCTGGT GCAGAAGTAC

8821 ACGGCGGTAT CCTCGGCTCT CAGGCTGTTG ATCTGCAGGT AGGCGGTGTT CTTGCTGTCG

8881 TCCAGGCTGA AGGTGAATCT GCCCTTAAAG CTATCGGCGT AGGTTGGCTC GCCGGTGTGG

8941 GTATTGATCC AGCCCATCCA CTCAAGGCCT TTTCCAGGGG CCTGTCGGAC CCAGTTCATG

9001 CCGTAGTTGG TGAAGGTGTA GCCGCTGGCG GCACAGCTGA TTCTGACAGA TCCGCCAGGT

9061 TTCACAAGTC CGCCGCCAGA CTGAACCAGC TGGATCTCAG AGATGCTACA GGCCACTGTT

9121 CCCAGCAGCA GCAGAGACTG CAGCCACATT CGAAGCTTGA GCTCGAGATC TGAGTCCGGT

9181 AGCGCTAGCG GATCTGACGG TTCACTAAAC CAGCTCTGCT TATATAGACC TCCCACCGTA

9241 CACGCCTACC GCCCATTTGC GTCAATGGGG CGGAGTTGTT ACGACATTTT GGAAAGTCCC

9301 GTTGATTTTG GTGCCAAAAC AAACTCCCAT TGACGTCAAT GGGGTGGAGA CTTGGAAATC

9361 CCCGTGAGTC AAACCGCTAT CCACGCCCAT TGATGTACTG CCAAAACCGC ATCACCATGG

9421 TAATAGCGAT GACTAATACG TAGATGTACT GCCAAGTAGG AAAGTCCCAT AAGGTCATGT

9481 ACTGGGCATA ATGCCAGGCG GGCCATTTAC CGTCATTGAC GTCAATAGGG GGCGTACTTG

9541 GCATATGATA CACTTGATGT ACTGCCAAGT GGGCAGTTTA CCGTAAATAC TCCACCCATT

9601 GACGTCAATG GAAAGTCCCT ATTGGCGTTA CTATGGGAAC ATACGTCATT ATTGACGTCA

9661 ATGGGCGGGG GTCGTTGGGC GGTCAGCCAG GCGGGCCATT TACCGTAAGT TATGTAACGC

9721 GGAACTCCAT ATATGGGCTA TGAACTAATG ACCCCGTAAT TGATTACTAT TAGCCCGGGG

9781 GATCCAGACA TGATAAGATA CATTGATGAG TTTGGACAAA CCACAACTAG AATGCAGTGA

9841 AAAAAATGCT TTATTTGTGA AATTTGTGAT GCTATTGCTT TATTTGTAAC CATTATAAGC
```

TABLE 8-continued

Plasmid and mRNA construct sequences

```
 9901 TGCAATAAAC AAGTTAACAA CAACAATTGC ATTCATTTTA TGTTTCAGGT TCAGGGGGAG

9961 GTGTGGGAGG TTTTTTAAAG CAAGTAAAAC CTCTACAAAT GTGGTATGGC TGATTATGAT

10021 CCGGCTGCCT CGCGCGTTTC GGTGATGACG GTGAAAACCT CTGACACATG CAGCTCCCGG

10081 AGACGGTCAC AGCTTGTCTG TAAGCGGATG CCGGGAGCAG ACAAGCCCGT CAGGGCGCGT

10141 CAGCGGGTGT TGGCGGGTGT CGGGGCGCAG CCATGAGGTC GATCGACTCT AGAGGATCGA

10201 TCCCCGCCCC GGACGAACTA AACCTGACTA CGACATCTCT GCCCCTTCTT CGCGGGGCAG

10261 TGCATGTAAT CCCTTCAGTT GGTTGGTACA ACTTGCCAAC TGGGCCCTGT TCCACATGTG

10321 ACACGGGGGG GGACCAAACA CAAAGGGGTT CTCTGACTGT AGTTGACATC CTTATAAATG

10381 GATGTGCACA TTTGCCAACA CTGAGTGGCT TTCATCCTGG AGCAGACTTT GCAGTCTGTG

10441 GACTGCAACA CAACATTGCC TTTATGTGTA ACTCTTGGCT GAAGCTCTTA CACCAATGCT

10501 GGGGGACATG TACCTCCCAG GGGCCCAGGA AGACTACGGG AGGCTACACC AACGTCAATC

10561 AGAGGGGCCT GTGTAGCTAC CGATAAGCGG ACCCTCAAGA GGGCATTAGC AATAGTGTTT

10621 ATAAGGCCCC CTTGTTAACC CTAAACGGGT AGCATATGCT TCCCGGGTAG TAGTATATAC

10681 TATCCAGACT AACCCTAATT CAATAGCATA TGTTACCCAA CGGGAAGCAT ATGCTATCGA

10741 ATTAGGGTTA GTAAAAGGGT CCTAAGGAAC AGCGATATCT CCCACCCCAT GAGCTGTCAC

10801 GGTTTTATTT ACATGGGGTC AGGATTCCAC GAGGGTAGTG AACCATTTTA GTCACAAGGG

10861 CAGTGGCTGA AGATCAAGGA GCGGGCAGTG AACTCTCCTG AATCTTCGCC TGCTTCTTCA

10921 TTCTCCTTCG TTTAGCTAAT AGAATAACTG CTGAGTTGTG AACAGTAAGG TGTATGTGAG

10981 GTGCTCGAAA ACAAGGTTTC AGGTGACGCC CCCAGAATAA AATTTGGACG GGGGGTTCAG

11041 TGGTGGCATT GTGCTATGAC ACCAATATAA CCCTCACAAA CCCCTTGGGC AATAAATACT

11101 AGTGTAGGAA TGAAACATTC TGAATATCTT TAACAATAGA AATCCATGGG GTGGGGACAA

11161 GCCGTAAAGA CTGGATGTCC ATCTCACACG AATTTATGGC TATGGGCAAC ACATAATCCT

11221 AGTGCAATAT GATACTGGGG TTATTAAGAT GTGTCCCAGG CAGGGACCAA GACAGGTGAA

11281 CCATGTTGTT ACACTCTATT TGTAACAAGG GGAAAGAGAG TGGACGCCGA CAGCAGCGGA

11341 CTCCACTGGT TGTCTCTAAC ACCCCCGAAA ATTAAACGGG GCTCCACGCC AATGGGGCCC

11401 ATAAACAAAG ACAAGTGGCC ACTCTTTTTT TTGAAATTGT GGAGTGGGGG CACGCGTCAG

11461 CCCCCACACG CCGCCCTGCG GTTTTGGACT GTAAAATAAG GGTGTAATAA CTTGGCTGAT

11521 TGTAACCCCG CTAACCACTG CGGTCAAACC ACTTGCCCAC AAAACCACTA ATGGCACCCC

11581 GGGGAATACC TGCATAAGTA GGTGGGCGGG CCAAGATAGG GGCGCGATTG CTGCGATCTG

11641 GAGGACAAAT TACACACACT TGCGCCTGAG CGCCAAGCAC AGGGTTGTTG GTCCTCATAT

11701 TCACGAGGTC GCTGAGAGCA CGGTGGGCTA ATGTTGCCAT GGGTAGCATA TACTACCCAA

11761 ATATCTGGAT AGCATATGCT ATCCTAATCT ATATCTGGGT AGCATAGGCT ATCCTAATCT

11821 ATATCTGGGT AGCATATGCT ATCCTAATCT ATATCTGGGT AGTATATGCT ATCCTAATTT

11881 ATATCTGGGT AGCATAGGCT ATCCTAATCT ATATCTGGGT AGCATATGCT ATCCTAATCT

11941 ATATCTGGGT AGTATATGCT ATCCTAATCT GTATCCGGGT AGCATATGCT ATCCTAATAG

12001 AGATTAGGGT AGTATATGCT ATCCTAATTT ATATCTGGGT AGCATATACT ACCCAAATAT

12061 CTGGATAGCA TATGCTATCC TAATCTATAT CTGGGTAGCA TATGCTATCC TAATCTATAT

12121 CTGGGTAGCA TAGGCTATCC TAATCTATAT CTGGGTAGCA TATGCTATCC TAATCTATAT

12181 CTGGGTAGTA TATGCTATCC TAATTTATAT CTGGGTAGCA TAGGCTATCC TAATCTATAT
```

TABLE 8-continued

Plasmid and mRNA construct sequences

```
12241 CTGGGTAGCA TATGCTATCC TAATCTATAT CTGGGTAGTA TATGCTATCC TAATCTGTAT

12301 CCGGGTAGCA TATGCTATCC TCATGCATAT ACAGTCAGCA TATGATACCC AGTAGTAGAG

12361 TGGGAGTGCT ATCCTTTGCA TATGCCGCCA CCTCCCAAGG GGGCGTGAAT TTTCGCTGCT

12421 TGTCCTTTTC CTGCATGCTG GTTGCTCCCA TTCTTAGGTG AATTTAAGGA GGCCAGGCTA

12481 AAGCCGTCGC ATGTCTGATT GCTCACCAGG TAAATGTCGC TAATGTTTTC CAACGCGAGA

12541 AGGTGTTGAG CGCGGAGCTG AGTGACGTGA CAACATGGGT ATGCCCAATT GCCCCATGTT

12601 GGGAGGACGA AAATGGTGAC AAGACAGATG GCCAGAAATA CACCAACAGC ACGCATGATG

12661 TCTACTGGGG ATTTATTCTT TAGTGCGGGG GAATACACGG CTTTTAATAC GATTGAGGGC

12721 GTCTCCTAAC AAGTTACATC ACTCCTGCCC TTCCTCACCC TCATCTCCAT CACCTCCTTC

12781 ATCTCCGTCA TCTCCGTCAT CACCCTCCGC GGCAGCCCCT TCCACCATAG GTGGAAACCA

12841 GGGAGGCAAA TCTACTCCAT CGTCAAAGCT GCACACAGTC ACCCTGATAT TGCAGGTAGG

12901 AGCGGGCTTT GTCATAACAA GGTCCTTAAT CGCATCCTTC AAAACCTCAG CAAATATATG

12961 AGTTTGTAAA AAGACCATGA AATAACAGAC AATGGACTCC CTTAGCGGGC CAGGTTGTGG

13021 GCCGGGTCCA GGGGCCATTC CAAAGGGGAG ACGACTCAAT GGTGTAAGAC GACATTGTGG

13081 AATAGCAAGG GCAGTTCCTC GCCTTAGGTT GTAAAGGGAG GTCTTACTAC CTCCATATAC

13141 GAACACACCG GCGACCCAAG TTCCTTCGTC GGTAGTCCTT TCTACGTGAC TCCTAGCCAG

13201 GAGAGCTCTT AAACCTTCTG CAATGTTCTC AAATTTCGGG TTGGAACCTC CTTGACCACG

13261 ATGCTTTCCA AACCACCCTC CTTTTTTGCG CCTGCCTCCA TCACCCTGAC CCCGGGGTCC

13321 AGTGCTTGGG CCTTCTCCTG GGTCATCTGC GGGGCCCTGC TCTATCGCTC CCGGGGGCAC

13381 GTCAGGCTCA CCATCTGGGC CACCTTCTTG GTGGTATTCA AAATAATCGG CTTCCCCTAC

13441 AGGGTGGAAA AATGGCCTTC TACCTGGAGG GGGCCTGCGC GGTGGAGACC CGGATGATGA

13501 TGACTGACTA CTGGGACTCC TGGGCCTCTT TTCTCCACGT CCACGACCTC TCCCCCTGGC

13561 TCTTTCACGA CTTCCCCCCC TGGCTCTTTC ACGTCCTCTA CCCCGGCGGC CTCCACTACC

13621 TCCTCGACCC CGGCCTCCAC TACCTCCTCG ACCCCGGCCT CCACTGCCTC CTCGACCCCG

13681 GCCTCCACCT CCTGCTCCTG CCCCTCCTGC TCCTGCCCCT CCTCCTGCTC CTGCCCCTCC

13741 TGCCCCTCCT GCTCCTGCCC CTCCTGCCCC TCCTGCTCCT GCCCCTCCTG CCCCTCCTGC

13801 TCCTGCCCCT CCTGCCCCTC CTCCTGCTCC TGCCCCTCCT GCCCCTCCTC CTGCTCCTGC

13861 CCCTCCTGCC CCTCCTGCTC CTGCCCCTCC TGCCCCTCCT GCTCCTGCCC CTCCTGCCCC

13921 TCCTGCTCCT GCCCCTCCTG CTCCTGCCCC TCCTGCTCCT GCCCCTCCTG CTCCTGCCCC

13981 TCCTGCCCCT CCTGCCCCTC CTCCTGCTCC TGCCCCTCCT GCTCCTGCCC CTCCTGCCCC

14041 TCCTGCCCCT CCTGCTCCTG CCCCTCCTCC TGCTCCTGCC CCTCCTGCCC CTCCTGCCCC

14101 TCCTCCTGCT CCTGCCCCTC CTGCCCCTCC TCCTGCTCCT GCCCCTCCTC CTGCTCCTGC

14161 CCCTCCTGCC CCTCCTGCCC CTCCTCCTGC TCCTGCCCCT CCTGCCCCTC CTCCTGCTCC

14221 TGCCCCTCCT CCTGCTCCTG CCCCTCCTGC CCCTCCTGCC CCTCCTGCTC CTCCTGCCCC

14281 TCCTCCTGCT CCTGCCCCTC CTGCCCCTCC TGCCCCTCCT GCCCCTCCTC CTGCTCCTGC

14341 CCCTCCTCCT GCTCCTGCCC CTCCTGCTCC TGCCCCTCCC GCTCCTGCTC CTGCTCCTGT

14401 TCCACCGTGG GTCCCTTTGC AGCCAATGCA ACTTGGACGT TTTTGGGGTC TCCGGACACC

14461 ATCTCTATGT CTTGGCCCTG ATCCTGAGCC GCCCGGGGCT CCTGGTCTTC CGCCTCCTCG

14521 TCCTCGTCCT CTTCCCCGTC CTCGTCCATG GTTATCACCC CCTCTTCTTT GAGGTCCACT
```

TABLE 8-continued

Plasmid and mRNA construct sequences

```
14581 GCCGCCGGAG CCTTCTGGTC CAGATGTGTC TCCCTTCTCT CCTAGGCCAT TTCCAGGTCC

14641 TGTACCTGGC CCCTCGTCAG ACATGATTCA CACTAAAAGA GATCAATAGA CATCTTTATT

14701 AGACGACGCT CAGTGAATAC AGGGAGTGCA GACTCCTGCC CCCTCCAACA GCCCCCCCAC

14761 CCTCATCCCC TTCATGGTCG CTGTCAGACA GATCCAGGTC TGAAAATTCC CCATCCTCCG

14821 AACCATCCTC GTCCTCATCA CCAATTACTC GCAGCCCGGA AAACTCCCGC TGAACATCCT

14881 CAAGATTTGC GTCCTGAGCC TCAAGCCAGG CCTCAAATTC CTCGTCCCCC TTTTTGCTGG

14941 ACGGTAGGGA TGGGGATTCT CGGGACCCCT CCTCTTCCTC TTCAAGGTCA CCAGACAGAG

15001 ATGCTACTGG GGCAACGGAA GAAAAGCTGG GTGCGGCCTG TGAGGATCAG CTTATCGATG

15061 ATAAGCTGTC AAACATGAGA ATTCTTGAAG ACGAAAGGGC CTCGTGATAC GCCTATTTTT

15121 ATAGGTTAAT GTCATGATAA TAATGGTTTC TTAGACGTCA GGTGGCACTT TTCGGGGAAA

15181 TGTGCGCGGA ACCCCTATTT GTTTATTTTT CTAAATACAT TCAAATATGT ATCCGCTCAT

15241 GAGACAATAA CCCTGATAAA TGCTTCAATA ATATTGAAAA AGGAAGAGTA TGAGTATTCA

15301 ACATTTCCGT GTCGCCCTTA TTCCCTTTTT TGCGGCATTT TGCCTTCCTG TTTTTGCTCA

15361 CCCAGAAACG CTGGTGAAAG TAAAAGATGC TGAAGATCAG TTGGGTGCAC GAGTGGGTTA

15421 CATCGAACTG GATCTCAACA GCGGTAAGAT CCTTGAGAGT TTTCGCCCCG AAGAACGTTT

15481 TCCAATGATG AGCACTTTTA AAGTTCTGCT ATGTGGCGCG GTATTATCCC GTGTTGACGC

15541 CGGGCAAGAG CAACTCGGTC GCCGCATACA CTATTCTCAG AATGACTTGG TTGAGTACTC

15601 ACCAGTCACA GAAAAGCATC TTACGGATGG CATGACAGTA AGAGAATTAT GCAGTGCTGC

15661 CATAACCATG AGTGATAACA CTGCGGCCAA CTTACTTCTG ACAACGATCG GAGGACCGAA

15721 GGAGCTAACC GCTTTTTTGC ACAACATGGG GGATCATGTA ACTCGCCTTG ATCGTTGGGA

15781 ACCGGAGCTG AATGAAGCCA TACCAAACGA CGAGCGTGAC ACCACGATGC CTGCAGCAAT

15841 GGCAACAACG TTGCGCAAAC TATTAACTGG CGAACTACTT ACTCTAGCTT CCCGGCAACA

15901 ATTAATAGAC TGGATGGAGG CGGATAAAGT TGCAGGACCA CTTCTGCGCT CGGCCCTTCC

15961 GGCTGGCTGG TTTATTGCTG ATAAATCTGG AGCCGGTGAG CGTGGGTCTC GCGGTATCAT

16021 TGCAGCACTG GGGCCAGATG GTAAGCCCTC CCGTATCGTA GTTATCTACA CGACGGGGAG

16081 TCAGGCAACT ATGGATGAAC GAAATAGACA GATCGCTGAG ATAGGTGCCT CACTGATTAA

16141 GCATTGGTAA CTGTCAGACC AAGTTTACTC ATATATACTT TAGATTGATT TAAAACTTCA

16201 TTTTTAATTT AAAAGGATCT AGGTGAAGAT CCTTTTTGAT AATCTCATGA CCAAAATCCC

16261 TTAACGTGAG TTTTCGTTCC ACTGAGCGTC AGACCCCGTA GAAAAGATCA AAGGATCTTC

16321 TTGAGATCCT TTTTTTCTGC GCGTAATCTG CTGCTTGCAA ACAAAAAAAC CACCGCTACC

16381 AGCGGTGGTT TGTTTGCCGG ATCAAGAGCT ACCAACTCTT TTTCCGAAGG TAACTGGCTT

16441 CAGCAGAGCG CAGATACCAA ATACTGTCCT TCTAGTGTAG CCGTAGTTAG GCCACCACTT

16501 CAAGAACTCT GTAGCACCGC CTACATACCT CGCTCTGCTA ATCCTGTTAC CAGTGGCTGC

16561 TGCCAGTGGC GATAAGTCGT GTCTTACCGG GTTGGACTCA AGACGATAGT TACCGGATAA

16621 GGCGCAGCGG TCGGGCTGAA CGGGGGGTTC GTGCACACAG CCCAGCTTGG AGCGAACGAC

16681 CTACACCGAA CTGAGATACC TACAGCGTGA GCTATGAGAA AGCGCCACGC TTCCCGAAGG

16741 GAGAAAGGCG GACAGGTATC CGGTAAGCGG CAGGGTCGGA ACAGGAGAGC GCACGAGGGA

16801 GCTTCCAGGG GGAAACGCCT GGTATCTTTA TAGTCCTGTC GGGTTTCGCC ACCTCTGACT

16861 TGAGCGTCGA TTTTTGTGAT GCTCGTCAGG GGGGCGGAGC CTATGGAAAA ACGCCAGCAA
```

TABLE 8-continued

Plasmid and mRNA construct sequences

16921 CGCGGCCTTT TTACGGTTCC TGGCCTTTTG CTGGCCTTTT GCTCACATGT TCTTTCCTGC

16981 GTTATCCCCT GATTCTGTGG ATAACCGTAT TACCGCCTTT GAGTGAGCTG ATACCGCTCG

17041 CCGCAGCCGA ACGACCGAGC GCAGCGAGTC AGTGAGCGAG GAAGCGGAAG AGCGCCTGAT

17101 GCGGTATTTT CTCCTTACGC ATCTGTGCGG TATTTCACAC CGCATATGGT GCACTCTCAG

17161 TACAATCTGC TCTGATGCCG CATAGTTAAG CCAGCTGTGG AATGTGTGTC AGTTAGGGTG

17221 TGGAAAGTCC CCAGGCTCCC CAGCAGGCAG AAGTATGCAA AGCATGCATC TCAATTAGTC

17281 AGCAACCAGG TGTGGAAAGT CCCCAGGCTC CCCAGCAGGC AGAAGTATGC AAAGCATGCA

17341 TCTCAATTAG TCAGCAACCA TAGTCCCGCC CCTAACTCCG CCCATCCCGC CCCTAACTCC

17401 GCCCAGTTCC GCCCATTCTC CGCCCCATGG CTGACTAATT TTTTTTATTT ATGCAGAGGC

17461 CGAGGCCGCC TCGGCCTCTG AGCTATTCCA GAAGTAGTGA GGAGGCTTTT TTGGAGGCCT

17521 AGGCTTTTGC AAAAAGCTTG CATGCCTGCA GGTCGGCCGC CACGACCGGT GCCGCCACCA

17581 TCCCCTGACC CACGCCCCTG ACCCCTCACA AGGAGACGAC CTTCCATGAC CGAGTACAAG

17641 CCCACGGTGC GCCTCGCCAC CCGCGACGAC GTCCCCGGG CCGTACGCAC CCTCGCCGCC

17701 GCGTTCGCCG ACTACCCCGC CACGCGCCAC ACCGTCGACC CGGACCGCCA CATCGAGCGG

17761 GTCACCGAGC TGCAAGAACT CTTCCTCACG CGCGTCGGGC TCGACATCGG CAAGGTGTGG

17821 GTCGCGGACG ACGGCGCCGC GGTGGCGGTC TGGACCACGC CGGAGAGCGT CGAAGCGGGG

17881 GCGGTGTTCG CCGAGATCGG CCCGCGCATG GCCGAGTTGA GCGGTTCCCG GCTGGCCGCG

17941 CAGCAACAGA TGGAAGGCCT CCTGGCGCCG CACCGGCCCA AGGAGCCCGC GTGGTTCCTG

18001 GCCACCGTCG GCGTCTCGCC CGACCACCAG GGCAAGGGTC TGGGCAGCGC CGTCGTGCTC

18061 CCCGGAGTGG AGGCGGCCGA GCGCGCCGGG GTGCCCGCCT TCCTGGAGAC CTCCGCGCCC

18121 CGCAACCTCC CCTTCTACGA GCGGCTCGGC TTCACCGTCA CCGCCGACGT CGAGGTGCCC

18181 GAAGGACCGC GCACCTGGTG CATGACCCGC AAGCCCGGTG CCTGACGCCC GCCCCACGAC

18241 CCGCAGCGCC CGACCGAAAG GAGCGCACGA CCCCATGGCT CCGACCGAAG CCGACCCGGG

18301 CGGCCCCGCC GACCCCGCAC CCGCCCCCGA GGCCCACCGA CTCTAGAGGA TCATAATCAG

18361 CCATACCACA TTTGTAGAGG TTTTACTTGC TTTAAAAAAC CTCCCACACC TCCCCCTGAA

18421 CCTGAAACAT AAAATGAATG CAATTGTTGT TGTTAACTTG TTTATTGCAG CTTATAATGG

18481 TTACAAATAA AGCAATAGCA TCACAAATTT CACAAATAAA GCATTTTTTT CACTGCATTC

18541 TAGTTGTGGT TTGTCCAAAC TCATCAATGT ATCTTATCAT GTCTGGATCA CTCGCCGATA

18601 GTGGAAACCG ACGCCCCAGC ACTCGTCCGA GGGCAAAGGA ATAGGGGAGA TGGGGGAGGC

18661 TAACTGAAAC ACGGAAGGAG ACAATACCGG AAGGAACCCG CGCTATGACG GCAATAAAAA

18721 GACAGAATAA AACGCACGGG TGTTGGGTCG TTTGTTCATA AACGCGGGGT TCGGTCCCAG

18781 GGCTGGCACT CTGTCGATAC CCCACCGAGA CCCCATTGGG GCCAATACGC CCGCGTTTCT

18841 TCCTTTTCCC CACCCCACCC CCCAAGTTCG GGTGAAGGCC CAGGGCTCGC AGCCAACGTC

18901 GGGGCGGCAG GCCCTGCCAT AGCCACTGGC CCCGTGGGTT AGGGACGGGG TCCCCCATGG

18961 GGAATGGTTT ATGGTTCGTG GGGGTTATTA TTTTGGGCGT TGCGTGGGGT CTGGTCCACG

19021 ACTGGACTGA GCAGACAGAC CCATGGTTTT TGGATGGCCT GGGCATGGAC CGCATGTACT

19081 GGCGCGACAC GAACACCGGG CGTCTGTGGC TGCCAAACAC CCCCGACCCC CAAAAACCAC

19141 CGCGCGGATT TCTGGCGTGC CAAGCTAGTC GACCAATTCT CATGTTTGAC AGCTTATCAT

19201 CGCAGATCCG GGCAACGTTG TTGCATTGCT GCAGGCGCAG AACTGGTAGG TATGGAAGAT

TABLE 8-continued

Plasmid and mRNA construct sequences

19261 CTCTAGAAGC TGGGTACCAG CTGCTAGCAA GCTTGCTAGC GGCCGGCTCG AGTTTACTCC

19321 CTATCAGTGA TAGAGAACGT ATGTCGAGTT TACTCCCTAT CAGTGATAGA GAACGATGTC

19381 GAGTTTACTC CCTATCAGTG ATAGAGAACG TATGTCGAGT TTACTCCCTA TCAGTGATAG

19441 AGAACGTATG TCGAGTTTAC TCCCTATCAG TGATAGAGAA CGTATGTCGA GTTTATCCCT

19501 ATCAGTGATA GAGAACGTAT GTCGAGTTTA CTCCCTATCA GTGATAGAGA ACGTATGTCG

19561 AGGTAGGCGT GTACGGTGGG AGGCCTATAT AAGCAGAGCT CGTTTAGTGA ACCGTCAGAT

19621 CGCCG
(SEQ ID NO: 40)

LINE-1 plasmid Her2-Cd3z-T2A GFPintron (SEQ ID NO: 41)

1 CGGCCGCGGG GGGAGGAGCC AAGATGGCCG AATAGGAACA GCTCCGGTCT CAGCTCCCA

61 GCGTGAGCGA CGCAGAAGAC GGTGATTTCT GCATTTCCAT CTGAGGTACC GGGTTCATCT

121 CACTAGGGAG TGCCAGACAG TGGGCGCAGG CCAGTGTGTG TGCGCACCGT GCGCGAGCCG

181 AAGCAGGGCG AGGCATTGCC TCACCTGGGA AGCGCAAGGG GTCAGGGAGT TCCCTTTCCG

241 AGTCAAAGAA AGGGGTGACG GACGCACCTG AAAATCGGG TCACTCCCAC CCGAATATTG

301 CGCTTTTCAG ACCGGCTTAA GAAACGGCGC ACCACGAGAC TATATCCCAC ACCTGGCTCG

361 GAGGGTCCTA CGCCCACGGA ATCTCGCTGA TTGCTAGCAC AGCAGTCTGA GATCAAACTG

421 CAAGGCGGCA ACGAGGCTGG GGGAGGGGCG CCCGCCATTG CCCAGGCTTG CTTAGGTAAA

481 CAAAGCAGCA GGGAAGCTCG AACTGGGTGG AGCCCACCAC AGCTCAAGGA GGCCTGCCTG

541 CCTCTGTAGG CTCCACCTCT GGGGGCAGGG CACAGACAAA CAAAAAGACA GCAGTAACCT

601 CTGCAGACTT AAGTGTCCCT GTCTGACAGC TTTGAAGAGA GCAGTGGTTC TCCCAGCACG

661 CAGCTGGAGA TCTGAGAACG GGCAGACTGC CTCCTCAAGT GGGTCCCTGA CCCCTGACCC

721 CCGAGCAGCC TAACTGGGAG GCACCCCCCA GCAGGGGCAC ACTGACACCT CACACGGCAG

781 GGTATTCCAA CAGACCTGCA GCTGAGGGTC CTGTCTGTTA GAAGGAAAAC TAACAACCAG

841 AAAGGACATC TACACCGAAA ACCCATCTGT ACATCACCAT CATCAAAGAC CAAAAGTAGA

901 TAAAACCACA AAGATGGGGA AAAACAGAA CAGAAAAACT GGAAACTCTA AAACGCAGAG

961 CGCCTCTCCT CCTCCAAAGG AACGCAGTTC CTCACCAGCA ACAGAACAAA GCTGGATGGA

1021 GAATGATTTT GATGAGCTGA GAGAAGAAGG CTTCAGACGA TCAAATTACT CTGAGCTACG

1081 GGAGGACATT CAAACCAAAG GCAAAGAAGT TGAAAACTTT GAAAAAAATT TAGAAGAATG

1141 TATAACTAGA ATAACCAATA CAGAGAAGTG CTTAAAGGAG CTGATGGAGC TGAAAACCAA

1201 GGCTCGAGAA CTACGTGAAG AATGCAGAAG CCTCAGGAGC CGATGCGATC AACTGGAAGA

1261 AAGGGTATCA GCAATGGAAG ATGAAATGAA TGAAATGAAG CGAGAAGGGA AGTTTAGAGA

1321 AAAAAGAATA AAAGAAATG AGCAAAGCCT CCAAGAAATA TGGGACTATG TGAAAAGACC

1381 AAATCTACGT CTGATTGGTG TACCTGAAAG TGATGTGGAG AATGGAACCA AGTTGGAAAA

1441 CACTCTGCAG GATATTATCC AGGAGAACTT CCCCAATCTA GCAAGGCAGG CCAACGTTCA

1501 GATTCAGGAA ATACAGAGAA CGCCACAAAG ATACTCCTCG AGAAGAGCAA CTCCAAGACA

1561 CATAATTGTC AGATTCACCA AAGTTGAAAT GAAGGAAAAA ATGTTAAGGG CAGCCAGAGA

1621 GAAAGGTCGG GTTACCCTCA AAGGAAAGCC CATCAGACTA ACAGCGGATC TCTCGGCAGA

1681 AACCCTACAA GCCAGAAGAG AGTGGGGGCC AATATTCAAC ATTCTTAAAG AAAAGAATTT

1741 TCAACCCAGA ATTTCATATC CAGCCAAACT AAGCTTCATA AGTGAAGGAG AAATAAAATA

1801 CTTTATAGAC AAGCAAATGT TGAGAGATTT TGTCACCACC AGGCCTGCCC TAAAAGAGCT

TABLE 8-continued

Plasmid and mRNA construct sequences

```
1861  CCTGAAGGAA GCGCTAAACA TGGAAAGGAA CAACCGGTAC CAGCCGCTGC AAAATCATGC

1921  CAAAATGTAA AGACCATCAA GACTAGGAAG AAACTGCATC AACTAATGAG CAAAATCACC

1981  AGCTAACATC ATAATGACAG GATCAACTTC ACACATAACA ATATTAACTT TAAATATAAA

2041  TGGACTAAAT TCTGCAATTA AAAGACACAG ACTGGCAAGT TGGATAAAGA GTCAAGACCC

2101  ATCAGTGTGC TGTATTCAGG AAACCCATCT CACGTGCAGA GACACACATA GGCTCAAAAT

2161  AAAAGGATGG AGGAAGATCT ACCAAGCCAA TGGAAAACAA AAAAAGGCAG GGGTTGCAAT

2221  CCTAGTCTCT GATAAAACAG ACTTTAAACC AACAAAGATC AAAAGAGACA AAGAAGGCCA

2281  TTACATAATG GTAAAGGGAT CAATTCAACA AGAGGAGCTA ACTATCCTAA ATATTTATGC

2341  ACCCAATACA GGAGCACCCA GATTCATAAA GCAAGTCCTC AGTGACCTAC AAAGAGACTT

2401  AGACTCCCAC ACATTAATAA TGGGAGACTT TAACACCCCA CTGTCAACAT TAGACAGATC

2461  AACGAGACAG AAAGTCAACA AGGATACCCA GGAATTGAAC TCAGCTCTGC ACCAAGCAGA

2521  CCTAATAGAC ATCTACAGAA CTCTCCACCC CAAATCAACA GAATATACAT TTTTTTCAGC

2581  ACCACACCAC ACCTATTCCA AAATTGACCA CATAGTTGGA AGTAAAGCTC TCCTCAGCAA

2641  ATGTAAAAGA ACAGAAATTA TAACAAACTA TCTCTCAGAC CACAGTGCAA TCAAACTAGA

2701  ACTCAGGATT AAGAATCTCA CTCAAAGCCG CTCAACTACA TGGAAACTGA ACAACCTGCT

2761  CCTGAATGAC TACTGGGTAC ATAACGAAAT GAAGGCAGAA ATAAAGATGT TCTTTGAAAC

2821  CAACGAGAAC AAAGACACCA CATACCAGAA TCTCTGGGAC GCATTCAAAG CAGTGTGTAG

2881  AGGGAAATTT ATAGCACTAA ATGCCTACAA GAGAAAGCAG GAAAGATCCA AAATTGACAC

2941  CCTAACATCA CAATTAAAAG AACTAGAAAA GCAAGAGCAA ACACATTCAA AAGCTAGCAG

3001  AAGGCAAGAA ATAACTAAAA TCAGAGCAGA ACTGAAGGAA ATAGAGACAC AAAAAACCCT

3061  TCAAAAAATC AATGAATCCA GGAGCTGGTT TTTTGAAAGG ATCAACAAAA TTGATAGACC

3121  GCTAGCAAGA CTAATAAAGA AAAAAGAGA GAAGAATCAA ATAGACACAA TAAAAAATGA

3181  TAAAGGGGAT ATCACCACCG ATCCCACAGA AATACAAACT ACCATCAGAG AATACTACAA

3241  ACACCTCTAC GCAAATAAAC TAGAAAATCT AGAAGAAATG GATACATTCC TCGACACATA

3301  CACTCTCCCA AGACTAAACC AGGAAGAAGT TGAATCTCTG AATCGACCAA TAACAGGCTC

3361  TGAAATTGTG GCAATAATCA ATAGTTTACC AACCAAAAAG AGTCCAGGAC CAGATGGATT

3421  CACAGCCGAA TTCTACCAGA GGTACAAGGA GGAACTGGTA CCATTCCTTC TGAAACTATT

3481  CCAATCAATA GAAAAAGAGG GAATCCTCCC TAACTCATTT TATGAGGCCA GCATCATTCT

3541  GATACCAAAG CCGGGCAGAG ACACAACCAA AAAAGAGAAT TTTAGACCAA TATCCTTGAT

3601  GAACATTGAT GCAAAAATCC TCAATAAAAT ACTGGCAAAC CGAATCCAGC AGCACATCAA

3661  AAAGCTTATC CACCATGATC AAGTGGGCTT CATCCCTGGG ATGCAAGGCT GGTTCAATAT

3721  ACGCAAATCA ATAAATGTAA TCCAGCATAT AAACAGAGCC AAAGACAAAA CCACATGAT

3781  TATCTCAATA GATGCAGAAA AAGCCTTTGA CAAAATTCAA CAACCCTTCA TGCTAAAAAC

3841  TCTCAATAAA TTAGGTATTG ATGGGACGTA TTTCAAAATA ATAAGAGCTA TCTATGACAA

3901  ACCCACAGCC AATATCATAC TGAATGGGCA AAAACTGGAA GCATTCCCTT TGAAAACCGG

3961  CACAAGACAG GGATGCCCTC TCTCACCGCT CCTATTCAAC ATAGTGTTGG AAGTTCTGGC

4021  CAGGGCAATC AGGCAGGAGA AGGAAATAAA GGGTATTCAA TTAGGAAAAG AGGAAGTCAA

4081  ATTGTCCCTG TTTGCAGACG ACATGATTGT TTATCTAGAA AACCCCATCG TCTCAGCCCA

4141  AAATCTCCTT AAGCTGATAA GCAACTTCAG CAAAGTCTCA GGATACAAAA TCAATGTACA
```

TABLE 8-continued

Plasmid and mRNA construct sequences

```
4201 AAAATCACAA GCATTCTTAT ACACCAACAA CAGACAAACA GAGAGCCAAA TCATGGGTGA

4261 ACTCCCATTC ACAATTGCTT CAAAGAGAAT AAAATACCTA GGAATCCAAC TTACAAGGGA

4321 TGTGAAGGAC CTCTTCAAGG AGAACTACAA ACCACTGCTC AAGGAAATAA AAGAGGAGAC

4381 AAACAAATGG AAGAACATTC CATGCTCATG GGTAGGAAGA ATCAATATCG TGAAAATGGC

4441 CATACTGCCC AAGGTAATTT ACAGATTCAA TGCCATCCCC ATCAAGCTAC CAATGACTTT

4501 CTTCACAGAA TTGGAAAAAA CTACTTTAAA GTTCATATGG AACCAAAAAA GAGCCCGCAT

4561 TGCCAAGTCA ATCCTAAGCC AAAAGAACAA AGCTGGAGGC ATCACACTAC CTGACTTCAA

4621 ACTATACTAC AAGGCTACAG TAACCAAAAC AGCATGGTAC TGGTACCAAA ACAGAGATAT

4681 AGATCAATGG AACAGAACAG AGCCCTCAGA AATAATGCCG CATATCTACA ACTATCTGAT

4741 CTTTGACAAA CCTGAGAAAA CAAGCAATG GGGAAAGGAT TCCCTATTTA ATAAATGGTG

4801 CTGGGAAAAC TGGCTAGCCA TATGTAGAAA GCTGAAACTG GATCCCTTCC TTACACCTTA

4861 TACAAAAATC AATTCAAGAT GGATTAAAGA TTTAAACGTT AAACCTAAAA CCATAAAAAC

4921 CCTAGAAGAA AACCTAGGCA TTACCATTCA GGACATAGGC GTGGGCAAGG ACTTCATGTC

4981 CAAAACACCA AAAGCAATGG CAACAAAAGA CAAAATTGAC AAATGGGATC TAATTAAACT

5041 AAAGAGCTTC TGCACAGCAA AAGAAACTAC CATCGAGTG AACAGGCAAC CTACAACATG

5101 GGAGAAAATT TTTGCAACCT ACTCATCTGA CAAAGGGCTA ATATCCAGAA TCTACAATGA

5161 ACTCAAACAA ATTTACAAGA AAAAAACAAA CAACCCCATC AAAAAGTGGG CGAAGGACAT

5221 GAACAGACAC TTCTCAAAAG AAGACATTTA TGCAGCCAAA AAACACATGA AGAAATGCTC

5281 ATCATCACTG GCCATCAGAG AAATGCAAAT CAAAACCACT ATGAGATATC ATCTCACACC

5341 AGTTAGAATG GCAATCATTA AAAAGTCAGG AAACAACAGG TGCTGGAGAG GATGCGGAGA

5401 AATAGGAACA CTTTTACACT GTTGGTGGGA CTGTAAACTA GTTCAACCAT TGTGGAAGTC

5461 AGTGTGGCGA TTCCTCAGGG ATCTAGAACT AGAAATACCA TTTGACCCAG CCATCCCATT

5521 ACTGGGTATA TACCCAAATG AGTATAAATC ATGCTGCTAT AAAGACACAT GCACACGTAT

5581 GTTTATTGCG GCACTATTCA CAATAGCAAA GACTTGGAAC CAACCCAAAT GTCCAACAAT

5641 GATAGACTGG ATTAAGAAAA TGTGGCACAT ATACACCATG GAATACTATG CAGCCATAAA

5701 AAATGATGAG TTCATATCCT TTGTAGGGAC ATGGATGAAA TTGGAAACCA TCATTCTCAG

5761 TAAACTATCG CAAGAACAAA AAACCAAACA CCGCATATTC TCACTCATAG GTGGGAATTG

5821 AACAATGAGA TCACATGGAC ACAGGAAGGG GAATATCACA CTCTGGGGAC TGTGGTGGGG

5881 TCGGGGGAGG GGGGAGGGAT AGCATTGGGA GATATACCTA ATGCTAGATG ACACATTAGT

5941 GGGTGCAGCG CACCAGCATG GCACATGTAT ACGGATCCGA ATTCTCGACG GATCGATCCG

6001 AACAAACGAC CCAACACCCG TGCGTTTTAT TCTGTCTTTT TATTGCCGAT CCCCTCAGAA

6061 GAACTCGTCA AGAAGGCGAT AGAAGGCGAT GCGCTGCGAA TCGGGAGCGG CGATACCGTA

6121 AAGCACGAGG AAGCGGTCAG CCCATTCGCC GCCAAGCTCT TCAGCAATAT CACGGGTAGC

6181 CAACGCTATG TCCTGATAGC GGTCGGCCGC TTTACTTGTA CAGCTCGTCC ATGCCGAGAG

6241 TGATCCCGGC GGCGGTCACG AACTCCAGCA GGACCATGTG ATCGCGCTTC TCGTTGGGGT

6301 CTTTGCTCAG GGCGGACTGG GTGCTCAGGT AGTGGTTGTC GGGCAGCAGC ACGGGGCCGT

6361 CGCCGATGGG GGTGTTCTGC TGGTAGTGGT CGGCCAGGTG AGTCCAGGAG ATGTTTCAGC

6421 ACTGTTGCCT TTAGTCTCGA GGCAACTTAG ACAACTGAGT ATTGATCTGA GCACAGCAGG

6481 GTGTGAGCTG TTTGAAGATA CTGGGGTTGG GGGTGAAGAA ACTGCAGAGG ACTAACTGGG
```

TABLE 8-continued

Plasmid and mRNA construct sequences

```
6541 CTGAGACCCA GTGGCAATGT TTTAGGGCCT AAGGAATGCC TCTGAAAATC TAGATGGACA

6601 ACTTTGACTT TGAGAAAAGA GAGGTGGAAA TGAGGAAAAT GACTTTTCTT TATTAGATTT

6661 CGGTAGAAAG AACTTTCATC TTTCCCCTAT TTTTGTTATT CGTTTTAAAA CATCTATCTG

6721 GAGGCAGGAC AAGTATGGTC ATTAAAAAGA TGCAGGCAGA AGGCATATAT TGGCTCAGTC

6781 AAAGTGGGGA ACTTTGGTGG CCAAACATAC ATTGCTAAGG CTATTCCTAT ATCAGCTGGA

6841 CACATATAAA ATGCTGCTAA TGCTTCATTA CAAACTTATA TCCTTTAATT CCAGATGGGG

6901 GCAAAGTATG TCCAGGGGTG AGGAACAATT GAAACATTTG GGCTGGAGTA GATTTTGAAA

6961 GTCAGCTCTG TGTGTGTGTG TGTGTGTGTG TGTGTGAGAG CGTGTGTTTC TTTTAACGTT

7021 TTCAGCCTAC AGCATACAGG GTTCATGGTG GCAAGAAGAT AACAAGATTT AAATTATGGC

7081 CAGTGACTAG TGCTGCAAGA AGAACAACTA CCTGCATTTA ATGGGAAAGC AAAATCTCAG

7141 GCTTTGAGGG AAGTTAACAT AGGCTTGATT CTGGGTGGAA GCTGGGTGTG TAGTTATCTG

7201 GAGGCCAGGC TGGAGCTCTC AGCTCACTAT GGGTTCATCT TTATTGTCTC CTTTCATCTC

7261 AACAGCTGCA CGCTGCCGTC CTCGATGTTG TGGCGGATCT TGAAGTTCAC CTTGATGCCG

7321 TTCTTCTGCT TGTCGGCCAT GATATAGACG TTGTGGCTGT TGTAGTTGTA CTCCAGCTTG

7381 TGCCCCAGGA TGTTGCCGTC CTCCTTGAAG TCGATGCCCT TCAGCTCGAT GCGGTTCACC

7441 AGGGTGTCGC CCTCGAACTT CACCTCGGCG CGGGTCTTGT AGTTGCCGTC GTCCTTGAAG

7501 AAGATGGTGC GCTCCTGGAC GTAGCCTTCG GGCATGGCGG ACTTGAAGAA GTCGTGCTGC

7561 TTCATGTGGT CGGGGTAGCG GCTGAAGCAC TGCACGCCGT AGGTCAGGGT GGTCACGAGG

7621 GTGGGCCAGG GCACGGGCAG CTTGCCGGTG GTGCAGATGA ACTTCAGGGT CAGCTTGCCG

7681 TAGGTGGCAT CGCCCTCGCC CTCGCCGGAC ACGCTGAACT TGTGGCCGTT TACGTCGCCG

7741 TCCAGCTCGA CCAGGATGGG CACCACCCCG GTGAACAGCT CCTCGCCCTT GCTCACCATA

7801 GGGCCGGGAT TCTCCTCCAC GTCACCGCAT GTTAGAAGAC TTCCTCTGCC CTCTCTTGGA

7861 GGCAGGGCCT GCATGTGCAG GGCATCGTAG GTATCCTTGG TGGCTGTGCT CAGTCCCTGG

7921 TACAGTCCAT CGTGGCCCTT GCCTCTTCTT CTCTCGCCCT TCATGCCGAT CTCGCTGTAG

7981 GCCTCGGCCA TCTTGTCTTT CTGCAGCTCA TTATACAGGC CCTCTTGAGG ATTCTTTCTC

8041 CGCTGGGGCT TGCCGCCCAT CTCAGGATCT CTGCCTCTCC GCTTATCCAG CACGTCGTAC

8101 TCTTCTCTTC TCCCCAGGTT CAGCTCGTTG TACAGCTGAT TCTGGCCCTG CTGGTAAGCA

8161 GGAGCGTCGG CGGATCTGCT GAACTTCACT CTGCAGTACA GGGTGATGAC CAGAGAGAGC

8221 AGCAGAACGC CACATGTGCC AGCCAGAGGG GCCCAAATGT AGATATCCAG GCCTCTGGTA

8281 TGCACAGCTC CGCCAGCTGC AGGTCTACAG GCTTCAGGTC TGAGAGACAG AGGCTGGCTG

8341 GCGATTGTAG GAGCTGGTGT AGGTGGTCTA GGAGCGGGTG TTGTTGTAGG CTTGGCGGGC

8401 AGAAACACGG GCACGAAGTG GCTGAAGTAC ATGATGCTAT TGCTCAGGGC TCCGCTTCCT

8461 CCGCCTCCGC TAGAAGAAAC TGTGACCAGG GTGCCCTGTC CCCAAACATC CATGGCGTAG

8521 AAGCCGTCGC CTCCCCATCT AGAACAGTAG TACACGGCGG TGTCCTCGGC TCTCAGGCTG

8581 TTCATCTGCA GGTAGGCGGT GTTCTTGCTG GTGTCGGCGC TGATGGTGAA TCTGCCCTTC

8641 ACGCTATCGG CGTATCTGGT GTAGCCGTTG GTGGGGTAGA TTCTGGCGAC CCATTCAAGT

8701 CCCTTTCCAG GGGCCTGTCG GACCCAGTGG ATGTAGGTGT CCTTGATGTT GAAGCCGCTG

8761 GCGGCACAAG ACAGTCTCAG AGAGCCGCCA GGCTGAACAA GTCCTCCGCC AGATTCAACC

8821 AGCTGCACCT CAGATCCTTC GCCAGATCCA GGCTTTCCAG AGCCGCTGGT GCTGCCTGTT
```

TABLE 8-continued

Plasmid and mRNA construct sequences

```
 8881 CTCTTGATTT CCACCTTGGT GCCCTGGCCA AAGGTTGGAG GTGTGGTGTA GTGCTGCTGG

8941 CAGTAGTAGG TGGCGAAGTC CTCAGGCTGC AGGCTAGAGA TGGTCAGGGT GAAGTCGGTG

9001 CCAGATCTGC TGCCGCTGAA TCTGCTTGGC ACGCCGCTGT ACAGAAAGCT GGCGCTGTAG

9061 ATCAGCAGCT TAGGGGCTTT TCCAGGCTTC TGCTGATACC AGGCCACGGC GGTATTCACA

9121 TCCTGGCTGG CTCTACAGGT GATGGTCACT CTATCGCCCA CAGAGGCAGA CAGGCTGCTA

9181 GGGCTCTGTG TCATCTGGAT GTCGCTGATG CTGCAGGCCA CTGTTCCCAG CAGCAGCAGA

9241 GACTGCAGCC ACATTCGAAG CTTGAGCTCG AGATCTGAGT CCGGTAGCGC TAGCGGATCT

9301 GACGGTTCAC TAAACCAGCT CTGCTTATAT AGACCTCCCA CCGTACACGC CTACCGCCCA

9361 TTTGCGTCAA TGGGGCGGAG TTGTTACGAC ATTTTGGAAA GTCCCGTTGA TTTTGGTGCC

9421 AAAACAAACT CCCATTGACG TCAATGGGGT GGAGACTTGG AAATCCCCGT GAGTCAAACC

9481 GCTATCCACG CCCATTGATG TACTGCCAAA ACCGCATCAC CATGGTAATA GCGATGACTA

9541 ATACGTAGAT GTACTGCCAA GTAGGAAAGT CCCATAAGGT CATGTACTGG GCATAATGCC

9601 AGGCGGGCCA TTTACCGTCA TTGACGTCAA TAGGGGGCGT ACTTGGCATA TGATACACTT

9661 GATGTACTGC CAAGTGGGCA GTTTACCGTA AATACTCCAC CCATTGACGT CAATGGAAAG

9721 TCCCTATTGG CGTTACTATG GGAACATACG TCATTATTGA CGTCAATGGG CGGGGGTCGT

9781 TGGGCGGTCA GCCAGGCGGG CCATTTACCG TAAGTTATGT AACGCGGAAC TCCATATATG

9841 GGCTATGAAC TAATGACCCC GTAATTGATT ACTATTAGCC CGGGGGATCC AGACATGATA

9901 AGATACATTG ATGAGTTTGG ACAAACCACA ACTAGAATGC AGTGAAAAAA ATGCTTTATT

9961 TGTGAAATTT GTGATGCTAT TGCTTTATTT GTAACCATTA TAAGCTGCAA TAAACAAGTT

10021 AACAACAACA ATTGCATTCA TTTTATGTTT CAGGTTCAGG GGGAGGTGTG GGAGGTTTTT

10081 TAAAGCAAGT AAAACCTCTA CAAATGTGGT ATGGCTGATT ATGATCCGGC TGCCTCGCGC

10141 GTTTCGGTGA TGACGGTGAA AACCTCTGAC ACATGCAGCT CCCGGAGACG GTCACAGCTT

10201 GTCTGTAAGC GGATGCCGGG AGCAGACAAG CCCGTCAGGG CGCGTCAGCG GGTGTTGGCG

10261 GGTGTCGGGG CGCAGCCATG AGGTCGATCG ACTCTAGAGG ATCGATCCCC GCCCCGGACG

10321 AACTAAACCT GACTACGACA TCTCTGCCCC TTCTTCGCGG GGCAGTGCAT GTAATCCCTT

10381 CAGTTGGTTG GTACAACTTG CCAACTGGGC CCTGTTCCAC ATGTGACACG GGGGGGGACC

10441 AAACACAAAG GGGTTCTCTG ACTGTAGTTG ACATCCTTAT AAATGGATGT GCACATTTGC

10501 CAACACTGAG TGGCTTTCAT CCTGGAGCAG ACTTTGCAGT CTGTGGACTG CAACACAACA

10561 TTGCCTTTAT GTGTAACTCT TGGCTGAAGC TCTTACACCA ATGCTGGGGG ACATGTACCT

10621 CCCAGGGGCC CAGGAAGACT ACGGGAGGCT ACACCAACGT CAATCAGAGG GGCCTGTGTA

10681 GCTACCGATA AGCGGACCCT CAAGAGGGCA TTAGCAATAG TGTTTATAAG GCCCCCTTGT

10741 TAACCCTAAA CGGGTAGCAT ATGCTTCCCG GGTAGTAGTA TATACTATCC AGACTAACCC

10801 TAATTCAATA GCATATGTTA CCCAACGGGA AGCATATGCT ATCGAATTAG GGTTAGTAAA

10861 AGGGTCCTAA GGAACAGCGA TATCTCCCAC CCCATGAGCT GTCACGGTTT TATTTACATG

10921 GGGTCAGGAT TCCACGAGGG TAGTGAACCA TTTTAGTCAC AAGGGCAGTG GCTGAAGATC

10981 AAGGAGCGGG CAGTGAACTC TCCTGAATCT TCGCCTGCTT CTTCATTCTC CTTCGTTTAG

11041 CTAATAGAAT AACTGCTGAG TTGTGAACAG TAAGGTGTAT GTGAGGTGCT CGAAAACAAG

11101 GTTTCAGGTG ACGCCCCCAG AATAAAATTT GGACGGGGGG TTCAGTGGTG GCATTGTGCT

11161 ATGACACCAA TATAACCCTC ACAAACCCCT TGGGCAATAA ATACTAGTGT AGGAATGAAA
```

TABLE 8-continued

Plasmid and mRNA construct sequences

```
11221 CATTCTGAAT ATCTTTAACA ATAGAAATCC ATGGGGTGGG GACAAGCCGT AAAGACTGGA

11281 TGTCCATCTC ACACGAATTT ATGGCTATGG GCAACACATA ATCCTAGTGC AATATGATAC

11341 TGGGGTTATT AAGATGTGTC CCAGGCAGGG ACCAAGACAG GTGAACCATG TTGTTACACT

11401 CTATTTGTAA CAAGGGGAAA GAGAGTGGAC GCCGACAGCA GCGGACTCCA CTGGTTGTCT

11461 CTAACACCCC CGAAAATTAA ACGGGGCTCC ACGCCAATGG GGCCCATAAA CAAAGACAAG

11521 TGGCCACTCT TTTTTTTGAA ATTGTGGAGT GGGGGCACGC GTCAGCCCCC ACACGCCGCC

11581 CTGCGGTTTT GGACTGTAAA ATAAGGGTGT AATAACTTGG CTGATTGTAA CCCCGCTAAC

11641 CACTGCGGTC AAACCACTTG CCCACAAAAC CACTAATGGC ACCCCGGGGA ATACCTGCAT

11701 AAGTAGGTGG GCGGGCCAAG ATAGGGGCGC GATTGCTGCG ATCTGGAGGA CAAATTACAC

11761 ACACTTGCGC CTGAGCGCCA AGCACAGGGT TGTTGGTCCT CATATTCACG AGGTCGCTGA

11821 GAGCACGGTG GGCTAATGTT GCCATGGGTA GCATATACTA CCCAAATATC TGGATAGCAT

11881 ATGCTATCCT AATCTATATC TGGGTAGCAT AGGCTATCCT AATCTATATC TGGGTAGCAT

11941 ATGCTATCCT AATCTATATC TGGGTAGTAT ATGCTATCCT AATTTATATC TGGGTAGCAT

12001 AGGCTATCCT AATCTATATC TGGGTAGCAT ATGCTATCCT AATCTATATC TGGGTAGTAT

12061 ATGCTATCCT AATCTGTATC CGGGTAGCAT ATGCTATCCT AATAGAGATT AGGGTAGTAT

12121 ATGCTATCCT AATTTATATC TGGGTAGCAT ATACTACCCA AATATCTGGA TAGCATATGC

12181 TATCCTAATC TATATCTGGG TAGCATATGC TATCCTAATC TATATCTGGG TAGCATAGGC

12241 TATCCTAATC TATATCTGGG TAGCATATGC TATCCTAATC TATATCTGGG TAGTATATGC

12301 TATCCTAATT TATATCTGGG TAGCATAGGC TATCCTAATC TATATCTGGG TAGCATATGC

12361 TATCCTAATC TATATCTGGG TAGTATATGC TATCCTAATC TGTATCCGGG TAGCATATGC

12421 TATCCTCATG CATATACAGT CAGCATATGA TACCCAGTAG TAGAGTGGGA GTGCTATCCT

12481 TTGCATATGC CGCCACCTCC CAAGGGGGCG TGAATTTTCG CTGCTTGTCC TTTTCCTGCA

12541 TGCTGGTTGC TCCCATTCTT AGGTGAATTT AAGGAGGCCA GGCTAAAGCC GTCGCATGTC

12601 TGATTGCTCA CCAGGTAAAT GTCGCTAATG TTTTCCAACG CGAGAAGGTG TTGAGCGCGG

12661 AGCTGAGTGA CGTGACAACA TGGGTATGCC CAATTGCCCC ATGTTGGGAG GACGAAAATG

12721 GTGACAAGAC AGATGGCCAG AAATACACCA ACAGCACGCA TGATGTCTAC TGGGGATTTA

12781 TTCTTTAGTG CGGGGGAATA CACGGCTTTT AATACGATTG AGGGCGTCTC CTAACAAGTT

12841 ACATCACTCC TGCCCTTCCT CACCCTCATC TCCATCACCT CCTTCATCTC CGTCATCTCC

12901 GTCATCACCC TCCGCGGCAG CCCCTTCCAC CATAGGTGGA AACCAGGGAG GCAAATCTAC

12961 TCCATCGTCA AAGCTGCACA CAGTCACCCT GATATTGCAG GTAGGAGCGG GCTTTGTCAT

13021 AACAAGGTCC TTAATCGCAT CCTTCAAAAC CTCAGCAAAT ATATGAGTTT GTAAAAAGAC

13081 CATGAAATAA CAGACAATGG ACTCCCTTAG CGGGCCAGGT TGTGGGCCGG TCCAGGGGC

13141 CATTCCAAAG GGGAGACGAC TCAATGGTGT AAGACGACAT TGTGGAATAG CAAGGGCAGT

13201 TCCTCGCCTT AGGTTGTAAA GGGAGGTCTT ACTACCTCCA TATACGAACA CACCGGCGAC

13261 CCAAGTTCCT TCGTCGGTAG TCCTTTCTAC GTGACTCCTA GCCAGGAGAG CTCTTAAACC

13321 TTCTGCAATG TTCTCAAATT TCGGGTTGGA ACCTCCTTGA CCACGATGCT TTCCAAACCA

13381 CCCTCCTTTT TTGCGCCTGC CTCCATCACC CTGACCCCGG GGTCCAGTGC TTGGGCCTTC

13441 TCCTGGGTCA TCTGCGGGGC CCTGCTCTAT CGCTCCCGGG GGCACGTCAG GCTCACCATC

13501 TGGGCCACCT TCTTGGTGGT ATTCAAAATA ATCGGCTTCC CCTACAGGGT GGAAAAATGG
```

TABLE 8-continued

Plasmid and mRNA construct sequences

```
13561  CCTTCTACCT GGAGGGGGCC TGCGCGGTGG AGACCCGGAT GATGATGACT GACTACTGGG

13621  ACTCCTGGGC CTCTTTTCTC CACGTCCACG ACCTCTCCCC CTGGCTCTTT CACGACTTCC

13681  CCCCCTGGCT CTTTCACGTC CTCTACCCCG GCGGCCTCCA CTACCTCCTC GACCCCGGCC

13741  TCCACTACCT CCTCGACCCC GGCCTCCACT GCCTCCTCGA CCCCGGCCTC CACCTCCTGC

13801  TCCTGCCCCT CCTGCTCCTG CCCCTCCTCC TGCTCCTGCC CCTCCTGCCC CTCCTGCTCC

13861  TGCCCCTCCT GCCCCTCCTG CTCCTGCCCC TCCTGCCCCT CCTGCTCCTG CCCCTCCTGC

13921  CCCTCCTCCT GCTCCTGCCC CTCCTGCCCC TCCTCCTGCT CCTGCCCCTC CTGCCCCTCC

13981  TGCTCCTGCC CCTCCTGCCC CTCCTGCTCC TGCCCCTCCT GCCCCTCCTG CTCCTGCCCC

14041  TCCTGCTCCT GCCCCTCCTG CTCCTGCCCC TCCTGCTCCT GCCCCTCCTG CCCCTCCTGC

14101  CCCTCCTCCT GCTCCTGCCC CTCCTGCTCC TGCCCCTCCT GCCCCTCCTG CCCCTCCTGC

14161  TCCTGCCCCT CCTCCTGCTC CTGCCCCTCC TGCCCCTCCT GCCCCTCCTC CTGCTCCTGC

14221  CCCTCCTGCC CCTCCTCCTG CTCCTGCCCC TCCTCCTGCT CCTGCCCCTC CTGCCCCTCC

14281  TGCCCCTCCT CCTGCTCCTG CCCCTCCTGC CCCTCCTCCT GCTCCTGCCC CTCCTCCTGC

14341  TCCTGCCCCT CCTGCCCCTC CTGCCCCTCC TCCTGCTCCT GCCCCTCCTC CTGCTCCTGC

14401  CCCTCCTGCC CCTCCTGCCC CTCCTGCCCC TCCTCCTGCT CCTGCCCCTC CTCCTGCTCC

14461  TGCCCCTCCT GCTCCTGCCC CTCCCGCTCC TGCTCCTGCT CCTGTTCCAC CGTGGGTCCC

14521  TTTGCAGCCA ATGCAACTTG GACGTTTTTG GGGTCTCCGG ACACCATCTC TATGTCTTGG

14581  CCCTGATCCT GAGCCGCCCG GGGCTCCTGG TCTTCCGCCT CCTCGTCCTC GTCCTCTTCC

14641  CCGTCCTCGT CCATGGTTAT CACCCCCTCT TCTTTGAGGT CCACTGCCGC CGGAGCCTTC

14701  TGGTCCAGAT GTGTCTCCCT TCTCTCCTAG GCCATTTCCA GGTCCTGTAC CTGGCCCCTC

14761  GTCAGACATG ATTCACACTA AAAGAGATCA ATAGACATCT TTATTAGACG ACGCTCAGTG

14821  AATACAGGGA GTGCAGACTC CTGCCCCCTC CAACAGCCCC CCCACCCTCA TCCCCTTCAT

14881  GGTCGCTGTC AGACAGATCC AGGTCTGAAA ATTCCCCATC CTCCGAACCA TCCTCGTCCT

14941  CATCACCAAT TACTCGCAGC CCGGAAAACT CCCGCTGAAC ATCCTCAAGA TTTGCGTCCT

15001  GAGCCTCAAG CCAGGCCTCA AATTCCTCGT CCCCCTTTTT GCTGGACGGT AGGGATGGGG

15061  ATTCTCGGGA CCCCTCCTCT TCCTCTTCAA GGTCACCAGA CAGAGATGCT ACTGGGGCAA

15121  CGGAAGAAAA GCTGGGTGCG GCCTGTGAGG ATCAGCTTAT CGATGATAAG CTGTCAAACA

15181  TGAGAATTCT TGAAGACGAA AGGGCCTCGT GATACGCCTA TTTTTATAGG TTAATGTCAT

15241  GATAATAATG GTTTCTTAGA CGTCAGGTGG CACTTTTCGG GGAAATGTGC GCGGAACCCC

15301  TATTTGTTTA TTTTTCTAAA TACATTCAAA TATGTATCCG CTCATGAGAC AATAACCCTG

15361  ATAAATGCTT CAATAATATT GAAAAAGGAA GAGTATGAGT ATTCAACATT TCCGTGTCGC

15421  CCTTATTCCC TTTTTTGCGG CATTTTGCCT TCCTGTTTTT GCTCACCCAG AAACGCTGGT

15481  GAAAGTAAAA GATGCTGAAG ATCAGTTGGG TGCACGAGTG GGTTACATCG AACTGGATCT

15541  CAACAGCGGT AAGATCCTTG AGAGTTTTCG CCCCGAAGAA CGTTTTCCAA TGATGAGCAC

15601  TTTTAAAGTT CTGCTATGTG GCGCGGTATT ATCCCGTGTT GACGCCGGGC AAGAGCAACT

15661  CGGTCGCCGC ATACACTATT CTCAGAATGA CTTGGTTGAG TACTCACCAG TCACAGAAAA

15721  GCATCTTACG GATGGCATGA CAGTAAGAGA ATTATGCAGT GCTGCCATAA CCATGAGTGA

15781  TAACACTGCG GCCAACTTAC TTCTGACAAC GATCGGAGGA CCGAAGGAGC TAACCGCTTT

15841  TTTGCACAAC ATGGGGGATC ATGTAACTCG CCTTGATCGT TGGGAACCGG AGCTGAATGA
```

TABLE 8-continued

Plasmid and mRNA construct sequences

```
15901 AGCCATACCA AACGACGAGC GTGACACCAC GATGCCTGCA GCAATGGCAA CAACGTTGCG

15961 CAAACTATTA ACTGGCGAAC TACTTACTCT AGCTTCCCGG CAACAATTAA TAGACTGGAT

16021 GGAGGCGGAT AAAGTTGCAG GACCACTTCT GCGCTCGGCC CTTCCGGCTG GCTGGTTTAT

16081 TGCTGATAAA TCTGGAGCCG GTGAGCGTGG GTCTCGCGGT ATCATTGCAG CACTGGGGCC

16141 AGATGGTAAG CCCTCCCGTA TCGTAGTTAT CTACACGACG GGGAGTCAGG CAACTATGGA

16201 TGAACGAAAT AGACAGATCG CTGAGATAGG TGCCTCACTG ATTAAGCATT GGTAACTGTC

16261 AGACCAAGTT TACTCATATA TACTTTAGAT TGATTTAAAA CTTCATTTTT AATTTAAAAG

16321 GATCTAGGTG AAGATCCTTT TTGATAATCT CATGACCAAA ATCCCTTAAC GTGAGTTTTC

16381 GTTCCACTGA GCGTCAGACC CCGTAGAAAA GATCAAAGGA TCTTCTTGAG ATCCTTTTTT

16441 TCTGCGCGTA ATCTGCTGCT TGCAAACAAA AAAACCACCG CTACCAGCGG TGGTTTGTTT

16501 GCCGGATCAA GAGCTACCAA CTCTTTTTCC GAAGGTAACT GGCTTCAGCA GAGCGCAGAT

16561 ACCAAATACT GTCCTTCTAG TGTAGCCGTA GTTAGGCCAC CACTTCAAGA ACTCTGTAGC

16621 ACCGCCTACA TACCTCGCTC TGCTAATCCT GTTACCAGTG GCTGCTGCCA GTGGCGATAA

16681 GTCGTGTCTT ACCGGGTTGG ACTCAAGACG ATAGTTACCG GATAAGGCGC AGCGGTCGGG

16741 CTGAACGGGG GGTTCGTGCA CACAGCCCAG CTTGGAGCGA ACGACCTACA CCGAACTGAG

16801 ATACCTACAG CGTGAGCTAT GAGAAAGCGC CACGCTTCCC GAAGGGAGAA AGGCGGACAG

16861 GTATCCGGTA AGCGGCAGGG TCGGAACAGG AGAGCGCACG AGGGAGCTTC CAGGGGGAAA

16921 CGCCTGGTAT CTTTATAGTC CTGTCGGGTT TCGCCACCTC TGACTTGAGC GTCGATTTTT

16981 GTGATGCTCG TCAGGGGGGC GGAGCCTATG GAAAAACGCC AGCAACGCGG CCTTTTTACG

17041 GTTCCTGGCC TTTTGCTGGC CTTTTGCTCA CATGTTCTTT CCTGCGTTAT CCCCTGATTC

17101 TGTGGATAAC CGTATTACCG CCTTTGAGTG AGCTGATACC GCTCGCCGCA GCCGAACGAC

17161 CGAGCGCAGC GAGTCAGTGA GCGAGGAAGC GGAAGAGCGC CTGATGCGGT ATTTTCTCCT

17221 TACGCATCTG TGCGGTATTT CACACCGCAT ATGGTGCACT CTCAGTACAA TCTGCTCTGA

17281 TGCCGCATAG TTAAGCCAGC TGTGGAATGT GTGTCAGTTA GGGTGTGGAA AGTCCCCAGG

17341 CTCCCCAGCA GGCAGAAGTA TGCAAAGCAT GCATCTCAAT TAGTCAGCAA CCAGGTGTGG

17401 AAAGTCCCCA GGCTCCCCAG CAGGCAGAAG TATGCAAAGC ATGCATCTCA ATTAGTCAGC

17461 AACCATAGTC CCGCCCCTAA CTCCGCCCAT CCCGCCCCTA ACTCCGCCCA GTTCCGCCCA

17521 TTCTCCGCCC CATGGCTGAC TAATTTTTTT TATTTATGCA GAGGCCGAGG CCGCCTCGGC

17581 CTCTGAGCTA TTCCAGAAGT AGTGAGGAGG CTTTTTTGGA GGCCTAGGCT TTTGCAAAAA

17641 GCTTGCATGC CTGCAGGTCG GCCGCCACGA CCGGTGCCGC CACCATCCCC TGACCCACGC

17701 CCCTGACCCC TCACAAGGAG ACGACCTTCC ATGACCGAGT ACAAGCCCAC GGTGCGCCTC

17761 GCCACCCGCG ACGACGTCCC CCGGGCCGTA CGCACCCTCG CCGCCGCGTT CGCCGACTAC

17821 CCCGCCACGC GCCACACCGT CGACCCGGAC CGCCACATCG AGCGGGTCAC CGAGCTGCAA

17881 GAACTCTTCC TCACGCGCGT CGGGCTCGAC ATCGGCAAGG TGTGGGTCGC GGACGACGGC

17941 GCCGCGGTGG CGGTCTGGAC CACGCCGGAG AGCGTCGAAG CGGGGGCGGT GTTCGCCGAG

18001 ATCGGCCCGC GCATGGCCGA GTTGAGCGGT TCCCGGCTGG CCGCGCAGCA ACAGATGGAA

18061 GGCCTCCTGG CGCCGCACCG GCCCAAGGAG CCCGCGTGGT TCCTGGCCAC CGTCGGCGTC

18121 TCGCCCGACC ACCAGGGCAA GGGTCTGGGC AGCGCCGTCG TGCTCCCCGG AGTGGAGGCG

18181 GCCGAGCGCG CCGGGGTGCC CGCCTTCCTG GAGACCTCCG CGCCCCGCAA CCTCCCCTTC
```

TABLE 8-continued

Plasmid and mRNA construct sequences

```
18241 TACGAGCGGC TCGGCTTCAC CGTCACCGCC GACGTCGAGG TGCCCGAAGG ACCGCGCACC

18301 TGGTGCATGA CCCGCAAGCC CGGTGCCTGA CGCCCGCCCC ACGACCCGCA GCGCCCGACC

18361 GAAAGGAGCG CACGACCCCA TGGCTCCGAC CGAAGCCGAC CCGGGCGGCC CCGCCGACCC

18421 CGCACCCGCC CCCGAGGCCC ACCGACTCTA GAGGATCATA ATCAGCCATA CCACATTTGT

18481 AGAGGTTTTA CTTGCTTTAA AAAACCTCCC ACACCTCCCC CTGAACCTGA AACATAAAAT

18541 GAATGCAATT GTTGTTGTTA ACTTGTTTAT TGCAGCTTAT AATGGTTACA AATAAAGCAA

18601 TAGCATCACA AATTTCACAA ATAAAGCATT TTTTTCACTG CATTCTAGTT GTGGTTTGTC

18661 CAAACTCATC AATGTATCTT ATCATGTCTG GATCACTCGC CGATAGTGGA AACCGACGCC

18721 CCAGCACTCG TCCGAGGGCA AAGGAATAGG GGAGATGGGG GAGGCTAACT GAAACACGGA

18781 AGGAGACAAT ACCGGAAGGA ACCCGCGCTA TGACGGCAAT AAAAAGACAG AATAAAACGC

18841 ACGGGTGTTG GGTCGTTTGT TCATAAACGC GGGGTTCGGT CCCAGGGCTG GCACTCTGTC

18901 GATACCCCAC CGAGACCCCA TTGGGGCCAA TACGCCCGCG TTTCTTCCTT TTCCCCACCC

18961 CACCCCCCAA GTTCGGGTGA AGGCCCAGGG CTCGCAGCCA ACGTCGGGGC GGCAGGCCCT

19021 GCCATAGCCA CTGGCCCCGT GGGTTAGGGA CGGGGTCCCC CATGGGGAAT GGTTTATGGT

19081 TCGTGGGGGT TATTATTTTG GGCGTTGCGT GGGGTCTGGT CCACGACTGG ACTGAGCAGA

19141 CAGACCCATG GTTTTTGGAT GGCCTGGGCA TGGACCGCAT GTACTGGCGC GACACGAACA

19201 CCGGGCGTCT GTGGCTGCCA AACACCCCCG ACCCCCAAAA ACCACCGCGC GGATTTCTGG

19261 CGTGCCAAGC TAGTCGACCA ATTCTCATGT TTGACAGCTT ATCATCGCAG ATCCGGGCAA

19321 CGTTGTTGCA TTGCTGCAGG CGCAGAACTG GTAGGTATGG AAGATCTCTA GAAGCTGGGT

19381 ACCAGCTGCT AGCAAGCTTG CTAGCGGCCG GCTCGAGTTT ACTCCCTATC AGTGATAGAG

19441 AACGTATGTC GAGTTTACTC CCTATCAGTG ATAGAACG ATGTCGAGTT TACTCCCTAT

19501 CAGTGATAGA GAACGTATGT CGAGTTTACT CCCTATCAGT GATAGAGAAC GTATGTCGAG

19561 TTTACTCCCT ATCAGTGATA GAGAACGTAT GTCGAGTTTA TCCCTATCAG TGATAGAGAA

19621 CGTATGTCGA GTTTACTCCC TATCAGTGAT AGAGAACGTA TGTCGAGGTA GGCGTGTACG

19681 GTGGGAGGCC TATATAAGCA GAGCTCGTTT AGTGAACCGT CAGATCGCCG
(SEQ ID NO: 41)
```

LINE-1 ORF2-NLS mRNA (SEQ ID NO: 42)

```
   1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT

361 CCAGGTGTGA CCAGCTCGAG GAGCGCGTGA GCGCGATGGA AGACGAGATG AACGAGATGA

421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA
```

TABLE 8-continued

Plasmid and mRNA construct sequences

```
 721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA

901 TCTCCGAGGG TGAGATTAAG TATTTCATCG ATAAACAGAT GCTGCGAGAC TTCGTGACAA

961 CTCGCCCAGC TCTCAAGGAA CTGCTCAAAG AGGCTCTTAA TATGGAGCGC AATAATAGAT

1021 ATCAACCCTT GCAGAACCAC GCAAAGATGT GAGACAGCCG TCAGACCATC AAGACTAGGA

1081 AGAAACTGCA TCAACTAATG AGCAAAATCA CCAGCTAACA TCATAGTATA CATGACCGGC

1141 TCTAACTCAC ATATCACCAT CCTTACACTT AACATTAACG GCCTCAACTC AGCTATCAAG

1201 CGCCATCGGC TGGCCAGCTG GATCAAATCA CAGGATCCAA GCGTTTGTTG CATCCAAGAG

1261 ACCCACCTGA CCTGTAGAGA TACTCACCGC CTCAAGATCA AGGGATGGCG AAAGATTTAT

1321 CAGGCGAACG GTAAGCAGAA GAAAGCCGGA GTCGCAATTC TGGTCTCAGA CAAGACGGAT

1381 TTCAAGCCCA CCAAAATTAA GCGTGATAAG GAAGGTCACT ATATTATGGT GAAAGGCAGC

1441 ATACAGCAGG AAGAACTTAC CATATTGAAC ATCTACGCGC CAAACACCGG CGCACCTCGC

1501 TTTATCAAAC AGGTCCTGTC CGATCTGCAG CGAGATCTGG ATTCTCATAC GTTGATTATG

1561 GGTGATTTCA ATACACCATT GAGCACCCTG GATCGCAGCA CCAGGCAAAA GGTAAATAAA

1621 GACACGCAAG AGCTCAATAG CGCACTGCAT CAGGCAGATC TCATTGATAT TTATCGCACT

1681 CTTCATCCTA AGAGTACCGA GTACACATTC TTCAGCGCCC CACATCATAC ATACTCAAAG

1741 ATCGATCATA TCGTCGGCTC AAAGGCTCTG CTGTCAAAGT GCAAGCGCAC AGAGATAATT

1801 ACAAATTACC TGTCAGATCA TAGCGCGATC AAGCTCGAGC TGAGAATCAA GAACCTGACC

1861 CAGAGCCGGA GTACCACTTG GAAGCTTAAT AACCTGCTGC TCAACGATTA TTGGGTCCAC

1921 AATGAGATGA AGGCAGAGAT TAAAATGTTC TTCGAAACAA ATGAGAATAA GGATACTACC

1981 TATCAAAACC TTTGGGATGC CTTTAAGGCC GTCTGCAGAG GCAAGTTCAT CGCCCTCAAC

2041 GCCTATAAAA GAAACAAGA GAGATCTAAG ATCGATACTC TCACCTCTCA GCTGAAGGAG

2101 TTGGAGAAAC AGGAACAGAC CCACTCCAAG GCGTCAAGAC GGCAGGAGAT CACAAAGATT

2161 CGCGCCGAGT TGAAAGAGAT CGAAACCCAA AAGACTCTTC AGAAAATTAA CGAGTCTCGT

2221 AGTTGGTTCT TCGAGCGGAT TAATAAGATA GACAGACCTC TGGCACGACT GATTAAGAAG

2281 AAGCGCGAAA AGAACCAGAT TGATACCATC AAGAACGACA AGGGCGACAT CACTACTGAC

2341 CCGACCGAGA TCCAGACCAC TATTCGGGAG TATTATAAGC ATTTGTATGC TAACAAGCTT

2401 GAGAACCTGG AAGAGATGGA CACTTTTCTG GATACCTATA CTCTGCCACG GCTTAATCAA

2461 GAGGAAGTCG AGTCCCTCAA CCGCCCAATT ACAGGAAGCG AGATTGTGGC CATAATTAAC

2521 TCCCTGCCGA CAAAGAAATC TCCTGGTCCG GACGGGTTTA CAGCTGAGTT TTATCAACGG

2581 TATATGGAAG AGCTTGTACC GTTTCTGCTC AAGCTCTTTC AGTCTATAGA AAAGGAAGGC

2641 ATCTTGCCCA ATTCCTTCTA CGAAGCTTCT ATAATACTTA TTCCCAAACC AGGACGCGAT

2701 ACCACAAAGA AGGAAAACTT CCGGCCCATT AGTCTCATGA ATATCGACGC TAAAATATTG

2761 AACAAGATTC TCGCCAACAG AATCCAACAA CATATTAAGA AATTGATACA TCACGACCAG

2821 GTGGGGTTTA TACCTGGCAT GCAGGGCTGG TTTAACATCC GGAAGAGTAT TAACGTCATT

2881 CAACACATTA ATAGAGCTAA GGATAAGAAT CATATGATCA TCTCTATAGA CGCGGAAAAG

2941 GCATTCGATA AGATTCAGCA GCCATTTATG CTCAAGACTC TGAACAAACT CGGCATCGAC

3001 GGAACATATT TTAAGATTAT TCGCGCAATT TACGATAAGC CGACTGCTAA CATTATCCTT
```

TABLE 8-continued

Plasmid and mRNA construct sequences

```
3061 AACGGCCAAA AGCTCGAGGC CTTTCCGCTC AAGACTGGAA CCCGCCAAGG CTGTCCCCTC

3121 TCCCCGCTTT TGTTTAATAT TGTACTCGAG GTGCTGGCTA GGGCTATTCG TCAAGAGAAA

3181 GAGATTAAAG GGATACAGCT CGGGAAGGAA GAGGTCAAGC TTTCCTTGTT CGCCGATGAT

3241 ATGATTGTGT ACCTGGAGAA TCCTATTGTG TCTGCTCAGA ACCTTCTTAA ACTTATTTCT

3301 AACTTTAGCA AGGTCAGCGG CTATAAGATT AACGTCCAGA AATCTCAGGC CTTTCTGTAC

3361 ACAAATAATC GACAGACCGA ATCCCAGATA ATGGGTGAGC TTCCGTTTGT CATAGCCAGC

3421 AAAAGGATAA AGTATCTCGG AATCCAGCTG ACACGAGACG TTAAAGATTT GTTTAAGGAA

3481 AATTACAAGC CTCTCCTGAA AGAGATTAAG GAAGATACTA ATAAGTGGAA GAATATCCCC

3541 TGTTCATGGG TTGGCAGAAT CAACATAGTG AAGATGGCAA TACTTCCTAA AGTGATATAT

3601 CGCTTTAACG CCATCCCAAT TAAACTGCCT ATGACCTTCT TTACGGAGCT CGAGAAAACA

3661 ACCCTTAAAT TTATATGGAA TCAAAAGAGA GCAAGAATAG CGAAGTCCAT CTTGAGCCAG

3721 AAGAATAAGG CCGGTGGGAT TACTTTGCCT GATTTTAAGT TGTATTATAA AGCCACAGTA

3781 ACTAAGACAG CCTGGTATTG GTATCAGAAT AGAGACATCG ACCAGTGGAA TCGGACCGAA

3841 CCATCAGAGA TAATGCCCCA CATCTATAAT TACCTTATAT TCGATAAGCC AGAAAAGAAT

3901 AAACAGTGGG GCAAAGACAG CCTCTTCAAC AAGTGGTGTT GGGAGAATTG GCTGGCCATA

3961 TGCCGGAAAC TCAAGCTCGA CCCCTTTCTT ACACCCTACA CTAAAATCAA CAGTAGGTGG

4021 ATCAAGGACT TGAATGTCAA GCCAAAGACT ATAAAGACAC TGGAAGAGAA TCTTGGGATC

4081 ACAATACAAG ATATAGGCGT CGGCAAAGAT TTTATGTCAA AGACGCCCAA GGCCATGGCC

4141 ACTAAGGATA AGATTGATAA GTGGGACCTT ATTAAGCTCA AAAGCTTCTG TACTGCCAAG

4201 GAGACCACGA TCAGAGTTAA TAGGCAGCCC ACTACATGGG AAAAGATTTT CGCCACTTAT

4261 TCATCAGATA AGGGGTTGAT AAGCAGAATA TATAACGAGC TGAAGCAGAT CTACAAGAAG

4321 AAAACGAATA ATCCCATCAA GAAGTGGGCA AAAGATATGA ACAGGCATTT TAGCAAAGAG

4381 GATATCTACG CCGCGAAGAA GCATATGAAG AAGTGTAGTT CAAGCTTGGC CATTCGTGAG

4441 ATGCAGATTA AGACGACCAT GCGATACCAC CTTACCCCAG TGAGGATGGC AATTATCAAG

4501 AAATCTGGCA ATAATAGATG TTGGCGGGGC TGTGGCGAGA TTGGCACCCT GCTCCATTGC

4561 TGGTGGGATT GCAAGCTGGT GCAGCCGCTT TGGAAATCAG TCTGGCGCTT TCTGAGGGAC

4621 CTCGAGCTTG AGATTCCCTT CGATCCCGCA ATTCCCTTGC TCGGAATCTA TCCTAACGAA

4681 TACAAGAGCT GTTGTTACAA GGATACGTGT ACCCGGATGT TCATCGCGGC CTTGTTTACG

4741 ATAGCTAAGA CGTGGAATCA GCCTAAGTGC CCCACAATGA TCGATTGGAT CAAGAAAATG

4801 TGGCATATTT ATACCATGGA GTATTACGCA GCAATTAAGA ATGACGAATT TATTTCCTTC

4861 GTTGGGACCT GGATGAAGCT GGAGACTATT ATTCTGAGCA AGCTGTCTCA GGAGCAAAAG

4921 ACAAAGCATA GAATCTTCTC TCTCATTGGT GGTAACGACT ACAAAGACGA TGACGACAAG

4981 CCCGCCGCCA AGAGGGTGAA GCTGGACTAA AGCGCTTCTA GAAGTTGTCT CCTCCTGCAC

5041 TGACTGACTG ATACAATCGA TTTCTGGATC CGCAGGCCTA ATCAACCTCT GGATTACAAA

5101 ATTTGTGAAA GATTGACTGG TATTCTTAAC TATGTTGCTC CTTTTACGCT ATGTGGATAC

5161 GCTGCTTTAA TGCCTTTGTA TCATGCTATT GCTTCCCGTA TGGCTTTCAT TTTCTCCTCC

5221 TTGTATAAAT CCTGGTTGCT GTCTCTTTAT GAGGAGTTGT GGCCCGTTGT CAGGCAACGT

5281 GGCGTGGTGT GCACTGTGTT TGCTGACGCA ACCCCCACTG GTTGGGGCAT TGCCACCACC

5341 TGTCAGCTCC TTTCCGGGAC TTTCGCTTTC CCCCTCCCTA TTGCCACGGC GGAACTCATC
```

TABLE 8-continued

Plasmid and mRNA construct sequences

```
5401 GCCGCCTGCC TTGCCCGCTG CTGGACAGGG GCTCGGCTGT TGGGCACTGA CAATTCCGTG

5461 GTGTTGTCGG GGAAGCTGAC GTCCTTTCCA TGGCTGCTCG CCTGTGTTGC CACCTGGATT

5521 CTGCGCGGGA CGTCCTTCTG CTACGTCCCT TCGGCCCTCA ATCCAGCGGA CCTTCCTTCC

5581 CGCTGAGAGA CACAAAAAAT TCCAACACAC TATTGCAATG AAAATAAATT TCCTTTATTA

5641 GCCAGAAGTC AGATGCTCAA GGGGCTTCAT GATGTCCCCA TAATTTTTGG CAGAGGGAAA

5701 AAGATCTCAG TGGTATTTGT GAGCCAGGGC ATTGGCCTTC TGATAGGCAG CCTGCACCTG

5761 AGGAGTGCGG CCGCTTTACT TGTACAGCTC GTCCATGCCG AGAGTGATCC CGGCGGCGGT

5821 CACGAACTCC AGCAGGACCA TGTGATCGCG CTTCTCGTTG GGGTCTTTGC TCAGGGCGGA

5881 CTGGGTGCTC AGGTAGTGGT TGTCGGGCAG CAGCACGGGG CCGTCGCCGA TGGGGGTGTT

5941 CTGCTGGTAG TGGTCGGCGA GCTGCACGCT GCCGTCCTCG ATGTTGTGGC GGATCTTGAA

6001 GTTCACCTTG ATGCCGTTCT TCTGCTTGTC GGCCATGATA TAGACGTTGT GGCTGTTGTA

6061 GTTGTACTCC AGCTTGTGCC CCAGGATGTT GCCGTCCTCC TTGAAGTCGA TGCCCTTCAG

6121 CTCGATGCGG TTCACCAGGG TGTCGCCCTC GAACTTCACC TCGGCGCGGG TCTTGTAGTT

6181 GCCGTCGTCC TTGAAGAAGA TGGTGCGCTC CTGGACGTAG CCTTCGGGCA TGGCGGACTT

6241 GAAGAAGTCG TGCTGCTTCA TGTGGTCGGG GTAGCGGCTG AAGCACTGCA CGCCGTAGGT

6301 CAGGGTGGTC ACGAGGGTGG GCCAGGGCAC GGGCAGCTTG CCGGTGGTGC AGATGAACTT

6361 CAGGGTCAGC TTGCCGTAGG TGGCATCGCC CTCGCCCTCG CCGGACACGC TGAACTTGTG

6421 GCCGTTTACG TCGCCGTCCA GCTCGACCAG GATGGGCACC ACCCCGGTGA ACAGCTCCTC

6481 GCCCTTGCTC ACCATGGTGG CGGGATCTGA CGGTTCACTA AACCAGCTCT GCTTATATAG

6541 ACCTCCCACC GTACACGCCT ACCGCCCATT TGCGTCAATG GGGCGGAGTT GTTACGACAT

6601 TTTGGAAAGT CCCGTTGATT TTGGTGCCAA AACAAACTCC CATTGACGTC AATGGGGTGG

6661 AGACTTGGAA ATCCCCGTGA GTCAAACCGC TATCCACGCC CATTGATGTA CTGCCAAAAC

6721 CGCATCACCA TGGTAATAGC GATGACTAAT ACGTAGATGT ACTGCCAAGT AGGAAAGTCC

6781 CATAAGGTCA TGTACTGGGC ATAATGCCAG GCGGGCCATT TACCGTCATT GACGTCAATA

6841 GGGGGCGTAC TTGGCATATG ATACACTTGA TGTACTGCCA AGTGGGCAGT TTACCGTAAA

6901 TACTCCACCC ATTGACGTCA ATGGAAAGTC CCTATTGGCG TTACTATGGG AACATACGTC

6961 ATTATTGACG TCAATGGGCG GGGGTCGTTG GGCGGTCAGC CAGGCGGGCC ATTTACCGTA

7021 AGTTATGTAA CGGGCCTGCT GCCGGCTCTG CGGCCTCTTC CGCGTCTTCG CCTTCGCCCT

7081 CAGACGAGTC GGATCTCCCT TTGGGCCGCC TCCCCGCCTG TCTAGCTTGA CTGACTGAGA

7141 TACAGCGTAC CTTCAGCTCA CAGACATGAT AAGATACATT GATGAGTTTG GACAAACCAC

7201 AACTAGAATG CAGTGAAAAA AATGCTTTAT TTGTGAAATT TGTGATGCTA TTGCTTTATT

7261 TGTAACCATT ATAAGCTGCA ATAAACAAGT T
(SEQ ID NO: 42)
```

LINE-1 alu mRNA GFP (SEQ ID NO: 43)

```
  1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT
```

TABLE 8-continued

Plasmid and mRNA construct sequences

```
 361 CCAGGTGTGA CCAGCTCGAG GAGCGCGTGA GCGCGATGGA AGACGAGATG AACGAGATGA

421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA

721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA

901 TCTCCGAGGG TGAGATTAAG TATTTCATCG ATAAACAGAT GCTGCGAGAC TTCGTGACAA

961 CTCGCCCAGC TCTCAAGGAA CTGCTCAAAG AGGCTCTTAA TATGGAGCGC AATAATAGAT

1021 ATCAACCCTT GCAGAACCAC GCAAAGATGT GAGACAGCCG TCAGACCATC AAGACTAGGA

1081 AGAAACTGCA TCAACTAATG AGCAAAATCA CCAGCTAACA TCATAGTATA CATGACCGGC

1141 TCTAACTCAC ATATCACCAT CCTTACACTT AACATTAACG GCCTCAACTC AGCTATCAAG

1201 CGCCATCGGC TGGCCAGCTG GATCAAATCA CAGGATCCAA GCGTTTGTTG CATCCAAGAG

1261 ACCCACCTGA CCTGTAGAGA TACTCACCGC CTCAAGATCA AGGGATGGCG AAAGATTTAT

1321 CAGGCGAACG GTAAGCAGAA GAAAGCCGGA GTCGCAATTC TGGTCTCAGA CAAGACGGAT

1381 TTCAAGCCCA CCAAAATTAA GCGTGATAAG GAAGGTCACT ATATTATGGT GAAAGGCAGC

1441 ATACAGCAGG AAGAACTTAC CATATTGAAC ATCTACGCGC CAAACACCGG CGCACCTCGC

1501 TTTATCAAAC AGGTCCTGTC CGATCTGCAG CGAGATCTGG ATTCTCATAC GTTGATTATG

1561 GGTGATTTCA ATACACCATT GAGCACCCTG GATCGCAGCA CCAGGCAAAA GGTAAATAAA

1621 GACACGCAAG AGCTCAATAG CGCACTGCAT CAGGCAGATC TCATTGATAT TTATCGCACT

1681 CTTCATCCTA AGAGTACCGA GTACACATTC TTCAGCGCCC CACATCATAC ATACTCAAAG

1741 ATCGATCATA TCGTCGGCTC AAAGGCTCTG CTGTCAAAGT GCAAGCGCAC AGAGATAATT

1801 ACAAATTACC TGTCAGATCA TAGCGCGATC AAGCTCGAGC TGAGAATCAA GAACCTGACC

1861 CAGAGCCGGA GTACCACTTG GAAGCTTAAT AACCTGCTGC TCAACGATTA TTGGGTCCAC

1921 AATGAGATGA AGGCAGAGAT TAAAATGTTC TTCGAAACAA ATGAGAATAA GGATACTACC

1981 TATCAAAACC TTTGGGATGC CTTTAAGGCC GTCTGCAGAG GCAAGTTCAT CGCCCTCAAC

2041 GCCTATAAAA GAAAACAAGA GAGATCTAAG ATCGATACTC TCACCTCTCA GCTGAAGGAG

2101 TTGGAGAAAC AGGAACAGAC CCACTCCAAG GCGTCAAGAC GGCAGGAGAT CACAAAGATT

2161 CGCGCCGAGT TGAAAGAGAT CGAAACCCAA AAGACTCTTC AGAAAATTAA CGAGTCTCGT

2221 AGTTGGTTCT TCGAGCGGAT TAATAAGATA GACAGACCTC TGGCACGACT GATTAAGAAG

2281 AAGCGCGAAA AGAACCAGAT TGATACCATC AAGAACGACA AGGGCGACAT CACTACTGAC

2341 CCGACCGAGA TCCAGACCAC TATTCGGGAG TATTATAAGC ATTTGTATGC TAACAAGCTT

2401 GAGAACCTGG AAGAGATGGA CACTTTTCTG GATACCTATA CTCTGCCACG GCTTAATCAA

2461 GAGGAAGTCG AGTCCCTCAA CCGCCCAATT ACAGGAAGCG AGATTGTGGC CATAATTAAC

2521 TCCCTGCCGA CAAAGAAATC TCCTGGTCCG GACGGGTTTA CAGCTGAGTT TTATCAACGG

2581 TATATGGAAG AGCTTGTACC GTTTCTGCTC AAGCTCTTTC AGTCTATAGA AAAGGAAGGC

2641 ATCTTGCCCA ATTCCTTCTA CGAAGCTTCT ATAATACTTA TTCCCAAACC AGGACGCGAT
```

TABLE 8-continued

Plasmid and mRNA construct sequences

```
2701 ACCACAAAGA AGGAAAACTT CCGGCCCATT AGTCTCATGA ATATCGACGC TAAAATATTG

2761 AACAAGATTC TCGCCAACAG AATCCAACAA CATATTAAGA AATTGATACA TCACGACCAG

2821 GTGGGGTTTA TACCTGGCAT GCAGGGCTGG TTTAACATCC GGAAGAGTAT TAACGTCATT

2881 CAACACATTA ATAGAGCTAA GGATAAGAAT CATATGATCA TCTCTATAGA CGCGGAAAAG

2941 GCATTCGATA AGATTCAGCA GCCATTTATG CTCAAGACTC TGAACAAACT CGGCATCGAC

3001 GGAACATATT TTAAGATTAT TCGCGCAATT TACGATAAGC CGACTGCTAA CATTATCCTT

3061 AACGGCCAAA AGCTCGAGGC CTTTCCGCTC AAGACTGGAA CCCGCCAAGG CTGTCCCCTC

3121 TCCCCGCTTT TGTTTAATAT TGTACTCGAG GTGCTGGCTA GGGCTATTCG TCAAGAGAAA

3181 GAGATTAAAG GGATACAGCT CGGGAAGGAA GAGGTCAAGC TTTCCTTGTT CGCCGATGAT

3241 ATGATTGTGT ACCTGGAGAA TCCTATTGTG TCTGCTCAGA ACCTTCTTAA ACTTATTTCT

3301 AACTTTAGCA AGGTCAGCGG CTATAAGATT AACGTCCAGA AATCTCAGGC CTTTCTGTAC

3361 ACAAATAATC GACAGACCGA ATCCCAGATA ATGGGTGAGC TTCCGTTTGT CATAGCCAGC

3421 AAAAGGATAA AGTATCTCGG AATCCAGCTG ACACGAGACG TTAAAGATTT GTTTAAGGAA

3481 AATTACAAGC CTCTCCTGAA AGAGATTAAG GAAGATACTA ATAAGTGGAA GAATATCCCC

3541 TGTTCATGGG TTGGCAGAAT CAACATAGTG AAGATGGCAA TACTTCCTAA AGTGATATAT

3601 CGCTTTAACG CCATCCCAAT TAAACTGCCT ATGACCTTCT TTACGGAGCT CGAGAAAACA

3661 ACCCTTAAAT TTATATGGAA TCAAAAGAGA GCAAGAATAG CGAAGTCCAT CTTGAGCCAG

3721 AAGAATAAGG CCGGTGGGAT TACTTTGCCT GATTTTAAGT TGTATTATAA AGCCACAGTA

3781 ACTAAGACAG CCTGGTATTG GTATCAGAAT AGAGACATCG ACCAGTGGAA TCGGACCGAA

3841 CCATCAGAGA TAATGCCCCA CATCTATAAT TACCTTATAT TCGATAAGCC AGAAAAGAAT

3901 AAACAGTGGG GCAAAGACAG CCTCTTCAAC AAGTGGTGTT GGGAGAATTG GCTGGCCATA

3961 TGCCGGAAAC TCAAGCTCGA CCCCTTTCTT ACACCCTACA CTAAAATCAA CAGTAGGTGG

4021 ATCAAGGACT TGAATGTCAA GCCAAAGACT ATAAAGACAC TGGAAGAGAA TCTTGGGATC

4081 ACAATACAAG ATATAGGCGT CGGCAAAGAT TTTATGTCAA AGACGCCCAA GGCCATGGCC

4141 ACTAAGGATA AGATTGATAA GTGGGACCTT ATTAAGCTCA AAAGCTTCTG TACTGCCAAG

4201 GAGACCACGA TCAGAGTTAA TAGGCAGCCC ACTACATGGG AAAAGATTTT CGCCACTTAT

4261 TCATCAGATA AGGGGTTGAT AAGCAGAATA TATAACGAGC TGAAGCAGAT CTACAAGAAG

4321 AAAACGAATA ATCCCATCAA GAAGTGGGCA AAAGATATGA ACAGGCATTT TAGCAAAGAG

4381 GATATCTACG CCGCGAAGAA GCATATGAAG AAGTGTAGTT CAAGCTTGGC CATTCGTGAG

4441 ATGCAGATTA AGACGACCAT GCGATACCAC CTTACCCCAG TGAGGATGGC AATTATCAAG

4501 AAATCTGGCA ATAATAGATG TTGGCGGGGC TGTGGCGAGA TTGGCACCCT GCTCCATTGC

4561 TGGTGGGATT GCAAGCTGGT GCAGCCGCTT TGGAAATCAG TCTGGCGCTT TCTGAGGGAC

4621 CTCGAGCTTG AGATTCCCTT CGATCCCGCA ATTCCCTTGC TCGGAATCTA TCCTAACGAA

4681 TACAAGAGCT GTTGTTACAA GGATACGTGT ACCCGGATGT TCATCGCGGC CTTGTTTACG

4741 ATAGCTAAGA CGTGGAATCA GCCTAAGTGC CCCACAATGA TCGATTGGAT CAAGAAAATG

4801 TGGCATATTT ATACCATGGA GTATTACGCA GCAATTAAGA ATGACGAATT TATTTCCTTC

4861 GTTGGGACCT GGATGAAGCT GGAGACTATT ATTCTGAGCA AGCTGTCTCA GGAGCAAAAG

4921 ACAAAGCATA GAATCTTCTC TCTCATTGGT GGTAACGACT ACAAAGACGA TGACGACAAG

4981 TAAAGCGGCC GGGCGCGGTG GCTCACGCCT GTAATCCCAG CACTTTGGGA GGCCGAGGCG
```

TABLE 8-continued

Plasmid and mRNA construct sequences

```
5041 GGAGGATCGC AGTTCGAGAC CAGCGCGAGA CCCCGTCTCT ACAAAAATAC AAAAATTAGC

5101 TTCTAGAAGT TGTCTCCTCC TGCACTGACT GACTGATACA ATCGATTTCT GGATCCGCAG

5161 GCCTAATCAA CCTCTGGATT ACAAAATTTG TGAAAGATTG ACTGGTATTC TTAACTATGT

5221 TGCTCCTTTT ACGCTATGTG GATACGCTGC TTTAATGCCT TTGTATCATG CTATTGCTTC

5281 CCGTATGGCT TTCATTTTCT CCTCCTTGTA TAAATCCTGG TTGCTGTCTC TTTATGAGGA

5341 GTTGTGGCCC GTTGTCAGGC AACGTGGCGT GGTGTGCACT GTGTTTGCTG ACGCAACCCC

5401 CACTGGTTGG GGCATTGCCA CCACCTGTCA GCTCCTTTCC GGGACTTTCG CTTTCCCCCT

5461 CCCTATTGCC ACGGCGGAAC TCATCGCCGC CTGCCTTGCC CGCTGCTGGA CAGGGGCTCG

5521 GCTGTTGGGC ACTGACAATT CCGTGGTGTT GTCGGGGAAG CTGACGTCCT TTCCATGGCT

5581 GCTCGCCTGT GTTGCCACCT GGATTCTGCG CGGGACGTCC TTCTGCTACG TCCCTTCGGC

5641 CCTCAATCCA GCGGACCTTC CTTCCCGCTG AGAGACACAA AAAATTCCAA CACACTATTG

5701 CAATGAAAAT AAATTTCCTT TATTAGCCAG AAGTCAGATG CTCAAGGGGC TTCATGATGT

5761 CCCCATAATT TTTGGCAGAG GGAAAAAGAT CTCAGTGGTA TTTGTGAGCC AGGGCATTGG

5821 CCTTCTGATA GGCAGCCTGC ACCTGAGGAG TGCGGCCGCT TTACTTGTAC AGCTCGTCCA

5881 TGCCGAGAGT GATCCCGGCG GCGGTCACGA ACTCCAGCAG GACCATGTGA TCGCGCTTCT

5941 CGTTGGGGTC TTTGCTCAGG GCGGACTGGG TGCTCAGGTA GTGGTTGTCG GGCAGCAGCA

6001 CGGGGCCGTC GCCGATGGGG GTGTTCTGCT GGTAGTGGTC GGCGAGCTGC ACGCTGCCGT

6061 CCTCGATGTT GTGGCGGATC TTGAAGTTCA CCTTGATGCC GTTCTTCTGC TTGTCGGCCA

6121 TGATATAGAC GTTGTGGCTG TTGTAGTTGT ACTCCAGCTT GTGCCCCAGG ATGTTGCCGT

6181 CCTCCTTGAA GTCGATGCCC TTCAGCTCGA TGCGGTTCAC CAGGGTGTCG CCCTCGAACT

6241 TCACCTCGGC GCGGGTCTTG TAGTTGCCGT CGTCCTTGAA GAAGATGGTG CGCTCCTGGA

6301 CGTAGCCTTC GGGCATGGCG GACTTGAAGA AGTCGTGCTG CTTCATGTGG TCGGGGTAGC

6361 GGCTGAAGCA CTGCACGCCG TAGGTCAGGG TGGTCACGAG GGTGGGCCAG GGCACGGGCA

6421 GCTTGCCGGT GGTGCAGATG AACTTCAGGG TCAGCTTGCC GTAGGTGGCA TCGCCCTCGC

6481 CCTCGCCGGA CACGCTGAAC TTGTGGCCGT TTACGTCGCC GTCCAGCTCG ACCAGGATGG

6541 GCACCACCCC GGTGAACAGC TCCTCGCCCT TGCTCACCAT GGTGGCGGGA TCTGACGGTT

6601 CACTAAACCA GCTCTGCTTA TATAGACCTC CCACCGTACA CGCCTACCGC CCATTTGCGT

6661 CAATGGGGCG GAGTTGTTAC GACATTTTGG AAAGTCCCGT TGATTTTGGT GCCAAAACAA

6721 ACTCCCATTG ACGTCAATGG GGTGGAGACT TGGAAATCCC CGTGAGTCAA ACCGCTATCC

6781 ACGCCCATTG ATGTACTGCC AAAACCGCAT CACCATGGTA ATAGCGATGA CTAATACGTA

6841 GATGTACTGC CAAGTAGGAA AGTCCCATAA GGTCATGTAC TGGGCATAAT GCCAGGCGGG

6901 CCATTTACCG TCATTGACGT CAATAGGGGG CGTACTTGGC ATATGATACA CTTGATGTAC

6961 TGCCAAGTGG GCAGTTTACC GTAAATACTC CACCCATTGA CGTCAATGGA AAGTCCCTAT

7021 TGGCGTTACT ATGGGAACAT ACGTCATTAT TGACGTCAAT GGGCGGGGGT CGTTGGGCGG

7081 TCAGCCAGGC GGGCCATTTA CCGTAAGTTA TGTAACGGGC CTGCTGCCGG CTCTGCGGCC

7141 TCTTCCGCGT CTTCGCCTTC GCCCTCAGAC GAGTCGGATC TCCCTTTGGG CCGCCTCCCC

7201 GCCTGTCTAG CTTGACTGAC TGAGATACAG CGTACCTTCA GCTCACAGAC ATGATAAGAT

7261 ACATTGATGA GTTTGGACAA ACCACAACTA GAATGCAGTG AAAAAAATGC TTTATTTGTG

7321 AAATTTGTGA TGCTATTGCT TTATTTGTAA CCATTATAAG CTGCAATAAA CAAGTT
```

TABLE 8-continued

| Plasmid and mRNA construct sequences |
| --- |

(SEQ ID NO: 43)

LINE-1 plasmid CVBE IRES GFP (SEQ ID NO: 44)

```
   1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT

361 CCAGGTGTGA CCAGCTCGAG GAGCGCGTGA GCGCGATGGA AGACGAGATG AACGAGATGA

421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA

721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA

901 TCTCCGAGGG TGAGATTAAG TATTTCATCG ATAAACAGAT GCTGCGAGAC TTCGTGACAA

961 CTCGCCCAGC TCTCAAGGAA CTGCTCAAAG AGGCTCTTAA TATGGAGCGC AATAATAGAT

1021 ATCAACCCTT GCAGAACCAC GCAAAGATGT GAGACAGTTA AAACAGCCTG TGGGTTGATC

1081 CCACCCACAG GCCCATTGGG CGCTAGCACT CTGGTATCAC GGTACCTTTG TGCGCCTGTT

1141 TTATACCCCC TCCCCCAACT GTAACTTAGA AGTAACACAC ACCGATCAAC AGTCAGCGTG

1201 GCACACCAGC CACGTTTTGA TCAAGCACTT CTGTTACCCC GGACTGAGTA TCAATAGACT

1261 GCTCACGCGG TTGAAGGAGA AAGCGTTCGT TATCCGGCCA ACTACTTCGA AAAACCTAGT

1321 AACACCGTGG AAGTTGCAGA GTGTTTCGCT CAGCACTACC CCAGTGTAGA TCAGGTCGAT

1381 GAGTCACCGC ATTCCCCACG GGCGACCGTG GCGGTGGCTG CGTTGGCGGC CTGCCCATGG

1441 GGAAACCCAT GGGACGCTCT AATACAGACA TGGTGCGAAG AGTCTATTGA GCTAGTTGGT

1501 AGTCCTCCGG CCCCTGAATG CGGCTAATCC TAACTGCGGA GCACACACCC TCAAGCCAGA

1561 GGGCAGTGTG TCGTAACGGG CAACTCTGCA GCGGAACCGA CTACTTTGGG TGTCCGTGTT

1621 TCATTTTATT CCTATACTGG CTGCTTATGG TGACAATTGA GAGATCGTTA CCATATAGCT

1681 ATTGGATTGG CCATCCGGTG ACTAATAGAG CTATTATATA TCCCTTTGTT GGGTTTATAC

1741 CACTTAGCTT GAAAGAGGTT AAAACATTAC AATTCATTGT TAAGTTGAAT ACAGCAAATA

1801 CATGACCGGC TCTAACTCAC ATATCACCAT CCTTACACTT AACATTAACG GCCTCAACTC

1861 AGCTATCAAG CGCCATCGGC TGGCCAGCTG GATCAAATCA CAGGATCCAA GCGTTTGTTG

1921 CATCCAAGAG ACCCACCTGA CCTGTAGAGA TACTCACCGC CTCAAGATCA AGGGATGGCG

1981 AAAGATTTAT CAGGCGAACG GTAAGCAGAA GAAAGCCGGA GTCGCAATTC TGGTCTCAGA

2041 CAAGACGGAT TTCAAGCCCA CCAAAATTAA GCGTGATAAG GAAGGTCACT ATATTATGGT

2101 GAAAGGCAGC ATACAGCAGG AAGAACTTAC CATATTGAAC ATCTACGCGC CAAACACCGG

2161 CGCACCTCGC TTTATCAAAC AGGTCCTGTC CGATCTGCAG CGAGATCTGG ATTCTCATAC
```

TABLE 8-continued

Plasmid and mRNA construct sequences

```
2221 GTTGATTATG GGTGATTTCA ATACACCATT GAGCACCCTG GATCGCAGCA CCAGGCAAAA

2281 GGTAAATAAA GACACGCAAG AGCTCAATAG CGCACTGCAT CAGGCAGATC TCATTGATAT

2341 TTATCGCACT CTTCATCCTA AGAGTACCGA GTACACATTC TTCAGCGCCC CACATCATAC

2401 ATACTCAAAG ATCGATCATA TCGTCGGCTC AAAGGCTCTG CTGTCAAAGT GCAAGCGCAC

2461 AGAGATAATT ACAAATTACC TGTCAGATCA TAGCGCGATC AAGCTCGAGC TGAGAATCAA

2521 GAACCTGACC CAGAGCCGGA GTACCACTTG GAAGCTTAAT AACCTGCTGC TCAACGATTA

2581 TTGGGTCCAC AATGAGATGA AGGCAGAGAT TAAAATGTTC TTCGAAACAA ATGAGAATAA

2641 GGATACTACC TATCAAAACC TTTGGGATGC CTTTAAGGCC GTCTGCAGAG GCAAGTTCAT

2701 CGCCCTCAAC GCCTATAAAA GAAAACAAGA GAGATCTAAG ATCGATACTC TCACCTCTCA

2761 GCTGAAGGAG TTGGAGAAAC AGGAACAGAC CCACTCCAAG GCGTCAAGAC GGCAGGAGAT

2821 CACAAAGATT CGCGCCGAGT TGAAAGAGAT CGAAACCCAA AAGACTCTTC AGAAAATTAA

2881 CGAGTCTCGT AGTTGGTTCT TCGAGCGGAT TAATAAGATA GACAGACCTC TGGCACGACT

2941 GATTAAGAAG AAGCGCGAAA AGAACCAGAT TGATACCATC AAGAACGACA AGGGCGACAT

3001 CACTACTGAC CCGACCGAGA TCCAGACCAC TATTCGGGAG TATTATAAGC ATTTGTATGC

3061 TAACAAGCTT GAGAACCTGG AAGAGATGGA CACTTTTCTG GATACCTATA CTCTGCCACG

3121 GCTTAATCAA GAGGAAGTCG AGTCCCTCAA CCGCCCAATT ACAGGAAGCG AGATTGTGGC

3181 CATAATTAAC TCCCTGCCGA CAAAGAAATC TCCTGGTCCG GACGGGTTTA CAGCTGAGTT

3241 TTATCAACGG TATATGGAAG AGCTTGTACC GTTTCTGCTC AAGCTCTTTC AGTCTATAGA

3301 AAAGGAAGGC ATCTTGCCCA ATTCCTTCTA CGAAGCTTCT ATAATACTTA TTCCCAAACC

3361 AGGACGCGAT ACCACAAAGA AGGAAAACTT CCGGCCCATT AGTCTCATGA ATATCGACGC

3421 TAAAATATTG AACAAGATTC TCGCCAACAG AATCCAACAA CATATTAAGA AATTGATACA

3481 TCACGACCAG GTGGGGTTTA TACCTGGCAT GCAGGGCTGG TTTAACATCC GGAAGAGTAT

3541 TAACGTCATT CAACACATTA ATAGAGCTAA GGATAAGAAT CATATGATCA TCTCTATAGA

3601 CGCGGAAAAG GCATTCGATA AGATTCAGCA GCCATTTATG CTCAAGACTC TGAACAAACT

3661 CGGCATCGAC GGAACATATT TTAAGATTAT TCGCGCAATT TACGATAAGC CGACTGCTAA

3721 CATTATCCTT AACGGCCAAA AGCTCGAGGC CTTTCCGCTC AAGACTGGAA CCCGCCAAGG

3781 CTGTCCCCTC TCCCCGCTTT TGTTTAATAT TGTACTCGAG GTGCTGGCTA GGGCTATTCG

3841 TCAAGAGAAA GAGATTAAAG GGATACAGCT CGGGAAGGAA GAGGTCAAGC TTTCCTTGTT

3901 CGCCGATGAT ATGATTGTGT ACCTGGAGAA TCCTATTGTG TCTGCTCAGA ACCTTCTTAA

3961 ACTTATTTCT AACTTTAGCA AGGTCAGCGG CTATAAGATT AACGTCCAGA AATCTCAGGC

4021 CTTTCTGTAC ACAAATAATC GACAGACCGA ATCCCAGATA ATGGGTGAGC TTCCGTTTGT

4081 CATAGCCAGC AAAAGGATAA AGTATCTCGG AATCCAGCTG ACACGAGACG TTAAAGATTT

4141 GTTTAAGGAA AATTACAAGC CTCTCCTGAA AGAGATTAAG GAAGATACTA ATAAGTGGAA

4201 GAATATCCCC TGTTCATGGG TTGGCAGAAT CAACATAGTG AAGATGGCAA TACTTCCTAA

4261 AGTGATATAT CGCTTTAACG CCATCCCAAT TAAACTGCCT ATGACCTTCT TTACGGAGCT

4321 CGAGAAAACA ACCCTTAAAT TTATATGGAA TCAAAAGAGA GCAAGAATAG CGAAGTCCAT

4381 CTTGAGCCAG AAGAATAAGG CCGGTGGGAT TACTTTGCCT GATTTTAAGT TGTATTATAA

4441 AGCCACAGTA ACTAAGACAG CCTGGTATTG GTATCAGAAT AGAGACATCG ACCAGTGGAA

4501 TCGGACCGAA CCATCAGAGA TAATGCCCCA CATCTATAAT TACCTTATAT CGATAAGCC
```

TABLE 8-continued

Plasmid and mRNA construct sequences

```
4561 AGAAAGAAT AAACAGTGGG GCAAAGACAG CCTCTTCAAC AAGTGGTGTT GGGAGAATTG

4621 GCTGGCCATA TGCCGGAAAC TCAAGCTCGA CCCCTTTCTT ACACCCTACA CTAAAATCAA

4681 CAGTAGGTGG ATCAAGGACT TGAATGTCAA GCCAAAGACT ATAAAGACAC TGGAAGAGAA

4741 TCTTGGGATC ACAATACAAG ATATAGGCGT CGGCAAAGAT TTTATGTCAA AGACGCCCAA

4801 GGCCATGGCC ACTAAGGATA AGATTGATAA GTGGGACCTT ATTAAGCTCA AAAGCTTCTG

4861 TACTGCCAAG GAGACCACGA TCAGAGTTAA TAGGCAGCCC ACTACATGGG AAAAGATTTT

4921 CGCCACTTAT TCATCAGATA AGGGGGTTGAT AAGCAGAATA TATAACGAGC TGAAGCAGAT

4981 CTACAAGAAG AAAACGAATA ATCCCATCAA GAAGTGGGCA AAAGATATGA ACAGGCATTT

5041 TAGCAAAGAG GATATCTACG CCGCGAAGAA GCATATGAAG AAGTGTAGTT CAAGCTTGGC

5101 CATTCGTGAG ATGCAGATTA AGACGACCAT GCGATACCAC CTTACCCCAG TGAGGATGGC

5161 AATTATCAAG AAATCTGGCA ATAATAGATG TTGGCGGGGC TGTGGCGAGA TTGGCACCCT

5221 GCTCCATTGC TGGTGGGATT GCAAGCTGGT GCAGCCGCTT TGGAAATCAG TCTGGCGCTT

5281 TCTGAGGGAC CTCGAGCTTG AGATTCCCTT CGATCCCGCA ATTCCCTTGC TCGGAATCTA

5341 TCCTAACGAA TACAAGAGCT GTTGTTACAA GGATACGTGT ACCCGGATGT TCATCGCGGC

5401 CTTGTTTACG ATAGCTAAGA CGTGGAATCA GCCTAAGTGC CCCACAATGA TCGATTGGAT

5461 CAAGAAAATG TGGCATATTT ATACCATGGA GTATTACGCA GCAATTAAGA ATGACGAATT

5521 TATTTCCTTC GTTGGGACCT GGATGAAGCT GGAGACTATT ATTCTGAGCA AGCTGTCTCA

5581 GGAGCAAAAG ACAAAGCATA GAATCTTCTC TCTCATTGGT GGTAACGACT ACAAAGACGA

5641 TGACGACAAG TAAAGCGCTT CTAGAAGTTG TCTCCTCCTG CACTGACTGA CTGATACAAT

5701 CGATTCTGG ATCCGCAGGC CTAATCAACC TCTGGATTAC AAAATTTGTG AAAGATTGAC

5761 TGGTATTCTT AACTATGTTG CTCCTTTTAC GCTATGTGGA TACGCTGCTT TAATGCCTTT

5821 GTATCATGCT ATTGCTTCCC GTATGGCTTT CATTTTCTCC TCCTTGTATA AATCCTGGTT

5881 GCTGTCTCTT TATGAGGAGT TGTGGCCCGT TGTCAGGCAA CGTGGCGTGG TGTGCACTGT

5941 GTTTGCTGAC GCAACCCCCA CTGGTTGGGG CATTGCCACC ACCTGTCAGC TCCTTTCCGG

6001 GACTTTCGCT TTCCCCCTCC CTATTGCCAC GGCGGAACTC ATCGCCGCCT GCCTTGCCCG

6061 CTGCTGGACA GGGGCTCGGC TGTTGGGCAC TGACAATTCC GTGGTGTTGT CGGGGAAGCT

6121 GACGTCCTTT CCATGGCTGC TCGCCTGTGT TGCCACCTGG ATTCTGCGCG GGACGTCCTT

6181 CTGCTACGTC CCTTCGGCCC TCAATCCAGC GGACCTTCCT TCCCGCGAAC AAACGACCCA

6241 ACACCCGTGC GTTTTATTCT GTCTTTTTAT TGCCGATCCC CTCAGAAGAA CTCGTCAAGA

6301 AGGCGATAGA AGGCGATGCG CTGCGAATCG GGAGCGGCGA TACCGTAAAG CACGAGGAAG

6361 CGGTCAGCCC ATTCGCCGCC AAGCTCTTCA GCAATATCAC GGGTAGCCAA CGCTATGTCC

6421 TGATAGCGGT CGGCCGCTTT ACTTGTACAG CTCGTCCATG CCGAGAGTGA TCCCGGCGGC

6481 GGTCACGAAC TCCAGCAGGA CCATGTGATC GCGCTTCTCG TTGGGGTCTT TGCTCAGGGC

6541 GGACTGGGTG CTCAGGTAGT GGTTGTCGGG CAGCAGCACG GGGCCGTCGC CGATGGGGGT

6601 GTTCTGCTGG TAGTGGTCGG CCAGGTGAGT CCAGGAGATG TTTCAGCACT GTTGCCTTTA

6661 GTCTCGAGGC AACTTAGACA ACTGAGTATT GATCTGAGCA CAGCAGGGTG TGAGCTGTTT

6721 GAAGATACTG GGGTTGGGGG TGAAGAAACT GCAGAGGACT AACTGGGCTG AGACCCAGTG

6781 GCAATGTTTT AGGGCCTAAG GAATGCCTCT GAAAATCTAG ATGGACAACT TTGACTTTGA

6841 GAAAGAGAG GTGGAAATGA GGAAAATGAC TTTTCTTTAT TAGATTTCGG TAGAAAGAAC
```

TABLE 8-continued

Plasmid and mRNA construct sequences

```
6901 TTTCATCTTT CCCCTATTTT TGTTATTCGT TTTAAAACAT CTATCTGGAG GCAGGACAAG

6961 TATGGTCATT AAAAAGATGC AGGCAGAAGG CATATATTGG CTCAGTCAAA GTGGGGAACT

7021 TTGGTGGCCA AACATACATT GCTAAGGCTA TTCCTATATC AGCTGGACAC ATATAAAATG

7081 CTGCTAATGC TTCATTACAA ACTTATATCC TTTAATTCCA GATGGGGGCA AAGTATGTCC

7141 AGGGGTGAGG AACAATTGAA ACATTTGGGC TGGAGTAGAT TTTGAAAGTC AGCTCTGTGT

7201 GTGTGTGTGT GTGTGTGTGT GTGAGAGCGT GTGTTTCTTT TAACGTTTTC AGCCTACAGC

7261 ATACAGGGTT CATGGTGGCA AGAAGATAAC AAGATTTAAA TTATGGCCAG TGACTAGTGC

7321 TGCAAGAAGA ACAACTACCT GCATTTAATG GGAAAGCAAA ATCTCAGGCT TTGAGGGAAG

7381 TTAACATAGG CTTGATTCTG GGTGGAAGCT GGGTGTGTAG TTATCTGGAG GCCAGGCTGG

7441 AGCTCTCAGC TCACTATGGG TTCATCTTTA TTGTCTCCTT TCATCTCAAC AGCTGCACGC

7501 TGCCGTCCTC GATGTTGTGG CGGATCTTGA AGTTCACCTT GATGCCGTTC TTCTGCTTGT

7561 CGGCCATGAT ATAGACGTTG TGGCTGTTGT AGTTGTACTC CAGCTTGTGC CCCAGGATGT

7621 TGCCGTCCTC CTTGAAGTCG ATGCCCTTCA GCTCGATGCG GTTCACCAGG GTGTCGCCCT

7681 CGAACTTCAC CTCGGCGCGG GTCTTGTAGT TGCCGTCGTC CTTGAAGAAG ATGGTGCGCT

7741 CCTGGACGTA GCCTTCGGGC ATGGCGGACT TGAAGAAGTC GTGCTGCTTC ATGTGGTCGG

7801 GGTAGCGGCT GAAGCACTGC ACGCCGTAGG TCAGGGTGGT CACGAGGGTG GGCCAGGGCA

7861 CGGGCAGCTT GCCGGTGGTG CAGATGAACT TCAGGGTCAG CTTGCCGTAG GTGGCATCGC

7921 CCTCGCCCTC GCCGGACACG CTGAACTTGT GGCCGTTTAC GTCGCCGTCC AGCTCGACCA

7981 GGATGGGCAC CACCCCGGTG AACAGCTCCT CGCCCTTGCT CACCATGGTG GCGAATTCGA

8041 AGCTTGAGCA CGAGATCTGA GTCCGGTAGG CCTAGCGGAT CTGACGGTTC ACTAAACCAG

8101 CTCTGCTTAT ATAGACCTCC CACCGTACAC GCCTACCGCC CATTTGCGTC AATGGGGCGG

8161 AGTTGTTACG ACATTTTGGA AAGTCCCGTT GATTTTGGTG CCAAAACAAA CTCCCATTGA

8221 CGTCAATGGG GTGGAGACTT GGAAATCCCC GTGAGTCAAA CCGCTATCCA CGCCCATTGA

8281 TGTACTGCCA AAACCGCATC ACCATGGTAA TAGCGATGAC TAATACGTAG ATGTACTGCC

8341 AAGTAGGAAA GTCCCATAAG GTCATGTACT GGGCATAATG CCAGGCGGGC CATTTACCGT

8401 CATTGACGTC AATAGGGGGC GTACTTGGCA TATGATACAC TTGATGTACT GCCAAGTGGG

8461 CAGTTTACCG TAAATACTCC ACCCATTGAC GTCAATGGAA AGTCCCTATT GGCGTTACTA

8521 TGGGAACATA CGTCATTATT GACGTCAATG GGCGGGGGTC GTTGGGCGGT CAGCCAGGCG

8581 GGCCATTTAC CGTAAGTTAT GTAACGGGCC TGCTGCCGGC TCTGCGGCCT CTTCCGCGTC

8641 TTCGCCTTCG CCCTCAGACG AGTCGGATCT CCCTTTGGGC CGCCTCCCCG CCTGTCTAGC

8701 TTGACTGACT GAGATACAGC GTACCTTCAG CTCACAGACA TGATAAGATA CATTGATGAG

8761 TTTGGACAAA CCACAACTAG AATGCAGTGA AAAAAATGCT TTATTTGTGA AATTTGTGAT

8821 GCTATTGCTT TATTTGTAAC CATTATAAGC TGCAATAAAC AAGTTAACAA CAACAATTGC

8881 ATTCATTTTA TGTTTCAGGT TCAGGGGGAG GTGTGGGAGG TTTTTTAAAG CAAGTAAAAC

8941 CTCTACAAAT GTGGTATTGG CCCATCTCTA TCGGTATCGT AGCATAACCC CTTGGGGCCT

9001 CTAAACGGGT CTTGAGGGGT TTTTTGTGCC CCTCGGGCCG GATTGCTATC TACCGGCATT

9061 GGCGCAGAAA AAAATGCCTG ATGCGACGCT GCGCGTCTTA TACTCCCACA TATGCCAGAT

9121 TCAGCAACGG ATACGGCTTC CCCAACTTGC CCACTTCCAT ACGTGTCCTC CTTACCAGAA

9181 ATTTATCCTT AAGGTCGTCA GCTATCCTGC AGGCGATCTC TCGATTTCGA TCAAGACATT
```

TABLE 8-continued

Plasmid and mRNA construct sequences

```
 9241 CCTTTAATGG TCTTTTCTGG ACACCACTAG GGGTCAGAAG TAGTTCATCA AACTTTCTTC

9301 CCTCCCTAAT CTCATTGGTT ACCTTGGGCT ATCGAAACTT AATTAAGCGA TCTGCATCTC

9361 AATTAGTCAG CAACCATAGT CCCGCCCCTA ACTCCGCCCA TCCCGCCCCT AACTCCGCCC

9421 AGTTCCGCCC ATTCTCCGCC CCATCGCTGA CTAATTTTTT TTATTTATGC AGAGGCCGAG

9481 GCCGCCTCGG CCTCTGAGCT ATTCCAGAAG TAGTGAGGAG GCTTTTTTGG AGGCCTAGGC

9541 TTTTGCAAAG GAGGTAGCCA ACATGATTGA ACAAGATGGA TTGCACGCAG GTTCTCCCGC

9601 CGCTTGGGTG GAGAGGCTAT TCGGCTATGA CTGGGCACAA CAGACAATCG GCTGCTCTGA

9661 TGCCGCCGTG TTCCGGCTGT CAGCGCAGGG GCGCCCGGTT CTTTTTGTCA AGACCGACCT

9721 GTCCGGTGCC CTGAATGAAC TCCAGGACGA GGCAGCGCGG CTATCGTGGC TGGCCACGAC

9781 GGGCGTTCCT TGCGCAGCTG TGCTCGACGT TGTCACTGAA GCGGGAAGGG ACTGGCTGCT

9841 ATTGGGCGAA GTGCCGGGGC AGGATCTCCT GTCATCTCAC CTTGCTCCTG CCGAGAAAGT

9901 ATCCATCATG GCTGATGCAA TGCGGCGGCT GCATACGCTT GATCCGGCTA CCTGCCCATT

9961 CGACCACCAA GCGAAACATC GCATCGAGCG AGCACGTACT CGGATGGAAG CCGGTCTTGT

10021 CGATCAGGAT GATCTGGACG AAGAGCATCA GGGGCTCGCG CCAGCCGAAC TGTTCGCCAG

10081 GCTCAAGGCG CGGATGCCCG ACGGCGAGGA TCTCGTCGTG ACCCACGGCG ATGCCTGCTT

10141 GCCGAATATC ATGGTGGAAA ATGGCCGCTT TTCTGGATTC ATCGACTGTG GCCGGCTGGG

10201 TGTGGCGGAC CGCTATCAGG ACATAGCGTT GGCTACCCGT GATATTGCTG AAGAGCTTGG

10261 CGGCGAATGG GCTGACCGCT TCCTCGTGCT TTACGGTATC GCCGCTCCCG ATTCGCAGCG

10321 CATCGCCTTC TATCGCCTTC TTGACGAGTT CTTCTAGTAT GTAAGCCCTG TGCCTTCTAG

10381 TTGCCAGCCA TCTGTTGTTT GCCCCTCCCC CGTGCCTTCC TTGACCCTGG AAGGTGCCAC

10441 TCCCACTGTC CTTTCCTAAT AAAATGAGGA AATTGCATCG CATTGTCTGA GTAGGTGTCA

10501 TTCTATTCTG GGGGGTGGGG TGGGGCAGGA CAGCAAGGGG GAGGATTGGG AAGACAATAG

10561 CAGGCATGCT GGGGATGCGG TGGGCTCTAT GGTTAATTAA CCAGTCAAGT CAGCTACTTG

10621 GCGAGATCGA CTTGTCTGGG TTTCGACTAC GCTCAGAATT GCGTCAGTCA AGTTCGATCT

10681 GGTCCTTGCT ATTGCACCCG TTCTCCGATT ACGAGTTTCA TTTAAATCAT GTGAGCAAAA

10741 GGCCAGCAAA AGGCCAGGAA CCGTAAAAAG GCCGCGTTGC TGGCGTTTTT CCATAGGCTC

10801 CGCCCCCCTG ACGAGCATCA CAAAAATCGA CGCTCAAGTC AGAGGTGGCG AAACCCGACA

10861 GGACTATAAA GATACCAGGC GTTTCCCCCT GGAAGCTCCC TCGTGCGCTC TCCTGTTCCG

10921 ACCCTGCCGC TTACCGGATA CCTGTCCGCC TTTCTCCCTT CGGGAAGCGT GGCGCTTTCT

10981 CATAGCTCAC GCTGTAGGTA TCTCAGTTCG GTGTAGGTCG TTCGCTCCAA GCTGGGCTGT

11041 GTGCACGAAC CCCCCGTTCA GCCCGACCGC TGCGCCTTAT CCGGTAACTA TCGTCTTGAG

11101 TCCAACCCGG TAAGACACGA CTTATCGCCA CTGGCAGCAG CCACTGGTAA CAGGATTAGC

11161 AGAGCGAGGT ATGTAGGCGG TGCTACAGAG TTCTTGAAGT GGTGGCCTAA CTACGGCTAC

11221 ACTAGAAGAA CAGTATTTGG TATCTGCGCT CTGCTGAAGC CAGTTACCTT CGGAAAAAGA

11281 GTTGGTAGCT CTTGATCCGG CAAACAAACC ACCGCTGGTA GCGGTGGTTT TTTTGTTTGC

11341 AAGCAGCAGA TTACGCGCAG AAAAAAAGGA TCTCAAGAAG ATCCTTTGAT CTTTTCTACG

11401 GGGTCTGACG CTCAGTGGAA CGAAAACTCA CGTTAAGGGA TTTTGGTCAT GAGATTATCA

11461 AAAAGGATCT TCACCTAGAT CCTTTTAAAT TAAAAATGAA GTTTTAAATC AATCTAAAGT

11521 ATATATGAGT AAACTTGGTC TGACAGTTAC CAATGCTTAA TCAGTGAGGC ACCTATCTCA
```

TABLE 8-continued

Plasmid and mRNA construct sequences

```
11581 GCGATCTGTC TATTTCGTTC ATCCATAGTT GCATTTAAAT TTCCGAACTC TCCAAGGCCC

11641 TCGTCGGAAA ATCTTCAAAC CTTTCGTCCG ATCCATCTTG CAGGCTACCT CTCGAACGAA

11701 CTATCGCAAG TCTCTTGGCC GGCCTTGCGC CTTGGCTATT GCTTGGCAGC GCCTATCGCC

11761 AGGTATTACT CCAATCCCGA ATATCCGAGA TCGGGATCAC CCGAGAGAAG TTCAACCTAC

11821 ATCCTCAATC CCGATCTATC CGAGATCCGA GGAATATCGA AATCGGGGCG CGCCTGGTGT

11881 ACCGAGAACG ATCCTCTCAG TGCGAGTCTC GACGATCCAT ATCGTTGCTT GGCAGTCAGC

11941 CAGTCGGAAT CCAGCTTGGG ACCCAGGAAG TCCAATCGTC AGATATTGTA CTCAAGCCTG

12001 GTCACGGCAG CGTACCGATC TGTTTAAACC TAGATATTGA TAGTCTGATC GGTCAACGTA

12061 TAATCGAGTC CTAGCTTTTG CAAACATCTA TCAAGAGACA GGATCAGCAG GAGGCTTTCG

12121 CATGAGTATT CAACATTTCC GTGTCGCCCT TATTCCCTTT TTTGCGGCAT TTTGCCTTCC

12181 TGTTTTTGCT CACCCAGAAA CGCTGGTGAA AGTAAAAGAT GCTGAAGATC AGTTGGGTGC

12241 GCGAGTGGGT TACATCGAAC TGGATCTCAA CAGCGGTAAG ATCCTTGAGA GTTTTCGCCC

12301 CGAAGAACGC TTTCCAATGA TGAGCACTTT TAAAGTTCTG CTATGTGGCG CGGTATTATC

12361 CCGTATTGAC GCCGGGCAAG AGCAACTCGG TCGCCGCATA CACTATTCTC AGAATGACTT

12421 GGTTGAGTAT TCACCAGTCA CAGAAAAGCA TCTTACGGAT GGCATGACAG TAAGAGAATT

12481 ATGCAGTGCT GCCATAACCA TGAGTGATAA CACTGCGGCC AACTTACTTC TGACAACGAT

12541 TGGAGGACCG AAGGAGCTAA CCGCTTTTTT GCACAACATG GGGGATCATG TAACTCGCCT

12601 TGATCGTTGG GAACCGGAGC TGAATGAAGC CATACCAAAC GACGAGCGTG ACACCACGAT

12661 GCCTGTAGCA ATGGCAACAA CCTTGCGTAA ACTATTAACT GGCGAACTAC TTACTCTAGC

12721 TTCCCGGCAA CAGTTGATAG ACTGGATGGA GGCGGATAAA GTTGCAGGAC CACTTCTGCG

12781 CTCGGCCCTT CCGGCTGGCT GGTTTATTGC TGATAAATCT GGAGCCGGTG AGCGTGGGTC

12841 TCGCGGTATC ATTGCAGCAC TGGGGCCAGA TGGTAAGCCC TCCCGTATCG TAGTTATCTA

12901 CACGACGGGG AGTCAGGCAA CTATGGATGA ACGAAATAGA CAGATCGCTG AGATAGGTGC

12961 CTCACTGATT AAGCATTGGT AACCGATTCT AGGTGCATTG GCGCAGAAAA AAATGCCTGA

13021 TGCGACGCTG CGCGTCTTAT ACTCCCACAT ATGCCAGATT CAGCAACGGA TACGGCTTCC

13081 CCAACTTGCC CACTTCCATA CGTGTCCTCC TTACCAGAAA TTTATCCTTA AGATCGTTTA

13141 AACTCGACTC TGGCTCTATC GAATCTCCGT CGTTTCGAGC TTACGCGAAC AGCCGTGGCG

13201 CTCATTTGCT CGTCGGGCAT CGAATCTCGT CAGCTATCGT CAGCTTACCT TTTTGGCAGC

13261 GATCGCGGCT CCCGACATCT TGGACCATTA GCTCCACAGG TATCTTCTTC CCTCTAGTGG

13321 TCATAACAGC AGCTTCAGCT ACCTCTCAAT TCAAAAAACC CCTCAAGACC CGTTTAGAGG

13381 CCCCAAGGGG TTATGCTATC AATCGTTGCG TTACACACAC AAAAAACCAA CACACATCCA

13441 TCTTCGATGG ATAGCGATTT TATTATCTAA CTGCTGATCG AGTGTAGCCA GATCTAGTAA

13501 TCAATTACGG GGTCATTAGT TCATAGCCCA TATATGGAGT TCCGCGTTAC ATAACTTACG

13561 GTAAATGGCC CGCCTGGCTG ACCGCCCAAC GACCCCCGCC CATTGACGTC AATAATGACG

13621 TATGTTCCCA TAGTAACGCC AATAGGGACT TTCCATTGAC GTCAATGGGT GGAGTATTTA

13681 CGGTAAACTG CCCACTTGGC AGTACATCAA GTGTATCATA TGCCAAGTAC GCCCCCTATT

13741 GACGTCAATG ACGGTAAATG GCCCGCCTGG CATTATGCCC AGTACATGAC CTTATGGGAC

13801 TTTCCTACTT GGCAGTACAT CTACGTATTA GTCATCGCTA TTACCATGCT GATGCGGTTT

13861 TGGCAGTACA TCAATGGGCG TGGATAGCGG TTTGACTCAC GGGGATTTCC AAGTCTCCAC
```

TABLE 8-continued

Plasmid and mRNA construct sequences

```
13921 CCCATTGACG TCAATGGGAG TTTGTTTTGG CACCAAAATC AACGGGACTT TCCAAAATGT

13981 CGTAACAACT CCGCCCCATT GACGCAAATG GGCGGTAGGC GTGTACGGTG GGAGGTCTAT

14041 ATAAGCAGAG CTGGTTTAGT GAACCGTCAG ATCAGATCTT TGTCGATCCT ACCATCCACT

14101 CGACACACCC GCCAGCGGCC GC
(SEQ ID NO: 44)
```

LINE-1 Plasmid EV71 IRES (SEQ ID NO: 45)

```
   1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT

361 CCAGGTGTGA CCAGCTCGAG GAGCGCGTGA GCGCGATGGA AGACGAGATG AACGAGATGA

421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA

721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA

901 TCTCCGAGGG TGAGATTAAG TATTTCATCG ATAAACAGAT GCTGCGAGAC TTCGTGACAA

961 CTCGCCCAGC TCTCAAGGAA CTGCTCAAAG AGGCTCTTAA TATGGAGCGC AATAATAGAT

1021 ATCAACCCTT GCAGAACCAC GCAAAGATGT GAGACAGTTA AAACAGCTGT GGGTTGTCAC

1081 CCACCCACAG GGTCCACTGG GCGCTAGTAC ACTGGTATCT CGGTACCTTT GTACGCCTGT

1141 TTTATACCCC CTCCCTGATT TGCAACTTAG AAGCAACGCA AACCAGATCA ATAGTAGGTG

1201 TGACATACCA GTCGCATCTT GATCAAGCAC TTCTGTATCC CCGGACCGAG TATCAATAGA

1261 CTGTGCACAC GGTTGAAGGA GAAAACGTCC GTTACCCGGC TAACTACTTC GAGAAGCCTA

1321 GTAACGCCAT TGAAGTTGCA GAGTGTTTCG CTCAGCACTC CCCCCGTGTA GATCAGGTCG

1381 ATGAGTCACC GCATTCCCCA CGGGCGACCG TGGCGGTGGC TGCGTTGGCG GCCTGCCTAT

1441 GGGGTAACCC ATAGGACGCT CTAATACGGA CATGGCGTGA AGAGTCTATT GAGCTAGTTA

1501 GTAGTCCTCC GGCCCCTGAA TGCGGCTAAT CCTAACTGCG GAGCACATAC CCTTAATCCA

1561 AAGGGCAGTG TGTCGTAACG GGCAACTCTG CAGCGGAACC GACTACTTTG GGTGTCCGTG

1621 TTTCTTTTTA TTCTTGTATT GGCTGCTTAT GGTGACAATT AAAGAATTGT TACCATATAG

1681 CTATTGGATT GGCCATCCAG TGTCAAACAG AGCTATTGTA TATCTCTTTG TTGGATTCAC

1741 ACCTCTCACT CTTGAAACGT TACACACCCT CAATTACATT ATACTGCTGA ACACGAAGCG

1801 TACATGACCG GCTCTAACTC ACATATCACC ATCCTTACAC TTAACATTAA CGGCCTCAAC

1861 TCAGCTATCA AGCGCCATCG GCTGGCCAGC TGGATCAAAT CACAGGATCC AAGCGTTTGT

1921 TGCATCCAAG AGACCCACCT GACCTGTAGA GATACTCACC GCCTCAAGAT CAAGGGATGG

1981 CGAAAGATTT ATCAGGCGAA CGGTAAGCAG AAGAAAGCCG GAGTCGCAAT TCTGGTCTCA
```

TABLE 8-continued

Plasmid and mRNA construct sequences

```
2041 GACAAGACGG ATTTCAAGCC CACCAAAATT AAGCGTGATA AGGAAGGTCA CTATATTATG

2101 GTGAAAGGCA GCATACAGCA GGAAGAACTT ACCATATTGA ACATCTACGC GCCAAACACC

2161 GGCGCACCTC GCTTTATCAA ACAGGTCCTG TCCGATCTGC AGCGAGATCT GGATTCTCAT

2221 ACGTTGATTA TGGGTGATTT CAATACACCA TTGAGCACCC TGGATCGCAG CACCAGGCAA

2281 AAGGTAAATA AAGACACGCA AGAGCTCAAT AGCGCACTGC ATCAGGCAGA TCTCATTGAT

2341 ATTTATCGCA CTCTTCATCC TAAGAGTACC GAGTACACAT TCTTCAGCGC CCCACATCAT

2401 ACATACTCAA AGATCGATCA TATCGTCGGC TCAAAGGCTC TGCTGTCAAA GTGCAAGCGC

2461 ACAGAGATAA TTACAAATTA CCTGTCAGAT CATAGCGCGA TCAAGCTCGA GCTGAGAATC

2521 AAGAACCTGA CCCAGAGCCG GAGTACCACT TGGAAGCTTA ATAACCTGCT GCTCAACGAT

2581 TATTGGGTCC ACAATGAGAT GAAGGCAGAG ATTAAAATGT TCTTCGAAAC AAATGAGAAT

2641 AAGGATACTA CCTATCAAAA CCTTTGGGAT GCCTTTAAGG CCGTCTGCAG AGGCAAGTTC

2701 ATCGCCCTCA ACGCCTATAA AAGAAACAA GAGAGATCTA AGATCGATAC TCTCACCTCT

2761 CAGCTGAAGG AGTTGGAGAA ACAGGAACAG ACCCACTCCA AGGCGTCAAG ACGGCAGGAG

2821 ATCACAAAGA TTCGCGCCGA GTTGAAAGAG ATCGAAACCC AAAAGACTCT TCAGAAAATT

2881 AACGAGTCTC GTAGTTGGTT CTTCGAGCGG ATTAATAAGA TAGACAGACC TCTGGCACGA

2941 CTGATTAAGA AGAAGCGCGA AAAGAACCAG ATTGATACCA TCAAGAACGA CAAGGGCGAC

3001 ATCACTACTG ACCCGACCGA GATCCAGACC ACTATTCGGG AGTATTATAA GCATTTGTAT

3061 GCTAACAAGC TTGAGAACCT GGAAGAGATG GACACTTTTC TGGATACCTA TACTCTGCCA

3121 CGGCTTAATC AAGAGGAAGT CGAGTCCCTC AACCGCCCAA TTACAGGAAG CGAGATTGTG

3181 GCCATAATTA ACTCCCTGCC GACAAAGAAA TCTCCTGGTC CGGACGGGTT TACAGCTGAG

3241 TTTTATCAAC GGTATATGGA AGAGCTTGTA CCGTTTCTGC TCAAGCTCTT TCAGTCTATA

3301 GAAAAGGAAG GCATCTTGCC CAATTCCTTC TACGAAGCTT CTATAATACT TATTCCCAAA

3361 CCAGGACGCG ATACCACAAA GAAGGAAAAC TTCCGGCCCA TTAGTCTCAT GAATATCGAC

3421 GCTAAAATAT TGAACAAGAT TCTCGCCAAC AGAATCCAAC AACATATTAA GAAATTGATA

3481 CATCACGACC AGGTGGGGT TATACCTGGC ATGCAGGGCT GGTTTAACAT CCGGAAGAGT

3541 ATTAACGTCA TTCAACACAT TAATAGAGCT AAGGATAAGA ATCATATGAT CATCTCTATA

3601 GACGCGGAAA AGGCATTCGA TAAGATTCAG CAGCCATTTA TGCTCAAGAC TCTGAACAAA

3661 CTCGGCATCG ACGGAACATA TTTTAAGATT ATTCGCGCAA TTTACGATAA GCCGACTGCT

3721 AACATTATCC TTAACGGCCA AAAGCTCGAG GCCTTTCCGC TCAAGACTGG AACCCGCCAA

3781 GGCTGTCCCC TCTCCCCGCT TTTGTTTAAT ATTGTACTCG AGGTGCTGGC TAGGGCTATT

3841 CGTCAAGAGA AAGAGATTAA AGGGATACAG CTCGGGAAGG AAGAGGTCAA GCTTTCCTTG

3901 TTCGCCGATG ATATGATTGT GTACCTGGAG AATCCTATTG TGTCTGCTCA GAACCTTCTT

3961 AAACTTATTT CTAACTTTAG CAAGGTCAGC GGCTATAAGA TTAACGTCCA GAAATCTCAG

4021 GCCTTTCTGT ACACAAATAA TCGACAGACC GAATCCCAGA TAATGGGTGA GCTTCCGTTT

4081 GTCATAGCCA GCAAAAGGAT AAAGTATCTC GGAATCCAGC TGACACGAGA CGTTAAAGAT

4141 TTGTTTAAGG AAAATTACAA GCCTCTCCTG AAAGAGATTA AGGAAGATAC TAATAAGTGG

4201 AAGAATATCC CCTGTTCATG GGTTGGCAGA ATCAACATAG TGAAGATGGC AATACTTCCT

4261 AAAGTGATAT ATCGCTTTAA CGCCATCCCA ATTAAACTGC CTATGACCTT CTTTACGGAG

4321 CTCGAGAAAA CAACCCTTAA ATTTATATGG AATCAAAAGA GAGCAAGAAT AGCGAAGTCC
```

TABLE 8-continued

Plasmid and mRNA construct sequences

```
4381 ATCTTGAGCC AGAAGAATAA GGCCGGTGGG ATTACTTTGC CTGATTTTAA GTTGTATTAT

4441 AAAGCCACAG TAACTAAGAC AGCCTGGTAT TGGTATCAGA ATAGAGACAT CGACCAGTGG

4501 AATCGGACCG AACCATCAGA GATAATGCCC CACATCTATA ATTACCTTAT ATTCGATAAG

4561 CCAGAAAAGA ATAAACAGTG GGGCAAAGAC AGCCTCTTCA ACAAGTGGTG TTGGGAGAAT

4621 TGGCTGGCCA TATGCCGGAA ACTCAAGCTC GACCCCTTTC TTACACCCTA CACTAAAATC

4681 AACAGTAGGT GGATCAAGGA CTTGAATGTC AAGCCAAAGA CTATAAAGAC ACTGGAAGAG

4741 AATCTTGGGA TCACAATACA AGATATAGGC GTCGGCAAAG ATTTTATGTC AAAGACGCCC

4801 AAGGCCATGG CCACTAAGGA TAAGATTGAT AAGTGGGACC TTATTAAGCT CAAAAGCTTC

4861 TGTACTGCCA AGGAGACCAC GATCAGAGTT AATAGGCAGC CCACTACATG GGAAAAGATT

4921 TTCGCCACTT ATTCATCAGA TAAGGGGTTG ATAAGCAGAA TATATAACGA GCTGAAGCAG

4981 ATCTACAAGA AGAAACGAA TAATCCCATC AAGAAGTGGG CAAAAGATAT GAACAGGCAT

5041 TTTAGCAAAG AGGATATCTA CGCCGCGAAG AAGCATATGA AGAAGTGTAG TTCAAGCTTG

5101 GCCATTCGTG AGATGCAGAT TAAGACGACC ATGCGATACC ACCTTACCCC AGTGAGGATG

5161 GCAATTATCA AGAAATCTGG CAATAATAGA TGTTGGCGGG GCTGTGGCGA GATTGGCACC

5221 CTGCTCCATT GCTGGTGGGA TTGCAAGCTG GTGCAGCCGC TTTGGAAATC AGTCTGGCGC

5281 TTTCTGAGGG ACCTCGAGCT TGAGATTCCC TTCGATCCCG CAATTCCCTT GCTCGGAATC

5341 TATCCTAACG AATACAAGAG CTGTTGTTAC AAGGATACGT GTACCCGGAT GTTCATCGCG

5401 GCCTTGTTTA CGATAGCTAA GACGTGGAAT CAGCCTAAGT GCCCCACAAT GATCGATTGG

5461 ATCAAGAAAA TGTGGCATAT TTATACCATG GAGTATTACG CAGCAATTAA GAATGACGAA

5521 TTTATTTCCT TCGTTGGGAC CTGGATGAAG CTGGAGACTA TTATTCTGAG CAAGCTGTCT

5581 CAGGAGCAAA AGACAAAGCA TAGAATCTTC TCTCTCATTG GTGGTAACGA CTACAAAGAC

5641 GATGACGACA AGTAAAGCGC TTCTAGAAGT TGTCTCCTCC TGCACTGACT GACTGATACA

5701 ATCGATTTCT GGATCCGCAG GCCTAATCAA CCTCTGGATT ACAAAATTTG TGAAAGATTG

5761 ACTGGTATTC TTAACTATGT TGCTCCTTTT ACGCTATGTG GATACGCTGC TTTAATGCCT

5821 TTGTATCATG CTATTGCTTC CCGTATGGCT TTCATTTTCT CCTCCTTGTA TAAATCCTGG

5881 TTGCTGTCTC TTTATGAGGA GTTGTGGCCC GTTGTCAGGC AACGTGGCGT GGTGTGCACT

5941 GTGTTTGCTG ACGCAACCCC CACTGGTTGG GGCATTGCCA CCACCTGTCA GCTCCTTTCC

6001 GGGACTTTCG CTTTCCCCCT CCCTATTGCC ACGGCGGAAC TCATCGCCGC CTGCCTTGCC

6061 CGCTGCTGGA CAGGGGCTCG GCTGTTGGGC ACTGACAATT CCGTGGTGTT GTCGGGGAAG

6121 CTGACGTCCT TTCCATGGCT GCTCGCCTGT GTTGCCACCT GGATTCTGCG CGGGACGTCC

6181 TTCTGCTACG TCCCTTCGGC CCTCAATCCA GCGGACCTTC CTTCCCGCGA ACAAACGACC

6241 CAACACCCGT GCGTTTTATT CTGTCTTTTT ATTGCCGATC CCCTCAGAAG AACTCGTCAA

6301 GAAGGCGATA GAAGGCGATG CGCTGCGAAT CGGGAGCGGC GATACCGTAA AGCACGAGGA

6361 AGCGGTCAGC CCATTCGCCG CCAAGCTCTT CAGCAATATC ACGGGTAGCC AACGCTATGT

6421 CCTGATAGCG GTCGGCCGCT TTACTTGTAC AGCTCGTCCA TGCCGAGAGT GATCCCGGCG

6481 GCGGTCACGA ACTCCAGCAG GACCATGTGA TCGCGCTTCT CGTTGGGGTC TTTGCTCAGG

6541 GCGGACTGGG TGCTCAGGTA GTGGTTGTCG GGCAGCAGCA CGGGGCCGTC GCCGATGGGG

6601 GTGTTCTGCT GGTAGTGGTC GGCCAGGTGA GTCCAGGAGA TGTTTCAGCA CTGTTGCCTT

6661 TAGTCTCGAG GCAACTTAGA CAACTGAGTA TTGATCTGAG CACAGCAGGG TGTGAGCTGT
```

TABLE 8-continued

Plasmid and mRNA construct sequences

```
6721 TTGAAGATAC TGGGGTTGGG GGTGAAGAAA CTGCAGAGGA CTAACTGGGC TGAGACCCAG

6781 TGGCAATGTT TTAGGGCCTA AGGAATGCCT CTGAAAATCT AGATGGACAA CTTTGACTTT

6841 GAGAAAAGAG AGGTGGAAAT GAGGAAAATG ACTTTTCTTT ATTAGATTTC GGTAGAAAGA

6901 ACTTTCATCT TTCCCCTATT TTTGTTATTC GTTTTAAAAC ATCTATCTGG AGGCAGGACA

6961 AGTATGGTCA TTAAAAAGAT GCAGGCAGAA GGCATATATT GGCTCAGTCA AAGTGGGGAA

7021 CTTTGGTGGC CAAACATACA TTGCTAAGGC TATTCCTATA TCAGCTGGAC ACATATAAAA

7081 TGCTGCTAAT GCTTCATTAC AAACTTATAT CCTTTAATTC CAGATGGGGG CAAAGTATGT

7141 CCAGGGGTGA GGAACAATTG AAACATTTGG GCTGGAGTAG ATTTTGAAAG TCAGCTCTGT

7201 GTGTGTGTGT GTGTGTGTGT GTGTGAGAGC GTGTGTTTCT TTTAACGTTT TCAGCCTACA

7261 GCATACAGGG TTCATGGTGG CAAGAAGATA ACAAGATTTA AATTATGGCC AGTGACTAGT

7321 GCTGCAAGAA GAACAACTAC CTGCATTTAA TGGGAAAGCA AAATCTCAGG CTTTGAGGGA

7381 AGTTAACATA GGCTTGATTC TGGGTGGAAG CTGGGTGTGT AGTTATCTGG AGGCCAGGCT

7441 GGAGCTCTCA GCTCACTATG GGTTCATCTT TATTGTCTCC TTTCATCTCA ACAGCTGCAC

7501 GCTGCCGTCC TCGATGTTGT GGCGGATCTT GAAGTTCACC TTGATGCCGT TCTTCTGCTT

7561 GTCGGCCATG ATATAGACGT TGTGGCTGTT GTAGTTGTAC TCCAGCTTGT GCCCCAGGAT

7621 GTTGCCGTCC TCCTTGAAGT CGATGCCCTT CAGCTCGATG CGGTTCACCA GGGTGTCGCC

7681 CTCGAACTTC ACCTCGGCGC GGGTCTTGTA GTTGCCGTCG TCCTTGAAGA AGATGGTGCG

7741 CTCCTGGACG TAGCCTTCGG GCATGGCGGA CTTGAAGAAG TCGTGCTGCT TCATGTGGTC

7801 GGGGTAGCGG CTGAAGCACT GCACGCCGTA GGTCAGGGTG GTCACGAGGG TGGGCCAGGG

7861 CACGGGCAGC TTGCCGGTGG TGCAGATGAA CTTCAGGGTC AGCTTGCCGT AGGTGGCATC

7921 GCCCTCGCCC TCGCCGGACA CGCTGAACTT GTGGCCGTTT ACGTCGCCGT CCAGCTCGAC

7981 CAGGATGGGC ACCACCCCGG TGAACAGCTC CTCGCCCTTG CTCACCATGG TGGCGAATTC

8041 GAAGCTTGAG CACGAGATCT GAGTCCGGTA GGCCTAGCGG ATCTGACGGT TCACTAAACC

8101 AGCTCTGCTT ATATAGACCT CCCACCGTAC ACGCCTACCG CCCATTTGCG TCAATGGGGC

8161 GGAGTTGTTA CGACATTTTG GAAAGTCCCG TTGATTTTGG TGCCAAAACA AACTCCCATT

8221 GACGTCAATG GGGTGGAGAC TTGGAAATCC CCGTGAGTCA AACCGCTATC CACGCCCATT

8281 GATGTACTGC CAAAACCGCA TCACCATGGT AATAGCGATG ACTAATACGT AGATGTACTG

8341 CCAAGTAGGA AAGTCCCATA AGGTCATGTA CTGGGCATAA TGCCAGGCGG GCCATTTACC

8401 GTCATTGACG TCAATAGGGG GCGTACTTGG CATATGATAC ACTTGATGTA CTGCCAAGTG

8461 GGCAGTTTAC CGTAAATACT CCACCCATTG ACGTCAATGG AAAGTCCCTA TTGGCGTTAC

8521 TATGGGAACA TACGTCATTA TTGACGTCAA TGGGCGGGGG TCGTTGGGCG TCAGCCAGG

8581 CGGGCCATTT ACCGTAAGTT ATGTAACGGG CCTGCTGCCG GCTCTGCGGC CTCTTCCGCG

8641 TCTTCGCCTT CGCCCTCAGA CGAGTCGGAT CTCCCTTTGG CCGCCTCCC CGCCTGTCTA

8701 GCTTGACTGA CTGAGATACA GCGTACCTTC AGCTCACAGA CATGATAAGA TACATTGATG

8761 AGTTTGGACA AACCACAACT AGAATGCAGT GAAAAAAATG CTTTATTTGT GAAATTTGTG

8821 ATGCTATTGC TTTATTTGTA ACCATTATAA GCTGCAATAA ACAAGTTAAC AACAACAATT

8881 GCATTCATTT TATGTTTCAG GTTCAGGGGG AGGTGTGGGA GGTTTTTTAA AGCAAGTAAA

8941 ACCTCTACAA ATGTGGTATT GGCCCATCTC TATCGGTATC GTAGCATAAC CCCTTGGGGC

9001 CTCTAAACGG GTCTTGAGGG GTTTTTTGTG CCCCTCGGGC CGGATTGCTA TCTACCGGCA
```

TABLE 8-continued

Plasmid and mRNA construct sequences

```
 9061 TTGGCGCAGA AAAAAATGCC TGATGCGACG CTGCGCGTCT TATACTCCCA CATATGCCAG

9121 ATTCAGCAAC GGATACGGCT TCCCCAACTT GCCCACTTCC ATACGTGTCC TCCTTACCAG

9181 AAATTTATCC TTAAGGTCGT CAGCTATCCT GCAGGCGATC TCTCGATTTC GATCAAGACA

9241 TTCCTTTAAT GGTCTTTTCT GGACACCACT AGGGGTCAGA AGTAGTTCAT CAAACTTTCT

9301 TCCCTCCCTA ATCTCATTGG TTACCTTGGG CTATCGAAAC TTAATTAAGC GATCTGCATC

9361 TCAATTAGTC AGCAACCATA GTCCCGCCCC TAACTCCGCC CATCCCGCCC CTAACTCCGC

9421 CCAGTTCCGC CCATTCTCCG CCCCATCGCT GACTAATTTT TTTTATTTAT GCAGAGGCCG

9481 AGGCCGCCTC GGCCTCTGAG CTATTCCAGA AGTAGTGAGG AGGCTTTTTT GGAGGCCTAG

9541 GCTTTTGCAA AGGAGGTAGC CAACATGATT GAACAAGATG GATTGCACGC AGGTTCTCCC

9601 GCCGCTTGGG TGGAGAGGCT ATTCGGCTAT GACTGGGCAC AACAGACAAT CGGCTGCTCT

9661 GATGCCGCCG TGTTCCGGCT GTCAGCGCAG GGGCGCCCGG TTCTTTTTGT CAAGACCGAC

9721 CTGTCCGGTG CCCTGAATGA ACTCCAGGAC GAGGCAGCGC GGCTATCGTG GCTGGCCACG

9781 ACGGGCGTTC CTTGCGCAGC TGTGCTCGAC GTTGTCACTG AAGCGGGAAG GGACTGGCTG

9841 CTATTGGGCG AAGTGCCGGG GCAGGATCTC CTGTCATCTC ACCTTGCTCC TGCCGAGAAA

9901 GTATCCATCA TGGCTGATGC AATGCGGCGG CTGCATACGC TTGATCCGGC TACCTGCCCA

9961 TTCGACCACC AAGCGAAACA TCGCATCGAG CGAGCACGTA CTCGGATGGA AGCCGGTCTT

10021 GTCGATCAGG ATGATCTGGA CGAAGAGCAT CAGGGGCTCG CGCCAGCCGA ACTGTTCGCC

10081 AGGCTCAAGG CGCGGATGCC CGACGGCGAG GATCTCGTCG TGACCCACGG CGATGCCTGC

10141 TTGCCGAATA TCATGGTGGA AAATGGCCGC TTTTCTGGAT TCATCGACTG TGGCCGGCTG

10201 GGTGTGGCGG ACCGCTATCA GGACATAGCG TTGGCTACCC GTGATATTGC TGAAGAGCTT

10261 GGCGGCGAAT GGGCTGACCG CTTCCTCGTG CTTTACGGTA TCGCCGCTCC CGATTCGCAG

10321 CGCATCGCCT TCTATCGCCT TCTTGACGAG TTCTTCTAGT ATGTAAGCCC TGTGCCTTCT

10381 AGTTGCCAGC CATCTGTTGT TTGCCCCTCC CCCGTGCCTT CCTTGACCCT GGAAGGTGCC

10441 ACTCCCACTG TCCTTTCCTA ATAAAATGAG GAAATTGCAT CGCATTGTCT GAGTAGGTGT

10501 CATTCTATTC TGGGGGGTGG GGTGGGGCAG GACAGCAAGG GGGAGGATTG GGAAGACAAT

10561 AGCAGGCATG CTGGGGATGC GGTGGGCTCT ATGGTTAATT AACCAGTCAA GTCAGCTACT

10621 TGGCGAGATC GACTTGTCTG GGTTTCGACT ACGCTCAGAA TTGCGTCAGT CAAGTTCGAT

10681 CTGGTCCTTG CTATTGCACC CGTTCTCCGA TTACGAGTTT CATTTAAATC ATGTGAGCAA

10741 AAGGCCAGCA AAAGGCCAGG AACCGTAAAA AGGCCGCGTT GCTGGCGTTT TTCCATAGGC

10801 TCCGCCCCCC TGACGAGCAT CACAAAAATC GACGCTCAAG TCAGAGGTGG CGAAACCCGA

10861 CAGGACTATA AAGATACCAG GCGTTTCCCC CTGGAAGCTC CCTCGTGCGC TCTCCTGTTC

10921 CGACCCTGCC GCTTACCGGA TACCTGTCCG CCTTTCTCCC TTCGGGAAGC GTGGCGCTTT

10981 CTCATAGCTC ACGCTGTAGG TATCTCAGTT CGGTGTAGGT CGTTCGCTCC AAGCTGGGCT

11041 GTGTGCACGA ACCCCCCGTT CAGCCCGACC GCTGCGCCTT ATCCGGTAAC TATCGTCTTG

11101 AGTCCAACCC GGTAAGACAC GACTTATCGC CACTGGCAGC AGCCACTGGT AACAGGATTA

11161 GCAGAGCGAG GTATGTAGGC GGTGCTACAG AGTTCTTGAA GTGGTGGCCT AACTACGGCT

11221 ACACTAGAAG AACAGTATTT GGTATCTGCG CTCTGCTGAA GCCAGTTACC TTCGGAAAAA

11281 GAGTTGGTAG CTCTTGATCC GGCAACAAAA CCACCGCTGG TAGCGGTGGT TTTTTTGTTT

11341 GCAAGCAGCA GATTACGCGC AGAAAAAAAG GATCTCAAGA AGATCCTTTG ATCTTTTCTA
```

TABLE 8-continued

Plasmid and mRNA construct sequences

```
11401 CGGGGTCTGA CGCTCAGTGG AACGAAAACT CACGTTAAGG GATTTTGGTC ATGAGATTAT

11461 CAAAAAGGAT CTTCACCTAG ATCCTTTTAA ATTAAAAATG AAGTTTTAAA TCAATCTAAA

11521 GTATATATGA GTAAACTTGG TCTGACAGTT ACCAATGCTT AATCAGTGAG GCACCTATCT

11581 CAGCGATCTG TCTATTTCGT TCATCCATAG TTGCATTTAA ATTTCCGAAC TCTCCAAGGC

11641 CCTCGTCGGA AAATCTTCAA ACCTTTCGTC CGATCCATCT TGCAGGCTAC CTCTCGAACG

11701 AACTATCGCA AGTCTCTTGG CCGGCCTTGC GCCTTGGCTA TTGCTTGGCA GCGCCTATCG

11761 CCAGGTATTA CTCCAATCCC GAATATCCGA GATCGGGATC ACCCGAGAGA AGTTCAACCT

11821 ACATCCTCAA TCCCGATCTA TCCGAGATCC GAGGAATATC GAAATCGGGC CGCGCCTGGT

11881 GTACCGAGAA CGATCCTCTC AGTGCGAGTC TCGACGATCC ATATCGTTGC TTGGCAGTCA

11941 GCCAGTCGGA ATCCAGCTTG GGACCCAGGA AGTCCAATCG TCAGATATTG TACTCAAGCC

12001 TGGTCACGGC AGCGTACCGA TCTGTTTAAA CCTAGATATT GATAGTCTGA TCGGTCAACG

12061 TATAATCGAG TCCTAGCTTT TGCAAACATC TATCAAGAGA CAGGATCAGC AGGAGGCTTT

12121 CGCATGAGTA TTCAACATTT CCGTGTCGCC CTTATTCCCT TTTTTGCGGC ATTTTGCCTT

12181 CCTGTTTTTG CTCACCCAGA AACGCTGGTG AAAGTAAAAG ATGCTGAAGA TCAGTTGGGT

12241 GCGCGAGTGG GTTACATCGA ACTGGATCTC AACAGCGGTA AGATCCTTGA GAGTTTTCGC

12301 CCCGAAGAAC GCTTTCCAAT GATGAGCACT TTTAAAGTTC TGCTATGTGG CGCGGTATTA

12361 TCCCGTATTG ACGCCGGGCA AGAGCAACTC GGTCGCCGCA TACACTATTC TCAGAATGAC

12421 TTGGTTGAGT ATTCACCAGT CACAGAAAAG CATCTTACGG ATGGCATGAC AGTAAGAGAA

12481 TTATGCAGTG CTGCCATAAC CATGAGTGAT AACACTGCGG CCAACTTACT TCTGACAACG

12541 ATTGGAGGAC CGAAGGAGCT AACCGCTTTT TTGCACAACA TGGGGGATCA TGTAACTCGC

12601 CTTGATCGTT GGGAACCGGA GCTGAATGAA GCCATACCAA ACGACGAGCG TGACACCACG

12661 ATGCCTGTAG CAATGGCAAC AACCTTGCGT AAACTATTAA CTGGCGAACT ACTTACTCTA

12721 GCTTCCCGGC AACAGTTGAT AGACTGGATG GAGGCGGATA AAGTTGCAGG ACCACTTCTG

12781 CGCTCGGCCC TTCCGGCTGG CTGGTTTATT GCTGATAAAT CTGGAGCCGG TGAGCGTGGG

12841 TCTCGCGGTA TCATTGCAGC ACTGGGGCCA GATGGTAAGC CCTCCCGTAT CGTAGTTATC

12901 TACACGACGG GGAGTCAGGC AACTATGGAT GAACGAAATA GACAGATCGC TGAGATAGGT

12961 GCCTCACTGA TTAAGCATTG GTAACCGATT CTAGGTGCAT GGCGCAGAA AAAAATGCCT

13021 GATGCGACGC TGCGCGTCTT ATACTCCCAC ATATGCCAGA TTCAGCAACG GATACGGCTT

13081 CCCCAACTTG CCCACTTCCA TACGTGTCCT CCTTACCAGA AATTTATCCT TAAGATCGTT

13141 TAAACTCGAC TCTGGCTCTA TCGAATCTCC GTCGTTTCGA GCTTACGCGA ACAGCCGTGG

13201 CGCTCATTTG CTCGTCGGGC ATCGAATCTC GTCAGCTATC GTCAGCTTAC CTTTTTGGCA

13261 GCGATCGCGG CTCCCGACAT CTTGGACCAT TAGCTCCACA GGTATCTTCT TCCCTCTAGT

13321 GGTCATAACA GCAGCTTCAG CTACCTCTCA ATTCAAAAAA CCCCTCAAGA CCCGTTTAGA

13381 GGCCCCAAGG GGTTATGCTA TCAATCGTTG CGTTACACAC ACAAAAAACC AACACACATC

13441 CATCTTCGAT GGATAGCGAT TTTATTATCT AACTGCTGAT CGAGTGTAGC CAGATCTAGT

13501 AATCAATTAC GGGGTCATTA GTTCATAGCC CATATATGGA GTTCCGCGTT ACATAACTTA

13561 CGGTAAATGG CCCGCCTGGC TGACCGCCCA ACGACCCCCG CCCATTGACG TCAATAATGA

13621 CGTATGTTCC CATAGTAACG CCAATAGGGA CTTTCCATTG ACGTCAATGG GTGGAGTATT

13681 TACGGTAAAC TGCCCACTTG GCAGTACATC AAGTGTATCA TATGCCAAGT ACGCCCCCTA
```

TABLE 8-continued

Plasmid and mRNA construct sequences

```
13741 TTGACGTCAA TGACGGTAAA TGGCCCGCCT GGCATTATGC CCAGTACATG ACCTTATGGG

13801 ACTTTCCTAC TTGGCAGTAC ATCTACGTAT TAGTCATCGC TATTACCATG CTGATGCGGT

13861 TTTGGCAGTA CATCAATGGG CGTGGATAGC GGTTTGACTC ACGGGGATTT CCAAGTCTCC

13921 ACCCCATTGA CGTCAATGGG AGTTTGTTTT GGCACCAAAA TCAACGGGAC TTTCCAAAAT

13981 GTCGTAACAA CTCCGCCCCA TTGACGCAAA TGGGCGGTAG GCGTGTACGG TGGGAGGTCT

14041 ATATAAGCAG AGCTGGTTTA GTGAACCGTC AGATCAGATC TTTGTCGATC CTACCATCCA

14101 CTCGACACAC CGCCAGCGG CCGC
(SEQ ID NO: 45)
```

LINE-1 plasmid ORF 1- E2A-ORF2 GFP (SEQ ID NO: 46)

```
   1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT

361 CCAGGTGTGA CCAGCTCGAG GAGCGCGTGA GCGCGATGGA AGACGAGATG AACGAGATGA

421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA

721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA

901 TCTCCGAGGG TGAGATTAAG TATTTCATCG ATAAACAGAT GCTGCGAGAC TTCGTGACAA

961 CTCGCCCAGC TCTCAAGGAA CTGCTCAAAG AGGCTCTTAA TATGGAGCGC AATAATAGAT

1021 ATCAACCCTT GCAGAACCAC GCAAAGATGG GAAGCGGACA GTGTACTAAT TATGCTCTCT

1081 TGAAATTGGC TGGAGATGTT GAGAGCAACC CTGGACCTAT GACCGGCTCT AACTCACATA

1141 TCACCATCCT TACACTTAAC ATTAACGGCC TCAACTCAGC TATCAAGCGC CATCGGCTGG

1201 CCAGCTGGAT CAAATCACAG GATCCAAGCG TTTGTTGCAT CCAAGAGACC CACCTGACCT

1261 GTAGAGATAC TCACCGCCTC AAGATCAAGG GATGGCGAAA GATTTATCAG GCGAACGGTA

1321 AGCAGAAGAA AGCCGGAGTC GCAATTCTGG TCTCAGACAA GACGGATTTC AAGCCCACCA

1381 AAATTAAGCG TGATAAGGAA GGTCACTATA TTATGGTGAA AGGCAGCATA CAGCAGGAAG

1441 AACTTACCAT ATTGAACATC TACGCGCCAA ACACCGGCGC ACCTCGCTTT ATCAAACAGG

1501 TCCTGTCCGA TCTGCAGCGA GATCTGGATT CTCATACGTT GATTATGGGT GATTTCAATA

1561 CACCATTGAG CACCCTGGAT CGCAGCACCA GGCAAAAGGT AAATAAAGAC ACGCAAGAGC

1621 TCAATAGCGC ACTGCATCAG GCAGATCTCA TTGATATTTA TCGCACTCTT CATCCTAAGA

1681 GTACCGAGTA CACATTCTTC AGCGCCCCAC ATCATACATA CTCAAAGATC GATCATATCG

1741 TCGGCTCAAA GGCTCTGCTG TCAAAGTGCA AGCGCACAGA GATAATTACA AATTACCTGT
```

TABLE 8-continued

| Plasmid and mRNA construct sequences |
| --- |

```
1801 CAGATCATAG CGCGATCAAG CTCGAGCTGA GAATCAAGAA CCTGACCCAG AGCCGGAGTA

1861 CCACTTGGAA GCTTAATAAC CTGCTGCTCA ACGATTATTG GGTCCACAAT GAGATGAAGG

1921 CAGAGATTAA AATGTTCTTC GAAACAAATG AGAATAAGGA TACTACCTAT CAAAACCTTT

1981 GGGATGCCTT TAAGGCCGTC TGCAGAGGCA AGTTCATCGC CCTCAACGCC TATAAAAGAA

2041 AACAAGAGAG ATCTAAGATC GATACTCTCA CCTCTCAGCT GAAGGAGTTG GAGAAACAGG

2101 AACAGACCCA CTCCAAGGCG TCAAGACGGC AGGAGATCAC AAAGATTCGC GCCGAGTTGA

2161 AAGAGATCGA AACCCAAAAG ACTCTTCAGA AAATTAACGA GTCTCGTAGT TGGTTCTTCG

2221 AGCGGATTAA TAAGATAGAC AGACCTCTGG CACGACTGAT TAAGAAGAAG CGCGAAAAGA

2281 ACCAGATTGA TACCATCAAG AACGACAAGG GCGACATCAC TACTGACCCG ACCGAGATCC

2341 AGACCACTAT TCGGGAGTAT TATAAGCATT TGTATGCTAA CAAGCTTGAG AACCTGGAAG

2401 AGATGGACAC TTTTCTGGAT ACCTATACTC TGCCACGGCT TAATCAAGAG GAAGTCGAGT

2461 CCCTCAACCG CCCAATTACA GGAAGCGAGA TTGTGGCCAT AATTAACTCC CTGCCGACAA

2521 AGAAATCTCC TGGTCCGGAC GGGTTTACAG CTGAGTTTTA TCAACGGTAT ATGGAAGAGC

2581 TTGTACCGTT TCTGCTCAAG CTCTTTCAGT CTATAGAAAA GGAAGGCATC TTGCCCAATT

2641 CCTTCTACGA AGCTTCTATA ATACTTATTC CCAAACCAGG ACGCGATACC ACAAAGAAGG

2701 AAAACTTCCG GCCCATTAGT CTCATGAATA TCGACGCTAA AATATTGAAC AAGATTCTCG

2761 CCAACAGAAT CCAACAACAT ATTAAGAAAT TGATACATCA CGACCAGGTG GGGTTTATAC

2821 CTGGCATGCA GGGCTGGTTT AACATCCGGA AGAGTATTAA CGTCATTCAA CACATTAATA

2881 GAGCTAAGGA TAAGAATCAT ATGATCATCT CTATAGACGC GGAAAAGGCA TTCGATAAGA

2941 TTCAGCAGCC ATTTATGCTC AAGACTCTGA ACAAACTCGG CATCGACGGA ACATATTTTA

3001 AGATTATTCG CGCAATTTAC GATAAGCCGA CTGCTAACAT TATCCTTAAC GGCCAAAAGC

3061 TCGAGGCCTT TCCGCTCAAG ACTGGAACCC GCCAAGGCTG TCCCCTCTCC CCGCTTTTGT

3121 TTAATATTGT ACTCGAGGTG CTGGCTAGGG CTATTCGTCA AGAGAAAGAG ATTAAAGGGA

3181 TACAGCTCGG GAAGGAAGAG GTCAAGCTTT CCTTGTTCGC CGATGATATG ATTGTGTACC

3241 TGGAGAATCC TATTGTGTCT GCTCAGAACC TTCTTAAACT TATTTCTAAC TTTAGCAAGG

3301 TCAGCGGCTA TAAGATTAAC GTCCAGAAAT CTCAGGCCTT TCTGTACACA AATAATCGAC

3361 AGACCGAATC CCAGATAATG GGTGAGCTTC CGTTTGTCAT AGCCAGCAAA AGGATAAAGT

3421 ATCTCGGAAT CCAGCTGACA CGAGACGTTA AAGATTTGTT TAAGGAAAAT TACAAGCCTC

3481 TCCTGAAAGA GATTAAGGAA GATACTAATA AGTGGAAGAA TATCCCCTGT TCATGGGTTG

3541 GCAGAATCAA CATAGTGAAG ATGGCAATAC TTCCTAAAGT GATATATCGC TTTAACGCCA

3601 TCCCAATTAA ACTGCCTATG ACCTTCTTTA CGGAGCTCGA GAAAACAACC CTTAAATTTA

3661 TATGGAATCA AAAGAGAGCA AGAATAGCGA AGTCCATCTT GAGCCAGAAG AATAAGGCCG

3721 GTGGGATTAC TTTGCCTGAT TTTAAGTTGT ATTATAAAGC CACAGTAACT AAGACAGCCT

3781 GGTATTGGTA TCAGAATAGA GACATCGACC AGTGGAATCG GACCGAACCA TCAGAGATAA

3841 TGCCCCACAT CTATAATTAC CTTATATTCG ATAAGCCAGA AAAGAATAAA CAGTGGGGCA

3901 AAGACAGCCT CTTCAACAAG TGGTGTTGGG AGAATTGGCT GGCCATATGC CGGAAACTCA

3961 AGCTCGACCC CTTTCTTACA CCCTACACTA AAATCAACAG TAGGTGGATC AAGGACTTGA

4021 ATGTCAAGCC AAAGACTATA AAGCACTGG AAGAGAATCT TGGGATCACA ATACAAGATA

4081 TAGGCGTCGG CAAAGATTTT ATGTCAAAGA CGCCCAAGGC CATGGCCACT AAGGATAAGA
```

TABLE 8-continued

Plasmid and mRNA construct sequences

```
4141 TTGATAAGTG GGACCTTATT AAGCTCAAAA GCTTCTGTAC TGCCAAGGAG ACCACGATCA

4201 GAGTTAATAG GCAGCCCACT ACATGGGAAA AGATTTTCGC CACTTATTCA TCAGATAAGG

4261 GGTTGATAAG CAGAATATAT AACGAGCTGA AGCAGATCTA CAAGAAGAAA ACGAATAATC

4321 CCATCAAGAA GTGGGCAAAA GATATGAACA GGCATTTTAG CAAAGAGGAT ATCTACGCCG

4381 CGAAGAAGCA TATGAAGAAG TGTAGTTCAA GCTTGGCCAT TCGTGAGATG CAGATTAAGA

4441 CGACCATGCG ATACCACCTT ACCCCAGTGA GGATGGCAAT TATCAAGAAA TCTGGCAATA

4501 ATAGATGTTG GCGGGGCTGT GGCGAGATTG GCACCCTGCT CCATTGCTGG TGGGATTGCA

4561 AGCTGGTGCA GCCGCTTTGG AAATCAGTCT GGCGCTTTCT GAGGGACCTC GAGCTTGAGA

4621 TTCCCTTCGA TCCCGCAATT CCCTTGCTCG GAATCTATCC TAACGAATAC AAGAGCTGTT

4681 GTTACAAGGA TACGTGTACC CGGATGTTCA TCGCGGCCTT GTTTACGATA GCTAAGACGT

4741 GGAATCAGCC TAAGTGCCCC ACAATGATCG ATTGGATCAA GAAAATGTGG CATATTTATA

4801 CCATGGAGTA TTACGCAGCA ATTAAGAATG ACGAATTTAT TTCCTTCGTT GGGACCTGGA

4861 TGAAGCTGGA GACTATTATT CTGAGCAAGC TGTCTCAGGA GCAAAAGACA AAGCATAGAA

4921 TCTTCTCTCT CATTGGTGGT AACGACTACA AAGACGATGA CGACAAGTAA AGCGCTTCTA

4981 GAAGTTGTCT CCTCCTGCAC TGACTGACTG ATACAATCGA TTTCTGGATC CGCAGGCCTA

5041 ATCAACCTCT GGATTACAAA ATTTGTGAAA GATTGACTGG TATTCTTAAC TATGTTGCTC

5101 CTTTTACGCT ATGTGGATAC GCTGCTTTAA TGCCTTTGTA TCATGCTATT GCTTCCCGTA

5161 TGGCTTTCAT TTTCTCCTCC TTGTATAAAT CCTGGTTGCT GTCTCTTTAT GAGGAGTTGT

5221 GGCCCGTTGT CAGGCAACGT GGCGTGGTGT GCACTGTGTT TGCTGACGCA ACCCCCACTG

5281 GTTGGGGCAT TGCCACCACC TGTCAGCTCC TTTCCGGGAC TTTCGCTTTC CCCCTCCCTA

5341 TTGCCACGGC GGAACTCATC GCCGCCTGCC TTGCCCGCTG CTGGACAGGG GCTCGGCTGT

5401 TGGGCACTGA CAATTCCGTG GTGTTGTCGG GGAAGCTGAC GTCCTTTCCA TGGCTGCTCG

5461 CCTGTGTTGC CACCTGGATT CTGCGCGGGA CGTCCTTCTG CTACGTCCCT TCGGCCCTCA

5521 ATCCAGCGGA CCTTCCTTCC CGCGAACAAA CGACCCAACA CCCGTGCGTT TTATTCTGTC

5581 TTTTTATTGC CGATCCCCTC AGAAGAACTC GTCAAGAAGG CGATAGAAGG CGATGCGCTG

5641 CGAATCGGGA GCGGCGATAC CGTAAAGCAC GAGGAAGCGG TCAGCCCATT CGCCGCCAAG

5701 CTCTTCAGCA ATATCACGGG TAGCCAACGC TATGTCCTGA TAGCGGTCGG CCGCTTTACT

5761 TGTACAGCTC GTCCATGCCG AGAGTGATCC CGGCGGCGGT CACGAACTCC AGCAGGACCA

5821 TGTGATCGCG CTTCTCGTTG GGGTCTTTGC TCAGGGCGGA CTGGGTGCTC AGGTAGTGGT

5881 TGTCGGGCAG CAGCACGGGG CCGTCGCCGA TGGGGGTGTT CTGCTGGTAG TGGTCGGCCA

5941 GGTGAGTCCA GGAGATGTTT CAGCACTGTT GCCTTTAGTC TCGAGGCAAC TTAGACAACT

6001 GAGTATTGAT CTGAGCACAG CAGGGTGTGA GCTGTTTGAA GATACTGGGG TTGGGGGTGA

6061 AGAAACTGCA GAGGACTAAC TGGGCTGAGA CCCAGTGGCA ATGTTTTAGG GCCTAAGGAA

6121 TGCCTCTGAA AATCTAGATG GACAACTTTG ACTTTGAGAA AAGAGAGGTG GAAATGAGGA

6181 AAATGACTTT TCTTTATTAG ATTTCGGTAG AAAGAACTTT CATCTTTCCC CTATTTTTGT

6241 TATTCGTTTT AAAACATCTA TCTGGAGGCA GGACAAGTAT GGTCATTAAA AAGATGCAGG

6301 CAGAAGGCAT ATATTGGCTC AGTCAAAGTG GGGAACTTTG GTGGCCAAAC ATACATTGCT

6361 AAGGCTATTC CTATATCAGC TGGACACATA TAAAATGCTG CTAATGCTTA TTACAAACT

6421 TATATCCTTT AATTCCAGAT GGGGGCAAAG TATGTCCAGG GGTGAGGAAC AATTGAAACA
```

TABLE 8-continued

Plasmid and mRNA construct sequences

6481 TTTGGGCTGG AGTAGATTTT GAAAGTCAGC TCTGTGTGTG TGTGTGTGTG TGTGTGTGTG

6541 AGAGCGTGTG TTTCTTTTAA CGTTTTCAGC CTACAGCATA CAGGGTTCAT GGTGGCAAGA

6601 AGATAACAAG ATTTAAATTA TGGCCAGTGA CTAGTGCTGC AAGAAGAACA ACTACCTGCA

6661 TTTAATGGGA AAGCAAAATC TCAGGCTTTG AGGGAAGTTA ACATAGGCTT GATTCTGGGT

6721 GGAAGCTGGG TGTGTAGTTA TCTGGAGGCC AGGCTGGAGC TCTCAGCTCA CTATGGGTTC

6781 ATCTTTATTG TCTCCTTTCA TCTCAACAGC TGCACGCTGC CGTCCTCGAT GTTGTGGCGG

6841 ATCTTGAAGT TCACCTTGAT GCCGTTCTTC TGCTTGTCGG CCATGATATA GACGTTGTGG

6901 CTGTTGTAGT TGTACTCCAG CTTGTGCCCC AGGATGTTGC CGTCCTCCTT GAAGTCGATG

6961 CCCTTCAGCT CGATGCGGTT CACCAGGGTG TCGCCCTCGA ACTTCACCTC GGCGCGGGTC

7021 TTGTAGTTGC CGTCGTCCTT GAAGAAGATG GTGCGCTCCT GGACGTAGCC TTCGGGCATG

7081 GCGGACTTGA AGAAGTCGTG CTGCTTCATG TGGTCGGGGT AGCGGCTGAA GCACTGCACG

7141 CCGTAGGTCA GGGTGGTCAC GAGGGTGGGC CAGGGCACGG GCAGCTTGCC GGTGGTGCAG

7201 ATGAACTTCA GGGTCAGCTT GCCGTAGGTG GCATCGCCCT CGCCCTCGCC GGACACGCTG

7261 AACTTGTGGC CGTTTACGTC GCCGTCCAGC TCGACCAGGA TGGGCACCAC CCCGGTGAAC

7321 AGCTCCTCGC CCTTGCTCAC CATGGTGGCG AATTCGAAGC TTGAGCACGA GATCTGAGTC

7381 CGGTAGGCCT AGCGGATCTG ACGGTTCACT AAACCAGCTC TGCTTATATA GACCTCCCAC

7441 CGTACACGCC TACCGCCCAT TTGCGTCAAT GGGGCGGAGT TGTTACGACA TTTTGGAAAG

7501 TCCCGTTGAT TTTGGTGCCA AAACAAACTC CCATTGACGT CAATGGGGTG GAGACTTGGA

7561 AATCCCCGTG AGTCAAACCG CTATCCACGC CCATTGATGT ACTGCCAAAA CCGCATCACC

7621 ATGGTAATAG CGATGACTAA TACGTAGATG TACTGCCAAG TAGGAAAGTC CCATAAGGTC

7681 ATGTACTGGG CATAATGCCA GGCGGGCCAT TTACCGTCAT TGACGTCAAT AGGGGGCGTA

7741 CTTGGCATAT GATACACTTG ATGTACTGCC AAGTGGGCAG TTTACCGTAA ATACTCCACC

7801 CATTGACGTC AATGGAAAGT CCCTATTGGC GTTACTATGG AACATACGTC CATTATTGAC

7861 GTCAATGGGC GGGGGTCGTT GGGCGGTCAG CCAGGCGGGC CATTTACCGT AAGTTATGTA

7921 ACGGGCCTGC TGCCGGCTCT GCGGCCTCTT CCGCGTCTTC GCCTTCGCCC TCAGACGAGT

7981 CGGATCTCCC TTTGGGCCGC CTCCCCGCCT GTCTAGCTTG ACTGACTGAG ATACAGCGTA

8041 CCTTCAGCTC ACAGACATGA TAAGATACAT TGATGAGTTT GGACAAACCA CAACTAGAAT

8101 GCAGTGAAAA AAATGCTTTA TTTGTGAAAT TTGTGATGCT ATTGCTTTAT TTGTAACCAT

8161 TATAAGCTGC AATAAACAAG TTAACAACAA CAATTGCATT CATTTTATGT TTCAGGTTCA

8221 GGGGGAGGTG TGGGAGGTTT TTTAAAGCAA GTAAACCTC TACAAATGTG GTATTGGCCC

8281 ATCTCTATCG GTATCGTAGC ATAACCCCTT GGGGCCTCTA AACGGGTCTT GAGGGGTTTT

8341 TTGTGCCCCT CGGGCCGGAT TGCTATCTAC CGGCATTGGC GCAGAAAAAA ATGCCTGATG

8401 CGACGCTGCG CGTCTTATAC TCCCACATAT GCCAGATTCA GCAACGGATA CGGCTTCCCC

8461 AACTTGCCCA CTTCCATACG TGTCCTCCTT ACCAGAAATT TATCCTTAAG GTCGTCAGCT

8521 ATCCTGCAGG CGATCTCTCG ATTTCGATCA AGACATTCCT TTAATGGTCT TTTCTGGACA

8581 CCACTAGGGG TCAGAAGTAG TTCATCAAAC TTTCTTCCCT CCCTAATCTC ATTGGTTACC

8641 TTGGGCTATC GAAACTTAAT TAAGCGATCT GCATCTCAAT TAGTCAGCAA CCATAGTCCC

8701 GCCCCTAACT CCGCCCATCC CGCCCCTAAC TCCGCCCAGT TCCGCCCATT CTCCGCCCCA

8761 TCGCTGACTA ATTTTTTTTA TTTATGCAGA GGCCGAGGCC GCCTCGGCCT CTGAGCTATT

TABLE 8-continued

Plasmid and mRNA construct sequences

```
 8821 CCAGAAGTAG TGAGGAGGCT TTTTTGGAGG CCTAGGCTTT TGCAAAGGAG GTAGCCAACA

8881 TGATTGAACA AGATGGATTG CACGCAGGTT CTCCCGCCGC TTGGGTGGAG AGGCTATTCG

8941 GCTATGACTG GGCACAACAG ACAATCGGCT GCTCTGATGC CGCCGTGTTC CGGCTGTCAG

9001 CGCAGGGGCG CCCGGTTCTT TTTGTCAAGA CCGACCTGTC CGGTGCCCTG AATGAACTCC

9061 AGGACGAGGC AGCGCGGCTA TCGTGGCTGG CCACGACGGG CGTTCCTTGC GCAGCTGTGC

9121 TCGACGTTGT CACTGAAGCG GGAAGGGACT GGCTGCTATT GGGCGAAGTG CCGGGGCAGG

9181 ATCTCCTGTC ATCTCACCTT GCTCCTGCCG AGAAAGTATC CATCATGGCT GATGCAATGC

9241 GGCGGCTGCA TACGCTTGAT CCGGCTACCT GCCCATTCGA CCACCAAGCG AAACATCGCA

9301 TCGAGCGAGC ACGTACTCGG ATGGAAGCCG GTCTTGTCGA TCAGGATGAT CTGGACGAAG

9361 AGCATCAGGG GCTCGCGCCA GCCGAACTGT TCGCCAGGCT CAAGGCGCGG ATGCCCGACG

9421 GCGAGGATCT CGTCGTGACC CACGGCGATG CCTGCTTGCC GAATATCATG GTGGAAAATG

9481 GCCGCTTTTC TGGATTCATC GACTGTGGCC GGCTGGGTGT GGCGGACCGC TATCAGGACA

9541 TAGCGTTGGC TACCCGTGAT ATTGCTGAAG AGCTTGGCGG CGAATGGGCT GACCGCTTCC

9601 TCGTGCTTTA CGGTATCGCC GCTCCCGATT CGCAGCGCAT CGCCTTCTAT CGCCTTCTTG

9661 ACGAGTTCTT CTAGTATGTA AGCCCTGTGC CTTCTAGTTG CCAGCCATCT GTTGTTTGCC

9721 CCTCCCCCGT GCCTTCCTTG ACCCTGGAAG GTGCCACTCC CACTGTCCTT TCCTAATAAA

9781 ATGAGGAAAT TGCATCGCAT TGTCTGAGTA GGTGTCATTC TATTCTGGGG GGTGGGGTGG

9841 GGCAGGACAG CAAGGGGGAG GATTGGGAAG ACAATAGCAG GCATGCTGGG GATGCGGTGG

9901 GCTCTATGGT TAATTAACCA GTCAAGTCAG CTACTTGGCG AGATCGACTT GTCTGGGTTT

9961 CGACTACGCT CAGAATTGCG TCAGTCAAGT TCGATCTGGT CCTTGCTATT GCACCCGTTC

10021 TCCGATTACG AGTTTCATTT AAATCATGTG AGCAAAAGGC CAGCAAAAGG CCAGGAACCG

10081 TAAAAAGGCC GCGTTGCTGG CGTTTTTCCA TAGGCTCCGC CCCCCTGACG AGCATCACAA

10141 AAATCGACGC TCAAGTCAGA GGTGGCGAAA CCCGACAGGA CTATAAAGAT ACCAGGCGTT

10201 TCCCCCTGGA AGCTCCCTCG TGCGCTCTCC TGTTCCGACC CTGCCGCTTA CCGGATACCT

10261 GTCCGCCTTT CTCCCTTCGG GAAGCGTGGC GCTTTCTCAT AGCTCACGCT GTAGGTATCT

10321 CAGTTCGGTG TAGGTCGTTC GCTCCAAGCT GGGCTGTGTG CACGAACCCC CCGTTCAGCC

10381 CGACCGCTGC GCCTTATCCG GTAACTATCG TCTTGAGTCC AACCCGGTAA GACACGACTT

10441 ATCGCCACTG GCAGCAGCCA CTGGTAACAG GATTAGCAGA GCGAGGTATG TAGGCGGTGC

10501 TACAGAGTTC TTGAAGTGGT GGCCTAACTA CGGCTACACT AGAAGAACAG TATTTGGTAT

10561 CTGCGCTCTG CTGAAGCCAG TTACCTTCGG AAAAAGAGTT GGTAGCTCTT GATCCGGCAA

10621 ACAAACCACC GCTGGTAGCG GTGGTTTTTT TGTTTGCAAG CAGCAGATTA CGCGCAGAAA

10681 AAAAGGATCT CAAGAAGATC CTTTGATCTT TTCTACGGGG TCTGACGCTC AGTGGAACGA

10741 AAACTCACGT TAAGGGATTT TGGTCATGAG ATTATCAAAA AGGATCTTCA CCTAGATCCT

10801 TTTAAATTAA AAATGAAGTT TTAAATCAAT CTAAAGTATA TATGAGTAAA CTTGGTCTGA

10861 CAGTTACCAA TGCTTAATCA GTGAGGCACC TATCTCAGCG ATCTGTCTAT TTCGTTCATC

10921 CATAGTTGCA TTTAAATTTC CGAACTCTCC AAGGCCCTCG TCGGAAAATC TTCAAACCTT

10981 TCGTCCGATC CATCTTGCAG GCTACCTCTC GAACGAACTA TCGCAAGTCT CTTGGCCGGC

11041 CTTGCGCCTT GGCTATTGCT TGGCAGCGCC TATCGCCAGG TATTACTCCA ATCCCGAATA

11101 TCCGAGATCG GGATCACCCG AGAGAAGTTC AACCTACATC CTCAATCCCG ATCTATCCGA
```

TABLE 8-continued

Plasmid and mRNA construct sequences

```
11161 GATCCGAGGA ATATCGAAAT CGGGGCGCGC CTGGTGTACC GAGAACGATC CTCTCAGTGC

11221 GAGTCTCGAC GATCCATATC GTTGCTTGGC AGTCAGCCAG TCGGAATCCA GCTTGGGACC

11281 CAGGAAGTCC AATCGTCAGA TATTGTACTC AAGCCTGGTC ACGGCAGCGT ACCGATCTGT

11341 TTAAACCTAG ATATTGATAG TCTGATCGGT CAACGTATAA TCGAGTCCTA GCTTTTGCAA

11401 ACATCTATCA AGAGACAGGA TCAGCAGGAG GCTTTCGCAT GAGTATTCAA CATTTCCGTG

11461 TCGCCCTTAT TCCCTTTTTT GCGGCATTTT GCCTTCCTGT TTTTGCTCAC CCAGAAACGC

11521 TGGTGAAAGT AAAAGATGCT GAAGATCAGT TGGGTGCGCG AGTGGGTTAC ATCGAACTGG

11581 ATCTCAACAG CGGTAAGATC CTTGAGAGTT TTCGCCCCGA AGAACGCTTT CCAATGATGA

11641 GCACTTTTAA AGTTCTGCTA TGTGGCGCGG TATTATCCCG TATTGACGCC GGGCAAGAGC

11701 AACTCGGTCG CCGCATACAC TATTCTCAGA ATGACTTGGT TGAGTATTCA CCAGTCACAG

11761 AAAAGCATCT TACGGATGGC ATGACAGTAA GAGAATTATG CAGTGCTGCC ATAACCATGA

11821 GTGATAACAC TGCGGCCAAC TTACTTCTGA CAACGATTGG AGGACCGAAG GAGCTAACCG

11881 CTTTTTTGCA CAACATGGGG GATCATGTAA CTCGCCTTGA TCGTTGGGAA CCGGAGCTGA

11941 ATGAAGCCAT ACCAAACGAC GAGCGTGACA CCACGATGCC TGTAGCAATG GCAACAACCT

12001 TGCGTAAACT ATTAACTGGC GAACTACTTA CTCTAGCTTC CCGGCAACAG TTGATAGACT

12061 GGATGGAGGC GGATAAAGTT GCAGGACCAC TTCTGCGCTC GGCCCTTCCG GCTGGCTGGT

12121 TTATTGCTGA TAAATCTGGA GCCGGTGAGC GTGGGTCTCG CGGTATCATT GCAGCACTGG

12181 GGCCAGATGG TAAGCCCTCC CGTATCGTAG TTATCTACAC GACGGGGAGT CAGGCAACTA

12241 TGGATGAACG AAATAGACAG ATCGCTGAGA TAGGTGCCTC ACTGATTAAG CATTGGTAAC

12301 CGATTCTAGG TGCATTGGCG CAGAAAAAAA TGCCTGATGC GACGCTGCGC GTCTTATACT

12361 CCCACATATG CCAGATTCAG CAACGGATAC GGCTTCCCCA ACTTGCCCAC TTCCATACGT

12421 GTCCTCCTTA CCAGAAATTT ATCCTTAAGA TCGTTTAAAC TCGACTCTGG CTCTATCGAA

12481 TCTCCGTCGT TTCGAGCTTA CGCGAACAGC CGTGGCGCTC ATTTGCTCGT CGGGCATCGA

12541 ATCTCGTCAG CTATCGTCAG CTTACCTTTT TGGCAGCGAT CGCGGCTCCC GACATCTTGG

12601 ACCATTAGCT CCACAGGTAT CTTCTTCCCT CTAGTGGTCA TAACAGCAGC TTCAGCTACC

12661 TCTCAATTCA AAAAACCCCT CAAGACCCGT TTAGAGGCCC CAAGGGGTTA TGCTATCAAT

12721 CGTTGCGTTA CACACACAAA AAACCAACAC ACATCCATCT TCGATGGATA GCGATTTTAT

12781 TATCTAACTG CTGATCGAGT GTAGCCAGAT CTAGTAATCA ATTACGGGGT CATTAGTTCA

12841 TAGCCCATAT ATGGAGTTCC GCGTTACATA ACTTACGGTA AATGGCCCGC CTGGCTGACC

12901 GCCCAACGAC CCCCGCCCAT TGACGTCAAT AATGACGTAT GTTCCCATAG TAACGCCAAT

12961 AGGGACTTTC CATTGACGTC AATGGGTGGA GTATTTACGG TAAACTGCCC ACTTGGCAGT

13021 ACATCAAGTG TATCATATGC CAAGTACGCC CCCTATTGAC GTCAATGACG GTAAATGGCC

13081 CGCCTGGCAT TATGCCCAGT ACATGACCTT ATGGGACTTT CCTACTTGGC AGTACATCTA

13141 CGTATTAGTC ATCGCTATTA CCATGCTGAT GCGGTTTTGG CAGTACATCA ATGGGCGTGG

13201 ATAGCGGTTT GACTCACGGG GATTTCCAAG TCTCCACCCC ATTGACGTCA ATGGGAGTTT

13261 GTTTTGGCAC CAAAATCAAC GGGACTTTCC AAAATGTCGT AACAACTCCG CCCCATTGAC

13321 GCAAATGGGC GGTAGGCGTG TACGGTGGGA GGTCTATATA AGCAGAGCTG GTTTAGTGAA

13381 CCGTCAGATC AGATCTTTGT CGATCCTACC ATCCACTCGA CACACCCGCC AGCGGCCGC
(SEQ ID NO: 46)
```

TABLE 8-continued

Plasmid and mRNA construct sequences

LINE-1 plasmid ORF 1- P2A-ORF2 GFP (SEQ ID NO: 47)

```
   1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT

361 CCAGGTGTGA CCAGCTCGAG GAGCGCGTGA GCGCGATGGA AGACGAGATG AACGAGATGA

421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA

721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA

901 TCTCCGAGGG TGAGATTAAG TATTTCATCG ATAAACAGAT GCTGCGAGAC TTCGTGACAA

961 CTCGCCCAGC TCTCAAGGAA CTGCTCAAAG AGGCTCTTAA TATGGAGCGC AATAATAGAT

1021 ATCAACCCTT GCAGAACCAC GCAAAGATGG GAAGCGGAGC TACTAACTTC AGCCTGCTGA

1081 AGCAGGCTGG AGACGTGGAG GAGAACCCTG GACCTATGAC CGGCTCTAAC TCACATATCA

1141 CCATCCTTAC ACTTAACATT AACGGCCTCA ACTCAGCTAT CAAGCGCCAT CGGCTGGCCA

1201 GCTGGATCAA ATCACAGGAT CCAAGCGTTT GTTGCATCCA AGAGACCCAC CTGACCTGTA

1261 GAGATACTCA CCGCCTCAAG ATCAAGGGAT GGCGAAAGAT TTATCAGGCG AACGGTAAGC

1321 AGAAGAAAGC CGGAGTCGCA ATTCTGGTCT CAGACAAGAC GGATTTCAAG CCCACCAAAA

1381 TTAAGCGTGA TAAGGAAGGT CACTATATTA TGGTGAAAGG CAGCATACAG CAGGAAGAAC

1441 TTACCATATT GAACATCTAC GCGCCAAACA CCGGCGCACC TCGCTTTATC AAACAGGTCC

1501 TGTCCGATCT GCAGCGAGAT CTGGATTCTC ATACGTTGAT TATGGGTGAT TTCAATACAC

1561 CATTGAGCAC CCTGGATCGC AGCACCAGGC AAAAGGTAAA TAAAGACACG CAAGAGCTCA

1621 ATAGCGCACT GCATCAGGCA GATCTCATTG ATATTTATCG CACTCTTCAT CCTAAGAGTA

1681 CCGAGTACAC ATTCTTCAGC GCCCCACATC ATACATACTC AAAGATCGAT CATATCGTCG

1741 GCTCAAAGGC TCTGCTGTCA AAGTGCAAGC GCACAGAGAT AATTACAAAT TACCTGTCAG

1801 ATCATAGCGC GATCAAGCTC GAGCTGAGAA TCAAGAACCT GACCCAGAGC CGGAGTACCA

1861 CTTGGAAGCT TAATAACCTG CTGCTCAACG ATTATTGGGT CCACAATGAG ATGAAGGCAG

1921 AGATTAAAAT GTTCTTCGAA ACAAATGAGA ATAAGGATAC TACCTATCAA AACCTTTGGG

1981 ATGCCTTTAA GGCCGTCTGC AGAGGCAAGT TCATCGCCCT CAACGCCTAT AAAAGAAAAC

2041 AAGAGAGATC TAAGATCGAT ACTCTCACCT CTCAGCTGAA GGAGTTGGAG AAACAGGAAC

2101 AGACCCACTC CAAGGCGTCA GACGGCAGG AGATCACAAA GATTCGCGCC GAGTTGAAAG

2161 AGATCGAAAC CCAAAAGACT CTTCAGAAAA TTAACGAGTC TCGTAGTTGG TTCTTCGAGC

2221 GGATTAATAA GATAGACAGA CCTCTGGCAC GACTGATTAA GAAGAAGCGC GAAAAGAACC
```

TABLE 8-continued

Plasmid and mRNA construct sequences

```
2281 AGATTGATAC CATCAAGAAC GACAAGGGCG ACATCACTAC TGACCCGACC GAGATCCAGA

2341 CCACTATTCG GGAGTATTAT AAGCATTTGT ATGCTAACAA GCTTGAGAAC CTGGAAGAGA

2401 TGGACACTTT TCTGGATACC TATACTCTGC CACGGCTTAA TCAAGAGGAA GTCGAGTCCC

2461 TCAACCGCCC AATTACAGGA AGCGAGATTG TGGCCATAAT TAACTCCCTG CCGACAAAGA

2521 AATCTCCTGG TCCGGACGGG TTTACAGCTG AGTTTTATCA ACGGTATATG GAAGAGCTTG

2581 TACCGTTTCT GCTCAAGCTC TTTCAGTCTA TAGAAAAGGA AGGCATCTTG CCCAATTCCT

2641 TCTACGAAGC TTCTATAATA CTTATTCCCA AACCAGGACG CGATACCACA AAGAAGGAAA

2701 ACTTCCGGCC CATTAGTCTC ATGAATATCG ACGCTAAAAT ATTGAACAAG ATTCTCGCCA

2761 ACAGAATCCA ACAACATATT AAGAAATTGA TACATCACGA CCAGGTGGGG TTTATACCTG

2821 GCATGCAGGG CTGGTTTAAC ATCCGGAAGA GTATTAACGT CATTCAACAC ATTAATAGAG

2881 CTAAGGATAA GAATCATATG ATCATCTCTA TAGACGCGGA AAAGGCATTC GATAAGATTC

2941 AGCAGCCATT TATGCTCAAG ACTCTGAACA AACTCGGCAT CGACGGAACA TATTTTAAGA

3001 TTATTCGCGC AATTTACGAT AAGCCGACTG CTAACATTAT CCTTAACGGC CAAAAGCTCG

3061 AGGCCTTTCC GCTCAAGACT GGAACCCGCC AAGGCTGTCC CCTCTCCCCG CTTTTGTTTA

3121 ATATTGTACT CGAGGTGCTG GCTAGGGCTA TTCGTCAAGA GAAAGAGATT AAAGGGATAC

3181 AGCTCGGGAA GGAAGAGGTC AAGCTTTCCT TGTTCGCCGA TGATATGATT GTGTACCTGG

3241 AGAATCCTAT TGTGTCTGCT CAGAACCTTC TTAAACTTAT TTCTAACTTT AGCAAGGTCA

3301 GCGGCTATAA GATTAACGTC CAGAAATCTC AGGCCTTTCT GTACACAAAT AATCGACAGA

3361 CCGAATCCCA GATAATGGGT GAGCTTCCGT TTGTCATAGC CAGCAAAAGG ATAAAGTATC

3421 TCGGAATCCA GCTGACACGA GACGTTAAAG ATTTGTTTAA GGAAAATTAC AAGCCTCTCC

3481 TGAAAGAGAT TAAGGAAGAT ACTAATAAGT GGAAGAATAT CCCCTGTTCA TGGGTTGGCA

3541 GAATCAACAT AGTGAAGATG GCAATACTTC CTAAAGTGAT ATATCGCTTT AACGCCATCC

3601 CAATTAAACT GCCTATGACC TTCTTTACGG AGCTCGAGAA AACAACCCTT AAATTTATAT

3661 GGAATCAAAA GAGAGCAAGA ATAGCGAAGT CCATCTTGAG CCAGAAGAAT AAGGCCGGTG

3721 GGATTACTTT GCCTGATTTT AAGTTGTATT ATAAAGCCAC AGTAACTAAG ACAGCCTGGT

3781 ATTGGTATCA GAATAGAGAC ATCGACCAGT GGAATCGGAC CGAACCATCA GAGATAATGC

3841 CCCACATCTA TAATTACCTT ATATTCGATA AGCCAGAAAA GAATAAACAG TGGGGCAAAG

3901 ACAGCCTCTT CAACAAGTGG TGTTGGGAGA ATTGGCTGGC CATATGCCGG AAACTCAAGC

3961 TCGACCCCTT TCTTACACCC TACACTAAAA TCAACAGTAG GTGGATCAAG GACTTGAATG

4021 TCAAGCCAAA GACTATAAAG ACACTGGAAG AGAATCTTGG GATCACAATA CAAGATATAG

4081 GCGTCGGCAA AGATTTTATG TCAAAGACGC CCAAGGCCAT GGCCACTAAG GATAAGATTG

4141 ATAAGTGGGA CCTTATTAAG CTCAAAAGCT TCTGTACTGC CAAGGAGACC ACGATCAGAG

4201 TTAATAGGCA GCCCACTACA TGGGAAAAGA TTTTCGCCAC TTATTCATCA GATAAGGGGT

4261 TGATAAGCAG AATATATAAC GAGCTGAAGC AGATCTACAA GAAGAAACG AATAATCCCA

4321 TCAAGAAGTG GGCAAAAGAT ATGAACAGGC ATTTTAGCAA AGAGGATATC TACGCCGCGA

4381 AGAAGCATAT GAAGAAGTGT AGTTCAAGCT TGGCCATTCG TGAGATGCAG ATTAAGACGA

4441 CCATGCGATA CCACCTTACC CCAGTGAGGA TGGCAATTAT CAAGAAATCT GGCAATAATA

4501 GATGTTGGCG GGGCTGTGGC GAGATTGGCA CCCTGCTCCA TTGCTGGTGG GATTGCAAGC

4561 TGGTGCAGCC GCTTTGGAAA TCAGTCTGGC GCTTTCTGAG GGACCTCGAG CTTGAGATTC
```

TABLE 8-continued

Plasmid and mRNA construct sequences

```
4621 CCTTCGATCC CGCAATTCCC TTGCTCGGAA TCTATCCTAA CGAATACAAG AGCTGTTGTT

4681 ACAAGGATAC GTGTACCCGG ATGTTCATCG CGGCCTTGTT TACGATAGCT AAGACGTGGA

4741 ATCAGCCTAA GTGCCCCACA ATGATCGATT GGATCAAGAA AATGTGGCAT ATTTATACCA

4801 TGGAGTATTA CGCAGCAATT AAGAATGACG AATTTATTTC CTTCGTTGGG ACCTGGATGA

4861 AGCTGGAGAC TATTATTCTG AGCAAGCTGT CTCAGGAGCA AAAGACAAAG CATAGAATCT

4921 TCTCTCTCAT TGGTGGTAAC GACTACAAAG ACGATGACGA CAAGTAAAGC GCTTCTAGAA

4981 GTTGTCTCCT CCTGCACTGA CTGACTGATA CAATCGATTT CTGGATCCGC AGGCCTAATC

5041 AACCTCTGGA TTACAAAATT TGTGAAAGAT TGACTGGTAT TCTTAACTAT GTTGCTCCTT

5101 TTACGCTATG TGGATACGCT GCTTTAATGC CTTTGTATCA TGCTATTGCT TCCCGTATGG

5161 CTTTCATTTT CTCCTCCTTG TATAAATCCT GGTTGCTGTC TCTTTATGAG GAGTTGTGGC

5221 CCGTTGTCAG GCAACGTGGC GTGGTGTGCA CTGTGTTTGC TGACGCAACC CCCACTGGTT

5281 GGGGCATTGC CACCACCTGT CAGCTCCTTT CCGGGACTTT CGCTTTCCCC CTCCCTATTG

5341 CCACGGCGGA ACTCATCGCC GCCTGCCTTG CCCGCTGCTG GACAGGGGCT CGGCTGTTGG

5401 GCACTGACAA TTCCGTGGTG TTGTCGGGGA AGCTGACGTC CTTTCCATGG CTGCTCGCCT

5461 GTGTTGCCAC CTGGATTCTG CGCGGGACGT CCTTCTGCTA CGTCCCTTCG GCCCTCAATC

5521 CAGCGGACCT TCCTTCCCGC GAACAAACGA CCCAACACCC GTGCGTTTTA TTCTGTCTTT

5581 TTATTGCCGA TCCCCTCAGA AGAACTCGTC AAGAAGGCGA TAGAAGGCGA TGCGCTGCGA

5641 ATCGGGAGCG GCGATACCGT AAAGCACGAG GAAGCGGTCA GCCCATTCGC CGCCAAGCTC

5701 TTCAGCAATA TCACGGGTAG CCAACGCTAT GTCCTGATAG CGGTCGGCCG CTTTACTTGT

5761 ACAGCTCGTC CATGCCGAGA GTGATCCCGG CGGCGGTCAC GAACTCCAGC AGGACCATGT

5821 GATCGCGCTT CTCGTTGGGG TCTTTGCTCA GGGCGGACTG GGTGCTCAGG TAGTGGTTGT

5881 CGGGCAGCAG CACGGGGCCG TCGCCGATGG GGGTGTTCTG CTGGTAGTGG TCGGCCAGGT

5941 GAGTCCAGGA GATGTTTCAG CACTGTTGCC TTTAGTCTCG AGGCAACTTA GACAACTGAG

6001 TATTGATCTG AGCACAGCAG GGTGTGAGCT GTTTGAAGAT ACTGGGGTTG GGGGTGAAGA

6061 AACTGCAGAG GACTAACTGG GCTGAGACCC AGTGGCAATG TTTTAGGGCC TAAGGAATGC

6121 CTCTGAAAAT CTAGATGGAC AACTTTGACT TTGAGAAAAG AGAGGTGGAA ATGAGGAAAA

6181 TGACTTTTCT TTATTAGATT TCGGTAGAAA GAACTTTCAT CTTTCCCCTA TTTTTGTTAT

6241 TCGTTTTAAA ACATCTATCT GGAGGCAGGA CAAGTATGGT CATTAAAAAG ATGCAGGCAG

6301 AAGGCATATA TTGGCTCAGT CAAAGTGGGG AACTTTGGTG CCAAACATA CATTGCTAAG

6361 GCTATTCCTA TATCAGCTGG ACACATATAA AATGCTGCTA ATGCTTCATT ACAAACTTAT

6421 ATCCTTTAAT TCCAGATGGG GGCAAAGTAT GTCCAGGGGT GAGGAACAAT TGAAACATTT

6481 GGGCTGGAGT AGATTTTGAA AGTCAGCTCT GTGTGTGTGT GTGTGTGTGT GTGTGTGAGA

6541 GCGTGTGTTT CTTTTAACGT TTTCAGCCTA CAGCATACAG GGTTCATGGT GGCAAGAAGA

6601 TAACAAGATT TAAATTATGG CCAGTGACTA GTGCTGCAAG AAGAACAACT ACCTGCATTT

6661 AATGGGAAAG CAAAATCTCA GGCTTTGAGG GAAGTTAACA TAGGCTTGAT TCTGGGTGGA

6721 AGCTGGGTGT GTAGTTATCT GGAGGCCAGG CTGGAGCTCT CAGCTCACTA TGGGTTCATC

6781 TTTATTGTCT CCTTTCATCT CAACAGCTGC ACGCTGCCGT CCTCGATGTT GTGGCGGATC

6841 TTGAAGTTCA CCTTGATGCC GTTCTTCTGC TTGTCGGCCA TGATATAGAC GTTGTGGCTG

6901 TTGTAGTTGT ACTCCAGCTT GTGCCCCAGG ATGTTGCCGT CCTCCTTGAA GTCGATGCCC
```

TABLE 8-continued

Plasmid and mRNA construct sequences

```
6961 TTCAGCTCGA TGCGGTTCAC CAGGGTGTCG CCCTCGAACT TCACCTCGGC GCGGGTCTTG

7021 TAGTTGCCGT CGTCCTTGAA GAAGATGGTG CGCTCCTGGA CGTAGCCTTC GGGCATGGCG

7081 GACTTGAAGA AGTCGTGCTG CTTCATGTGG TCGGGGTAGC GGCTGAAGCA CTGCACGCCG

7141 TAGGTCAGGG TGGTCACGAG GGTGGGCCAG GGCACGGGCA GCTTGCCGGT GGTGCAGATG

7201 AACTTCAGGG TCAGCTTGCC GTAGGTGGCA TCGCCCTCGC CCTCGCCGGA CACGCTGAAC

7261 TTGTGGCCGT TTACGTCGCC GTCCAGCTCG ACCAGGATGG GCACCACCCC GGTGAACAGC

7321 TCCTCGCCCT TGCTCACCAT GGTGGCGAAT TCGAAGCTTG AGCACGAGAT CTGAGTCCGG

7381 TAGGCCTAGC GGATCTGACG GTTCACTAAA CCAGCTCTGC TTATATAGAC CTCCCACCGT

7441 ACACGCCTAC CGCCCATTTG CGTCAATGGG GCGGAGTTGT TACGACATTT TGGAAAGTCC

7501 CGTTGATTTT GGTGCCAAAA CAAACTCCCA TTGACGTCAA TGGGGTGGAG ACTTGGAAAT

7561 CCCCGTGAGT CAAACCGCTA TCCACGCCCA TTGATGTACT GCCAAAACCG CATCACCATG

7621 GTAATAGCGA TGACTAATAC GTAGATGTAC TGCCAAGTAG GAAAGTCCCA TAAGGTCATG

7681 TACTGGGCAT AATGCCAGGC GGGCCATTTA CCGTCATTGA CGTCAATAGG GGGCGTACTT

7741 GGCATATGAT ACACTTGATG TACTGCCAAG TGGGCAGTTT ACCGTAAATA CTCCACCCAT

7801 TGACGTCAAT GGAAAGTCCC TATTGGCGTT ACTATGGGAA CATACGTCAT TATTGACGTC

7861 AATGGGCGGG GGTCGTTGGG CGGTCAGCCA GGCGGGCCAT TTACCGTAAG TTATGTAACG

7921 GGCCTGCTGC CGGCTCTGCG GCCTCTTCCG CGTCTTCGCC TTCGCCCTCA GACGAGTCGG

7981 ATCTCCCTTT GGGCCGCCTC CCCGCCTGTC TAGCTTGACT GACTGAGATA CAGCGTACCT

8041 TCAGCTCACA GACATGATAA GATACATTGA TGAGTTTGGA CAAACCACAA CTAGAATGCA

8101 GTGAAAAAAA TGCTTTATTT GTGAAATTTG TGATGCTATT GCTTTATTTG TAACCATTAT

8161 AAGCTGCAAT AAACAAGTTA ACAACAACAA TTGCATTCAT TTTATGTTTC AGGTTCAGGG

8221 GGAGGTGTGG GAGGTTTTTT AAAGCAAGTA AAACCTCTAC AAATGTGGTA TTGGCCCATC

8281 TCTATCGGTA TCGTAGCATA ACCCCTTGGG GCCTCTAAAC GGGTCTTGAG GGGTTTTTTG

8341 TGCCCCTCGG GCCGGATTGC TATCTACCGG CATTGGCGCA GAAAAAAATG CCTGATGCGA

8401 CGCTGCGCGT CTTATACTCC CACATATGCC AGATTCAGCA ACGGATACGG CTTCCCCAAC

8461 TTGCCCACTT CCATACGTGT CCTCCTTACC AGAAATTTAT CCTTAAGGTC GTCAGCTATC

8521 CTGCAGGCGA TCTCTCGATT TCGATCAAGA CATTCCTTTA ATGGTCTTTT CTGGCACCA

8581 CTAGGGGTCA GAAGTAGTTC ATCAAACTTT CTTCCCTCCC TAATCTCATT GGTTACCTTG

8641 GGCTATCGAA ACTTAATTAA GCGATCTGCA TCTCAATTAG TCAGCAACCA TAGTCCCGCC

8701 CCTAACTCCG CCCATCCCGC CCCTAACTCC GCCCAGTTCC GCCCATTCTC CGCCCCATCG

8761 CTGACTAATT TTTTTATTT ATGCAGAGGC CGAGGCCGCC TCGGCCTCTG AGCTATTCCA

8821 GAAGTAGTGA GGAGGCTTTT TTGGAGGCCT AGGCTTTTGC AAAGGAGGTA GCCAACATGA

8881 TTGAACAAGA TGGATTGCAC GCAGGTTCTC CCGCCGCTTG GGTGGAGAGG CTATTCGGCT

8941 ATGACTGGGC ACAACAGACA ATCGGCTGCT CTGATGCCGC CGTGTTCCGG CTGTCAGCGC

9001 AGGGGCGCCC GGTTCTTTTT GTCAAGACCG ACCTGTCCGG TGCCCTGAAT GAACTCCAGG

9061 ACGAGGCAGC GCGGCTATCG TGGCTGGCCA CGACGGGCGT TCCTTGCGCA GCTGTGCTCG

9121 ACGTTGTCAC TGAAGCGGGA AGGGACTGGC TGCTATTGGG CGAAGTGCCG GGGCAGGATC

9181 TCCTGTCATC TCACCTTGCT CCTGCCGAGA AAGTATCCAT CATGGCTGAT GCAATGCGGC

9241 GGCTGCATAC GCTTGATCCG GCTACCTGCC CATTCGACCA CCAAGCGAAA CATCGCATCG
```

TABLE 8-continued

Plasmid and mRNA construct sequences

```
 9301 AGCGAGCACG TACTCGGATG GAAGCCGGTC TTGTCGATCA GGATGATCTG GACGAAGAGC

9361 ATCAGGGGCT CGCGCCAGCC GAACTGTTCG CCAGGCTCAA GGCGCGGATG CCCGACGGCG

9421 AGGATCTCGT CGTGACCCAC GGCGATGCCT GCTTGCCGAA TATCATGGTG GAAAATGGCC

9481 GCTTTTCTGG ATTCATCGAC TGTGGCCGGC TGGGTGTGGC GGACCGCTAT CAGGACATAG

9541 CGTTGGCTAC CCGTGATATT GCTGAAGAGC TTGGCGGCGA ATGGGCTGAC CGCTTCCTCG

9601 TGCTTTACGG TATCGCCGCT CCCGATTCGC AGCGCATCGC CTTCTATCGC CTTCTTGACG

9661 AGTTCTTCTA GTATGTAAGC CCTGTGCCTT CTAGTTGCCA GCCATCTGTT GTTTGCCCCT

9721 CCCCCGTGCC TTCCTTGACC CTGGAAGGTG CCACTCCCAC TGTCCTTTCC TAATAAAATG

9781 AGGAAATTGC ATCGCATTGT CTGAGTAGGT GTCATTCTAT TCTGGGGGGT GGGGTGGGGC

9841 AGGACAGCAA GGGGGAGGAT TGGGAAGACA ATAGCAGGCA TGCTGGGGAT GCGGTGGGCT

9901 CTATGGTTAA TTAACCAGTC AAGTCAGCTA CTTGGCGAGA TCGACTTGTC TGGGTTTCGA

9961 CTACGCTCAG AATTGCGTCA GTCAAGTTCG ATCTGGTCCT TGCTATTGCA CCCGTTCTCC

10021 GATTACGAGT TTCATTTAAA TCATGTGAGC AAAAGGCCAG CAAAAGGCCA GGAACCGTAA

10081 AAAGGCCGCG TTGCTGGCGT TTTTCCATAG GCTCCGCCCC CCTGACGAGC ATCACAAAAA

10141 TCGACGCTCA AGTCAGAGGT GGCGAAACCC GACAGGACTA TAAAGATACC AGGCGTTTCC

10201 CCCTGGAAGC TCCCTCGTGC GCTCTCCTGT TCCGACCCTG CCGCTTACCG GATACCTGTC

10261 CGCCTTTCTC CCTTCGGGAA GCGTGGCGCT TTCTCATAGC TCACGCTGTA GGTATCTCAG

10321 TTCGGTGTAG GTCGTTCGCT CCAAGCTGGG CTGTGTGCAC GAACCCCCCG TTCAGCCCGA

10381 CCGCTGCGCC TTATCCGGTA ACTATCGTCT TGAGTCCAAC CCGGTAAGAC ACGACTTATC

10441 GCCACTGGCA GCAGCCACTG GTAACAGGAT TAGCAGAGCG AGGTATGTAG GCGGTGCTAC

10501 AGAGTTCTTG AAGTGGTGGC CTAACTACGG CTACACTAGA AGAACAGTAT TTGGTATCTG

10561 CGCTCTGCTG AAGCCAGTTA CCTTCGGAAA AAGAGTTGGT AGCTCTTGAT CCGGCAAACA

10621 AACCACCGCT GGTAGCGGTG GTTTTTTTGT TTGCAAGCAG CAGATTACGC GCAGAAAAAA

10681 AGGATCTCAA GAAGATCCTT TGATCTTTTC TACGGGGTCT GACGCTCAGT GGAACGAAAA

10741 CTCACGTTAA GGGATTTTGG TCATGAGATT ATCAAAAAGG ATCTTCACCT AGATCCTTTT

10801 AAATTAAAAA TGAAGTTTTA AATCAATCTA AAGTATATAT GAGTAAACTT GGTCTGACAG

10861 TTACCAATGC TTAATCAGTG AGGCACCTAT CTCAGCGATC TGTCTATTTC GTTCATCCAT

10921 AGTTGCATTT AAATTTCCGA ACTCTCCAAG GCCCTCGTCG AAAATCTTC AAACCTTTCG

10981 TCCGATCCAT CTTGCAGGCT ACCTCTCGAA CGAACTATCG CAAGTCTCTT GGCCGGCCTT

11041 GCGCCTTGGC TATTGCTTGG CAGCGCCTAT CGCCAGGTAT TACTCCAATC CCGAATATCC

11101 GAGATCGGGA TCACCCGAGA GAAGTTCAAC CTACATCCTC AATCCCGATC TATCCGAGAT

11161 CCGAGGAATA TCGAAATCGG GGCGCGCCTG GTGTACCGAG AACGATCCTC TCAGTGCGAG

11221 TCTCGACGAT CCATATCGTT GCTTGGCAGT CAGCCAGTCG GAATCCAGCT TGGGACCCAG

11281 GAAGTCCAAT CGTCAGATAT TGTACTCAAG CCTGGTCACG GCAGCGTACC GATCTGTTTA

11341 AACCTAGATA TTGATAGTCT GATCGGTCAA CGTATAATCG AGTCCTAGCT TTTGCAAACA

11401 TCTATCAAGA GACAGGATCA GCAGGAGGCT TTCGCATGAG TATTCAACAT TTCCGTGTCG

11461 CCCTTATTCC CTTTTTTGCG GCATTTTGCC TTCCTGTTTT TGCTCACCCA GAAACGCTGG

11521 TGAAAGTAAA AGATGCTGAA GATCAGTTGG GTGCGCGAGT GGGTTACATC GAACTGGATC

11581 TCAACAGCGG TAAGATCCTT GAGAGTTTTC GCCCCGAAGA ACGCTTTCCA ATGATGAGCA
```

TABLE 8-continued

Plasmid and mRNA construct sequences

```
11641 CTTTTAAAGT TCTGCTATGT GGCGCGGTAT TATCCCGTAT TGACGCCGGG CAAGAGCAAC

11701 TCGGTCGCCG CATACACTAT TCTCAGAATG ACTTGGTTGA GTATTCACCA GTCACAGAAA

11761 AGCATCTTAC GGATGGCATG ACAGTAAGAG AATTATGCAG TGCTGCCATA ACCATGAGTG

11821 ATAACACTGC GGCCAACTTA CTTCTGACAA CGATTGGAGG ACCGAAGGAG CTAACCGCTT

11881 TTTTGCACAA CATGGGGGAT CATGTAACTC GCCTTGATCG TTGGGAACCG GAGCTGAATG

11941 AAGCCATACC AAACGACGAG CGTGACACCA CGATGCCTGT AGCAATGGCA ACAACCTTGC

12001 GTAAACTATT AACTGGCGAA CTACTTACTC TAGCTTCCCG GCAACAGTTG ATAGACTGGA

12061 TGGAGGCGGA TAAAGTTGCA GGACCACTTC TGCGCTCGGC CCTTCCGGCT GGCTGGTTTA

12121 TTGCTGATAA ATCTGGAGCC GGTGAGCGTG GGTCTCGCGG TATCATTGCA GCACTGGGGC

12181 CAGATGGTAA GCCCTCCCGT ATCGTAGTTA TCTACACGAC GGGGAGTCAG GCAACTATGG

12241 ATGAACGAAA TAGACAGATC GCTGAGATAG GTGCCTCACT GATTAAGCAT TGGTAACCGA

12301 TTCTAGGTGC ATTGGCGCAG AAAAAAATGC CTGATGCGAC GCTGCGCGTC TTATACTCCC

12361 ACATATGCCA GATTCAGCAA CGGATACGGC TTCCCCAACT TGCCCACTTC CATACGTGTC

12421 CTCCTTACCA GAAATTTATC CTTAAGATCG TTTAAACTCG ACTCTGGCTC TATCGAATCT

12481 CCGTCGTTTC GAGCTTACGC GAACAGCCGT GGCGCTCATT TGCTCGTCGG GCATCGAATC

12541 TCGTCAGCTA TCGTCAGCTT ACCTTTTTGG CAGCGATCGC GGCTCCCGAC ATCTTGGACC

12601 ATTAGCTCCA CAGGTATCTT CTTCCCTCTA GTGGTCATAA CAGCAGCTTC AGCTACCTCT

12661 CAATTCAAAA AACCCCTCAA GACCCGTTTA GAGGCCCCAA GGGGTTATGC TATCAATCGT

12721 TGCGTTACAC ACACAAAAAA CCAACACACA TCCATCTTCG ATGGATAGCG ATTTTATTAT

12781 CTAACTGCTG ATCGAGTGTA GCCAGATCTA GTAATCAATT ACGGGGTCAT TAGTTCATAG

12841 CCCATATATG GAGTTCCGCG TTACATAACT TACGGTAAAT GGCCCGCCTG GCTGACCGCC

12901 CAACGACCCC CGCCCATTGA CGTCAATAAT GACGTATGTT CCCATAGTAA CGCCAATAGG

12961 GACTTTCCAT TGACGTCAAT GGGTGGAGTA TTTACGGTAA ACTGCCCACT TGGCAGTACA

13021 TCAAGTGTAT CATATGCCAA GTACGCCCCC TATTGACGTC AATGACGGTA AATGGCCCGC

13081 CTGGCATTAT GCCCAGTACA TGACCTTATG GGACTTTCCT ACTTGGCAGT ACATCTACGT

13141 ATTAGTCATC GCTATTACCA TGCTGATGCG GTTTTGGCAG TACATCAATG GGCGTGGATA

13201 GCGGTTTGAC TCACGGGGAT TTCCAAGTCT CCACCCCATT GACGTCAATG GGAGTTTGTT

13261 TTGGCACCAA AATCAACGGG ACTTTCCAAA ATGTCGTAAC AACTCCGCCC CATTGACGCA

13321 AATGGGCGGT AGGCGTGTAC GGTGGGAGGT CTATATAAGC AGAGCTGGTT TAGTGAACCG

13381 TCAGATCAGA TCTTTGTCGA TCCTACCATC CACTCGACAC ACCCGCCAGC GGCCGC
```
(SEQ ID NO: 47)

LINE-1 plasmid ORF1- T2A ORF2 GFP (SEQ ID NO: 48)

```
   1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT

361 CCAGGTGTGA CCAGCTCGAG GAGCGCGTGA GCGCGATGGA AGACGAGATG AACGAGATGA
```

TABLE 8-continued

Plasmid and mRNA construct sequences

```
 421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA

721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA

901 TCTCCGAGGG TGAGATTAAG TATTTCATCG ATAAACAGAT GCTGCGAGAC TTCGTGACAA

961 CTCGCCCAGC TCTCAAGGAA CTGCTCAAAG AGGCTCTTAA TATGGAGCGC AATAATAGAT

1021 ATCAACCCTT GCAGAACCAC GCAAAGATGG GAAGCGGAGA GGGCAGAGGA AGTCTGCTAA

1081 CATGCGGTGA CGTCGAGGAG AATCCTGGAC CTATGACCGG CTCTAACTCA CATATCACCA

1141 TCCTTACACT TAACATTAAC GGCCTCAACT CAGCTATCAA GCGCCATCGG CTGGCCAGCT

1201 GGATCAAATC ACAGGATCCA AGCGTTTGTT GCATCCAAGA GACCCACCTG ACCTGTAGAG

1261 ATACTCACCG CCTCAAGATC AAGGGATGGC GAAAGATTTA TCAGGCGAAC GGTAAGCAGA

1321 AGAAAGCCGG AGTCGCAATT CTGGTCTCAG ACAAGACGGA TTTCAAGCCC ACCAAAATTA

1381 AGCGTGATAA GGAAGGTCAC TATATTATGG TGAAAGGCAG CATACAGCAG GAAGAACTTA

1441 CCATATTGAA CATCTACGCG CCAAACACCG GCGCACCTCG CTTTATCAAA CAGGTCCTGT

1501 CCGATCTGCA GCGAGATCTG GATTCTCATA CGTTGATTAT GGGTGATTTC AATACACCAT

1561 TGAGCACCCT GGATCGCAGC ACCAGGCAAA AGGTAAATAA AGACACGCAA GAGCTCAATA

1621 GCGCACTGCA TCAGGCAGAT CTCATTGATA TTTATCGCAC TCTTCATCCT AAGAGTACCG

1681 AGTACACATT CTTCAGCGCC CCACATCATA CATACTCAAA GATCGATCAT ATCGTCGGCT

1741 CAAAGGCTCT GCTGTCAAAG TGCAAGCGCA CAGAGATAAT TACAAATTAC CTGTCAGATC

1801 ATAGCGCGAT CAAGCTCGAG CTGAGAATCA AGAACCTGAC CCAGAGCCGG AGTACCACTT

1861 GGAAGCTTAA TAACCTGCTG CTCAACGATT ATTGGGTCCA CAATGAGATG AAGGCAGAGA

1921 TTAAAATGTT CTTCGAAACA AATGAGAATA AGGATACTAC CTATCAAAAC CTTTGGGATG

1981 CCTTTAAGGC CGTCTGCAGA GGCAAGTTCA TCGCCCTCAA CGCCTATAAA AGAAACAAG

2041 AGAGATCTAA GATCGATACT CTCACCTCTC AGCTGAAGGA GTTGGAGAAA CAGGAACAGA

2101 CCCACTCCAA GGCGTCAAGA CGGCAGGAGA TCACAAAGAT TCGCGCCGAG TTGAAAGAGA

2161 TCGAAACCCA AAAGACTCTT CAGAAAATTA ACGAGTCTCG TAGTTGGTTC TTCGAGCGGA

2221 TTAATAAGAT AGACAGACCT CTGGCACGAC TGATTAAGAA GAAGCGCGAA AAGAACCAGA

2281 TTGATACCAT CAAGAACGAC AAGGGCGACA TCACTACTGA CCCGACCGAG ATCCAGACCA

2341 CTATTCGGGA GTATTATAAG CATTTGTATG CTAACAAGCT TGAGAACCTG AAGAGATGG

2401 ACACTTTTCT GGATACCTAT ACTCTGCCAC GGCTTAATCA AGAGGAAGTC GAGTCCCTCA

2461 ACCGCCCAAT TACAGGAAGC GAGATTGTGG CCATAATTAA CTCCCTGCCG ACAAAGAAAT

2521 CTCCTGGTCC GGACGGGTTT ACAGCTGAGT TTTATCAACG GTATATGGAA GAGCTTGTAC

2581 CGTTTCTGCT CAAGCTCTTT CAGTCTATAG AAAAGGAAGG CATCTTGCCC AATTCCTTCT

2641 ACGAAGCTTC TATAATACTT ATTCCCAAAC CAGGACGCGA TACCACAAAG AAGGAAAACT

2701 TCCGGCCCAT TAGTCTCATG AATATCGACG CTAAAATATT GAACAAGATT CTCGCCAACA
```

TABLE 8-continued

Plasmid and mRNA construct sequences

```
2761 GAATCCAACA ACATATTAAG AAATTGATAC ATCACGACCA GGTGGGGTTT ATACCTGGCA

2821 TGCAGGGCTG GTTTAACATC CGGAAGAGTA TTAACGTCAT TCAACACATT AATAGAGCTA

2881 AGGATAAGAA TCATATGATC ATCTCTATAG ACGCGGAAAA GGCATTCGAT AAGATTCAGC

2941 AGCCATTTAT GCTCAAGACT CTGAACAAAC TCGGCATCGA CGGAACATAT TTTAAGATTA

3001 TTCGCGCAAT TTACGATAAG CCGACTGCTA ACATTATCCT TAACGGCCAA AAGCTCGAGG

3061 CCTTTCCGCT CAAGACTGGA ACCCGCCAAG GCTGTCCCCT CTCCCCGCTT TTGTTTAATA

3121 TTGTACTCGA GGTGCTGGCT AGGGCTATTC GTCAAGAGAA AGAGATTAAA GGGATACAGC

3181 TCGGGAAGGA AGAGGTCAAG CTTTCCTTGT TCGCCGATGA TATGATTGTG TACCTGGAGA

3241 ATCCTATTGT GTCTGCTCAG AACCTTCTTA AACTTATTTC TAACTTTAGC AAGGTCAGCG

3301 GCTATAAGAT TAACGTCCAG AAATCTCAGG CCTTTCTGTA CACAAATAAT CGACAGACCG

3361 AATCCCAGAT AATGGGTGAG CTTCCGTTTG TCATAGCCAG CAAAAGGATA AAGTATCTCG

3421 GAATCCAGCT GACACGAGAC GTTAAAGATT TGTTTAAGGA AAATTACAAG CCTCTCCTGA

3481 AAGAGATTAA GGAAGATACT AATAAGTGGA AGAATATCCC CTGTTCATGG GTTGGCAGAA

3541 TCAACATAGT GAAGATGGCA ATACTTCCTA AAGTGATATA TCGCTTTAAC GCCATCCCAA

3601 TTAAACTGCC TATGACCTTC TTTACGGAGC TCGAGAAAAC AACCCTTAAA TTTATATGGA

3661 ATCAAAAGAG AGCAAGAATA GCGAAGTCCA TCTTGAGCCA GAAGAATAAG GCCGGTGGGA

3721 TTACTTTGCC TGATTTTAAG TTGTATTATA AAGCCACAGT AACTAAGACA GCCTGGTATT

3781 GGTATCAGAA TAGAGACATC GACCAGTGGA TCGGACCGA ACCATCAGAG ATAATGCCCC

3841 ACATCTATAA TTACCTTATA TTCGATAAGC CAGAAAAGAA TAAACAGTGG GGCAAAGACA

3901 GCCTCTTCAA CAAGTGGTGT TGGGAGAATT GGCTGGCCAT ATGCCGGAAA CTCAAGCTCG

3961 ACCCCTTTCT TACACCCTAC ACTAAAATCA ACAGTAGGTG GATCAAGGAC TTGAATGTCA

4021 AGCCAAAGAC TATAAAGACA CTGGAAGAGA ATCTTGGGAT CACAATACAA GATATAGGCG

4081 TCGGCAAAGA TTTTATGTCA AAGACGCCCA AGGCCATGGC CACTAAGGAT AAGATTGATA

4141 AGTGGGACCT TATTAAGCTC AAAAGCTTCT GTACTGCCAA GGAGACCACG ATCAGAGTTA

4201 ATAGGCAGCC CACTACATGG GAAAAGATTT CGCCACTTA TTCATCGAT AAGGGGGTTGA

4261 TAAGCAGAAT ATATAACGAG CTGAAGCAGA TCTACAAGAA GAAAACGAAT AATCCCATCA

4321 AGAAGTGGGC AAAAGATATG AACAGGCATT TTAGCAAAGA GGATATCTAC GCCGCGAAGA

4381 AGCATATGAA GAAGTGTAGT TCAAGCTTGG CCATTCGTGA GATGCAGATT AAGACGACCA

4441 TGCGATACCA CCTTACCCCA GTGAGGATGG CAATTATCAA GAAATCTGGC AATAATAGAT

4501 GTTGGCGGGG CTGTGGCGAG ATTGGCACCC TGCTCCATTG CTGGTGGAT TGCAAGCTGG

4561 TGCAGCCGCT TTGGAAATCA GTCTGGCGCT TTCTGAGGGA CCTCGAGCTT GAGATTCCCT

4621 TCGATCCCGC AATTCCCTTG CTCGGAATCT ATCCTAACGA ATACAAGAGC TGTTGTTACA

4681 AGGATACGTG TACCCGGATG TTCATCGCGG CCTTGTTTAC GATAGCTAAG ACGTGGAATC

4741 AGCCTAAGTG CCCCACAATG ATCGATTGGA TCAAGAAAAT GTGGCATATT TATACCATGG

4801 AGTATTACGC AGCAATTAAG AATGACGAAT TTATTTCCTT CGTTGGGACC TGGATGAAGC

4861 TGGAGACTAT TATTCTGAGC AAGCTGTCTC AGGAGCAAAA GACAAAGCAT AGAATCTTCT

4921 CTCTCATTGG TGGTAACGAC TACAAAGACG ATGACGACAA GTAAAGCGCT TCTAGAAGTT

4981 GTCTCCTCCT GCACTGACTG ACTGATACAA TCGATTTCTG GATCCGCAGG CCTAATCAAC

5041 CTCTGGATTA CAAAATTTGT GAAAGATTGA CTGGTATTCT TAACTATGTT GCTCCTTTTA
```

TABLE 8-continued

Plasmid and mRNA construct sequences

```
5101 CGCTATGTGG ATACGCTGCT TTAATGCCTT TGTATCATGC TATTGCTTCC CGTATGGCTT

5161 TCATTTTCTC CTCCTTGTAT AAATCCTGGT TGCTGTCTCT TTATGAGGAG TTGTGGCCCG

5221 TTGTCAGGCA ACGTGGCGTG GTGTGCACTG TGTTTGCTGA CGCAACCCCC ACTGGTTGGG

5281 GCATTGCCAC CACCTGTCAG CTCCTTTCCG GGACTTTCGC TTTCCCCCTC CCTATTGCCA

5341 CGGCGGAACT CATCGCCGCC TGCCTTGCCC GCTGCTGGAC AGGGGCTCGG CTGTTGGGCA

5401 CTGACAATTC CGTGGTGTTG TCGGGGAAGC TGACGTCCTT CCATGGCTG CTCGCCTGTG

5461 TTGCCACCTG GATTCTGCGC GGGACGTCCT TCTGCTACGT CCCTTCGGCC CTCAATCCAG

5521 CGGACCTTCC TTCCCGCGAA CAAACGACCC AACACCCGTG CGTTTTATTC TGTCTTTTTA

5581 TTGCCGATCC CCTCAGAAGA ACTCGTCAAG AAGGCGATAG AAGGCGATGC GCTGCGAATC

5641 GGGAGCGGCG ATACCGTAAA GCACGAGGAA GCGGTCAGCC CATTCGCCGC CAAGCTCTTC

5701 AGCAATATCA CGGGTAGCCA ACGCTATGTC CTGATAGCGG TCGGCCGCTT TACTTGTACA

5761 GCTCGTCCAT GCCGAGAGTG ATCCCGGCGG CGGTCACGAA CTCCAGCAGG ACCATGTGAT

5821 CGCGCTTCTC GTTGGGGTCT TTGCTCAGGG CGGACTGGGT GCTCAGGTAG TGGTTGTCGG

5881 GCAGCAGCAC GGGGCCGTCG CCGATGGGGG TGTTCTGCTG GTAGTGGTCG GCCAGGTGAG

5941 TCCAGGAGAT GTTTCAGCAC TGTTGCCTTT AGTCTCGAGG CAACTTAGAC AACTGAGTAT

6001 TGATCTGAGC ACAGCAGGGT GTGAGCTGTT TGAAGATACT GGGGTTGGGG GTGAAGAAAC

6061 TGCAGAGGAC TAACTGGGCT GAGACCCAGT GGCAATGTTT TAGGGCCTAA GGAATGCCTC

6121 TGAAAATCTA GATGGACAAC TTTGACTTTG AGAAAGAGA GGTGGAAATG AGGAAAATGA

6181 CTTTTCTTTA TTAGATTTCG GTAGAAAGAA CTTTCATCTT TCCCCTATTT TTGTTATTCG

6241 TTTTAAAACA TCTATCTGGA GGCAGGACAA GTATGGTCAT TAAAAAGATG CAGGCAGAAG

6301 GCATATATTG GCTCAGTCAA AGTGGGGAAC TTTGGTGGCC AAACATACAT TGCTAAGGCT

6361 ATTCCTATAT CAGCTGGACA CATATAAAAT GCTGCTAATG CTTCATTACA AACTTATATC

6421 CTTTAATTCC AGATGGGGGC AAAGTATGTC CAGGGGTGAG GAACAATTGA AACATTTGGG

6481 CTGGAGTAGA TTTTGAAAGT CAGCTCTGTG TGTGTGTGTG TGTGTGTGTG TGTGAGAGCG

6541 TGTGTTTCTT TTAACGTTTT CAGCCTACAG CATACAGGGT TCATGGTGGC AAGAAGATAA

6601 CAAGATTTAA ATTATGGCCA GTGACTAGTG CTGCAAGAAG AACAACTACC TGCATTTAAT

6661 GGGAAAGCAA AATCTCAGGC TTTGAGGGAA GTTAACATAG GCTTGATTCT GGGTGGAAGC

6721 TGGGTGTGTA GTTATCTGGA GGCCAGGCTG GAGCTCTCAG CTCACTATGG GTTCATCTTT

6781 ATTGTCTCCT TTCATCTCAA CAGCTGCACG CTGCCGTCCT CGATGTTGTG GCGGATCTTG

6841 AAGTTCACCT TGATGCCGTT CTTCTGCTTG TCGGCCATGA TATAGACGTT GTGGCTGTTG

6901 TAGTTGTACT CCAGCTTGTG CCCCAGGATG TTGCCGTCCT CCTTGAAGTC GATGCCCTTC

6961 AGCTCGATGC GGTTCACCAG GGTGTCGCCC TCGAACTTCA CCTCGGCGCG GGTCTTGTAG

7021 TTGCCGTCGT CCTTGAAGAA GATGGTGCGC TCCTGGACGT AGCCTTCGGG CATGGCGGAC

7081 TTGAAGAAGT CGTGCTGCTT CATGTGGTCG GGGTAGCGGC TGAAGCACTG CACGCCGTAG

7141 GTCAGGGTGG TCACGAGGGT GGGCCAGGGC ACGGGCAGCT TGCCGGTGGT GCAGATGAAC

7201 TTCAGGGTCA GCTTGCCGTA GGTGGCATCG CCCTCGCCCT CGCCGGACAC GCTGAACTTG

7261 TGGCCGTTTA CGTCGCCGTC CAGCTCGACC AGGATGGGCA CCACCCCGGT GAACAGCTCC

7321 TCGCCCTTGC TCACCATGGT GGCGAATTCG AAGCTTGAGC ACGAGATCTG AGTCCGGTAG

7381 GCCTAGCGGA TCTGACGGTT CACTAAACCA GCTCTGCTTA TATAGACCTC CCACCGTACA
```

TABLE 8-continued

Plasmid and mRNA construct sequences

```
7441 CGCCTACCGC CCATTTGCGT CAATGGGGCG GAGTTGTTAC GACATTTTGG AAAGTCCCGT

7501 TGATTTTGGT GCCAAAACAA ACTCCCATTG ACGTCAATGG GGTGGAGACT TGGAAATCCC

7561 CGTGAGTCAA ACCGCTATCC ACGCCCATTG ATGTACTGCC AAAACCGCAT CACCATGGTA

7621 ATAGCGATGA CTAATACGTA GATGTACTGC CAAGTAGGAA AGTCCCATAA GGTCATGTAC

7681 TGGGCATAAT GCCAGGCGGG CCATTTACCG TCATTGACGT CAATAGGGGG CGTACTTGGC

7741 ATATGATACA CTTGATGTAC TGCCAAGTGG GCAGTTTACC GTAAATACTC CACCCATTGA

7801 CGTCAATGGA AAGTCCCTAT TGGCGTTACT ATGGGAACAT ACGTCATTAT TGACGTCAAT

7861 GGGCGGGGGT CGTTGGGCGG TCAGCCAGGC GGGCCATTTA CCGTAAGTTA TGTAACGGGC

7921 CTGCTGCCGG CTCTGCGGCC TCTTCCGCGT CTTCGCCTTC GCCCTCAGAC GAGTCGGATC

7981 TCCCTTTGGG CCGCCTCCCC GCCTGTCTAG CTTGACTGAC TGAGATACAG CGTACCTTCA

8041 GCTCACAGAC ATGATAAGAT ACATTGATGA GTTTGGACAA ACCACAACTA GAATGCAGTG

8101 AAAAAAATGC TTTATTTGTG AAATTTGTGA TGCTATTGCT TTATTTGTAA CCATTATAAG

8161 CTGCAATAAA CAAGTTAACA ACAACAATTG CATTCATTTT ATGTTTCAGG TTCAGGGGGA

8221 GGTGTGGGAG GTTTTTTAAA GCAAGTAAAA CCTCTACAAA TGTGGTATTG GCCCATCTCT

8281 ATCGGTATCG TAGCATAACC CCTTGGGGCC TCTAAACGGG TCTTGAGGGG TTTTTTGTGC

8341 CCCTCGGGCC GGATTGCTAT CTACCGGCAT TGGCGCAGAA AAAAATGCCT GATGCGACGC

8401 TGCGCGTCTT ATACTCCCAC ATATGCCAGA TTCAGCAACG GATACGGCTT CCCCAACTTG

8461 CCCACTTCCA TACGTGTCCT CCTTACCAGA AATTTATCCT TAAGGTCGTC AGCTATCCTG

8521 CAGGCGATCT CTCGATTTCG ATCAAGACAT TCCTTTAATG GTCTTTTCTG GACACCACTA

8581 GGGGTCAGAA GTAGTTCATC AAACTTTCTT CCCTCCCTAA TCTCATTGGT TACCTTGGGC

8641 TATCGAAACT TAATTAAGCG ATCTGCATCT CAATTAGTCA GCAACCATAG TCCCGCCCCT

8701 AACTCCGCCC ATCCCGCCCC TAACTCCGCC CAGTTCCGCC CATTCTCCGC CCCATCGCTG

8761 ACTAATTTTT TTTATTTATG CAGAGGCCGA GGCCGCCTCG GCCTCTGAGC TATTCCAGAA

8821 GTAGTGAGGA GGCTTTTTTG GAGGCCTAGG CTTTTGCAAA GGAGGTAGCC AACATGATTG

8881 AACAAGATGG ATTGCACGCA GGTTCTCCCG CCGCTTGGGT GGAGAGGCTA TTCGGCTATG

8941 ACTGGGCACA ACAGACAATC GGCTGCTCTG ATGCCGCCGT GTTCCGGCTG TCAGCGCAGG

9001 GGCGCCCGGT TCTTTTTGTC AAGACCGACC TGTCCGGTGC CCTGAATGAA CTCCAGGACG

9061 AGGCAGCGCG GCTATCGTGG CTGGCCACGA CGGGCGTTCC TTGCGCAGCT GTGCTCGACG

9121 TTGTCACTGA AGCGGGAAGG GACTGGCTGC TATTGGGCGA AGTGCCGGGG CAGGATCTCC

9181 TGTCATCTCA CCTTGCTCCT GCCGAGAAAG TATCCATCAT GGCTGATGCA ATGCGGCGGC

9241 TGCATACGCT TGATCCGGCT ACCTGCCCAT TCGACCACCA AGCGAAACAT CGCATCGAGC

9301 GAGCACGTAC TCGGATGGAA GCCGGTCTTG TCGATCAGGA TGATCTGGAC GAAGAGCATC

9361 AGGGGCTCGC GCCAGCCGAA CTGTTCGCCA GGCTCAAGGC GCGGATGCCC GACGGCGAGG

9421 ATCTCGTCGT GACCCACGGC GATGCCTGCT TGCCGAATAT CATGGTGGAA AATGGCCGCT

9481 TTTCTGGATT CATCGACTGT GGCCGGCTGG GTGTGGCGGA CCGCTATCAG GACATAGCGT

9541 TGGCTACCCG TGATATTGCT GAAGAGCTTG GCGGCGAATG GGCTGACCGC TTCCTCGTGC

9601 TTTACGGTAT CGCCGCTCCC GATTCGCAGC GCATCGCCTT CTATCGCCTT CTTGACGAGT

9661 TCTTCTAGTA TGTAAGCCCT GTGCCTTCTA GTTGCCAGCC ATCTGTTGTT TGCCCCTCCC

9721 CCGTGCCTTC CTTGACCCTG GAAGGTGCCA CTCCCACTGT CCTTTCCTAA TAAAATGAGG
```

TABLE 8-continued

Plasmid and mRNA construct sequences

```
 9781 AAATTGCATC GCATTGTCTG AGTAGGTGTC ATTCTATTCT GGGGGGTGGG GTGGGGCAGG

9841 ACAGCAAGGG GGAGGATTGG GAAGACAATA GCAGGCATGC TGGGGATGCG GTGGGCTCTA

9901 TGGTTAATTA ACCAGTCAAG TCAGCTACTT GGCGAGATCG ACTTGTCTGG GTTTCGACTA

9961 CGCTCAGAAT TGCGTCAGTC AAGTTCGATC TGGTCCTTGC TATTGCACCC GTTCTCCGAT

10021 TACGAGTTTC ATTTAAATCA TGTGAGCAAA AGGCCAGCAA AAGGCCAGGA ACCGTAAAAA

10081 GGCCGCGTTG CTGGCGTTTT TCCATAGGCT CCGCCCCCCT GACGAGCATC ACAAAAATCG

10141 ACGCTCAAGT CAGAGGTGGC GAAACCCGAC AGGACTATAA AGATACCAGG CGTTTCCCCC

10201 TGGAAGCTCC CTCGTGCGCT CTCCTGTTCC GACCCTGCCG CTTACCGGAT ACCTGTCCGC

10261 CTTTCTCCCT TCGGGAAGCG TGGCGCTTTC TCATAGCTCA CGCTGTAGGT ATCTCAGTTC

10321 GGTGTAGGTC GTTCGCTCCA AGCTGGGCTG TGTGCACGAA CCCCCCGTTC AGCCCGACCG

10381 CTGCGCCTTA TCCGGTAACT ATCGTCTTGA GTCCAACCCG GTAAGACACG ACTTATCGCC

10441 ACTGGCAGCA GCCACTGGTA ACAGGATTAG CAGAGCGAGG TATGTAGGCG GTGCTACAGA

10501 GTTCTTGAAG TGGTGGCCTA ACTACGGCTA CACTAGAAGA ACAGTATTTG GTATCTGCGC

10561 TCTGCTGAAG CCAGTTACCT TCGGAAAAAG AGTTGGTAGC TCTTGATCCG GCAAACAAAC

10621 CACCGCTGGT AGCGGTGGTT TTTTTGTTTG CAAGCAGCAG ATTACGCGCA GAAAAAAAGG

10681 ATCTCAAGAA GATCCTTTGA TCTTTTCTAC GGGGTCTGAC GCTCAGTGGA ACGAAAACTC

10741 ACGTTAAGGG ATTTTGGTCA TGAGATTATC AAAAAGGATC TTCACCTAGA TCCTTTTAAA

10801 TTAAAAATGA AGTTTTAAAT CAATCTAAAG TATATATGAG TAAACTTGGT CTGACAGTTA

10861 CCAATGCTTA ATCAGTGAGG CACCTATCTC AGCGATCTGT CTATTTCGTT CATCCATAGT

10921 TGCATTTAAA TTTCCGAACT CTCCAAGGCC CTCGTCGGAA AATCTTCAAA CCTTTCGTCC

10981 GATCCATCTT GCAGGCTACC TCTCGAACGA ACTATCGCAA GTCTCTTGGC CGGCCTTGCG

11041 CCTTGGCTAT TGCTTGGCAG CGCCTATCGC CAGGTATTAC TCCAATCCCG AATATCCGAG

11101 ATCGGGATCA CCCGAGAGAA GTTCAACCTA CATCCTCAAT CCCGATCTAT CCGAGATCCG

11161 AGGAATATCG AAATCGGGGC GCGCCTGGTG TACCGAGAAC GATCCTCTCA GTGCGAGTCT

11221 CGACGATCCA TATCGTTGCT TGGCAGTCAG CCAGTCGGAA TCCAGCTTGG GACCCAGGAA

11281 GTCCAATCGT CAGATATTGT ACTCAAGCCT GGTCACGGCA GCGTACCGAT CTGTTTAAAC

11341 CTAGATATTG ATAGTCTGAT CGGTCAACGT ATAATCGAGT CCTAGCTTTT GCAAACATCT

11401 ATCAAGAGAC AGGATCAGCA GGAGGCTTTC GCATGAGTAT TCAACATTTC CGTGTCGCCC

11461 TTATTCCCTT TTTTGCGGCA TTTTGCCTTC CTGTTTTTGC TCACCCAGAA ACGCTGGTGA

11521 AAGTAAAAGA TGCTGAAGAT CAGTTGGGTG CGCGAGTGGG TTACATCGAA CTGGATCTCA

11581 ACAGCGGTAA GATCCTTGAG AGTTTTCGCC CCGAAGAACG CTTTCCAATG ATGAGCACTT

11641 TTAAAGTTCT GCTATGTGGC GCGGTATTAT CCCGTATTGA CGCCGGGCAA GAGCAACTCG

11701 GTCGCCGCAT ACACTATTCT CAGAATGACT TGGTTGAGTA TTCACCAGTC ACAGAAAAGC

11761 ATCTTACGGA TGGCATGACA GTAAGAGAAT TATGCAGTGC TGCCATAACC ATGAGTGATA

11821 ACACTGCGGC CAACTTACTT CTGACAACGA TTGGAGGACC GAAGGAGCTA ACCGCTTTTT

11881 TGCACAACAT GGGGGATCAT GTAACTCGCC TTGATCGTTG GGAACCGGAG CTGAATGAAG

11941 CCATACCAAA CGACGAGCGT GACACCACGA TGCCTGTAGC AATGGCAACA ACCTTGCGTA

12001 AACTATTAAC TGGCGAACTA CTTACTCTAG CTTCCCGGCA ACAGTTGATA GACTGGATGG

12061 AGGCGGATAA AGTTGCAGGA CCACTTCTGC GCTCGGCCCT TCCGGCTGGC TGGTTTATTG
```

TABLE 8-continued

Plasmid and mRNA construct sequences

```
12121 CTGATAAATC TGGAGCCGGT GAGCGTGGGT CTCGCGGTAT CATTGCAGCA CTGGGGCCAG

12181 ATGGTAAGCC CTCCCGTATC GTAGTTATCT ACACGACGGG GAGTCAGGCA ACTATGGATG

12241 AACGAAATAG ACAGATCGCT GAGATAGGTG CCTCACTGAT TAAGCATTGG TAACCGATTC

12301 TAGGTGCATT GGCGCAGAAA AAAATGCCTG ATGCGACGCT GCGCGTCTTA TACTCCCACA

12361 TATGCCAGAT TCAGCAACGG ATACGGCTTC CCCAACTTGC CCACTTCCAT ACGTGTCCTC

12421 CTTACCAGAA ATTTATCCTT AAGATCGTTT AAACTCGACT CTGGCTCTAT CGAATCTCCG

12481 TCGTTTCGAG CTTACGCGAA CAGCCGTGGC GCTCATTTGC TCGTCGGGCA TCGAATCTCG

12541 TCAGCTATCG TCAGCTTACC TTTTTGGCAG CGATCGCGGC TCCCGACATC TTGGACCATT

12601 AGCTCCACAG GTATCTTCTT CCCTCTAGTG GTCATAACAG CAGCTTCAGC TACCTCTCAA

12661 TTCAAAAAAC CCCTCAAGAC CCGTTTAGAG GCCCCAAGGG GTTATGCTAT CAATCGTTGC

12721 GTTACACACA CAAAAAACCA ACACACATCC ATCTTCGATG GATAGCGATT TTATTATCTA

12781 ACTGCTGATC GAGTGTAGCC AGATCTAGTA ATCAATTACG GGGTCATTAG TTCATAGCCC

12841 ATATATGGAG TTCCGCGTTA CATAACTTAC GGTAAATGGC CCGCCTGGCT GACCGCCCAA

12901 CGACCCCCGC CCATTGACGT CAATAATGAC GTATGTTCCC ATAGTAACGC CAATAGGGAC

12961 TTTCCATTGA CGTCAATGGG TGGAGTATTT ACGGTAAACT GCCCACTTGG CAGTACATCA

13021 AGTGTATCAT ATGCCAAGTA CGCCCCCTAT TGACGTCAAT GACGGTAAAT GGCCCGCCTG

13081 GCATTATGCC CAGTACATGA CCTTATGGGA CTTTCCTACT TGGCAGTACA TCTACGTATT

13141 AGTCATCGCT ATTACCATGC TGATGCGGTT TTGGCAGTAC ATCAATGGGC GTGGATAGCG

13201 GTTTGACTCA CGGGGATTTC CAAGTCTCCA CCCCATTGAC GTCAATGGGA GTTTGTTTTG

13261 GCACCAAAAT CAACGGGACT TTCCAAAATG TCGTAACAAC TCCGCCCCAT TGACGCAAAT

13321 GGGCGGTAGG CGTGTACGGT GGGAGGTCTA TATAAGCAGA GCTGGTTTAG TGAACCGTCA

13381 GATCAGATCT TTGTCGATCC TACCATCCAC TCGACACACC CGCCAGCGGC CGC
(SEQ ID NO: 48)
```

LINE-1_ORF2-MCP_MS2_mRNA (SEQ ID NO: 49)

```
  1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT

361 CCAGGTGTGA CCAGCTCGAG GAGCGCGTGA GCGCGATGGA AGACGAGATG AACGAGATGA

421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA

721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA

901 TCTCCGAGGG TGAGATTAAG TATTTCATCG ATAAACAGAT GCTGCGAGAC TTCGTGACAA
```

TABLE 8-continued

Plasmid and mRNA construct sequences

```
 961 CTCGCCCAGC TCTCAAGGAA CTGCTCAAAG AGGCTCTTAA TATGGAGCGC AATAATAGAT

1021 ATCAACCCTT GCAGAACCAC GCAAAGATGT GAGACAGCCG TCAGACCATC AAGACTAGGA

1081 AGAAACTGCA TCAACTAATG AGCAAAATCA CCAGCTAACA TCATAGTATA CATGACCGGC

1141 TCTAACTCAC ATATCACCAT CCTTACACTT AACATTAACG GCCTCAACTC AGCTATCAAG

1201 CGCCATCGGC TGGCCAGCTG GATCAAATCA CAGGATCCAA GCGTTTGTTG CATCCAAGAG

1261 ACCCACCTGA CCTGTAGAGA TACTCACCGC CTCAAGATCA AGGGATGGCA AAAGATTTAT

1321 CAGGCGAACG GTAAGCAGAA GAAAGCCGGA GTCGCAATTC TGGTCTCAGA CAAGACGGAT

1381 TTCAAGCCCA CCAAAATTAA GCGTGATAAG GAAGGTCACT ATATTATGGT GAAAGGCAGC

1441 ATACAGCAGG AAGAACTTAC CATATTGAAC ATCTACGCGC CAAACACCGG CGCACCTCGC

1501 TTTATCAAAC AGGTCCTGTC CGATCTGCAG CGAGATCTGG ATTCTCATAC GTTGATTATG

1561 GGTGATTTCA ATACACCATT GAGCACCCTG GATCGCAGCA CCAGGCAAAA GGTAAATAAA

1621 GACACGCAAG AGCTCAATAG CGCACTGCAT CAGGCAGATC TCATTGATAT TTATCGCACT

1681 CTTCATCCTA AGAGTACCGA GTACACATTC TTCAGCGCCC CACATCATAC ATACTCAAAG

1741 ATCGATCATA TCGTCGGCTC AAAGGCTCTG CTGTCAAAGT GCAAGCGCAC AGAGATAATT

1801 ACAAATTACC TGTCAGATCA TAGCGCGATC AAGCTCGAGC TGAGAATCAA GAACCTGACC

1861 CAGAGCCGGA GTACCACTTG GAAGCTTAAT AACCTGCTGC TCAACGATTA TTGGGTCCAC

1921 AATGAGATGA AGGCAGAGAT TAAAATGTTC TTCGAAACAA ATGAGAATAA GGATACTACC

1981 TATCAAAACC TTTGGGATGC CTTTAAGGCC GTCTGCAGAG GCAAGTTCAT CGCCCTCAAC

2041 GCCTATAAAA GAAAACAAGA GAGATCTAAG ATCGATACTC TCACCTCTCA GCTGAAGGAG

2101 TTGGAGAAAC AGGAACAGAC CCACTCCAAG GCGTCAAGAC GGCAGGAGAT CACAAAGATT

2161 CGCGCCGAGT TGAAAGAGAT CGAAACCCAA AAGACTCTTC AGAAAATTAA CGAGTCTCGT

2221 AGTTGGTTCT TCGAGCGGAT TAATAAGATA GACAGACCTC TGGCACGACT GATTAAGAAG

2281 AAGCGCGAAA AGAACCAGAT TGATACCATC AAGAACGACA AGGGCGACAT CACTACTGAC

2341 CCGACCGAGA TCCAGACCAC TATTCGGGAG TATTATAAGC ATTTGTATGC TAACAAGCTT

2401 GAGAACCTGG AAGAGATGGA CACTTTTCTG GATACCTATA CTCTGCCACG GCTTAATCAA

2461 GAGGAAGTCG AGTCCCTCAA CCGCCCAATT ACAGGAAGCG AGATTGTGGC CATAATTAAC

2521 TCCCTGCCGA CAAAGAAATC TCCTGGTCCG GACGGGTTTA CAGCTGAGTT TTATCAACGG

2581 TATATGGAAG AGCTTGTACC GTTTCTGCTC AAGCTCTTTC AGTCTATAGA AAAGGAAGGC

2641 ATCTTGCCCA ATTCCTTCTA CGAAGCTTCT ATAATACTTA TTCCCAAACC AGGACGCGAT

2701 ACCACAAAGA AGGAAAACTT CCGGCCCATT AGTCTCATGA ATATCGACGC TAAAATATTG

2761 AACAAGATTC TCGCCAACAG AATCCAACAA CATATTAAGA AATTGATACA TCACGACCAG

2821 GTGGGGTTTA TACCTGGCAT GCAGGGCTGG TTTAACATCC GGAAGAGTAT TAACGTCATT

2881 CAACACATTA ATAGAGCTAA GGATAAGAAT CATATGATCA TCTCTATAGA CGCGGAAAAG

2941 GCATTCGATA AGATTCAGCA GCCCATTTATG CTCAAGACTC TGAACAAACT CGGCATCGAC

3001 GGAACATATT TTAAGATTAT TCGCGCAATT TACGATAAGC CGACTGCTAA CATTATCCTT

3061 AACGGCCAAA AGCTCGAGGC CTTTCCGCTC AAGACTGGAA CCCGCCAAGG CTGTCCCCTC

3121 TCCCCGCTTT TGTTTAATAT TGTACTCGAG GTGCTGGCTA GGGCTATTCG TCAAGAGAAA

3181 GAGATTAAAG GGATACAGCT CGGGAAGGAA GAGGTCAAGC TTTCCTTGTT CGCCGATGAT

3241 ATGATTGTGT ACCTGGAGAA TCCTATTGTG TCTGCTCAGA ACCTTCTTAA ACTTATTTCT
```

TABLE 8-continued

Plasmid and mRNA construct sequences

```
3301 AACTTTAGCA AGGTCAGCGG CTATAAGATT AACGTCCAGA AATCTCAGGC CTTTCTGTAC

3361 ACAAATAATC GACAGACCGA ATCCCAGATA ATGGGTGAGC TTCCGTTTGT CATAGCCAGC

3421 AAAAGGATAA AGTATCTCGG AATCCAGCTG ACACGAGACG TTAAAGATTT GTTTAAGGAA

3481 AATTACAAGC CTCTCCTGAA AGAGATTAAG GAAGATACTA ATAAGTGGAA GAATATCCCC

3541 TGTTCATGGG TTGGCAGAAT CAACATAGTG AAGATGGCAA TACTTCCTAA AGTGATATAT

3601 CGCTTTAACG CCATCCCAAT TAAACTGCCT ATGACCTTCT TTACGGAGCT CGAGAAAACA

3661 ACCCTTAAAT TTATATGGAA TCAAAAGAGA GCAAGAATAG CGAAGTCCAT CTTGAGCCAG

3721 AAGAATAAGG CCGGTGGGAT TACTTTGCCT GATTTTAAGT TGTATTATAA AGCCACAGTA

3781 ACTAAGACAG CCTGGTATTG GTATCAGAAT AGAGACATCG ACCAGTGGAA TCGGACCGAA

3841 CCATCAGAGA TAATGCCCCA CATCTATAAT TACCTTATAT TCGATAAGCC AGAAAAGAAT

3901 AAACAGTGGG GCAAAGACAG CCTCTTCAAC AAGTGGTGTT GGGAGAATTG GCTGGCCATA

3961 TGCCGGAAAC TCAAGCTCGA CCCCTTTCTT ACACCCTACA CTAAAATCAA CAGTAGGTGG

4021 ATCAAGGACT TGAATGTCAA GCCAAAGACT ATAAAGACAC TGGAAGAGAA TCTTGGGATC

4081 ACAATACAAG ATATAGGCGT CGGCAAAGAT TTTATGTCAA AGACGCCCAA GGCCATGGCC

4141 ACTAAGGATA AGATTGATAA GTGGGACCTT ATTAAGCTCA AAAGCTTCTG TACTGCCAAG

4201 GAGACCACGA TCAGAGTTAA TAGGCAGCCC ACTACATGGG AAAAGATTTT CGCCACTTAT

4261 TCATCAGATA AGGGGTTGAT AAGCAGAATA TATAACGAGC TGAAGCAGAT CTACAAGAAG

4321 AAAACGAATA ATCCCATCAA GAAGTGGGCA AAAGATATGA ACAGGCATTT TAGCAAAGAG

4381 GATATCTACG CCGCGAAGAA GCATATGAAG AAGTGTAGTT CAAGCTTGGC CATTCGTGAG

4441 ATGCAGATTA AGACGACCAT GCGATACCAC CTTACCCCAG TGAGGATGGC AATTATCAAG

4501 AAATCTGGCA ATAATAGATG TTGGCGGGGC TGTGGCGAGA TTGGCACCCT GCTCCATTGC

4561 TGGTGGGATT GCAAGCTGGT GCAGCCGCTT TGGAAATCAG TCTGGCGCTT TCTGAGGGAC

4621 CTCGAGCTTG AGATTCCCTT CGATCCCGCA ATTCCCTTGC TCGGAATCTA TCCTAACGAA

4681 TACAAGAGCT GTTGTTACAA GGATACGTGT ACCCGGATGT TCATCGCGGC CTTGTTTACG

4741 ATAGCTAAGA CGTGGAATCA GCCTAAGTGC CCCACAATGA TCGATTGGAT CAAGAAAATG

4801 TGGCATATTT ATACCATGGA GTATTACGCA GCAATTAAGA ATGACGAATT TATTTCCTTC

4861 GTTGGGACCT GGATGAAGCT GGAGACTATT ATTCTGAGCA AGCTGTCTCA GGAGCAAAAG

4921 ACAAAGCATA GAATCTTCTC TCTCATTGGT GGTAACGCTT CTAACTTTAC TCAGTTCGTT

4981 CTCGTCGACA ATGGCGGAAC TGGCGACGTG ACTGTCGCCC CAAGCAACTT CGCTAACGGG

5041 ATCGCTGAAT GGATCAGCTC TAACTCGCGT TCACAGGCTT ACAAAGTAAC CTGTAGCGTT

5101 CGTCAGAGCT CTGCGCAGAA TCGCAAATAC ACCATCAAAG TCGAGGTGCC TAAAGGCGCC

5161 TGGCGTTCGT ACTTAAATAT GGAACTAACC ATTCCAATTT CGCCACGAA TTCCGACTGC

5221 GAGCTTATTG TTAAGGCAAT GCAAGGTCTC CTAAAAGATG GAAACCCGAT TCCCTCAGCA

5281 ATCGCAGCAA ACTCCGGCAT CTACGCCATG GCCAGCAACT TCACCCAGTT CGTGCTGGTG

5341 GACAACGGCG GCACCGGCGA CGTGACCGTG GCCCCAGCA ACTTCGCCAA CGGCATCGCC

5401 GAGTGGATCA GCAGCAACAG CAGAAGCCAG GCCTACAAGG TGACCTGCAG CGTGAGACAG

5461 AGCAGCGCCC AGAACAGAAA GTACACCATC AAGGTGGAGG TGCCCAAGGG CGCCTGGAGA

5521 AGCTACCTGA ACATGGAGCT GACCATCCCC ATCTTCGCCA CCAACAGCGA CTGCGAGCTG

5581 ATCGTGAAGG CCATGCAGGG CCTGCTGAAG GACGGCAACC CCATCCCCAG CGCCATCGCC
```

TABLE 8-continued

Plasmid and mRNA construct sequences

```
5641 GCCAACAGCG GCATCTACGA CTACAAAGAC GATGACGACA AGTAAAGCAA CCTACAAACG

5701 GGTGGAGGAT CACCCCACCC GACACTTCAC AATCAAGGGG TACAATACAC AAGGGTGGAG

5761 GAACACCCCA CCCTCCAGAC ACATTACACA GAAATCCAAT CAAACAGAAG CACCATCAGG

5821 GCTTCTGCTA CCAAATTTAT CTCAAAAAAC TACAACAAGG AATCACCATC AGGGATTCCC

5881 TGTGCAATAT ACGTCAAACG AGGGCCACGA CGGGAGGACG ATCACGCCTC CCGAATATCG

5941 GCATGTCTGG CTTTCGAATT CAGTGCGTGG AGCATCAGCC CACGCAGCCA ATCAGAGTCG

6001 AATACAAGTC GACTTTCGCG AAGAGCATCA GCCTTCGCGC CATTCTTACA CAAACCACAC

6061 TCTCCCCTAC AGGAACAGCA TCAGCGTTCC TGCCCAGTAC CCAACTCAAG AAAATTTATG

6121 TCCCCATGCA GCATCAGCGC ATGGGCCCCA AGAATACATC CCCAACAAAA TCACATCCGA

6181 GCACCAACAG GGCTCGGAGT GTTGTTTCTT GTCCAACTGG ACAAACCCTC CATGGACCAT

6241 CAGGCCATGG ACTCTCACCA ACAAGACAAA AACTACTCTT CTCGAAGCAG CATCAGCGCT

6301 TCGAAACACT CGAGCATACA TTGTGCCTAT TTCTTGGGTG GACGATCACG CCACCCATGC

6361 TCTCACGAAT TTCAAAACAC GGACAAGGAC GAGCACCACC AGGGCTCGTC GTTCCACGTC

6421 CAATACGATT ACTTACCTTT CGGGATCACG ATCACGGATC CCGCAGCTAC ATCACTTCCA

6481 CTCAGGACAT TCAAGCATGC ACGATCACGG CATGCTCCAC AAGTCTCAAC CACAGAAACT

6541 ACCAAATGGG TTCAGCACCA GCGAACCCAC TCCTACCTCA AACCTCTTCC CACAAAACTG

6601 GCAAGCAGGA TCACCGCTTG CCCATTCCAA CATACCAAAT CAAAAACAAT TACTGGTACA

6661 GCATCAGCGT ACCAGCCCAC ATCTCTCACT ACTATCAAAA ACCAAACCGT TCAGCAACAG

6721 CGAACGGTAC ACACGGAAAA ATCAACTGGT TTACAAATAC GAAAGACGAT CACGCTTTCG

6781 TCCAGCGCAA ACTATTACGA AAAACATCCG ACGGGAAGAG CAACAGCCTT CCCGCGGCGG

6841 AAAACCTCAC AAAAACACGA CAAACGGATG CACGAACACG GCATCCGCCG ACAACCCACA

6901 AACTTACAAC CAGGCAAACG GTGCAGGATC ACCGCACCGT ACATCAAACA CCTCAGATCT

6961 CATGCTTCTA GAAGTTGTCT CCTCCTGCAC TGACTGACTG ATACAATCGA TTTCTGGATC

7021 CGCAGGCCTA ATCAACCTCT GGATTACAAA ATTTGTGAAA GATTGACTGG TATTCTTAAC

7081 TATGTTGCTC CTTTTACGCT ATGTGGATAC GCTGCTTTAA TGCCTTTGTA TCATGCTATT

7141 GCTTCCCGTA TGGCTTTCAT TTTCTCCTCC TTGTATAAAT CCTGGTTGCT GTCTCTTTAT

7201 GAGGAGTTGT GGCCCGTTGT CAGGCAACGT GGCGTGGTGT GCACTGTGTT TGCTGACGCA

7261 ACCCCCACTG GTTGGGGCAT TGCCACCACC TGTCAGCTCC TTTCCGGGAC TTTCGCTTTC

7321 CCCCTCCCTA TTGCCACGGC GGAACTCATC GCCGCCTGCC TTGCCCGCTG CTGGACAGGG

7381 GCTCGGCTGT TGGGCACTGA CAATTCCGTG GTGTTGTCGG GGAAGCTGAC GTCCTTTCCA

7441 TGGCTGCTCG CCTGTGTTGC CACCTGGATT CTGCGCGGGA CGTCCTTCTG CTACGTCCCT

7501 TCGGCCCTCA ATCCAGCGGA CCTTCCTTCC CGCTGAGAGA CACAAAAAAT TCCAACACAC

7561 TATTGCAATG AAAATAAATT TCCTTTATTA GCCAGAAGTC AGATGCTCAA GGGGCTTCAT

7621 GATGTCCCCA TAATTTTTGG CAGAGGGAAA AAGATCTCAG TGGTATTTGT GAGCCAGGGC

7681 ATTGGCCTTC TGATAGGCAG CCTGCACCTG AGGAGTGCGG CCGCTTTACT TGTACAGCTC

7741 GTCCATGCCG AGAGTGATCC CGGCGGCGGT CACGAACTCC AGCAGGACCA TGTGATCGCG

7801 CTTCTCGTTG GGGTCTTTGC TCAGGGCGGA CTGGGTGCTC AGGTAGTGGT TGTCGGGCAG

7861 CAGCACGGGG CCGTCGCCGA TGGGGGTGTT CTGCTGGTAG TGGTCGGCGA GCTGCACGCT

7921 GCCGTCCTCG ATGTTGTGGC GGATCTTGAA GTTCACCTTG ATGCCGTTCT TCTGCTTGTC
```

TABLE 8-continued

Plasmid and mRNA construct sequences

```
7981 GGCCATGATA TAGACGTTGT GGCTGTTGTA GTTGTACTCC AGCTTGTGCC CCAGGATGTT

8041 GCCGTCCTCC TTGAAGTCGA TGCCCTTCAG CTCGATGCGG TTCACCAGGG TGTCGCCCTC

8101 GAACTTCACC TCGGCGCGGG TCTTGTAGTT GCCGTCGTCC TTGAAGAAGA TGGTGCGCTC

8161 CTGGACGTAG CCTTCGGGCA TGGCGGACTT GAAGAAGTCG TGCTGCTTCA TGTGGTCGGG

8221 GTAGCGGCTG AAGCACTGCA CGCCGTAGGT CAGGGTGGTC ACGAGGGTGG GCCAGGGCAC

8281 GGGCAGCTTG CCGGTGGTGC AGATGAACTT CAGGGTCAGC TTGCCGTAGG TGGCATCGCC

8341 CTCGCCCTCG CCGGACACGC TGAACTTGTG GCCGTTTACG TCGCCGTCCA GCTCGACCAG

8401 GATGGGCACC ACCCCGGTGA ACAGCTCCTC GCCCTTGCTC ACCATGGTGG CGGGATCTGA

8461 CGGTTCACTA AACCAGCTCT GCTTATATAG ACCTCCCACC GTACACGCCT ACCGCCCATT

8521 TGCGTCAATG GGGCGGAGTT GTTACGACAT TTTGGAAAGT CCCGTTGATT TTGGTGCCAA

8581 AACAAACTCC CATTGACGTC AATGGGGTGG AGACTTGGAA ATCCCCGTGA GTCAAACCGC

8641 TATCCACGCC CATTGATGTA CTGCCAAAAC CGCATCACCA TGGTAATAGC GATGACTAAT

8701 ACGTAGATGT ACTGCCAAGT AGGAAAGTCC CATAAGGTCA TGTACTGGGC ATAATGCCAG

8761 GCGGGCCATT TACCGTCATT GACGTCAATA GGGGGCGTAC TTGGCATATG ATACACTTGA

8821 TGTACTGCCA AGTGGGCAGT TTACCGTAAA TACTCCACCC ATTGACGTCA ATGGAAAGTC

8881 CCTATTGGCG TTACTATGGG AACATACGTC ATTATTGACG TCAATGGGCG GGGGTCGTTG

8941 GGCGGTCAGC CAGGCGGGCC ATTTACCGTA AGTTATGTAA CGGGCCTGCT GCCGGCTCTG

9001 CGGCCTCTTC CGCGTCTTCG CCTTCGCCCT CAGACGAGTC GGATCTCCCT TTGGGCCGCC

9061 TCCCCGCCTG TCTAGCTTGA CTGACTGAGA TACAGCGTAC CTTCAGCTCA CAGACATGAT

9121 AAGATACATT GATGAGTTTG GACAAACCAC AACTAGAATG CAGTGAAAAA AATGCTTTAT

9181 TTGTGAAATT TGTGATGCTA TTGCTTTATT TGTAACCATT ATAAGCTGCA ATAAACAAGT

9241 T
(SEQ ID NO: 49)
```

LINE 1 ORF2-minke mRNA GFP (SEQ ID NO: 50)

```
   1 TAATACGACT CACTATAGGG AGAAGTACTG CCACCATGGG CAAGAAGCAA AATCGCAAGA

61 CGGGGAATTC CAAGACACAA TCCGCTAGCC CACCACCTAA AGAGCGTTCT AGCTCCCCTG

121 CTACTGAGCA GTCCTGGATG GAAAACGACT TCGATGAACT CCGGGAAGAG GGATTTAGGC

181 GATCCAACTA TTCAGAACTC CGCGAAGATA TCCAGACAAA GGGGAAGGAA GTCGAGAATT

241 TCGAGAAGAA CCTCGAGGAG TGCATCACCC GTATCACAAA CACTGAGAAA TGTCTCAAAG

301 AACTCATGGA ACTTAAGACA AAAGCCAGGG AGCTTCGAGA GGAGTGTCGG AGTCTGAGAT

361 CCAGGTGTGA CCAGCTCGAG GAGCGCGTGA GCGCGATGGA AGACGAGATG AACGAGATGA

421 AAAGAGAGGG CAAATTCAGG GAGAAGCGCA TTAAGAGGAA CGAACAGAGT CTGCAGGAGA

481 TTTGGGATTA CGTCAAGAGG CCTAACCTGC GGTTGATCGG CGTCCCCGAG AGCGACGTAG

541 AAAACGGGAC TAAACTGGAG AATACACTTC AAGACATCAT TCAAGAAAAT TTTCCAAACC

601 TGGCTCGGCA AGCTAATGTG CAAATCCAAG AGATCCAACG CACACCCCAG CGGTATAGCT

661 CTCGGCGTGC CACCCCTAGG CATATTATCG TGCGCTTTAC TAAGGTGGAG ATGAAAGAGA

721 AGATGCTGCG AGCCGCTCGG GAAAAGGGAA GGGTGACTTT GAAGGGCAAA CCTATTCGGC

781 TGACGGTTGA CCTTAGCGCC GAGACACTCC AGGCACGCCG GGAATGGGGC CCCATCTTTA

841 ATATCCTGAA GGAGAAGAAC TTCCAGCCAC GAATCTCTTA CCCTGCAAAG TTGAGTTTTA
```

TABLE 8-continued

Plasmid and mRNA construct sequences

```
 901 TCTCCGAGGG TGAGATTAAG TATTTCATCG ATAAACAGAT GCTGCGAGAC TTCGTGACAA

961 CTCGCCCAGC TCTCAAGGAA CTGCTCAAAG AGGCTCTTAA TATGGAGCGC AATAATAGAT

1021 ATCAACCCTT GCAGAACCAC GCAAAGATGT GAGACAGCCG TCAGACCATC AAGACTAGGA

1081 AGAAACTGCA TCAACTAATG AGCAAAATCA CCAGCTAACA TCATAGTATA CATGGTCATA

1141 GGAACTTACA TTTCGATTAT TACCTTAAAC GTGAATGGGT TAAATGCCCC AACCAAGAGA

1201 CATCGGCTGG CTGAATGGAT TCAGAAACAG GACCCCTATA TTTGCTGTCT GCAGGAGACC

1261 CACTTCCGTC CTCGCGCACAC ATACAGACTG AAAGTGAGGG GCTGGAAAAA GATCTTCCAT

1321 GCCAATGGAA ATCAAAGAA AGCTGGAGTG GCTATTCTCA TCTCAGATAA AATTGACTTC

1381 AAAATAAAGA ATGTTACTCG AGATAAGGAG GGACACTACA TAATGATCCA GGGGTCCATC

1441 CAAGAAGAGG ATATAACTAT TATTAATATT TATGCACCCA ACATTGGCGC CCCTCAGTAC

1501 ATCAGGCAGC TGCTTACAGC TATCAAGGAG GAAATCGACA GTAACACGAT TATCGTGGGG

1561 GACTTTAACA CCAGCCTTAC TCCGATGGAT AGATCATCCA AAATGAAAAT AAATAAGGAA

1621 ACAGAGGCTC TTAATGACAC CATTGACCAG ATAGATCTGA TTGATATATA TAGGACATTC

1681 CATCCAAAAA CTGCCGATTA CACTTTCTTC AGCAGTGCGC ATGGAACCTT CTCCAGGATA

1741 GATCACATCT TGGGTCACAA AAGTAGCCTC AGTAAGTTTA AGAAAATTGA AATCATTAGC

1801 AGCATCTTTT CTGACCATAA CGCTATGCGC CTGGAGATGA ATCACAGGGA GAAGAACGTA

1861 AAGAAGACAA ACACCTGGAG GCTGAACAAT ACGCTGCTAA ATAACCAAGA GATCACTGAG

1921 GAAATCAAAC AGGAAATAAA AAAATACTTG GAGACAAATG ACAATGAAAA CACGACCACC

1981 CAGAACTTGT GGGATGCAGC TAAAGCGGTT CTGAGAGGGA AGTTTATAGC TATTCAAGCC

2041 TACCTTAAGA AACAGGAAAA ATCTCAAGTG AACAATTTGA CCTTACACCT AAAGAAACTG

2101 GAGAAGGAGG AGCAGACCAA ACCCAAAGTG AGCAGGAGGA AAGAAATCAT CAAGATCAGA

2161 GCCGAAATCA ATGAAATAGA AACTAAGAAG ACAATTGCCA AGATCAATAA AACTAAATCC

2221 TGGTTCTTTG AGAAGATCAA CAAAATTGAT AAGCCATTAG CCAGACTCAT CAAGAAAAAG

2281 AGGGAGAGGA CTCAGATCAA TAAGATCAGA AATGAGAAAG GGGAAGTTAC AACCGACACC

2341 GCGGAGATTC AGAACATCCT GAGAGACTAC TACAAGCAAC TTTATGCCAA TAAAATGGAC

2401 AACCTGGAAG AAATGGACAA ATTCCTGGAA AGGTATAACC TTCCCCGGCT GAACCAGGAG

2461 GAGACTGAAA ATATCAACCG CCCAATCACA AGTAATGAGA TTGAGACTGT GATTAAGAAT

2521 CTTCCAACTA ACAAAAGTCC CGGCCCCGAT GGCTTCACAG GTGAATTCTA TCAGACCTTT

2581 CGGGAGGAGT TGACACCCAT CCTTCTCAAG CTCTTCCAAA AAATTGCAGA GGAGGGCACA

2641 CTCCCGAACT CATTCTATGA GGCCACCATC ACCCTGATCC CAAAGCCCGA CAAGGACACT

2701 ACAAAGAAAG AAAATTACCG ACCAATTTCC CTGATGAATA TCGATGCCAA GATCCTCAAC

2761 AAAATCTTGG CAAACAGAAT CCAGCAGCAC ATTAAGAGGA TCATACACCA CGATCAGGTG

2821 GGCTTTATCC CGGGGATGCA AGGATTCTTC AATATCCGCA AATCAATCAA TGTGATCCAC

2881 CATATTAACA AGTTGAAGAA GAAGAACCAT ATGATCATCT CCATCGATGC AGAGAAAGCT

2941 TTTGACAAAA TTCAACACCC ATTTATGATC AAAACTCTCC AGAAGGTGGG CATCGAGGGG

3001 ACCTACCTCA ACATAATTAA GGCCATCTAT GATAAGCCCA CAGCCAACAT CATTCTCAAT

3061 GGTGAAAAGC TGAAGGCATT TCCTCTGCGG TCCGGAACGA GACAGGGATG TCCTCTCTCT

3121 CCTCTTCTGT TCAACATCGT TCTGGAAGTC CTAGCCACCG CTATCCGCGA GGAAAAGGAA

3181 ATTAAAGGCA TACAGATTGG AAAGGAAGAG GTAAAACTGT CTCTGTTTGC GGATGATATG
```

TABLE 8-continued

Plasmid and mRNA construct sequences

```
3241 ATACTGTACA TAGAGAATCC TAAAACTGCC ACCCGGAAGC TGTTGGAGCT AATTAATGAG

3301 TATGGTAAGG TCGCCGGTTA CAAGATTAAT GCTCAGAAGT CTCTTGCTTT CCTGTACACT

3361 AATGATGAAA AGTCTGAACG GGAAATTATG GAGACACTCC CCTTTACCAT TGCAACCAAA

3421 CGTATTAAAT ACCTTGGCAT TAACCTGCCT AAGGAGACAA AAGACCTGTA TGCTGAAAAC

3481 TATAAGACAC TGATGAAAGA GATTAAAGAT GATACCAACC GGTGGCGGGA TATCCCATGT

3541 TCTTGGATTG GCAGAATCAA CATTGTGAAG ATGAGCATCC TGCCCAAGGC CATCTACAGA

3601 TTCAATGCCA TCCCTATCAA ATTACCTATG GCATTTTTTA CGGAGCTGGA ACAGATCATC

3661 TTAAAATTTG TGTGGCGCCA CAAGCGGCCC CGAATCGCCA AGCGGTCTT GAGGCAGAAG

3721 AATGGCGCTG GGGGAATCCG ACTCCCTGAC TTCAGATTGT ACTACAAAGC TACCGTCATC

3781 AAGACAATCT GGTACTGGCA CAAGAACAGA AACATCGATC AGTGGAACAA GATCGAAAGC

3841 CCTGAGATTA ACCCCCGCAC CTATGGTCAA CTGATCTATG ACAAAGGGGG CAAGGATATA

3901 CAATGGCGCA AGGACAGCCT CTTCAATAAG TGGTGCTGGG AAAACTGGAC AGCCACCTGC

3961 AAGCGTATGA AGCTGGAGTA CTCCCTGACA CCATACACAA AAATAAACTC AAAGTGGATT

4021 CGAGACCTCA ATATTCGGCT GGACACTATA AAACTCCTGG AGGAGAACAT TGGGCGTACA

4081 CTCTTTGACA TTAATCATAG CAAGATCTTT TTCGATCCCC CTCCTCGTGT AATGGAAATA

4141 AAAACAAAAA TAAACAAGTG GGATCTGATG AAACTTCAGA GCTTTTGCAC CGCAAAGGAG

4201 ACCATAAACA AGACGAAGCG CCAACCCTCA GAATGGGAGA AAATATTTGC GAATGAGTCT

4261 ACGGACAAAG GCTTAATCTC CAAAATATAT AAGCAGCTCA TTCAGCTCAA TATCAAGGAA

4321 ACAAACACCC CGATCCAAAA GTGGGCAGAG GACCTAAATC GGCATTTCTC CAAGGAAGAC

4381 ATCCAGACGG CCACGAAGCA CATGAAGCGA TGCTCAACTT CCCTGATTAT TCGCGAAATG

4441 CAGATCAAGA CTACTATGCG CTATCACCTC ACTCCTGTTC GGATGGGCAT CATCCGGAAA

4501 TCTACAAACA ACAAGTGCTG GAGAGGGTGT GGCGAAAAGG GAACCCTCTT GCATTGTTGG

4561 TGGGAGTGTA AGTTGATCCA GCCACTATGG CGGACCATAT GGAGGTTCCT TAAAAAACTG

4621 AAGATTGAGC TGCCATATGA CCCAGCAATC CCACTGCTGG GCATATACCC GGAGAAAACC

4681 GTGATTCAGA AAGACACTTG CACCCGAATG TTCATTGCAG CATTGTTTAC AATAGCCAGG

4741 TCATGGAAGC AGCCTAAGTG CCCCTCGACA GACGAGTGGA TCAAGAAGAT GTGGTACATT

4801 TATACTATGG AATATTACAG CGCCATCAAA CGCAACGAAA TTGGGTCTTT TCTGGAGACG

4861 TGGATGGATC TAGAGACTGT CATCCAGAGT GAGGTAAGTC AGAAAGAGAA GAACAAATAT

4921 CGTATTTTAA CGCATATTTG TGGAACCTGG AAGAATGGTA CAGATGAGCC GGTCTGCCGA

4981 ACCGAGATTG AGACCCAGAT GGACTACAAA GACGATGACG ACAAGTGAAG CGCTTCTAGA

5041 AGTTGTCTCC TCCTGCACTG ACTGACTGAT ACAATCGATT CTGGATCCG CAGGCCTAAT

5101 CAACCTCTGG ATTACAAAAT TTGTGAAAGA TTGACTGGTA TTCTTAACTA TGTTGCTCCT

5161 TTTACGCTAT GTGGATACGC TGCTTTAATG CCTTTGTATC ATGCTATTGC TTCCCGTATG

5221 GCTTTCATTT TCTCCTCCTT GTATAAATCC TGGTTGCTGT CTCTTTATGA GGAGTTGTGG

5281 CCCGTTGTCA GGCAACGTGG CGTGGTGTGC ACTGTGTTTG CTGACGCAAC CCCCACTGGT

5341 TGGGGCATTG CCACCACCTG TCAGCTCCTT TCCGGGACTT TCGCTTTCCC CCTCCCTATT

5401 GCCACGGCGG AACTCATCGC CGCCTGCCTT GCCCGCTGCT GGACAGGGGC TCGGCTGTTG

5461 GGCACTGACA ATTCCGTGGT GTTGTCGGGG AAGCTGACGT CCTTTCCATG GCTGCTCGCC

5521 TGTGTTGCCA CCTGGATTCT GCGCGGGACG TCCTTCTGCT ACGTCCCTTC GGCCCTCAAT
```

TABLE 8-continued

Plasmid and mRNA construct sequences

```
5581 CCAGCGGACC TTCCTTCCCG CTGAGAGACA CAAAAAATTC CAACACACTA TTGCAATGAA

5641 AATAAATTTC CTTTATTAGC CAGAAGTCAG ATGCTCAAGG GGCTTCATGA TGTCCCCATA

5701 ATTTTTGGCA GAGGGAAAAA GATCTCAGTG GTATTTGTGA GCCAGGGCAT TGGCCTTCTG

5761 ATAGGCAGCC TGCACCTGAG GAGTGCGGCC GCTTTACTTG TACAGCTCGT CCATGCCGAG

5821 AGTGATCCCG GCGGCGGTCA CGAACTCCAG CAGGACCATG TGATCGCGCT TCTCGTTGGG

5881 GTCTTTGCTC AGGGCGGACT GGGTGCTCAG GTAGTGGTTG TCGGGCAGCA GCACGGGGCC

5941 GTCGCCGATG GGGGTGTTCT GCTGGTAGTG GTCGGCGAGC TGCACGCTGC CGTCCTCGAT

6001 GTTGTGGCGG ATCTTGAAGT TCACCTTGAT GCCGTTCTTC TGCTTGTCGG CCATGATATA

6061 GACGTTGTGG CTGTTGTAGT TGTACTCCAG CTTGTGCCCC AGGATGTTGC CGTCCTCCTT

6121 GAAGTCGATG CCCTTCAGCT CGATGCGGTT CACCAGGGTG TCGCCCTCGA ACTTCACCTC

6181 GGCGCGGGTC TTGTAGTTGC CGTCGTCCTT GAAGAAGATG GTGCGCTCCT GGACGTAGCC

6241 TTCGGGCATG GCGGACTTGA AGAAGTCGTG CTGCTTCATG TGGTCGGGGT AGCGGCTGAA

6301 GCACTGCACG CCGTAGGTCA GGGTGGTCAC GAGGGTGGGC CAGGGCACGG GCAGCTTGCC

6361 GGTGGTGCAG ATGAACTTCA GGGTCAGCTT GCCGTAGGTG GCATCGCCCT CGCCCTCGCC

6421 GGACACGCTG AACTTGTGGC CGTTTACGTC GCCGTCCAGC TCGACCAGGA TGGGCACCAC

6481 CCCGGTGAAC AGCTCCTCGC CCTTGCTCAC CATGGTGGCG GGATCTGACG GTTCACTAAA

6541 CCAGCTCTGC TTATATAGAC CTCCCACCGT ACACGCCTAC CGCCCATTTG CGTCAATGGG

6601 GCGGAGTTGT TACGACATTT TGGAAAGTCC CGTTGATTTT GGTGCCAAAA CAAACTCCCA

6661 TTGACGTCAA TGGGGTGGAG ACTTGGAAAT CCCCGTGAGT CAAACCGCTA TCCACGCCCA

6721 TTGATGTACT GCCAAAACCG CATCACCATG GTAATAGCGA TGACTAATAC GTAGATGTAC

6781 TGCCAAGTAG GAAAGTCCCA TAAGGTCATG TACTGGGCAT AATGCCAGGC GGGCCATTTA

6841 CCGTCATTGA CGTCAATAGG GGGCGTACTT GGCATATGAT ACACTTGATG TACTGCCAAG

6901 TGGGCAGTTT ACCGTAAATA CTCCACCCAT TGACGTCAAT GGAAAGTCCC TATTGGCGTT

6961 ACTATGGGAA CATACGTCAT TATTGACGTC AATGGGCGGG GGTCGTTGGG CGGTCAGCCA

7021 GGCGGGCCAT TTACCGTAAG TTATGTAACG GGCCTGCTGC CGGCTCTGCG GCCTCTTCCG

7081 CGTCTTCGCC TTCGCCCTCA GACGAGTCGG ATCTCCCTTT GGGCCGCCTC CCCGCCTGTC

7141 TAGCTTGACT GACTGAGATA CAGCGTACCT TCAGCTCACA GACATGATAA GATACATTGA

7201 TGAGTTTGGA CAAACCACAA CTAGAATGCA GTGAAAAAAA TGCTTTATTT GTGAAATTTG

7261 TGATGCTATT GCTTTATTTG TAACCATTAT AAGCTGCAAT AAACAAGTT
(SEQ ID NO: 50)
```

Example 17. Enriching Stably Retrotransposed Cells

In an effort to increase the cell yield having stably integrated nucleic acid sequence a method of sorting and culturing was attempted, as described in this example. 293T cells were electroporated with LINE1-GFP mRNA produced by IVT and cultured in vitro for at least 3 days. Expression of GFP was determined periodically using flow cytometry, as shown in FIG. 40. Genomic integration per genome was evaluated using quantitative PCR. Interpolations of nucleic acid encoding GFP in the genome per genome were evaluated using standard curves for GFP and a housekeeping gene (FAU). In a sorting and enrichment culture of GFP positive cells, shown in FIG. 40, it was evident that integration was stable for multiple cell passages (at least 18 days post EP), and considerable enrichment was possible. GFP expression was detectable in ~1% of 293T cells 5 days post-EP. GFP+ cells were enriched to ~28% after first sorting and was further enriched up to ~74% of cells after 2nd sorting. (FIG. 40, FIG. 41C).

Standard curves and exemplary quantitation of genomic integrations are shown in FIGS. 41A and 41B respectively. FIG. 41C shows average number of GFP integrations per genome when gated at $10^3$ units of GFP fluorescence intensity and at $10^4$ units of GFP fluorescence intensity.

Example 18. Titration of mRNA Concentration for Increased Transposon Mediated Integration The concentration of LINE1-GFP mRNA used for electroporation was titrated for optimum genomic integration per cell in different cell types, 293T cells, K562 and THP-1 cells (FIGS. 42-46). 100, 500, 1000, 1500 and 2000 ng/μL of mRNA were tested for GFP expression and number of integrations per cell. Concentrations higher than 1000 ng/μl cause cell death. From the results shown in FIGS. 42, 43 and 44 that 1000 ng/μl causes a higher and long-term expression of GFP encoded by the retrotransposed integrated nucleic acid. Integrated DNA encoded protein expression starts to be detectable at day 3 and peaks around day 6-7 (FIG. 45). However, genomic integration and expression of the LINE-1 GFP mRNA in K562 and THP-1 was quite low; integration was detected at about 0.067-0.155 per cell in K562 cells (FIG. 46). (THP-1 data not shown). Higher LINE1-GFP mRNA concentrations (1500 and 2000 ng/μl) caused cell death in these cells. GFP mRNA expression in PD-0015 monocytes was detected at day 3 post electroporation, with detectable integration per cell. (FIG. 47). Steps were to be taken for more extensive DNase 1 treatment, and test mRNA batches were to be evaluated for residual plasmid before electroporation. Accuracy in determination of integration levels in the genome could be improved by first enriching for integrated DNA sequence by PCR followed by paired end sequencing leading to mapping the integration sites within the genome. Next generation sequencing is considered the gold standard in this respect, which involves gDNA extraction→shearing by sonication→DNA linkers ligated onto DNA ends→nested PCR (1: one primer for linker, second to integrated DNA, 2: Illumina sequencing adapters added)→paired-end sequencing.

Example 19. Improvement of Integration Efficiency by Knockdown of Candidates that Prevent Transposon Mediated Integration In this example, a number of endogenous candidates were knocked down using siRNA to determine if the knockdown could result in higher integration of test nucleic acid encoding GFP. Candidates included inhibitors of LINE1 retrotransposition: ADAR1, ADAR2 (ADAR1B), APOBEC3C, BRCA1, let-7 miRNA, RNase L, TASOR (HUSH complex). siRNAs (3 per target candidate) were made, electroporated in test cells along with LINE1-GFP mRNA and tested for alteration of the LINE-1 GFP expression by flow cytometry and its genome integration by qPCR and a cocktail of the siRNA that help increase LINE-1 GFP integration and expression was selected for further titration. Results from the different siRNAs tested are shown in FIGS. 48-51. Knockdown of ADAR1, BRCA and RNASEL tested individually induced about 2-fold increase in integration of LINE 1-GFP. ADAR2 and APOEBEC3C each led to less than 1.5-fold increase, and let7 miRNA and TASOR each led to no increase. In the study shown in FIG. 48, LINE-1 GFP (2000 ng/μL) was electroporated with an siBRCA at 100, 200 and 300 ng/μL in 293 cells, data shown at 4 days post electroporation. With 100 ng/μL, the integration rate was approximately ~0.06 GFP copies per cell, and siBRCA1_s459 (100 ng/μl) increases integration by ~2-fold. Data shown in FIG. 49 demonstrates that at day 6 post electroporation, each of siRNASEL and siADAR1 siRNAs separately increased integration about 2-fold. On the other hand, siAPOBEC3C_s2617 increases GFP integration<1.5-fold (FIG. 50) at 6 days post electroporation.

TABLE 11

Effect of specific knockdowns on genomic integration rate.

| Target | GFP integration fold change in 293T cells |
|---|---|
| ADAR1 | ~2 fold increase |
| ADAR2 | <1.5-fold increase |
| APOEBEC3C | <1.5-fold increase |
| BRCA | ~2 fold increase |
| Let7 miRNA | No increase |
| RNASEL | ~2 fold increase |
| TASOR (Hush complex) | No increase | siRNA against ADAR, APOBEC3C, BRCA and RNASEL were chosen for the siRNA cocktail. Using 1000 ng/μL and 1500 ng/μL LINE1-GFP mRNA in two sets of experiments, the concentration of the siRNAs for electroporation was titrated next. It was observed that LINE 1-GFP mRNA at 1500 ng/μL was slightly toxic (FIG. 51). With 1000 ng/μL, 75 ng/uL of each siRNA resulted in ~5-fold improvement of integration of GFP in 293T cells. These results were highly encouraging and support further development. Results from a similar experiment in K562 cells are shown in FIG. 52.

What is claimed is:

1. A method of expressing an exogenous human therapeutic polypeptide from a genomically integrated DNA sequence of a target human cell, the method comprising:

(a) contacting a plurality of the target human cell with a composition comprising:

(I) a nanoparticle delivery vehicle comprising:

one or more exogenous RNA molecules, wherein the one or more exogenous RNA molecules comprises a first RNA molecule, comprising:

(i) a first RNA sequence that is a reverse complement of a sequence encoding the exogenous human therapeutic polypeptide, and (ii) a second RNA sequence comprising a mobile genetic element that is not controlled by a promoter; comprising a sequence that encodes a human LINE-1 open reading frame 2 (ORF2p) polypeptide or fragment thereof, wherein the human LINE-1 ORF2p polypeptide or the fragment thereof has a human LINE-1 ORF2p reverse transcriptase or a functional fragment thereof and a human LINE-1 ORF2p endonuclease domain that lacks a endonuclease activity, and a sequence encoding a heterologous RNA guided endonuclease, wherein the heterologous RNA guided endonuclease comprises a CRISPR-Cas (Cas) endonuclease;

wherein the human LINE-1 ORF2p polypeptide or the fragment thereof that has the human LINE-1 ORF2p reverse transcriptase or a functional fragment thereof and the human LINE-1 ORF2p endonuclease domain that lacks endonuclease activity is fused to the Cas endonuclease;

and (II) a guide RNA;

wherein a target human cell uptakes the one or more exogenous RNA molecules and the guide RNA, (b) translating the sequence of the second RNA sequence of (a)(I)(ii), thereby producing the heterologous RNA guided endonuclease and the human LINE-1 ORF2p reverse transcriptase;

(c) (i) cutting genomic DNA of the target human cell by the heterologous RNA guided endonuclease, thereby producing a DNA cut site in the genomic DNA of the target human cell; and (ii) reverse transcribing the sequence of (a)(i) by the human LINE-1 ORF2p reverse transcriptase translated in step (b), thereby producing a DNA sequence encoding the exogenous human therapeutic polypeptide;

(d) integrating via the human LINE-1 ORF2p mediated target primed reverse transcription (TPRT), the DNA sequence encoding the exogenous human therapeutic polypeptide into the genomic DNA of the target human cell at the DNA cut site; and (e) after step (d) expressing the exogenous human therapeutic polypeptide from the DNA sequence integrated into the genomic DNA of step (d) in the target human cell, wherein the exogenous human therapeutic polypeptide expresses from the DNA sequence integrated into the genomic DNA in at least 2% target human cells of the plurality of the target human cell.

2. The method of claim 1, wherein the one or more exogenous RNA molecules further comprises an RNA sequence encoding a human LINE-1 ORF1p polypeptide or a functional fragment thereof.

3. The method of claim 2, wherein the one or more exogenous RNA molecules comprises:

(a) a first RNA molecule comprising the sequence encoding the human LINE-1 ORF1p polypeptide, and (b) a second RNA molecule comprising:

(A) the first RNA sequence that is the reverse complement of a sequence encoding the exogenous human therapeutic polypeptide, and (B) the second RNA sequence comprising the mobile genetic element that is not controlled by a promoter, comprising the sequence encoding the human LINE-1 ORF2p polypeptide or fragment thereof, wherein the human LINE-1 ORF2p polypeptide or the fragment thereof has a human LINE-1 ORF2p reverse transcriptase or a functional fragment thereof and a human LINE-1 ORF2p endonuclease that lacks endonuclease activity, and the sequence encoding the heterologous RNA guided site-specific endonuclease.

4. The method of claim 3, wherein ratio of the first RNA molecule to the second RNA molecule in the composition is at least 2:1, and less than 10:1.

5. The method of claim 4, wherein the ratio of the first RNA molecule to the second RNA molecule in the composition is about 3:1.

6. The method of claim 1, wherein the reverse transcriptase comprises a C-terminal nuclear localization signal (NLS) or an N-terminal NLS.

7. The method of claim 1, wherein the target human cell is an immune cell selected from the group consisting of a T cell, a B cell, a myeloid cell, a monocyte, a macrophage and a dendritic cell.

8. The method of claim 1, wherein the one or more exogenous RNA molecules comprises homology arms complementary to a target site that is a sequence surrounding the DNA cut site in the genomic DNA.

9. The method of claim 1, wherein integrating comprises integrating the DNA sequence encoding the exogenous human therapeutic polypeptide into non-ribosomal genomic DNA (rDNA) of the target human cell or integrating the DNA sequence encoding the exogenous human therapeutic polypeptide into the genomic DNA at a locus that is not an rDNA locus.

10. The method of claim 1, wherein the guide RNA targets a DNA target site of the genomic DNA that is not an rDNA locus.

11. The method of claim 1, wherein the exogenous human therapeutic polypeptide is selected from the group consisting of a ligand, an antibody, a receptor, an enzyme, a transport protein, a structural protein, a hormone, a contractile protein, a storage protein and a transcription factor.

12. The method of claim 1, wherein the exogenous human therapeutic polypeptide is a receptor selected from the group consisting of a chimeric antigen receptor (CAR) and a T cell receptor (TCR).

13. The method of claim 1, wherein the DNA sequence encoding the exogenous human therapeutic polypeptide does not comprise introns.

14. The method of claim 1, wherein the one or more exogenous RNA molecules comprises a 5' UTR sequence, a 3' UTR sequence and a poly A sequence; wherein:

(i) the 5' UTR sequence is upstream of the second RNA sequence comprising the mobile genetic element comprising the sequence encoding the human LINE-1 ORF2p reverse transcriptase, (ii) the 3' UTR sequence is downstream of the sequence encoding the exogenous human therapeutic polypeptide;

(iii) the 3' UTR is upstream of the poly A sequence; and wherein, (a) the 5' UTR comprises a 5' UTR from LINE-1; and/or (b) the 3' UTR comprises a 3' UTR from LINE-1.

15. The method of claim 1 wherein the Cas endonuclease is Cas9, Cas6, Cas7, or Cas8.

16. The method of claim 1, wherein contacting comprises administering the composition to a human subject.

17. The method of claim 1, wherein the one or more exogenous RNA molecules comprises a glycosylated RNA molecule, a circular RNA molecule or a self-replicating RNA molecule.

18. The method of claim 1, wherein the exogenous therapeutic polypeptide is expressed from a non-ribosomal safe harbor locus of the genomically integrated DNA sequence.

19. The method of claim 1, wherein the Cas endonuclease is a mutated form thereof comprising a Cas nickase.

20. The method of claim 1, wherein the DNA cut site is a single strand nick.

21. The method of claim 1, wherein the reverse transcriptase and the heterologous RNA guided endonuclease promote integration of the DNA sequence encoding the exogenous human therapeutic polypeptide into the genomic DNA of the target human cell of the target human cell via TPRT.

22. The method of claim 1, wherein the human LINE-1 ORF2p polypeptide comprising human LINE-1 ORF2p reverse transcriptase comprises a sequence that has at least 80% sequence identity to SEQ ID NO: 55.

* * * * *

SEQUENCE LISTING

```
Sequence total quantity: 87
SEQ ID NO: 1            moltype = AA  length = 116
FEATURE                 Location/Qualifiers
REGION                  1..116
                        note = Description of Artificial Sequence: Synthetic
                        polypeptide
source                  1..116
                        mol_type = protein
                        organism = synthetic construct
SEQUENCE: 1
EIQLVQSGGG LVKPGGSVRI SCAASGYTFT NYGMNWVRQA PGKGLEWMGW INTHTGEPTY  60
ADSFKGRFTF SLDDSKNTAY LQINSLRAED TAVYFCTRRG YDWYFDVWGQ GTTVTV      116

SEQ ID NO: 2            moltype = AA  length = 107
FEATURE                 Location/Qualifiers
REGION                  1..107
                        note = Description of Artificial Sequence: Synthetic
                        polypeptide
source                  1..107
                        mol_type = protein
```

-continued

```
                          organism = synthetic construct
SEQUENCE: 2
DIQMTQSPSS LSASVGDRVT ITCRASQDIN SYLSWFQQKP GKAPKTLIYR ANRLESGVPS    60
RFSGSGSGTD YTLTISSLQY EDFGIYYCQQ YDESPWTFGG GTKLEIK                  107

SEQ ID NO: 3              moltype = AA   length = 46
FEATURE                   Location/Qualifiers
REGION                    1..46
                          note = Description of Artificial Sequence: Synthetic
                           polypeptide
source                    1..46
                          mol_type = protein
                          organism = synthetic construct
SEQUENCE: 3
LYCRRLKIQV RKAAITSYEK SDGVYTGLST RNQETYETLK HEKPPQ                   46

SEQ ID NO: 4              moltype = AA   length = 35
FEATURE                   Location/Qualifiers
REGION                    1..35
                          note = Description of Artificial Sequence: Synthetic
                           polypeptide
source                    1..35
                          mol_type = protein
                          organism = synthetic construct
SEQUENCE: 4
YEDMRGILYA APQLRSIRGQ PGPNHEEDAD SYENM                               35

SEQ ID NO: 5              moltype = AA   length = 62
FEATURE                   Location/Qualifiers
REGION                    1..62
                          note = Description of Artificial Sequence: Synthetic
                           polypeptide
source                    1..62
                          mol_type = protein
                          organism = synthetic construct
SEQUENCE: 5
KKVAKKPTNK APHPKQEPQE INFPDDLPGS NTAAPVQETL HGCQPVTQED GKESRISVQE    60
RQ                                                                   62

SEQ ID NO: 6              moltype = AA   length = 21
FEATURE                   Location/Qualifiers
REGION                    1..21
                          note = Description of Artificial Sequence: Synthetic peptide
source                    1..21
                          mol_type = protein
                          organism = synthetic construct
SEQUENCE: 6
IYIWAPLAGT CGVLLLSLVI T                                              21

SEQ ID NO: 7              moltype = AA   length = 62
FEATURE                   Location/Qualifiers
REGION                    1..62
                          note = Description of Artificial Sequence: Synthetic
                           polypeptide
source                    1..62
                          mol_type = protein
                          organism = synthetic construct
SEQUENCE: 7
ALSNSIMYFS HFVPVFLPAK PTTTPAPRPP TPAPTIASQP LSLRPEACRP AAGGAVHTRG    60
LD                                                                   62

SEQ ID NO: 8              moltype = AA   length = 130
FEATURE                   Location/Qualifiers
REGION                    1..130
                          note = Description of Artificial Sequence: Synthetic
                           polypeptide
source                    1..130
                          mol_type = protein
                          organism = synthetic construct
SEQUENCE: 8
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTG STSGSGKPGS    120
GEGSEVQLVE                                                           130

SEQ ID NO: 9              moltype = AA   length = 108
FEATURE                   Location/Qualifiers
REGION                    1..108
                          note = Description of Artificial Sequence: Synthetic
                           polypeptide
```

```
source                   1..108
                         mol_type = protein
                         organism = synthetic construct
SEQUENCE: 9
LVQPGGSLRL SCAASGFNIK DTYIHWVRQA PGKGLEWVAR IYPTNGYTRY ADSVKGRFTI   60
SADTSKNTAY LQMNSLRAED TAVYYCSRWG GDGFYAMDVW GQGTLVTV               108

SEQ ID NO: 10            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 10
SSGGGGSGGG GSGGGGS                                                  17

SEQ ID NO: 11            moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 11
SGGGGSG                                                              7

SEQ ID NO: 12            moltype = AA  length = 4
FEATURE                  Location/Qualifiers
REGION                   1..4
                         note = Description of Artificial Sequence: Synthetic peptide
source                   1..4
                         mol_type = protein
                         organism = synthetic construct
SEQUENCE: 12
SGGG                                                                 4

SEQ ID NO: 13            moltype = AA  length = 4
FEATURE                  Location/Qualifiers
REGION                   1..4
                         note = Description of Artificial Sequence: Synthetic peptide
source                   1..4
                         mol_type = protein
                         organism = synthetic construct
SEQUENCE: 13
GSGS                                                                 4

SEQ ID NO: 14            moltype = AA  length = 432
FEATURE                  Location/Qualifiers
REGION                   1..432
                         note = Description of Artificial Sequence: Synthetic
                          polypeptide
source                   1..432
                         mol_type = protein
                         organism = synthetic construct
SEQUENCE: 14
MWLQSLLLLG TVACSISEIQ LVQSGGGLVK PGGSVRISCA ASGYTFTNYG MNWVRQAPGK   60
GLEWMGWINT HTGEPTYADS FKGRFTFSLD DSKNTAYLQI NSLRAEDTAV YFCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RRLKIQVRKA  360
AITSYEKSDG VYTGLSTRNQ ETYETLKHEK PPQGSGSYED MRGILYAAPQ LRSIRGQPGP  420
NHEEDADSYE NM                                                      432

SEQ ID NO: 15            moltype = AA  length = 436
FEATURE                  Location/Qualifiers
REGION                   1..436
                         note = Description of Artificial Sequence: Synthetic
                          polypeptide
source                   1..436
                         mol_type = protein
                         organism = synthetic construct
SEQUENCE: 15
MWLQSLLLLG TVACSISDIQ MTQSPSSLSA SVGDRVTITC RASQDVNTAV AWYQQKPGKA   60
PKLLIYSASF LYSGVPSRFS GSRSGTDFTL TISSLQPEDF ATYYCQQHYT TPPTFGQGTK  120
VEIKRTGSTS GSGKPGSGEG SEVQLVESGG GLVQPGGSLR LSCAASGFNI KDTYIHWVRQ  180
APGKGLEWVA RIYPTNGYTR YADSVKGRFT ISADTSKNTA YLQMNSLRAE DTAVYYCSRW  240
GGDGFYAMDV WGQGTLVTVS SSGGGGSGAL SNSIMYFSHF VPVFLPAKPT TTPAPRPPTP  300
```

-continued

```
APTIASQPLS LRPEACRPAA GGAVHTRGLD IYIWAPLAGT CGVLLLSLVI TLYCRRLKIQ  360
VRKAAITSYE KSDGVYTGLS TRNQETYETL KHEKPPQGSG SYEDMRGILY AAPQLRSIRG  420
QPGPNHEEDA DSYENM                                                  436

SEQ ID NO: 16          moltype = AA  length = 454
FEATURE                Location/Qualifiers
REGION                 1..454
                       note = Description of Artificial Sequence: Synthetic
                        polypeptide
source                 1..454
                       mol_type = protein
                       organism = synthetic construct
SEQUENCE: 16
MWLQSLLLLG TVACSISEIQ LVQSGGGLVK PGGSVRISCA ASGYTFTNYG MNWVRQAPGK  60
GLEWMGWINT HTGEPTYADS FKGRFTFSLD DSKNTAYLQI NSLRAEDTAV YFCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RLKIQVRKAA  360
ITSYEKSDGV YTGLSTRNQE TYETLKHEKP PQKKVAKKPT NKAPHPKQEP QEINFPDDLP  420
GSNTAAPVQE TLHGCQPVTQ EDGKESRISV QERQ                              454

SEQ ID NO: 17          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 17
MWLQSLLLLG TVACSIS                                                 17

SEQ ID NO: 18          moltype = AA  length = 27
FEATURE                Location/Qualifiers
REGION                 1..27
                       note = Description of Artificial Sequence: Synthetic peptide
source                 1..27
                       mol_type = protein
                       organism = synthetic construct
SEQUENCE: 18
FWVLVVVGGV LACYSLLVTV AFIIFWV                                      27

SEQ ID NO: 19          moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 19
ILLPLIIGLI LLGLLALVLI AFCII                                        25

SEQ ID NO: 20          moltype = AA  length = 45
FEATURE                Location/Qualifiers
REGION                 1..45
                       note = Description of Artificial Sequence: Synthetic
                        polypeptide
source                 1..45
                       mol_type = protein
                       organism = synthetic construct
SEQUENCE: 20
LYCRLKIQVR KAAITSYEKS DGVYTGLSTR NQETYETLKH EKPPQ                  45

SEQ ID NO: 21          moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 21
QRWKSKLYSI VCGKSTPEKE GELEGTTTKP LAPNPSFSPT PGFTPTLGFS PVPSSTFTSS  60
STYTPGDCPN FAAPRREVAP PYQGADPILA TALASDPIPN PLQKWEDSAH KPQSLDTDDP  120
ATLYAVVENV PPLRWKEFVR RLGLSDHEID RLELQNGRCL REAQYSMLAT WRRRTPRREA  180
TLELLGRVLR DMDLLGCLED IEEALCGPAA LPPAPSLLR                         219

SEQ ID NO: 22          moltype = AA  length = 171
FEATURE                Location/Qualifiers
```

```
REGION                    1..171
                          note = Description of Artificial Sequence: Synthetic
                           polypeptide
source                    1..171
                          mol_type = protein
                          organism = synthetic construct
SEQUENCE: 22
PLCLQREAKV PHLPADKARG TQGPEQQHLL ITAPSSSSSS LESSASALDR RAPTRNQPQA    60
PGVEASGAGE ARASTGSSDS SPGGHGTQVN VTCIVNVCSS SDHSSQCSSQ ASSTMGDTDS   120
SPSESPKDEQ VPFSKEECAF RSQLETPETL LGSTEEKPLP LGVPDAGMKP S            171

SEQ ID NO: 23             moltype = AA  length = 211
FEATURE                   Location/Qualifiers
REGION                    1..211
                          note = Description of Artificial Sequence: Synthetic
                           polypeptide
source                    1..211
                          mol_type = protein
                          organism = synthetic construct
SEQUENCE: 23
MSNGYSTDEN FRYLISCFRA RVKMYIQVEP VLDYLTFLPA EVKEQIQRTV ATSGNMQAVE    60
LLLSTLEKGV WHLGWTREFV EALRRTGSPL AARYMNPELT DLPSPSFENA HDEYLQLLNL   120
LQPTLVDKLL VRDVLDKCME EELLTIEDRN RIAAAENNGN ESGVRELLKR IVQKENWFSA   180
FLNVLRQTGN NELVQELTGS DCSESNAEIE N                                  211

SEQ ID NO: 24             moltype = AA  length = 607
FEATURE                   Location/Qualifiers
REGION                    1..607
                          note = Description of Artificial Sequence: Synthetic
                           polypeptide
source                    1..607
                          mol_type = protein
                          organism = synthetic construct
SEQUENCE: 24
MWLQSLLLLG TVACSISEIQ LVQSGGGLVK PGGSVRISCA ASGYTFTNYG MNWVRQAPGK    60
GLEWMGWINT HTGEPTYADS FKGRFTFSLD DSKNTAYLQI NSLRAEDTAV YFCTRRGYDW   120
YFDVWGQGTT VTVSSGGGGS GGGGSGGGGS DIQMTQSPSS LSASVGDRVT ITCRASQDIN   180
SYLSWFQQKP GKAPKTLIYR ANRLESGVPS RFSGSGSGTD YTLTISSLQY EDFGIYYCQQ   240
YDESPWTFGG GTKLEIKSGG GGSGALSNSI MYFSHFVPVF LPAKPTTTPA PRPPTPAPTI   300
ASQPLSLRPE ACRPAAGGAV HTRGLDIYIW APLAGTCGVL LLSLVITLYC RLKIQVRKAA   360
ITSYEKSDGV YTGLSTRNQE TYETLKHEKP PQGSGSMSNG YSTDENFRYL ISCFRARVKM   420
YIQVEPVLDY LTFLPAEVKE QIQRTVATSG NMQAVELLLS TLEKGVWHLG WTREFVEALR   480
RTGSPLAARY MNPELTDLPS PSFENAHDEY LQLLNLLQPT LVDKLLVRDV LDKCMEEELL   540
TIEDRNRIAA AENNGNESGV RELLKRIVQK ENWFSAFLNV LRQTGNNELV QELTGSDCSE   600
SNAEIEN                                                            607

SEQ ID NO: 25             moltype = AA  length = 615
FEATURE                   Location/Qualifiers
REGION                    1..615
                          note = Description of Artificial Sequence: Synthetic
                           polypeptide
source                    1..615
                          mol_type = protein
                          organism = synthetic construct
SEQUENCE: 25
MWLQSLLLLG TVACSISEIQ LVQSGGGLVK PGGSVRISCA ASGYTFTNYG MNWVRQAPGK    60
GLEWMGWINT HTGEPTYADS FKGRFTFSLD DSKNTAYLQI NSLRAEDTAV YFCTRRGYDW   120
YFDVWGQGTT VTVSSGGGGS GGGGSGGGGS DIQMTQSPSS LSASVGDRVT ITCRASQDIN   180
SYLSWFQQKP GKAPKTLIYR ANRLESGVPS RFSGSGSGTD YTLTISSLQY EDFGIYYCQQ   240
YDESPWTFGG GTKLEIKSGG GGSGALSNSI MYFSHFVPVF LPAKPTTTPA PRPPTPAPTI   300
ASQPLSLRPE ACRPAAGGAV HTRGLDIYIW APLAGTCGVL LLSLVITLYC RLKIQVRKAA   360
ITSYEKSDGV YTGLSTRNQE TYETLKHEKP PQGSGSQRWK SKLYSIVCGK STPEKEGELE   420
GTTTKPLAPN PSFSPTPGFT PTLGFSPVPS STFTSSSTYT PGDCPNFAAP RREVAPPYQG   480
ADPILATALA SDPIPNPLQK WEDSAHKPQS LDTDDPATLY AVVENVPPLR WKEFVRRLGL   540
SDHEIDRLEL QNGRCLREAQ YSMLATWRRR TPRREATLEL LGRVLRDMDL LGCLEDIEEA   600
LCGPAALPPA PSLLR                                                   615

SEQ ID NO: 26             moltype = AA  length = 567
FEATURE                   Location/Qualifiers
REGION                    1..567
                          note = Description of Artificial Sequence: Synthetic
                           polypeptide
source                    1..567
                          mol_type = protein
                          organism = synthetic construct
SEQUENCE: 26
MWLQSLLLLG TVACSISEIQ LVQSGGGLVK PGGSVRISCA ASGYTFTNYG MNWVRQAPGK    60
GLEWMGWINT HTGEPTYADS FKGRFTFSLD DSKNTAYLQI NSLRAEDTAV YFCTRRGYDW   120
YFDVWGQGTT VTVSSGGGGS GGGGSGGGGS DIQMTQSPSS LSASVGDRVT ITCRASQDIN   180
```

-continued

```
SYLSWFQQKP GKAPKTLIYR ANRLESGVPS RFSGSGSGTD YTLTISSLQY EDFGIYYCQQ 240
YDESPWTFGG GTKLEIKSGG GGSGALSNSI MYFSHFVPVF LPAKPTTTPA PRPPTPAPTI 300
ASQPLSLRPE ACRPAAGGAV HTRGLDIYIW APLAGTCGVL LLSLVITLYC RLKIQVRKAA 360
ITSYEKSDGV YTGLSTRNQE TYETLKHEKP PQGSGSPLCL QREAKVPHLP ADKARGTQGP 420
EQQHLLITAP SSSSSSLESS ASALDRRAPT RNQPQAPGVE ASGAGEARAS TGSSDSSPGG 480
HGTQVNVTCI VNVCSSSDHS SQCSSQASST MGDTDSSPSE SPKDEQVPFS KEECAFRSQL 540
ETPETLLGST EEKPLPLGVP DAGMKPS                                    567

SEQ ID NO: 27           moltype = AA  length = 42
FEATURE                 Location/Qualifiers
REGION                  1..42
                        note = Description of Artificial Sequence: Synthetic
                         polypeptide
source                  1..42
                        mol_type = protein
                        organism = synthetic construct
SEQUENCE: 27
RLKIQVRKAA ITSYEKSDGV YTGLSTRNQE TYETLKHEKP PQ                    42

SEQ ID NO: 28           moltype = AA  length = 42
FEATURE                 Location/Qualifiers
REGION                  1..42
                        note = Description of Artificial Sequence: Synthetic
                         polypeptide
source                  1..42
                        mol_type = protein
                        organism = synthetic construct
SEQUENCE: 28
RLKIQVRKAA ITSYEKSDGV YTGLSTRNQE TYETLKHEKP PQ                    42

SEQ ID NO: 29           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 29
IYIWAPLAGT CGVLLLSLVI TLYC                                        24

SEQ ID NO: 30           moltype = AA  length = 86
FEATURE                 Location/Qualifiers
REGION                  1..86
                        note = Description of Artificial Sequence: Synthetic
                         polypeptide
source                  1..86
                        mol_type = protein
                        organism = synthetic construct
SEQUENCE: 30
ALSNSIMYFS HFVPVFLPAK PTTTPAPRPP TPAPTIASQP LSLRPEACRP AAGGAVHTRG 60
LDIYIWAPLA GTCGVLLLSL VITLYC                                      86

SEQ ID NO: 31           moltype = AA  length = 83
FEATURE                 Location/Qualifiers
REGION                  1..83
                        note = Description of Artificial Sequence: Synthetic
                         polypeptide
source                  1..83
                        mol_type = protein
                        organism = synthetic construct
SEQUENCE: 31
ALSNSIMYFS HFVPVFLPAK PTTTPAPRPP TPAPTIASQP LSLRPEACRP AAGGAVHTRG 60
LDIYIWAPLA GTCGVLLLSL VIT                                         83

SEQ ID NO: 32           moltype = AA  length = 255
FEATURE                 Location/Qualifiers
REGION                  1..255
                        note = Description of Artificial Sequence: Synthetic
                         polypeptide
source                  1..255
                        mol_type = protein
                        organism = synthetic construct
SEQUENCE: 32
DIQMTQSPSS LSASVGDRVT ITCRASQDVN TAVAWYQQKP GKAPKLLIYS ASFLYSGVPS 60
RFSGSRSGTD FTLTISSLQP EDFATYYCQQ HYTTPPTFGQ GTKVEIKRTG STSGSGKPGS 120
GEGSEVQLVE SSGGGGSGGG GSGGGGSLVQ PGGSLRLSCA ASGFNIKDTY IHWVRQAPGK 180
GLEWVARIYP TNGYTRYADS VKGRFTISAD TSKNTAYLQM NSLRAEDTAV YYCSRWGGDG 240
FYAMDVWGQG TLVTV                                                  255
```

-continued

```
SEQ ID NO: 33           moltype = AA   length = 240
FEATURE                 Location/Qualifiers
REGION                  1..240
                        note = Description of Artificial Sequence: Synthetic
                        polypeptide
source                  1..240
                        mol_type = protein
                        organism = synthetic construct
SEQUENCE: 33
EIQLVQSGGG LVKPGGSVRI SCAASGYTFT NYGMNWVRQA PGKGLEWMGW INTHTGEPTY  60
ADSFKGRFTF SLDDSKNTAY LQINSLRAED TAVYFCTRRG YDWYFDVWGQ GTTVTVSSGG  120
GGSGGGGSGG GGSDIQMTQS PSSLSASVGD RVTITCRASQ DINSYLSWFQ QKPGKAPKTL  180
IYRANRLESG VPSRFSGSGS GTDYTLTISS LQYEDFGIYY CQQYDESPWT FGGGTKLEIK  240

SEQ ID NO: 34           moltype = AA   length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 34
IYLIIGICGG GSLLMVFVAL LVFYIT                                       26

SEQ ID NO: 35           moltype = DNA   length = 1075
FEATURE                 Location/Qualifiers
misc_feature            1..1075
                        note = Description of Artificial Sequence: Synthetic
                        polynucleotide
source                  1..1075
                        mol_type = other DNA
                        organism = synthetic construct
SEQUENCE: 35
taatacgact cactataggg agaaagacgc caccatgggc aagaagcaaa atcgcaagac  60
ggggaattcc aagacacaat ccgctagccc accacctaaa gagcgttcta gctcccctgc  120
tactgagcag tcctggatgg aaaacgactt cgatgaactc cgggaagagg gatttaggcg  180
atccaactat tcagaactcc gcgaagatat ccagacaaag gggaaggaag tcgagaattt  240
cgagaagaac ctcgaggagt gcatcacccg tatcacaaac actgagaaat gtctcaaaga  300
actcatggaa cttaagacaa aagccaggga gcttcgagag gagtgtcgga gtctgagatc  360
caggtgtgac cagctcgagg agcgcgtgag cgcgatggaa gacgagatga acagatgaa  420
aagagagggc aaattcaggg agaagcgcat taagaggaac gaacagagtc tgcaggagat  480
ttgggattac gtcaagaggc ctaacctgcg gttgatcggc gtccccgaga gcgacgtaga  540
aaacgggact aaactggaga atacacttca agacatcatt caagaaaatt ttccaaacct  600
ggctcggcaa gctaatgtgc aaatccaaga gatccaacgc acacccagc ggtatagctc  660
tcggcgtgcc accccaggc atattatcgt gcgctttact aaggtggaga tgaaagagaa  720
gatgctgcga gccgctcggg aaaagggaag ggtgactttg aagggcaaac ctattcggct  780
gacggttgac cttagcgccg agacactcca ggcacgccgg aatggggcc ccatctttaa  840
tatcctgaag gagaagaact tccagccacg aatctcttac cctgcaaagt tgagttttat  900
ctccgagggt gagattaagt atttcatcga taaacagatg ctgcgagact tcgtgacaac  960
tcgcccagct ctcaaggaac tgctcaaaga ggctcttaat atggagcgca ataatagata  1020
tcaacccttg cagaaccacg caaagatgga ttataaggat gacgatgata aatga        1075

SEQ ID NO: 36           moltype = DNA   length = 5751
FEATURE                 Location/Qualifiers
misc_feature            1..5751
                        note = Description of Artificial Sequence: Synthetic
                        polynucleotide
source                  1..5751
                        mol_type = other DNA
                        organism = synthetic construct
SEQUENCE: 36
taatacgact cactataggg agaaagacgc caccatgaca ggttcaaata gtcacattac  60
gattctcact ctgaatataa atgggctgaa ttctgcaatt aaacggcaca ggcttgcttc  120
ctggataaag tctcaagacc cctcagtgtg ctgtattcag gaaacgcatc tcacgtgcag  180
ggacacccat cggctgaaaa taaaaggctg gcggaagatc taccaagcca atggaaaaca  240
aaagaaggct ggggtggcga tacttgtaag cgataaaaca gactttaaac caactaagat  300
caaacgggac aaagagggcc attacatcat ggtaaagggt agtattcaac aagaggagct  360
gactatcctg aatatttatg cacctaatac tggagccccc agattcataa agcaagtgtt  420
gagtgacctt caacgcgacc tcgactccca cactctgatc atgggagact ttaacaccct  480
gctgtccact ctcgacagat ctactagaca gaaagtcaac aaggatacac aggaactgaa  540
cagtgctctc caccaagcgg accttatcga catctacaga acactccacc ccaaaagcac  600
agaatatacc ttcttttcag ccctcacca cacctattcc aaaattgacc acattgtggg  660
gagtaaagcc cttctctcca aatgtaaacg gaccgaaatt atcactaact atctctccga  720
ccacagtgca ataaaacttg aattgcgaat taagaatctc actcaaagta gatccacgac  780
atggaaactg aacaatctcc tcttgaatga ctactgggtg cataacgaaa tgaaggctga  840
aataaagatg ttctttgaga ccaacgaaa caaagacacc acgtaccaga atctctggga  900
cgctttcaaa gcagtgtgtc gaggaaaatt tattgcactg aatgcttaca gcggaagca  960
ggaaagatca aaaatagaca ccctgactag ccaacttaaa gaactggaaa agcaagagca  1020
aactcatagc aaagctagcc gtcgccaaga aattacgaaa atcagagctg aactgaagga  1080
```

```
aattgagaca cagaaaaccc tgcaaaagat aaatgaaagc cgcagctggt tctttgaacg   1140
catcaacaaa atcgataggc cacttgctcg ccttatcaag aagaaaaggg agaagaatca   1200
aatcgacact ataaagaatg ataaaggcga tataaccacc gatcccacag aaaattcaaac  1260
aaccatacgc gaatactaca aacacctcta cgccaataaa ctcgaaaatc tcgaggaaat   1320
ggatacattc ctcgacacgt acacccttcc caggctgaac caggaagaag ttgaatcact   1380
gaatcggcct atcacgggga gtgaaatagt agctatcatc aattcactcc ctaccaagaa   1440
gtcacccgga cctgatggat tcaccgccga attctaccag agatacatgg aagaactggt   1500
gcccttcttg ctgaaacttt tccaaagtat tgagaaagag ggaatacttc caaactcatt   1560
ttatgaggca tccatcattc tgatcccgaa gcccggcagg gacacgacca agaaagagaa   1620
ttttcgacca atctcattga tgaacattga tgcaaagatc ctcaataaaa tactggcaaa   1680
tcggattcag cagcacataa agaagctgat ccaccatgat caagtaggct tcatccccgg   1740
tatgcaaggt tggttcaata tacgaaaatc aatcaatgtt atccagcata taaaccgggc   1800
caaagacaag aaccacatga ttattagtat cgatgctgag aaagcctttg acaaaataca   1860
acaacccttc atgctgaaaa cattgaataa gctgggaatt gatggcacct acttcaaaat   1920
catcagagcc atatatgaca aaccaacagc aaatatcatt ctgaatggtc agaaattgga   1980
agcattcccc ttgaaaaccg gcacacggca gggttgccct ctgtcaccac tcctcttcaa   2040
catcgtgttg gaagttcttg cccgcgcaat ccggcaggaa aaggaaatca agggcattca   2100
actgggcaaa gaggaagtta aattgagcct gtttgcagac gacatgatcg tctatttgga   2160
aaacccccata gttagtgcac aaaatctgct gaagttgatc agtaatttct ccaaagtgag   2220
tgggtacaaa atcaatgtgc aaaagagcca agctttcttg tacaccaaca acaggcaaac   2280
tgagtctcaa atcatgggcg aactcccctt cgtgattgca tccaagcgga tcaaatacct   2340
ggggattcaa ttgactcgtg atgtgaagga cctcttcaag aggaactaca aacccctgct   2400
caaggaaatc aaagaggaca caaacaaatg gaagaacatt ccatgctctt gggtggggaag   2460
gatcaatatc gtcaaaatgg ccatcctgcc caaggtaatt tacaggttca atgctatacc   2520
catcaagctc cccatgacat tcttcacaga acttgaaaag acgacgctga agttcatttg   2580
gaaccagaaa cgtgccagga ttgctaaatc tattctctcc caaaagaaca aagctggcgg   2640
aatcacactc ccagacttca aactttacta caaggcgacc gtgacgaaaa cggcttggta   2700
ctggtaccaa aacagggata tagatcaatg gaaccgaacg gagcccagcg aaattatgcc   2760
tcatatatac aactatctga tctttgacaa accggagaag aacaagcaat ggggaaagga   2820
tagtctgttt aataaatggt gctgggaaaa ctggctcgca atctgtagga agctgaaact   2880
ggatccattc ttgacgcctt atacaaagat aaattcccga tggattaaag atctcaacgt   2940
gaaacccaaa acaattaaaa ccctcgagga aaacctgggt attacgattc aggacattgg   3000
ggtgggaaag gacttcatgt ccaaaacccc aaaagcgatg gcaaccaaag acaaaatcga   3060
caaatgggat ctcataaaac ttaagtcatt ttgcacagct aaagaaacga caattgggt   3120
gaaccgacaa ccgaccactt gggagaaaat cttcgcaaca tacagttctg acaaaggcct   3180
gatttccagg atctacaatg aattgaaaca aatttacaag aagaagacga acaaccctat   3240
aaagaaatgg gccaaggaca tgaacagaca cttctctaag gaagacattt atgcagccaa   3300
gaaacacatg aagaaatgca gctcttcact ggcaatcagg gaaatgcaaa tcaaaacaac   3360
aatgagatat catctcacac ccgtcagaat ggccatcatt aagaagagcg gaaacaaccg   3420
gtgctggcgt ggttgcggag aaatcggtac tctccttcac tgttggtggg actgtaaact   3480
cgttcaacca ctgtgtgaagt ctgtgtggcg gttcctcaga gatctggaac tcgaaatccc   3540
atttgaccca gccatccctc tcctgggtat atacccgaat gagtataaat cctgctgcta   3600
taaagacacc tgcacaagga tgtttattgc agctctcttc acaatcgcga agacgtggaa   3660
ccaacccaaa tgtccgacta tgattgactg gattaagaag atgtggcaca tatacactat   3720
ggaatactat gctgcgatca agaacgatga gttcatatca tttgtgggca catggatgaa   3780
actcgaaacc atcatactct ctaaattgag tcaagaacag aaaactaaac accgtatatt   3840
ttccctgatc ggtgggaatt agctacaaag acgatgacga caaggaccat gagacggtg    3900
agagacacaa aaaattccaa cacactattg caatgaaaat aaatttcctt tattagccag   3960
aagtcagatg ctcaagggggc ttcatgatgt ccccataatt tttggcagag ggaaaaagat   4020
ctcagtggta tttgtgagcc aagggcattgg ccttctgata ggcagcctgc acctgaggag   4080
tgcggccgct ttacttgtac agctcgtcca tgccgagagt gatccccggcg gcggtcacga   4140
actccagcag gaccatgtga tcgcgcttct cgttgggggtc tttgctcagg cggactgggg   4200
tgctcaggta gtggttgtcg ggcagcagca cggggccgtc gccgatgggg gtgttctgct   4260
ggtagtggtc ggcgagctgc acgctgccgt cctcgatgtt gtggcggatc ttgaagttca   4320
ccttgatgcc gttcttctgc ttgtcggcca tgatatagac gttgtggctg ttgtagttgt   4380
actccagctt gtgccccagg atgttgccgt cctccttgaa gtcgatgccc ttcagctcga   4440
tgcggttcac cagggtgtcg ccctcgaact tcacctcggc gcgggtcttg tagttgccgt   4500
cgtccttgaa gaagatggtg cgctcctgga cgtagccttc gggcatggcg gacttgaaga   4560
agtcgtgctg cttcatgtgg tcggggtagc ggctgaagca ctgcacgccg taggtcaggg   4620
tggtcacgag ggtgggccag ggcacgggca gcttgccggt ggtgcagatg aacttcaggg   4680
tcagcttgcc gtaggtggca tcgccctcgc cctcgccgga cacgctgaac ttgtggccgt   4740
ttacgtcgcc gtccagctcg accaggatgg gcaccacccc ggtgaacagc tcctcgccct   4800
tgctcaccat ggtggcggga tctgacggtt cactaaacca gctctgctta tatagacctc   4860
ccaccgtaca cgcctaccgc ccatttgcgt caatgggcga ggttgttac gacattttgg    4920
aaagtcccgt tgattttggt gccaaaacaa actcccattg acgtcaatgg ggtggagact   4980
tggaaatccc cgtgagtcaa accgctatcc acgcccattg atgtactgcc aaaaccgcat   5040
caccatggta atagcgatga ctaatacgta gatgtactgc caagtaggaa agtcccataa   5100
ggtcatgtac tgggcataat gccaggcggg ccatttaccg tcattgacgt caataggggg   5160
cgtacttggc atatgataca cttgatgtac tgccaagtgg gcagtttacc gtaaatactc   5220
cacccattga cgtcaatgga aagtccctat tggcgttact atgggaacat acgtcattat   5280
tgacgtcaat gggcgggggt cgttgggcgg tcagccaggc gggccattta ccgtaagtta   5340
tgtaacgacg tctcagctga caatgagatc acatggacac aggaaggggga atatcacact   5400
ctggggactg tggtggggtc gggggagggg gagggtag cattgggaga tatacctaat     5460
gctagatgac acattagtgg gtgcagcgca ccagcatgac acatgtatac atatgtaact   5520
aacctgcaca atgtgcacat gtaccctaaa acttagagta taatggatcc gcaggcctct   5580
gctagcttga ctgactgaga tacagcgtac cttcagctca cagacatgat aagatacatt   5640
gatgagtttg gacaaaccac aactagaatg cagtgaaaaa aatgctttat ttgtgaaatt   5700
tgtgatgcta ttgctttatt tgtaaccatt ataagctgca ataaacaagt t            5751
```

-continued

```
SEQ ID NO: 37          moltype = DNA   length = 18285
FEATURE                Location/Qualifiers
misc_feature           1..18285
                       note = Description of Artificial Sequence: Synthetic
                       polynucleotide
source                 1..18285
                       mol_type = other DNA
                       organism = synthetic construct
SEQUENCE: 37
cggccgcggg gggaggagcc aagatggccg aataggaaca gctccggtct acagctccca   60
gcgtgagcga cgcagaagac ggtgatttct gcatttccat ctgaggtacc gggttcatct  120
cactagggag tgccagacag tgggcgcagg ccagtgtgtg tgcgcaccgt gcgcgagccg  180
aagcagggcg aggcattgcc tcacctggga agcgcaaggg gtcagggagt tccctttccg  240
agtcaaagaa aggggtgacg gacgcacctg gaaaatcggt tcactcccac ccgaatattg  300
cgcttttcag accggcttaa gaaacgcgcg accacgagac tatatcccac acctggctcg  360
gagggtccta cgcccacgga atctcgctga ttgctagcac agcagtctga gatcaaactg  420
caaggcggca acgaggctgg gggaggggcg cccgccattg cccaggcttg cttaggtaaa  480
caaagcagca gggaagctcg aactgggtgg agcccaccac agctcaagga ggcctgcctg  540
cctctgtagg ctccacctct gggggcaggg cacagacaaa caaaaagaca gcagtaacct  600
ctgcagactt aagtgtccct gtctgacagc tttgaagaga gcagtggttc tcccagcacg  660
cagctggaga tctgagaacg ggcagactgc ctcctcaagt gggtccctga cccctgaccc  720
ccgagcagcc taactgggag gcacccccca gcaggggcac actgacacct cacacggcag  780
ggtattccaa cagacctgca gctgagggtc ctgtctgtta gaaggaaaac taacaaccag  840
aaaggacatc tacaccgaaa acccatctgt acatcaccat catcaaagac caaaagtaga  900
taaaaccaca aagatgggga aaaacagaa cagaaaaact ggaaactcta aaacgcagag  960
cgcctctcct cctccaaagg aacgcagttc ctcaccagca acagaacaaa gctggatgga  1020
gaatgatttt gatgagctga gagaagaagg cttcagacga tcaaattact ctgagctacg  1080
ggaggacatt caaaccaaag gcaaagaagt tgaaaacttt gaaaaaaatt tagaagaatg  1140
tataactaga ataaccaata cagagaagtg cttaaaggag ctgatggagc tgaaaaccaa  1200
ggctcgagaa ctacgtgaag aatgcagaag cctcaggagc cgatgcgatc aactggaaga  1260
aagggtatca gcaatggaag atgaaatgaa tgaaatgaag cgagaaggga gtttagaga   1320
aaaaagaata aaaagaaatg agcaaagcct ccaagaaata tgggactatg tgaaaagacc  1380
aaatctacgt ctgattggtg tacctgaaag tgatgtggag aatggaacca agttggaaaa  1440
cactctgcag gatattatcc aggagaactt ccccaatctg gcaaggcagg ccaacgttca  1500
gattcaggaa atacagagaa cgccacaaag atactcctcg agaagagcaa ctccaagaca  1560
cataattgtc agattcacca aagttgaaat gaaggaaaaa atgttaaggg cagccagaga  1620
gaaaggtcgg gttaccctca aaggaaagcc catcagacta acagcggatc tctcggcaga  1680
aaccctacaa gccagaagag agtgggggcc aatattcaac attcttaaag aaaagaattt  1740
tcaacccaga atttcatatc cagccaaact aagcttcata agtgaaggag aaataaaata  1800
ctttatagac aagcaaatgt tgagagattt tgtcaccacc aggcctgccc taaaagagct  1860
cctgaaggaa gcgctaaaca tggaaaggaa caaccggtac cagccgctgc aaaatcatgc  1920
caaaatgtaa agaccatcaa gactaggaag aaactgcatc aactaatgag caaaatcacc  1980
agctaacatc ataatgacag gatcaacttc acacataaca attaactt taaatataaa  2040
tggactaaat tctgcaatta aaagacacag actggcaagt tggataaaga gtcaagaccc  2100
atcagtgtgc tgtattcagg aaacccatct cacgtgcaga gacacacata ggctcaaaat  2160
aaaaggatgg aggaagatct accaagccaa tggaaaacaa aaaaaggcag gggttgcaat  2220
cctagtctct gataaaacag actttaaacc aacaaagatc aaaagagaca aagaaggcca  2280
ttacataatg gtaaagggat caattcaaca agaggagcta actatcctaa atatttatgc  2340
acccaataca ggagcaccca gattcataaa gcaagtcctc agtgacctac aaagagactt  2400
agactcccac acattaataa tgggagactt taacaccca ctgtcaacat tagacagatc  2460
aacgagacag aaagtcaaca aggatcccca ggaattgaac tcagctctgc accaagcaga  2520
cctaatagac atctacagaa ctctccaccc caaatcaaca gaatatacat ttttttcagc  2580
accacaccac acctattcca aaattgacca catagttgga agtaaagctc tcctcagcaa  2640
atgtaaaaga acagaaatta taacaaacta tctctcagac cacagtgcaa tcaaactaga  2700
actcaggatt aagaatctca ctcaaagccg ctcaactaca tggaaactga acaacctgct  2760
cctgaatgac tactgggtac ataacgaaat gaaggcagaa ataaagatgt tctttgaaac  2820
caacgagaac aaagacacca cataccagaa tctctgggac gcattcaaag cagtgtgtag  2880
agggaaattt atagcactaa atgcctacaa gagaaagcag gaaagatcca aaattgacac  2940
cctaacatca caattaaaag aactagaaa gcaagaacaa acacattcaa aagctagcag  3000
aaggcaagaa ataactaaaa tcagagcaga actgaaggaa atagagacac aaaaaaccct  3060
tcaaaaaatc aatgaatcca ggagctggtt ttttgaaagg atcaacaaaa ttgatagacc  3120
gctagcaaga ctaataaaga aaaaagaga gaagaatcaa atagacacaa taaaaaatga  3180
taaaggggat atcaccaccg atcccacaga aatacaaact accatcagag aatactacaa  3240
acacctctac gcaaataaac tagaaaatct agaagaaatg gatacattcc tcgacacata  3300
cactctccca agactaaacc aggaagaagt tgaatctctg aatcgaccaa taacaggctc  3360
tgaaattgtg gcaataatca atagtttacc aaccaaaaag agtccaggac cagatggatt  3420
cacagccgaa ttctaccaga ggtacaagga ggaactggta ccattccttc tgaaactatt  3480
ccaatcaata gaaaaagagg gaatcctccc taactcattt tatgaggcca gcatcattct  3540
gataccaaag ccgggcagag acacaaccaa aaaagagaat tttagaccaa tatccttgat  3600
gaacattgat gcaaaaatcc tcaataaaat actggcaaac cgaatccagc agcacatcaa  3660
aaagcttatc caccatgatc aagtgggctt catccctggg atgcaaggct ggttcaatat  3720
acgcaaatca ataaatgtaa tccagcatat aaacagagcc aaagacaaaa accacatgat  3780
tatctcaata gatgcagaaa aagcctttga caaaattcaa caaccttca tgctaaaaac  3840
tctcaataaa ttaggtattg atgggacgta tttcaaaata ataagagcta tctatgacaa  3900
acccacagcc aatatcatac tgaatgggca aaaactggaa gcattccctt tgaaaaccgg  3960
cacaagacag gatgccctc tctcaccgct cctattcaac atagtgttgg aagttctggc  4020
cagggcaatc aggcaggaga aggaaataaa gggtattcaa ttaggaaaag aggaagtcaa  4080
attgtccctg tttgcagacg acatgattgt ttatctagaa aaccccatcg tctcagccca  4140
aaatctcctt aagctgataa gcaacttcag caaagtctca ggatacaaaa tcaatgtaca  4200
```

-continued

```
aaaatcacaa gcattcttat acaccaacaa cagacaaaca gagagccaaa tcatgggtga  4260
actcccattc acaattgctt caaagagaat aaaataccta ggaatccaac ttacaaggga  4320
tgtgaaggac ctcttcaagg agaactacaa accactgctc aaggaaataa aagaggagac  4380
aaacaaatgg aagaacattc catgctcatg ggtaggaaga atcaatatcg tgaaaatggc  4440
catactgccc aaggtaattt acagattcaa tgccatcccc atcaagctac caatgacttt  4500
cttcacagaa ttggaaaaaa ctactttaaa gttcatatgg aaccaaaaaa gagcccgcat  4560
tgccaagtca atcctaagcc aaaagaacaa agctggaggc atcacactac ctgacttcaa  4620
actatactac aaggctacag taaccaaaac agcatggtac tggtaccaaa acagagatat  4680
agatcaatga aacagaacag agccctcaga aataatgccg catatctaca actatctgat  4740
ctttgacaaa cctgagaaaa caaagcaatg gggaaaggat tccctattta ataaatggtg  4800
ctgggaaaac tggctagcca tatgtagaaa gctgaaactg gatcccttcc ttacacctta  4860
tacaaaaatc aattcaagat ggattaaaga tttaaacgtt aaacctaaaa ccataaaaac  4920
cctagaagaa aacctaggca ttaccattca ggacataggc gtgggcaagg acttcatgtc  4980
caaaacacca aaagcaatgg caacaaaaga caaaattgac aaatgggatc taattaaact  5040
aaaagagcttc tgcacagcaa aagaaactac catcagagtg aacaggcaac ctacaacatg  5100
ggagaaaatt tttgcaacct actcatctga caaagggcta atatccagaa tctacaatga  5160
actcaaacaa atttacaaga aaaaaacaaa caaccccatc aaaaagtggg cgaaggacat  5220
gaacagacac ttctcaaaag aagacattta tgcagccaaa aaacacatga agaaatgctc  5280
atcatcactg gccatcagag aaatgcaaat caaaaccact atgagatatc atctcacacc  5340
agttagaatg gcaatcatta aaaagtcagg aaacaacagg tgctggagag gatgcggaga  5400
aataggaaca cttttacact gttggtggga ctgtaaacta gttcaaccat tgtggaagtc  5460
agtgtggcga ttcctcaggg atctagaact agaaatacca tttgacccag ccatcccatt  5520
actgggtata tacccaaatg agtataaatc atgctgctat aaagacacat gcacacgtat  5580
gtttattgcg gcactattca caatagcaaa gacttggaac caacccaaat gtccaacaat  5640
gatagactgg attaagaaaa tgtggcacat atacaccatg gaatactatg cagccataaa  5700
aaatgatgag ttcatatcct ttgtagggac atggatgaaa ttggaaacca tcattctcag  5760
taaactatcg caagaacaaa aaaccaaaca ccgcatattc tcactcatag gtgggaattg  5820
aacaatgaga tcacatggac acaggaaggg gaatatcaca ctctggggac tgtggtgggg  5880
tcggggggagg ggggaggggat agcattggga gatataccta atgctagatg acacattagt  5940
gggtgcagcg caccagcatg gcacatgtat acggatccga attctcgacg gatcgatccg  6000
aacaaacgac ccaacacccg tgcgtttat tctgtctttt tattgccgat cccctcagaa  6060
gaactcgtca agaaggcgat agaaggcgat gcgctgcgaa tcgggagcgg cgataccgta  6120
aagcacgagg aagcggtcag cccattcgcc gccaagctct tcagcaatat cacgggtagc  6180
caacgctatg tcctgatagc ggtcggccgc tttacttgta cagctcgtcc atgccgagag  6240
tgatcccggc ggcggtcacg aactccagca ggaccatgtg atcgcgcttc tcgttgggat  6300
ctttgctcag ggcggactgg gtgctcaggt agtggttgtc gggcagcagc acggggccgt  6360
cgccgatggg ggtgttctgc tggtagtggt cggccaggtg agtccaggag atgtttcagc  6420
actgttgcct ttagtctcga ggcaacttag acaactgagt attgatctga gcacagcagg  6480
gtgtgagctg tttgaagata ctgggggttgg gggtgaagaa actgcagagg actaactggg  6540
ctgagaccca gtggcaatgt tttagggcct aaggaatgcc tctgaaaatc tagatggaca  6600
actttgactt tgagaaaaga gaggtggaaa tgaggaaaat gacttttctt tattagattt  6660
cggtagaaag aactttcatc tttcccctat tttttgttatt cgtttttaaaa catctatctg  6720
gaggcaggac aagtatggtc attaaaaaga tgcaggcaga agcacatat tggctcagtc  6780
aaagtgggga actttggtgg ccaaacatac attgctaagg ctattcctat atcagctgga  6840
cacatataaa atgctgctaa tgcttcatta caaacttata tcctttaatt ccagatgggg  6900
gcaaagtatg tccagggggtg aggaacaatt gaaacatttg ggctggagta gattttgaaa  6960
gtcagctctg tgtgtgtgtg tgtgtgtgag cgtgtgtttc ttttaacgtt  7020
ttcagcctac agcatacagg gttcatggtg gcaagaagat aacaagattt aaattatggc  7080
cagtgactag tgctgcaaga agaacaacta cctgcattta atgggaaagc aaaatctcag  7140
gctttgaggg aagttaacat aggcttgatt ctgggtggaa gctgggtgtg tagttatctg  7200
gaggccaggc tggagctctc agctcactat gggttcatct ttattgtctc ctttcatctc  7260
aacagctgca cgctgccgtc ctcgatgttg tggcggatct tgaagttcac cttgatgccg  7320
ttcttctgct tgtcggccat gatatagacg ttgtggctgt tgtagttgta ctccagcttg  7380
tgccccagga tgttgccgtc ctccttgaag tcgatgccct tcagctcgat gcggttcacc  7440
agggtgtcgc cctcgaactt cacctcggcg cgggtcttgt agttgccgtc gtccttgaag  7500
aagatggtgc gctcctggac gtagccttcg ggcatggcgg acttgaagaa gtcgtgctgc  7560
ttcatgtggt cggggtagcg gctgaagcac tgcacgccgt aggtcagggt ggtcacgagg  7620
gtgggccagg gcacgggcag cttgccggtg gtgcagatga acttcagggt cagcttgccg  7680
taggtggcat cgccctcgcc ctcgccggac acgctgaact tgtggccgtt tacgtcgccg  7740
tccagctcga ccaggatggg caccacccg gtgaacagct cctcgccctt gctcaccatg  7800
gtggcgaatt cgaagcttga gctcgagatc tgagtccggt agcgctagcg gatctgacgg  7860
ttcactaaac cagctctgct tatatagacc tcccaccgta cacgcctacc gcccatttgc  7920
gtcaatgggg cggagttgtt acgacatttt ggaaagtccc gttgatttg gtgccaaaac  7980
aaactcccat tgacgtcaat ggggtggaga cttggaaatc cccgtgagtc aaaccgctat  8040
ccacgcccat tgatgtactg ccaaaaccgc atcaccatgg taatagcgat gactaatacg  8100
tagatgtact gccaagtagg aaagtcccat aaggtcatgt actgggcata atgccaggcg  8160
ggccatttac cgtcattgac gtcaataggg gcgtacttg gcatatgata cacttgatgt  8220
actgccaagt gggcagttta ccgtaaatac tccacccatt gacgtcaatg gaaagtccct  8280
attggcgtta ctatgggaac atacgtcatt attgacgtca atgggcgggg gtcgttgggc  8340
ggtcagccag gcgggccatt taccgtaagt tatgtaacgc ggaactccat atatgggcta  8400
tgaactaatg accccgtaat tgattactat tagcccgggg gatccagaca tgataagata  8460
cattgatgag tttggacaaa ccacaactag aatgcagtga aaaaaatgct ttatttgtga  8520
aatttgtgat gctattgctt tatttgtaac cattataagc tgcaataaac aagttaacaa  8580
caacaattgc attcatttta tgtttcaggt tcagggggag gtgtgggagg ttttttaaag  8640
caagtaaaac ctctacaaat gtggtatggc tgattatgat ccggctgcct cgcgcgtttc  8700
ggtgatgacg gtgaaaacct ctgacacatg cagctcccgg agacggtcac agcttgtctg  8760
taagcggatg ccgggagcag acaagcccgt caggcgcgt cagcgggtgt tggcgggtgt  8820
cggggcgcag ccatgaggtc gatcgactct agaggatcga tccccgcccc ggacgaacta  8880
aacctgacta cgacatctct gccccttctt cgcggggcag tgcatgtaat cccttcagtt  8940
```

-continued

```
ggttggtaca acttgccaac tgggccctgt tccacatgtg acacgggggg ggaccaaaca  9000
caaaggggtt ctctgactgt agttgacatc cttataaatg gatgtgcaca tttgccaaca  9060
ctgagtggct ttcatcctgg agcagacttt gcagtctgtg gactgcaaca caacattgcc  9120
tttatgtgta actcttggct gaagctctta caccaatgct gggggacatg tacctcccag  9180
gggcccagga agactacggg aggctacacc aacgtcaatc aaggggcct gtgtagctac  9240
cgataagcgg accctcaaga gggcattagc aatagtgttt ataaggcccc cttgttaacc  9300
ctaaacgggt agcatatgct tcccgggtag tagtatatac tatccagact aaccctaatt  9360
caatagcata tgttacccaa cgggaagcat atgctatcga attagggtta gtaaaagggt  9420
cctaaggaac agcgatatct cccaccccat gagctgtcac ggttttattt acatggggtc  9480
aggattccac gagggtagtg aaccatttta gtcacaaggg cagtggctga agatcaagga  9540
gcgggcagtg aactctcctg aatcttcgcc tgcttcttca ttctccttcg tttagctaat  9600
agaataactg ctgagttgtg aacagtaagg tgtatgtgag gtgctcgaaa acaaggtttc  9660
aggtgacgcc cccagaataa aatttggacg gggggttcag tggtggcatt gtgctatgac  9720
accaatataa ccctcacaaa ccccttgggc aataaatact agtgtaggaa tgaaacattc  9780
tgaatatctt taacaataga aatccatggg gtgggggacaa gccgtaaaga ctggatgtcc  9840
atctcacacg aatttatggc tatgggcaac acataatcct agtgcaatat gatactgggg  9900
ttattaagat gtgtcccagg cagggaccaa gacaggtgaa ccatgttgtt acactctatt  9960
tgtaacaagg ggaaagagag tggacgccga cagcagcgga ctccactggt tgtctctaac  10020
accccgaaa attaaacggg gctccacgcc aatggggccc ataaacaaag acaagtggcc  10080
actctttttt ttgaaattgt ggagtggggg cacgcgtcag cccccacacg ccgccctgcg  10140
gttttggact gtaaaataag ggtgtaataa cttggctgat tgtaaccccg ctaaccactg  10200
cggtcaaacc acttgcccac aaaaccacta atggcacccc ggggaatacc tgcataagta  10260
ggtgggcggg ccaagatagg ggcgcgattg ctgcgatctg gaggacaaat tacacacact  10320
tgcgcctgag cgccaagcac agggttgttg gtcctcatat tcacgaggtc gctgagagca  10380
cggtgggcta atgttgccat gggtagcata tactacccaa atatctggat agcatatgct  10440
atcctaatct atatctgggt agcataggct atcctaatct atatctgggt agcatatgct  10500
atcctaatct atatctgggt agtatatgct atcctaattt atatctgggt agcataggct  10560
atcctaatct atatctgggt agcatatgct atcctaatct atatctgggt agtatatgct  10620
atcctaatct gtatccgggt agcatatgct atcctaatag agattagggt agtatatgct  10680
atcctaattt atatctgggt agcatatact acccaaatat ctggatagca tatgctatcc  10740
taatctatat ctgggtagca tatgctatcc taatctatat ctgggtagca taggctatcc  10800
taatctatat ctgggtagca tatgctatcc taatctatat ctgggtagta tatgctatcc  10860
taatttatat ctgggtagca taggctatcc taatctatat ctgggtagca tatgctatcc  10920
taatctatat ctgggtagta tatgctatcc taatctgtat ctgggtagca tatgctatcc  10980
tcatgcatat acagtcagca tatgataccc agtagtagag tgggagtgct atcctttgca  11040
tatgccgcca cctcccaagg gggcgtgaat tttcgctgct tgtccttttc ctgcatgctg  11100
gttgctccca ttcttaggtg aatttaagga ggccaggcta aagccgtcgc atgtctgatt  11160
gctcaccagg taaatgtcgc taatgttttc caacgcgaga aggtgttgag cgcggagctg  11220
agtgacgtga caacatgggt atgcccaatt gccccatgtt gggaggacga aaatggtgac  11280
aagacagatg gccagaaata caccaacagc acgcatgatg tctactgggg atttattctt  11340
tagtgcgggg gaatacacgg cttttaatac gattgagggc gtctcctaac aagttacatc  11400
actcctgccc ttcctcaccc tcatctccat cacctccttc atctccgtca tctccgtcat  11460
caccctccgc ggcagcccct tccaccatag gtggaaacca ggaggcaaa tctactccat  11520
cgtcaaagct gcacacagtc accctgatat tgcaggtagg agcgggcttt gtcataacaa  11580
ggtccttaat cgcatccttc aaaacctcag caaatatatg agtttgtaaa aagaccatga  11640
aataacagac aatggactcc cttagcgggc caggttgtgg gccgggtcca ggggccattc  11700
caaaggggag acgactcaat ggtgtaagac gacattgtgg aatagcaagg gcagttcctc  11760
gccttaggtt gtaaagggag gtcttactac ctccatatac gaacacaccg gcgacccaag  11820
ttccttcgtc ggtagtcctt tctacgtgac tcctagccag gagagctctt aaaccttctg  11880
caatgttctc aaatttcggg ttggaacctc cttgaccacg atgctttcca aaccaccctc  11940
ctttttgcg cctgcctcca tcaccctgac ccgggggtcc agtgcttggg ccttctcctg  12000
ggtcatctgc ggggccctgc tctatcgctc ccgggggcac gtcaggctca ccatctgggc  12060
caccttcttg gtggtattca aaataatcgg cttcccctac agggtggaaa aatggccttc  12120
tacctggagg gggcctgcgc ggtggagacc cggatgatga tgactgacta ctgggactcc  12180
tgggcctctt ttctccacgt ccacgacctc tcccctggc tctttcacga cttcccccccc  12240
tggctctttc acgtcctcta ccccggcggc ctccactacc tcctcgaccc cggcctccac  12300
tacctcctcg accccggcct ccactgcctc ctcgaccccg gcctccacct cctgctcctg  12360
cccctcctgc tcctgcccct cctcctgctc ctgcccctcc tgccctcct gctcctgccc  12420
ctcctgcccc tcctgctcct gccccctcctg ccctcctgc tcctgccctc cctgctcctc  12480
ctcctgctcc tgccctcct gccccctcctc ctgctcctgc cctcctgcc tcctgctctc  12540
ctgcccctcc tgcccctcct gctcctgccc ctcctgcccc tcctgctcct gccccctcctg  12600
ctcctgcccc tcctgctcct gccccctcctg ctcctgcccc tcctgcccct cctgcccctc  12660
ctcctgctcc tgcccctcct gctcctgccc ctcctgcccc tcctgcccct cctgctcctg  12720
cccctcctgc tcctgccc ctcctgcccc tcctgcccct cctgctcctg ccccctcctg  12780
ctgcccctcc tcctgctcct gccccctcctg ctcctgccc cctcctgcc cctcctgccc  12840
ctcctcctgc tcctgcccct cctgcccctc ctcctgctcc tgcccctcct cctgctcctg  12900
cccctcctgc ccctcctgcc cctcctcctg ctcctgcccc tcctcctgct cctgccccctc  12960
ctgcccctcc tgcccctcct gctcctgctc ctgcccctcc tcctgctcct gctgcccctc  13020
ctcctgctcc tgcccctccc gctcctgctc ctgctcctgt tccaccgtgg gtccctttgc  13080
agccaatgca acttggacgt tttgggggtc tccggacacc atctctatgt cttggccctg  13140
atcctgagcc gcccggggct cctggtcttc cgcctcctcg tcctcgtcct cttccccgtc  13200
ctcgtccatg gttatcaccc cctcttcttt gaggtccact gccgccggag ccttctggtc  13260
cagatgtgtc tcccttctct cctaggccat ttccaggtcc tgtacctggc ccctcgtcag  13320
acatgattca cactaaaaga gatcaataga catctttatt agacgacgct cagtgaatac  13380
agggagtgca gactcctgcc ccctccaaca gcccccccac cctcatcccc ttcatggtcg  13440
ctgtcagaca gatccaggtc tgaaaattcc ccatcctccg aaccatcctc gtcctcatca  13500
ccaattactc gcagcccgga aaactcccgc tgaacatcct caagatttgc gtcctgagcc  13560
tcaagccagg cctcaaattc ctcgtccccc ttttgctgg acggtaggga tggggattct  13620
cgggacccct cctcttcctc ttcaaggtca ccagacagag atgctactgg ggcaacgaa  13680
```

```
gaaaagctgg gtgcggcctg tgaggatcag cttatcgatg ataagctgtc aaacatgaga   13740
attcttgaag acgaaagggc ctcgtgatac gcctattttt ataggttaat gtcatgataa   13800
taatggtttc ttagacgtca ggtggcactt ttcggggaaa tgtgcgcgga acccctattt   13860
gtttattttt ctaaatacat tcaaatatgt atccgctcat gagacaataa ccctgataaa   13920
tgcttcaata atattgaaaa aggaagagta tgagtattca acatttccgt gtcgccctta   13980
ttcccttttt tgcggcattt tgccttcctg tttttgctca cccagaaacg ctggtgaaag   14040
taaaagatgc tgaagatcag ttgggtgcac gagtgggtta catcgaactg gatctcaaca   14100
gcggtaagat ccttgagagt tttcgccccg aagaacgttt tccaatgatg agcacttttt   14160
aagttctgct atgtggcgcg gtattatccc gtgttgacgc cgggcaagag caactcggtc   14220
gccgcataca ctattctcag aatgacttgg ttgagtactc accagtcaca gaaaagcatc   14280
ttacggatgg catgacagta agagaattat gcagtgctgc cataaccatg agtgataaca   14340
ctgcggccaa cttacttctg acaacgatcg gaggaccgaa ggagctaacc gcttttttgc   14400
acaacatggg ggatcatgta actcgccttg atcgttggga accggagctg aatgaagcca   14460
taccaaacga cgagcgtgac accacgatgc ctgcagcaat ttgcgcaaac   14520
tattaactgg cgaactactt actctagctt cccggcaaca attaatagac tggatggagg   14580
cggataaagt tgcaggacca cttctgcgct cggcccttcc ggctggctgg tttattgctg   14640
ataaatctgg agccggtgag cgtgggtctc gcggtatcat tgcagcactg gggccagatg   14700
gtaagccctc ccgtatcgta gttatctaca cgacggggag tcaggcaact atggatgaac   14760
gaaatagaca gatcgctgag ataggtgcct cactgattaa gcattggtaa ctgtcagacc   14820
aagtttactc atatatactt tagattgatt taaaacttca ttttttaattt aaaaggatct   14880
aggtgaagat cctttttgat aatctcatga ccaaaatccc ttaacgtgag ttttcgttcc   14940
actgagcgtc agaccccgta gaaaagatca aaggatcttc ttgagatcct tttttttctgc   15000
gcgtaatctg ctgcttgcaa acaaaaaaac caccgctacc agcggtggtt tgtttgccgg   15060
atcaagagct accaactctt tttccgaagg taactggctt cagcagagcg cagataccaa   15120
atactgtcct tctagtgtag ccgtagttag gccaccactt caagaactct gtagcaccgc   15180
ctacatacct cgctctgcta atcctgttac cagtggctgc tgccagtggc gataagtcgt   15240
gtcttaccgg gttggactca agacgatagt taccggataa ggcgcagcgg tcgggctgaa   15300
cggggggttc gtgcacacag cccagcttgg agcgaacgac ctacaccgaa ctgagatacc   15360
tacagcgtga gctatgagaa agcgccacgc ttcccgaagg gagaaaggcg gacaggtatc   15420
cggtaagcgg cagggtcgga acaggagagc gcacgaggga gcttccaggg gaaacgcct   15480
ggtatcttta gtgtcctgtc gggtttcgcc acctctgact tgagcgtcga ttttttgtgat   15540
gctcgtcagg gggggcggagc ctatggaaaa acgccagcaa cgcggccttt ttacggttcc   15600
tggccttttg ctggcctttt gctcacatgt tctttcctgc gttatcccct gattctgtgg   15660
ataaccgtat taccgccttt gagtgagctg ataccgctcg ccgcagccga acgaccgagc   15720
gcagcgagtc agtgagcgag gaagcggaag agcgcctgat gcggtatttt ctccttacgc   15780
atctgtgcgg tatttcacac cgcatatggt gcactctcag tacaatctgc tctgatgccg   15840
catagttaag ccagctgtgg aatgtgtgtc agttagggtg tggaaagtcc ccaggctccc   15900
cagcaggcag aagtatgcaa agcatgcatc tcaattagtc agcaaccagg tgtggaaagt   15960
ccccaggctc cccagcaggc agaagtatgc aaagcatgca tctcaattag tcagcaacca   16020
tagtcccgcc cctaactccg cccatcccgc ccctaactcc gcccagttcc gcccattctc   16080
cgccccatgg ctgactaatt tttttatttt atgcagaggc cgaggccgcc tcggcctctg   16140
agctattcca gaagtagtga ggaggctttt ttggaggcct aggcttttgc aaaaagcttg   16200
catgctgtgca ggtcggccgc cacgaccggt gccgccacca tcccctgacc cacgccccctg   16260
acccctcaca aggagacgac cttccatgac cgagtacaag cccacggtgc gcctcgccac   16320
ccgcgacgac gtccccgggg ccgtacgcac cctcgccgcc gcgttcgccg actacccgc   16380
cacgcgccac accgtcgacc cggaccgcca catcgagcgg gtcaccgagc tgcaagaact   16440
cttcctcacg cgcgtcgggc tcgacatcgg caaggtgtgg gtcgcggagaa acggcgccga   16500
ggtggcggtc tggaccacgc cggagagcgt cgaagcgggg gcggtgttcg ccagatcgg   16560
cccgcgcatg gccgagttga gcggttcccg gctggccgcg cagcaacaga tggaaggcct   16620
cctggcgccg caccggccca aggagcccgc gtggttcctg gccaccgtcg gcgtctcgcc   16680
cgaccaccag ggcaagggtc tgggcagcgc cgtcgtgctc cccggagtgg aggcggcgca   16740
gcgcgccggg gtgcccgcct tcctggagac ctccgcgccc cgcaacctcc ccttctacga   16800
gcggctcggc ttcaccgtca ccgccgacgt cgaggtgccc gaaggaccgc gcacctggtg   16860
catgacccgc aagcccggtg cctgacgccc gccccacgac ccgcagcgcc cgaccgaaag   16920
gagcgcacga ccccatggct ccgaccgaag ccgacccggg cggccccgcc gaccccgcac   16980
ccgcccccga ggcccaccga ctctagagga tcataatcag ccataccaca tttgtagagg   17040
ttttacttgc tttaaaaaac ctcccacacc tccccctgaa cctgaaacat aaaatgaatg   17100
caattgttgt tgttaacttg tttattgcag cttataatgg ttacaaataa agcaatagca   17160
tcacaaattt cacaaataaa gcattttttt cactgcattc tagttgtggt ttgtccaaac   17220
tcatcaatgt atcttatcat gtctggatca ctcgccgata gtggaaaccg acgccccagc   17280
actcgtccga gggcaaagga ataggggaga tggggaggc taactgaaac acggaaggag   17340
acaataccgg aaggaacccg cgctatgacg gcaataaaaa gacagaataa aacgcacggg   17400
tgttgggtcg tttgttcata aacgcggggt tcggtccag gctggcact ctgtcgatac   17460
cccaccgaga ccccattggg gccaatacgc ccgcgtttct tccttttccc cacccaccc   17520
cccaagttcg ggtgaaggcc cagggctcgc agccaacgtc ggggcggcag gccctgccat   17580
agccactggc cccgtgggtt agggacgggg tcccccatgg ggaatggttt atggttcgtg   17640
ggggttatta ttttgggcgt tgcgtggggt ctggtccacg actggactga gcagacagac   17700
ccatggtttt tggatggcct gggcatggac cgcatgtact ggcgcgacac gaacaccggg   17760
cgtctgtggc tgccaaacac ccccgacccc caaaaaccac gacgcggatt tctggcgtgc   17820
caagctagtc gaccaattct catgtttgac agcttatcat cgcagatccg ggcaacgttg   17880
ttgcattgct gcaggcgcag aactggtagg tatggaagat ctctagaagc tgggtaccag   17940
ctgctagcaa gcttgctagc ggccggctcg agttactcc ctatcagtga tagagaacgt   18000
atgtcgagtt tactccctat cagtgataga gaacgatgtc gagtttactc cctatcagtg   18060
atagagaacg tatgtcgagt ttactcccta tcagtgatag agaacgtatg tcgagtttac   18120
tccctatcag tgatagagaa cgtatgtcga gtttatccct atcagtgata gagaacgtat   18180
gtcgagttta ctccctatca gtgatagaga acgtatgtcg aggtaggcgt gtacggtggg   18240
aggcctatat aagcagagct cgtttagtga accgtcagat cgccg                    18285
```

SEQ ID NO: 38         moltype = DNA   length = 7264

-continued

```
FEATURE              Location/Qualifiers
misc_feature         1..7264
                     note = Description of Artificial Sequence: Synthetic
                      polynucleotide
source               1..7264
                     mol_type = other DNA
                     organism = synthetic construct SEQUENCE: 38
taatacgact cactataggg agaagtactg ccaccatggg caagaagcaa aatcgcaaga   60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacacccag cggtatagct   660
ctcggcgtgc caccctagg catattatcg tgcgctttac taaggtggag atgaaagaga   720
agatgctgcg agccgctcgg gaaaagggaa gggtgacttt gaagggcaaa cctattcggc   780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgt gagacagcg tcagaccatc aagactagga  1080
agaaactgca tcaactaatg agcaaaatca ccagctaaca tcatagtata catgaccggc  1140
tctaactcac atatcaccat ccttacactt aacattaacg gcctcaactc agctatcaag  1200
cgccatcggc tggccagctg gatcaaatca caggatccaa gcgtttgttg catccaagag  1260
acccacctga cctgtagaga tactcaccgc ctcaagatca agggatggcg aaagatttat  1320
caggcgaacg gtaagcagaa gaaagccgga gtcgcaattc tggtctcaga caagacggat  1380
ttcaagccca ccaaaattaa gcgtgataag gaaggtcact atattatggt gaaaggcagc  1440
atacagcagg aagaacttac catattgaac atctacgcgc caaacaccgg cgcacctcgc  1500
tttatcaaac aggtcctgtc cgatctgcag cggagatcgg attctcatac gttgattatg  1560
ggtgatttca atacaccatt gagcaccctg gatcgcagca ccaggcaaaa ggtaaataaa  1620
gacacgcaag agctcaatag cgcactgcat caggcagatc tcattgatat ttatcgcact  1680
cttcatccta agagtaccga gtacacattc ttcagcgccc cacatcatac atactcaaag  1740
atcgatcata tcgtcggctc aaaggctctg ctgtcaaagt gcaagcgcac agagataatt  1800
acaaattacc tgtcagatca tagcgcgatc aagctcagac tgaagaatcaa gaacctgacc  1860
cagagccgga gtaccacttg gaagcttaat aacctgctgc tcaacgatta ttgggtccac  1920
aatgagatga aggcagagat taaaatgttc ttcgaaacaa atgagaataa ggatactacc  1980
tatcaaaacc tttgggatgc ctttaaggcc gtctgcagag gcaagttcat cgccctcaac  2040
gcctataaaa gaaaacaaga gagatctaag atcgatacct tcacctctca gctgaaggag  2100
ttggagaaac aggaacagac ccactccaag gcgtcaagac ggcaggagat cacaaagatt  2160
cgcgccgagt tgaaagagat cgaaacccaa aagactcttc agaaaattaa cgagtctcgt  2220
agttggttct tcgagcggat taataagata gacagacctg tggcacgact gattaagaag  2280
aagcgcgaaa agaaccagat tgataccatc aagaacgaca agggcgacat cactactgac  2340
ccgaccgaga tccagaccac tattcggag tattataagc atttgtatgc taacaagctt  2400
gagaacctgg aagagatgga cactttctg gatacctata ctctgccacg gcttaatcaa  2460
gaggaagtcg agtccctcaa ccgcccaatt acaggaagcg agattgtggc cataattaac  2520
tccctgccga caaagaaatc tcctggtccg gacggggttta cagctgagtt ttatcaacgg  2580
tatatggaag agcttgtacc gtttctgctc aagctctttc agtctataga aaaggaaggc  2640
atcttgccca attccttcta cgaagcttct ataatactta ttcccaaacc aggacgcgat  2700
accacaaaga aggaaaactt ccggcccatt agtctcatga atatcgacgc taaaatattg  2760
aacaagattc tcgccaacag aatccaacaa catattaaga aattgataca tcacgaccag  2820
gtggggttta tacctggcat gcagggctgg tttaacatcc ggaagagtat taacgtcatt  2880
caacacatta atagagctaa ggataagaat catatgatca tctctataga cgcggaaaag  2940
gcattcgata agattcagca gccatttatg ctcaagactc tgaacaaact cggcatcgac  3000
ggaacatatt ttaagattat tcgcgcaatt tacgataagc cgactgctaa cattatcctt  3060
aacggccaaa agctcgaggc ctttccgctc aagactggaa cccgccaagg ctgtccctc  3120
tcccgctttt tgtttaatat tgtactcgag gtgctggcta gggctattcg tcaagagaaa  3180
gagattaaag ggatacagct cgggaaggaa gaggtcaagc tttccttgtt cgccgatgat  3240
atgattgtgt acctggagaa tcctattgtg tctgctcaga accttcttaa acttatttct  3300
aactttagca aggtcagcgg ctataagatt aacgtccaga aatctcaggc ctttctgtac  3360
acaaataatc gacagaccga atcccagata atgggtgagc ttccgtttgt catagccagc  3420
aaaaggataa agtatctcgg aatccagctg acacgagacg ttaaagattt gtttaaggaa  3480
aattacaagc ctctcctgaa agagattaag gaagatacta ataagtggaa gaatatcccc  3540
tgttcatggg ttggcagaat caacatagtg aagatgacaa tacttcctaa agtagatatat  3600
cgctttaacg ccatcccaat taaactgcct atgaccttct ttacggacgt cgagaaaaca  3660
acccttaaat ttatatggaa tcaaaagaga gcaagaatag cgaagtccat cttgagccag  3720
aagaataagg ccggtgggat tactttgcct gatttaagt tgtattataa agccacagta  3780
actaagacag cctggtattg gtatcagaat agagacatcg accagtggaa tcggaccgaa  3840
ccatcagaga taatgccca catctataat taccttatat tcgataagcc agaaaagaat  3900
aaacagtggg gcaaagacag cctcttcaac aagtggtgtt gacggaatg gctggccata  3960
tgccggaaac tcaagctcga ccccttctctt acaccctaca ctaaaatcaa cagtaggtgt  4020
atcaaggact tgaatgtcaa gccaaagact ataaagacac tggaagagaa tcttgggatc  4080
acaatacaag atataggcgt cggcaaagat tttatgtcaa agacgcccaa ggccatggcc  4140
actaaggata agattgataa gtgggacctt attaagctca aaagcttctg tactgccaag  4200
gagaccacga tcagagttaa taggcagccc actacatggg aaaagatttt cgccacttat  4260
```

-continued

```
tcatcagata aggggttgat aagcagaata tataacgagc tgaagcagat ctacaagaag   4320
aaaacgaata atcccatcaa gaagtgggca aaagatatga acaggcattt tagcaaaagag  4380
gatatctacg ccgcgaagaa gcatatgaag aagtgtagtt caagcttggc cattcgtgag   4440
atgcagatta agacgaccat gcgataccac cttaccccag tgaggatggc aattatcaag   4500
aaatctggca ataatagatg ttggcggggc tgtggcgaga ttggcaccct gctccattgc   4560
tggtgggatt gcaagctggt gcagccgctt tggaaatcag tctggcgctt tctgagggac   4620
ctcgagcttg agattccctt cgatcccgca attcccttgc tcggaatcta tcctaacgaa   4680
tacaagagct gttgttacaa ggatacgtgt acccggatgt tcatcgcggc cttgtttacg   4740
atagctaaga cgtggaatca gcctaagtgc cccacaatga tcgattggat caagaaaatg   4800
tggcatattt ataccatgga gtattacgca gcaattaaga atgacgaatt tatttccttc   4860
gttgggacct ggatgaagct ggagactatt attctgagca agctgtctca ggagcaaaag   4920
acaaagcata gaatcttctc tctcattggt ggtaacgact acaaagacga tgacgacaag   4980
taaagcgctt ctagaagttg tctcctcctg cactgactga ctgatacaat cgatttctgg   5040
atccgcaggc ctaatcaacc tctggattac aaaatttgtg aaagattgac tggtattctt   5100
aactatgttg ctccttttac gctatgtgga tacgctgctt taatgccttt gtatcatgct   5160
attgcttccc gtatggcttt cattttctcc tccttgtata aatcctggtt gctgtctctt   5220
tatgaggagt tgtggcccgt tgtcaggcaa cgtggcgtgg tgtgcactgt gtttgctgac   5280
gcaaccccca ctggttgggg cattgccacc acctgtcagc tcctttccgg gactttcgct   5340
ttcccctcc ctattgccac ggcggaactc atcgccgcct gccttgcccg ctgctggaca    5400
ggggctcggc tgttgggcac tgacaattcc gtggtgttgt cggggaagct gacgtccttt   5460
ccatggctgc tcgcctgtgt tgccacctgg attctgcgcg ggacgtcctt ctgctacgtc   5520
ccttcggccc tcaatccagc ggaccttcct tcccgctgag agacacaaaa aattccaaca   5580
cactattgca atgaaaataa atttccttta ttagccagaa gtcagatgct caaggggctt   5640
catgatgtcc ccataatttt tggcagaggg aaaaagatct cagtggtatt tgtgagccag   5700
ggcattggcc ttctgatagg cagcctgcac ctgaggagtg cggccgcttt acttgtacag   5760
ctcgtccatg ccgagagtga tcccggccggc ggtcacgaac tgcacagga ccatgtgatc    5820
gcgcttctcg ttggggtctt tgctcagggc ggactgggtg ctcaggtagt ggttgtcggg   5880
cagcagcacg gggccgtcgc cgatggggggt gttctgctgg tagtggtcgg cgagctgcac   5940
gctgccgtcc tcgatgttgt ggcggatctt gaagttcacc ttgatgccgt tcttctgctt   6000
gtcggccatg atatagacgt tgtggctgtt gtagttgtac tccagcttgt gccccaggat   6060
gttgccgtcc tccttgaagt cgatgcccttt cagctcgatg cggttcacca gggtgtcgcc   6120
ctcgaacttc acctcggcgc gggtcttgta gttgccgtcg tccttgaaga gatggtgcg    6180
ctcctggacg tagccttcgg gcatggcgga cttgaagaag tcgtgctgct tcatgtggtc   6240
ggggtagcgg ctgaagcact gcacgccgta ggtcagggtg gtcacgaggg tgggccaggg   6300
cacgggcagc ttgccggtgg tgcagatgaa cttcagggtc agcttgccgt aggtggcatc   6360
gccctcgccc tcgccggaca cgctgaactt gtggccgttt acgtcgccgt ccagctcgac   6420
caggatgggc accacccggg tgaacagctc ctcgcccttg ctcaccatgg tggcgggatc   6480
tgacggttca ctaaaccagc tctgcttata tagacctccc accgtacacg cctaccgccc   6540
atttgcgtca atggggcgga gttgttacga catttttggaa agtcccgttg attttggttgc   6600
caaaacaaac tcccattgac gtcaatgggg tggagacttg gaaatccccg tgagtcaaac   6660
cgctatccac gcccattgat gtactgccaa aaccgcatca ccatggtaat agcgatgact   6720
aatacgtaga tgtactgcca agtaggaaag tcccataagg tcatgtactg ggcataatgc   6780
caggcgggcc atttaccgtc attgacgtca atagggggcg tacttggcat gatatacact   6840
tgatgtactg ccaagtgggc agtttaccgt aaatactcca cccattgacg tcaatggaaa   6900
gtccctattg gcgttactat gggaacatac gtcattattg acgtcaatgg gcgggggtcg   6960
ttgggcggtc agccaggcgg gccatttacc gtaagttatg taacgggcct gctgccggct   7020
ctgcggcctc ttccgcgtct tcgccttcgc cctcagacga gtcggatctc cctttgggcc   7080
gcctccccgc ctgtctagct tgactgactg agatacagcg taccttcagc tcacagacat   7140
gataagatac attgatgagt ttggacaaac cacaactaga atgcagtgaa aaaaatgctt   7200
tatttgtgaa atttgtgatg ctattgcttt atttgtaacc attataagct gcaataaaca   7260
agtt                                                                7264
```

SEQ ID NO: 39          moltype = DNA   length = 18852
FEATURE                Location/Qualifiers
misc_feature          1..18852
                       note = Description of Artificial Sequence: Synthetic
                       polynucleotide
source                1..18852
                       mol_type = other DNA
                       organism = synthetic construct
SEQUENCE: 39
```
cggccgcggg gggaggagcc aagatggccg aataggaaca gctccggtct acagctccca    60
gcgtgagcga cgcagaagac ggtgatttct gcatttccat ctgaggtacc gggttcatct   120
cactagggag tgccagacag tgggcgcagg ccagtgtgtg cgcgcaccct gcgcgagccg   180
aagcagggcg aggcattgcc tcacctggga agcgcaaggg gtcaggagt tccctttccg     240
agtcaaagaa aggggtgacg gacgcacctg gaaaatcggg tcactcccac ccgaatattg    300
cgcttttcag accggcttaa gaaacggcgc accacgagac tatatcccac acctggctcg    360
gagggtccta cgcccacgga atctcgctga ttgctagcac agcagtctga gatcaaactg    420
caaggcggca acgaggctgg gggaggggcg cccgccattg cccaggcttg cttaggtaaa    480
caaagcagca gggaagctcg aactgggtgg agcccaccac agctcaagga ggcctgcctg    540
cctctgtagg ctccacctct gggggcaggg cacagacaaa caaaaagaca gcagtaacct    600
ctgcagactt aagtgtccct gtctgacagc tttgaagaga gcagtggttc tcccagcacg    660
cagctggaga tctgagaacg ggcagactgc ctcctcaagt gggtccctga ccctgaccc     720
ccgagcagcc taactgggag gcaccccca gcaggggcac actgacacct cacacgcag      780
ggtattccaa cagacctgca gctgagggtc ctgtctgtta aaggaaaac taacaaccag     840
aaaggacatc tacaccgaaa acccatctgt acatcaccat catcaaagac caaaagtaga    900
taaaaccaca aagatgggga aaaaacagaa cagaaaaact ggaaactcta aaacgcagag    960
cgcctctcct cctccaaagg aacgcagttc ctcaccagca acagaacaaa gctggatgga   1020
gaatgatttt gatgagctga gagaagaagg cttcagacga tcaaattact ctgagctacg   1080
```

```
ggaggacatt caaaccaaag gcaaagaagt tgaaaacttt gaaaaaaatt tagaagaatg   1140
tataactaga ataaccaata cagagaagtg cttaaaggag ctgatggagc tgaaaaccaa   1200
ggctcgagaa ctacgtgaag aatgcagaag cctcaggagc cgatgcgatc aactggaaga   1260
aagggtatca gcaatggaag atgaaatgaa tgaaatgaag cgagaaggga agtttagaga   1320
aaaaagaata aaaagaaatg agcaaagcct ccaagaaata tgggactatg tgaaaagacc   1380
aaatctacgt ctgattggtg tacctgaaag tgatgtggag aatggaacca agttggaaaa   1440
cactctgcag gatattatcc aggagaactt ccccaatcta gcaaggcagg ccaacgttca   1500
gattcaggaa atacagagaa cgccacaaag atactcctcg agaagagcaa ctccaagaca   1560
cataattgtc agattcacca aagttgaaat gaaggaaaaa atgttaaggg cagccagaga   1620
gaaaggtcgg gttaccctca aaggaaagcc catcagacta acagcggatc tctcggcaga   1680
aaccctacaa gccagaagag agtgggggggc aatattcaac attcttaaag aaaagaattt   1740
tcaacccaga atttcatatc cagccaaact aagcttcata agtgaaggag aaataaaata   1800
ctttatagac aagcaaatgt tgagagattt tgtcaccacc aggcctgccc taaaagagct   1860
cctgaaggaa gcgctaaaca tggaaaggaa caaccggatc cagccgctgc aaaatcatgc   1920
caaaatgtaa agaccatcaa gactaggaag aaactgcatc aactaatgag caaaatcacc   1980
agctaacatc ataatgacag gatcaacttc acacataaca atattaactt aaatataaaa   2040
tggactaaat tctgcaatta aaagacacag actggcaagt tggataaaga gtcaagaccc   2100
atcagtgtgc tgtattcagg aaacccatct cacgtgcaga gacacacata ggctcaaaat   2160
aaaaggatgg aggaagatct accaagccaa tggaaaacaa aaaaaggcag gggttgcaat   2220
cctagtctct gataaaacag actttaaacc aacaaagatc aaaagagaca aagaaggcca   2280
ttacataatg gtaaagggat caattcaaca agaggagcta actatcctaa atatttatgc   2340
acccaataca ggagcaccca gattcataaa gcaagtcctc agtgacctac aaagagactt   2400
agactcccac acattaataa tgggagactt taacaccccca ctgtcaacat tagacagatc   2460
aacgagacag aaagtcaaca aggatacca ggaattgaac tcagctctgc accaagcaga   2520
cctaatagac atctacagaa ctctccaccc caaatcaaca gaatatacat ttttttcagc   2580
accacaccac acctattcca aaattgacca catagttgga agtaaagctc tcctcagcaa   2640
atgtaaaaga acagaaatta taacaaacta tctctcagac cacagtgcaa tcaaactaga   2700
actcaggatt aagaatctca ctcaaagccg ctcaactaca tggaaactga acaacctgct   2760
cctgaatgac tactgggtac ataacgaaat gaaggcagaa ataaagatgt tctttgaaac   2820
caacgagaac aaagacacca cataccagga tctctggaac gcattcaaag cagtgtgtaga   2880
agggaaattt atagcactaa atgcctacaa gagaaagcag gaaagatcca aaattgacac   2940
cctaacatca caattaaaag aactagaaaa gcaagagcaa acacattcaa aagctagcag   3000
aaggcaagaa ataactaaaa tcagagcaga actgaaggaa atagagacac aaaaaaccct   3060
tcaaaaaatc aatgaatcca ggagctggtt ttttgaaagg atcaacaaaa ttgatagacc   3120
gctagcaaga ctaataaaga aaaaagaga gaagaatcaa atagacacaa taaaaaatga   3180
taaaggggggat atcaccaccg atcccacaga aatacaaact accatcagag aatactacaa   3240
acacctctac gcaaataaac tagaaaatct agaagaaatg gatacattcc tcgacacata   3300
cactctccca agactaaacc aggaagaagt tgaatctctg aatcgaccaa taacaggctc   3360
tgaaattgtg gcaataatca atagtttacc aaccaaaaag agtccaggac cagatggatt   3420
cacagccgaa ttctaccaga ggtacaagga ggaactggta ccattcctct tgaaactatt   3480
ccaatcaata gaaaaagagg gaatcctccc taactcattt tatgaggcca gcatcattct   3540
gataccaaag ccgggcagag acacaaccaa aaaagagaat tttagaccaa tatccttgat   3600
gaacattgat gcaaaaatcc tcaataaaat actggcaaac actgccgaat ccagcatcaa   3660
aaagcttatc caccatgatc aagtgggctt catccctggg atgcaaggct ggttcaatat   3720
acgcaaatca ataaatgtaa tccagcatat aaacagagcc aaagacaaaa accacatgat   3780
tatctcaata gatgcagaaa aagcctttga caaaattcaa caacccttca tgctaaaaac   3840
tctcaataaa ttaggtattg atgggacgta tttcaaaata ataagagcta tctatgacaa   3900
acccacagcc aatatcatac tgaatgggca aaaactggaa gcattcectt tgaaaaccgg   3960
cacaagacag ggatgccctc tctcaccgct cctattcaac atagtgttgg aagttctggc   4020
cagggcaatc aggcaggaga aggaaataaa gggtattcaa ttaggaaaag aggaagtcaa   4080
attgtccctg tttgcagacg acatgattgt ttatctagaa aaccccatcg tctcagccca   4140
aaatctcctt aagctgataa gcaacttcag caaagtctca ggatacaaaa tcaatgtaca   4200
aaaatcacaa gcattcttat acaccaacaa cagacaaaca gagagccaaa tcatgggtga   4260
actcccattc acaattgctt caaagagaat aaaataccta ggaatccaac ttacaaggga   4320
tgtgaaggac ctcttcaagg agaactacaa accactgctc aaggaaataa aagaggagac   4380
aaacaaatgg aagaacattc catgctcatg ggtaggaaga atcaatatcg tgaaaatggc   4440
catactgccc aaggtaattt acagattcaa tgccatcccc atcaagctac caatgacttt   4500
cttcacagaa ttggaaaaaa ctactttaaa gttcatatgg aaccaaaaaa gagcccgcat   4560
tgccaagtca atcctaagcc aaaagaacaa agctggaggc atcacactac ctgacttcaa   4620
actatactac aaggctacag taaccaaaac agcatggtac tggtaccaaa acagagatat   4680
agatcaatgg aacagaacag agccctcaga ataatgccg catatctaca actatctgat   4740
ctttgacaaa cctgagaaaa acaagcaatg gggaaaggat tccctattta ataaatggtg   4800
ctgggaaaac tggctagcca tatgtagaaa gctgaaactg gatccttcc ttacacctta   4860
tacaaaaatc aattcaagat ggattaaaga tttaaacgtt aaaacctaaaa ccataaaaac   4920
cctagaagaa aacctaggca ttaccattca ggacataggc gtgggcaagg acttcatgtc   4980
caaaacacca aaagcaatgg caacaaaaga caaaattgac aaatgggatc taattaaact   5040
aaagagcttc tgcacagcaa aagaaactac catcagagtg aacaggcaac ctacaacatg   5100
ggagaaaatt tttgcaacct actcatctga caaagggcta atatccagaa tctacaatga   5160
actcaaacaa atttacaaga aaaaaacaaa caaccccatc aaaaagtggg cgaaggacat   5220
gaacagacac ttctcaaaag aagacattta tgcagccaaa aaacacatga agaaatgctc   5280
atcatcactg gccatcagag aaatgcaaat caaaaccact atgagatatc atctcacacc   5340
agttagaatg gcaatcatta aaagtcagg aaacaacagg tgctggagag gatgcggaga   5400
aataggaaca cttttacact gttggtggga ctgtaaacta gttcaaccat tgtggaagtc   5460
agtgtggcga ttcctcaggg atctagaact agaaatacca tttgacccag ccatcccatt   5520
actgggtata tacccaaatg agtataaatc atgctgctat aaagacacat gcacacgtat   5580
gtttattgcg gcactattca caatagcaaa gacttggaac caacccaaat gtccaacaat   5640
gatagactgg attaagaaaa tgtggcacat atacaccatg gaatactatg cagccataaa   5700
aaatgatgag ttcatatcct ttgtagggac atggatgaaa ttggaaacca tcattctcag   5760
taaactatcg caagaacaaa aaaccaaaca ccgcatattc tcactcatag gtgggaattg   5820
```

-continued

```
aacaatgaga tcacatggac acaggaaggg gaatatcaca ctctgggac tgtggtgggg   5880
tcggggagg ggggagggat agcattggga gatataccta atgctagatg acacattagt   5940
gggtgcagcg caccagcatg gcacatgtat acggatccga attctcgacg gatcgatccg   6000
aacaaacgac ccaacacccg tgcgttttat tctgtctttt tattgccgat cccctcagaa   6060
gaactcgtca agaaggcgat agaaggcgat gcgctgcgaa tcgggagcgg cgataccgta   6120
aagcacgagg aagcggtcag cccattcgcc gccaagctct tcagcaatat cacgggtagc   6180
caacgctatg tcctgatagc ggtcggccgc tcatgttctc gtaggagtcg gcgtcctctt   6240
cgtggttagg tccaggttgg cctctgatag accgcagctg aggagcggcg tacagaatgc   6300
ctctcatgtc ctcatagctg ccgctgcctt gtggaggctt ctcgtgcttc agtgtctcgt   6360
atgtctcttg attccgggtg ctcaggccgg tgtacacgcc atcagatttc tcgtagctgg   6420
tgatggcggc cttccggcact tggatcttca gccgtctgca gtacagggtg atgaccagag   6480
acagcagcag gacaccacat gtgccagcca gaggggccca aatgtagata tccaggcctc   6540
tggtatgcac agctccgcct gcagcaggtc tacaggcttc aggtctgaga gacagaggct   6600
ggctggcgat tgtaggagct ggtgtaggtg gtctaggagc gggtgttgtt gtaggcttgg   6660
cgggcagaaa cacgggcacg aagtggctga agtacatgat gctattgctc agggctccgc   6720
ttcctccgcc gcctgatttg atttccagct tggtgcctcc gccaaatgtc caagggctct   6780
cgtcgtactg ctggcagtag tagatgccga agtcctcgta ctgcaggctg ctgattgtca   6840
gggtgtagtc ggtgccagag ccgctgccag aaaatctgct tggcacgccg cttccagtc   6900
tgttggcccg gtagatcagt gtcttagggg ccttgccagg cttctgctgg aaccagctca   6960
ggtagctgtt gatgtcctgg ctggctctac aggtgatggt cactctatcg cccacagagg   7020
cagacaggct gctagggctc tgtgtcatct ggatatcaga gccaccaccg ccagatccac   7080
cgccacctga tcctccgcct ccgctagaaa ctgtcactgt ggtgccctgg ccccacacat   7140
cgaagtacca gtcgtagcct cttctggtgc agaagtacac ggcggtatcc tcggctctca   7200
ggctgttgat ctgcaggtag gcggtgttct tgctgtcgtc caggctgaag gtgaatctgc   7260
ccttaaagct atcggcgtag gttggctcgc cggtgtgggg attgatccag cccatccact   7320
caaggccagg tgagtccagg agatgtttca gcactgttgc ctttagtctc gaggcaactt   7380
agacaactga gtattgatct gagcacagca gggtgtgagc tgtttgaaga tactgggGtt   7440
gggggtgaag aaactgcaga ggactaactg ggctgagacc cagtggcaat gttttagggc   7500
ctaaggaatg cctctgaaaa tctagatgga caactttgac tttgagaaaa gagaggtgga   7560
aatgaggaaa atgactttc tttattagat ttcggtagaa agaactttca tcttccct     7620
attttttgtta ttcgttttaa aacatctatc tggaggcagg acaagtatgg tcattaaaaa   7680
gatgcaggca gaaggcatat attggctcag tcaaagtggg gaactttggt ggccaaacat   7740
acattgctaa ggctattcct atatcagctg gacacatata aaatgctgct aatgcttcat   7800
tacaaactta tatcctttaa ttccagatgg gggcaaagta tgtccagggg tgaggaacaa   7860
ttgaaacatt tgggctggag tagatttga aagtcagctc tgtgtgtgtg tgtgtgtgtg   7920
tgtgtgtgag agcgtgtgtt tcttttaacg ttttcagcct acagcataca gggttcatgg   7980
tggcaagaag ataacaagat ttaaaattatg gccagtgact agtgctgcaa gaagaacaac   8040
tacctgcatt taatgggaaa gcaaaatctc aggctttgag ggaagttaac ataggcttga   8100
ttctggggtg aagctgggtg tgtagttatc tggaggccag gctggagctc tcagctcact   8160
atgggttcat ctttattgtc tccttttcc aggggcctgt cggacccagt tcatgccgta   8220
gttggtgaag gtgtagccgc tggcggcaca gctgattctg acagatccgc caggtttcac   8280
aagtccgccg ccagactgaa ccagctggat ctcagagatg ctacaggcca ctgttcccag   8340
cagcagcaga gactgcagcc acatctggtg gcgaattcga agcttgacct gcgagatctga   8400
gtccggtagc gctagcggat ctgacgggtc actaaaccag ctctgcttat atagacctcc   8460
caccgtacac gcctaccgcc catttgcgtc aatggggcgg agttgttacg acattttgga   8520
aagtcccgtt gattttggtg ccaaaacaaa ctcccattga cgtcaatggg gtggagactt   8580
ggaaatcccc gtgagtcaaa ccgctatcca cgcccattga tgtactgcca aaaccgcatc   8640
accatggtaa tagcgatgac taatacgtag atgtactgcc aagtaggaaa gtcccataag   8700
gtcatgtact gggcataatg ccaggcgggc catttaccgt cattgacgtc aataggggc    8760
gtacttggca tatgatacac ttgatgtact gccaagtggg cagtttaccg taaatactcc   8820
acccattgac gtcaatggaa agtccctatt ggcgttacta tgggaacata cgtcattatt   8880
gacgtcaatg ggcggggggtc gttgggcggt cagccaggcg ggccatttac cgtaagttat   8940
gtaacgcgga actccatata tgggctatga actaatgacc ccgtaattga ttactattag   9000
cccgggggat ccagacatga taagatacat tgatgagttt ggacaaacca caactagaat   9060
gcagtgaaaa aaatgcttta tttgtgtgaaat ttgtgatgct attgctttat ttgtaaccat   9120
tataagctgc aataaacaag ttaacaacaa caattgcatt cattttatgt ttcaggttca   9180
gggggaggtg tggggaggtt tttaaagcaa gtaaaacctc tacaaatgtg gtatggctga   9240
ttatgatccg gctgcctcgc gcgtttcggt gatgacggtg aaaacctctg acacatgcag   9300
ctcccggaga cggtcacagc ttgtctgtaa gcggatgccg ggagcagaca agcccgtcag   9360
ggcgcgtcag cgggtgttgg cgggtgtcgg gcgcagcca tgagggtcgat cgactctaga   9420
ggatcgatcc ccgcccgga cgaactaaac ctgactacga catctctgcc ccttcttcgc   9480
ggggcagtgc atgtaatccc ttcagttggt tggtacaact tgccaactgg gccctgttcc   9540
acatgtgaca cggggggggga ccaaacacaa aggggttctc tgactgtagt tgacatcctt   9600
ataaatggat gtgcacattt gccaacactg agtggcttc atcctggagac agactttgca   9660
gtctgtggac tgcaacacaa cattgcctt atgtgtaact cttggctgaa gctcttacac   9720
caatgctggg ggacatgtac ctcccagggg cccaggaaga ctacgggagg ctacaccaac   9780
gtcaatcaga ggggcctgtg tagctaccga taagcggacc ctcaagaggg cattagcaat   9840
agtgtttata aggcccccctt gttaaccota aacgggtagc atatgcttcc cgggtagtag   9900
tatatactat ccagactaac cctaattcaa tagcatatgt tacccaacgg gaagcatatg   9960
ctatcgaatt agggttagta aaaggggtcct aaggaacagc gatatctccc accccatgag  10020
ctgtcacggt tttatttaca tggggtcagg attccacgag ggtagtgaac catttttagtc  10080
acaagggcag tggctgaaga tcaaggagcg ggcagtgaac tctcctgaat cttcgcctgc  10140
ttcttcattc tccttcgttt agctaataga ataactgctg agttgtgaac agtaaggtgt  10200
atgtgagtg ctcgaaaaca aggtttcagg tgacgccccc agaataaaat ttggacgggg  10260
ggttcagtgg tggcattgtg ctatgacacc aatataaccc tcacaaaccc cttgggcaat  10320
aaatactagt gtaggaatga aacattctga atatctttaa caatagaaat ccatgggtg   10380
gggacaagcc gtaaagactg gatgtccatc tcacacgaat ttatggctat gggcaacaca  10440
taatcctagt gcaatatgat actgggggtta ttaagatgtg tcccaggcag ggaccaagac  10500
aggtgaacca tgttgttaca ctctatttgt aacaagggga aagagagtgg acgccgacag  10560
```

-continued

```
cagcggactc cactggttgt ctctaacacc cccgaaaatt aaacggggct ccacgccaat  10620
gggggcccata aacaaagaca agtgccact  ctttttttttg aaattgtgga gtggggggcac  10680
gcgtcagccc ccacacgccg ccctgcggtt ttggactgta aaataagggt gtaataactt  10740
ggctgattgt aaccccgcta accactgcgg tcaaaccact tgcccacaaa accactaatg  10800
gcaccccggg gaatacctgc ataagtaggt gggcgggcca agataggggc gcgattgctg  10860
cgatctggag gacaaattac acacacttgc gcctgagcgc caagcacagg gttgttggtc  10920
ctcatattca cgaggtcgct gagagcacgg tgggctaatg ttgccatggg tagcatatac  10980
tacccaaata tctggatagc atatgctatc ctaatctata tctgggtagc ataggctatc  11040
ctaatctata tctgggtagc atatgctatc ctaatctata tctgggtagt atatgctatc  11100
ctaatttata tctgggtagc ataggctatc ctaatctata tctgggtagc atatgctatc  11160
ctaatctata tctgggtagt atatgctatc ctaatctgta tccgggtagc atatgctatc  11220
ctaatagaga ttagggtagt atatgctatc ctaatttata tctgggtagc atatactacc  11280
caaatatctg gatagcatat gctatcctaa tctatatctg ggtagcatat gctatcctaa  11340
tctatatctg ggtagcatag gctatcctaa tctatatctg ggtagcatat gctatcctaa  11400
tctatatctg ggtagtatat gctatcctaa tttatatctg ggtagcatag gctatcctaa  11460
tctatatctg ggtagcatat gctatcctaa tctatatctg ggtagtatat gctatcctaa  11520
tctgtatccg ggtagcatat gctatcctca tgcatataca gtcagcatat gatacccagt  11580
agtagagtgg gagtgctatc ctttgcatat gccgccacct cccaagggggg cgtgaatttt  11640
cgctgcttgt cctttttcctg catgctggtt gctcccattc ttaggtgaat ttaaggaggc  11700
caggctaaag ccgtcgcatg tctgattgct caccaggtaa atgtcgctaa tgttttccaa  11760
cgcgagaagg tgttgagcgc ggagctgagt gacgtgacaa catgggtatg cccaattgcc  11820
ccatgttggg aggacgaaaa tggtgacaag acagatggcc agaaatacac caacagcacg  11880
catgatgtct actgggggatt tattctttag tgcgggggaa tacacggctt ttaatacgat  11940
tgagggcgtc tcctaacaag ttacatcact cctgcccttc ctcaccctca tctccatcac  12000
ctccttcatc tccgtcatct ccgtcatcac cctccgcggc agccccttcc accataggtg  12060
gaaaccaggg aggcaaatct actccatcgt caaagctgca cagtcacc ctgatattgc  12120
aggtaggagc gggctttgtc ataacaaggt ccttaatcgc atccttcaaa acctcagcaa  12180
atatatgagt ttgtaaaaag accatgaaat aacagacaat ggactcccctt agcgggccag  12240
gttgtgggcc gggtccaggg gccattccaa aggggagacg actcaatggt gtaagacgac  12300
attgtggaat agcaagggca gttcctcgcc ttaggttgta aagggaggtc ttactacctc  12360
catatacgaa cacaccggcg acccaagttc cttcgtcggt agtcctttct acgtgactcc  12420
tagccaggag agctcttaaa ccttctgcaa tgttctcaaa tttcggggttg gaacctcctt  12480
gaccacgatg ctttccaaac caccctcctt ttttgcgcct gcctccatca ccctgacccc  12540
ggggtccagt gcttgggcct tctcctgggt catctgcggg gccctgctct atcgctcccg  12600
ggggcacgtc aggctcacca tctgggccac cttcttggtg gtattcaaaa taatcggctt  12660
cccctacagg gtggaaaaat ggccttctac ctggagggg cctgcgcggt ggagacccgg  12720
atgatgatga ctgactactg ggactcctgg gcctctttttc tccacgtcca cgacctctcc  12780
ccctggctct ttcacgactt ccccccctgg ctctttcacg tcctctaccc cggcggcctc  12840
cactacctcc tcgacccccgg cctccactac ctcctcgacc ccggcctcca ctgcctcctc  12900
gaccccggcc tccacctcct gctcctgccc ctcctgctcc tgcccctcct cctgctcctg  12960
ccctcctgc ccctcctgct cctgcccctc ctgcccctcc tgctcctgcc cctcctgccc  13020
ctcctgctcc tgcccctcct gcccctcctc ctgctcctgc ccctcctgcc cctcctgctg  13080
ctcctgcccc tcctgcctctg ccctcctgcc cctcctgctg  13140
ctgcccctcc tgctcctgcc cctcctgctc ctgcccctcc tgctcctgcc cctcctgctc  13200
ctgcccctcc tgctcctgcc ccctcctgc cctcctgctg ctgcccctcc tgcccctcc  13260
ctgcccctcc tgctcctgcc ctcctcctgc tcctgccccct cctgcccctc  13320
ctgcccctcc tcctgctcct gccctctg ccctcctgc tgctcctgc  13380
ctcctgcccc tcctgcccct cctgcccctc ctcctgctcc tgcccctcct gccctcctc  13440
ctgctcctgc ccctcctcct gctcctgccc ctcctgcccc tcctgcccct cctcctgctc  13500
ctgcccctcc tcctgctcct gccccctgc ccctcctgc cctcctgcc cctcctcctg  13560
ctcctgcccc tcctcctgct cctgcccctc ctgctcctgc cctcctgctg  13620
ctcctgttcc accgtgggtc cctttgcagc caatgcaact tggacgtttt tggggtctcc  13680
ggacaccatc tctatgtctt ggccctgatc ctgagccgcc cgggggctcct ggtcttccgc  13740
ctcctcgtcc tcgtcctctt ccccgtcctc gtccatggtt atcacccct cttctttgag  13800
gtccactgcc gccggagcct tctggtccag atgtgtctcc cttctctcct aggccatttc  13860
caggtcctgt acctggcccc tcgtcagaca tgattcacac taaaagagat caatagacat  13920
ctttattaga cgacgctcag tgaatacagg gagtgcagac tcctgccccc tccaacagcc  13980
ccccacccct catcccctttc atggtcgctg tcagacagat ccaggtctga aaattccccca  14040
tcctccgaac catcctcgtc ctcatcacca attactcgca gcccggaaaa ctcccgctga  14100
acatcctcaa gatttgcgtc ctgagcctca agccaggcct caaattcctc gtccccctttt  14160
ttgctggacg gtagggatgg ggattctcgg gaccctcct cttcctcttc aaggtcacca  14220
gacagagatg ctactggggc aacggaagaa aagctgggtg cggcctgtga ggatcagctt  14280
atcgatgata agctgtcaaa catgagaatt cttgaagacg aaagggcctc gtgatacgcc  14340
tattttttata ggttaatgtc atgataataa tggtttctta gacgtcaggt ggcacttttca  14400
gggggaaatgt gcgcggaacc cctatttgtt tattttttcta aatacattca aaatatgtatc  14460
cgctcatgag acaataaccc tgataaatgc ttcaataata ttgaaaaagg aagagtatga  14520
gtattcaaca tttccgtgtc gcccttattc ccttttttgc ggcattttgc cttcctgttt  14580
ttgctcaccc agaaacgctg gtgaaagtaa aagatgctga agatcagttg ggtgcacgag  14640
tgggttacat cgaactggat ctcaacagcg gtaagatcct tgagagtttt cgccccgaag  14700
aacgttttcc aatgatgagc acttttaaag ttctgctatg tggcgcggta ttatcccgtg  14760
ttgacgccgg gcaagagcaa ctcggtcgcc gcatacacta ttctcagaat gacttggttg  14820
agtactcacc agtcacagaa aagcatctta cggatggcat gacagtaaga gaattatgca  14880
gtgctgccat aaccatgagt gataacactg cggccaactt acttctgaca acgatcggag  14940
gaccgaagga gctaaccgct tttttgcaca acatgggggga tcatgtaact cgccttgatc  15000
gttgggaacc ggagctgaat gaagccatac caaacgacga gcgtgacacc acgatgcctg  15060
cagcaatggc aacaacgttg cgcaaactat taactggcga actacttact ctagcttccc  15120
ggcaacaatt aatagactgg atggaggcgg ataaagttgc aggaccactt ctgcgctcgg  15180
cccttccggc tggctggttt attgctgata aatctggagc cggtgagcgt gggtctcgcg  15240
gtatcattgc agcactgggg ccagatggta agccctcccg tatcgtagtt atctacacga  15300
```

```
cggggagtca ggcaactatg gatgaacgaa atagacagat cgctgagata ggtgcctcac   15360
tgattaagca ttggtaactg tcagaccaag tttactcata tatactttag attgatttaa   15420
aacttcattt ttaatttaaa aggatctagg tgaagatcct ttttgataat ctcatgacca   15480
aaatccctta acgtgagttt tcgttccact gagcgtcaga ccccgtagaa aagatcaaag   15540
gatcttcttg agatcctttt tttctgcgcg taatctgctg cttgcaaaca aaaaaaccac   15600
cgctaccagc ggtggtttgt ttgccggatc aagagctacc aactcttttt ccgaaggtaa   15660
ctggcttcag cagagcgcag ataccaaata ctgtccttct agtgtagccg tagttaggcc   15720
accacttcaa gaactctgta gcaccgccta catacctcgc tctgctaatc ctgttaccag   15780
tggctgctgc cagtggcgat aagtcgtgtc ttaccgggtt ggactcaaga cgatagttac   15840
cggataaggc gcagcggtcg ggctgaacgg ggggttcgtg cacacagccc agcttggagc   15900
gaacgaccta caccgaactg agatacctac agcgtgagct atgagaaagc gccacgcttc   15960
ccgaagggag aaaggcggac aggtatccgg taagcggcag ggtcggaaca ggagagcgca   16020
cgagggagct tccaggggga aacgcctggt atctttatag tcctgtcggg tttcgccacc   16080
tctgacttga gcgtcgattt ttgtgatgct cgtcagggggg gcggagccta tggaaaaacg   16140
ccagcaacgc ggcctttttta cggttcctgg ccttttgctg gccttttgct cacatgttct   16200
ttcctgcgtt atcccctgat tctgtggata accgtattac cgcctttgag tgagctgata   16260
ccgctcgccg cagccgaacg accgagcgca gcgagtcagt gagcgaggaa gcggaagagc   16320
gcctgatgcg gtattttctc cttacgcatc tgtgcggtat ttcacaccgc atatggtgca   16380
ctctcagtac aatctgctct gatgccgcat agttaagcca gctgtggaat gtgtgtcagt   16440
tagggtgtgg aaagtcccca ggctccccag caggcagaag tatgcaaagc atgcatctca   16500
attagtcagc aaccaggtgt ggaaagtccc caggctcccc agcaggcaga agtatgcaaa   16560
gcatgcatct caattagtca gcaaccatag tcccgcccct aactccgccc atcccgcccc   16620
taactccgcc cagttccgcc cattctccgc cccatggctg actaatttttt tttatttatg   16680
cagaggccga ggccgcctcg gcctctgagc tattccagaa gtagtgagga ggcttttttg   16740
gaggcctagg cttttgcaaa aagcttgcat gcctgcaggt cggccgccac gaccggtgcc   16800
gccaccatcc cctgacccac gcccctgacc cctcacaagg agacgacctt ccatgaccga   16860
gtacaagccc acggtgcgcc tcgcacccg cgacgacgtc ccccgggccg tacgcaccct   16920
cgccgccgcg ttcgccgact acccccgcca cgcgccacacc gtcgacccgg accgccacat   16980
cgagcgggtc accgagctgc aagaactctt cctcacgcgc gtcgggctcg acatcggcaa   17040
ggtgtgggtc gcggacgacg gcgcccgcggt ggcggtctgg accacgccgg agagcgtcga   17100
agcggggggcg gtgttcgccg agatcggccc gcgcatggcc gagttgagcg gttcccggct   17160
ggccgcgcag caacagatgg aaggcctcct ggcgccgcac cggcccaagg agcccgcgtg   17220
gttcctggcc accgtcggcg tctcgcccga ccaccagggc aagggtctgg gcagcgccgt   17280
cgtgctcccc ggagtggagg cggccgagcg cgccgggggtg cccgccttcc tggagacctc   17340
cgcgccccgc aacctccect tctacgagcg gctcggcttc accgtcaccg ccgacgtcga   17400
ggtgcccgaa ggaccgcgca cctggtgcat gacccgcaag cccggtgcct gacgcccgcc   17460
ccacgacccg cagcgcccga ccgaaaggag cgcacgaccc catggctccg accgaagccg   17520
acccgggcgg ccccgccgac cccgcacccg ccccccgaggc ccaccgactc tagaggatca   17580
taatcagcca taccacattt gtagaggttt tacttgcttt aaaaaacctc ccacacctcc   17640
ccctgaacct gaaacataaa atgaatgcaa ttgttgttgt taacttgttt attgcagctt   17700
ataatggtta caaataaagc aatagcatca caaatttcac aaataaagca ttttttttcac   17760
tgcattctag ttgtggtttg tccaaactca tcaatgtatc ttatcatgtc tggatcactc   17820
gccgatagtg aaaaccgacg ccccagcact cgtccgaggg caaaggaata ggggagatgg   17880
gggaggctaa ctgaaacacg gaaggagaca ataccggaag gaacccgcgc tatgacggca   17940
ataaaaagac agaataaaac gcacgggtgt tgggtcgttt gttcataaac gcggggttcg   18000
gtcccagggc tggcactctg tcgatacccc accgagaccc cattgggcc aatacgcccg   18060
cgtttcttcc ttttccccac cccacccccc aagttcgggt gaaggcccag ggctcgcagc   18120
caacgtcggg gcggcaggcc ctgccatagc cactggcccc gtgggttagg gacggggtcc   18180
cccatgggga atggtttatg gttcgtgggg gttattattt tgggcgttgc gtggggtctg   18240
gtccacgact ggactgagca gacagaccca tggttttttgg atggcctggg catggaccgc   18300
atgtactggc gcgacacgaa caccggggcgt ctgtggctgc caaacacccc cgaccccaa   18360
aaaccaccgc gcggatttct ggcgtgccaa gctagtcgac caattctcat gtttgacagc   18420
ttatcatcgc agatccgggc aacgttgttg cattgctgca ggcgcagaac tggtaggtat   18480
ggaagatctc tagaagctgg gtaccagctg ctagcaagct tgctagcggc cggctcgagt   18540
ttactcccta tcagtgatag agaacgtatg tcgagtttac tcccttatca tgatagagaa   18600
cgatgtcgag tttactccct atcagtgata gagaacgtat gtcgagttta ctccctatca   18660
gtgatagaga acgtatgtcg agtttactcc ctatcagtga tagagaacgt atgtcgagtt   18720
tatccctatc agtgatagag aacgtatgtc gagtttactc cctatcagtg atagagaacg   18780
tatgtcgagg taggcgtgta cggtgggagg cctatataag cagagctcgt ttagtgaacc   18840
gtcagatcgc cg                                                       18852

SEQ ID NO: 40              moltype = DNA   length = 19625
FEATURE                    Location/Qualifiers
misc_feature              1..19625
                          note = Description of Artificial Sequence: Synthetic
                           polynucleotide
source                    1..19625
                          mol_type = other DNA
                          organism = synthetic construct
SEQUENCE: 40
cggccgcggg gggaggagcc aagatggccg aataggaaca gctccggtct acagctccca   60
gcgtgagcga cgcagaagac ggtgatttct gcatttccat ctgaggtacc gggttcatct   120
cactaggggag tgccagacag tgggcgcagg ccagtgtgtg tgcgcaccgt gcgcgagccg   180
aagcagggcg aggcattgcc tcacctggga agcgcaaggg gtcagggagt tccctttccg   240
agtcaaagaa aggggtgacg gacgcacctg gaaaatcggg tcactcccac ccgaatattg   300
cgcttttcag accggcttaa gaaacggcgc accacgagac tatatcccac acctggctcg   360
gagggtcctc gcccacggaa tctcgctga ttgctagcac agcagtctga gatcaaactg   420
caaggcggca acgaggctgg gggaggggcg cccgccattg cccaggcttg cttaggtaaa   480
caaagcagca gggaagctcg aactgggtgg agcccaccac agctcaagga ggcctgcctg   540
```

-continued

```
cctctgtagg ctccacctct gggggcaggg cacagacaaa caaaaagaca gcagtaacct    600
ctgcagactt aagtgtccct gtctgacagc tttgaagaga gcagtggttc tcccagcacg    660
cagctggaga tctgagaacg ggcagactgc ctcctcaagt gggtccctga cccctgaccc    720
ccgagcagcc taactgggag gcaccccca gcagggcac actgacacct cacacggcag    780
ggtattccaa cagacctgca gctgagggtc ctgtctgtta gaaggaaaac taacaaccag    840
aaaggacatc tacaccgaaa acccatctgt acatcaccat catcaaagac caaaagtaga    900
taaaaccaca aagatgggga aaaaacagaa cagaaaaact ggaaactcta aaacgcagag    960
cgcctctcct cctccaaagg aacgcagttc ctcaccagca acagaacaaa gctggatgga   1020
gaatgatttt gatgagctga gagaagaagg cttcagacga tcaaattact ctgagctacg   1080
ggaggacatt caaaccaaag gcaaagaagt tgaaaacttt gaaaaaaatt tagaagaatg   1140
tataactaga ataaccaata cagagaagtg cttaaaggag ctgatggagc tgaaaaccaa   1200
ggctcgagaa ctacgtgaag aatgcagaag cctcaggagc cgatgcgatc aactggaaga   1260
aagggtatca gcaatggaag atgaaatgaa tgaaatgaag cgagaaggga agtttagaga   1320
aaaaagaata aaaagaaatg agcaaagcct ccaagaaata tgggactatg tgaaaagacc   1380
aaatctacgt ctgattggtg tacctgaaag tgatgtggag aatggaacca agttggaaaa   1440
cactctgcag gatattatcc aggagaactt ccccaatcta gcaaggcagg ccaacgttca   1500
gattcaggaa atacagagaa cgccacaaag atactcctcg agaagagcaa ctccaagaca   1560
cataattgtc agattcacca aagttgaaat gaaggaaaaa atgttaaggg cagccagaga   1620
gaaaggtcgg gttaccctca aaggaaagcc catcagacta acagcggatc tctcggcaga   1680
aaccctacaa gccagaagag agtgggggcc aatattcaac attcttaaag aaaagaattt   1740
tcaacccaga atttcatatc cagccaaact aagcttcata agtgaaggag aaataaaata   1800
ctttatagac aagcaaatgt tgagagattt tgtcaccacc aggcctgccc taaaagagct   1860
cctgaaggaa gcgctaaaca tggaaaggaa caaccggtac cagccgctgc aaaatcatgc   1920
caaaatgtaa agaccatcaa gactaggaag aaactgcatc aactaatgag caaaatcacc   1980
agctaacatc ataatgacag gatcaacttc acacataaca atattaactt taaatataaa   2040
tggactaaat tctgcaatta aaagacacag actggcaagt tggataaaga gtcaagaccc   2100
atcagtgtgc tgtattcagg aaacccatct cacgtgcaga gacacacata ggctcaaaat   2160
aaaaggatgg aggaagatct accaagccaa tggaaaacaa aaaaaggcag gggttgcaat   2220
cctagtctct gataaaacag actttaaacc aacaaagatc aaaagagaca aagaaggcca   2280
ttacataatg gtaaagggat caattcaaca agaggagcta actatcctaa atatttatgc   2340
acccaataca ggagcaccca gattcataaa gcaagtcctc agtgacctac aaagagactt   2400
agactcccac acattaataa tgggagactt taacaccccca ctgtcaacat tagacagatc   2460
aacgagacag aaagtcaaca aggatcccca ggaattgaac tcagctctgc accaagcaga   2520
cctaatagac atctacagaa ctctccaccc caaatcaaca gaatatacat ttttttcagc   2580
accacaccac acctattcca aaattgacca catagttgga agtaaagctc tcctcagcaa   2640
atgtaaaaga acagaaatta taacaaacta tctctcagac cacagtgcaa tcaaactaga   2700
actcaggatt aagaatctca ctcaaagccg ctcaactaca tggaaactga acaacctgct   2760
cctgaatgac tactgggtac ataacgaaat gaaggcagaa ataaagatgt tctttgaaac   2820
caacgagaac aaagacacca cataccagaa tctctgggac gcattcaaag cagtgtgtga   2880
agggaaattt atagcactaa atgcctacaa gagaaagcag gaaagatcca aaattgacac   2940
cctaacatca caattaaaag aactagaaaa gcaagagcaa acacattcaa aagctagcag   3000
aaggcaagaa ataactaaaa tcagagcaga actgaaggaa atagagacac aaaaaaccct   3060
tcaaaaaatc aatgaatcca ggagctggtt ttttgaaagg atcaacaaaa ttgataqacc   3120
gctagcaaga ctaataaaga aaaaagaga gaagaatcaa atagacacaa taaaaaatga   3180
taaaggggat atcaccaccg atcccacaga aatacaaact accatcagag aatactacaa   3240
acacctctac gcaaataaac tagaaaatct agaagaaatg gatacattcc tcgacacata   3300
cactctccca agactctctg aggaagaagt tgaatctctg aatcgaccaa taacaggctc   3360
tgaaattgtg gcaataatca atagtttacc aaccaaaaag agtccaggac cagatggatt   3420
cacagccgaa ttctaccaga ggtacaagga ggaactggta ccattccttc tgaaactatt   3480
ccaatcaata gaaaaagagg gaatcctccc taactcattt tatgaggcca gcatcattct   3540
gataccaaag ccgggcagag acacaaccaa aaaagacaat tttagaccaa tatccttgat   3600
gaacattgat gcaaaaatcc tcaataaaat actggcaaac cgaatccagc agcacatcaa   3660
aaagcttatc caccatgatc aagtgggctt catccctggg atgcaaggct ggttcaatat   3720
acgcaaatca ataaatgtaa tccagcatat aaacagagcc aaagacaaaa accacatgat   3780
tatctcaata gatgcagaaa aagcctttga caaaattcaa caccttca tgctaaaaac   3840
tctcaataaa ttaggtattg atgggacgta tttcaaaata ataagagcta tctatgacaa   3900
acccacagcc aatatcatac tgaatgggca aaaactggaa gcattccctt tgaaaaccgg   3960
cacaagacag ggatgccctc tctcaccgct cctattcaac atagtgttgg aagttctggc   4020
cagggcaatc aggcaggaga aggaaataaa gggtattcaa ttaggaaaag aggaagtcaa   4080
attgtccctg tttgcagacg acatgattgt ttatctagaa aaccccatcg tctcagccca   4140
aaatctcctt aagctgataa gcaacttcag caaagtctca ggatacaaaa tcaatgtaca   4200
aaaatcacaa gcattcttat acaccaacaa cagacaaaca gagagccaaa tcatgggtga   4260
actcccattc acaattgctt caaagagaat aaaaatacct ggaatccaac ttacaaggga   4320
tgtgaaggac ctcttcaagg agaactacaa accactgctc aaagaaataa aagaggaac   4380
aaacaaatgg aagaacattc catgctcatg gtaggaagaa tcaatatcg tgaaaatggc   4440
catactgccc aaggtaattt acagattcaa tgccatcccc atcaagctac caatgacttt   4500
cttcacagaa ttggaaaaaa ctactttaaa gttcatatgg aaccaaaaaa gagcccgcat   4560
tgccagtca atcctaagcc aaaagaacaa agctggaggc atcacactac ctgacttcaa   4620
actatactac aaggctacag taaccaaaac agcatggtat tggtaccaaa acagagatat   4680
agatcaatgg aacagaacag agccctcaga ataatgccg catatctaca actatctgat   4740
ctttgacaaa cctgagaaaa acaagcaatg gggaaaggat tccctattta ataaatggtg   4800
ctgggaaaac tggctagcca tatgtagaaa gctgaaactg gatcccttcc ttacacctta   4860
tacaaaaatc aattcaagat ggattaaaga tttaaacgtt aaacctaaaa ccataaaaac   4920
cctagaagaa aacctaggca ttaccattca ggacatagga gtgggcaagg acttcatgtc   4980
caaaacacca aaagcaatgg caacaaaaga caaattgac aaatgggatc taattaaact   5040
aaaagagcttc tgcacagcaa aagaaactac catcagagtg aacaggcaac ctacaacatg   5100
ggagaaaatt tttgcaacct actcatctga caaagggcta atatccagaa tctacaatga   5160
actcaaacaa atttacaaga aaaaaacaaa caacccatc aaaaagtggg cgaaggacat   5220
gaacagacac ttctcaaaag aagacattta tgcagccaaa aaacacatga agaaatgctc   5280
```

-continued

```
atcatcactg gccatcagag aaatgcaaat caaaaccact atgagatatc atctcacacc  5340
agttagaatg gcaatcatta aaaagtcagg aaacaacagg tgctggagag gatgcggaga  5400
aataggaaca cttttacact gttggtggga ctgtaaacta gttcaaccat tgtggaagtc  5460
agtgtggcga ttcctcaggg atctagaact agaaatacca tttgacccag ccatcccatt  5520
actgggtata tacccaaatg agtataaatc atgctgctat aaagacacat gcacacgtat  5580
gtttattgcg gcactattca caatagcaaa gacttggaac caacccaaat gtccaacaat  5640
gatagactgg attaagaaaa tgtggcacat atacaccatg gaatactatg cagccataaa  5700
aaatgatgag ttcatatcct ttgtagggac atggatgaaa ttggaaacca tcattctcag  5760
taaactatcg caagaacaaa aaaccaaaca ccgcatattc tcactcatag gtgggaattg  5820
aacaatgaga tcacatggac acaggaaggg gaatatcaca ctctggggac tgtggtgggg  5880
tcggggggagg ggggagggat agcattggga gatataccta atgctagatg acacattagt  5940
gggtgcagcg caccagcatg gcacatgtat acggatccga attctcgacg gatcgatccg  6000
aacaaacgac ccaacacccg tgcgttttat tctgtctttt tattgccgat cccctcagaa  6060
gaactcgtca agaaggcgat agaaggcgag gcgctgcgaa tcgggagcgg cgataccgta  6120
aagcacgagg aagcggtcag cccattcgcc gccaagctct tcagcaatat cacgggtagc  6180
caacgctatg tcctgatagc ggtcggccgc tttacttgta cagctcgtcc atgccgagag  6240
tgatcccggc ggcggtcacg aactccagca ggaccatgtg atcgcgcttc tcgttggggt  6300
ctttgctcag ggcggactgg gtgctcaggt agtggttgtc gggcagcagc acggggccgt  6360
cgccgatggg ggtgttctgc tggtagtggt cggccaggtg agtccaggag atgtttcagc  6420
actgttgcct ttagtctcga ggcaacttag acaactgagt attgatctga gcacagcagg  6480
gtgtgagctg tttgaagata ctggggttgg gggtgaagaa actgcagagg actaactggg  6540
ctgagaccca gtggcaatgt tttaggggcct aaggaatgcc tctgaaaatc tagatggaca  6600
actttgactt tgagaaaaga gaggtggaaa tgaggaaaat gacttttctt tattagattt  6660
cggtagaaag aactttcatc tttcccctat ttttgttatt cgttttaaaa catctatctg  6720
gaggcaggac aagtatggtc attaaaaaga tgcaggcaga aggcatatat tggctcagtc  6780
aaagtgggga actttggtgg ccaaacatac attgctaagg ctattcctat atcagctgga  6840
cacatataaa atgctgctaa tgcttcatta caaacttata tcctttaatt ccagatgggg  6900
gcaaagtatg tccaggggtg aggaacaatt gaaacatttg ggctggagta gattttgaaa  6960
gtcagctctg tgtgtgtgtg tgtgtgtgtg tgtgtgagag cgtgtgtttc ttttaacgtt  7020
ttcagcctac agcatacagg gttcatggtg gcaagaagat aacaagattt aaattatggc  7080
cagtgactag tgctgcaaga agaacaacta cctgcattta atgggaaagc aaaatctcag  7140
gctttgaggg aagttaacat aggcttgatt ctgggtggaa gctgggtgtg tagttatctg  7200
gaggccaggc tggagctctc agctcactat gggttcatct ttattgtctc ctttcatctc  7260
aacagctgca cgctgccgtc ctcgatgttg tggcggatct tgaagttcac cttgatgccg  7320
ttcttctgct tgtcggccat gatatagacg ttgtggctgt tgtagttgta ctccagcttg  7380
tgccccagga tgttgccgtc ctccttgaag tcgatgccct tcagctcgat gcggttcacc  7440
agggtgtcgc cctcgaactt cacctcggcg cgggtcttgt agttgccgtc gtccttgaag  7500
aagatggtgc gctcctggac gtagccttcg ggcatggcgg acttgaagaa gtcgtgctgc  7560
ttcatgtggt cggggtagcg gctgaagcac tgcacgccgt aggtcaggt ggtcacgagg  7620
gtgggccagg gcacgggcag cttgccggtg gtgcagatga acttcagggt cagcttgccg  7680
taggtggcat cgccctcgcc ctcgccggac acgctgaact tgtggccgtt tacgtcgccg  7740
tccagctcga ccaggatggg caccaccccg gtgaacagct cctcgccctt gctccaccata  7800
gggccgggat tctcctccac gtcaccgcat gttagaagac ttcctctgcc ctccatgttc  7860
tcgtaggagt cggcgtcctc ttcgtggtta ggtccaggtt ggcctctgat agaccgcagc  7920
tgaggagcgg cgtacagaat gcctctcatg tcctcatagc tgccgctgcc ttgtggaggc  7980
ttctcgtgct tcagtgtctc gtatgtctct tgattccggg tgctcaggcc ggtgtacacg  8040
ccatcagatt tctcgtagct ggtgatggcg gccttccgca cttggatctt cagccgtctg  8100
cagtacaggg tgatgaccag agacagcagc aggacaccac atgtgccagc cagagggggcc  8160
caaatgtaga tatccaggcc tctggtatgc acagctccgc ctgcagcagg tctacaggct  8220
tcaggtctga gagacagagg ctggctggcg attgtaggag ctggtgtagg tggtctagga  8280
gcgggtgttg ttgtaggctt ggcgggcaga aacacgggca cgaagtggct gaagtacatg  8340
atgctattgc tcaggctcc gcttcctccg ccgcctgatt tgatttccag cttggtgcct  8400
ccgccaaatg tccaagggct ctcgtcgtac tgctggcagt agtagatgcc gaagtcctcg  8460
tactgcaggc tgctgattgt cagggtgtag tcggtgccag agccgctgcc agaaaatctg  8520
cttggcacgc cgctttccag tctgttggcc cggtagatca gtgtcttagg ggccttgcca  8580
ggcttctgct ggaaccagct caggtagctg ttgatgtcct ggctggctct acaggtgatg  8640
gtcactctat cgcccacaga ggcagacagg ctgctagggc tctgtgtcat ctggatatca  8700
gagccaccac cgccagatcc accgccacct gatcctccgc ctccgctaga aactgtcact  8760
gtggtgccct ggcccacac atcgaagtac cagtcgtagc ctcttctggt gcagaagtac  8820
acggcggtat cctcggctct caggctgttg atctgcaggt aggcgggtgtt cttgctgtcg  8880
tccaggctga aggtgaatct gcccttaaag ctatcggcgt aggtggctc gccggtgtgg  8940
gtattgatcc agcccatcca ctcaaggcct ttttccaggg cctgtcggac ccagttcatg  9000
ccgtagttgg tgaaggtgta gccgctggcg gcacagctga ttctgacaga tccgccaggt  9060
ttcacaagtc cgccgccaga ctgaaccagc tggatctcag agatgctaca ggccactgtt  9120
cccagcagca gcagagactg cagccacatt cgaagcttgg gctcgagatc tgagtccggt  9180
agcgctagcg gatctgacgg ttcactaaac cagctctgct tatatagacc tcccaccgta  9240
cacgcctacc gcccatttgc gtcaatgggg cggagttgtt acgacatttt ggaaagtccc  9300
gttgattttg gtgccaaaac aaactcccat tgacgtcaat ggggtggaga cttggaaatc  9360
cccgtgagtc aaaccgctat ccacgcccat tgatgtactg ccaaaaccgc atcaccatgg  9420
taatagcgat gactaatacg tagatgtact gccaagtagg aaagtcccat aaggtcatgt  9480
actgggcata atgccaggcg ggccatttac cgtcattgac gtcaataggg ggcgtacttg  9540
gcatatgata cacttgatgt actgccaagt gggcagttta ccgtaaatac tccacccatt  9600
gacgtcaatg gaaagtccct attggcgtta ctatgggaac atacgtcatt attgacgtca  9660
atgggcgtggg gtcgttgggc ggtcagccag gcgggccatt taccgtaagt tatgtaacgc  9720
ggaactccat atatgggcta tgaactaatg accccgtaat tgattactat tagcccgggg  9780
gatccagaca tgataagata cattgatgag tttggacaaa ccacaactag aatgcagtga  9840
aaaaaatgct ttatttgtga aatttgtgat gctattgctt tatttgtaac cattataagc  9900
tgcaataaac aagttaacaa caacaattgc attcattta tgtttcaggt tcagggggag  9960
gtgtgggagg tttttttaaag caagtaaaac ctctacaaat gtggtatggc tgattatgat  10020
```

```
ccggctgcct cgcgcgtttc ggtgatgacg gtgaaaacct ctgacacatg cagctcccgg    10080
agacggtcac agcttgtctg taagcggatg ccgggagcag acaagcccgt cagggcgcgt    10140
cagcgggtgt tggcgggtgt cggggcgcag ccatgaggtc gatcgactct agaggatcga    10200
tccccgcccc ggacgaacta aacctgacta cgacatctct gccccttctt cgcggggcag    10260
tgcatgtaat cccttcagtt ggttagtaca acttgccaac tgggccctgt tccacatgtg    10320
acacgggggg ggaccaaaca caaagggggtt ctctgactgt agttgacatc cttataaatg    10380
gatgtgcaca tttgccaaca ctgagtggct ttcatcctgg agcagacttt gcagtctgtg    10440
gactgcaaca caacattgcc tttatgtgta actcttggct gaagctctta caccaatgct    10500
gggggacatg tacctcccag gggcccagga agactacggg aggctacacc aacgtcaatc    10560
agagggggcct gtgtagctac cgataagcgg accctcaaga gggcattagc aatagtgttt    10620
ataaggcccc cttgttaacc ctaaacgggt agcatatgct tcccgggtag tagtatatac    10680
tatccagact aaccctaatt caatagcata tgttacccaa cgggaagcat atgctatcga    10740
attagggtta gtaaaagggt cctaaggaac agcgatatct cccaccccat gagctgtcac    10800
ggtttattt acatggggtc aggattccac gagggtagtg aaccattta gtcacaaggg    10860
cagtggctga agatcaagga gcgggcagtg aactctcctg aatcttcgcc tgcttcttca    10920
ttctccttcg tttagctaat agaataactg ctgagttgtg aacagtaagg tgtatgtgag    10980
gtgctcgaaa acaaggtttc aggtgacgcc cccagaataa aatttggacg gggggttcag    11040
tggtggcatt gtgctatgac accaatataa ccctcacaaa cccctgggc aataaatact    11100
agtgtaggaa tgaaacattc tgaatatctt taacaataga aatccatggg gtggggacaa    11160
gccgtaaaga ctggatgtcc atctcacacg aatttatggc tatgggcaac acataatcct    11220
agtgcaatat gatactgggg ttattaagat gtgtcccagg cagggaccaa gacaggtgaa    11280
ccatgttgtt acactctatt tgtaacaagg ggaaagagag tggacgccga cagcagcgga    11340
ctccactggt tgtctctaac acccccgaaa attaaacggg gctccacgcc aatggggccc    11400
ataaacaaag acaagtggcc actctttttt ttgaaattgt ggagtggggg cacgcgtcag    11460
cccccacacg ccgccctgcg gttttggact gtaaaataag ggtgtaataa cttggctgat    11520
tgtaaccccg ctaaccactg cggtcaaacc acttgcccac aaaaccacta atggcacccc    11580
ggggaatacc tgcataagta ggtgggcggg ccaagatagg ggcgcgattg ctgcgatctg    11640
gaggacaaat tacacacact tgcgcctgag cgccaagcac agggttgttg gtcctcatat    11700
tcacgaggtc gctgagagca cggtgggcta atgttgccat gggtagcata tactacccaa    11760
atatctggat agcatatgct atcctaatct atatctgggt agcataggct atcctaatct    11820
atatctgggt agcataggct atcctaatct atatctgggt agtatatgct atcctaattt    11880
atatctgggt agcataggct atcctaatct atatctgggt agcatatgct atcctaatct    11940
atatctgggt agtatatgct atcctaatct gtatccgggt agcatatgct atcctaatag    12000
agattagggt agtatatgct atcctaattt atatctgggt agcatatact acccaaatat    12060
ctggatagca tatgctatcc taatctatat ctgggtagca tatgctatcc taatctatat    12120
ctgggtagca taggctatcc taatctatat ctgggtagca tatgctatcc taatctatat    12180
ctgggtagta tatgctatcc taatttatat ctgggtagca taggctatcc taatctatat    12240
ctgggtagca tatgctatcc taatctatat ctgggtagta tatgctatcc taatctgtat    12300
ccgggtagca tatgctatcc tcatgcatat acagtcagca tatgataccc agtagtagag    12360
tgggagtgct atcctttgca tatgccgcca cctcccaagg gggcgtgaat tttcgctgct    12420
tgtccttttc ctgcatgctg gttgctccca ttcttaggtg aatttaagga ggccaggcta    12480
aagccgtcgc atgtctgatt gctcaccagg taaatgtcgc taatgttttc caacgcgaga    12540
aggtgttgag cgcggagctg agtgacgtga caacatgggt atgcccaatt gccccatgtt    12600
gggaggacga aaatggtgac aagacagatg gccagaaata caccaacagc acgcatgatg    12660
tctactgggg atttattctt tagtgcgggg gaatacacgg cttttaatac gattgagggc    12720
gtctcctaac aagttacatc actcctgccc ttcctcaccc tcatctccat cacctccttc    12780
atctccgtca tctccgtcat caccctccgc ggcagcccct tccaccatag gtggaaacca    12840
gggaggcaaa tctactccat cgtcaaagct gcacacagtc accctgatat tgcaggtagg    12900
agcgggcttt gtcataacaa ggtccttaat cgcatccttc aaaacctcag caaatatatg    12960
agtttgtaaa aagaccatga aataacagac aatggactcc cttagcgggc caggttgtgg    13020
gccgggtcca ggggccattc caaagggag acgactcaat ggtgtaagac gacattgtgg    13080
aatagcaagg gcagttcctc gccttaggtt gtaaagggag gtcttactac ctccatatac    13140
gaacacaccg gcgacccaag ttccttcgtc ggtagtcctt tctacgtgac tcctagccag    13200
gagagctctt aaaccttctg caatgttctc aaatttcggg ttggaacctc cttgaccacg    13260
atgctttcca aaccaccctc cttttttgcg cctgcctcca tcaccctgac cccggggtcc    13320
agtgcttggg ccttctcctg ggtcatctgc ggggccctgc tctatcgctc ccggggggcac    13380
gtcaggctca ccatctgggc caccttcttg gtggtattca aaataatcgg cttcccctac    13440
agggtggaaa aatggccttc tacctggagg gggcctgcgc ggtggagacc cggatgatga    13500
tgactgacta ctgggactcc tgggcctctt ttctccacgt ccacgacctc tcccctggc    13560
tctttcacga cttccccccc tggctctttc acgtcctcta ccccggcggc ctccactacc    13620
tcctcgaccc cggcctccac tacctcctcg accccggcct ccactgcctc ctcgaccccg    13680
gcctccacct cctgctcctg cccctcctgc tcctgcccct cctcctgctc ctgccctcc    13740
tgcccctcct gctcctgccc ctcctgcccc tcctgctcct gccctcctg cccctcctgc    13800
tcctgcccct cctgccccctc ctgctcctgc cccctcctgc tcctgctct cctgctctgc    13860
ccctcctgcc cctcctgctc ctgcccctcc tgcccctcct gctcctgccc ctcctgcccc    13920
tcctgctcct gccctcctg tcctgcccc tcctgctcct gccctcctg tcctgcccc    13980
tcctgcccct cctgccctc ctcctgctcc tgcccctcct gctcctgccc ctcctgcccc    14040
tcctgcccct cctgctcctg cccctcctgc tcctgcccct cctgctcctg cccctcctgc    14100
tcctgctcct cctgccccctc ctgcccctcc tcctgcccct cctgctct cctgcccctc    14160
cctcctgcc cctcctgccc ctcctcctgc tcctgccccct cctgcccctc ctcctgctcc    14220
tgccctcct cctgctcctg ccccctcctgc ccctcctgcc cctcctcctg ctcctgcccc    14280
tcctgctcct cctgcccctc ctgcccctcc tgcccctcct gcccctcctc ctgctcctgc    14340
ccctcctgct cctgcccctc ctgctcctgc cccctcctgct cctgctctgt    14400
tccaccgtgg gtcccttgc agccaatgca acttggacgt ttttggggtc tccggacacc    14460
atctctatgt cttggccctg atcctgagcc gcccggggcc cctggttctt cgcctcctcg    14520
tcctcgtcct cttcccccgtc ctcgtccatg gttatcaccc cctcttcttt gaggtccact    14580
gccgccggag ccttctggtc cagatgtgtc tcccttctct cctaggccat ttccaggtcc    14640
tgtacctggc ccctcgtcag acatgattca cactaaaaga gatcaataga catctttatt    14700
agacgacgct cagtgaatac aggggagtgca gactcctgcc ccctccaaca gccccccac    14760
```

-continued

```
cctcatcccc ttcatggtcg ctgtcagaca gatccaggtc tgaaaattcc ccatcctccg   14820
aaccatcctc gtcctcatca ccaattactc gcagcccgga aaactcccgc tgaacatcct   14880
caagatttgc gtcctgagcc tcaagccagg cctcaaattc ctcgtccccc tttttgctgg   14940
acggtaggga tggggattct cgggacccct cctcttcctc ttcaaggtca ccagacagag   15000
atgctactgg ggcaacggaa gaaaagctgg gtgcggcctg tgaggatcag cttatcgatg   15060
ataagctgtc aaacatgaga attcttgaag acgaaagggc ctcgtgatac gcctattttt   15120
ataggttaat gtcatgataa taatggtttc ttagacgtca ggtggcactt ttcggggaaa   15180
tgtgcgcgga acccctattt gtttattttt ctaaatacat tcaaatatgt atccgctcat   15240
gagacaataa ccctgataaa tgcttcaata atattgaaaa aggaagagta tgagtattca   15300
acatttccgt gtcgccctta ttcccttttt tgcggcattt tgccttcctg tttttgctca   15360
cccagaaacg ctggtgaaag taaaagatgc tgaagatcag ttgggtgcac gagtgggtta   15420
catcgaactg gatctcaaca gcggtaagat ccttgagagt tttcgccccg aagaacgttt   15480
tccaatgatg agcactttta aagttctgct atgtggcgcg gtattatccc gtgttgacgc   15540
cgggcaagag caactcggtc gccgcataca ctattctcag aatgacttgg ttgagtactc   15600
accagtcaca gaaaagcatc ttacggatgg catgacagta agagaattat gcagtgctgc   15660
cataaccatg agtgataaca ctgcggccaa cttacttctg acaacgatcg gaggaccgaa   15720
ggagctaacc gcttttttgc acaacatggg ggatcatgta actcgccttg atcgttggga   15780
accggagctg aatgaagcca taccaaacga cgagcgtgac accacgatgc ctgcagcaat   15840
ggcaacaacg ttgcgcaaac tattaactgg cgaactactt actctagctt cccggcaaca   15900
attaatagac tggatggagg cggataaagt tgcaggacca cttctgcgct cggcccttcc   15960
ggctggctgg tttattgctg ataaatctgg agccggtgag cgtgggtctc gcggtatcat   16020
tgcagcactg gggccagatg gtaagccctc ccgtatcgta gttatctaca cgacggggag   16080
tcaggcaact atggatgaac gaaatagaca gatcgctgag ataggtgcct cactgattaa   16140
gcattggtaa ctgtcagacc aagtttactc atatatactt tagattgatt taaaacttca   16200
tttttaattt aaaaggatct aggtgaagat cctttttgat aatctcatga ccaaaatccc   16260
ttaacgtgag ttttcgttcc actgagcgtc agaccccgta gaaaagatca aaggatcttc   16320
ttgagatcct ttttttctgc gcgtaatctg ctgcttgcaa acaaaaaaac caccgctacc   16380
agcggtggtt tgtttgccgg atcaagagct accaactctt tttccgaagg taactggctt   16440
cagcagagcg cagataccaa atactgtcct tctagtgtag ccgtagttag gccaccactt   16500
caagaactct gtagcaccgc ctacatacct cgctctgcta atcctgttac cagtggctgc   16560
tgccagtggc gataagtcgt gtcttaccgg gttggactca agacgatagt taccggataa   16620
ggcgcagcgg tcgggctgaa cggggggttc gtgcacacag cccagcttgg agcgaacgac   16680
ctacaccgaa ctgagatacc tacagcgtga gctatgagaa agcgccacgc ttcccgaagg   16740
gagaaaggcg gacaggtatc cggtaagcgg cagggtcgga acaggagagc gcacgaggga   16800
gcttccaggg ggaaacgcct ggtatcttta gtgtcctgtc gggtttcgcc acctctgact   16860
tgagcgtcga tttttgtgat gctcgtcagg ggggcggagc ctatggaaaa acgccagcaa   16920
cgcggccttt ttacggttcc tggccttttg ctggcctttt gctcacatgt tctttcctgc   16980
gttatcccct gattctgtgg ataaccgtat taccgccttt gagtgagctg ataccgctcg   17040
ccgcagccga acgaccgagc gcagcgagtc agtgagcgag gaagcggaag agcgcctgat   17100
gcggtatttt ctccttacgc atctgtgcgg tatttcacac cgcatatggt gcactctcag   17160
tacaatctgc tctgatgccg catagttaag ccagctgtgg aatgtgtgtc agttagggtg   17220
tggaaagtcc ccaggctccc cagcaggcag aagtatgcaa agcatgcatc tcaattagtc   17280
agcaaccagg tgtggaaagt ccccaggctc cccagcaggc agaagtatgc aaagcatgca   17340
tctcaattag tcagcaacca tagtcccgcc cctaactccg cccatcccgc ccctaactcc   17400
gcccagttcc gcccattctc cgccccatgg ctgactaatt tttttattt atgcagaggc   17460
cgaggccgcc tcggcctctg agctattcca gaagtagtga ggaggctttt ttggaggcct   17520
aggcttttgc aaaaagcttg catgcctgca ggtcggccgc cacgaccggt gccgccacca   17580
tcccctgacc cacgcccctg accctcaca aggagacgac cttccatgac cgagtacaag   17640
cccacggtgc gcctcgccac ccgcgacgac gtccccgggg ccgtacgcac cctcgccgcc   17700
gcgttcgccg actacccgc cacgcgccac accgtcgacc cggaccgcca catcgagcgg   17760
gtcaccgaac tgcaagaact cttcctcacg cgcgtcgggc tcgacatcgg caaggtgtgg   17820
gtcgcgacg acggcgccgc ggtgcggagt tggaccacgc cggagagcgt cgaagcgggg   17880
gcggtgttcg ccgagatcgg cccgcgcatg gccgagttga gcggttcccg gctggccgcg   17940
cagcaacaga tggaaggcct cctggcgccg caccggccca aggagcccgc gtggttcctg   18000
gccaccgtcg gcgtctcgcc cgaccaccag ggcaaggtct gggcagcggt gccgccacca   18060
cccggagtgg aggcggccga gcgcgccggg gtgcccgcct tcctggagac ctccgcgccc   18120
cgcaacctcc ccttctacga gcggctcggc ttcaccgtca ccgccgacgt cgaggtgccc   18180
gaaggaccgc gcacctggtg catgacccgc aagcccggtg cctgacgccc gccccacgac   18240
ccgcagcgcc cgaccgaaag gagcgcacga ccccatggct ccgaccgaag ccgacccggg   18300
cggccccgcc gaccccgcac ccgccccgg gcccaccagg ctctagagga tcataatcag   18360
ccataccaca tttgtagagg ttttacttgc tttaaaaaac ctcccacacc tccccctgaa   18420
cctgaaacat aaaatgaatg caattgttgt tgttaacttg tttattgcag cttataatgg   18480
ttacaaataa agcaatagca tcacaaattt cacaaataa gcattttttt cactgcattc   18540
tagttgtggt ttgtccaaac tcatcaatgt atcttatcat gtctggatca ctcgccgata   18600
gtggaaaccg acgccccagc actcgtccga gggcaaagga ataggggaga tgggggaggc   18660
taactgaaac acggaaggag acaataccgg aaggaacccg cgctatgacg gcaataaaaa   18720
gacagaataa aacgcacggg tgttgggtcg tttgttcata aacgcggggt tcggtcccag   18780
ggctggcact ctgtcgatac cccaccgaga ccccattggg gccaatacgc ccgcgtttct   18840
tcctttttcc caccccaccc ccaagttcg gtgaaggcc cagggctcgc agccaacgtc   18900
ggggcggcag gccctgccat agccactggc cccgtgggtt agggacgggg tcccccatgg   18960
ggaatggttt atggttcgtg ggggttatta ttttgggcgt tgcgtggggt ctggtccacg   19020
actggactga gcagacagac ccatggtttt tggatggcct gggcatggac cgcatgtact   19080
ggcgcgacac gaacaccggg cgtctgtggc tgccaaacac ccccgacccc caaaaaccac   19140
cgcgcggatt tctggcgtgc caagctagtc gaccaattct catgtttgac agcttatcat   19200
cgcagatccg gcaacgttgt tgcattgct gcaggcgcag aactggtagg tatggaagat   19260
ctctagaagc tgggtaccag ctgctagcaa gcttgctagc ggcggctcg agttactcc   19320
ctatcagtga tagagaacgt atgtcgagtt tactccctat cagtgataga gaacgatgtc   19380
gagtttactc cctatcagtg atagagaacg tatgtcgagt ttactcccta tcagtgatag   19440
agaacgtatg tcgagtttac tccctatcag tgatagagaa cgtatgtcga gtttatccct   19500
```

```
atcagtgata gagaacgtat gtcgagttta ctccctatca gtgatagaga acgtatgtcg   19560
aggtaggcgt gtacggtggg aggcctatat aagcagagct cgtttagtga accgtcagat   19620
cgccg                                                                19625

SEQ ID NO: 41          moltype = DNA  length = 19730
FEATURE                Location/Qualifiers
misc_feature           1..19730
                       note = Description of Artificial Sequence: Synthetic
                        polynucleotide
source                 1..19730
                       mol_type = other DNA
                       organism = synthetic construct
SEQUENCE: 41
cggccgcggg gggaggagcc aagatggccg aataggaaca gctccggtct acagctccca   60
gcgtgagcga cgcagaagac ggtgatttct gcatttccat ctgaggtacc gggttcatct   120
cactagggag tgccagacag tgggcgcagg ccagtgtgtg tgcgcaccgt gcgcgagccg   180
aagcaggcg aggcattgcc tcacctggga agcgcaaggg gtcagggagt tccctttccg   240
agtcaaagaa aggggtgacg gacgcacctg gaaaatcggg tcactcccac ccgaatattg   300
cgcttttcag accggcttaa gaaacggcgc accacgagac tatatcccac acctggctcg   360
gagggtccta cgcccacgga atctcgctga ttgctagcac agcagtctga gatcaaactg   420
caaggcggca acgaggctgg gggaggggcg cccgccattg cccaggcttg cttaggtaaa   480
caaagcagca gggaagctcg aactgggtgg agcccaccac agctcaagga ggcctgcctg   540
cctctgtagg ctccacctct gggggcaggg cacagacaaa caaaaagaca gcagtaacct   600
ctgcagactt aagtgtccct gtctgacagc tttgaagaga gcagtggttc tcccagcacg   660
cagctggaga tctgagaacg ggcagactgc ctcctcaagt gggtccctga cccctgaccc   720
ccgagcagcc taactgggag gcacccccca gcaggggcac actgacacct cacacgggca   780
ggtattccaa cagacctgca gctgagggtc ctgtctgtta gaaggaaaac taacaaccag   840
aaaggacatc tacaccgaaa acccatctgt acatcaccat catcaaagac caaaagtaga   900
taaaaccaca aagatgggga aaaaacagaa cagaaaaact ggaaactcta aaacgcagag   960
cgcctctcct cctccaaagg aacgcagttc ctcaccagca acagaacaaa gctggatgga   1020
gaatgatttt gatgagctga gagaagaagg cttcagacga tcaaattact ctgagctacg   1080
ggaggacatt caaaccaaag gcaaagaagt tgaaaacttt gaaaaaaatt tagaagaatg   1140
tataactaga ataaccaata cagagaagtg cttaaaggag ctgatggagc tgaaaaccaa   1200
ggctcgagaa ctacgtgaag aatgcagaag cctcaggagc cgatgcgatc aactggaaga   1260
aagggtatca gcaatggaag atgaaatgaa tgaaatgcag cgagaaggga agttttagaga   1320
aaaaagaata aaaagaaatg agcaaagcct ccaagaaata tgggactatg tgaaaagacc   1380
aaatctacgt ctgattggtg tacctgaaag tgatgtggag aatggaacca agttggaaaa   1440
cactctgcag gatattatcc aggagaactt ccccaatcta gcaaggcagg ccaacgttca   1500
gattcaggaa atacagagaa cgccacaaag atactcctcg agagagcaa ctccaagaca   1560
cataattgtc agattcacca aagttgaaat gaaggaaaaa atgttaaggg cagccagaga   1620
gaaaggtcgg gttaccctca aaggaaagcc catcagacta acagcggatc tctcggcaga   1680
aaccctacaa gccagaagag agtgggggcc aatattcaac attcttaaag aaaagaattt   1740
tcaacccaga atttcatatc cagccaaact aagcttcata agtgaaggag aaataaaata   1800
ctttatagac aagcaaatgt tgagagattt tgtcaccacc aggcctgccc taaaagagct   1860
cctgaaggaa gcgctaaaca tggaaaggaa caaccggtac cagccgctgc aaaatcatgc   1920
caaaatgtaa agaccatcaa gactaggaag aaactgcatc aactaatgag caaaatcacc   1980
agctaacatc ataatgacag gatcaacttc acacataaca atattaactt taaatataaa   2040
tggactaaat tctgcaatta aaagacacag actggcaagt tggataaaga gtcaagaccc   2100
atcagtgtgc tgtattcagg aaacccatct cacgtgcaga gacacacata ggctcaaaat   2160
aaaaggatgg aggaagatct accaagccaa tggaaaacaa aaaaaggcag gggttgcaat   2220
cctagtctct gataaaacag actttaaacc aacaaagatc aaaagagaca aagaaggcca   2280
ttacataatg gtaaagggat caattcaaca agaggagcta actatcctaa atatttatgc   2340
acccaataca ggagcaccca gattcataaa gcaagtcctc agtgacctac aaagagactt   2400
agactcccac acattaataa tgggagactt taacaccccca ctgtcaacat tagacagatc   2460
aacgagacag aaagtcaaca aggatcccca ggaattgaac tcagctctgc accaagcaga   2520
cctaatagac atctacagaa ctctccaccc caaatcaaca gaatatacat tttttcagc   2580
accacaccac acctattcca aaattgacca catagttgga agtaaagctc tcctcagcaa   2640
atgtaaaaga acagaaatta taacaaacta tctctcagac cacagtgcaa tcaaactaga   2700
actcaggatt aagaatctca ctcaaagccg ctcaactaca tggaaactga acaacctgct   2760
cctgaatgac tactgggtac ataacgaaat gaaggcagaa ataaagatgt tctttgaaac   2820
caacgagaac aaagacacca cataccagaa tctctgggac gcattcaaag cagtgtgtag   2880
agggaaattt atagcactaa atgcctacaa gagaaagcag gaaagatcca aaattgacac   2940
cctaacatca caattaaaag aactagaaaa gcaagagcaa acacattcaa aagctagcag   3000
aaggcaagaa ataactaaaa tcagagcaga actgaaggaa atagagacag aaaaaaccct   3060
tcaaaaaatc aatgaatcca ggagctggtt ttttgaaagg atcaacaaaa ttgatagacc   3120
gctagcaaga ctaataaaga aaaaagagaa gaatcaa atagacacaa taaaaaatga   3180
taaaggggat atcaccaccg atcccacaga aatacaaact accatcagag aatactacaa   3240
acacctctac gcaaataaac tagaaaatct agaagaaatg gatacattcc tcgacacata   3300
cactctccca agactaaacc aggaagaagt tgaatctctg aatcgaccaa taacaggctc   3360
tgaaattgtg gcaataatca atagtttacc aaccaaaaag agtccaggac cagatggatt   3420
cacagccgaa ttctaccaga ggtacaagga ggaactggta ccattccttc tgaaactatt   3480
ccaatcaata gaaaaagagg gaatcctccc taactcattt tatgaggcca gcatcattct   3540
gataccaaag ccgggcagag acacaaccaa aaaagagaat tttagaccaa tatccttgat   3600
gaacattgat gcaaaaatcc tcaataaaat actggcaaac cgaatccagc agcacatcaa   3660
aaagcttatc caccatgatc aagtgggctt catccctggg atgcaaggct ggttcaatat   3720
acgcaaatca ataaatgtaa tccagcatat aaacagagcc aaagacaaaa ccacatgat   3780
tatctcaata gatgcagaaa aagccttga caaaattcaa caacccttca tgctaaaaac   3840
tctcaataaa ttaggtattg atgggacgta tttcaaaata ataagagcta tctatgacaa   3900
acccacagcc aatatcatac tgaatgggca aaaactggaa gcattcccctt tgaaaaccgg   3960
```

-continued

```
cacaagacag ggatgccctc tctcaccgct cctattcaac atagtgttgg aagttctggc  4020
caggggaatc aggcaggaga aggaaataaa gggtattcaa ttaggaaaag aggaagtcaa  4080
attgtccctg tttgcagacg acatgattgt ttatctagaa aaccccatcg tctcagccca  4140
aaatctcctt aagctgataa gcaacttcag caaagtctca ggatacaaaa tcaatgtaca  4200
aaaatcacaa gcattcttat acaccaacaa cagacaaaca gagagccaaa tcatgggtga  4260
actcccattc acaattgctt caaagagaat aaaataccta ggaatccaac ttacaaggga  4320
tgtgaaggac ctcttcaagg agaactacaa accactgctc aaggaaataa aagaggagac  4380
aaacaaatgg aagaacattc catgctcatg ggtaggaaga atcaatatcg tgaaaatggc  4440
catactgccc aagtaattt acagattcaa tgccatcccc atcaagctac caatgacttt  4500
cttcacagaa ttggaaaaaa ctactttaaa gttcatatgg aaccaaaaaa gagcccgcat  4560
tgccaagtca atcctaagcc aaaagaacaa agctggaggc atcacactac ctgacttcaa  4620
actatactac aaggctacag taaccaaaac agcatggtac tggtaccaaa acagagatat  4680
agatcaatgg aacagaacag agccctcaga aataatgccg catatctaca actatctgat  4740
ctttgacaaa cctgagaaaa acaagcaatg gggaaaggat tccctattta ataaatggtg  4800
ctggaaaac tggctagcca tatgtagaaa gctgaaactg gatcccttcc ttacacctta  4860
tacaaaaatc aattcaagat ggattaaaga tttaaacgtt aaacctaaaa ccataaaaac  4920
cctagaagaa aacctaggca ttaccattca ggacataggc gtgggcaagg acttcatgtc  4980
caaaacacca aaagcaatgg caacaaaaga caaaattgac aaatgggatc taattaaact  5040
aaagagcttc tgcacagcaa aagaaactac catcagagtg aacaggcaac ctacaacatg  5100
ggagaaaatt tttgcaacct actcatctga caaagggcta atatccagaa tctacaatga  5160
actcaaacaa atttacaaga aaaaaacaaa caaccccatc aaaaagtggg cgaaggacat  5220
gaacagacac ttctcaaaag aagacattta tgcagccaaa aaacacatga aaaatgctc  5280
atcatcactg gccatcagag aaatgcaaat caaaaccact atgagatatc atctcacacc  5340
agttagaatg gcaatcatta aaaagtcagg aaacaacagg tgctggagag gatgcggaga  5400
aataggaaca cttttacact gttggtggga ctgtaaacta gttcaaccat tgtggaagtc  5460
agtgtggcga ttcctcaggg atctagaact agaaatacca tttgacccag ccatcccatt  5520
actgggtata tacccaaatg agtataaatc atgctgctat aaagacacat gcacacgtat  5580
gtttattgcg gcactattca caatagcaaa gacttggaac caacccaaat gtccaacaat  5640
gatagactgg attaagaaaa tgtggcacat atacaccatg gaatactatg cagccataaa  5700
aaatgatgag ttcatatcct ttgtagggac atggatggaa ttggaaacca tcattctcag  5760
taaactatcg caagaacaaa aaaccaaaca ccgcatattc tcactcatag gtgggaattg  5820
aacaatgaga tcacatggac acaggaaggg gaatatcaca ctctggggac tgtggtgggg  5880
tcgggggagg ggggagggat agcattggga gatataccta atgctagatg acacattagt  5940
gggtgcagcg caccagcatg gcacatgtat acggatccga attctcgacg gatcgatcca  6000
aacaaacgac ccaacacccg tgcgttttat tctgtctttt tattgccgat cccctcagaa  6060
gaactcgtca agaaggcgat agaaggcgat gcgctgcgaa tcgggagcgg cgataccgta  6120
aagcacgagg aagcggtcag cccattcgcc gccaagctct tcagcaatat cacgggtagc  6180
caacgctatg tcctgatagc ggtcggccgc tttacttgta cagctcgtcc atgccgagag  6240
tgatccggc ggcggtcacg aactccagca ggaccatgtg atcgcgcttc tcgttgggg  6300
ctttgctcag ggcggactgg gtgctcaggt agtggttgtc gggcagcagc acggggccgt  6360
cgccgatggg ggtgttctgc tggtagtggt cggccaggtg agtccaggag atgtttcagc  6420
actgttgcct ttagtctcga ggcaacttag acaactgagt attgatctga gcacagcagg  6480
gtgtgagctg tttgaagata ctggggttgg gggtgaagaa actgcagagg actaactggg  6540
ctgagaccca gtggcaatgt tttagggcct aaggaatgcc tctgaaaatc tagatggaca  6600
actttgactt tgagaaaaga gaggtggaaa tgaggaaaat gacttttctt tattagattt  6660
cggtagaaag aactttcatc tttcccctat ttttgttatt cgtttttaaaa catctatctg  6720
gaggcaggac aagtatggtc attaaaaaga tgcaggcaga aggcatatat tggctcagtc  6780
aaagtgggga actttggtgg ccaaacatac attgctaagg ctattcctat atcagctgga  6840
cacatataaa atgctgctaa tgcttcatta caaacttata tcctttaatt ccagatgggg  6900
gcaaagtatg tccaggggtg aggaacaatt gaaacatttg ggctggagta gattttgaaa  6960
gtcagctctg tgtgtgtgtg tgtgtgtgag cgtgtgtttc ttttaacgtt  7020
ttcagcctac agcatacagg gttcatggtg gcaagaagat aacaagattt aaattatggc  7080
cagtgactag tgctgcaaga agaacaacta cctgcattta atgggaaagc aaaatctcag  7140
gctttgaggg aagttaacat aggcttgatt ctgggtggaa gctgggtgtg tagttatctg  7200
gaggccaggc tggagctctc agctcactat gggttcatct ttattgtctc ctttcatctc  7260
aacagctgca cgctgccgtc ctcgatgttg tggcggatct tgaagttcac cttgatgccg  7320
ttcttctgct tgtcggccat gatatagacg ttgtggctgt tgtagttgta ctccagcttg  7380
tgccccagga tgttgccgtc ctccttgaag tcgatgccct tcagctcgat gcggttcacc  7440
agggtgtcgc cctcgaactt cacctcggcg cgggtcttgt agttgccgtc gtccttgaag  7500
aagatggtgc gctcctggac gtagccttcg ggcatggcgg acttgaagaa gtcgtgctgc  7560
ttcatgtggt cggggtagcg gctgaagcac tgcacgccgt aggtcagggt ggtcacgagg  7620
gtgggccagg gcacgggcag cttgccggtg gtgcagatga acttcagggt cagcttgccg  7680
taggtggcat cgccctcgcc ctcgccgac acgctgaact tgtggccgtt tacgtcgccg  7740
tccagctcga ccaggatggg caccaccccg gtgaacagct cctcgccctt gctcaccata  7800
gggccgggat tctcctccac gtcaccgcat gttagaagac ttcctctgcc ctctcttgga  7860
ggcagggcct gcatgtgcag ggcatcgtag gtatccttgg tggctgtgct cagtccctgg  7920
tacagtccat cgtggccctt gcctcttctt ctctcgccct tcatgccgat ctcgctgtag  7980
gcctcggcca tcttgtcttt ctgcagctca ttatacaggc cctcttgagg attctttctc  8040
cgctggggct tgccgcccat ctcaggatct ctgcctccc gcttatccag cacgtcgtac  8100
tcttctcttc tccccaggtt cagctcgttg tacagctgat tctggccctg ctggtaagca  8160
ggagcgtcgg cggatctgct gaacttcact ctgcagtaca gggtgatgac cagagagagc  8220
agcagaacgc cacatgtgcc agccagaggg gcccaaatgt agatatccag gcctctggta  8280
tgcacagctc cgccagctgc aggtctcag gcttcaggtc tgagagacag aggctggctg  8340
gcgattgtag gagctggtgt aggtggtcta ggagcgggtg ttgttgtagg cttggcgggc  8400
agaaacacgg gcacgaagtg gctgaagtac atgatgctat tgctcagggc tccgcttcct  8460
ccgcctccgc tagaagaaac tgtgaccagg gtgccctgtc cccaaacatc catggcgtag  8520
aagccgtcgc ctccccatct agaacagtag tacacggcgg tgtcctcggc tctcaggctg  8580
ttcatctgca ggtaggcggt gttcttgctg gtgtcggcgc tgatggtgaa tctgcccttc  8640
acgctatcgg cgtatctggt gtagccgttg gtggggtaga ttctggcgac ccattcaagt  8700
```

```
ccctttccag gggcctgtcg gacccagtgg atgtaggtgt ccttgatgtt gaagccgctg   8760
gcggcacaag acagtctcag agagccgcca ggctgaacaa gtcctccgcc agattcaacc   8820
agctgcacct cagatccttc gccagatcca ggctttccag agccgctggt gctgcctgtt   8880
ctcttgattt ccaccttggt gccctggcca aaggttggag gtgtggtgta gtgctgctgt   8940
cagtagtagg tggcgaagtc ctcaggctgc aggctagaga tggtcagggt gaagtcggtg   9000
ccagatctgc tgccgctgaa tctgcttggc acgccgctgt acagaaagct ggcgctgtag   9060
atcagcagct taggggcttt tccaggcttc tgctgatacc aggccacggc ggtattcaca   9120
tcctggctgg ctctacaggt gatggtcact ctatcgccca cagaggcaga caggctgcta   9180
gggctctgtg tcatctggat gtcgctgatg ctgcaggcca ctgttcccag cagcagcaga   9240
gactgcagcc acattcgaag cttgagctcg agatctgagt ccggtagcgc tagcggatct   9300
gacggttcac taaaccagct ctgctttatat agacctccca ccgtacacgc ctaccgccca   9360
tttgcgtcaa tggggcggag ttgttacgac attttggaaa gtcccgttga ttttggtgcc   9420
aaaacaaact cccattgacg tcaatggggt ggagacttgg aaatccccgt gagtcaaacc   9480
gctatccacg cccattgatg tactgccaaa accgcatcac catggtaata gcgatgacta   9540
atacgtagat gtactgccaa gtaggaaagt cccataaggt catgtactgg gcataatgcc   9600
aggcgggcca tttaccgtca ttgacgtcaa tagggggcgt acttggcata tgatacactt   9660
gatgtactgc caagtgggca gtttaccgta aatactccac ccattgacgt caatggaaag   9720
tccctattgg cgttactatg ggaacatacg tcattattga cgtcaatggg cgggggtcgt   9780
tgggcggtca gccaggcggg ccatttaccg taagttatgt aacgcggaac tccatatatg   9840
ggctatgaac taatgacccc gtaattgatt actattagcc cggggatcc agacatgata   9900
agatacattg atgagtttgg acaaaccaca actagaatgc agtgaaaaaa atgctttatt   9960
tgtgaaattt gtgatgctat tgctttattt gtaaccatta taagctgcaa taaacaagtt  10020
aacaacaaca attgcattca ttttatgttt caggttcagg gggaggtgtg ggaggttttt  10080
taaagcaagt aaaacctcta caaatgtggt atggctgatt atgatccggc tgcctcgcgc  10140
gtttcggtga tgacggtgaa aacctctgac acatgcagct cccggagacg gtcacagctt  10200
gtctgtaagc ggatgccggg agcagacaag cccgtcaggg cgcgtcagcg ggtgttggcg  10260
ggtgtcgggg cgcagccatg aggtcgatcg actctagaga atcgatcccc gccccgacg  10320
aactaaacct gactacgaca tctctgcccc ttcttcgcgg ggcagtgcat gtaatccctt  10380
cagttggttg gtacaacttg ccaactgggc cctgttccac atgtgacacg gggggggacc  10440
aaacacaaag gggttctctg actgtagttg acatccttat aaatggatgt gcacatttgc  10500
caacactgag tggctttcat cctggagcag actttgcagt ctgtggactg caacacaaca  10560
ttgcctttat gtgtaactct tggctgaagc tcttacacca atgctggggg acatgtacct  10620
cccaggggcc caggaagact acgggaggct acaccaacgt caatcagagg ggcctgtgta  10680
gctaccgata agcggaccct caagagggca ttagcaatag tgtttataag gccccccttgt  10740
taaccctaaa cgggtagcat atgcttcccg ggtagtagta tatactatcc agactaaccc  10800
taattcaata gcatatgtta cccaacggga agcatatgct atcgaattag ggttagtaaa  10860
agggtcctaa ggaacagcga tatctcccac cccatgagct gtcacggttt tatttacatg  10920
gggtcaggat tccacgaggg tagtgaacca tttagtcac aagggcagtg gctgaagatc  10980
aaggagcgga cagtgaactc tcctgaatct tcgcctgctt cttcattctc cttcgtttag  11040
ctaatagaat aactgctgag ttgtgaacag taaggtgtat gtgaggtgct cgaaaacaag  11100
gtttcaggtg acgcccccag aataaaattt ggacgggggg ttcagtggtg gcattgtgct  11160
atgacaccaa tataaccctc acaaaccct tgggcaataa atactagtgt aggaatgaaa  11220
cattctgaat atctttaaca atagaaatcc atggggtggg gcaagccgt aaagactgga  11280
tgtccatctc acacgaattt atggctatgg gcaacacata atcctagtgc aatatgatac  11340
tggggttatt aagatgtgtc ccaggcaggg accaagacag gtgaaccatg ttgttacact  11400
ctatttgtaa caagggggaa gagagtggac gccgacagca gcggactcca ctggttgtct  11460
ctaacacccc cgaaaattaa acggggctcc acgccaatag ggcccataaa caaagacaag  11520
tggccactct tttttttgaa attgtggagt gggggcacgc gtcagccccc acacgccgcc  11580
ctgcggtttt ggactgtaaa ataagggtgt aataacttgg ctgattgtaa ccccgctaac  11640
cactgcggtc aaaccacttg cccacaaaac cactaatggc accccgggga atacctgcat  11700
aagtaggtgg gcgggccaag ataggggcgc gattgctgcg atctggagga caaattacac  11760
acacttgcgc ctgagcgcca agcacagggt tgttggtcct catattcacg aggtcgctga  11820
gagcacggtg ggctaatgtt gccatgggta gcatatacta cccaaatatc tggatagcat  11880
atgctatcct aatctatatc tgggtagcat aggctatcct aatctatatc tgggtagcat  11940
atgctatcct aatctatatc tgggtagtat atgctatcct aatttatatc tgggtagcat  12000
aggctatcct aatctatatc tgggtagcat atgctatcct aatctatatc tgggtagtat  12060
atgctatcct aatctgtatc cgggtagcat atgctatcct aatagagatt agggtagtat  12120
atgctatcct aatttatatc tgggtagcat atactaccca aatatctgga tagcatatgc  12180
tatcctaatc tatatctggg tagcatatgc tatcctaatc tatatctggg tagcataggc  12240
tatcctaatc tatatctggg tagcatatgc tatcctaatc tatatctggg tagtatatgc  12300
tatcctaatt tatatctggg tagcataggc tatcctaatc tatatctggg tagcatatgc  12360
tatcctaatc tatatctggg tagtatatgc tatcctaatc tgtatccggg tagcatatgc  12420
tatcctcatg catatacagt cagcatatga tacccagtag tagagtggga gtgctatcct  12480
ttgcatatgc cgccacctcc caaggggggcg tgaattttcg tgcttgtcc ttttcctgca  12540
tgctggttgc tccattctt aggtgaattt aaggaggcca ggctaaagcc gtcgcatgtc  12600
tgattgctca ccaggtaaat gtcgctaatg ttttccaacg cgagaaggtg ttgagcgcgg  12660
agctgagtga cgtgacaaca tgggtatgcc caattgcccc atgttgggag gacgaaatg  12720
gtgacaagac agatggccag aaatacacca acagcacgca tgatgtctac tggggattta  12780
ttcttttagtg cgggggaata cacggctttt aatacgattg agggcgtctc ctaacaagtt  12840
acatcactcc tgcccttcct caccctcatc tccatcacct ccttcatctc cgtcatctcc  12900
gtcatcaccc tccgcggcag ccccttccac cataggtgga aaccaggggag gcaaatctac  12960
tccatcgtca aagctgcaca cagtcaccct gatattgcag gtaggagcgg gctttgtcat  13020
aacaaggtcc ttaatcgcat ccttcaaaac ctcagcaaat atatgagttt gtaaaaagac  13080
catgaaataa cagacaatgg actccttag cgggcaggt tgtgggcgg gtccagggac  13140
cattccaaag gggagacgac tcaatggtgt aagacgacat tgtggaatag caagggcagt  13200
tcctcgcctt aggttgtaaa gggaggtctt actacctcca tatacgaaca caccggcgac  13260
ccaagttcct tcgtcggtag tcctttctac gtgactccta gccaggagag ctcttaaacc  13320
ttctgcaatg ttctcaaatt tcgggttgga acctccttga ccacgatgct ttccaaacca  13380
ccctcctttt ttgcgcctgc ctccatcacc ctgacccccg ggtccagtgc ttgggccttc  13440
```

-continued

```
tcctgggtca tctgcggggc cctgctctat cgctcccggg ggcacgtcag gctcaccatc   13500
tgggccacct tcttggtggt attcaaaata atcggcttcc cctacagggt ggaaaaatgg   13560
ccttctacct ggaggggggcc tgcgcggtgg agacccggat gatgatgact gactactggg   13620
actcctgggc ctcttttctc cacgtccacg acctctcccc ctggctcttt cacgacttcc   13680
ccccctggct ctttcacgtc ctctaccccg gcggcctcca ctacctcctc gaccccggcc   13740
tccactacct cctcgacccc ggcctccact gcctcctcga ccccggcctc cacctcctgc   13800
tcctgcccct cctgctcctg cccctcctcc tgctcctgcc cctcctgccc ctcctgctcc   13860
tgccctcct gccctcctg ctcctgcccc tcctgcccct cctgctcctg cccctcctgc   13920
ccctcctcct gctcctgccc ctcctgcccc tcctgctgct cctgccctcc ctgcccctcc   13980
tgctcctgcc cctcctgccc ctcctgctcc tgccctcctg gccctcctg ctcctgcccc   14040
tcctgctcct gccctcctg ctcctgcccc tcctgctcct gccctcctg ccctcctgc   14100
ccctcctcct gctcctgccc ctcctgctcc tgccctcctc gccctcctg ccctcctgc   14160
tcctgcccct cctcctgctc ctgccctcct gccctcctg gccctcctc ctgctcctgc   14220
ccctcctgcc cctcctcctg ctcctgcccc tcctcctgct cctgccctc ctgctcctcc   14280
tgccctcctc cctgctcctg cccctcctgc ccctcctcct gctcctgccc ctcctgctgc   14340
tcctgcccct cctgccctc ctgccctcc tcctgctcct gccctcctc ctgctcctgc   14400
ccctcctgcc cctcctgccc ctcctgccc tcctcctgct cctgccctc ctcctgctcc   14460
tgccctcct gctcctgccc tcctgctcc tgctcctgct cctgttccac cgtgggtccc   14520
tttgcagcca atgcaacttg gacgtttttg gggtctccgg acaccatctc tatgtcttgg   14580
ccctgatcct gagccgcccg gggctcctgg tcttccgcct cctcgtcctc gtcctcttcc   14640
ccgtcctcgt ccatggttat cacccctct tctttgaggt ccactgccgc cggagccttc   14700
tggtccagat gtgtctccct tctctcctag gccatttcca ggtcctgtac ctggcccctc   14760
gtcagacatg attcacacta aaagagatca atagacatct ttattagacg acgctcagtg   14820
aatacaggga gtgcagactc ctgcccctc caacagcccc cccaccctca tcccttcat   14880
ggtcgctgtc agacagatcc aggtctgaaa attcccatc ctccgaacca tcctcgtcct   14940
catcaccaat tactcgcagc ccggaaaact cccgctgaac atcctcaaga tttgcgtcct   15000
gagcctcaag ccaggcctca aattcctcgt ccccctttt gctggacggt agggatgggg   15060
attctcggga cccctcctct tcctcttcaa ggtcaccaga cagagatgct actggggcaa   15120
cggaagaaaa gctgggtgcg gcctgtgagg atcagcttat cgatgataag ctgtcaaaca   15180
tgagaattct tgaagacgaa agggcctcgt gatacgccta tttttatagg ttaatgtcat   15240
gataataatg gtttcttaga cgtcaggtgg cacttttcgg ggaaatgtgc gcggaacccc   15300
tatttgttta tttttctaaa tacattcaaa tatgtatccg ctcatgagac aataaccctg   15360
ataaatgctt caataatatt gaaaaaggaa gagtatgagt attcaacatt ccgtgtcgc   15420
ccttattccc tttttttgcgg cattttgcct tcctgttttt gctcacccag aaacgctggt   15480
gaaagtaaaa gatgctgaag atcagttggg tgcacgagtg ggttacatcg aactggatct   15540
caacagcggt aagatccttg agagttttcg ccccgaagaa cgttttccaa tgatgagcac   15600
ttttaaagtt ctgctatgtg gcgcggtatt atcccgtgtt gacgccgggc aagagcaact   15660
cggtcgccgc atacactatt ctcagaatga cttggttgag tactcaccag tcacagaaaa   15720
gcatcttacg gatggcatga cagtaagaga attatgcagt gctgccataa ccatgagtga   15780
taacactgcg gccaacttac ttctgacaac gatcggagga ccgaaggagc taaccgcttt   15840
tttgcacaac atggggggatc atgtaactcg ccttgatcgt tgggaaccgg agctgaatga   15900
agccatacca aacgacgagc gtgacaccac gatgcctgca gcaatggcaa caacgttgcg   15960
caaactatta actggcgaac tacttactct agcttcccgg caacaattaa tagactggat   16020
ggaggcggat aaagttgcag gaccacttct gcgctcggcc cttccggctg gctggtttat   16080
tgctgataaa tctggagccg gtgagcgtgg gtctcgcggt atcattgcag cactggggcc   16140
agatggtaag ccctcccgta tcgtagttat ctacacgacg gggagtcagg caactatgga   16200
tgaacgaaat agacagatcg ctgagatagg tgcctcactg attaagcatt ggtaactgtc   16260
agaccaagtt tactcatata tactttagat tgatttaaaa cttcattttt aatttaaaag   16320
gatctaggtg aagatccttt ttgataatct catgaccaaa atcccttaac gtgagttttc   16380
gttccactga gcgtcagacc ccgtagaaaa gatcaaagga tcttcttgag atccttttt   16440
tctgcgcgta atctgctgct tgcaaacaaa aaaaccaccg ctaccagcgg tggtttgttt   16500
gccggatcaa gagctaccaa ctctttttcc gaaggtaact ggcttcagca gagcgcagat   16560
accaaatact gtccttctag tgtagccgta gttaggccac cacttcaaga actctgtagc   16620
accgcctaca tacctcgctc tgctaatcct gttaccagtg gctgctgcca gtggcgataa   16680
gtcgtgtctt accgggttgg actcaagacg atagttaccg gataaggcgc agcggtcggg   16740
ctgaacgggg ggttcgtgca cacagcccag cttggagcga acgacctaca ccgaactgag   16800
atacctacag cgtgagctat gagaaagcgc cacgcttccc gaaggagaa aggcggacag   16860
gtatccggta agcggcaggg tcggaacagg agagcgcacg agggagcttc caggggggaaa   16920
cgcctggtat ctttatagtc ctgtcgggtt tcgccacctc tgacttgagc gtcgatttt   16980
gtgatgctcg tcaggggggc ggagccatg gaaaaacgcc agcaacgcgg ccttttttacg   17040
gttcctggcc ttttgctggc cttttgctca catgttcttt cctgcgttat ccctgattc   17100
tgtggataac cgtattaccg cctttgagtg agctgatacc gctcgccgca gccgaacgac   17160
cgagcgcagc gagtcagtga gcgaggaagc ggaagagcgc ctgatgcggt attttctcct   17220
tacgcatctg tgcggtattt cacaccgcat atggtgcact ctcagtacaa tctgctctga   17280
tgccgcatag ttaagccagc tgtggaatgt gtgtcagtta gggtgtggaa agtccccagg   17340
ctccccagca ggcagaagta tgcaaagcat gcatctcaat tagtcagcaa ccaggtgtgg   17400
aaagtccccca ggctcccag caggcagaag tatgcaaagc atgcatctca attagtcagc   17460
aaccatagtc ccgccctaa ctccgcccat cccgccccca actccgccca gttccgccca   17520
ttctccgccc catggctgac taatttttt tatttatgca gaggccgagg ccgcctcggc   17580
ctctgagcta ttccagaagt agtgaggagg cttttttgga ggcctaggct tttgcaaaaa   17640
gcttgcatgc ctgcaggtcg gccgccacga ccggtgccgc caccatcccc tgacccacgc   17700
ccctgacccc tcacaaggag acgaccttcc atgaccgagt acaagcccac ggtgcgcctc   17760
gccaccgcg acgacgtccc ccgggccgta cgcaccctcg ccgccgcgtt cgccgactac   17820
cccgccacgc gccacaccgt cgacccggac cgccacatcg acggcacgct gccggtgcaa   17880
gaactcttcc tcacgcgcgt cgggctcgac atcggcaagg tgtgggtcgc ggacgacggc   17940
gccgcggtgg cggtctggac cacgccggag agcgtcgaag cgggggcggt gttcgccgag   18000
atcggcccgc gcatggccga gttgagcggt tcccggctgg ccgcgcagca acagatggaa   18060
ggcctcctgg cgccgcaccg gcccaaggag cccgcgtggt cctgccac cgtcggcgtc   18120
tcgcccgacc accagggcaa gggtctgggc agcgccgtcg tgctccccgg agtggaggcg   18180
```

```
gccgagcgcg ccgggtgcc cgccttcctg gagacctccg cgccccgcaa cctcccttc      18240
tacgagcggc tcggcttcac cgtcaccgcc gacgtcgagg tgcccgaagg accgcgcacc    18300
tggtgcatga cccgcaagcc cggtgcctga cgcccgcccc acgacccgca gcgcccgacc    18360
gaaaggagcg cacgacccca tggctccgac cgaagccgac ccgggcggcc ccgccgaccc    18420
cgcacccgcc cccgaggccc accgactcta gaggatcata atcagccata ccacatttgt    18480
agaggttta cttgctttaa aaaacctccc acacctcccc ctgaacctga aacataaaat     18540
gaatgcaatt gttgttgtta acttgtttat tgcagcttat aatggttaca aataaagcaa    18600
tagcatcaca aatttcacaa ataaagcatt tttttcactg cattctagtt gtggtttgtc    18660
caaactcatc aatgtatctt atcatgtctg gatcactcgc cgatagtgga aaccgacgcc    18720
ccagcactcg tccgagggca aaggaatagg ggagatgggg gaggctaact gaaacacgga    18780
aggagacaat accggaagga acccgcgcta tgacggcaat aaaaagacag aataaaacgc    18840
acgggtgttg ggtcgtttgt tcataaacgc ggggttcggt cccagggctg gcactctgtc    18900
gatacccac cgagacccca ttggggccaa tacgcccgcg tttcttcctt ttccccaccc     18960
cacccccaa gttcgggtga aggcccaggg ctcgcagcca acgtcgggcg ggcaggccct     19020
gccatagcca ctggcccgt gggttaggga cggggtcccc catgggaat ggtttatggt      19080
tcgtggggt tattattttg ggcgttgcgt ggggtctggt ccacgactgg actgagcaga     19140
cagacccatg gttttttggat ggcctgggca tggaccgcat gtactggcgc gacacgaaca   19200
ccgggcgtct gtggctgcca aacacccccg acccccaaaa accaccgccg ggatttctgg    19260
cgtgccaagc tagtcgacca attctcatgt ttgacagctt atcatcgcag atccgggcaa    19320
cgttgttgca ttgctgcagg cgcagaactg gtaggtatgg aagatctcta gaagctgggt    19380
accagctgct agcaagcttg ctagcggccg gctcgagttt actccctatc agtgatagag    19440
aacgtatgtc gagtttactc cctatcagtg atagagaacg acgtcgagtt tactccctat    19500
cagtgataga gaacgtatgt cgagtttact ccctatcagt gatagagaac gtatgtcgag    19560
tttactccct atcagtgata gagaacgtat gtcgagttta tccctatcag tgatagaaa    19620
cgtatgtcga gtttactccc tatcagtgat agagaacgta tgtcgaggta ggcgtgtacg    19680
gtgggaggc tatataagca gagctcgttt agtgaaccg cagatcgccg                 19730
```

SEQ ID NO: 42          moltype = DNA   length = 7291
FEATURE                Location/Qualifiers
misc_feature           1..7291
                       note = Description of Artificial Sequence: Synthetic
                       polynucleotide
source                 1..7291
                       mol_type = other DNA
                       organism = synthetic construct
SEQUENCE: 42

```
taatacgact cactataggg agaagtactg ccaccatggg caagaagcaa aatcgcaaga      60
cggggaattc caagacacaa tccgctagcc caccacctaa agagcgttct agctcccctg     120
ctactgagca gtcctggatg gaaaacgact tcgatgaact ccgggaagag ggatttaggc     180
gatccaacta ttcagaactc cgcgaagata tccagacaa ggggaaggaa gtcgagaatt       240
tcgagaagaa cctcgaggag tgcatcaccc gtatcacaaa cactgagaaa tgtctcaaag     300
aactcatgga acttaagaca aaagccaggg agcttcgaga ggagtgtcgg agtctgagat     360
ccaggtgtga ccagctcgag gagcgcgtga gcgcgatgga agacgagatg aacgagatga    420
aaagagaggg caaattcagg gagaagcgca ttaaggagaa cgaacagagt ctgcaggaga    480
tttgggatta cgtcaagagg cctaacctgc ggttgatcgg cgtccccgag agcgacgtag    540
aaaacggac taaactggag aatacacttc aagacatcat tcaagaaaat tttccaaacc      600
tggctcggca agctaatgtg caaatccaag agatccaacg cacacccag cggtatagct       660
ctcggcgtgc caccctagg catattatcg tgcgctttac taaggtggag atgaaagaga      720
agatgctgcg agccgctcgg gaaaagggaa gggtgacttt gaaggcaaa cctattcggc      780
tgacggttga ccttagcgcc gagacactcc aggcacgccg ggaatggggc cccatcttta    840
atatcctgaa ggagaagaac ttccagccac gaatctctta ccctgcaaag ttgagtttta    900
tctccgaggg tgagattaag tatttcatcg ataaacagat gctgcgagac ttcgtgacaa    960
ctcgcccagc tctcaaggaa ctgctcaaag aggctcttaa tatggagcgc aataatagat    1020
atcaacctt gcagaaccac gcaaagatgt gagacagccg tcagaccatc aagactagga    1080
agaaactgca tcaactaatg agcaaaatca ccagctacaa tcatagtata catgaccggc    1140
tctaactcac atatcaccat ccttacactt aacattaacg gcctcaactc agctatcaag    1200
cgccatcggc tggccagctg gatcaaatca caggatccaa gcgtttgttg catccaagag    1260
acccacctga cctgtagaga tactcaccgc ctcaagatca agggatggcg aaaagattat    1320
caggcgaacg gtaagcagaa gaaagccgga gtcgcaattc tggtctcaga caagacggat    1380
ttcaagccca ccaaaattaa gcgtgataag gaaggtcact atattatggt gaaaggcagc    1440
atacagcagg aagaacttac catattgaac atctacgcgc caaacaccgg cgcacctcgc    1500
tttatcaaac aggtcctgtc cgatctgcag cgagatctgg attctcatac gttgattatg    1560
ggtgatttca atacaccatt gagcaccctg gatcgcagca ccaggcaaaa ggtaaataaa     1620
gacacgcaag agctcaatag cgcactgcat caggcagatc tcattgatat ttatcgcact    1680
cttcatccta agagtaccga gtacacattc ttcagcgccc cacatcatac atactcaaag    1740
atcgatcata tcgtcggctc aaaggctctg ctgtcaaagt gcaagcgcac agagataatt    1800
acaaattacc tgtcagatca tagcgcgatc aagctcgagc tgagaatcaa gaacctgacc    1860
cagagccgga gtaccacttg gaagcttaat aacctgctgc tcaacgatta ttgggtccac    1920
aatgagatga aggcagagat taaaatgttc ttcgaaacaa atgagaataa ggatactacc    1980
tatcaaaacc tttgggatgc ctttaaggcc gtctgcagag gcaagttcat cgccctcaac    2040
gcctataaaa gaaaacaaga gagatctaag atcgatactc tcacctctca gctgaaggag    2100
ttggagaaac aggaacagac ccactccaag gcgtcaagac ggcaggagat cacaaagatt    2160
cgcgccgagt tgaaagagat cgaaacccaa aagactcttc agaaaattaa cgagtctcgt    2220
agttggttct tcgagcggat taataagata gacagacgct tggcacgact gattaagaag    2280
aagcgcgaaa agaaccagat tgataccatc aagaacgaca agggcgacat cactactgac    2340
ccgaccgaga tccagaccac tattcgggag tattataagc atttgtatgc taacaagctt    2400
gagaacctgg aagagatgga cactttctgt gatacctata ctctgccacg gcttaatcaa    2460
gaggaagtcg agtccctcaa ccgcccaatt acaggaagcg agattgtggc cataattaac    2520
tccctgccga caaagaaatc tcctggtccg gacgggttta cagctgagtt ttatcaacgg    2580
```

-continued

```
tatatggaag agcttgtacc gtttctgctc aagctctttc agtctataga aaaggaaggc   2640
atcttgccca attccttcta cgaagcttct ataatactta ttcccaaacc aggacgcgat   2700
accacaaaga aggaaaactt ccggcccatt agtctcatga atatcgacgc taaaatattg   2760
aacaagattc tcgccaacag aatccaacaa catattaaga aattgataca tcacgaccag   2820
gtgggttta tacctggcat gcagggctgg tttaacatcc ggaagagtat taacgtcatt    2880
caacacatta atagagctaa ggataagaat catatgatca tctctataga cgcgggaaaag   2940
gcattcgata agattcagca gccatttatg ctcaagactc tgaacaaact cggcatcgac   3000
ggaacatatt ttaagattat tcgcgcaatt tacgataagc cgactgctaa cattatcctt   3060
aacggccaaa agctcgaggc ctttccgctc aagactggaa cccgccaagg ctgtcccctc   3120
tccccgcttt tgtttaatat tgtactcgag gtgctggcta gggctattcg tcaagagaaa   3180
gagattaaag ggatacagct cgggaaggaa gaggtcaagc tttccttgtt cgccgatgat   3240
atgattgtgt acctggagaa tcctattgtg tctgctcaga accttcttaa acttatttct   3300
aactttagca aggtcagcgg ctataagatt aacgtccaga aatctcaggc ctttctgtac   3360
acaaataatc gacagaccga atcccagata atgggtgagc ttccgtttgt catagccagc   3420
aaaaggataa agtatctcgg aatccagctg acacgagacg ttaaagattt gtttaaggaa   3480
aattacaagc ctctcctgaa agagattaag gaagatacta ataagtggaa gaatatcccc   3540
tgttcatggg ttggcagaat caacatagtg aagatggcaa tacttcctaa agtgatatat   3600
cgctttaacg ccatcccaat taaactgcct atgaccttct ttacggagct cgagaaaaca   3660
acccttaaat ttatatggaa tcaaaagaga gcaagaatag cgaagtccat cttgagccag   3720
aagaataagg ccggtgggat tactttgcct gattttaagt tgtattataa agccacagta   3780
actaagacag cctggtattg gtatcagaat agagacatcg accagtggaa tcggaccgaa   3840
ccatcagaga taatgcccca catctataat taccttatat tcgataagcc agaaaagaat   3900
aaacagtggg gcaaagacag cctcttcaac aagtggtgtt gggagaattg gctggccata   3960
tgccggaaac tcaagctcga cccctttctt acaccctaca ctaaaatcaa cagtaggtgg   4020
atcaaggact tgaatgtcaa gccaaagact ataaagacac tggaagagaa tcttgggatc   4080
acaatacaag atataggcgt cggcaaagat tttatgtcaa agacgcccaa ggccatggcc   4140
actaaggata agattgataa gtgggacctt attaagctca aaagcttctg tactgccaag   4200
gagaccacga tcagagttaa taggcagccc actacatggg aaaagatttt cgccacttat   4260
tcatcagata aggggttgat aagcagaata tataacgagc tgaagcagat ctacaagaag   4320
aaaacgaata atcccatcaa gaagtgggca aaagatatga acaggcattt tagcaaagag   4380
gatatctacg ccgcgaagaa gcatatgaag aagtgtagtt caagcttggc cattcgtgag   4440
atgcagatta agacgaccat gcgataccac cttaccccag tgaggatggc aattatcaag   4500
aaatctggca ataatagatg ttggcgggc tgtggcgaga ttggcaccct gctccattgc   4560
tggtgggatt gcaagctggt gcagccgctt tggaaatcag tctggcgctt tctgagggac   4620
ctcgagcttg agattcccct cgatcccgca attcccttgc tcggaatcta tcctaacgaa   4680
tacaagagct gttgttacaa ggatacgtgt acccggatgt tcatcgcggc cttgtttacg   4740
atagctaaga cgtggaatca gcctaagtgc cccacaatga tcgattggat caagaaaatg   4800
tggcatattt ataccatgga gtattacgca gcaattaaga atgacgaatt tatttccttc   4860
gttgggacct ggatgaagct ggagactatt attctgagca agctgtctca ggagcaaaag   4920
acaaagcata gaatcttctc tctcattggt ggtaacgact acaaagacga tgacgacaag   4980
cccgccgcca agagggtgaa gctggactaa agcgcttcta gaagttgtct cctcctgcac   5040
tgactgactg atacaatcga tttctggatc cgcaggccta atcaacctct ggattacaaa   5100
atttgtgaaa gattgactgg tattcttaac tatgttgctc ctttacgct atgtggatac   5160
gctgctttaa tgcctttgta tcatgctatt gcttcccgta tggctttcat tttctcctcc   5220
ttgtataaat cctggttgct gtctctttat gaggagttgt ggcccgttgt caggcaacgt   5280
ggcgtggtgt gcactgtgtt tgctgacgca acccccactg gttggggcat tgccaccacc   5340
tgtcagctcc tttccgggac tttcgctttc ccctccctta ttgccacggc ggaactcatc   5400
gccgcctgcc ttgcccgctg ctggacaggg gctcggctgt tgggcactga caattccgtg   5460
gtgttgtcgg ggaagctgac gtcctttcca tggctgctcg cctgtgttgc cacctggatt   5520
ctgcgcggga cgtccttctg ctacgtccct tcggccctca atccagcgga ccttccttcc   5580
cgctgagaga cacaaaaaat tccaacacac tattgcaatg aaaataaatt tcctttatta   5640
gccagaagtc agatgctcaa ggggcttcat gatgtcccca taattttttgg cagagggaaa   5700
aagatctcag tggtatttgt gagccagggc attggccttc tgataggcag cctgcacctg   5760
aggagtgcgg ccgctttact tgtacagctc gtccatgccg agagtgatcc cggcggcggt   5820
cacgaactcc agcaggacca tgtgatcgcg cttctcgttg gggtctttgc tcagggcgga   5880
ctgggtgctc aggtagtggt tgtcgggcag cagcacgggg ccgtcgccga tgggggtgtt   5940
ctgctggtag tggtcggcga gctgcacgct gccgtcctcg atgttgtggc ggatcttgaa   6000
gttcaccttg atgccgttct tctgcttgtc ggccatgata tagacgttgt ggctgttgta   6060
gttgtactcc agcttgtgcc ccaggatgtt gccgtcctcc ttgaagtcga tgcccttcag   6120
ctcgatgcgg ttcaccaggg tgtcgccctc gaacttcacc tcggcgcggg tcttgtagtt   6180
gccgtcgtcc ttgaagaaga tggtgcgctc ctggacgtag ccttcgggca tggcggactt   6240
gaagaagtcg tgctgcttca tgtggtcggg gtagcggctg aagcactgca cgccgtaggt   6300
cagggtggtc acgagggtgg gccagggcac gggcagcttg ccggtggtgc agatgaactt   6360
cagggtcagc ttgccgtagg tggcatcgcc ctcgccctcg ccggacacgc tgaacttgtg   6420
gccgtttacg tcgccgtcca gctcgaccag gatgggcacc accccggtga acagctcctc   6480
gcccttgctc accatggtgg cgggatctga cggttcacta aaccagctct gcttatatag   6540
acctccaccg gtacacgcct accgcccatt gcgtcaatg gggcggagtt gttacgacat    6600
tttggaaagt cccgttgatt ttggtgccaa aacaaactcc cattgacgtc aatgggggtgg   6660
agacttggaa atccccgtga tcaaaccgc tatccacgcc cattgatgta ctgccaaaac    6720
cgcatcacca tggtaatagc gatgactaat acgtagatgt actgccaagt aggaaagtcc   6780
cataaggtca tgtactgggc ataatgccag gcgggccatt taccgtcatt gacgtcaata   6840
gggggcgtac ttggcatatg atacacttga tgtactgcca gtgggcagt ttaccgtaaa    6900
tactccaccc attgacgtca atggaaagtc cctattggcg ttactatggg aacatacgtc   6960
attattgacg tcaatgggcg ggggtcgttg ggcggtcagc caggcgggcc atttaccgta   7020
agttatgtaa cgggcctgct gccggctctg cggcctcttc cgcgtcttcg ccttcgccct   7080
cagacgagtc ggatctccct ttgggccgcc tccccgcctg tctagcttga ctgactgaga   7140
tacagcgtac cttcagctca cagacatgat aagatacatt gatgagtttg gacaaaccac   7200
aactagaatg cagtgaaaaa aatgctttat ttgtgaaatt tgtgatgcta ttgctttatt   7260
tgtaaccatt ataagctgca ataaacaagt t                                 7291
```

```
SEQ ID NO: 43          moltype = DNA  length = 7376
FEATURE                Location/Qualifiers
misc_feature           1..7376
                       note = Description of Artificial Sequence: Synthetic
                       polynucleotide
source                 1..7376
                       mol_type = other DNA
                       organism = synthetic construct
SEQUENCE: 43
taatacgact cactataggg agaagtactg ccaccatggg caagaagcaa aatcgcaaga    60
cggggaattc caagacacaa tccgctagcc caccacctaa agagcgttct agctccctg    120
ctactgagca gtcctggatg gaaaacgact tcgatgaact ccgggaagag ggatttaggc   180
gatccaacta ttcagaactc cgcgaagata tccagacaag gggaaggaa gtcgagaatt    240
tcgagaagaa cctcgaggag tgcatcaccc gtatcacaaa cactgagaaa tgtctcaaag    300
aactcatgga acttaagaca aaagccaggg agcttcgaga ggagtgtcgg agtctgagat    360
ccaggtgtga ccagctcgag gagcgcgtga gcgcgatgga agacgagatg aacgagatga    420
aaagagaggg caaattcagg gagaagcgca ttaagaggaa cgaacagagt ctgcaggaga    480
tttgggatta cgtcaagagg cctaacctgc ggttgatcgg cgtccccgag agcgacgtag    540
aaaacgggac taaactggag aatacacttc aagacatcat tcaagaaaat tttccaaacc    600
tggctcggca agctaatgtg caaatccaag agatccaacg cacaccccag cggtatagct    660
ctcggcgtgc cacccctagg catattatcg tgcgctttac taaggtggag atgaaagaga    720
agatgctgcg agccgctcgg gaaaaggaa gggtgacttt gaagggcaaa cctattcggc    780
tgacggttga ccttagcgcc gagacactcc aggcacgccg ggaatggggc cccatcttta    840
atatcctgaa ggagaagaac ttccagccac gaatctctta ccctgcaaag ttgagtttta    900
tctccgaggg tgagattaag tatttcatcg ataaacagat gctgcgagac ttcgtgacaa    960
ctcgcccagc tctcaaggaa ctgctcaaag aggctcttaa tatggagcgc aataatagat   1020
atcaaccctt gcagaaccac gcaaagatgt gagacagccg tcagaccatc aagactagga   1080
agaaactgca tcaactaatg agcaaaatca ccagctaaca tcatagtata catgaccggc   1140
tctaactcac atatcaccat ccttacactt aacattaacg gcctcaactc agctatcaag   1200
cgccatcggc tggccagctg gatcaaatca caggatccaa gcgtttgttg catccaagag   1260
acccacctga cctgtagaga tactcaccgc ctcaagatca agggatggcg aaagatttat   1320
caggcgaacg gtaagcagaa gaaagccgga gtcgcaattc tggtctcaga caagacggat   1380
ttcaagccca ccaaaattaa gcgtgataag gaaggtcact atattatggt gaaaggcagc   1440
atacagcagg aagaacttac catattgaac atctacgcgc aaacaccggg cgcacctcgc   1500
tttatcaaac aggtcctgtc cgatctgcag cgagatctgg attctcatac gttgattatg   1560
ggtgatttca atacaccatt gagcaccctg gatcgcagca ccaggcaaaa ggtaaataaa   1620
gacacgcaag agctcaatag cgcactgcat caggcagatc tcattgatat ttatcgcact   1680
cttcatccta agagtaccga gtacacattc ttcagcgccc cacatcatac atactcaaag   1740
atcgatcata tcgtcggctc aaaggctctg ctgtcaaagt gcaagcgcac agagataatt   1800
acaaattacc tgtcagatca tagcgcgatc aagctcgagc tgagaatcaa gaacctgacc   1860
cagagccgga gtaccacttg gaagcttaat aacctgctgc tcaacgatta ttgggtccac   1920
aatgagatga aggcagagat taaaatgttc ttcgaaacaa atgagaataa ggatactacc   1980
tatcaaaacc tttgggatgc ctttaaggcc gtctgcagag gcaagttcat cgccctcaac   2040
gcctataaaa gaaaacaaga gagatctaag atcgatactc tcacctctca gctgaaggag   2100
ttggagaaac aggaacagac ccactccaag gcgtcaagac ggcaggagat cacaaagatt   2160
cgcgccgagt tgaaagagat cgaaacccaa aagactcttc agaaaattaa cgagtctcgt   2220
agttggttct tcgagcggat taataagata gacagacctc tggcacgact gattaagaag   2280
aagcgcgaaa agaaccagat tgataccatc aagaacgaca agggcgacat cactactgac   2340
ccgaccgaga tccagaccac tattcgggag tattataagc atttgtatgc taacaagctt   2400
gagaacctgg aagagatgga cacttttctg gatacctata ctctgccacg gcttaatcaa   2460
gaggaagtcg agtccctcaa ccgcccaatt acaggaagcg agattgtggc cataattaac   2520
tccctgccga caaagaaatc tcctggtccg gacgggttta cagctgagtt ttatcaacgg   2580
tatatggaag agcttgtacc gtttctgctc aagctctttc agtctataga aaaggaaggc   2640
atcttgccaa attccttcta cgaagcttct ataatactta ttcccaaacc aggacgcgat   2700
accacaaaga aggaaaactt ccggcccatt agtctcatga atatcgacgc taaaatattg   2760
aacaagattc tcgccaacag aatccaacaa catattaaga aattgataca tcacgaccag   2820
gtgggggttta tacctggcat gcagggctgg tttaacatcc ggaagagtat taacgtcatt   2880
caacacata atagagctaa ggataagaat catatgatca tctctataga cgcggaaaag   2940
gcattcgata agattcagca gccatttatg ctcaagactc tgaacaaact cggcatcgac   3000
ggaacatatt ttaagattat tcgcgcaatt tacgataagc cgactgctaa cattatcctt   3060
aacgccaaa agctcgaggc ctttccgctc aagactggaa cccgccaagg ctgtcccctc   3120
tccccgcttt tgtttaatat tgtactcgag gtgctggcta gggctattcg tcaagagaaa   3180
gagattaaag ggatacagct cgggaaggaa gaggtcaagc tttccttgtt cgccgatgat   3240
atgattgtgt acctggagaa tcctattgtg tctgctcaga accttcttaa acttatttct   3300
aactttagca aggtcagcgg ctataagatt aacgtccaga aatctcaggc ctttctgtac   3360
acaaataatc gacagaccga tcccagata atgggtgagc ttccgtttgt catagccagc   3420
aaaaggataa agtatctcgg aatccagctg cacgagacg ttaaagattt gtttaaggaa   3480
aattacaagc ctctcctgaa agagattaag gaagatacta ataagtggaa gaatatcccc   3540
tgttcatggg ttggcagaat caacatagtg aagatggcaa tacttcctaa agtgatatat   3600
cgctttaacg ccatcccaat taaactgcct atgaccttct ttacggagct cgagaaaaca   3660
acccttaaat ttatatggaa tcaaaagaga gcaagaatag cgagtccat cttgagccag   3720
aagaataagg ccggtgggat tactttgcct gattttaagt gtattataaa agccacagta   3780
actaagacag cctggtattg gtatcagaat agagacatcg accagttgga tcggaccgaa   3840
ccatcagaga taatgccca catctataat taccttatat tcgataagcc agaaaagaat   3900
aaacagtggg gcaaagacag cctcttcaac aagtggtgtt gggagaattg gctggccata   3960
tgccggaaac tcaagctcga ccccctttctt acaccctaca ctaaaatcaa cagtaggtgg   4020
atcaaggact tgaatgtcaa gccaaagact ataaagacac tggaagagaa tcttgggatc   4080
acaatacaag atataggcgt cggcaaagat tttatgtcaa agacgcccaa ggccatggcc   4140
```

-continued

```
actaaggata agattgataa gtgggacctt attaagctca aaagcttctg tactgccaag  4200
gagaccacga tcagagttaa taggcagccc actacatggg aaaagatttt cgccacttat  4260
tcatcagata aggggttgat aagcagaata tataacgagc tgaagcagat ctacaagaag  4320
aaaacgaata atcccatcaa gaagtgggca aaagatatga acaggcattt tagcaaagag  4380
gatatctacg ccgcgaagaa gcatatgaag aagtgtagtt caagcttggc cattcgtgag  4440
atgcagatta agacgaccat gcgataccac cttaccccag tgaggatggc aattatcaag  4500
aaatctggca ataatagatg ttggcggggc tgtggcgaga ttggcaccct gctccattgc  4560
tggtgggatt gcaagctggt gcagccgctt tggaaatcag tctggcgctt tctgagggac  4620
ctcgagcttg agattccctt cgatcccgca attcccttgc tcggaatcta tcctaacgaa  4680
tacaagagct gttgttacaa ggatacgtgt acccggatgt tcatcgcggc cttgtttacg  4740
atagctaaga cgtggaatca gcctaagtgc cccacaatga tcgattggat caagaaaatg  4800
tggcatattt ataccatgga gtattacgca gcaattaaga atgacgaatt tatttccttc  4860
gttgggacct ggatgaagct ggagactatt attctgagca agctgtctca ggagcaaaag  4920
acaaagcata gaatcttctc tctcattggt ggtaacgact acaaagacga tgacgacaag  4980
taaagcggcc gggcgcggtg gctcacgcct gtaatcccag cactttggga ggccgaggcg  5040
ggaggatcgc agttcgagac cagcgcgaga ccccgtctct acaaaaatac aaaaattagc  5100
ttctagaagt tgtctcctcc tgcactgact gactgataca atcgatttct ggatccgcag  5160
gcctaatcaa cctctggatt acaaaatttg tgaaagattg actggtattc ttaactatgt  5220
tgctcctttt acgctatgtg gatacgctgc tttaatgcct ttgtatcatg ctattgcttc  5280
ccgtatggct ttcattttct cctccttgta taaatcctgg ttgctgtctc tttatgagga  5340
gttgtggccc gttgtcaggc aacgtggcgt ggtgtgcact gtgtttgctg acgcaacccc  5400
cactggttgg ggcattgcca ccacctgtca gctcctttcc gggactttcg ctttccccct  5460
ccctattgcc acggcggaac tcatcgccgc ctgccttgcc cgctgctgga caggggctcg  5520
gctgttgggc actgacaatt ccgtggtgtt gtcggggaag ctgacgtcct ttccatggct  5580
gctcgcctgt gttgccacct ggattctgcg cgggacgtcc ttctgctacg tcccttcggc  5640
cctcaatcca gcggaccttc cttcccgctg agagacacaa aaattccaa cacactattg  5700
caatgaaaat aaatttcctt tattagccag aagtcagatg ctcaaggggc ttcatgatgt  5760
ccccataatt tttggcagag ggaaaaagat ctcagtggta tttgtgagcc agggcattgg  5820
ccttctgata ggcagcctgc acctgaggag tgcggccgct ttacttgtac agctcgtcca  5880
tgccgagagt gatcccggcg gcggtcacga actccagcag gaccatgtga tcgcgcttct  5940
cgttggggtc tttgctcagg gcggactggg tgctcaggta gtggttgtcg ggcagcagca  6000
cggggccgtc gccgatgggg gtgttctgct ggtagtggtc ggcgagctgc acgctgccgt  6060
cctcgatgtt gtggcggatc ttgaagttca ccttgatgcc gttcttctgc ttgtcggcca  6120
tgatatagac gttgtggctg ttgtagttgt actccagctt gtgccccagg atgttgccgt  6180
cctccttgaa gtcgatgccc ttcagctcga tgcggttcac cagggtgtcg ccctcgaact  6240
tcacctcggc gcgggtcttg tagttgccgt cgtccttgaa gaagatggtg cgctcctgga  6300
cgtagccttc gggcatggcg gacttgaaga agtcgtgctg cttcatgtgg tcggggtagc  6360
ggctgaagca ctgcacgccg taggtcaggg tggtcacgag ggtgggccag ggcacgggca  6420
gcttgccggt ggtgcagatg aacttcaggg tcagcttgcc gtaggtggca tcgccctcgc  6480
cctcgccgga cacgctgaac ttgtggccgt ttacgtcgcc gtccagctcg accaggatgg  6540
gcaccacccc ggtgaacagc tcctcgccct tgctcaccat ggtggcggga tctgacggtt  6600
cactaaacca gctctgctta tatagacctc ccaccgtaca cgcctaccgc ccatttgcgt  6660
caatggggag ttgttac gacattttgg aaagtcccgt tgattttggt gccaaaacaa  6720
actcccattg acgtcaatgg ggtggagact tggaaatccc cgtgagtcaa accgctatcc  6780
acgcccattg atgtactgcc aaaaccgcat caccatggta atagcgatga ctaatacgta  6840
gatgtactgc caagtaggaa agtcccataa ggtcatgtac tgggcataat gccaggcggg  6900
ccatttaccg tcattgacgt caataggggg cgtacttggc atatgataca cttgatgtac  6960
tgccaagtgg gcagtttacc gtaaatactc cacccattga cgtcaatgga aagtccctat  7020
tggcgttact atgggaacat acgtcattat tgacgtcaat gggcggggt cgttgggcgg  7080
tcagccagcg gggccattta ccgtaagtta tgtaacgggc ctgctgccgg ctctgcggcc  7140
tcttccgcgt cttcgccttc gccctcagac gagtcggatc tccctttggg ccgcctcccc  7200
gcctgtctag cttgactgac tgagatacag cgtaccttca gctcacgaca atgataagat  7260
acattgatga gtttggacaa accacaacta gaatgcagtg aaaaaaatgc tttatttgtg  7320
aaatttgtga tgctattgct ttatttgtaa ccattataag ctgcaataaa caagtt  7376
```

SEQ ID NO: 44          moltype = DNA   length = 14122
FEATURE                Location/Qualifiers
misc_feature           1..14122
                       note = Description of Artificial Sequence: Synthetic
                       polynucleotide
source                 1..14122
                       mol_type = other DNA
                       organism = synthetic construct
SEQUENCE: 44

```
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaaggaaga cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc cacccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatctta  840
atatcctgaa ggagaagaac ttccagccac gaatctctta ccctgcaaag ttgagtttta  900
```

-continued

```
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaacccctt gcagaaccac gcaaagatgt gagacagtta aaacagcctg tgggttgatc  1080
ccacccacag gcccattggg cgctagcact ctggtatcac ggtacctttg tgcgcctgtt  1140
ttatacccce tcccccaact gtaacttaga agtaacacac accgatcaac agtcagcgtg  1200
gcacaccagc cacgttttga tcaagcactt ctgttacccc ggactgagta tcaatagact  1260
gctcacgcgg ttgaaggaga aagcgttcgt tatccggcca actacttcga aaaacctagt  1320
aacaccgtgg aagttgcaga gtgtttcgct cagcactacc ccagtgtaga tcaggtcgat  1380
gagtcaccgc attccccacg ggcgaccgtg gcggtggctg cgttggcggc ctgcccatgg  1440
ggaaacccat gggacgctct aatacagaca tggtgcgaag agtctattga gctagttggt  1500
agtcctccgg ccccctgaatg cggctaatcc taactgcgga gcacacaccc tcaagccaga  1560
gggcagtgtg tcgtaacggg caactctgca gcggaaccga ctactttggg tgtccgtgtt  1620
tcattttatt cctatactgg ctgcttatgg tgacaattga gagatcgtta ccatatagct  1680
attggattgg ccatccggtg actaatagag ctattatata tcccttttgtt gggtttatac  1740
cacttagctt gaaagaggtt aaaacattac aattcattgt taagttgaat acagcaaata  1800
catgaccggc tctaactcac atatcaccat ccttacactt aacattaacg gcctcaactc  1860
agctatcaag cgccatcggc tggccagctg gatcaaatca caggatccaa gcgtttgttg  1920
catccaagag acccacctga cctgtagaca tactcaccgc ctcaagatca agggatggcg  1980
aaagatttat caggcgaacg gtaagcagaa gaaagccgga gtcgcaattc tggtctcaga  2040
caagacggat ttcaagccca ccaaaattaa gcgtgataag gaaggtcact atattatggt  2100
gaaaggcagc atacagcagg aagaacttac catattgaac atctacgcgc caaacaccgg  2160
cgcacctcgc tttatcaaac aggtcctgtc cgatctgcag cggagatctg attctcatac  2220
gttgattatg ggtgatttca atacaccatt gagcaccctg gatcgcagca ccaggcaaaa  2280
ggtaaataaa gacacgcaag agctcaatag cgcactgcat caggcagatc tcattgatat  2340
ttatcgcact cttcatccta agagtaccga gtacacattc ttcagcgccc cacatcatac  2400
atactcaaag atcgatcata tcgtcggctc aaaggctctg ctgtcaaagt gcaagcgcac  2460
agagataatt acaaattacc tgtcagatca tagcgcgatc aagctcgagc tgagaatcaa  2520
gaacctgacc cagagccgga gtaccacttg gaagcttaat aacctgctgc tcaacgatta  2580
ttgggtccac aatgagatga aggcagagat taaaatgttc ttcgaaacaa atgagaataa  2640
ggatactacc tatcaaaacc tttgggatgc ctttaaggcc gtctgcagag gcaagttcat  2700
cgccctcaac gcctataaaa gaaaacaaga gagatctaag atcgatactc tcacctctca  2760
gctgaaggag ttggagaaac aggaacagac ccactccaag gcgtcaagac ggcaggagat  2820
cacaaagatt cgcgccgagt tgaaagagat cgaaacccaa aagactcttc agaaaattaa  2880
cgagtctcgt agttggttct tcgagcggat taataagata gacagacctc tggcacgact  2940
gattaagaag aagcgcgaaa agaaccagat tgataccatc aagaacgaca agggcgacat  3000
cactactgac ccgaccgaga tccagaccac tattcgggag tattataagc atttgtatgc  3060
taacaagctt gagaacctgg aagagatgga cacttttctg gatacctata ctctgccacg  3120
gcttaatcaa gaggaagtcg agtccctcaa ccgcccaatt acaggaagcg agattgtggc  3180
cataattaac tccctgccga caaagaaatc tcctggtccg gacgggttta cagctgagtt  3240
ttatcaacgg tatatggaag agcttgtacc gtttctgctc aagctctttc agtctataga  3300
aaaggaaggc atcttgccca attccttcta cgaagcttct ataatactta ttcccaaacc  3360
aggacgcgat accacaaaga aggaaaactt ccggcccatt agtctcatga atatcgacgc  3420
taaaatattg aacaagattc tcgccaacag aatccaacaa aattgataca  3480
tcacgaccag gtggggttta tacctggcat gcagggctgg tttaacatcc ggaagagtat  3540
taacgtcatt caacacatta atagagctaa ggataagaat catatgatca tctctataga  3600
cgcggaaaag gcattcgata agattcagca gccatttatg ctcaagactc tgaacaaact  3660
cggcatcgac ggaacatatt ttaagattat tcgcgcaatt tacgataagc cgactgctaa  3720
cattatcctt aacggccaaa agctcgaggc ctttccgctc aagactggaa cccgccaagg  3780
ctgtcccctc tccccgcttt tgtttaatat tgtactcgag gtgctggcta gggctattcg  3840
tcaagagaaa gagattaaag ggatacagct cgggaaggaa gaggtcaagc tttccttgtt  3900
cgccgatgat atgattgtgt acctggagaa tcctattgtg tctgctcaga accttcttaa  3960
acttatttct aactttagca aggtcagcgg ctataagatt aacgtccaga aatctcaggc  4020
cttttctgtac acaaataatc gacagaccga atcccagata atgggtgagc ttccgtttgt  4080
catagccagc aaaaaggataa agtatctcgg aatccagctg acacgagacg ttaaagattt  4140
gtttaaggaa aattacaagc ctctcctgaa agagattaag gaagtacta ataagtggaa  4200
gaatatcccc tgttcatggg ttggcagaat caacatagtg aagatggcaa tacttcctaa  4260
agtgatatat cgctttaacg ccatcccaat taaactgcct atgaccttct ttacggagct  4320
cgagaaaaca acccttaaat ttatatggaa tcaaaagaga gcaagaatag cgaagtccat  4380
cttgagccag aagaataagg ccggtggaat tactttgcct gattttaagt tgtattataa  4440
agccacagta actaagacag cctggtattg gtatcagaat agagacatcg accagtggaa  4500
tcggaccgaa ccatcagaga taatgcccca catctataat taccttatat tcgataagcc  4560
agaaaagaat aaacagtggg gcaaagacag cctcttcaac aagtggtgtt gggagaattg  4620
gctggccata tgccggaaac tcaagctcga ccccttttctt acaccctaca ctaaaatcaa  4680
cagtaggtgg atcaaggact tgaatgtcaa gccaaagact ataagacac tggaagagaa  4740
tcttgggatc acaatacaag atataggcgt cggcaaagat tttatgtcaa agacgcccaa  4800
ggccatggcc actaaggata agattgataa gtgggacctt attaagctca aaagcttctg  4860
tactgccaag gagaccacga tcagagttaa taggcagccc actacatggg aaaagatttt  4920
cgccacttat tcatcagata aggggttgat aagcagaata tataacgagc tgaagcagat  4980
ctacaagaag aaaacgaata atcccatcaa gaagtgggca aaagatatga acaggcattt  5040
tagcaaagag gatatctacg ccgcgaagaa gcatatgaag aagtgtagtt caagcttggc  5100
cattcgtgag atgcagatta agacgaccat gcgataccac cttaccccag tgaggatggc  5160
aattatcaag aaatctggca ataatagatg ttggcggggc tgtggcgaga ttggcaccct  5220
gctccattgc tggtgggatt gcaagctggt gcagccgctt tggaaatcag tctggcgctt  5280
tctgagggac ctcgagcttg agattccctt cgatcccgca attcccttgc tcggaatcta  5340
tcctaacgaa tacaagagct gttgttacaa ggatacgtgt acccggatgt tcatcgcggc  5400
cttgtttacg atagctaaga cgtggaatca gcctaagtgc cccacaatga tcgattggat  5460
caagaaaatg tggcatattt ataccatgga gtattacgca gcaattaaga atgacgaatt  5520
tatttccttc gttgggacct ggatgaagct ggagactatt attctgagca agctgtctca  5580
ggagcaaaag acaaagcata gaatcttctc tctcattggt ggtaacgact acaaagacga  5640
```

-continued

```
tgacgacaag taaagcgctt ctagaagttg tctcctcctg cactgactga ctgatacaat   5700
cgatttctgg atccgcaggc ctaatcaacc tctggattac aaaatttgtg aaagattgac   5760
tggtattctt aactatgttg ctccttttac gctatgtgga tacgctgctt taatgccttt   5820
gtatcatgct attgcttccc gtatggcttt cattttctcc tccttgtata aatcctggtt   5880
gctgtctctt tatgaggagt tgtggcccgt tgtcaggcaa cgtggcgtgg tgtgcactgt   5940
gtttgctgac gcaacccca ctggttgggg cattgccacc acctgtcagc tcctttccgg   6000
gactttcgct ttccccctcc ctattgccac ggcggaactc atcgccgcct gccttgcccg   6060
ctgctggaca ggggctcggc tgttgggcac tgacaattcc gtggtgttgt cggggaagct   6120
gacgtccttt ccatggctgc tcgcctgtgt tgccacctgg attctgcgcg ggacgtcctt   6180
ctgctacgtc ccttcggccc tcaatccagc ggaccttcct tcccgcgaac aaacgaccca   6240
acacccgtgc gttttattct gtcttttat tgccgatccc ctcagaagaa ctcgtcaaga   6300
aggcgataga aggcgatgcg ctgcgaatcg ggagcggcga taccgtaaag cacgaggaag   6360
cggtcagccc attcgccgcc aagctcttca gcaatatcac gggtagccaa cgctatgtcc   6420
tgatagcggt cggccgcttt acttgtacag ctcgtccatg ccgagagtga tcccggcggc   6480
ggtcacgaac tccagcagga ccatgtgatc gcgcttctcg ttggggtctt tgctcagggc   6540
ggactgggtg ctcaggtagt ggttgtcggg cagcagcacg gggccgtcgc cgatgggggt   6600
gttctgctgg tagtggtcgg ccaggtgagt ccaggagatg tttcagcact gttgcctta   6660
gtctcgaggc aacttagaca actgagtatt gatctgagca cagcagggtg tgagctgttt   6720
gaagatactg gggttggggg tgaagaaact gcagaggact aactgggctg agacccagtg   6780
gcaatgtttt agggcctaag gaatgcctct gaaaatctag atggacaact ttgactttga   6840
gaaaagagag gtggaaatga ggaaaatgac ttttctttat tagatttcgg tagaaagaac   6900
tttcatcttt cccctatttt tgttattcgt tttaaaacat ctatctggag gcaggacaag   6960
tatggtcatt aaaaagatgc aggcagaagg catatattgg ctcagtcaaa gtggggaact   7020
ttggtggcca aacatacatt gctaaggcta ttcctatatc agctggacac atataaaatg   7080
ctgctaatgc ttcattacaa acttatatcc tttaattcca gatgggggca aagtatgtcc   7140
aggggtgagg aacaattgaa acatttgggc tggagtagat tttgaaagtc agctctgtgt   7200
gtgtgtgtgt gtgtgtgtgt gtgagagcgt gtgtttcttt taacgttttc agcctacagc   7260
atacagggtt catggtggca agaagataac aagatttaaa ttatgccag tgactagtgc   7320
tgcaagaaga acaactacct gcatttaatg ggaaagcaaa atctcaggct ttgagggaag   7380
ttaacatagg cttgattctg ggtggaagct gggtgtgtag ttatctggag gccaggctgg   7440
agctctcagc tcactatggg ttcatctttg ttgtctcctt tcatctcaac agctgcacgc   7500
tgccgtcctc gatgttgtgg cggatcttga agttcacctt gatgccgttc ttctgcttgt   7560
cggccatgat atagacgttg tggctgttgt agttgtactc cagcttgtgc cccaggatgt   7620
tgccgtcctc cttgaagtcg atgcccttca gctcgatgcg gttcaccagg gtgtcgccat   7680
cgaacttcac ctcggcgcgg gtcttgtagt tgccgtcgtc cttgaagaag atggtgcgct   7740
cctggacgta gccttcgggc atggcggact tgaagaagtc gtgctgcttc atgtggtcgg   7800
ggtagcggct gaagcactgc acgccgtagg tcagggtggt cacgagggtg ggccagggca   7860
cgggcagctt gccggtggtg cagatgaact tcagggtcag cttgccgtag gtggcatcgc   7920
cctcgcctc gccggacacg ctgaacttgt ggccgtttac gtcgccgtcc agctcgacca   7980
ggatgggcac cacccggtg aacagctcct cgcccttgct caccatggtg gcgaattcga   8040
agcttgagca cgagatctga gtccggtagg cctagcggat ctgacggttc actaaaccag   8100
ctctgcttat atagacctcc caccgtacac gcctaccgcc catttgcgtc aatggggcgg   8160
agttgttacg acattttgga aagtcccgtt gattttggtg ccaaaacaaa ctcccattga   8220
cgtcaatggg gtggagactt ggaaatcccc gtgagtcaaa ccgctatcca cgcccattga   8280
tgtactgcca aaaccgcatc accatggtaa tagcgatgac taatacgtag atgtactgcc   8340
aagtaggaaa gtcccataag gtcatgtact gggcataatg ccaggcgggc catttaccgt   8400
cattgacgtc aatagggggc gtacttggca tatgatacac ttgatgtact gccaagtggg   8460
cagtttaccg taaatactcc acccattgac gtcaatggaa agtccctatt ggcgttacta   8520
tgggaacata cgtcattatt gacgtcaatg ggcgggggtc gttgggcggt cagccaggcg   8580
ggccatttac cgtaagttat gtaacgggcc tgctgccggc tctgcggcct cttccgcgtc   8640
ttcgccttcg ccctcagacg agtcggatct ccctttggc cgcctccccg cctgtcctga   8700
ttgactgact gagatacagc gtaccttcag ctcacagaca tgataagata cattgatgag   8760
tttgacaaa ccacaactag aatgcagtga aaaaaatgct ttatttgtga aatttgtgat   8820
gctattgctt tatttgtaac cattataagc tgcaataaac aagttaacaa caacaattgc   8880
attttttta tgtttcaggt tcaggggggag gtgtgggagg ttttttaaag caagtaaaac   8940
ctctacaaat gtggtattgg cccatctcta tcggtatcgt agcataaccc cttggggcct   9000
ctaaacgggt cttgaggggt ttttttgtgcc cctcgggccg gattgctatc taccggcatt   9060
ggcgcagaaa aaaatgcctg atgcgacgct gcgcgtctta tactcccaca tatgccagat   9120
tcagcaacgg cctacggctt cccaacttgc ccacttccat acgtgtcctc cttaccagaa   9180
atttatcctt aaggtcgtca gctatcctgc aggcgatctc tcgatttcga tcaagacatt   9240
cctttaatgg tctttctgg acaccactag gggtcagaag tagttcatca aactttcttc   9300
cctcccctaat ctcattggtt accttgggct atcgaaactt aattaagcga tctgcatctc   9360
aattagtcag caaccatagt cccgccccta actccgccca tcccgcccct aactccgccc   9420
agttccgccc attctccgcc ccatcgctga ctaattttat gcagaggccga ggccgcctcgg   9480
gccgcctcgg cctctgagct attccagaag tagtgaggag gcttttttgg aggcctaggc   9540
ttttgcaaag gaggtagcca acatgattga acaagatgga ttgcacgcag gttctcccgc   9600
cgcttgggtg gagaggctat tcggctatga ctgggcacaa cagacaatcg gctgctctga   9660
tgccgccgtg ttccggctgt cagcgcaggg gcgcccggtt ctttttgtca agaccgacct   9720
gtccggtgcc ctgaatgaac tccaggacga ggcagcgcgg ctatcgtggc tggccacgac   9780
gggcgttcct tgcgcagctg tgctcgacgt tgtcactgaa gcgggaaggg actggctgct   9840
attgggcgaa gtgccggggc aggatctcct gtcatctcac cttgctcctg ccgagaaagt   9900
atccatcatg gctgatgcaa tgcggcggct gcatacgctt gatccggcta cctgcccatt   9960
cgaccaccaa gcgaaacatc gcatcgagcg agcacgtact cggatggaag ccggtcttgt   10020
cgatcaggat gatctggacg aagagcatca ggggctcgcg ccagccgaac tgttcgccag   10080
gctcaaggcg cggatgcccg acggcgagga tctcgtcgtg acccacgcg atgcctgctt   10140
gccgaatatc atggtggaaa atggccgctt ttctggattc atcgactgtg gccggctggg   10200
tgtggcggac cgctatcagg acatagcgtt ggctacccgt gatattgctg aagagcttgg   10260
cggcgaatgg gctgaccgct tcctcgtgct ttacggtatc gccgctcccg attcgcagcg   10320
catcgccttc tatcgccttc ttgacgagtt cttctagtat gtaagcccctg tgccttctag   10380
```

```
ttgccagcca tctgttgttt gcccctcccc cgtgccttcc ttgaccctgg aaggtgccac   10440
tcccactgtc ctttcctaat aaaatgagga aattgcatcg cattgtctga gtaggtgtca   10500
ttctattctg gggggtgggg tggggcagga cagcaagggg gaggattggg aagacaatag   10560
caggcatgct ggggatgcgg tgggctctat ggttaattaa ccagtcaagt cagctacttg   10620
gcgagatcga cttgtctggg tttcgactac gctcagaatt gcgtcagtca agttcgatct   10680
ggtccttgct attgcacccg ttctccgatt acgagtttca tttaaatcat gtgagcaaaa   10740
ggccagcaaa aggccaggaa ccgtaaaaag gccgcgttgc tggcgttttt ccataggctc   10800
cgcccccctg acgagcatca caaaaatcga cgctcaagtc agaggtggcg aaacccgaca   10860
ggactataaa gataccaggc gtttcccct ggaagctccc tcgtgcgctc tcctgttccg   10920
accctgccgc ttaccggata cctgtccgcc tttctccctt cgggaagcgt ggcgctttct   10980
catagctcac gctgtaggta tctcagttcg gtgtaggtcg ttcgctccaa gctgggctgt   11040
gtgcacgaac ccccgttca gcccgaccgc tgcgccttat ccggtaacta tcgtcttgag   11100
tccaacccgg taagacacga cttatcgcca ctggcagcag ccactggtaa caggattagc   11160
agagcgaggt atgtaggcgg tgctacagag ttcttgaagt ggtggcctaa ctacggctac   11220
actagaagaa cagtatttgg tatctgcgct ctgctgaagc cagttacctt cggaaaaaga   11280
gttggtagct cttgatccgg caaacaaacc accgctggta gcggtggttt ttttgtttgc   11340
aagcagcaga ttacgcgcag aaaaaaagga tctcaagaag atcctttgat cttttctacg   11400
gggtctgacg ctcagtggaa cgaaaactca cgttaaggga ttttggtcat gagattatca   11460
aaaaggatct tcacctagat ccttttaaat taaaaatgaa gttttaaatc aatctaaagt   11520
atatatgagt aaacttggtc tgacagttac caatgcttaa tcagtgaggc acctatctca   11580
gcgatctgtc tatttcgttc atccatagtt gcatttaaat ttccgaactc tccaaggccc   11640
tcgtcggaaa atcttcaaac ctttcgtccg atccatcttg caggtacctt ctcgaacgaa   11700
ctatcgcaag tctcttggcc ggccttgcgc cttggctatt gcttggcagc gcctatcgcc   11760
aggtattact ccaatcccga atatccgaga tcgggatcac ccgagagaag ttcaacctac   11820
atcctcaatc ccgatctatc cgagatccga ggaatatcga aatcggggcg cgcctggtgt   11880
accgaaacg atcctctcag tgcgagtctc gacgatccat atcgttgctt ggcagtcagc   11940
cagtcggaat ccagcttggg acccaggaag tccaatcgtc agatattgta ctcaagcctg   12000
gtcacggcag cgtaccgatc tgtttaaacc tagatattga tagtctgatc ggtcaacgta   12060
taatcgagtc ctagcttttg caaacatcta tcaagagaca ggatcagcag gaggctttcg   12120
catgagtatt caacatttcc gtgtcgccct tattcccttt tttgcggcat tttgccttcc   12180
tgttttttgct cacccagaaa cgctggtgaa agtaaaagat gctgaagatc agttgggtgc   12240
gcgagtgggt tacatcgaac tggatctcaa cagcggtaag atccttgaga gttttcgccc   12300
cgaagaacgc tttccaatga tgagcacttt taaagttctg ctatgtggcg cggtattatc   12360
ccgtattgac gccgggcaag agcaactcgg tcgccgcata cactattctc agaatgactt   12420
ggttgagtat tcaccagtca cagaaaagca tcttacggat ggcatgacag taagagaatt   12480
atgcagtgct gccataacca tgagtgataa cactgcggcc aacttacttc tgacaacgat   12540
tggaggaccg aaggagctaa ccgcttttt gcacaacatg gggatcatg taactcgcct   12600
tgatcgttgg gaaccggagc tgaatgaagc cataccaaac gacgagcgtg acaccacgat   12660
gcctgtagca atggcaacaa ccttgcgtaa actattaact ggcgaactac ttactctagc   12720
ttcccggcaa cagttgatag actggatgga ggcggataaa gttgcaggac cacttctgcg   12780
ctcggccctt ccggctggct ggtttattgc tgataaatct ggagccggtg agcgtgggtc   12840
tcgcggtatc attgcagcac tggggccaga tggtaagccc tcccgtatcg tagttatcta   12900
cacgacgggg agtcaggcaa ctatggatga acgaaataga cagatcgctg agataggtgc   12960
ctcactgatt aagcattggt aaccgattct aggtgcattg gcgcagaaaa aaatgcctga   13020
tgcgacgctg cgcgtcttat actcccacat atgccagatt cagcaacgga tacggcttcc   13080
ccaacttgcc cacttccata cgtgtcctcc ttaccagaaa tttatcctta agatcgttta   13140
aactcgactc tggctctatc gaatctccgt cgtttcgagc ttacgcgaac agccgtggcg   13200
ctcatttgct cgtcgggcat cgaatctcgt cagctatcgt cagcttacct ttttggcagc   13260
gatcgcggct cccgacatct tggaccatta gctccacagg tatcttcttc cctctagtgg   13320
tcataacagc agcttcagct acctctcaat tcaaaaaacc cctcaagacc cgtttagagg   13380
ccccaaggg ttatgctatc aatcgttgcg ttacacacat aaaaaaccaa cacacatcca   13440
tcttcgatgg atagcgattt tattatctaa ctgctgatcg agtgtagcca gatctagtaa   13500
tcaattacgg ggtcattagt tcatagccca tatatggagt tccgcgttac ataacttacg   13560
gtaaatggcc cgcctggctg accgcccaac gacccccgcc cattgacgtc aataatgacg   13620
tatgttccca tagtaacgcc aatagggact tccattgac gtcaatgggt ggagtattta   13680
cggtaaactg cccacttggc agtacatcaa gtgtatcata tgccaagtac gccccctatt   13740
gacgtcaatg acggtaaatg gcccgcctgg cattatgccc agtacatgac cttatgggac   13800
tttcctactt ggcagtacat ctacgtatta gtcatcgcta ttaccatgct gatgcggttt   13860
tggcagtaca tcaatgggcg tggatagcgg tttgactcac ggggatttcc aagtctccac   13920
cccattgacg tcaatgggag tttgttttgg caccaaaatc aacgggactt tccaaaatgt   13980
cgtaacaact ccgccccatt gacgcaaatg ggcggtaggc gtgtacggtg ggaggtctat   14040
ataagcagag ctggtttagt gaaccgtcag atcagatctt tgtcgatcct accatccact   14100
cgacacaccc gccagcggcc gc                                            14122
```

```
SEQ ID NO: 45       moltype = DNA   length = 14124
FEATURE             Location/Qualifiers
misc_feature        1..14124
                    note = Description of Artificial Sequence: Synthetic
                     polynucleotide
source              1..14124
                    mol_type = other DNA
                    organism = synthetic construct
SEQUENCE: 45
taatacgact cactataggg agaagtactg ccaccatggg caagaagcaa aatcgcaaga   60
cggggaattc caagacacaa tccgctagcc caccacctaa agagcgttct agctcccctg   120
ctactgagca gtcctggatg gaaaacgact tcgatgaact ccgggaagag ggatttaggc   180
gatccaacta ttcagaactc cgcgaagata tccagacaaa ggggaaggaa gtcgagaatt   240
tcgagaagaa cctcgaggag tgcatcaccc gtatcacaaa cactgagaaa tgtctcaaag   300
aactcatgga acttaagaca aaagccaggg agcttcgaga ggagtgtcgg agtctgagat   360
```

-continued

```
ccaggtgtga ccagctcgag gagcgcgtga gcgcgatgga agacgagatg aacgagatga   420
aaagagaggg caaattcagg gagaagcgca ttaagaggaa cgaacagagt ctgcaggaga   480
tttgggatta cgtcaagagg cctaacctgc ggttgatcgg cgtccccgag agcgacgtag   540
aaaacgggac taaactggag aatacacttc aagacatcat tcaagaaaat tttccaaacc   600
tggctcggca agctaatgtg caaatccaag agatccaacg cacacccag cggtatagct    660
ctcggcgtgc caccctagg catattatcg tgcgctttac taaggtggag atgaaagaga    720
agatgctgcg agccgctcgg gaaaagggaa gggtgacttt gaagggcaaa cctattcggc   780
tgacggttga ccttagcgcc gagacactcc aggcacgccg ggaatggggc cccatcttta   840
atatcctgaa ggagaagaac ttccagccac gaatctctta ccctgcaaag ttgagtttta   900
tctccgaggg tgagattaag tatttcatcg ataaacagat gctgcgagac ttcgtgacaa   960
ctcgcccagc tctcaaggaa ctgctcaaag aggctcttaa tatggagcgc aataatagat  1020
atcaacccct tgcagaaccac gcaaagatgt gagacagtta aaacagctgt gggttgtcac  1080
ccacccacag ggtccactgg gcgctagtac actggtatct cggtacccttt gtacgcctgt  1140
tttataccc ctccctgatt tgcaacttag aagcaacgca aaccagatca atagtaggtg    1200
tgacatacca gtcgcatctt gatcaagcac ttctgtatcc ccggaccgag tatcaataga   1260
ctgtgcacac ggttgaagga gaaaacgtcc gttaccggc taactacttc gagaagccta    1320
gtaacgccat tgaagttgca gagtgtttcg ctcagcactc cccccgtgta gatcaggtcg   1380
atgagtcacc gcattcccca cgggcgaccg tggcggtggc tgcgttggcg gcctgcctat   1440
ggggtaaccc ataggacgct ctaatacgga catggcgtga agagtctatt gagctagtta   1500
gtagtcctcc ggcccctgaa tgcggctaat cctaactgcg gagcacatac ccttaatcca   1560
aagggcagtg tgtcgtaacg ggcaactctg cagcggaacc gactactttg ggtgtccgtg   1620
tttctttta ttcttgtatt ggctgcttat ggtgacaatt aaagaattgt taccatatag    1680
ctattggatt ggccatccag tgtcaaacag agctattgta tatctctttg ttggattcac   1740
acctctcact cttgaaacgt tacacaccct caattacatt atactgctga acacgaagcg   1800
tacatgaccg gctctaactc acatatcacc atccttacac ttaacattaa cggcctcaac   1860
tcagctatca agcgccatcg gctggccagc tggatcaaat cacaggatcc aagcgtttgt   1920
tgcatccaag agaccacct gacctgtaga gatactcacc gcctcaagat caagggatgg   1980
cgaaagattt atcaggcgaa cggtaagcag aagaaagccg gagtcgcaat tctggtctca   2040
gacaagacgg atttcaagcc caccaaaatt aagcgtgata aggaaggtca ctatattatg   2100
gtgaaaggca gcatacagca ggaagaactt accatattga acatctacgc gccaaacacc   2160
ggcgcacctc gctttatcaa acaggtcctg tccgatctgc agcgagatct ggattctcat   2220
acgttgatta tgggtgattt caatacacca ttgagcaccc tggatcgcag caccaggcaa   2280
aaggtaaata aagacacgca agagctcaat agcgcactgc atcaggcaga tctcattgat   2340
atttatcgca ctcttcatcc taagagtacc gagtacacat tcttcagcgc cccacatcat   2400
acatactcaa agatcgatca tatcgtcggc tcaaaggctc tgctgtcaaa gtgcaagcgc   2460
acagagataa ttacaaatta cctgtcagat catagcgcga tcaagctcga gctgagaatc   2520
aagaacctga cccagagccg gagtaccact tggaagctta ataacctgct gctcaacgat   2580
tattgggtcc acaatgagat gaaggcagag attaaaatgt tcttcgaaac aaatgagaat   2640
aaggatacta cctatcaaaa cctttgggat gcctttaagg ccgtctgcag aggcaagttc   2700
atcgccctca acgcctataa aagaaaacaa gagagatcta agatcgatac tctcacctct   2760
cagctgaagg agttggagaa acaggaacag acccactcca aggcgtcaag acggcaggag   2820
atcacaaaga ttcgcgccga gttgaaagag atcgaaaccc aaaagactct tcagaaaatt   2880
aacgagtctc gtagttggtt cttcgagcgg attaataaga tagacagacc tctggcacga   2940
ctgattaaga agaagcgcga aaagaaccag attgatacca tcaagaacga caagggcgac   3000
atcactactg acccgaccga gatccagacc actattcggg agtattataa gcatttgtat   3060
gctaacaagc ttgagaacct ggaagagatg gacacttttc tggatacctaa tactctgcca   3120
cggcttaatc aagaggaagt cgagtccctc aaccgcccaa ttacaggaag cgagattgtg   3180
gccataatta actccctgcc gacaaagaaa tctcctggtc cggacgggtt tacagctgag   3240
ttttatcaac ggtatatgga agagcttgta ccgtttctgc tcaagctctt tcagtctata   3300
gaaaaggaag gcatcttgcc caattccttc tacgaagctt ctataatact tattcccaaa   3360
ccaggacgcg ataccacaaa gaaggaaaac ttccggccca ttagtctcat gaatatcgac   3420
gctaaaatat tgaacaagat tctcgccaac agaatccaac aacatattaa gaaattgata   3480
catcacgacc aggtgggggtt tatacctggc atgcagggct ggtttaacat ccggaagagt   3540
attaacgtca ttcaacacat taatagagct aaggataaga atcatatgat catctctata   3600
gacgcggaaa aggcattcga taagattcag cagccattta tgctcaagac tctgaacaaa   3660
ctcggcatcg acggaacata tttttaagatt attcgcgcaa tttacgataa gccgactgct   3720
aacattatcc ttaacggcca aaagctcgag gcctttccgc tcaagactgg aacccgccaa   3780
ggctgtcccc tctccccgct tttgtttaat attgtactcg aggtgctggc tagggctatt   3840
cgtcaagaga aagagattaa agggatacag ctcgggaagg aagaggtcaa gctttccttg   3900
ttcgccgatg atatgattgt gtacctggag aatcctattg tgtctgctca gaaccttctt   3960
aaacttattt ctaactttag caaggtcagc ggctataaga ttaacgtcca gaaatctcag   4020
gcctttctgt acacaaataa tcgacagacc gaatcccaga taatgggtga gcttccgttt   4080
gtcatagcca gcaaaaggat aaagtatctc ggaatccagc tgacacgaga cgttaaagat   4140
ttgtttaagg aaaattacaa gcctctcctg aaagagatta aggaagatac taataagtgg   4200
aagaatatcc cctgttcatg ggttggcaga atcaacatag tgaagatggc aatacttcct   4260
aaagtgatat atcgctttaa cgccatccca attaaactgc ctatgacctt ctttacggag   4320
ctcgagaaaa caacccttaa atttatatgg aatcaaaaga gagcaagaat agcgaagtcc   4380
atcttgagcc agaagaataa ggccggtggg attactttgc ctgattttaa gttgtattat   4440
aaagccacag taactaagac agcctggtat tggtatcaga atagagacac cgaccagtga   4500
aatcggaccg aaccatcaga gataatgccc cacatctata attaccttat attcgataag   4560
ccagaaaaga ataaacagtg gggcaaagac agcctcttca acaagtggtg ttgggagaat   4620
tggctggcca tatgccggaa actcaagctc gacccctttc ttacacccta cactaaaatc   4680
aacagtaggg ggatcaagga cttgaatgtc aagccaaaga ctataaagac actgaagag    4740
aatcttggga tcacaataca agatataggc gtcggcaaga attttatgtc aaagacgccc   4800
aaggccatgg ccactaagga taagattgat aagtgggacc ttattaagct caaaagcttc   4860
tgtactgcca aggagaccac gatcagagtt aataggcagc ccactacatg ggaaaagatt   4920
ttcgccactt attcatcaga taaggggttg ataagcagaa tatataacga gctgaagcag   4980
atctacaaga agaaaacgaa taatcccatc aagaagtggg caaagatat gaacaggcat   5040
tttagcaaag aggatatcta cgccgcgaag aagcatatga agaagtgtag ttcaagcttg   5100
```

-continued

```
gccattcgtg agatgcagat taagacgacc atgcgatacc accttacccc agtgaggatg   5160
gcaattatca agaaatctgg caataataga tgttggcggg gctgtggcga gattggcacc   5220
ctgctccatt gctggtggga ttgcaagctg gtgcagccgc tttggaaatc agtctggcgc   5280
tttctgaggg acctcgagct tgagattccc ttcgatcccg caattccctt gctcggaatc   5340
tatcctaacg aatacaagag ctgttgttac aaggatacgt gtacccggat gttcatcgcg   5400
gccttgttta cgatagctaa gacgtggaat cagcctaagt gccccacaat gatcgattgg   5460
atcaagaaaa tgtggcatat ttataccatg gagtattacg cagcaattaa gaatgacgaa   5520
tttatttcct tcgttgggac ctggatgaag ctggagacta ttattctgag caagctgtct   5580
caggagcaaa agacaaagca tagaatcttc tctctcattg gtggtaacga ctacaaagac   5640
gatgacgaca agtaaagcgc ttctagaagt tgtctcctcc tgcactgact gactgataca   5700
atcgatttct ggatccgcag gcctaatcaa cctctggatt acaaaatttg tgaaagattg   5760
actggtattc ttaactatgt tgctcctttt acgctatgtg gatacgctgc tttaatgcct   5820
ttgtatcatg ctattgcttc ccgtatggct ttcattttct cctccttgta taaatcctgg   5880
ttgctgtctc tttatgagga gttgtggccc gttgtcaggc aacgtggcgt ggtgtgcact   5940
gtgtttgctg acgcaacccc cactggttgg ggcattgcca ccacctgtca gctcctttcc   6000
gggactttcg ctttccccct ccctattgcc acggcggaac tcatcgccgc ctgccttgcc   6060
cgctgctgga caggggctcg gctgttgggc actgacaatt ccgtggtgtt gtcggggaag   6120
ctgacgtcct ttccatggct gctcgcctgt gttgccacct ggattctgcg cgggacgtcc   6180
ttctgctacg tcccttcggc cctcaatcca gcggaccttc cttcccgcga acaaacgacc   6240
caacaccgt gcgttttatt ctgtcttttt attgccgatc ccctcagaag aactcgtcaa   6300
gaaggcgata gaaggcgatg cgctgcgaat cgggagcggc gataccgtaa agcacgagga   6360
agcggtcagc ccattcgccg ccaagctctt cagcaatatc acgggtagcc aacgctatgt   6420
cctgatagcg gtcggccgct ttacttgtac agctcgtcca tgccgagagt gatcccggcg   6480
gcggtcacga actccagcag gaccatgtga tcgcgcttct cgttggggtc tttgctcagg   6540
gcggactggg tgctcaggta gtggttgtcg ggcagcagca cggggccgtc gccgatgggg   6600
gtgttctgct ggtagtggtc ggccaggtga gtccaggaga tgtttcagca ctgttgcctt   6660
tagtctcgag gcaacttaga caactgagta ttgatctgag cacagcaggg tgtgagctgt   6720
ttgaagatac tggggttggg ggtgaagaaa ctgcagagga ctaactgggc tgagacccag   6780
tggcaatgtt ttagggccta aggaatgcct ctgaaaatct agatggacaa ctttgacttt   6840
gagaaaagag aggtggaaat gaggaaaatg actttcttt attagatttc ggtagaaaga   6900
actttcatct ttcccctatt tttgttattc gttttaaaac atctatctgg aggcaggaca   6960
agtatggtca ttaaaaagat gcaggcagaa ggcatatatt ggctcagtca aagtggggaa   7020
ctttggtggc caaacataca ttgctaaggc tattcctata tcagctggac acatataaaa   7080
tgctgctaat gcttcattac aaacttatat cctttaattc cagatggggg caaagtatgt   7140
ccaggggtga ggaacaattg aaacatttgg gctggagtag attttgaaag tcagctctgt   7200
gtgtgtgtgt gtgtgtgtgt gtgtgagagc gtgtgtttct tttaacgttt tcagcctaca   7260
gcatacaggg ttcatggtgg caagaagata acaagattta aattatggcc agtgactagt   7320
gctgcaagaa gaacaactac ctgcatttaa tgggaaagca aaatctcagg ctttgaggga   7380
agttaacata ggcttgattc tgggtgtgaa gctgggtgtgt agttatctgg aggccaggct   7440
ggagctctca gctcactatg ggttcatctt tattgtctcc tttcatctca acagctgcac   7500
gctgccgtcc tcgatgttgt ggcggatctt gaagttcacc ttgatgccgt tcttctgctt   7560
gtcggccatg atatagacgt tgtggctgtt gtagttgtac tccagcttgt gccccaggat   7620
gttgcgtcc tccttgaagt cgatgccctt cagctcgatg cggttcacca gggtgtcgcc   7680
ctcgaacttc acctcggcgc gggtcttgta gttgccgtcg tccttgaaga agatggtgcg   7740
ctcctggacg tagccttcgg gcatggcgga cttgaagaag tcgtgctgct tcatgtggtc   7800
ggggtagcgg ctgaagcact gcacgccgta ggtcagggtg gtcacgaggg tgggccaggg   7860
cacgggcagc ttgccggtgg tgcagatgaa cttcagggtc agcttgccgt aggtggcatc   7920
gccctcgccc tcgccggaca cgctgaactt gtggccgttt acgtcgccgt ccagctcgac   7980
caggatgggc accaccccgg tgaacagctc ctcgcccttg ctcaccatgg tggcgaattc   8040
gaagcttgag cacgagatct gagtccggta ggcctagcgg atctgacggt tcactaaacc   8100
agctctgctt atatagacct cccaccgtac acgcctaccg cccatttgcg tcaatgggac   8160
ggagttgtta cgacattttg gaaagtcccg ttgattttgg tgccaaaaca aactcccatt   8220
gacgtcaatg gggtggagac ttggaaatcc ccgtgagtca aaccgctatc cacgcccatt   8280
gatgtactgc caaaaccgca tcaccatggt aatagcgatg actaatacgt agatgtactg   8340
ccaagtagga aagtcccata aggtcatgta ctgggcataa tgccaggcgg gccatttacc   8400
gtcattgacg tcaatagggg cgtacttggc catatgatac acttgatgta ctgccaagtg   8460
ggcagtttac cgtaaatact ccacccattg acgtcaatgg aaagtcccta ttggcgttac   8520
tatgggaaca tacgtcatta ttgacgtcaa tgggcggggg tcgttgggcg gtcagccagg   8580
cgggccattt accgtaagtt atgtaacggg cctgctgccg gctctgcggg ctcttccgcg   8640
tcttcgcctt cgccctcaga cgagtcggat ctccctttgg gccgcctccc cgcctgtcta   8700
gcttgactga ctgagataca gcgtaccttc agctcacaga catgataaga tacattgatg   8760
agtttggaca aaccacaact agaatgcagt gaaaaaaatg ctttatttgt gaaatttgtg   8820
atgctattgc tttatttgta accattataa gctgcaataa acaagttaac aacaacaatt   8880
gcattcattt tatgtttcag gttcagggggg aggtgtggga aggtttttta agcaagtaaa   8940
acctctacaa atgtggtatt ggcccatctc tatcggtatc gtagcataac cccttggggc   9000
ctctaaacgg gtcttgaggg gttttttgtg cccctcgggc cggattgcta tctaccggca   9060
ttggcgcaga aaaaaatgcc tgatgcgacg ctgcgcgtct tatactccca catatgccag   9120
attcagcaac ggatacggct tccccaactt gcccacttcc atacgtgtcc tccttaccag   9180
aaatttatcc ttaaggtcgt cagctatcct gcaggcgatc tctcagtttc gatcaagaca   9240
ttcctttaat ggtcttttct ggacaccact aggggtcaga agtagttcat caaactttct   9300
tccctcccta atctcattgg ttaccttggg ctatcgaaac ttaattaagc gatctgcatc   9360
tcaattagtc agcaaccata gtcccgcccc taactccgcc catcccgccc ctaactccgc   9420
ccagttccgc ccattctccg ccccatcgct gactaatttt ttttatttat gcagaggccg   9480
aggccgcctc ggcctctgag ctattccaga agtagtgagg aggcttttt ggaggcctaa   9540
gcttttgcaa aggaggtagc caacatgatt gaacaagatg gattgcacgc aggttctccc   9600
gccgcttggg tggagaggct attcggctat gactgggcac aacagacaat cggctgctct   9660
gatgccgccg tgttccggct gtcagcgcag gggcgcccgg ttcttttgt caagaccgac   9720
ctgtccggtg ccctgaatga actccaggac gaggcagcgc ggctatcgtg ctggccacg   9780
acgggcgttc cttgcgcagc tgtgctcgac gttgtcactg aagcgggaag ggactggctg   9840
```

```
ctattgggcg aagtgccggg gcaggatctc ctgtcatctc accttgctcc tgccgagaaa  9900
gtatccatca tggctgatgc aatgcggcgg ctgcatacgc ttgatccggc tacctgccca  9960
ttcgaccacc aagcgaaaca tcgcatcgag cgagcacgta ctcggatgga agccggtctt  10020
gtcgatcagg atgatctgga cgaagagcat caggggctcg cgccagccga actgttcgcc  10080
aggctcaagg cgcggatgcc cgacggcgag gatctcgtcg tgacccacgg cgatgcctgc  10140
ttgccgaata tcatggtgga aaatggccgc ttttctggat tcatcgactg tggccggctg  10200
ggtgtggcgg accgctatca ggacatagcg ttggctaccc gtgatattgc tgaagagctt  10260
ggcggcgaat gggctgaccg cttcctcgtg ctttacggta tcgccgctcc cgattcgcag  10320
cgcatcgcct tctatcgcct tcttgacgag ttcttctagt atgtaagccc tgtgccttct  10380
agttgccagc catctgttgt ttgcccctcc cccgtgcctt ccttgaccct ggaaggtgcc  10440
actcccactg tcctttccta ataaaatgag gaaattgcat cgcattgtct gagtaggtgt  10500
cattctattc tggggggtgg ggtgggggcag gacagcaagg gggaggattg ggaagacaat  10560
agcaggcatg ctggggatgc ggtgggctct atggttaatt aaccagtcaa gtcagctact  10620
tggcgagatc gacttgtctg ggtttcgact acgctcagaa ttgcgtcagt caagttcgat  10680
ctggtccttg ctattgcacc cgttctccga ttacgagttt catttaaatc atgtgagcaa  10740
aaggccagca aaaggccagg aaccgtaaaa aggccgcgtt gctggcgttt ttccataggc  10800
tccgcccccc tgacgagcat cacaaaaatc gacgctcaag tcagaggtgg cgaaacccga  10860
caggactata aagataccag gcgtttcccc ctggaagctc cctcgtgcgc tctcctgttc  10920
cgaccctgcc gcttaccgga tacctgtccg cctttctccc ttcgggaagc gtggcgcttt  10980
ctcatagctc acgctgtagg tatctcagtt cggtgtaggt cgttcgctcc aagctgggct  11040
gtgtgcacga accccccgtt cagcccgacc gctgcgcctt atccggtaac tatcgtcttg  11100
agtccaaccc ggtaagacac gacttatcgc cactggcagc agccactggt aacaggatta  11160
gcagagcgag gtatgtaggc ggtgctacag agttcttgaa gtggtggcct aactacggct  11220
acactagaag aacagtattt ggtatctgcg ctctgctgaa gccagttacc ttcggaaaaa  11280
gagttggtag ctcttgatcc ggcaaacaaa ccaccgctgg tagcggtggt ttttttgttt  11340
gcaagcagca gattacgcgc agaaaaaaag gatctcaaga agatcctttg atcttttcta  11400
cggggtctga cgctcagtgg aacgaaaact cacgttaagg gattttggtc atgagattat  11460
caaaaaggat cttcacctag atccttttaa attaaaaatg aagttttaaa tcaatctaaa  11520
gtatatatga gtaaacttgg tctgacagtt accaatgctt aatcagtgag gcacctatct  11580
cagcgatctg tctatttcgt tcatccatag ttgcatttaa atttccgaac tctccaaggc  11640
cctcgtcgga aaatcttcaa accttttcgtc cgatccatct tgcaggctac ctctcgaacg  11700
aactatcgca agtctcttgg ccggccttgc gccttggcta ttgcttggca gcgcctatcg  11760
ccaggtatta ctccaatccc gaatatccga gatcgggatc acccgagaga agttcaacct  11820
acatcctcaa tccccgatcta tccgagatcc gaggaatatc gaaatcgggg cgcgcctggt  11880
gtaccgagaa cgatcctctc agtgcgagtc tcgacgatcc atatcgttgc ttggcagtca  11940
gccagtcgga atccagcttg ggacccagga agtccaatcg tcagatattg tactcaagcc  12000
tggtcacggc agcgtaccga tctgtttaaa cctagatatt gatagtctga tcggtcaacg  12060
tataatcgag tcctagcttt tgcaaacatc tatcaagaga caggatcagc aggaggcttt  12120
cgcatgagta ttcaacattt ccgtgtcgcc cttattccct tttttgcggc attttgcctt  12180
cctgtttttg ctcacccaga aacgctggtg aaagtaaaag atgctgaaga tcagttgggt  12240
gcgcgagtgg gttacatcga actggatctc aacagcggta agatccttga gagttttcgc  12300
cccgaagaac gctttccaat gatgagcact tttaaagttc tgctatgtgg cgcggtatta  12360
tcccgtattg acgccgggca agagcaactc ggtcgccgca tacactattc tcagaatgac  12420
ttggttgagt attcaccagt cacagaaaag catcttacgg atggcatgac agtaagagaa  12480
ttatgcagtg ctgccataac catgagtgat aacactgcgg ccaacttact tctgacaacg  12540
attggaggac cgaaggagct aaccgctttt ttgcacaaca tgggggatca tgtaactcgc  12600
cttgatcgtt gggaaccgga gctgaatgaa gccataccaa acgacgagcg tgacaccacg  12660
atgcctgtag caatggcaac aaccttgcgt aaactattaa ctggcgaact acttactcta  12720
gcttcccggc aacagttgat agactggatg gaggcggata agttgcagg accacttctg  12780
cgctcggccc ttccggctgg ctggtttatt gctgataaat ctggagccgg tgagcgtggg  12840
tctcgcggta tcattgcagc actggggcca gatggtaagc cctcccgtat cgtagttatc  12900
tacacgacgg ggagtcaggc aactatggat gaacgaaata gacagatcgc tgagataggt  12960
gcctcactga ttaagcattg gtaaccgatt ctaggtgcat tggcgcagaa aaaaatgcct  13020
gatgcgacgc tgcgcgtctt atactcccac atatgccaga ttcagcaacg gatacggctt  13080
ccccaacttg cccacttcca tacgtgtcct ccttaccaga aatttatcct taagatcgtt  13140
taaactcgac tctggctcta tcgaatctcc gtcgtttcga gcttacgcga acagccgtgg  13200
cgctcatttg ctcgtcgggc atcgaatctc gtcagctatc gtcagcttac ctttttggca  13260
gcgatcgcgg ctcccgacat cttggaccat tagctccaca ggtatcttct tccctctagt  13320
ggtcataaca gcagcttcag ctacctctca attcaaaaaa cccctcaaga cccgtttaga  13380
ggccccaagg ggttatgcta tcaatcgttg cgttacacac acaaaaaacc aacacacatc  13440
catcttcgat ggatagcgat tttattatct aactgctgat cgagtgtagc cagatcagt  13500
aatcaattac ggggtcatta gttcatagcc catatatgga gttccgcgtt acataactta  13560
cggtaaatgg cccgcctggc tgaccgccca acgaccccg cccattgacg tcaataatga  13620
cgtatgttcc catagtaacg ccaataggga ctttccattg acgtcaatgg gtggagtatt  13680
tacggtaaac tgcccacttg gcagtacatc aagtgtatca tatgccaagt acgcccccta  13740
ttgacgtcaa tgacggtaaa tggcccgcct ggcattatgc ccagtacatg accttatggg  13800
actttcctac ttggcagtac atctacgtat tagtcatcgc tattaccatg ctgatgcggt  13860
tttggcagta catcaatggg cgtggatagc ggtttgactc acggggattt ccaagtctcc  13920
accccattga cgtcaatggg agtttgtttt ggcaccaaaa tcaacgggac tttccaaaat  13980
gtcgtaacaa ctccgcccca ttgacgcaaa tgggcggtag gcgtgtacgg tgggaggtct  14040
atataagcag agctggttta gtgaaccgtc agatcagatc tttgtcgatc ctaccatcca  14100
ctcgacacac ccgccagcgg ccgc                                         14124
```

SEQ ID NO: 46            moltype = DNA   length = 13439
FEATURE                  Location/Qualifiers
misc_feature            1..13439
                        note = Description of Artificial Sequence: Synthetic
                        polynucleotide
source                  1..13439

```
                    mol_type = other DNA
                    organism = synthetic construct
SEQUENCE: 46
taatacgact cactataggg agaagtactg ccaccatggg caagaagcaa aatcgcaaga   60
cggggaattc caagacacaa tccgctagcc caccacctaa agagcgttct agctccctg   120
ctactgagca gtcctggatg gaaaacgact tcgatgaact ccgggaagag ggatttaggc   180
gatccaacta ttcagaactc cgcgaagata tccagacaaa ggggaaggaa gtcgagaatt   240
tcgagaagaa cctcgaggag tgcatcaccc gtatcacaaa cactgagaaa tgtctcaaag   300
aactcatgga acttaagaca aaagccaggg agcttcgaga ggagtgtcgg agtctgagat   360
ccaggtgtga ccagctcgag gagcgcgtga gcgcgatgga agacgagatg aacgagatga   420
aaagagaggg caaattcagg gagaagcgca ttaagaggaa cgaacagagt ctgcaggaga   480
tttgggatta cgtcaagagg cctaacctgc ggttgatcgg cgtccccgag agcgacgtag   540
aaaacgggac taaactggag aatacacttc aagacatcat tcaagaaaat tttccaaacc   600
tggctcggca agctaatgtg caaatccaag agatccaacg cacacCCcag cggtatagct   660
ctcggcgtgc cacccctagg catattatcg tgcgctttac taaggtggag atgaaagaga   720
agatgctgcg agccgctcgg gaaaagggaa gggtgacttt gaagggcaaa cctattcggc   780
tgacggttga ccttagcgcc gagacactcc aggcacgccg ggaatggggc cccatcttta   840
atatcctgaa ggagaagaac ttccagccac gaatctctta ccctgcaag ttgagtttta   900
tctccgaggg tgagattaag tatttcatcg ataaacagat gctgcgagac ttcgtgacaa   960
ctcgcccagc tctcaaggaa ctgctcaaag aggctcttaa tatggagcgc aataatagat   1020
atcaaccctt gcagaaccac gcaaagatgg gaagcggaca gtgtactaat tatgctctct   1080
tgaaattggc tggagatgtt gagagcaacc ctggacctat gaccggctct aactcacata   1140
tcaccatcct tacacttaac attaacggcc tcaactcagc tatcaagcgc catcggctgg   1200
ccagctggat caaatcacag gatccaagcg tttgttgcat ccaagagacc cacctgacct   1260
gtagagatac tcaccgcctc aagatcaagg gatggcgaaa gatttatcag gcgaacggta   1320
agcagaagaa agccggagtc gcaattctgg tctcagacaa gacggatttc aagcccacca   1380
aaattaagcg tgataaggaa ggtcactata ttatggtgaa aggcagcata cagcaggaag   1440
aacttaccat attgaacatc tacgcgccaa acaccggcgc acctcgcttt atcaaacagg   1500
tcctgtccga tctgcagcga gatctggatt ctcatacgtt gattatgggt gatttcaata   1560
caccattgag caccctggat cgcagcacca ggcaaaaggt aaataaagac acgcaagagc   1620
tcaatagcgc actgcatcag gcagatctca ttgatattta tcgcactctt catcctaaga   1680
gtaccgagta cacattcttc agcgccccac atcatacata ctcaaagatc gatcatatcg   1740
tcggctcaaa ggctctgctg tcaaagtgca agcgcacaga gataattaca aattacctgt   1800
cagatcatag cgcgatcaag ctcgagctga gaatcaagaa cctgacccag agccggagta   1860
ccacttggaa gcttaataac ctgctgctca acgattattg ggtccacaat gagatgaagg   1920
cagagattaa aatgttcttc gaaacaaatg agaataagga tactacctat caaaaccttt   1980
gggatgcctt taaggccgtc tgcagaggca agttcatcgc cctcaacgcc tataaaagaa   2040
aacaagagag atctaagatc gatactctca cctctcagct gaaggagttg gagaaacagg   2100
aacagaccca ctccaaggcg tcaagacggc aggagatcac aaagattcgc gccgagttga   2160
aagagatcga aacccaaaag actcttcaga aaattaacga gtctcgtagt tggttcttcg   2220
agcggattaa taagatagac agacctctgg cacgactgat taagaagaag cgcgaaaaga   2280
accagattga taccatcaag aacgacaagg gcgacatcac tactgacccg accgagatcc   2340
agaccactat tcgggagtat tataagcatt tgtatgctaa caagcttgag aacctggaag   2400
agatggacac ttttctggat acctatactc tgccacggct taatcaagag gaagtcgagt   2460
ccctcaaccg cccaattaca ggaagcgaga ttgtggccat aattaactcc ctgccgacaa   2520
agaaatctcc tggtccggac gggtttacag ctgagttta tcaacggtat atggaagagc   2580
ttgtaccgtt tctgctcaag ctctttcagt ctatagaaaa ggaaggcatc ttgcccaatt   2640
ccttctacga agcttctata atacttattc ccaaaccagg acgcgatacc acaaagaagg   2700
aaaacttccg gcccattagt ctcatgaata tcgacgctaa aatattgaac aagattctcg   2760
ccaacagaat ccaacaacat attaagaaat tgatacatca cgaccaggtg gggtttatac   2820
ctggcatgca gggctggttt aacatccgga agagtattaa cgtcattcaa cacattaata   2880
gagctaagga taagaatcat atgatcatct ctatagacgc ggaaaaggca ttcgataaga   2940
ttcagcagcc atttatgctc aagactctga acaaactcgg catcgacgga acatattta   3000
agattattcg cgcaatttac gataagccga ctgctaacat tatccttaac ggccaaaagc   3060
tcgaggcctt tccgctcaag actggaaccc gccaaggctg tcccctctcc ccgcttttgt   3120
ttaatattgt actcgaggtg ctggctaggg ctattcgtca agagaaagag attaaaggga   3180
tacagctcgg gaaggaagag gtcaagcttt ccttgttcgc cgatgatatg attgtgtacc   3240
tggagaatcc tattgtgtct gctcagaacc ttcttaaact tatttctaac tttagcaagg   3300
tcagcggcta taagattaac gtccagaaat ctcaggcctt tctgtacaca aataatcgac   3360
agaccgaatc ccagataatg ggtgagcttc cgtttgtcat agccagcaaa aggataaagt   3420
atctcggaat ccagctgaca cgagacgtta aagatttgtt taaggaaaat tacaagcctc   3480
tcctgaaaga gattaaggaa gatactaata agtggaagaa tatccctgt tcatgggttg   3540
gcagaatcaa catagtgaag atggcaatac ttcctaaagt gatatatcgc tttaacgcca   3600
tcccaattaa actgcctatg accttctta cggagctgaa gaaaacaacc cttaaattta   3660
tatggaatca aaagagagca agaatagcga agtccatctt gagccagaag aataaggccg   3720
gtgggattac tttgcctgat tttaagttgt attataaagc cacagtaact aagacagcct   3780
ggtattggta tcagaataga gacatcgacc agtggaatcg gaccgaacca tcagagataa   3840
tgcccacat ctataattac cttatattcg ataagccaga aaagaataaa cagtggggca   3900
aagacagcct cttcaacaag tggtgttggg agaattggct ggccatatgc cggaaactca   3960
agctcgaccc ctttcttaca ccctacacta aaatcaacag taggtggatc aaggacttga   4020
atgtcaagcc aaagactata aagacactgg aagagaatct tgggatcaca atacaagata   4080
taggcgtcgg caaagatttt atgtcaaaga cgcccaaggc catggccact aaggataaga   4140
ttgataagtg ggaccttatt aagctcaaaa gcttctgtac tgccaaggag accacgatca   4200
gagttaatag gcagcccact acatgggaaa agattttcgc cacttattca tcagataagg   4260
ggttgataag cagaatatat aacgagctga gcagatctca caagaagaaa acgaataatc   4320
ccatcaagaa gtgggcaaaa gatatgaaca ggcatttag caaagaggat atctacgccg   4380
cgaagaagca tatgaagaag tgtagttcaa gcttggccat tcgtgagatg cagattaaga   4440
cgaccatgcg ataccacctt accccagtga ggatggcaat tatcaagaaa tctggcaata   4500
atagatgttg gcggggctgt ggcgagattg gcaccctgct ccattgctgg tgggattgca   4560
```

-continued

```
agctggtgca gccgctttgg aaatcagtct ggcgctttct gaggggacctc gagcttgaga   4620
ttcccttcga tcccgcaatt cccttgctcg gaatctatcc taacgaatac aagagctgtt   4680
gttacaagga tacgtgtacc cggatgttca tcgcggcctt gtttacgata gctaagacgt   4740
ggaatcagcc taagtgcccc acaatgatcg attggatcaa gaaaatgtgg catatttata   4800
ccatggagta ttacgcagca attaagaatg acgaatttat ttccttcgtt gggacctgga   4860
tgaagctgga gactattatt ctgagcaagc tgtctcagga gcaaaagaca aagcatagaa   4920
tcttctctct cattggtggt aacgactaca aagacgatga cgacaagtaa agcgcttcta   4980
gaagttgtct cctcctgcac tgactgactg atacaatcga tttctggatc cgcaggccta   5040
atcaacctct ggattacaaa atttgtgaaa gattgactgg tattcttaac tatgttgctc   5100
cttttacgct atgtggatac gctgctttaa tgcctttgta tcatgctatt gcttcccgta   5160
tggctttcat tttctcctcc ttgtataaat cctggttgct gtctctttat gaggagttgt   5220
ggcccgttgt caggcaacgt ggcgtggtgt gcactgtgtt tgctgacgca accccccactg  5280
gttggggcat tgccaccacc tgtcagctcc tttccgggac tttcgctttc ccctcccta    5340
ttgccacggc ggaactcatc gccgcctgcc ttgcccgctg ctggacaggg gctcggctgt   5400
tgggcactga caattccgtg gtgttgtcgg ggaagctgac gtcctttcca tggctgctcg   5460
cctgtgttgc cacctggatt ctgcgcggga cgtccttctg ctacgtccct tcggccctca   5520
atccagcgga ccttccttcc cgcgaacaaa cgacccaaca cccgtgcgtt ttattctgtc   5580
tttttattgc cgatcccctc agaagaactc gtcaagaagg cgatagaagg cgatgcgctg   5640
cgaatcggga gcggcgatac cgtaaagcac gaggaagcgg tcagcccatt cgccgccaag   5700
ctcttcagca atatcacggg tagccaacgc tatgtcctga tagcggtcgg ccgctttact   5760
tgtacagctc gtccatgccg agagtgatcc cggcggcggt cacgaactcc agcaggacca   5820
tgtgatcgcg cttctcgttg gggtctttgc tcagggcgga ctgggtgctc aggtagtgat   5880
tgtcgggcag cagcacgggg ccgtcgccga tgggggtgtt ctgctggtag tggtcggcca   5940
ggtgagtcca ggagatgttt cagcactgtt gcctttagtc tcgaggcaac ttagacaact   6000
gagtattgat ctgagcacag cagggtgtga gctgtttgaa gatactgggg ttgggggtga   6060
agaaactgca gaggactaac tgggctgaga cccagtgaca atgtttaggg gcctaaggaa   6120
tgcctctgaa aatctagatg gacaactttg actttgagaa aagagaggtg gaaatgagga   6180
aaatgacttt tctttattag atttcggtag aaagaacttt catctttccc ctatttttgt   6240
tattcgtttt aaaacatcta tctggaggca ggacaagtat ggtcattaaa aagatgcagg   6300
cagaaggcat atattggctc agtcaaagtg gggaactttg gtggccaaac atacattgct   6360
aaggctattc ctatatcagc tggacacata taaaatgctg ctaatgcttc attacaaact   6420
tatatccttt aattccagat gggggcaaag tatgtccagg ggtgaggaac aattgaaaca   6480
tttgggctgg agtagatttt gaaagtcagc tctgtgtgtg tgtgtgtgtg tgtgtgtgtg   6540
agagcgtgtg tttctttaa cgtttttcagc ctacagcata cagggttcat ggtggcaaga   6600
agataacaag atttaaatta tggccagtga ctagtgctgc aagaagaaca actacctgca   6660
tttaatggga aagcaaaatc tcaggctttg agggaagtta acataggctt gattctgggt   6720
ggaagctggg tgtgtagtta tctggaggcc aggctggagc tctcagctca ctatgggttc   6780
atctttattg tctcctttca tctcaacagc tgcacgctgc cgtcctcgat gttgtggcgg   6840
atcttgaagt tcaccttgat gccgttcttc tgcttgtcgg ccatgatata gacgttgtgg   6900
ctgttgtagt tgtactccag cttgtgcccc aggatgttgc cgtcctcctt gaagtcgatg   6960
cccttcagct cgatgcggtt caccaggggtg tcgccctcga acttcacctc ggcgcgggtc   7020
ttgtagttgc cgtcgtcctt gaagaagatg gtgcgctcct ggacgtagcc ttcgggcatg   7080
gcggacttga agaagtcgtg ctgcttcatg tggtcggggt agcggctgaa gcactgcacg   7140
ccgtaggtca gggtggtcac gagggtgggc cagggcacgg gcagcttgcc ggtggtgcag   7200
atgaacttca gggtcagctt gccgtaggtg gcatcgccct cgccctcgcc ggacacgctg   7260
aacttgtggc cgtttacgtc gccgtccagc tcgaccagga tgggcaccac cccggtgaac   7320
agctcctcga ccttgctcac catggtggcg aattcgaagc ttgagcacga atctgagtc   7380
cggtaggcct agcggatctg acggttcact aaaccagctc tgcttatata gacctcccac   7440
cgtacacgcc taccgcccat ttgcgtcaat ggggcggagt tgttacgaca ttttggaaag   7500
tcccgttgat tttggtgcca aaacaaactc ccattgacgt caatggggtg gagacttgga   7560
aatccccgtg agtcaaaccg ctatccacgc ccattgatgt actgccaaaa ccgcatcacc   7620
atggtaatag cgatgactaa tacgtagatg tactgccaag taggaaagtc ccataaggtc   7680
atgtactggg cataatgcca ggcgggccat ttaccgtcat tgacgtcaat agggggcgta   7740
cttggcatat gatacacttg atgtactgcc aagtgggcag tttaccgtaa atactccacc   7800
cattgacgtc aatggaaagt ccctattggc gttactatgg gaacatacgt cattattgac   7860
gtcaatgggc gggggtcgtt gggcggtcag ccaggcgggc catttaccgt aagttatgta   7920
acgggcctgc tgccggctct gcggcctctt ccgcgtcttc gccttcgccc tcagacgagt   7980
cggatctccc tttgggccgc ctccccgcct gtctagcttg actgactgag atacagcgta   8040
ccttcagctc acagacatga taagatacat tgatgagttt ggacaaacca caactagaat   8100
gcagtgaaaa aaatgcttta tttgtgaaat ttgtgatgct attgctttat ttgtaaccat   8160
tataagctgc aataaacaag ttaacaacaa caattgcatt cattttatgt ttcaggttca   8220
gggggaggtg tgggaggttt tttaaagcaa gtaaaacctc tacaaatgtg gtattggccc   8280
atctctatcg gtatcgtagc ataacccctt ggggcctcta aacgggtctt gaggggtttt   8340
ttgtgcccct cgggccggat tgctatctac cggcattggc gcagaaaaaa atgcctgatg   8400
cgacgctgcg cgtcttatac tcccacatat gccagattca gcaacggata cggcttcccc   8460
aacttgccca cttccatacg tgtcctcctt accagaaatt tatccttaag gtcgtcagct   8520
atcctgcagg cgatctctcg atttcgatca agacattcct ttaatggtct tttctggaca   8580
ccactagggg tcagaagtag ttcatcaaac tttcttccct ccctaatctc attggttacc   8640
ttgggctatc gaaacttaat taagcgatct gcatctcaat tagtcagcaa ccatagtccc   8700
gcccctaact ccgcccatcc cgcccctaac tccgcccagt tccgcccatt ctccgcccca   8760
tcgctgacta atttttttta tttatgcaga ggccgaggcc gcctcggcct ctgagctatt   8820
ccagaagtag tgaggaggct ttttttggagg cctaggcttt tgcaaaggag gtagccaaca   8880
tgattgaaca agatggattg cacgcaggtt ctccgccgc ttgggtggag aggctattcg    8940
gctatgactg ggcacaacag acaatcggct gctctgatgc cgccgtgttc cggctgtcag   9000
cgcaggggcg cccggttctt tttgtcaaga ccgacctgtc cggtgccctg aatgaactcc   9060
aggacgagge agcgcggcta tcgtggctgg ccacgacggg cgttccttgc gcagctgtgc   9120
tcgacgttgt cactgaagcg ggaagggact ggctgctatt gggcgaagtg ccggggcagg   9180
atctcctgtc atctcacctt gctcctgccg agaaagtatc catcatggct gatgcaatgc   9240
ggcggctgca tacgcttgat ccggctacct gcccattcga ccaccaagcg aaacatcgca   9300
```

-continued

```
tcgagcgagc acgtactcgg atggaagccg gtcttgtcga tcaggatgat ctggacgaag    9360
agcatcaggg gctcgcgcca gccgaactgt tcgccaggct caaggcgcgg atgcccgacg    9420
gcgaggatct cgtcgtgacc cacggcgatg cctgcttgcc gaatatcatg gtggaaaatg    9480
gccgcttttc tggattcatc gactgtggcc ggctgggtgt ggcggaccgc tatcaggaca    9540
tagcgttggc tacccgtgat attgctgaag agcttggcgg cgaatgggct gaccgcttcc    9600
tcgtgctttta cggtatcgcc gctcccgatt cgcagcgcat cgccttctat cgccttcttg    9660
acgagttctt ctagtatgta agccctgtgc cttctagttg ccagccatct gttgtttgcc    9720
cctccccgt gccttccttg accctggaag gtgccactcc cactgtcctt tcctaataaa    9780
atgaggaaat tgcatcgcat tgtctgagta ggtgtcattc tattctgggg ggtggggtgg    9840
ggcaggacag caaggggag gattgggaag acaatagcag gcatgctggg gatgcggtgg    9900
gctctatggt taattaacca gtcaagtcag ctacttggcg agatcgactt gtctgggttt    9960
cgactacgct cagaattgcg tcagtcaagt tcgatctggt ccttgctatt gcacccgttc    10020
tccgattacg agtttcattt aaatcatgtg agcaaaaggc cagcaaaagg ccaggaaccg    10080
taaaaaggcc gcgttgctgg cgtttttcca taggctccgc ccccctgacg gagcatcacaa    10140
aaatcgacgc tcaagtcaga ggtggcgaaa cccgacagga ctataaagat accaggcgtt    10200
tccccctgga agctccctcg tgcgctctcc tgttccgacc ctgccgctta ccggatacct    10260
gtccgccttt ctcccttcgg gaagcgtggc gctttctcat agctcacgct gtaggtatct    10320
cagttcggtg taggtcgttc gctccaagct gggctgtgtg cacgaacccc ccgttcagcc    10380
cgaccgctgc gccttatccg gtaactatcg tcttgagtcc aacccggtaa gacacgactt    10440
atcgccactg gcagcagcca ctggtaacag gattagcaga gcgaggtatg taggcggtgc    10500
tacagagttc ttgaagtggt ggcctaacta cggctacact agaagaacag tatttggtat    10560
ctgcgctctg ctgaagccag ttaccttcgg aaaaagagtt ggtagctctt gatccggcaa    10620
acaaaccacc gctggtagcg gtggtttttt tgtttgcaag cagcagatta cgcgcagaaa    10680
aaaaggatct caagaagatc ctttgatctt ttctacgggg tctgacgctc agtggaacga    10740
aaactcacgt taagggattt tggtcatgag attatcaaaa aggatcttca cctagatcct    10800
tttaaattaa aaatgaagtt ttaaatcaat ctaaagtaaa tatgagtaaa cttggtctga    10860
cagttaccaa tgcttaatca gtgaggcacc tatctcagcg atctgtctat ttcgttcatc    10920
catagttgca tttaaatttc cgaactctcc aaggccctcg tcggaaaatc ttcaaacctt    10980
tcgtccgatc catcttgcag gctacctctc gaacgaacta tcgcaagtct cttggccggc    11040
cttgcgcctt ggctattgct tggcagcgcc tatcgccagg tattactcca atcccgaata    11100
tccgagatcg ggatcacccg agagaagttc aacctacatc ctcaatcccg atctatccga    11160
gatccgagga atatcgaaat cggggcgcgc ctggtgtacc gagaacgatc ctctcagtgc    11220
gagtctcgac gatccatatc gttgcttggc agtcagccag tcggaatcca gcttgggacc    11280
caggaagtcc aatcgtcaga tattgtactc aagcctggtc acggcagcgt accgatctgt    11340
ttaaacctag atattgatag tctgatcggt caacgtataa tcgagtccta gcttttgcaa    11400
acatctatca agagacagga tcagcaggag gctttcgcat gagtattcaa catttccgtg    11460
tcgcccttat tccctttttt gcggcatttt gccttcctgt ttttgctcac ccagaaacgc    11520
tggtgaaagt aaaagatgct gaagatcagt tgggtgcgcg agtgggttac atcgaactgg    11580
atctcaacag cggtaagatc cttgagagtt ttcgccccga gaacgctttt ccaatgatga    11640
gcactttaa agttctgcta tgtggcgcgg tattatcccg tattgacgcc gggcaagagc    11700
aactcggtcg ccgcatacac tattctcaga atgacttggt tgagtattca ccagtcacag    11760
aaaagcatct tacggatggc atgacagtaa gagaattatg cagtgctgcc ataaccatga    11820
gtgataacac tgcggccaac ttacttctga caacgattgg aggaccgaag gagctaaccg    11880
cttttttgca caacatgggg gatcatgtaa ctcgccttga tcgttgggaa ccggagctga    11940
atgaagccat accaaacgac gagcgtgaca ccacgatgcc tgtagcaatg gcaacaacct    12000
tgcgtaaact attaactggc gaactactta ctctagcttc ccggcaacag ttgatagact    12060
ggatggaggc ggataaagtt gcaggaccac ttctgcgctc ggcccttccg gctggctggt    12120
ttattgctga taaatctgga gccggtgagc gtgggtctcg cggtatcatt gcagcactgg    12180
ggccagatgg taagccctcc cgtatcgtag ttatctacac gacggggagt caggcaacta    12240
tggatgaacg aaatagacag atcgctgaga taggtgcctc actgattaag cattggtaac    12300
cgattctagg tgcattggcg cagaaaaaaa tgcctgatgc gacgctgcgc gtcttatact    12360
cccacatatg ccagattcag caacggatac ggcttcccca acttgcccac ttccatacgt    12420
gtcctcctta ccagaaattt atccttaaga tcgtttaaac tcgactctgg ctctatcgaa    12480
tctccgtcgt ttcgagctta cgcgaacagc cgtggcgctc atttgctcgt cgggcatcga    12540
atctcgtcag ctatcgtcag cttacctttt tggcagcgat cgcggctccc gacatcttgg    12600
accattagct ccacaggtat cttcttccct ctagtggtca taacagcagc ttcagctacc    12660
tctcaattca aaaaacccct caagacccgt ttagaggccc caaggggtta tgctatcaat    12720
cgttgcgtta cacacacaaa aaaccaacac acatccatct tcgatggata gcgattttat    12780
tatctaactg ctgatcgagt gtagccagat ctagtaatca attacggggt cattagttca    12840
tagcccatat atggagttcc gcgttacata acttacggta aatggcccgc ctggctgacc    12900
gcccaacgac ccccgcccat tgacgtcaat aatgacgtat gttcccatag taacgccaat    12960
agggactttc cattgacgtc aatgggtgga gtatttacgg taaactgccc acttggcagt    13020
acatcaagtg tatcatatgc caagtacgcc ccctattgac gtcaatgacg gtaaatggcc    13080
cgcctggcat tatgcccagt acatgacctt atgggacttt cctacttggc agtacatcta    13140
cgtattagtc atcgctatta ccatgctgat gcggtttttgg cagtacatca atgggcgtgg    13200
atagcggttt gactcacggg gatttccaag tctccacccc attgacgtca atgggagttt    13260
gttttggcac caaaatcaac gggactttcc aaaatgtcgt aacaactccg ccccattgac    13320
gcaaatgggc ggtaggcgtg tacggtggga ggtctatata agcagagctg gtttagtgaa    13380
ccgtcagatc agatctttgt cgatcctacc atccactcga cacacccgcc agcggccgc    13439
```

SEQ ID NO: 47            moltype = DNA   length = 13436
FEATURE                  Location/Qualifiers
misc_feature            1..13436
                         note = Description of Artificial Sequence: Synthetic
                          polynucleotide
source                  1..13436
                         mol_type = other DNA
                         organism = synthetic construct

SEQUENCE: 47

-continued

```
taatacgact cactatagag agaagtactg ccaccatggg caagaagcaa aatcgcaaga   60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacacccag cggtatagct  660
ctcggcgtgc caccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat 1020
atcaaccctt gcagaaccac gcaaagatgg gaagcggagc tactaacttc agcctgctga 1080
agcaggctgg agacgtggag gagaaccctg gacctatgac cggctctaac tcacatatca 1140
ccatccttac acttaacatt aacggcctca actcagctat caagcgccat cggctggcca 1200
gctggatcaa atcacaggat ccaagcgttt gttgcatcca agagacccac ctgacctgta 1260
gagatactca ccgcctcaag atcaagggat ggcgaaagat ttatcaggcg aacggtaagc 1320
agaagaaagc cggagtcgca attctggtct cagacaagac ggatttcaag cccaccaaaa 1380
ttaagcgtga taaggaaggt cactatatta tggtgaaagg cagcatacag caggaagaac 1440
ttaccatatt gaacatctac gcgccaaaca ccggcgcacc tcgctttatc aaacaggtcc 1500
tgtccgatct gcagcgagat ctggattctc atacgttgat tatgggtgat ttcaatacac 1560
cattgagcac cctggatcgc agcaccaggc aaaaggtaaa taaagacacg caagagctca 1620
atagcgcact gcatcaggca gatctcattg atatttatcg cactcttcat cctaagagta 1680
ccgagtacac attcttcagc gccccacatc atacatactc aaagatcgat catatcgtcg 1740
gctcaaaggc tctgctgtca aagtgcaagc gcacagagat aattacaaat tacctgtcag 1800
atcatagcgc gatcaagctc gagctgagaa tcaagaacct gacccagagc cggagtacca 1860
cttggaagct taataacctg ctgctcaacg attattgggt ccacaatgag atgaaggcag 1920
agattaaaat gttcttcgaa acaaatgaga ataaggatac tacctatcaa aacctttggg 1980
atgcctttaa ggccgtctgc agaggcaagt tcatcgccct caacgcctat aaaagaaaac 2040
aagagagatc taagatcgat actctcacct ctcagctgaa ggagttggag aaacaggaac 2100
agacccactc caaggcgtca agacggcagg agatcacaaa gattcgcgcc gagttgaaag 2160
agatcgaaac ccaaaagact cttcagaaaa ttaacgagtc tcgtagttgg ttcttcgagc 2220
ggattaataa gatagacaga cctctggcac gactgattaa gaagaagcgc gaaaagaacc 2280
agattgatac catcaagaac gacaagggcg acatcactac tgacccgacc gagatccaga 2340
ccactattcg ggagtattat aagcatttgt atgctaacaa gcttgagaac ctggaagaga 2400
tggacacttt tctggatacc tatactctgc cacggcttaa tcaagaggaa gtcgagtccc 2460
tcaaccgccc aattacagga agcgagattg tggccataat taactccctg ccgacaaaga 2520
aatctcctgg tccggacggg tttacagctg agttttatca acggtatatg gaagagcttg 2580
taccgtttct gctcaagctc tttcagtcta tagaaaagga aggcatcttg cccaattcct 2640
tctacgaagc ttctataata cttattccca aaccaggacg cgataccaca aagaaggaaa 2700
acttccggcc cattagtctc atgaatatcg acgctaaaat attgaacaag attctcgcca 2760
acagaatcca acaacatatt aagaaattga tacatcacga ccaggtgagg tttatacctg 2820
gcatgcaggg ctggtttaac atccggaaga gtattaacgt cattcaacac attaatagag 2880
ctaaggataa gaatcatatg atcatctcta tagacgcgga aaaggcattc gataagattc 2940
agcagccatt tatgctcaag actctgaaca aactcggcat cgacggaaca tatttaagaa 3000
ttattcgcgc aatttacgat aagccgactc ctaacattat ccttaacggc caaaagctcg 3060
aggcctttcc gctcaagact ggaaccgcc aaggctgtcc cctctccccg cttttgtttta 3120
atattgtact cgaggtgctg gctagggcta ttcgtcaaga gaaagagatt aaagggatac 3180
agctcgggaa ggaagaggtc aagctttcct tgttcgccga tgatatgatt gtgtacctgg 3240
agaatcctat tgtgtctgct cagaaccttc ttaaacttat ttctaacttt agcaaggtca 3300
gcggctataa gattaacgtc cagaaatctc aggcctttct gtacacaaat aatcgacaga 3360
ccgaatccca gataatgggt gagcttccgt ttgtcatagc cagcaaaagg ataaagtatc 3420
tcggaatcca gctgacacga gacgttaaag atttgtttaa ggaaaattac aagcctctcc 3480
tgaaagagat taaggaagat actaataagt ggaagaatat cccctgttca tgggttggca 3540
gaatcaacat agtgaagatg gcaatacttc ctaaagtgat atatcgcttt aacgccatcc 3600
caattaaact gcctatgacc ttctttacgg agctcgagaa aacaacccct aaatttatat 3660
ggaatcaaaa gagagcaaga atagcgaagt ccatcttgag ccagaagaat aaggccggtg 3720
ggattacttt gcctgatttt aagttgtatt ataaagccac agtaactaag acagcctggt 3780
attggtatca gaatagagac atcgaccagt ggaatcggac cgaaccatca gagataatgc 3840
cccacatcta taattacctt atattcgata agccagaaaa gaataaacag tggggcaaag 3900
acagcctctt caacaagtgg tgttgggaga attggctggc catatgccgg aaactcaagc 3960
tcgacccctt tcttacaccc tacactaaaa tcaacagtag gtggatcaag gacttgaatg 4020
tcaagccaaa gactataaag acactggaag agaatcttgg gatcacaata caagatatag 4080
gcgtcggcaa agattttatg tcaaagacgc ccaaggccgt ggccactaag gataagattg 4140
ataagtggga cccttattaag ctcaaaaagct tctgtactgc caaggagacc acgatcagag 4200
ttaataggca gcccactaca tgggaaaaga ttttcgccac ttattcatca gataaggggt 4260
tgataagcag aatatataac gagctgaagc agatctacaa gaagaaacg aataatccca 4320
tcaagaagtg ggcaaaagat atgaacaggc attttagcaa agaggatatc tacgccgcga 4380
agaagcatat gaagaagtgt agttcaagct tggccattcg tgatgcag attaagacga 4440
ccatgcgata ccaccttacc ccagtgagga tggcaattat caagaaatct ggcaataata 4500
gatgttggcg gggctgtggc gagattggca ccctgctcca ttgctggtgg gattgcaagc 4560
tggtgcagcc gctttggaaa tcagtctggc gctttctgag ggacctcgag cttgagattc 4620
ccttcgatcc cgcaattcc ttgctcggaa tctatcctaa cgaatacaag agctgttgtt 4680
acaaggatac gtgtacccgg atgttcatcg cggccttgtt tacgatagct aagacgtgga 4740
```

-continued

```
atcagcctaa gtgccccaca atgatcgatt ggatcaagaa aatgtggcat atttatacca  4800
tggagtatta cgcagcaatt aagaatgacg aatttatttc cttcgttggg acctggatga  4860
agctggagac tattattctg agcaagctgt ctcaggagca aaagacaaag catagaatct  4920
tctctctcat tggtggtaac gactacaaag acgatgacga caagtaaagc gcttctagaa  4980
gttgtctcct cctgcactga ctgactgata caatcgattt ctggatccgc aggcctaatc  5040
aacctctgga ttacaaaatt tgtgaaagat tgactggtat tcttaactat gttgctcctt  5100
ttacgctatg tggatacgct gctttaatgc ctttgtatca tgctattgct tcccgtatgg  5160
cttttcatttt ctcctccttg tataaatcct ggttgctgtc tctttatgag gagttgtggc  5220
ccgttgtcag gcaacgtggc gtggtgtgca ctgtgtttgc tgacgcaacc cccactggtt  5280
ggggcattgc caccacctgt cagctccttt ccgggacttt cgctttcccc ctccctattg  5340
ccacggcgga actcatcgcc gcctgccttg cccgctgctg gacaggggct cggctgttgg  5400
gcactgacaa ttccgtggtg ttgtcgggga agctgacgtc ctttccatgg ctgctcgcct  5460
gtgttgccac ctggattctg cgcgggacgt ccttctgcta cgtcccttcg gccctcaatc  5520
cagcggacct tccttcccgc gaacaaacga cccaacacc gtgcgttta ttctgtcttt  5580
ttattgccga tcccctcaga agaactcgtc aagaaggcga tagaaggcga tgcgctgcga  5640
atcgggagcg gcgataccgt aaagcacgag gaagcggtca gcccattcgc cgccaagctc  5700
ttcagcaata tcacgggtag ccaacgctat gtcctgatag cggtcggccg ctttacttgt  5760
acagctcgtc catgccgaga gtgatcccgg cggcggtcac gaactccagc aggaccatgt  5820
gatcgcgctt ctcgttgggg tctttgctca gggcggactg ggtgctcagg tagtggttgt  5880
cgggcagcag cacggggccg tcgccgatgg gggtgttctg ctggtagtgg tcggccaggt  5940
gagtccagga gatgtttcag cactgttgcc tttagtctcg aggcaactta gacaactgag  6000
tattgatctg agcacagcag ggtgtgagct gtttgaagat actggggttg ggggtgaaga  6060
aactgcagag gactaactgg gctgagaccc agtggcaatg ttttagggcc taaggaatgc  6120
ctctgaaaat ctagatggac aactttgact ttgagaaaag agaggtggaa atgaggaaaa  6180
tgactttttct ttattagatt tcggtagaaa gaactttcat ctttcccta tttttgttat  6240
tcgttttaaa acatctatct ggaggcagga caagtatggt cattaaaaag atgcaggcag  6300
aaggcatata ttggctcagt caaagtgggg aactttggtg gccaaacata cattgctaag  6360
gctattccta tatcagctgg acacatataa aatgctgcta atgcttcatt acaaacttat  6420
atcctttaat tccagatggg ggcaaagtat gtccaggggt gaggaacaat tgaaacattt  6480
gggctggagt agattttgaa agtcagctct gtgtgtgtgt gtgtgtgtgt gtgtgtgaga  6540
gcgtgtgttt cttttaacgt tttcagccta cagcatacag ggttcatggt ggcaagaaga  6600
taacaagatt taaattatgg ccagtgacta gtgctgcaag aagaacaact acctgcattt  6660
aatgggaaag caaaatctca ggctttgagg gaagttaaca taggcttgat tctgggtgga  6720
agctgggtgt gtagttatct ggaggccagg ctggagctct cagctcacta tgggttcatc  6780
tttattgtct cctttcatct caacagctgc acgctgccgt cctcgatgtt gtggcggatc  6840
ttgaagttca ccttgatgcc gttcttctgc ttgtcggcca tgatatagac gttgtggctg  6900
ttgtagttgt actccagctt gtgccccagg atgttgccgt cctccttgaa gtcgatgccc  6960
ttcagctcga tgcggttcac cagggtgtcg ccctcgaact tcacctcggc gcgggtcttg  7020
tagttgccgt cgtccttgaa gaagatggtg cgctcctgga cgtagccttc gggcatggcg  7080
gacttgaaga agtcgtgctg cttcatgtgg tcggggtagc ggctgaagca ctgcacgccg  7140
taggtcaggg tggtcacgag ggtgggccag ggcacgggca gcttgccggt ggtgcagatg  7200
aacttcaggg tcagcttgcc gtaggtggca tcgccctcgc cctcgccgga cacgctgaac  7260
ttgtggccgt ttacgtcgcc gtccagctcg accaggatgg gcaccacccc ggtgaacagc  7320
tcctcgccct tgctcaccat ggtggcgaat tcgaagcttg agcacgagat ctgagtccgg  7380
taggcctagc ggatctgacg gttgcactaaa ccagctctgc ttatatagac ctcccaccgt  7440
acacgcctac cgcccatttg cgtcaatggg gcggagttgt tacgacattt tggaaagtcc  7500
cgttgatttt ggtgccaaaa caaactccca ttgacgtcaa tggggtggag acttggaaat  7560
ccccgtgagt caaaccgcta tccacgccca ttgatgtact gccaaaaccg catcaccatg  7620
gtaatagcga tgactaatac gtagatgtac tgccaagtag gaaagtccca taaggtcatg  7680
tactgggcat aatgccaggc gggccattta ccgtcattga cgtcaatagg gggcgtactt  7740
ggcatatgat acacttgatg tactgccaag tgggcagttt accgtaaata ctccacccat  7800
tgacgtcaat ggaaagtccc tattggcgtt actatgggaa catacgtcat tattgacgtc  7860
aatgggcggg ggtcgttggg cggtcagcca ggcgggccat ttaccgtaag ttatgtaacg  7920
ggcctgctgc cggctctgcg gcctcttccg cgtcttcgcc ttcgccctca gacgagtcgg  7980
atctcccttt gggccgcctc cccgcctgtc tagcttgact gactgagata cagcgtacct  8040
tcagctcaca gacatgataa gatacattga tgagtttgga caaaccacaa ctagaatgca  8100
gtgaaaaaaa tgctttattt gtgaaatttg tgatgctatt gctttatttg taaccattat  8160
aagctgcaat aaacaagtta acaacaacaa ttgcattcat tttatgtttc aggttcaggg  8220
ggaggtgtgg gaggtttttt aaagcaagta aaacctctac aaatgtggta ttggcccatc  8280
tctatcggta tcgtagcata acccttggg gcctctaaac gggtcttgag gggtttttg  8340
tgccctcgg gccggattgc tatctaccgg cattggcgca gaaaaaaatg cctgatgcga  8400
cgctgcgcgt cttatactcc cacatatgcc agattcagca acggatacg cttccccaac  8460
ttgcccactt ccatacgtgt cctccttacc agaaatttat cctaaggtc gtcagctatc  8520
ctgcaggcga tctctcgatt tcgatcaaga cattccttta atggtcttt ctggacacca  8580
ctaggggtca gaagtagttc atcaaacttt cttccctccc taatctcatt ggttaccttg  8640
ggctatcgaa acttaattaa gcgatctgca tctcaattag tcagcaacca tagtcccgcc  8700
cctaactccg cccatcccgc ccctaactcc gcccagttcc gcccattctc cgccccatcg  8760
ctgactaatt ttttttattt atgcagaggc cgaggccgcc tcggcctctg agctattcca  8820
gaagtagtga ggaggctttt ttggaggcct aggcttttgc aaaggaggta gccaacatga  8880
ttgaacaaga tggattgcac gcaggttctc ccgccgcttg ggtggagagg ctattcggct  8940
atgactgggc acaacagaca atcggctgct ctgatgccgc cgtgttccgg ctgtcagcgc  9000
aggggcgccc ggttcttttt gtcaagaccg acctgtccgg tgccctgaat gaactccagg  9060
acgaggcagc gcggctatcg tggctggcca cgacgggcgt tccttgcgca gctgtgctcg  9120
acgttgtcac tgaagcggga agggactgga ctgtattgga gggcgggcca gccaggaatca  9180
tcctgtcatc tcaccttgct cctgccgaga aagtatccat catggctgat gcaatgcggc  9240
ggctgcatac gcttgatccg gctacctgcc cattcgacca ccaagcgaaa catcgcatcg  9300
agcgagcacg tactcggatg gaagccggtc ttgtcgatca ggatgatctg gacgaagagc  9360
atcagggct cgcgccagcc gaactgttcg ccaggctcaa ggcgcggatg cccgacggcg  9420
aggatctcgt cgtgacccac ggcgatgcct gcttgccgaa tatcatggtg gaaaatggcc  9480
```

-continued

```
gcttttctgg attcatcgac tgtggccggc tgggtgtggc ggaccgctat caggacatag    9540
cgttggctac ccgtgatatt gctgaagagc ttggcggcga atgggctgac cgcttcctcg    9600
tgctttacgg tatcgccgct cccgattcgc agccgcatcgc cttctatcgc cttcttgacg    9660
agttcttcta gtatgtaagc cctgtgcctt ctagttgcca gccatctgtt gtttgccct     9720
cccccgtgcc ttccttgacc ctggaaggtg ccactcccac tgtccttcc taataaaatg     9780
aggaaattgc atcgcattgt ctgagtaggt gtcattctat tctgggggt ggggtggggc     9840
aggacagcaa gggggaggat tgggaagaca atagcaggca tgctggggat gcggtgggct    9900
ctatggttaa ttaaccagtc aagtcagcta cttggcgaga tcgacttgtc tgggtttcga    9960
ctacgctcag aattgcgtca gtcaagttcg atctggtcct tgctattgca cccgttctcc    10020
gattacgagt ttcatttaaa tcatgtgagc aaaaggccag caaaaggcca ggaaccgtaa    10080
aaaggccgcg ttgctggcgt ttttccatag gctccgcccc cctgacgagc atcacaaaaa    10140
tcgacgctca agtcagaggt ggcgaaaccc gacaggacta aaagatacc aggcgtttcc    10200
ccctggaagc tccctcgtgc gctctcctgt tccgaccctg ccgcttaccg gatacctgtc    10260
cgcctttctc cttcgggaa gcgtggcgct ttctcatagc tcacgctgta ggtatctcag    10320
ttcggtgtag tcgttcgct ccaagctggg ctgtgtgcac gaaccccccg ttcagcccga    10380
ccgctcgcc ttatccggta actatcgtct tgagtccaac ccggtaagac acgacttatc    10440
gccactggca gcagccactg gtaacaggat tagcagagcg aggtatgtag gcggtgctac    10500
agagttcttg aagtggtggc ctaactacgg ctacactaga agaacagtat ttggtatctg    10560
cgctctgctg aagccagtta ccttcggaaa aagagttggt agctcttgat ccggcaaaca    10620
aaccaccgct ggtagcggtg gtttttttgt ttgcaagcag cagattacgc gcagaaaaaa    10680
aggatctcaa gaagatcctt tgatctttc tacgggtct gacgctcagt ggaacgaaaa    10740
ctcacgttaa gggattttgg tcatgagatt atcaaaaagg atcttcacct agatccttt     10800
aaattaaaaa tgaagtttta aatcaatcta agtatatat gagtaaactt ggtctgacag    10860
ttaccaatgc ttaatcagtg aggcacctat ctcagcgatc tgtctatttc gttcatccat    10920
agttgcattt aaatttccga actctccaag gccctcgtcg gaaaatcttc aaacctttcg    10980
tccgatccat cttgcaggct acctctcgaa cgaactatcg caagtctctt ggccggcctt    11040
gcgccttggc tattgcttgg cagcgcctat cgccaggtat tactccaatc ccgaatatc     11100
gagatcggga tcacccgaga gaagttcaac ctacatcctc aatcccgatc tatccgagat    11160
ccgaggaata tcgaaatcgg ggcgcgcctg gtgtaccgag aacgatcctc tcagtgcgag    11220
tctcgacgat ccatatcgtt gcttggcagt cagccagtcg gaatccagct tgggacccag    11280
gaagtccaat cgtcagatat tgtactcaag cctggtcacg gcagcgtacc gatctgttta    11340
aacctagata ttgatagtct gatcggtcaa cgtataatcg agtcctagct tttgcaaaca    11400
tctatcaaga gacaggatca gcaggaggct ttcgcatgag tattcaacat ttccgtgtcg    11460
cccttattcc cttttttgcg gcattttgcc ttcctgtttt tgctcaccca gaaacgctgg    11520
tgaaagtaaa agatgctgaa gatcagttgg gtgcgcgagt gggttacatc gaactggatc    11580
tcaacagcgg taagatcctt gagagttttc gccccgaaga acgctttcca atgatgagca    11640
cttttaaagt tctgctatgt ggcgcggtat tatcccgtat tgacgccggg caagagcaac    11700
tcggtcgccg catacactat tctcagaatg acttggttga gtattcacca gtcacagaaa    11760
agcatcttac ggatggcatg acagtaagag aattatgcag tgctgccata accatgagtg    11820
ataacactgc ggccaactta cttctgacaa cgattggagg accgaaggag ctaaccgctt    11880
ttttgcacaa catgggggat catgtaactc gccttgatcg ttgggaaccg gagctgaatg    11940
aagccatacc aaacgacgag cgtgacacca cgatgcctgt agcaatggca acaaccttgc    12000
gtaaactatt aactggcgaa ctacttactc tagcttcccg gcaacagttg atagactgga    12060
tggaggcgga taaagttgca ggaccacttc tgcgctcggc ccttccggct ggctggttta    12120
ttgctgataa atctggagcc ggtgagcgtg ggtctcgcgg tatcattgca gcactggggc    12180
cagatggtaa gccctcccgt atcgtagtta tctacacgac ggggagtcag gcaactatgg    12240
atgaacgaaa tagacagatc gctgagatag gtgcctcact gattaagcat tggtaaccga    12300
ttctaggtgc attggcgcag aaaaaaatgc ctgatgcgac gctgcgcgtc ttatactccc    12360
acatatgcca gattcagcaa cggatacggc ttccccaact gcccacttc catacgtgtc    12420
ctccttacca gaaatttatc cttaagatcg tttaaactcg actctggctc tatcgaatct    12480
ccgtcgtttc gagcttacgc gaacagccgt ggcgctcatt tgctcgtcgg gcatcgaatct    12540
tcgtcagcta tcgtcagctt accttttttg cagcgatcgc ggctcccgac atcttggacc    12600
attagctcca caggtatctt cttccctcta gtggtcataa cagcagcttc agctacctct    12660
caattcaaaa aaccccctcaa gacccgttta gaggccccaa ggggttatgc tatcaatcgt    12720
tgcgttacac acacaaaaaa ccaacacaca tccatcttcg atggatagcg atttttattat    12780
ctaactgctg atcgagtgta gccagatcta gtaatcaatt acggggtcat tagttcatag    12840
cccatatatg gagttccgcg ttacataact tacggtaaat ggcccgcctg gctgaccgcc    12900
caacgacccc cgcccattga cgtcaataat gacgtatgtt cccatagtaa cgccaatagg    12960
gactttccat tgacgtcaat gggtggagta tttacggtaa actgcccact tggcagtaca    13020
tcaagtgtat catatgccaa gtacgccccc tattgacgtc aatgacggta aatggcccgc    13080
ctggcattat gcccagtaca tgaccttatg ggactttcct acttggcagt acatctacgt    13140
attagtcatc gctattacca tgctgatgcg gtttttggcag tacatcaatg ggcgtggata    13200
gcggtttgac tcacggggat ttccaagtct ccaccccatt gacgtcaatg ggagtttgtt    13260
ttggcaccaa aatcaacggg actttccaaa atgtcgtaac cattgacgca a13320
aatgggcggt aggcgtgtac ggtgggaggt ctatataagc agagctggtt tagtgaaccg    13380
tcagatcaga tctttgtcga tcctaccatc cactcgacac acccgccagc ggccgc       13436
```

SEQ ID NO: 48          moltype = DNA   length = 13433
FEATURE                Location/Qualifiers
misc_feature           1..13433
                       note = Description of Artificial Sequence: Synthetic
                       polynucleotide
source                 1..13433
                       mol_type = other DNA
                       organism = synthetic construct
SEQUENCE: 48
taatacgact cactataggg agaagtactg ccaccatggg caagaagcaa aatcgcaaga    60
cggggaattc caagacacaa tccgctagcc caccacctaa agagcgttct agctcccctg    120
ctactgagca gtcctggatg gaaaacgact tcgatgaact ccgggaagag ggatttaggc    180
```

-continued

```
gatccaacta ttcagaactc cgcgaagata tccagacaaa ggggaaggaa gtcgagaatt   240
tcgagaagaa cctcgaggag tgcatcaccc gtatcacaaa cactgagaaa tgtctcaaag   300
aactcatgga acttaagaca aaagccaggg agcttcgaga ggagtgtcgg agtctgagat   360
ccaggtgtga ccagctcgag gagcgcgtga gcgcgatgga agacgagatg aacgagatga   420
aaagagaggg caaattcagg gagaagcgca ttaagaggaa cgaacagagt ctgcaggaga   480
tttgggatta cgtcaagagg cctaacctgc ggttgatcgg cgtccccgag agcgacgtag   540
aaaacgggac taaactggag aatacacttc aagacatcat tcaagaaaat tttccaaacc   600
tggctcggca agctaatgtg caaatccaag agatccaacg cacaccccag cggtatagct   660
ctcggcgtgc cacccctagg catattatcg tgcgctttac taaggtggag atgaaagaga   720
agatgctgcg agccgctcgg gaaaagggaa gggtgacttt gaagggcaaa cctattcggc   780
tgacggttga ccttagcgcc gagacactcc aggcacgccg ggaatggggc cccatcttta   840
atatcctgaa ggagaagaac ttccagccac gaatctctta ccctgcaaag ttgagtttta   900
tctccgaggg tgagattaag tatttcatcg ataaacagat gctgcgagac ttcgtgacaa   960
ctcgcccagc tctcaaggaa ctgctcaaag aggctcttaa tatggagcgc aataatagat  1020
atcaaccctt gcagaaccac gcaaagatgg gaagcggaga gggcagagga agtctgctaa  1080
catgcggtga cgtcgaggag aatcctggac ctatgaccgg ctctaactca catatccacca  1140
tccttacact taacattaac ggcctcaact cagctatcaa gcgccatcgg ctggccagct  1200
ggatcaaatc acaggatcca agcgtttgtt gcatccaaga gacccacctg acctgtagag  1260
atactcaccg cctcaagatc aagggatggc gaaagattta tcaggcgaac ggtaagcaga  1320
agaaagccgg agtcgcaatt ctggtctcag acaagacgga tttcaagccc accaaaatta  1380
agcgtgataa ggaaggtcac tatattatgg tgaaaggcag catacagcag gaagaactta  1440
ccatattgaa catctacgcg ccaaacaccg gcgcacctcg ctttatcaaa caggtcctgt  1500
ccgatctgca gcgagatctg gattctcata cgttgattat gggtgatttc aatacaccat  1560
tgagcaccct ggatcgcagc accaggcaaa aggtaaataa agacacgcaa gagctcaata  1620
gcgcactgca tcaggcagat ctcattgata tttatcgcac tcttcatcct aagagtaccg  1680
agtacacatt cttcagcgcc ccacatcata catactcaaa gatcgatcat atcgtcggct  1740
caaaggctct gctgtcaaag tgcaagcgca cagagataat tacaaattac ctgtcagatc  1800
atagcgcgat caagctcgag ctgagaatca agaacctgac ccagagccgg agtaccactt  1860
ggaagcttaa taacctgctg ctcaacgatt attgggtcca caatgagatg aaggcagaga  1920
ttaaaatgtt cttcgaaaca aatgagaata aggatactac ctatcaaaac ctttgggatg  1980
cctttaaggc cgtctgcaga ggcaagttca tcgccctcca cgcctataaa agaaaacaag  2040
agagatctaa gatcgatact ctcacctctc agctgaagga gttggagaaa caggaacaga  2100
cccactccaa ggcgtcaaga cggcaggaga tcacaaagat tcgcgccgag ttgaaagaga  2160
tcgaaaccca aaagactctt cagaaaatta acgagtctcg tagttggttc ttcgagcgga  2220
ttaataagat agacagacct ctggcacgac tgattaagaa gaagcgcgaa aagaaccaga  2280
ttgataccat caagaacgac aagggcgaca tcactactga cccgaccgag atccagacca  2340
ctattcggga gtattataag catttgtatg ctaacaagct tgagaacctg gaagagatgg  2400
acacttttct ggataccctat actctgccac ggcttaatca agaggaagtc gagtccctca  2460
accgcccaat tacaggaagc gagattgtgg ccataattaa ctccctgccg acaaagaaat  2520
ctcctggtcc ggacgggttt acagctgagt tttatcaacg gtatatggaa gagcttgtac  2580
cgtttctgct caagctcttt cagtctatag aaaaggaagg catcttgccc aattccttct  2640
acgaagcttc tataatactt attcccaaac caggacgcga taccacaaag aaggaaaact  2700
tccggcccat tagtctcatg aatatcgacg ctaaaatatt gaacaagatt ctcgccaaca  2760
gaatccaaca acatattaag aaattgatca atcacgacca ggtggggttt atacctggca  2820
tgcagggctg gtttaacatc cggaagagta ttaacgtcat tcaacacatt aatagagcta  2880
aggataagaa tcatatgatc atctctatag acgcggaaaa ggcattcgat aagattcagc  2940
agccatttat gctcaagact ctgaacaaac tcggcatcga cggaacatat tttaagatta  3000
ttcgcgcaat ttacgataag ccgactgcta acattatcct taacggccaa aagctcgagg  3060
cctttccgct caagactgga acccgccaag gctgtcccct ctccccgctt ttgtttaata  3120
ttgtactcga ggtgctggct agggctattc gtcaagagaa agagattaaa gggatacagc  3180
tcgggaagga agaggtcaag cttttccttg tcgccgatga tatgattgtg tacctggaga  3240
atcctattgt gtctgctcag aaccttctta aacttatttc taactttagc aaggtcagcg  3300
gctataagat taacgtccag aaatctcagg cctttctgta cacaaataat cgacagaccg  3360
aatcccagat aatgggtgag cttccgtttg tcatagccag caaaaggata aagtatctcg  3420
gaatccagct gacacgagac gttaaagatt tgtttaagga aaattacaag cctctcctga  3480
aagagattaa ggaagatact aataagtgga gaaatatccc ctgttcatgg gttggcagaa  3540
tcaacatagt gaagatggca atacttccta aagtgatata tcgctttaac gccatcccaa  3600
ttaaactgcc tatgaccttc tttacggagc tcgagaaaac aacccttaaa tttatatgga  3660
atcaaaagag agcaagaata gcgaagtcca tcttgagcca gaagaataag gccggtggga  3720
ttactttgcc tgattttaag ttgtattata agccacagt aactaagaca gcctggtatt  3780
ggtatcagaa tagagacatc gaccagtgga atcggaccga accatcagag ataatgcccc  3840
acatctataa ttaccttata ttcgataagc cagaaaagaa taaacagtgg ggcaaagaca  3900
gcctcttcaa caagtggtgt tgggagaatt ggctggccat atgccggaaa ctcaagctcg  3960
accccttttct tacaccctac actaaaatca acagtaggtg gatcaaggac ttgaatgtca  4020
agccaaagac tataaagaca ctggaagaga atcttgggat cacaatacaa gatataggca  4080
tcggcaaaga tttttatgtca aagacgccca aggccatggc cactaaggat aagattgata  4140
agtgggacct tattaagctc aaaagcttct gtactgccaa ggagaccacg atcagagtta  4200
ataggcagcc cactacatgg gaaaagattt cgccactta ttcatcagat aaggggttga  4260
taagcagaat atataacgac ctgaagcaga tctacaagaa gaaaacgaat aatcccatca  4320
agaagtgggc aaaagatatg aacaggcatt ttagcaaaga ggatatctac gccgcgaaga  4380
agcatatgaa gaagtgtagt tcaagcttgg ccattcgtga gatgcagatt aagacgacca  4440
tgcgatacca ccttacccca gtgaggatgg caattatcaa gaaatctggc aataatagat  4500
gttggcgggg ctgtggcgag attggcaccc tgctccattg ctggtgggat tgcaagctgg  4560
tgcagcgat ttggaaatca gtctggcgct ttctgaggga cctcgagctt gagattcct  4620
tcgatcccgc aattcccttg ctcggaatct atcctaacga atacaagagc tgttgttaca  4680
aggatacgtg tacccggatg ttcatcgcgg cctttgttta cgatagctaag acgtggaatc  4740
agcctaagtg ccccacaatg atcgattgga tcaagaaaat gtggcatatt tataccatgg  4800
agtattacgc agcaattaag aatgacgaat ttatttcctt cgttgggacc tggatgaagc  4860
tggagactat tattctgagc aagctgtctc aggagcaaaa gacaaagcat agaatcttct  4920
```

-continued

```
ctctcattgg tggtaacgac tacaaagacg atgacgacaa gtaaagcgct tctagaagtt   4980
gtctcctcct gcactgactg actgatacaa tcgatttctg gatccgcagg cctaatcaac   5040
ctctggatta caaaatttgt gaaagattga ctggtattct taactatgtt gctcctttta   5100
cgctatgtgg atacgctgct ttaatgcctt tgtatcatgc tattgcttcc cgtatggctt   5160
tcattttctc ctccttgtat aaatcctggt tgctgtctct ttatgaggag ttgtggcccg   5220
ttgtcaggca acgtggcgtg gtgtgcactg tgtttgctga cgcaaccccc actggttggg   5280
gcattgccac cacctgtcag ctcctttccg ggactttcgc tttcccccctc cctattgcca   5340
cggcggaact catcgccgcc tgccttgccc gctgctggac aggggctcgg ctgttgggca   5400
ctgacaattc cgtggtgttg tcggggaagc tgacgtcctt tccatggctg ctcgcctgtg   5460
ttgccacctg gattctgcgc gggacgtcct tctgctacgt cccttcggcc ctcaatccag   5520
cggaccttcc ttcccgcgaa caaacgaccc aacacccgtg cgtttttattc tgtctttta    5580
ttgccgatcc cctcagaaga actcgtcaag aaggcgatag aaggcgatgc gctgcgaatc   5640
gggagcggcg ataccgtaaa gcacgaggaa gcggtcagcc cattcgccgc caagctcttc   5700
agcaatatca cgggtagcca acgctatgtc ctgatagcgg tcggccgctt tacttgtaca   5760
gctcgtccat gccgagagtg atcccggcgg cggtcacgaa ctccagcagg accatgtgat   5820
cgcgcttctc gttggggtct ttgctcaggg cggactgggt gctcaggtag tggttgtcgg   5880
gcagcagcac ggggccgtcg ccgatggggg tgttctgctg gtagtggtcg gccaggtgag   5940
tccaggagat gtttcagcac tgttgccttt agtctcgagg caacttagac aactgagtat   6000
tgatctgagc acagcagggt gtgagctgtt tgaagatact ggggttgggg gtgaagaaac   6060
tgcagaggac taactgggct gagacccagt ggcaatgttt tagggcctaa ggaatgcctc   6120
tgaaaatcta gatggacaac tttgactttg agaaaagaga ggtggaaatg aggaaaatga   6180
cttttcttta ttagatttcg gtagaaagaa ctttcatctt tcccctattt ttgttattcg   6240
ttttaaaaca tctatctgga ggcaggacaa gtatggtcat taaaaagatg caggcagaag   6300
gcatatattg gctcagtcaa agtggggaac tttggtggcc aaacatacat tgctaaggct   6360
attcctatat cagctggaca catataaaat gctgctaatg cttcattaca aacttatatc   6420
ctttaattcc agatgggggc aaagtatgtc caggggtgaag gacaattga aacatttggg   6480
ctggagtaga tttgaaagt cagctctgtg tgtgtgtgtg tgtgtgtgtg tgtgagagcg   6540
tgtgtttctt ttaacgtttt cagcctacag catacagggt tcatggtggc aagaagataa   6600
caagatttaa attatggcca gtgactagtg ctgcaagaag aacaactacc tgcatttaat   6660
gggaaagcaa aatctcaggc tttgggggaa gttaacatag gcttgattct gggtggaagc   6720
tgggtgtgta gttatctgga ggccaggctg gagctctcag ctcactatgg gttcatcttt   6780
attgtctcct ttcatctcaa cagctgcacg ctgccgtcct cgatgttgtg gcggatcttg   6840
aagttcacct tgatgccgtt cttctgcttg tcggccatga tatagacgtt gtggctgttg   6900
tagttgtact ccagcttgtg ccccaggatg ttgccgtcct ccttgaagtc gatgcccttc   6960
agctcgatgc ggttcaccag ggtgtcgccc tcgaacttca cctcggcgcg ggtcttgtag   7020
ttgccgtcgt ccttgaagaa gatggtgcgc tcctggacgt agccttcggg catggcggac   7080
ttgaagaagt cgtgctgctt catgtggtcg gggtagcggc tgaagcactg cacgccgtag   7140
gtcagggtgg tcacgagggt gggccagggc acggcagct tgccggtggt gcagatgaac   7200
ttcagggtca gcttgccgta ggtggcatcg ccctcgccct cgccggacac gctgaacttg   7260
tggccgttta cgtcgccgtc cagctcgacc aggatgggca ccaccccggt gaacagctcc   7320
tcgcccttgc tcaccatggt ggcgaattcg aagcttgagc acgagatctg agtccggtag   7380
gcctagcgga tctgacggtt cactaaacca gctctgctta tatagacctc ccaccgtaca   7440
cgcctaccgc ccatttgcgt caatggggcg gagttgttac gacattttgg aaagtcccgt   7500
tgattttggt gccaaacaa actcccattg acgtcaatgg ggtggagact tggaaatccc   7560
cgtgagtcaa accgctatcc acgcccattg atgtactgcc aaaaccgcat caccatggta   7620
atagcgatga ctaatacgta gatgtactgc caagtaggaa agtcccataa ggtcatgtac   7680
tgggcataat gccaggcggg ccatttaccg tcattgacg caatagggg cgtacttggc    7740
atatgataca cttgatgtac tgccaagtgg gcagtttacc gtaaatactc cacccattga   7800
cgtcaatgga aagtccctat tggcgttact atgggaacat acgtcattat tgacgtcaat   7860
gggcggggt cgttgggcgg tcagccaggc gggccattta ccgtaagtta tgtaacgggc   7920
ctgctgccgg ctctgcggcc tcttccgcgt cttcgccttc gccctcagac gagtcggatc   7980
tccctttggg ccgcctcccc gcctgtctag cttgactgac tgagatacag cgtaccttca   8040
gctcacagac atgataagat acattgatga gtttggacaa accacaacta gaatgcagtg   8100
aaaaaaatgc tttatttgtg aaatttgtga tgctattgct ttatttgtaa ccattataag   8160
ctgcaataaa caagttaaca acaacaattg cattcatttt atgtttcagg ttcagggggga   8220
ggtgtgggag gttttttaaa gcaagtaaaa cctctacaaa tgtggtattg gcccatctct   8280
atcggtatcg tagcataacc ccttggggcc tctaaacggg tcttgagggg ttttttgtgc   8340
ccctcgggcc ggattgctat ctaccggcat ggcgcagaaa aaaatgcct gatgcgacgc   8400
tgcgcgtctt atactcccac atatgccaga ttcagcaacg gatacggtct ccccaacttg   8460
cccacttcca tacgtgtcct ccttaccaga aatttatcct taaggtcgtc agctatcctg   8520
caggcgatct ctcgatttcg atcaagacat tcctttaatg gtcttttctg gacaccacta   8580
ggggtcagaa gtagttcatc aaactttctt ccctccctaa tctcattggt taccttgggc   8640
tatcgaaact taattaagcg atctgcatct caattagtca gcaaccatag tcccgcccct   8700
aactccgccc atcccgcccc taactccgcc cagttccgcc cattctccgc cccatggctg   8760
actaattttt tttatttatg cagaggccga ggccgcctcg gcctctgagc tattccagaa   8820
gtagtgagga ggcttttttg gaggcctagg cttttgcaaa ggaggtagcc aacatgattg   8880
aacaagatgg attgcacgca ggttctcccg ccgcttgggt ggagaggcta ttcggctatg   8940
actgggcaca acagacaatc ggctgctctg atgccgccgt gttccggctg tcagcgcagg   9000
ggcgcccggt tctttttgtc aagaccgacc tgtccggtgc cctgaatgaa ctccaggacg   9060
aggcagcgcg gctatcgtgg ctggccacga cgggcgttcc ttgcgcagct gtgctcgacg   9120
ttgtcactga gcgggaagg gactggctgc tattgggcga agtgccgggg caggatctcc   9180
tgtcatctca ccttgctcct gccgagaaag tatccatcat ggctgatgca atgcggcggc   9240
tgcatacgct tgatccggct acctgcccat tcgaccacca agcgaaacat cgcatcgagc   9300
gagcacgtac tcggatggaa gccggtcttg tcgatcagga tgatctggac gaagagcatc   9360
aggggctcgc gccagccgaa ctgttcgcca ggctcaaggc gcggatgccc gacgggcgagg   9420
atctcgtcgt gacccacggc gatgcctgct tgccgaatat catggtggaa aatggccgct   9480
tttctggatt catcgactgt ggccggctgg gtgtggcgga ccgctatcag gacatagcgt   9540
tggctacccg tgatattgct gaagagcttg gcggcgaatg ggctgaccgc ttcctcgtgc   9600
tttacggtat cgccgctccc gattcgcagc gcatcgcctt ctatcgcctt cttgacgagt   9660
```

-continued

```
tcttctagta tgtaagccct gtgccttcta gttgccagcc atctgttgtt tgccctccc   9720
ccgtgccttc cttgaccctg gaaggtgcca ctcccactgt cctttcctaa taaaatgagg   9780
aaattgcatc gcattgtctg agtaggtgtc attctattct gggggtggg gtggggcagg    9840
acagcaaggg ggaggattgg gaagacaata gcaggcatgc tggggatgcg gtgggctcta   9900
tggttaatta accagtcaag tcagctactt ggcgagatcg acttgtctgg gtttcgacta   9960
cgctcagaat tgcgtcagtc aagttcgatc tggtccttgc tattgcaccc gttctccgat  10020
tacgagtttc atttaaatca tgtgagcaaa aggccagcaa aaggccagga accgtaaaaa  10080
ggccgcgttg ctggcgtttt tccataggct ccgcccccct gacgagcatc acaaaaatcg  10140
acgctcaagt cagaggtggc gaaacccgac aggactataa agataccagg cgtttccccc  10200
tggaagctcc ctcgtgcgct ctcctgttcc gaccctgccg cttaccggat acctgtccgc  10260
ctttctccct tcgggaagcg tggcgctttc tcatagctca cgctgtaggt atctcagttc  10320
ggtgtaggtc gttcgctcca agctgggctg tgtgcacgaa ccccccgttc agcccgaccg  10380
ctgcgcctta tccggtaact atcgtcttga gtccaacccg gtaagacacg acttatcgcc  10440
actggcagca gccactggta acaggattag cagagcgagg tatgtaggcg gtgctacaga  10500
gttcttgaag tggtggccta actacggcta cactagaaga acagtatttg gtatctgcgc  10560
tctgctgaag ccagttacct tcggaaaaag agttggtagc tcttgatccg gcaaacaaac  10620
caccgctggt agcggtggtt tttttgtttg caagcagcag attacgcgca gaaaaaaagg  10680
atctcaagaa gatcctttga tcttttctac ggggtctgac gctcagtgga acgaaaactc  10740
acgttaaggg attttggtca tgagattatc aaaaaggatc ttcacctaga tccttttaaa  10800
ttaaaaatga agttttaaat caatctaaag tatatatgag taaacttggt ctgacagtta  10860
ccaatgctta atcagtgagg cacctatctc agcgatctgt ctatttcgtt catccatagt  10920
tgcatttaaa tttccgaact ctccaaggcc tcgtcggaaa aatcttcaaa cctttcgtcc  10980
gatccatctt gcaggctacc tctcgaacga actatcgcaa gtctcttggc cggccttgcg  11040
ccttggctat tgcttggcag cgcctatcgc caggtattac tccaatcccg aatatccgag  11100
atcgggatca cccgagagaa gttcaaccta catcctcaat cccgatctat ccgagatccg  11160
aggaatatcg aaatcggggc gcgcctggtg taccgagaac gatcctctca gtgcgagtct  11220
cgacgatcca tatcgttgct tggcagtcag ccagtcggaa tccagcttgg gacccaggaa  11280
gtccaatcgt cagatattgt actcaagcct ggtcacggca gcgtaccgat ctgtttaaac  11340
ctagatattg atagtctgat cggtcaacgt ataatcgagt cctagctttt gcaaacatct  11400
atcaagagac aggatcagca ggaggctttc gcatgagtat tcaacatttc cgtgtcgccc  11460
ttattccctt ttttgcggca ttttgccttc ctgtttttgc tcacccagaa acgctggtga  11520
aagtaaaaga tgctgaagat cagttgggtg cgcgagtggg ttacatcgaa ctggatctca  11580
acagcggtaa gatccttgag agttttcgcc ccgaagaacg ctttccaatg atgagcactt  11640
ttaaagttct gctatgtggc gcggtattat cccgtattga cgccgggcaa gagcaactcg  11700
gtcgccgcat acactattct cagaatgact tggttgagta ttcaccagtc acagaaaagc  11760
atcttacgga tggcatgaca gtaagagaat tatgcagtgc tgccataacc atgagtgata  11820
acactgcggc caacttactt ctgacaacga ttggaggacc gaaggagcta accgcttttt  11880
tgcacaacat gggggatcat gtaactcgcc ttgatcgttg ggaaccggag ctgaatgaag  11940
ccatcccaaa cgacgagcgt gacaccacga tgcctgtagc aatggcaaca acgttgcgta  12000
aactattaac tggcgaacta cttactctag cttcccggca acagttgata gactggatgg  12060
aggcggataa agttgcagga ccacttctgc gctcggccct tccggctggc tggtttattg  12120
ctgataaatc tggagccggt gagcgtgggt ctcgcggtat cattgcagca ctggggccag  12180
atggtaagcc ctcccgtatc gtagttatct acacgacggg gagtcaggca actatggatg  12240
aacgaaatag acagatcgct gagataggtg cctcactgat taagcattgg taaccgattc  12300
taggtgcatt ggcgcagaaa aaaatgcctg atgcgacgct gcgcgtctta tactcccaca  12360
tatgccagat tcagcaacgg atacggcttc cccaacttgc ccacttccat acgtgtcctc  12420
cttaccagaa atttatcctt aagatcgttt aaactgctgg ctggcacgga cgaatctccg  12480
tcgtttcgag cttacgcgaa cagccgtggc gctcatttgc tcgtcgggca tcgaatctcg  12540
tcagctatcg tcagcttacc tttttggcag cgatcgcggc tcccgacatc ttggaccatt  12600
agctccacg gtatcttctt ccctctagtg tcataacag cagcttcagc tacctctcaa  12660
ttcaaaaaac ccctcaagac ccgtttagag gccccaaggg gttatgctat caatcgttgc  12720
gttacacaca caaaaaacca acacacatcc atcttcgatg gatagcgatt ttattatcta  12780
actgctgatc gagtgtagcc agatctagta atcaattacg gggtcattag ttcatagccc  12840
atatatggag ttccgcgtta cataacttac ggtaaatggc ccgcctggct gaccgcccaa  12900
cgacccccgc ccattgacgt caataatgac gtatgttccc atagtaacgc caatagggac  12960
tttccattga cgtcaatggg tggagtattt acggtaaact gcccacttgg cagtacatca  13020
agtgtatcat atgccaagta cgccccctat tgacgtcaat gacggtaaat ggcccgcctg  13080
gcattatgcc cagtacatga ccttatggga ctttcctact tggcagtaca tctacgtatt  13140
agtcatcgct attaccatgc tgatgcggtt ttggcagtac atcaatgggc gtggatagcg  13200
gtttgactca cggggatttc caagtctcca ccccattgac gtcaatggga gtttgttttg  13260
gcaccaaaat caacgggact ttccaaaatg tcgtaacaac tccgccccat tgacgcaaat  13320
gggcggtagg cgtgtacggt gggaggtcta tataagcaga gctggtttag tgaaccgtca  13380
gatcagatct ttgtcgatcc taccatccac tcgacacacc cgccagcggc cgc          13433
```

```
SEQ ID NO: 49         moltype = DNA   length = 9241
FEATURE               Location/Qualifiers
misc_feature         1..9241
                     note = Description of Artificial Sequence: Synthetic
                      polynucleotide
source               1..9241
                     mol_type = other DNA
                     organism = synthetic construct
SEQUENCE: 49
taatacgact cactataggg agaagtactg ccaccatggg caagaagcaa aatcgcaaga   60
cggggaattc caagacacaa tccgctagcc caccacctaa agagcgttct agctcccctg   120
ctactgagca gtcctggatg gaaaacgact tcgatgaact ccgggaagag ggatttaggc   180
gatccaacta ttcagaactc cgcgaagata tccagacaaa ggggaaggaa gtcgagaatt   240
tcgagaagaa cctcgaggag tgcatcaccc gtatcacaaa cactgagaaa tgtctcaaag   300
aactcatgga acttaagaca aaagccaggg agcttcgaga ggagtgtcgg agtctgagat   360
```

-continued

```
ccaggtgtga ccagctcgag gagcgcgtga gcgcgatgga agacgagatg aacgagatga    420
aaagagaggg caaattcagg gagaagcgca ttaagaggaa cgaacagagt ctgcaggaga    480
tttgggatta cgtcaagagg cctaacctgc ggttgatcgg cgtcccccgag agcgacgtag    540
aaaacgggac taaactggag aatacacttc aagacatcat tcaagaaaat tttccaaacc    600
tggctcggca agctaatgtg caaatccaag agatccaacg cacacccag cggtatagct    660
ctcggcgtgc caccctagg catattatcg tgcgctttac taaggtggag atgaaagaga    720
agatgctgcg agccgctcgg gaaaagggaa gggtgacttt gaaggggcaaa cctattcggc    780
tgacggttga ccttagcgcc gagacactcc aggcacgccg ggaatggggc cccatcttta    840
atatcctgaa ggagaagaac ttccagccac gaatctctta ccctgcaaag ttgagttta    900
tctccgaggg tgagattaag tatttcatcg ataaacagat gctgcgagac ttcgtgacaa    960
ctcgcccagc tctcaaggaa ctgctcaaag aggctcttaa tatggagcgc aataatagat   1020
atcaaccctt gcagaaccac gcaaagatgt gagacagccg tcagaccatc aagactagga   1080
agaaactgca tcaactaatg agcaaaatca ccagctaaca tcatagtata catgaccggc   1140
tctaactcac atatcaccat ccttacactt aacattaacg gcctcaactc agctatcaag   1200
cgccatcggc tggccagctg gatcaaatca caggatccaa gcgtttgttg catccaagag   1260
acccacctga cctgtagaga tactcaccgc ctcaagatca agggatggcg aaaagatttat   1320
caggcgaacg gtaagcagaa gaaagccgga gtcgcaattc tggtctcaga caagacggat   1380
ttcaagccca ccaaaattaa gcgtgataag gaaggtcact atattatggt gaaaggcagc   1440
atacagcagg aagaacttac catattgaac atctacgcgc caaacaccgg cgcacctcgc   1500
tttatcaaac aggtcctgtc cgatctgcag cgagatctgg attctcatac gttgattatg   1560
ggtgatttca atacaccatt gagcaccctg gatcgcagca ccaggcaaaa ggtaaataaa   1620
gacacgcaag agctcaatag cgcactgcat caggcagatc tcattgatat ttatcgcact   1680
cttcatccta agagtaccga gtacacattc ttcagcgccc cacatcatac atactcaaag   1740
atcgatcata tcgtcggctc aaaggctctg ctgtcaaagt gcaagcgcac agagataatt   1800
acaaattacc tgtcagatca tagcgcgatc aagctcgagc tgagaatcaa gaacctgacc   1860
cagagccgga gtaccacttg gaagcttaat aacctgctgc tcaacgatta ttgggtccaa   1920
aatgagatga aggcagagat taaaatgttc ttcgaaacaa atgagaataa ggatactacc   1980
tatcaaaacc tttgggatgc ctttaaggcc gtctgcagag gcaagttcat cgccctcaac   2040
gcctataaaa gaaaacaaga gagatctaag atcgatactc tcacctctca gctgaaggag   2100
ttggagaaac aggaacagac ccactccaag gcgtcaagac ggcaggagat cacaaagatt   2160
cgcgccgagt tgaaagagat cgaaacccaa aagactcttc agaaaattaa cgagtctcgt   2220
agttggttct tcgagcggat taataagata gacagacctc tggcacgact gattaagaag   2280
aagcgcgaaa agaaccagat tgataccatc aagaacgaca agggcgacat cactactgac   2340
ccgaccgaga tccagaccac tattcgggag tattataagc atttgtatgc taacaagcat   2400
gagaacctgg aagagatgga cactttctg gatacctata ctctgccacg gcttaatcaa   2460
gaggaagtcg agtccctcaa ccgcccaatt acaggaagcg agattgtggc cataattaac   2520
tccctgccga caaagaaatc tcctggtccg gacgggttta cagctgagtt ttatcaacgg   2580
tatatggaag agcttgtacc gtttctgctc aagctctttc agtctataga aaaggaaggc   2640
atcttgccca attccttcta cgaagcttct ataatactta ttcccaaacc aggacgcgat   2700
accacaaaga aggaaaactt ccggcccatt agtctcatga atatcgacgc taaaatattg   2760
aacaagattc tcgccaacag aatccaacaa catattaaga aattgataca tcacgaccag   2820
gtgggggttta tacctggcat gcagggctgg tttaacatcc ggaagagtat taacgtcatt   2880
caacacatta atagagctaa ggataagaat catatgatca tctctataga cgcggaaaag   2940
gcattcgata agattcagca gccatttatg ctcaagactc tgaacaaact cggcatcgac   3000
ggaacatatt ttaagattat tcgcgcaatt tacgataagc cgactgctaa cattatcctt   3060
aacggccaaa agctcgaggc ctttccgctc aagactggaa cccgccaagg ctgtcccctc   3120
tccccgcttt tgtttaatat tgtactcgag gtgctggcta gggctattcg tcaagagaaa   3180
gagattaaag ggatacagct cgggaaggaa gaggtcaagc tttccttgtt cgccgatgat   3240
atgattgtgt acctggagaa tcctattgtg tctgctcaga accttcttaa acttatttct   3300
aactttagca aggtcagcgg ctataagatt aacgtccaga aatctcaggc ctttctgtac   3360
acaaataatc gacagaccga atcccagata atgggtaagc ttccgtttgt catagccagt   3420
aaaaggataa agtatctcgg aatccagctg acacgagacg ttaaagattt gtttaaggaa   3480
aattacaagc ctctcctgaa agagattaag gaagatacta ataagtggaa gaatatcccc   3540
tgttcatggg ttggcagaat caacatagtg aagatggcaa tacttcctaa agtgatatat   3600
cgcttttacg ccatcccaat taaactgcct atgaccttct ttacggagct cgagaaaaca   3660
acccttaaat ttatatggaa tcaaaagaga gcaagaatag cgaagtccat cttgagccag   3720
aagaataagg ccggtgggat tactttgcct gattttaagt tgtattataa agccacagta   3780
actaagacag cctggtattg gtatcagaat agagacatcg accagtggaa tcggaccgaa   3840
ccatcagaga taatgcccca catctataat taccttatat tcgataagcc agaaaagaat   3900
aaacagtggg gcaaagacag cctcttcaac aagtggtgtt gggagaattg gctggccata   3960
tgccggaaac tcaagctcga cccctttctt acaccctaca ctaaaatcaa cagtaggtgg   4020
atcaaggact tgaatgtcaa gccaaagact ataaagacac tggaagagaa tcttgggatc   4080
acaatacaag atataggcgt cggcaaagat tttatgtcaa agacgcccaa ggccatggcc   4140
actaaggata agattgataa gtgggacctt attaagctca aagcttctg tactgccaag   4200
gagaccacga tcagagttaa taggcagccc actacatggg aaaagatttt cgccacttat   4260
tcatcagata aggggttgat aagcagaata tataacgagc tgaagcagat ctacaagaag   4320
aaaacgaata atcccatcaa gaagtgggca aaagatatga caggcattt tagcaaagag   4380
gatatctacg ccgcgaagaa gcatatgaag aagtgtagt caagcttggc cattcgtgag   4440
atgcagatta agacgaccat gcgataccac cttacccag tgaggatggc aattatcaag   4500
aaatctggca ataatagatg ttggcgggc tgtggcgaga ttggcaccct gctccattgc   4560
tggtgggatt gcaagctggt gcagccgctt tggaaatcag tctggcgctt tctgagggac   4620
ctcgagcttg agattccctt cgatcccgca attcccttgc tcggaatcta tcctaacgaa   4680
tacaagagct gttgttacaa ggatacgtgt acccggatgt tcatcgcggc cttgtttacg   4740
atagctaaga cgtggaatca gcctaagtgc cccacaatga tcgattggat caagaaaatg   4800
tggcatattt ataccatgga gtattacgca gcaattaaga atgacgaatt tatttccttc   4860
gttgggacct ggatgaagct ggagactatt attctgagca agctgtctca ggagcaaaag   4920
acaaagcata gaatcttctc tctcattggt ggtaacgctt ctaactttac tcagttcgtt   4980
ctcgtcgaca atggcggaac tggcgacgtg actgtcgcc caagcaactt cgctaacggg   5040
atcgctgaat ggatcagctc taactcgcgt tcacaggctt acaaagtaac ctgtagcgtt   5100
```

```
cgtcagagct ctgcgcagaa tcgcaaatac accatcaaag tcgaggtgcc taaaggcgcc   5160
tggcgttcgt acttaaatat ggaactaacc attccatttt tcgccacgaa ttccgactgc   5220
gagcttattg ttaaggcaat gcaaggtctc ctaaaagatg gaaacccgat tccctcagca   5280
atcgcagcaa actccggcat ctacgccatg gccagcaact tcacccagtt cgtgctggtg   5340
gacaacggcg gcaccggcga cgtgaccgtg gcccccaaga acttcgccaa cggcatcgcc   5400
gagtggatca gcagcaacag cagaagccag gcctacaagg tgacctgcag cgtgagacag   5460
agcagcgccc agaacagaaa gtacaccatc aaggtggagg tgcccaaggg cgcctggaga   5520
agctacctga acatggagct gaccatcccc atcttcgcca ccaacagcga ctgcgagctg   5580
atcgtgaagg ccatgcaggg cctgctgaag gacggcaacc ccatccccag cgccatcgcc   5640
gccaacagcg gcatctacga ctacaaagac gatgacgaca agtaaagcaa cctacaaacg   5700
ggtggaggat caccccaccc gacacttcac aatcaagggg tacaatacac aagggtggag   5760
gaacacccca ccctccagac acattacaca gaaatccaat caaacagaag caccatcagg   5820
gcttctgcta ccaaatttat ctcaaaaaac tacaacaagg aatcaccatc agggattccc   5880
tgtgcaatat acgtcaaacg agggccacga cgggaggacg atcacgcctc ccgaatatcg   5940
gcatgtctgg ctttcgaatt cagtgcgtgg agcatcagcc cacgcagcca atcagagtcg   6000
aatacaagtc gactttcgcg aagagcatca gccttcgcgc cattcttaca caaaccacac   6060
tctcccctac aggaacagca tcagcgttcc tgcccagtac ccaactcaag aaaatttatg   6120
tccccatgca gcatcagcgc atgggcccca agaatacatc cccaacaaaa tcacatccga   6180
gcaccaacag ggctcggagt gttgtttctt gtccaactgg acaaaccctc catggaccat   6240
caggccatgg actctcacca acaagacaaa aactactctt ctcgaagcag catcagcgct   6300
tcgaaacact cgagcataca ttgtgcctat ttcttgggtg gacgatcacg ccacccatgc   6360
tctcacgaat ttcaaaacac ggacaaggac gagcaccacc agggctcgtc gttccacgtc   6420
caatacgatt acttaccttt cgggatcacg atcacggatc ccgcagctac atcacttcca   6480
ctcaggacat tcaagcatgc acgatcacgg catgctccac aagtctcaac cacagaaact   6540
accaaatggg ttcagcacca gcgaacccac tcctacctca aacctcttcc cacaaaaactg   6600
gcaagcagga tcaccgcttg cccattccaa cataccaagt caaaaacaat tactggtaca   6660
gcatcagcgt accagcccac atctctcact actatcaaaa accaaaccgt tcagcaacag   6720
cgaacggtac acacggaaaa atcaactggt ttacaaatac gaaagacgat cacgctttcg   6780
tccagcgcaa actattacga aaaacatccg acgggaagag caacagcctt cccgcggcgg   6840
aaaacctcac aaaaacacga caaacggatg cacgaacacg gcatccgccg acaacccaca   6900
aacttacaac caggcaaacg gtgcaggatc accgcaccgt acatcaaaca cctcagatct   6960
catgcttcta gaagttgtct cctcctgcac tgactgactg atacaatcga tttctggatc   7020
cgcaggccta atcaacctct ggattacaaa atttgtgaaa gattgactgg tattcttaac   7080
tatgttgctc cttttacgct atgtggatac gctgctttaa tgcctttgta tcatgctatt   7140
gcttccgta  tggctttcat tttctcctcc ttgtataaat cctggttgct gtctctttat   7200
gaggagttgt ggcccgttgt caggcaacgt ggcgtggtgt gcactgtgtt tgctgacgca   7260
acccccactg gttggggcat tgccaccacc tgtcagctcc tttccgggac tttcgctttc   7320
ccctcccta  ttgccacggc ggaactcatc gccgcctgcc ttgcccgctg ctggacaggg   7380
gctcggctgt tgggcactga caattccgtg gtgttgttcac ggaagctgac gtcctttcca   7440
tggctgctcg cctgtgttgc cacctggatt ctgcgcggga cgtccttctg ctacgtccct   7500
tcggccctca atccagcgga ccttccttcc cgctgagaga cacaaaaaat tccaacacac   7560
tattgcaatg aaaataaatt tcctttatta gccagaagtc agatgctcaa ggggcttcat   7620
gatgtcccca taattttttgg cagagggaaa aagatctcag tggtatttgt gagccaggcc   7680
attggccttc tgataggcag cctgcacctg aggagtgcgg ccgctttact tgtacagctc   7740
gtccatgccg agagtgatcc cggcggcggt cacgaactcc agcaggacca tgtgatcgcg   7800
cttctcgttg gggtctttgc tcaggcggga ctgggtgctc aggtagtggt tgtcgggcag   7860
cagcacggga ccgtcgccga tggggggtgtt ctgctggtag tggtcggcga gctgcacgct   7920
gccgtcctcg atgttgtggc ggatcttgaa gttcaccttg atgccgttct tctgcttgtc   7980
ggccatgata tagacgttgt ggctgttgta gttgtactcc agcttgtgcc ccaggatgtt   8040
gccgtcctcc ttgaagtcga tgcccttcag ctcgatgcgg ttcaccaggg tgtcgccctc   8100
gaacttcacc tcggcgcggg tcttgtagtt gccgtcgtcc ttgaagaaga tggtgcgctc   8160
ctggacgtag ccttcgggca tggcggactt gaagaagtcg tgctgcttca tgtggtcggg   8220
gtagcggctg aagcactgca cgccgtaggt caggtggtc  acgagggtgg gccagggcac   8280
gggcagcttg ccggtggtgc agatgaactt cagggtcagc ttgccgtagg tggcatcgcg   8340
ctcgccccg  ccggacacgc tgaacttgtg gccgtttacg tcgccgtcca gctcgaccag   8400
gatgggcacc accccggtga acagctcctc gcccttgctc accatggtgg cgggatctga   8460
cggttcacta aaccagctct gcttatatag acctcccacc gtacacgcct accgcccatt   8520
tgcgtcaatg gggcggagtt gttacgacat tttggaaagt cccgttgatt ttggtgccaa   8580
aacaaactcc cattgacgtc aatgggtgg  agacttggaa atccccgtga gtcaaaccgc   8640
tatccacgcc cattgatgta ctgccaaaac cgcatcacca tggtaatagc gatgactaat   8700
acgtagatgt actgccaagt aggaaagtcc cataaggtca tgtactgggc ataatgccaa   8760
gcgggccatt taccgtcatt gacgtcaata ggggggcgtac ttggcatatg atacacttga   8820
tgtactgcca agtgggcagt ttaccgtaaa tactccaccc attgacgtca atggaaagtc   8880
cctattggcg ttactatggg aacatacgtc attattgacg tcaatgggcg ggggtcgttg   8940
ggcggtcagc caggcgggcc atttaccgta agttatgtaa cgggcctgct gccggctctg   9000
cggcctcttc cgcgtcttcg ccttcgccct cagacgagtc ggatctccct ttgggccgcc   9060
tccccgcctg tctagcttga ctgactgaga tacacgcgtac cttcagctca cagacatgat   9120
aagatacatt gatgagtttg gacaaaccac aactagaatg cagtgaaaaa aatgctttat   9180
ttgtgaaatt tgtgatgcta ttgctttatt tgtaaccatt ataagctgca ataaacaagt   9240
t                                                                    9241
```

SEQ ID NO: 50           moltype = DNA   length = 7309
FEATURE              Location/Qualifiers
misc_feature        1..7309
                        note = Description of Artificial Sequence: Synthetic
                        polynucleotide
source                1..7309
                        mol_type = other DNA
                        organism = synthetic construct -continued

```
SEQUENCE: 50
taatacgact cactatagggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagagaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc caccccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatctta  840
atatcctgaa ggagaagaac ttccagccac gaatctctta ccctgcaaag ttgagttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaacccctt gcagaaccac gcaaagatgt gagacagccg tcagaccatc aagactagga  1080
agaaactgca tcaactaatg agcaaaatca ccagctaaca tcatagtata catggtcata  1140
ggaacttaca tttcgattat taccttaaac gtgaatgggt taaatgcccc aaccaagaga  1200
catcggctgg ctgaatggat tcagaaacag gacccctata tttgctgtct gcaggagacc  1260
cacttccgtc ctcgcgacac atacagactg aaagtgaggg gctggaaaaa gatcttccat  1320
gccaatggaa atcaaaagaa agctggagtg gctattctca tctcagataa aattgacttc  1380
aaaataaaga atgttactcg agataaggag ggacactaca taatgatcca ggggtccatc  1440
caagaagagg atataacatat tattaatatt tatgcaccca acattggcgc ccctcagtac  1500
atcaggcagc tgcttacagc tatcaaggag gaaatcgaca gtaacacgat tatcgtgggg  1560
gactttaaca ccagccttac tccgatggat agatcatcca aaatgaaaat aaataaggaa  1620
acagaggctc ttaatgacac cattgaccag atagatctga ttgatatata taggacattc  1680
catccaaaaa ctgccgatta cactttcttc agcagtgcgc atggaacctt ctccaggata  1740
gatcacatct tgggtcacaa aagtagcctc agtaagttta agaaaattga aatcattagc  1800
agcatctttt ctgaccataa cgctatgcgc ctggagatga atcacaggga gaagaacgta  1860
aagaagacaa acacctggag gctgaacaat acgctgctaa ataaccaaga gatcactgag  1920
gaaatcaaac aggaaataaa aaaatacttg gagacaaatg acaatgaaaa cacgacaccc  1980
cagaacttgt gggatgcagc taaagcggtt ctgagaggga agtttatagc tattcaagcc  2040
taccttaaga aacaggaaaa atctcaagtg aacaatttga ccttacacct aaagaaactg  2100
gagaaggagg agcagaccaa acccaaagtg agcaggagga agaaatcat caagatcaga  2160
gccgaaatca atgaaataga aactaagaag acaattgcca agatcaataa aactaaatcc  2220
tggttctttg agaagatcaa caaaattgat aagccattag ccagactcat caagaaaaag  2280
agggagagga ctcagatcaa taagatcaga aatgagaaag gggaagttac aaccgacacc  2340
gcggagattc agaacatcct gagagactac tacaagcaac tttatgccaa taaaatggac  2400
aacctggaag aaatggacaa attcctggaa aggtataacc ttccccggct gaaccaggag  2460
gagactgaaa atatcaaccg cccaatcaca agtaatgaga ttgagactgt gattaagaat  2520
cttccaacta acaaaagtcc cggccccgat ggcttcacag gtgaattcta tcagaccttt  2580
cgggaggagt tgacacccat ccttctcaag ctcttccaaa aaattgcaga ggagggcaca  2640
ctcccgaact cattctatga ggccaccatc accctgatcc caaagcccga caaggacact  2700
acaaagaaag aaaattaccg accaatttcc ctgatgaata tcgatgccaa gatcctcaac  2760
aaaatcttgg caaacagaat ccagcagcac attaagagga tcatacacca cgatcaggtg  2820
ggctttatcc cggggatgca aggattcttc aatatccgca aatcaatcaa tgtgatccac  2880
catattaaca agttgaagaa gaagaaccat atgatcatct ccatcgatgc agagaaagct  2940
tttgacaaaa ttcaacaccc atttatgatc aaaactctcc agaaggtggg catcgagggg  3000
acctacctca acataattaa ggccatctat gataagccca cagccaacat cattctcaat  3060
ggtgaaaagc tgaaggcatt tcctctgcgg tccggaacga gacagggatg tcctctctct  3120
cctcttctgt tcaacatcgt tctggaagtc ctagccaccg ctatccgcga ggaaaaggaa  3180
attaaaggca tacagattgg aaaggaagag gtaaaactgt ctctgtttgc ggatgatatg  3240
atactgtaca tagagaatcc taaaactgcc acccggaacg ctgttggagct aattaatgag  3300
tatggtaagg tcgccggtta caagattaat gctcagaagt ctcttgcttt cctgtacact  3360
aatgatgaaa agtctgaacg ggaaattatg gagacactcc cctttaccat tgcaaccaaa  3420
cgtattaaat accttggcat taacctgcct aaggagacaa aagacctgta tgctgaaaac  3480
tataagacac tgatgaaaga gattaaagat gataccaacc ggtggcggga tatcccatgt  3540
tcttggattg gcagaatcaa cattgtgaag atgagcatcc tgcccaaggc catctacaga  3600
ttcaatgcca tccctatcaa attacctatg gcattttta cggagctgga acagatcatc  3660
ttaaaatttg tgtggcgcca caagcggccc cgaatcgcca aagcggtctt gaggcagaag  3720
aatggcgtg ggggaatccg actccctgac ttcagattgt actacaaagc taccgtcatc  3780
aagacaatct ggtactggca caagaacaga aacatcgatc agtggaacaa gatcgaaagc  3840
cctgagatta accccgcac ctatggtcaa ctgatctatg acaaaggggg caaggatata  3900
caatggcgca aggacagcct cttcaataag tggtgctggg aaaactggac agccacctgc  3960
aagcgtatga agctggagta ctccctgaca ccatacacaa aaataaactc aaagtggatt  4020
cgagacctca atattcggct ggacactata aaactcctgg aggagaacat tgggcgtaca  4080
ctctttgaca ttaatcatag caagatcttt ttcgatcccc ctcctcgtgt aatggaaata  4140
aaaacaaaaa taaacaagtg ggatctgatg aaacttcaga gcttttgcac cgcaaaggag  4200
accataaaca agacgaagcg ccaaccctca gaatgggaga aaaatatttgc gaatgagtct  4260
acggacaaag gcttaatctc caaaatatat aagcagctca ttcagctcaa tatcaaggaa  4320
acaaacaccc cgatccaaaa gtgggcagag gacctaaatc ggcatttctc caaggaagac  4380
atccagacgc ccacgaagca catgaagcga tgctcaactt ccctgattat tcgcgaaatg  4440
cagatcaaga ctactatgcg ctatcacctc actcctgttc ggatgggcat catccggaaa  4500
tctacaaaca acaagtgctg gagagggtgt ggcgaaaagg gaaccctctt gcattgttgg  4560
tgggagtgta agttgatcca gccactatgg cggaccatat ggaggttcct taaaaaaactg  4620
aagattgagc tgccatatga cccagcaatc ccactgctgg gcatataccc ggagaaaacc  4680
```

-continued

```
gtgattcaga aagacacttg cacccgaatg ttcattgcag cattgtttac aatagccagg    4740
tcatggaagc agcctaagtg cccctcgaca gacgagtgga tcaagaagat gtggtacatt    4800
tatactatgg aatattacag cgccatcaaa cgcaacgaaa ttgggtcttt tctggagacg    4860
tggatggatc tagagactgt catccagagt gaggtaagtc agaaagagaa gaacaaatat    4920
cgtattttaa cgcatatttg tggaacctgg aagaatgata cagatgagcc ggtctgccga    4980
accgagattg agacccagat ggactacaaa gacgatgacg acaagtgaag cgcttctaga    5040
agttgtctcc tcctgcactg actgactgat acaatcgatt tctggatccg caggcctaat    5100
caacctctgg attacaaaat ttgtgaaaga ttgactggta ttcttaacta tgttgctcct    5160
tttacgctat gtggatacgc tgctttaatg cctttgtatc atgctattgc ttcccgtatg    5220
gctttcattt tctcctcctt gtataaatcc tggttgctgt ctctttatga ggagttgtgg    5280
cccgttgtca ggcaacgtgg cgtggtgtgc actgtgtttg ctgacgcaac ccccactggt    5340
tggggcattg ccaccacctg tcagctcctt tccgggactt tcgctttccc cctccctatt    5400
gccacggcgg aactcatcgc cgcctgcctt gcccgctgct ggacagggggc tcggctgttg    5460
ggcactgaca attccgtggt gttgtcgggg aagctgacgt cctttccatg gctgctcgcc    5520
tgtgttgcca cctggattct gcgcggggacg tccttctgct acgtcccttc ggccctcaat    5580
ccagcggacc ttccttcccg ctgagagaca caaaaaattc caacacacta ttgcaatgaa    5640
aataaatttc ctttattagc cagaagtcag atgctcaagg ggcttcatga tgtccccata    5700
atttttggca gagggaaaaa gatctcagtg gtatttgtga gccagggcat tggccttctg    5760
ataggcagcc tgcacctgag gagtgcggcc gctttacttg tacagctcgt ccatgccgag    5820
agtgatcccg gcggcggtca cgaactccac caggaccatg tgatcgcgct tctcgttggg    5880
gtctttgctc agggcggact gggtgctcag gtagtggttc tcgggcagca gcacggggggc    5940
gtcgccgatg ggggtgttct gctggtagtg tcggccgagc tgcacgctgc cgtcctcgat    6000
gttgtggcgg atcttgaagt tcaccttgat gccgttcttc tgcttgtcgg ccatgatata    6060
gacgttgtgg ctgttgtagt tgtactccag cttgtgcccc aggatgttgc cgtcctcctt    6120
gaagtcgatg cccttcagct cgatgcggtt caccagggtg tcgccctcga acttcacctc    6180
ggcgcgggtc ttgtagttgc cgtcgtcctt gaagaagatg gtgcgctcct ggacgtagcc    6240
ttcgggcatg gcggacttga agaagtcgtg ctgcttcatg tggtcggggt agcggctgaa    6300
gcactgcacg ccgtaggtca gggtggtcac gagggtgggc cagggcacgg gcagcttgcc    6360
ggtggtgcag atgaacttca gggtcagctt gccgtaggtg gcatcgccct cgccctcgcc    6420
ggacacgctg aacttgtggc cgtttacgtc gccgtccagc tcgaccagga tgggcaccac    6480
cccggtgaac agctcctcgc ccttgctcac catggtggcg ggatctgacg gttcactaaa    6540
ccagctctgc ttatatagac ctcccaccgt acacgcctac cgcccatttg cgtcaatggg    6600
gcggagttgt tacgacattt tggaaagtcc cgttgatttt ggtgccaaaa caaactccca    6660
ttgacgtcaa tggggtggag acttggaaat ccccgtgagt caaaccgcta tccacgccca    6720
ttgatgtact gccaaaaccg catcaccatg gtaatagcga tgactaatac gtagatgtac    6780
tgccaagtag gaaagtccca taaggtcatg tactgggcat aatgccaggc gggccattta    6840
ccgtcattga cgtcaatagg gggcgtactt ggcatatgat acacttgatg tactgccaag    6900
tgggcagttt accgtaaata ctccacccat tgacgtcaat ggaaagtccc tattggcgtt    6960
actatggtca ttattgacgtc aatgggcggg ggtcgttggg ggtcagcca    7020
ggcgggccat ttaccgtaag ttatgtaacg ggcctgctgc cggctctgcg gcctcttccg    7080
cgtcttcgcc ttcgccctca gacgagtcgg atctcccttt gggccgcctc cccgcctgtc    7140
tagcttgact gactgagata cagcgtacct tcagctcaca gacatgataa gatacattga    7200
tgagtttgga caaaccacaa ctagaatgca gtgaaaaaaa tgctttattt gtgaaatttg    7260
tgatgctatt gctttatttg taaccattat aagctgcaat aaacaagtt    7309
```

```
SEQ ID NO: 51              moltype = DNA   length = 19
FEATURE                    Location/Qualifiers
C_region                   1..19
source                     1..19
                           mol_type = other DNA
                           organism = synthetic construct
SEQUENCE: 51
agatgtgtat aagagacag                                                  19

SEQ ID NO: 52              moltype = DNA   length = 19
FEATURE                    Location/Qualifiers
misc_feature               1..19
                           note = Description of Unknown: transposon end sequence
source                     1..19
                           mol_type = other DNA
                           organism = synthetic construct
SEQUENCE: 52
ctgtctctta tacacatct                                                  19

SEQ ID NO: 53              moltype = AA   length = 338
FEATURE                    Location/Qualifiers
REGION                     1..338
                           note = Description of Artificial Sequence: Synthetic
                            polypeptide
source                     1..338
                           mol_type = protein
                           organism = synthetic construct
SEQUENCE: 53
MGKKQNRKTG NSKTQSASPP PKERSSSPAT EQSWMENDFD ELREEGFRRS NYSELREDIQ     60
TKGKEVENFE KNLEECITRI TNTEKCLKEL MELKTKAREL REECRSLRSR CDQLEERVSA    120
MEDEMNEMKR EGKFREKRIK RNEQSLQEIW DYVKRPNLRL IGVPESDVEN GTKLENTLQD    180
IIQENFPNLA RQANVQIQEI QRTPQRYSSR RATPRHIIVR FTKVEMKEKM LRAAREKGRV    240
TLKGKPIRLT VDLSAETLQA RREWGPIFNI LKEKNFQPRI SYPAKLSFIS EGEIKYFIDK    300
QMLRDFVTTR PALKELLKEA LNMERNNRYQ PLQNHAKM                            338
```

```
SEQ ID NO: 54             moltype = DNA  length = 1017
FEATURE                   Location/Qualifiers
misc_feature              1..1017
                          note = Description of Artificial Sequence: Synthetic
                          polynucleotide
source                    1..1017
                          mol_type = other DNA
                          organism = synthetic construct
SEQUENCE: 54
atgggcaaga agcaaaatcg caagacgggg aattccaaga cacaatccgc tagcccacca   60
cctaaagagc gttctagctc ccctgctact gagcagtcct ggatggaaaa cgacttcgat  120
gaactccggg aagagggatt taggcgatcc aactattcag aactccgcga agatatccag  180
acaaagggga aggaagtcga gaatttcgag aagaacctcg aggagtgcat cacccgtatc  240
acaaacactg agaaatgtct caaagaactc atggaactta agacaaaagc caggggagctt  300
cgagaggagt gtcggagtct gagatccagg tgtgaccagc tcgaggagcg cgtgagcgcg  360
atggaagacg agatgaacga gatgaaaaga gagggcaaat tcagggagaa gcgcattaag  420
aggaacgaac agagtctgca ggagatttgg gattacgtca gaggcctaa cctgcgggtg  480
atcggcgtcc ccgagagcga cgtagaaaac gggactaaac tggagaatac acttcaagac  540
atcattcaag aaaatttccc aaacctggct cggcaagcta atgtgcaaat ccaagagatc  600
caacgcacac cccagcggta tagctctcgg cgtgccaccc ctaggcatat tatcgtgcgc  660
tttactaagg tggagatgaa agagaagatg ctgcgagccg gcggggaaaa gggaagggtg  720
actttgaagg gcaaacctat tcggctgacg gttgaccta gcgccgagac actccaggca  780
cgccgggaat ggggcccat ctttaatatc ctgaaggaga agaacttcca gccacgaatc  840
tcttaccctg caaagttgag ttttatctcc gagggtgaga ttaagtattt catcgataaa  900
cagatgctgc gagacttcgt gacaactcgc ccagctctca aggaactgct caaagaggct  960
cttaatatgg agcgcaataa tagatatcaa cccttgcaga accacgcaaa gatgtga     1017

SEQ ID NO: 55             moltype = AA  length = 1275
FEATURE                   Location/Qualifiers
REGION                    1..1275
                          note = Description of Artificial Sequence: Synthetic
                          polypeptide
source                    1..1275
                          mol_type = protein
                          organism = synthetic construct
SEQUENCE: 55
MTGSNSHITI LTLNINGLNS AIKRHRLASW IKSQDPSVCC IQETHLTCRD THRLKIKGWR   60
KIYQANGKQK KAGVAILVSD KTDFKPTKIK RDKEGHYIMV KGSIQQEELT ILNIYAPNTG  120
APRFIKQVLS DLQRDLDSHT LIMGDFNTPL STLDRSTRQK VNKDTQELNS ALHQADLIDI  180
YRTLHPKSTE YTFFSAPHHT YSKIDHIVGS KALLSKCKRT EIITNYLSDH SAIKLELRIK  240
NLTQSRSTTW KLNNLLLNDY WVHNEMKAEI KMFFETNENK DTTYQNLWDA FKAVCRGKFI  300
ALNAYKRKQE RSKIDTLTSQ LKELEKQEQT HSKASRRQEI TKIRAELKEI ETQKTLQKIN  360
ESRSWFFERI NKIDRPLARL IKKKREKNQI DTIKNDKGDI TTDPTEIQTT IREYYKHLYA  420
NKLENLEEMD TFLDTYTLPR LNQEEVESLN RPITGSEIVA IINSLPTKKS PGPDGFTAEF  480
YQRYMEELVP FLLKLFQSIE KEGILPNSFY EASIILIPKP GRDTTKKENF RPISLMNIDA  540
KILNKILANR IQQHKKLIH HDQVGFIPGM QGWFNIRKSI NVIQHINRAK DKNHMIISID  600
AEKAFDKIQQ PFMLKTLNKL GIDGTYFKII RAIYDKPTAN IILNGQKLEA FPLKTGTRQG  660
CPLSPLLFNI VLEVLARAIR QEKEIKGIQL GKEEVKLSLF ADDMIVYLEN PIVSAQNLLK  720
LISNFSKVSG YKINVQKSQA FLYTNNRQTE SQIMGELPFV IASKRIKYLG IQLTRDVKDL  780
FKENYKPLLK EIKEDTNKWK NIPCSWVGRI NIVKMAILPK VIYRFNAIPI KLPMTFFTEL  840
EKTTLKFIWN QKRARIAKSI LSQKNKAGGI TLPDFKLYYK ATVTKTAWYW YQNRDIDQWN  900
RTEPSEIMPH IYNYLIFDKP EKNKQWGKDS LFNKWCWENW LAICRKLKLD PFLTPYTKIN  960
SRWIKDLNVK PKTIKTLEEN LGITIQDIGV GKDFMSKTPK AMATKDKIDK WDLIKLKSFC 1020
TAKETTIRVN RQPTTWEKIF ATYSSDKGLI SRIYNELKQI YKKKTNNPIK KWAKDMNRHF 1080
SKEDIYAAKK HMKKCSSSLA IREMQIKTTM RYHLTPVRMA IIKKSGNNRC WRGCGEIGTL 1140
LHCWWDCKLV QPLWKSVWRF LRDLELEIPF DPAIPLLGIY PNEYKSCCYK DTCTRMFIAA 1200
LFTIAKTWNQ PKCPTMIDWI KKMWHIYTME YYAAIKNDEF ISFVGTWMKL ETIILSKLSQ 1260
EQKTKHRIFS LIGGN                                                  1275

SEQ ID NO: 56             moltype = DNA  length = 3828
FEATURE                   Location/Qualifiers
misc_feature              1..3828
                          note = Description of Artificial Sequence: Synthetic
                          polynucleotide
source                    1..3828
                          mol_type = other DNA
                          organism = synthetic construct
SEQUENCE: 56
atgaccggct ctaactcaca tatcaccatc cttacactta acattaacgg cctcaactca   60
gctatcaagc gccatcggct ggccagctgg atcaaatcac aggatccaag cgtttgttgc  120
atccaagaga cccacctgac ctgtagagat actcaccgcc tcaagatcaa gggatggcga  180
aagatttatc aggcgaacgg taagcagaag aaagccggga tcgcaattct ggtctcagac  240
aagacggatt tcaagcccac caaaattaag cgtgataagg aagtcacta tattatggtg  300
aaaggcagca tacagcagga agaacttacc atattgaaca tctacgcgcc aaacaccggc  360
gcacctcgct ttatcaaaca ggtcctgtcc gatctgcagc gagatctgga ttctcatacg  420
ttgattatgg gtgatttcaa tacaccttg agcaccctgg atcgcagcac caggcaaaag  480
gtaaataaag acacgcaaga gctcaatagc gcactgcatc aggcagatct cattgatatt  540
tatcgcactc ttcatcctaa gagtaccgag tacacattct tcagcgcccc acatcataca  600
```

-continued

```
tactcaaaga tcgatcatat cgtcggctca aaggctctgc tgtcaaagtg caagcgcaca  660
gagataatta caaattacct gtcagatcat agcgcgatca agctcgagct gagaatcaag  720
aacctgaccc agagccggag taccacttgg aagcttaata acctgctgct caacgattat  780
tgggtccaca atgagatgaa ggcagagatt aaaatgttct tcgaaacaaa tgagaataag  840
gatactacct atcaaaacct ttgggatgcc tttaaggccg tctgcagagg caagttcatc  900
gccctcaacg cctataaaag aaaacaagag agatctaaga tcgatactct cacctctcag  960
ctgaaggagt tggagaaaca ggaacagacc cactccaagg cgtcaagacg gcaggagatc 1020
acaaagattc gcgccgagtt gaaagagatc gaaacccaaa agactcttca gaaaattaac 1080
gagtctcgta gttggttctt cgagcggatt aataagatag acagacctct ggcacgactg 1140
attaagaaga agcgcgaaaa gaaccagatt gataccatca agaacgacaa gggcgacatc 1200
actactgacc cgaccgagat ccagaccact attcgggagt attataagca tttgtatgct 1260
aacaagcttg agaacctgga agagatggac acttttctgg ataccatac tctgccacgg 1320
cttaatcaag aggaagtcga gtccctcaac cgcccaatta caggaagcga gattgtggcc 1380
ataattaact ccctgccgac aaagaaatct cctggtccgg acgggtttac agctgagttt 1440
tatcaacggt atatggaaga gcttgtaccg tttctgctca agctctttca gtctatagaa 1500
aaggaaggca tcttgcccaa ttccttctac gaagcttcta taatacttat tcccaaacca 1560
ggacgcgata ccacaaagaa ggaaaacttc cggcccatta gtctcatgaa tatcgacgct 1620
aaaatattga acaagattct cgccaacaga atccaacaac atattaagaa attgatacat 1680
cacgaccagg tggggtttat acctggcatg cagggctggt ttaacatccg gaagagtatt 1740
aacgtcattc aacacattaa tagagctaag gataagaatc atatgatcat ctctatagac 1800
gcggaaaagg cattcgataa gattcagcag ccatttatgc tcaagactct gaacaaactc 1860
ggcatcgacg gaacatattt taagattatt cgcgcaattc acgataagcc tgctgctaac 1920
attatcctta acggccaaaa gctcgaggcc tttccgctca agactggaac ccgccaaggc 1980
tgtcccctct ccccgctttt gtttaatatt gtactcgagg tgctggctag ggctattcgt 2040
caagagaaag agattaaagg gatacagctc gggaaggaag aggtcaagct ttccttgttc 2100
gccgatgata tgattgtgta cctggagaat cctattgtgt ctgctcagaa ccttcttaaa 2160
cttatttcta actttagcaa ggtcagcggc tataagatta acgtccagaa atctcaggcc 2220
tttctgtaca caaataatcg acagaccgaa tcccagataa tgggtgagct tccgtttgtc 2280
atagccagca aaaggataaa gtatctcgga atccagctga cacgagacgt taaagatttg 2340
tttaaggaaa attacaagcc tctcctgaaa gagattaagg aagatactaa taagtggaag 2400
aatatcccct gttcatgggg tggcagaatc aacatagtga agatggcaat acttcctaaa 2460
gtgatatatc gctttaacgc catcccaatt aaactgccta tgaccttctt tacggagctc 2520
gagaaaacaa cccttaaatt tatatggaat caaaagagag caagaatagc gaagtccatc 2580
ttgagccaga agaataaggc cggtgggatt actttgcctg attttaagtt gtattataaa 2640
gccacagtaa ctaagacagc ctggtattgg tatcagaata gagacatcga ccagtggaat 2700
cggaccgaac catcagagat aatgccccac atctataatt accttatatt cgataagcca 2760
gaaaagaata aacagtgggg caaagacagc ctcttcaaca agtggtgttg ggagaattgg 2820
ctggccatat gccggaaact caagctcgac cccttttctta caccctacac taaaatcaac 2880
agtaggtgga tcaaggactt gaatgtcaag ccaaagacta taaagacact ggaagagaat 2940
cttgggatca caatcaaga tataggcgtc ggcaaagatt ttatgtcaaa gacgcccaag 3000
gccatggcca ctaaggataa gattgataag tgggacctta ttaagctcaa aagcttctgt 3060
actgccaagg agaccacgat cagagttaat aggcagccca ctacatggga aaagattttc 3120
gccacttatt catcagataa ggggttgata agcagaaatat aaccgagct gaagcagatc 3180
tacaagaaga aaacgaataa tcccatcaag aagtgggcaa aagatatgaa caggcatttt 3240
agcaaagagg atatctacgc cgcgaagaag catatgaaga agtgtagttc aagcttggcc 3300
attcgtgaga tgcagattaa gacgaccatg cgataccacc ttaccccagt gaggatggca 3360
attatcaaga aatctggcaa taatagatgt tggcgggcgt gtggcgagat tggcaccctg 3420
ctccattgct ggtgggattg caagctggtg cagccgcttt ggaaatcagt ctggcgcttt 3480
ctgagggacc tcgagcttga gattcccttc gatcccgcaa ttcccttgct cggaatctat 3540
cctaacgaat acaagagctg ttgttacaag gatacgtgta cccggatgtt catcgcggcc 3600
ttgtttacga tagctaagac gtggaatcag cctaagtgcc ccacaatgat cgattggatc 3660
aagaaaatgt ggcatattta taccatggag tattacgcag caattaagaa tgacgaattt 3720
atttccttcg ttgggacctg gatgaagctg gagactatta ttctgagcaa gctgtctcag 3780
gagcaaaaga caaagcatag aatcttctct ctcattggtg gtaactaa              3828
```

SEQ ID NO: 57          moltype = AA   length = 1290
FEATURE                Location/Qualifiers
REGION                 1..1290
                       note = Description of Artificial Sequence: Synthetic
                         polypeptide
source                 1..1290
                       mol_type = protein
                       organism = synthetic construct
SEQUENCE: 57

```
MVIGTYISII TLNVNGLNAP TKRHRLAEWI QKQDPYICCL QETHFRPRDT YRLKVRGWKK  60
IPHANGNQKK AGVAILISDK IDFKIKNVTR DKEGHYIMIQ GSIQEEDITI INIYAPNIGA 120
PQYIRQLLTA IKEEIDSNTI IVGDFNTSLT PMDRSSKMKI NKETEALNDT IDQIDLIDIY 180
RTFHPKTADY TFFSSAHGTF SRIDHILGHK SSLSKFKKIE IISSIFSDHN AMRLEMNHRE 240
KNVKKTNTWR LNNTLLNNQE ITEEIKQEIK KYLETNDNEN TTTQNLWDAA KAVLRGKFIA 300
IQAYLKKQEK SQVNNLTLHL KKLEKEEQTK PKVSRRKEII KIRAEINEIE TKKTIAKINK 360
TKSWFFEKIN KIDKPLARLI KKKRERTQIN KIRNEKGEVT TDTAEIQNIL RDYYKQLYAN 420
KMDNLEEMDK FLERYNLPRL NQEETENINR PITSNEIETV IKNLPTNKSP GPDGFTGEFY 480
QTFREELTPI LLKLFQKIAE EGTLPNSFYE ATITLIPKPD KDTTKKENYR PISLMNIDAK 540
ILNKILANRI QQHIKRIIHH DQVGFIPGMQ GFFNIRKSIN VIHHINKLKK KNHMIISIDA 600
EKAFDKIQHP FMIKTLQKVG IEGTYLNIIK AIYDKPTANI ILNGEKLKAF PLRSGTRQGC 660
PLSPLLFNIV LEVLATAIRE EKEIKGIQIG KEEVKLSLFA DDMILYIENP KTATRKLLEL 720
INEYGKVAGY KINAQKSLAF LYTNDEKSER EIMETLPFTI ATKRIKYLGI NLPKETKDLY 780
AENYKTLMKE IKDDTNRWRD IPCSWIGRIN IVKMSILPKA IYRFNAIPIK LPMAFFTELE 840
QIILKFVWRH KRPRIAKAVL RQKNGAGGIR LPDFRLYYKA TVIKTIWYWH KNRNIDQWNK 900
```

```
IESPEINPRT YGQLIYDKGG KDIQWRKDSL FNKWCWENWT ATCKRMKLEY SLTPYTKINS    960
KWIRDLNIRL DTIKLLEENI GRTLFDINHS KIFFDPPPRV MEIKTKINKW DLMKLQSFCT   1020
AKETINKTKR QPSEWEKIFA NESTDKGLIS KIYKQLIQLN IKETNTPIQK WAEDLNRHFS   1080
KEDIQTATKH MKRCSTSLII REMQIKTTMR YHLTPVRMGI IRKSTNNKCW RGCGEKGTLL   1140
HCWWECKLIQ PLWRTIWRFL KKLKIELPYD PAIPLLGIYP EKTVIQKDTC TRMFIAALFT   1200
IARSWKQPKC PSTDEWIKKM WYIYTMEYYS AIKRNEIGSF LETWMDLETV IQSEVSQKEK   1260
NKYRILTHIC GTWKNGTDEP VCRTEIETQM                                   1290

SEQ ID NO: 58              moltype = DNA   length = 3873
FEATURE                    Location/Qualifiers
misc_feature               1..3873
                           note = Description of Artificial Sequence: Synthetic
                            polynucleotide
source                     1..3873
                           mol_type = other DNA
                           organism = synthetic construct
SEQUENCE: 58
atggtcatag gaacatacat atcgataatt accttaaacg tgaatggatt aaatgcccca    60
accaaaagac atagactggc tgaatggata caaaaacaag acccatatat atgctgtcta   120
caagagaccc acttcagacc tagggacaca tacagactga aagtgagggg atggaaaaag   180
atattccatg caaatggaaa tcaaaagaaa gctggagtag ctatactcat atcagataaa   240
atagacttta aaataaagaa tgttacaaga gacaaggaag gacactacat aatgatccag   300
ggatcaatcc aagaagaaga tataacaatt ataaatatat atgcacccaa cataggagca   360
cctcaataca taaggcaact gctaacagct ataaagaggg aaatcgacag taacacaata   420
atagtggggg actttaacac ctcacttaca ccaatggaca gatcatccaa aatgaaaata   480
aataaggaaa cagaagcttt aaatgacaca atagaccaga tagatttaat tgatatatat   540
aggacattcc atccaaaaac agcagattac acgttcttct caagtgcgca cggaacattc   600
tccaggatag atcacatctt gggtcacaaa tcaagcctca gtaaatttaa gaaaattgaa   660
atcatatcaa gcatcttttc tgaccacaac gctatgagat tagaaatgaa tcacaggga   720
aaaaacgtaa aaaagacaaa cacatggagg ctaaacaata cgttactaaa taaccaagag   780
atcactgaag aaatcaaaca ggaaataaaa aaatacctag agacaaatga caatgaaaac   840
acgacgaccc aaaacctatg ggatgcagca aaagcggttc taagagggaa gtttatagct   900
atacaagcct acctaaagaa acaagaaaaa tctcaagtaa acaatctaac cttacaccta   960
aagaaactag agaaagaaga acaaacaaaa cccaaagtta gcagaaggaa agaaatcata  1020
aagatcagag cagaaataaa tgaaataaaa acaaagaaaa caatagcaaa gatcaataaa  1080
actaaaagtt ggttctttga gaagataaac aaaattgata agccattagc cagactcatc  1140
aagaaaaaga gggagaggac tcaaatcaat aaaatcagaa atgaaaaagg agaagttaca  1200
acagacaccg cagaaataca aacatcctta agagactact acaagcaact ttatgccaat  1260
aaaatggaca acctggaaga aatggacaaa ttcttagaaa ggtataacct tccaagactg  1320
aaccaggaag aaacagaaaa tatcaacaga ccaatcacaa gtaatgaaat tgaaactgtg  1380
attaaaaatc ttccaacaaa caaaagtcca ggaccagatg gcttcacagg tgaattctat  1440
caaacattta gagaagagct aacacccatc cttctcaaac tcttccaaaa aattgcagaa  1500
gaaggaacac tcccaaactc attctatgag gccaccatca ccctgatacc aaaaccagac  1560
aaagacacta caaaaaaaga aaattacaga ccaatatcac tgatgaatat agatgcaaaa  1620
atcctcaaca aaatactagc aaacagaatc caacaacaca ttaaaaggat catacaccac  1680
gatcaagtgg gatttatccc agggatgcaa ggattcttca atatacgaa atcaatcaat  1740
gtgatacacc atattaacaa attgaagaag aaaaaccata tgatcatctc aatagatgca  1800
gaaaaagctt ttgacaaaat tcaacaccca tttatgataa aaactctcca gaaagtgggc  1860
atagagggaa cctacctcaa cataataaag gccatatatg acaaacccac agcaaacatc  1920
attctcaatg gtgaaaaact gaaagcattt cctctaagat caggaacgag acaaggatgt  1980
ccactctcac cactattatt caacatagtt ctggaagtcc tagccacggc aaactcagaa  2040
gaaaagaaa taaaggaat acaaattgga aagaagaag taaaactgtc actgtttgcg  2100
gatgacatga tactatacat agagaatcct aaaactgcca ccagaaaact gctagagcta  2160
attaatgaat atggtaaagt tgcaggttac aaaattaatg cacagaaatc tcttgcattc  2220
ctatacacta atgatgaaaa atctgaaaga aaattatgg aaacactccc atttaccatt  2280
gcaacaaaaa gaataaaata cctaggaata aacctaccta aggagacaaa agacctgtat  2340
gcagaaaact ataagacact gatgaaagaa attaaagatg ataccaacag atggagagat  2400
ataccatgtt cttggattgg aagaatcaac attgtgaaaa tgagtatact acccaaagca  2460
atctacagat tcaatgcaat ccctatcaaa ttaccaatgt cattttttac ggagctagaa  2520
caaatcatct taaaatttgt atggagacac aaaagacccc gaatagccaa agcagtcttg  2580
aggcaaaaaa atggagctgg aggaatcaga ctccctgact tcagactata ctacaaagct  2640
acagtaatca agacaatatg gtactggcac aaaaacagaa acatagatca atggaacaag  2700
atagaaagcc cagagattaa cccacgcacc tatggtcaac taatctatga caaaggaggc  2760
aaagatatac aatggagaaa agacagtctc ttcaataagt ggtgctggaa aactggaca  2820
gccacatgta aaagaatgaa attagaatac tccctaacac catacacaaa aataaactca  2880
aaatggatta gagacctaaa tataagactg gacactataa aactcttaga ggaaacata  2940
ggaagaacac tctttgacat aaatcacagc aagatctttt cgatccacc tcctagagta  3000
atggaaataa aaacaaaaat aaacaagtgg gacctaatga aacttcaaag cttttgcaca  3060
gcaaaggaaa ccataaacaa gacgaaaaga caaccctcag aatgggagaa aatatttgca  3120
aatgaatcaa cggacaaagg attaatctcc aaaatatata aacagctcat tcagctcaat  3180
atcaaagaaa caaacacccc aatccaaaaa tgggcagaag acctaaatag acatttctcc  3240
aaagaagaca tacagacggc cacgaagcac atgaaaagat gctcaacatc actaattatt  3300
agagaaatgc aaatcaaaac tacaatgagg tatcacctca ctcctgttag aatgggcatc  3360
atcagaaaat ctacaaacaa caaatgctgg agaggtgtg gagaaaaggg aaccctcttg  3420
cactgttggt gggaatgtaa attgatacag ccactatgga gaacaatatg gaggttcctt  3480
aaaaaactaa aatagaatt accatatgac ccagcaatcc cactactggg catataccca  3540
gagaaaccg taattcaaaa agacacatgc acccgaatgt tcattgcagc actatttaca  3600
atagccaggt catggaagca acctaaatgc ccatcgacac acgaatggat aaagaagatg  3660
tggtacatat atacaatgga atattactca gccataaaaa ggaacgaaat tgggtcattt  3720
```

-continued

```
ttagagacgt ggatggatct agagactgtc atacagagtg aagtaagtca gaaagagaaa   3780
aacaaatatc gtatattaac gcatatatgt ggaacctgga aaaatggtac agatgaaccg   3840
gtctgcagga cagaaattga gacacaaatg taa                                3873

SEQ ID NO: 59            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 59
PAAKRVKLD                                                            9

SEQ ID NO: 60            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 60
DYKDDDDK                                                             8

SEQ ID NO: 61            moltype = AA  length = 234
FEATURE                  Location/Qualifiers
REGION                   1..234
                         note = Description of Artificial Sequence: Synthetic
                          polypeptide
source                   1..234
                         mol_type = protein
                         organism = synthetic construct
SEQUENCE: 61
ASNFTQFVLV DNGGTGDVTV APSNFANGIA EWISSNSRSQ AYKVTCSVRQ SSAQNRKYTI   60
KVEVPKGAWR SYLNMELTIP IFATNSDCEL IVKAMQGLLK DGNPIPSAIA ANSGIYAMAS   120
NFTQFVLVDN GGTGDVTVAP SNFANGIAEW ISSNSRSQAY KVTCSVRQSS AQNRKYTIKV   180
EVPKGAWRSY LNMELTIPIF ATNSDCELIV KAMQGLLKDG NPIPSAIAAN SGIY         234

SEQ ID NO: 62            moltype = AA  length = 9
FEATURE                  Location/Qualifiers
REGION                   1..9
                         note = Description of Unknown: "LAGLIDADG" family motif
                          peptide
source                   1..9
                         mol_type = protein
                         organism = unidentified
SEQUENCE: 62
LAGLIDADG                                                            9

SEQ ID NO: 63            moltype = AA  length = 116
FEATURE                  Location/Qualifiers
REGION                   1..116
                         note = Description of Artificial Sequence: Synthetic
                          polypeptide
source                   1..116
                         mol_type = protein
                         organism = synthetic construct
SEQUENCE: 63
EIQLVQSGGG LVKPGGSVRI SCAASGYTFT NYGMNWVRQA PGKGLEWMGW INTHTGEPTY   60
ADSFKGRFTF SLDDSKNTAY LQINSLRAED TAVYFCTRRG YDWYFDVWGQ GTTVTV       116

SEQ ID NO: 64            moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 64
DIQMTQSPSS LSASVGDRVT ITCRASQDIN SYLSWFQQKP GKAPKTLIYR ANRLESGVPS   60
RFSGSGSGTD YTLTISSLQY EDFGIYYCQQ YDESPWTFGG GTKLEIK                 107

SEQ ID NO: 65            moltype = AA  length = 45
FEATURE                  Location/Qualifiers
REGION                   1..45
                         note = Description of Artificial Sequence: Synthetic
                          polypeptide
source                   1..45
```

```
                              mol_type = protein
                              organism = synthetic construct
SEQUENCE: 65
LYCRRLKIQV RKAAITSYEK SDGVYTGLST RNQETYETLK HEKPP                  45

SEQ ID NO: 66           moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 66
YEDMRGILYA APQLRSIRGQ PGPNHEEDAD SYENM                             35

SEQ ID NO: 67           moltype = AA  length = 61
FEATURE                 Location/Qualifiers
REGION                  1..61
                        note = Description of Artificial Sequence: Synthetic
                         polypeptide
source                  1..61
                        mol_type = protein
                        organism = synthetic construct
SEQUENCE: 67
KVAKKPTNKA PHPKQEPQEI NFPDDLPGSN TAAPVQETLH GCQPVTQEDG KESRISVQER  60
Q                                                                 61

SEQ ID NO: 68           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 68
IYIWAPLAGT CGVLLLSLVI T                                            21

SEQ ID NO: 69           moltype = AA  length = 62
FEATURE                 Location/Qualifiers
REGION                  1..62
                        note = Description of Artificial Sequence: Synthetic
                         polypeptide
source                  1..62
                        mol_type = protein
                        organism = synthetic construct
SEQUENCE: 69
ALSNSIMYFS HFVPVFLPAK PTTTPAPRPP TPAPTIASQP LSLRPEACRP AAGGAVHTRG  60
LD                                                                62

SEQ ID NO: 70           moltype = AA  length = 415
FEATURE                 Location/Qualifiers
REGION                  1..415
                        note = Description of Artificial Sequence: Synthetic
                         polypeptide
source                  1..415
                        mol_type = protein
                        organism = synthetic construct
SEQUENCE: 70
EIQLVQSGGG LVKPGGSVRI SCAASGYTFT NYGMNWVRQA PGKGLEWMGW INTHTGEPTY  60
ADSFKGRFTF SLDDSKNTAY LQINSLRAED TAVYFCTRRG YDWYFDVWGQ GTTVTVSSGG  120
GGSGGGGSGG GGSDIQMTQS PSSLSASVGD RVTITCRASQ DINSYLSWFQ QKPGKAPKTL  180
IYRANRLESG VPSRFSGSGS GTDYTLTISS LQYEDFGIYY CQQYDESPWT FGGGTKLEIK  240
SGGGGSGALS NSIMYFSHFV PVFLPAKPTT TPAPRPPTPA PTIASQPLSL RPEACRPAAG  300
GAVHTRGLDI YIWAPLAGTC GVLLLSLVIT LYCRRLKIQV RKAAITSYEK SDGVYTGLST  360
RNQETYETLK HEKPPQGSGS YEDMRGILYA APQLRSIRGQ PGPNHEEDAD SYENM       415

SEQ ID NO: 71           moltype = AA  length = 437
FEATURE                 Location/Qualifiers
REGION                  1..437
                        note = Description of Artificial Sequence: Synthetic
                         polypeptide
source                  1..437
                        mol_type = protein
                        organism = synthetic construct
SEQUENCE: 71
EIQLVQSGGG LVKPGGSVRI SCAASGYTFT NYGMNWVRQA PGKGLEWMGW INTHTGEPTY  60
ADSFKGRFTF SLDDSKNTAY LQINSLRAED TAVYFCTRRG YDWYFDVWGQ GTTVTVSSGG  120
GGSGGGGSGG GGSDIQMTQS PSSLSASVGD RVTITCRASQ DINSYLSWFQ QKPGKAPKTL  180
```

-continued

```
IYRANRLESG VPSRFSGSGS GTDYTLTISS LQYEDFGIYY CQQYDESPWT FGGGTKLEIK   240
SGGGGSGALS NSIMYFSHFV PVFLPAKPTT TPAPRPPTPA PTIASQPLSL RPEACRPAAG   300
GAVHTRGLDI YIWAPLAGTC GVLLLSLVIT LYCRLKIQVR KAAITSYEKS DGVYTGLSTR   360
NQETYETLKH EKPPQKKVAK KPTNKAPHPK QEPQEINFPD DLPGSNTAAP VQETLHGCQP   420
VTQEDGKESR ISVQERQ                                                 437

SEQ ID NO: 72            moltype = AA  length = 438
FEATURE                  Location/Qualifiers
REGION                   1..438
                         note = Description of Artificial Sequence: Synthetic
                          polypeptide
source                   1..438
                         mol_type = protein
                         organism = synthetic construct
SEQUENCE: 72
EIQLVQSGGG LVKPGGSVRI SCAASGYTFT NYGMNWVRQA PGKGLEWMGW INTHTGEPTY   60
ADSFKGRFTF SLDDSKNTAY LQINSLRAED TAVYFCTRRG YDWYFDVWGQ GTTVTVSSGG   120
GGSGGGGSGG GGSDIQMTQS PSSLSASVGD RVTITCRASQ DINSYLSWFQ QKPGKAPKTL   180
IYRANRLESG VPSRFSGSGS GTDYTLTISS LQYEDFGIYY CQQYDESPWT FGGGTKLEIK   240
SGGGGSGALS NSIMYFSHFV PVFLPAKPTT TPAPRPPTPA PTIASQPLSL RPEACRPAAG   300
GAVHTRGLDI YIWAPLAGTC GVLLLSLVIT LYCRRLKIQV RKAAITSYEK SDGVYTGLST   360
RNQETYETLK HEKPPQKKVA KKPTNKAPHP KQEPQEINFP DDLPGSNTAA PVQETLHGCQ   420
PVTQEDGKES RISVQERQ                                                438

SEQ ID NO: 73            moltype = AA  length = 44
FEATURE                  Location/Qualifiers
REGION                   1..44
                         note = Description of Artificial Sequence: Synthetic
                          polypeptide
source                   1..44
                         mol_type = protein
                         organism = synthetic construct
SEQUENCE: 73
MRNKKILKED ELLSETQQAA FHQIAMEPFE INVPKPKRRN GVNF                   44

SEQ ID NO: 74            moltype = AA  length = 50
FEATURE                  Location/Qualifiers
REGION                   1..50
                         note = Description of Artificial Sequence: Synthetic
                          polypeptide
source                   1..50
                         mol_type = protein
                         organism = synthetic construct
SEQUENCE: 74
MEQWDHFHNQ QEDTDSCSES VKFDARSMTA LLPPNPKNSP SLQEKLKSFK             50

SEQ ID NO: 75            moltype = AA  length = 33
FEATURE                  Location/Qualifiers
REGION                   1..33
                         note = Description of Artificial Sequence: Synthetic
                          polypeptide
source                   1..33
                         mol_type = protein
                         organism = synthetic construct
SEQUENCE: 75
GAAPAAAPAK QEAAAPAPAA KAEAPAAAPA AKA                               33

SEQ ID NO: 76            moltype = AA  length = 20
FEATURE                  Location/Qualifiers
REGION                   1..20
                         note = Description of Artificial Sequence: Synthetic peptide
REGION                   1..20
                         note = MISC_FEATURE - This sequence may encompass 1-4 "Gly
                          Gly Gly Gly Ser" repeating units
REGION                   1..20
                         note = See specification as filed for detailed description
                          of substitutions and preferred embodiments
source                   1..20
                         mol_type = protein
                         organism = synthetic construct
SEQUENCE: 76
GGGGSGGGGS GGGGSGGGGS                                              20

SEQ ID NO: 77            moltype = AA  length = 6
FEATURE                  Location/Qualifiers
REGION                   1..6
                         note = Description of Artificial Sequence: Synthetic peptide
source                   1..6
                         mol_type = protein
```

```
                        organism = synthetic construct
SEQUENCE: 77
GGGGGG                                                              6

SEQ ID NO: 78          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 78
GGGGGGGG                                                            8

SEQ ID NO: 79          moltype = AA   length = 20
FEATURE                Location/Qualifiers
REGION                 1..20
                       note = Description of Artificial Sequence: Synthetic peptide
REGION                 1..20
                       note = MISC_FEATURE - This sequence may encompass 1-4 "Glu
                        Ala Ala Ala Lys" repeating units
REGION                 1..20
                       note = See specification as filed for detailed description
                        of substitutions and preferred embodiments
source                 1..20
                       mol_type = protein
                       organism = synthetic construct
SEQUENCE: 79
EAAAKEAAAK EAAAKEAAAK                                               20

SEQ ID NO: 80          moltype = RNA   length = 48
FEATURE                Location/Qualifiers
misc_feature           1..48
                       note = Description of Artificial Sequence: Synthetic
                        oligonucleotide
source                 1..48
                       mol_type = other RNA
                       organism = synthetic construct
SEQUENCE: 80
ctaggaatct ggaagtaccg aggaaactcg gtacttcctg tgtcctag               48

SEQ ID NO: 81          moltype = RNA   length = 37
FEATURE                Location/Qualifiers
misc_feature           1..37
                       note = Description of Artificial Sequence: Synthetic
                        oligonucleotide
source                 1..37
                       mol_type = other RNA
                       organism = synthetic construct
SEQUENCE: 81
atatggaaga tcctggggaa ctgggatctt cctaagt                           37

SEQ ID NO: 82          moltype = DNA   length = 76
FEATURE                Location/Qualifiers
misc_feature           1..76
                       note = Description of Artificial Sequence: Synthetic
                        oligonucleotide
modified_base          16..17
                       mod_base = OTHER
                       note = dihydrouridine
variation              37
                       note = a, c, t, g or u
modified_base          39
                       mod_base = OTHER
                       note = Pseudouridine
modified_base          55
                       mod_base = OTHER
                       note = Pseudouridine
source                 1..76
                       mol_type = other DNA
                       organism = synthetic construct
SEQUENCE: 82
gcgcatttag ctcagnnggg agagcgccag actgaananc tggagctcct gtgtncgatc  60
cacagaattc gcacca                                                  76

SEQ ID NO: 83          moltype = RNA   length = 203
FEATURE                Location/Qualifiers
misc_feature           1..203
                       note = Description of Artificial Sequence: Synthetic
```

-continued

```
                       polynucleotide
misc_difference        66..185
                       note = a, t, c, g or u
misc_feature           1..203
                       note = See specification as filed for detailed description
                       of substitutions and preferred embodiments
source                 1..203
                       mol_type = other RNA
                       organism = synthetic construct
SEQUENCE: 83
gctgggtttt tccttgttcg caccggacac ctccagtgac cagacggcaa ggtttttatc  60
ccagtnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnaaaaa aaaaaaaaaa aaa                                          203

SEQ ID NO: 84          moltype = RNA  length = 93
FEATURE                Location/Qualifiers
misc_feature           1..93
                       note = Description of Artificial Sequence: Synthetic
                       oligonucleotide
source                 1..93
                       mol_type = other RNA
                       organism = synthetic construct
SEQUENCE: 84
gaaggttttt cttttcctga gaaaacaaca cgtattgttt tctcaggttt tgcttttttgg  60
ccttttttcta gcttaaaaaa aaaaaaagca aaa                              93

SEQ ID NO: 85          moltype = RNA  length = 76
FEATURE                Location/Qualifiers
misc_feature           1..76
                       note = Description of Artificial Sequence: Synthetic
                       oligonucleotide
source                 1..76
                       mol_type = other RNA
                       organism = synthetic construct
SEQUENCE: 85
ggaaggtttt tcttttcctg aggcgaaagt ctcaggtttt gcttttttggc ctttcttaaa  60
aaaaaaaaaa gcaaaa                                                  76

SEQ ID NO: 86          moltype = RNA  length = 61
FEATURE                Location/Qualifiers
source                 1..61
                       mol_type = other RNA
                       organism = synthetic construct
SEQUENCE: 86
actcctcccc atcctctccc tctgtccctc tgtccctctg accctgcact gtcccagcac  60
c                                                                 61

SEQ ID NO: 87          moltype = RNA  length = 118
FEATURE                Location/Qualifiers
source                 1..118
                       mol_type = other RNA
                       organism = synthetic construct
SEQUENCE: 87
caggacacag ccttggatca ggacagagac ttgggggcca tcctgcccct ccaacccgac  60
atgtgtacct cagctttttc cctcacttgc atcaataaag cttctgtgtt tggaacag    118
```